(12) United States Patent
Dasgupta et al.

(10) Patent No.: US 9,433,611 B2
(45) Date of Patent: Sep. 6, 2016

(54) OXAZOLE AND THIAZOLE COMPOUNDS AS β-CATENIN MODULATORS AND USES THEREOF

(75) Inventors: Ramanuj Dasgupta, New York, NY (US); Foster Gonsalves, Brooklyn, NY (US)

(73) Assignee: New York University, New York, NY (US)

( * ) Notice: Subject to any disclaimer, the term of this patent is extended or adjusted under 35 U.S.C. 154(b) by 750 days.

(21) Appl. No.: 13/595,336

(22) Filed: Aug. 27, 2012

(65) Prior Publication Data
US 2013/0109675 A1    May 2, 2013

Related U.S. Application Data

(63) Continuation of application No. 12/322,070, filed on Jan. 28, 2009, now Pat. No. 8,252,823.

(60) Provisional application No. 61/062,772, filed on Jan. 28, 2008, provisional application No. 61/084,681, filed on Jul. 30, 2008, provisional application No. 61/147,715, filed on Jan. 27, 2009.

(51) Int. Cl.
| | | |
|---|---|---|
| A61K 31/42 | (2006.01) | |
| A61K 31/497 | (2006.01) | |
| A61K 31/47 | (2006.01) | |
| A61K 31/421 | (2006.01) | |
| A61K 31/422 | (2006.01) | |
| A61K 31/426 | (2006.01) | |
| A61K 31/427 | (2006.01) | |
| A61K 31/428 | (2006.01) | |
| A61K 31/433 | (2006.01) | |
| A61K 31/435 | (2006.01) | |
| A61K 31/4439 | (2006.01) | |
| A61K 31/454 | (2006.01) | |
| A61K 31/4545 | (2006.01) | |
| A61K 31/4709 | (2006.01) | |
| A61K 31/4725 | (2006.01) | |
| A61K 31/496 | (2006.01) | |
| A61K 31/498 | (2006.01) | |
| A61K 31/506 | (2006.01) | |
| A61K 31/5377 | (2006.01) | |
| A61K 31/55 | (2006.01) | |

(52) U.S. Cl.
CPC ........... *A61K 31/421* (2013.01); *A61K 31/422* (2013.01); *A61K 31/426* (2013.01); *A61K 31/427* (2013.01); *A61K 31/428* (2013.01); *A61K 31/433* (2013.01); *A61K 31/435* (2013.01); *A61K 31/4439* (2013.01); *A61K 31/454* (2013.01); *A61K 31/4545* (2013.01); *A61K 31/4709* (2013.01); *A61K 31/4725* (2013.01); *A61K 31/496* (2013.01); *A61K 31/498* (2013.01); *A61K 31/506* (2013.01); *A61K 31/5377* (2013.01); *A61K 31/55* (2013.01)

(58) Field of Classification Search
CPC .................................................. A61K 31/422
USPC ........................... 514/374, 254.04, 307, 314
See application file for complete search history.

(56) References Cited

U.S. PATENT DOCUMENTS

| | | |
|---|---|---|
| 6,762,185 B1 | 7/2004 | Kahn et al. |
| 7,067,474 B1 | 6/2006 | Birchmeier et al. |
| 2005/0256076 A1 | 11/2005 | Bumcrot |
| 2006/0165699 A1 | 7/2006 | Colland et al. |
| 2011/0251144 A1 | 10/2011 | Moon et al. |

FOREIGN PATENT DOCUMENTS

| | | |
|---|---|---|
| JP | 60-208971 | 10/1985 |
| WO | 2006116503 | 11/2006 |

OTHER PUBLICATIONS

Clemens et al., "Use of double-stranded RNA interference in *Drosophila* cell lines to dissect signal transduction pathways", Proceedings of National Academy of Sciences of the United States of America, 2000, vol. 97, No. 12, pp. 6499-6503.

Dasgupta et al., "High-throughput RNAi screen in *Drosophila*", In Wnt Signaling, 2008, vol. II: Pathway Models, (E. Vincan, ed.), vol. 469, pp. 163-184.

Eggert et al., "Parallel chemical genetic and genome-wide RNAi screens identify cytokinesis inhibitors and targets", PLoS Biology, 2004, vol. 2, No. 12, pp. 2135-2143.

Kleino et al., "Pirk is a negative regulator of the *Drosophila* Imd pathway", The Journal of Immunology, 2008, vol. 180, pp. 5413-5422.

Perrimon et al., "Drug-target identification in *Drosophila* cells: combining high-throughout RNAi and small-molecule screens", Drug Discovery Today, 2007, vol. 12, Nos. 1-2, pp. 28-33.

Luu et al., "Wnt/Beta-catenin signaling pathway as novel cancer drug targets", Current Cancer Drug Targets, 2004, vol. 4, pp. 653-671.

Lepourcelet et al., "Small-molecule antagonists of the oncogenic Tcf/Beta-catenin protein complex", Cancer Cell, 2004, vol. 5, pp. 91-102.

Barker et al., "Mining the Wnt pathway for cancer therapeutics", Nature Reviews Drug Discovery, 2006, vol. 5, pp. 997-1014.

(Continued)

*Primary Examiner* — Shengjun Wang
(74) *Attorney, Agent, or Firm* — Klauber & Jackson LLC

(57) ABSTRACT

A series of oxazole and thiazole compounds are shown herein to be small molecule inhibitors of the Wnt pathway that specifically target the activity of the stabilized pool of β-cat oxazole and thiazole compounds are disclosed that have a formula represented by the following:

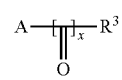

The compounds may be prepared as pharmaceutical compositions, and may be used for the prevention and treatment of a variety of conditions in mammals including humans, including by way of non-limiting example, cancer, and others.

18 Claims, 10 Drawing Sheets

(56) References Cited

OTHER PUBLICATIONS

Watanabe et al., "Winning WNT: Race to Wnt signaling inhibitors", Proc Natl Academy Sciences, 2011, vol. 108, No. 15, pp. 5929-5930.

Gonsalves et al., "An RNAi-based chemical genetic screen identifies three small-molecule inhibitors of the Wnt/wingless signaling pathway", Proc Natl Academy Sciences, 2011, vol. 108, pp. 5954-5973 and Supplemental Information, pp. 1-8.

ACS registration RN 902585-79-9.

OXAZOLE AND THIAZOLE COMPOUNDS AS β-CATENIN MODULATORS AND USES THEREOF

RELATED APPLICATIONS

The present application is a Continuation Application of U.S. application Ser. No. 12/322,070, filed Jan. 28, 2009 now U.S. Pat. No. 8,252,823, issued Aug. 28, 2012, which in turn claims the benefit under 35 U.S.C. §119 of U.S. Provisional Application Ser. No. 61/062,772 filed Jan. 28, 2008; Ser. No. 61/084,681 filed Jul. 30, 2008; and Ser. No. 61/147,715 filed Jan. 27, 2009. The contents of each of said applications is hereby incorporated by reference in its entirety.

GOVERNMENT RIGHTS

This invention was made with government support under Grant No. W81XWH-04-1-0460 awarded by the Department of Defense. Accordingly, the United States Government has certain rights in the invention.

FIELD OF THE INVENTION

This invention relates to oxazole and thiazole compounds capable of modulating β-catenin activity and uses of such compounds to modulate the activity of the Wnt/wingless (wg) signaling pathway.

BACKGROUND OF THE INVENTION

Wnts/wingless (wg) are a family of conserved signaling molecules that have been shown to regulate a plethora of fundamental developmental and cell biological processes, including cell proliferation, differentiation and cell polarity [Miller et al. Oncogene 18, 7860-72 (1999); Polakis. Genes Dev 14, 1837-51 (2000); Wodarz et al. Annu Rev Cell Dev Biol 14, 59-88 (1998)]. Mutations in the Wnt genes or in those genes encoding regulators of the Wnt/wg signaling pathway can cause devastating birth defects, including debilitating abnormalities of the central nervous system, axial skeleton, limbs, and occasionally other organs [Ciruna et al. Nature 439, 220-4 (2006); Grove et al. Development 125, 2315-25 (1998); Jiang et al. Dev Dyn 235, 1152-66 (2006); Kokubu et al. Development 131, 5469-80 (2004); Miyoshi et al. Breast Cancer Res 5, 63-8 (2003); Shu et al. Development 129, 4831-42 (2002); Staal et al. Hematol J I, 3-6 (2000)]. Aberrant Wnt signaling has also been linked to human disease, such as hepatic, colorectal, breast and skin cancers [Miyoshi et al. supra (2003); Miyoshi et al. Oncogene 21, 5548-56 (2002); Moon et al. Nat Rev Genet 5, 691-701 (2004)].

Wnts/wg encode secreted glycoproteins that activate receptor-mediated pathways leading to numerous transcriptional and cellular responses [Wodarz et al. supra (1998); Moon et al. supra (2004); Nusse. Trends Genet 15, 1-3 (1999)]. The main function of the canonical Wnt pathway is to stabilize the cytoplasmic pool of a key mediator, β-catenin (β-cat)/armadillo (arm), which is otherwise degraded by the proteosome pathway (See FIG. 1). Initially identified as a key player in stabilizing cell-cell adherens junctions, β-cat/arm is also known to act as a transcription factor by forming a complex with the LEF/TCF (Lymphoid Enhancer Factor/T Cell Factor) family of HMG-box (High mobility group) transcription factors. Upon Wnt stimulation, stabilized β-cat/arm translocates to the nucleus, wherein together with LEF/TCF transcription factors, it activates downstream target genes [Miller et al. supra (1999); Staal et al. supra (2000); Nusse. supra (1999); Schweizer et al. Proc Natl Acad Sci USA 100, 5846-51 (2003)]. Catenin responsive transcription (CRT), which is the activation of transcriptional targets of β-cat, has been shown to regulate many aspects of cell growth, proliferation, differentiation and death. The Wnt/wg pathway can also be activated by inhibiting negative regulators such as GSK-3β (Glycogen Synthase Kinase-3β), APC (Adenomatous Polyposis Coli) and Axin that promote β-cat/arm degradation, or by introducing activating mutations in β-cat that render it incapable of interacting with the degradation complex, thus stabilizing its cytosolic pool [Logan et al. Annu Rev Cell Dev Biol 20, 781-810 (2004); Nusse et al. Cell Res 15, 28-32 (2005)]. Wnt/wg signaling can also activate an alternative "non-canonical" pathway that may lead to PKC (Protein Kinase C) and JNK (c-Jun N-terminal Kinase) activation resulting in calcium release and cytoskeletal rearrangements [Miller et al. supra (1999)].

At the plasma membrane, Wnt proteins bind to their receptor, belonging to the Frizzled family of proteins and the co-receptor encoded by LDL-related-protein-5, 6 (LRP5, LRP6)/arrow (arr, in *Drosophila*) [Schweizer et al. BMC Cell Biol 4, 4 (2003); Tamai et al. Mol Cell 13, 149-56 (2004)]. In the absence of the Wnt stimulus, GSK-3β is known to phosphorylate β-cat/arm, which marks it for ubiquitination and subsequent proteosome-mediated degradation. Activation of the receptor/co-receptor complex upon Wnt binding initiates a signal transduction cascade, which results in phosphorylation and subsequent inactivation of GSK-31324.

Recent evidence has uncovered a new branch in the canonical Wnt/wg pathway whereby β-cat/arm can be stabilized in a GSK-3β independent fashion suggesting that regulated degradation of β-cat/arm (by GSK-3β) is not necessary for Wnt/wg signaling [Tolwinski et al. Dev Cell 4, 407-18 (2003); Tolwinski et al. Trends Genet 20, 177-81 (2004)]. Specifically, upon Wg binding, Arr directly recruits Axin (a scaffold protein which acts as a negative regulator) to the plasma membrane and causes its degradation. As a consequence, Arm no longer binds Axin or the degradation complex, resulting in nuclear accumulation and signaling by β-cat/Arm42.

A large number of oxazole and thiazole compounds are commercially available.

In view of the above, a need exists for therapeutic agents, and corresponding pharmaceutical compositions and related methods of treatment that address conditions causally related to aberrant Wnt pathway activity and CRT activity, and it is toward the fulfillment and satisfaction of that need, that the present invention is directed.

SUMMARY OF THE INVENTION

Accordingly, the present invention provides a method for preventing, treating or ameliorating in a mammal a disease or condition that is causally related to the aberrant activity of the Wnt pathway in vivo, which comprises administering to the mammal an effective disease-treating or condition-treating amount of a compound according to formula I:

wherein A is $A^1$, $A^2$ or $A^3$;

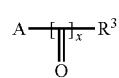

I $A^1$ is

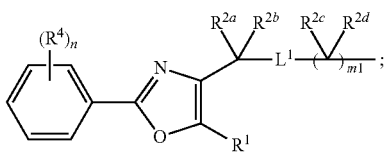

$A^2$ is

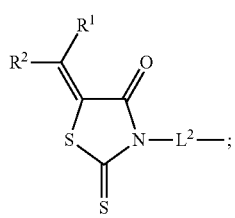

$A^3$ is

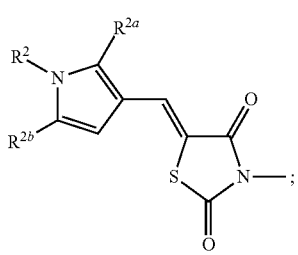

x is 1, when A is $A^1$ or $A^2$; or x is 0, when A is $A^3$;
$L^1$ is S, SO or $SO_2$;
m1 is 1, 2 or 3; n is 1, 2, 3, 4 or 5;
$L^2$ is substituted or unsubstituted $C_1$-$C_6$, alkylene or heteroalkylene;
each $R^1$, $R^{2a}$, $R^{2b}$, $R^{2c}$, and $R^{2d}$ is independently selected from hydrogen, halo, and substituted or unsubstituted $C_1$-$C_6$ alkyl;
$R^2$ is selected from aryl or heteroaryl, unsubstituted or substituted with one or more $R^4$;
$R^3$ is hydroxy, alkoxy, substituted or unsubstituted amino or cycloheteroalkyl; or when A is $A^3$, $R^3$ is $R^5$;
each $R^4$ and $R^{5a}$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and
$R^5$ is selected from aryl or heteroaryl, unsubstituted or substituted with one or more $R^{5a}$; or a pharmaceutically acceptable salt, solvate or prodrug thereof;
and stereoisomers, isotopic variants and tautomers thereof.

In one particular embodiment, with respect to compounds of formula I, $A^1$ is

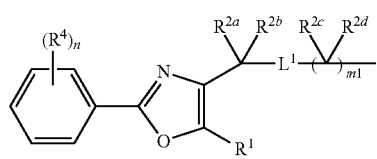

In one particular embodiment, with respect to compounds of formula I, $A^2$ is

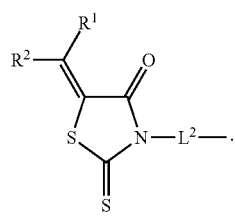

In one particular embodiment, with respect to compounds of formula I, $A^3$ is

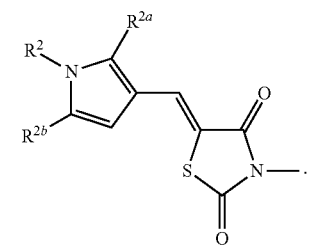

In one particular embodiment, with respect to compounds of formula I, the compound is according to formula IIa:

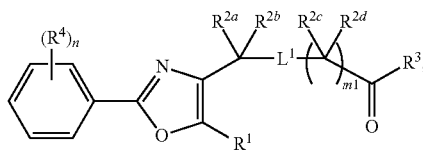

and wherein $L^1$, m1, n, $R^1$, $R^{2a}$, $R^{2b}$, $R^{2c}$, $R^{2d}$, $R^3$, and $R^4$ are as described for formula I.

In one particular embodiment, with respect to compounds of formula I, the compound is according to formula IIb:

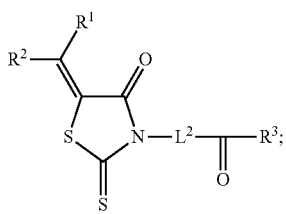

and wherein $L^2$, $R^1$, $R^2$, $R^3$, and $R^4$ are as described for formula I.

In one particular embodiment, with respect to compounds of formula I, the compound is according to formula IIc:

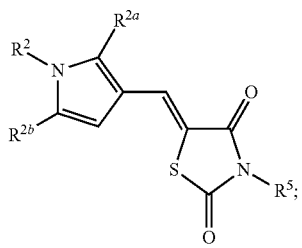

and wherein $R^{2a}$, $R^{2b}$, $R^2$, $R^4$ and $R^5$ are as described for formula I.

In a further aspect, the present invention provides pharmaceutical compositions comprising an oxazole or an thiazole compound of the invention, and a pharmaceutically acceptable carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, this invention provides the compounds of the invention and other agents for use in the treatment of mammals susceptible to or afflicted with a condition from those listed herein, and particularly, such conditions as may be associated with alterations or aberrations in Wnt/wg pathway signaling.

In addition to the methods of treatment set forth above, the present invention extends to the use of any of the compounds of the invention for the preparation of medicaments that may be administered for such treatments, as well as to such compounds for the treatments disclosed and specified.

A further aspect and object of the invention, is to provide a method of treating a mammal susceptible to or afflicted with a condition from among those listed herein, and particularly, such condition as may be associated with e.g. altered Wnt/wg pathway signaling, by administering to such mammal a an effective disease-treating or condition-treating amount of a compound or composition of the invention. Such conditions include, without limitation, a variety of hyperproliferative disorders and cancers, including hepatic, colorectal, breast and skin cancers. Additional support for this aspect of the invention is presented in the fact that most cancers of the skin, intestine, and breast epithelial tissue are a result of increased levels of the activated/signaling pool of β-catenin. A number of birth defects are also associated with altered Wnt/wg pathway signaling, including debilitating abnormalities of the central nervous system, axial skeleton, limbs, and occasionally other organs.

Other objects and advantages will become apparent to those skilled in the art from a consideration of the ensuing detailed description, which proceeds with reference to the following illustrative drawings.

DETAILED DESCRIPTION OF THE INVENTION

General Introduction

Figure 1:
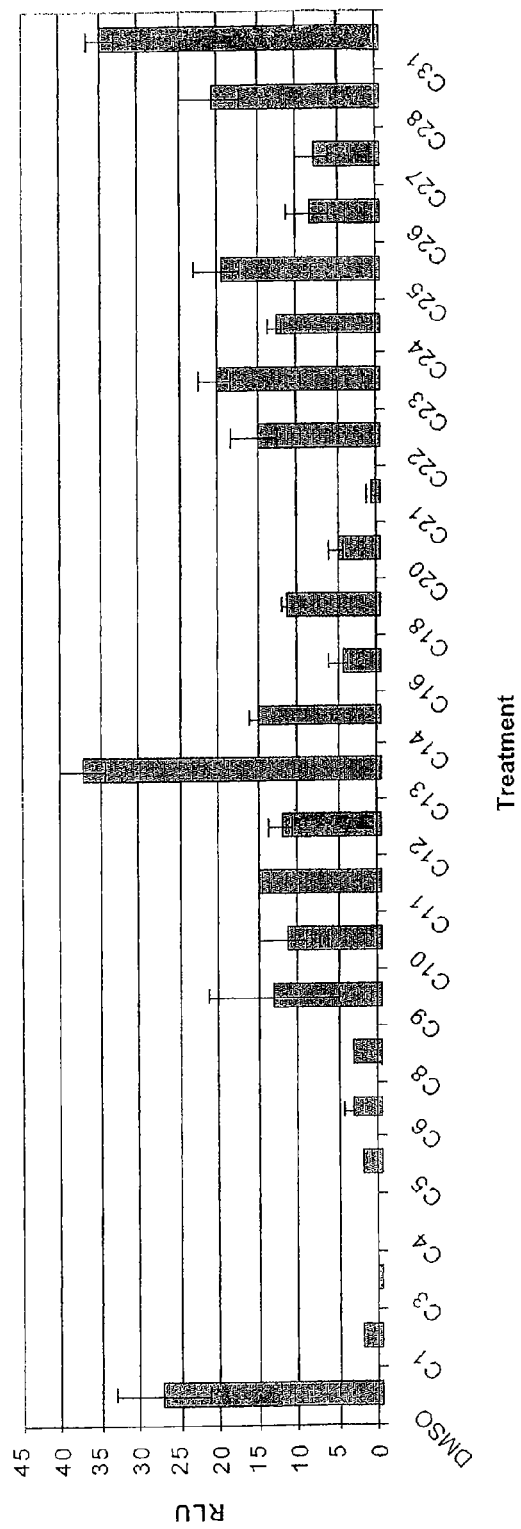
FIG. 1 shows a bar graph depicting the activity of candidate inhibitors on TOP12-LF in Clone 8 cells.

As indicated above, the Wnt pathway is one of a core set of evolutionarily conserved signaling pathways that regulates many aspects of metazoan development. Misregulation or aberrant regulation of the Wnt pathway can lead to adverse effects as demonstrated by the causal relationship identified between mutations in several components of the pathway and tumorigenesis of the liver, colon, breast and the skin. One of the most important effectors of the Wnt pathway is encoded by β-catenin (β-cat)/armadillo (arm). Induction by Wnt ligands leads to stabilization of cytosolic β-cat, which subsequently translocates into the nucleus to activate target genes that regulate many aspects of cell proliferation, growth, differentiation and death.

Since Catenin Responsive Transcription (CRT) has been implicated in the genesis of many cancers, this effector step of the pathway provides a good target for developing therapeutics that could modulate Wnt pathway activity, and more particularly, the nuclear activity of β-cat. Notably, the family of compounds disclosed herein are inhibitors that specifically target the activity of the signaling pool of β-catenin.

DEFINITIONS

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)$R^{20}$, where $R^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)$R^{21}$, wherein $R^{21}$ is independently
  $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —N$R^{22}$C(O)$R^{23}$, where $R^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl and $R^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Particular exemplary 'acylamino' groups are —N$R^{24}$C(O)—$C_1$-$C_8$ alkyl, —N$R^{24}$C(O)—(CH$_2$)$_t$($C_6$-$C_{10}$ aryl), (O)—(CH$_2$)$_t$(5-10 membered heteroaryl), —N$R^{24}$C(O)—(CH$_2$)$_t$($C_3$-$C_{10}$ cycloalkyl), and —N$R^{24}$C(O)—(CH$_2$)$_t$(4-10 membered heterocycloalkyl), wherein t is an integer from 0 to 4, and each $R^{24}$ independently represents H or $C_1$-$C_8$ alkyl.

'Substituted Acylamino' refers to a radical —N$R^{25}$C(O)$R^{26}$, wherein:
  $R^{25}$ is independently
  H, $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; and
  $R^{26}$ is independently
  H, $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;
provided at least one of $R^{25}$ and $R^{26}$ is other than H.

'Acyloxy' refers to a radical —OC(O)$R^{27}$, where $R^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyloxy' refers to a radical —OC(O)$R^{28}$, wherein $R^{28}$ is independently
  $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —O$R^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkoxycarbonyl' refers to a radical —C(O)—O$R^{30}$ where $R^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—(CH$_2$)$_t$($C_6$-$C_{10}$ aryl), —C(O)O—(CH$_2$)$_t$(5-10 membered heteroaryl), —C(O)O—(CH$_2$)$_t$($C_3$-

$C_{10}$ cycloalkyl), and —C(O)O—(CH$_2$)$_t$(4-10 membered heterocycloalkyl), wherein t is an integer from 1 to 4.

'Substituted Alkoxycarbonyl' refers to a radical —C(O)—OR$^{31}$ where R$^{31}$ represents:

$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or $C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—OR$^{32}$ where R$^{32}$ represents an $C_6$-$C_{10}$ aryl, as defined herein. Exemplary "aryloxycarbonyl" groups is —C(O)O—($C_6$-$C_{10}$ aryl).

'Substituted Aryloxycarbonyl' refers to a radical —C(O)—OR$^{33}$ where R$^{33}$ represents $C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—OR$^{34}$ where R$^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—OR$^{35}$ where R$^{35}$ represents:

5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

"Alkoxycarbonylamino" refers to the group —NR$^{36}$C(O)OR$^{37}$, where R$^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and R$^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl,—S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R''', —SO$_2$NR"R''', —C(O)R'', —C(O)OR'', —OC(O)R'', —NR'''C(O)R'', —C(O)NR"R''', or —(CR'''R'''')$_m$OR'''; wherein each R'' is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Substituted alkenyl" refers to those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —NH$_2$.

'Substituted amino' refers to an amino group substituted with one or more of those groups recited in the definition of 'substituted' herein, and particularly refers to the group —N(R$^{38}$)$_2$ where each R$^{38}$ is independently selected from:

hydrogen, C$_1$-C$_8$ alkyl, C$_6$-C$_{10}$ aryl, 5-10 membered heteroaryl, 4-10 membered heterocycloalkyl, or C$_3$-C$_{10}$ cycloalkyl; or C$_1$-C$_8$ alkyl, substituted with halo or hydroxy; or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl) or —(CH$_2$)$_t$(4-10 membered heterocycloalkyl) wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group. When both R$^{38}$ groups are hydrogen, —N(R$^{38}$)$_2$ is an amino group. Exemplary 'substituted amino' groups are —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocycloalkyl), wherein t is an integer from 0 to 4, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{40}$, wherein R$^{40}$ is C$_1$-C$_8$ alkyl;

'Substituted Alkylamino' refers to the group —NHR$^{41}$, wherein R$^{41}$ is C$_1$-C$_8$ alkyl; and the alkyl group is substituted with halo, substituted or unsubstituted amino, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Alkylarylamino' refers to the group —NR$^{42}$R$^{43}$, wherein R$^{42}$ is aryl and R$^{43}$ is C$_1$-C$_8$ alkyl.

'Substituted Alkylarylamino' refers to the group —NR$^{44}$R$^{45}$, wherein R$^{44}$ is aryl and R$^{45}$ is C$_1$-C$_8$ alkyl; and the alkyl group is substituted with halo, substituted or unsubstituted amino, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Arylamino' means a radical —NHR$^{46}$ where R$^{46}$ is selected from C$_6$-C$_{10}$ aryl and 5-10 membered heteroaryl as defined herein.

'Substituted Arylamino' refers to the group —NHR$^{47}$, wherein R$^{47}$ is independently selected from C$_6$-C$_{10}$ aryl and 5-10 membered heteroaryl; and any aryl or heteroaryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Dialkylamino' refers to the group —NR$^{48}$R$^{49}$, wherein each of R$^{48}$ and R$^{49}$ are independently selected from C$_1$-C$_8$ alkyl.

'Substituted Dialkylamino' refers to the group —NR$^{50}$R$^{51}$, wherein each of R$^{59}$ and R$^{51}$ are independently selected from C$_1$-C$_8$ alkyl; and at least one of the alkyl groups is independently substituted with halo, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_{1-4}$ haloalkyl, unsubstituted C$_1$-C$_4$ hydroxyalkyl, or unsubstituted C$_1$-C$_4$ haloalkoxy or hydroxy.

'Diarylamino' refers to the group —N$^{52}$R$^{53}$, wherein each of R$^{52}$ and R$^{53}$ are independently selected from C$_6$-C$_{10}$ aryl.

"Aminosulfonyl" or "Sulfonamide" refers to the radical —S(O$_2$)NH$_2$.

"Substituted aminosulfonyl" or "substituted sulfonamide" refers to a radical such as —S(O$_2$)N(R$^{54}$)$_2$ wherein each R$^{548}$ is independently selected from:

H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{54}$ is other than H.

Exemplary 'substituted aminosulfonyl' or 'substituted sulfonamide' groups are —S(O$_2$)N(R$^{55}$)—C$_1$-C$_8$ alkyl, —S(O$_2$)N(R$^{55}$)—(CH$_2$)$_t$(C$_6$-C$_{10}$ aryl), —S(O$_2$)N(R$^{55}$)—(CH$_2$)$_t$(5-10 membered heteroaryl), —S(O$_2$)N(R$^{55}$)—(CH$_2$)$_t$ (C$_3$-C$_{10}$ cycloalkyl), and —S(O$_2$)N(R$^{55}$)—(CH$_2$)$_t$(4-10 membered heterocycloalkyl), wherein t is an integer from 0 to 4; each R$^{55}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

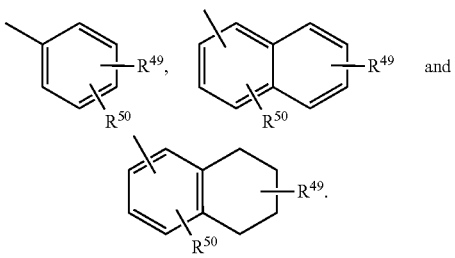

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}OR^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$, and $R^{61}$ are independently hydrogen, $C_1$-$C_8$ alkyl, $C_1$-$C_4$ haloalkyl, $C_3$-$C_{10}$ cycloalkyl, 4-10 membered heterocloalkyl, $C_6$-$C_{10}$ aryl, substituted aryl, 5-10 membered heteroaryl.

"Fused Aryl" refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted $C_1$-$C_4$ alkyl, halo, cyano, unsubstituted $C_1$-$C_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Azido' refers to the radical —$N_3$.

'Carbamoyl or amido' refers to the radical —C(O)$NH_2$.

'Substituted Carbamoyl or substituted amido' refers to the radical —C(O)N($R^{62}$)$_2$ wherein each $R^{62}$ is independently
  H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;
provided that at least one $R^{62}$ is other than H.

Exemplary 'Substituted Carbamoyl' groups are —C(O)$NR^{64}$—$C_1$-$C_8$ alkyl, —C(O)$NR^{64}$—$(CH_2)_t$($C_6$-$C_{10}$ aryl), —C(O)$N^{64}$—$(CH_2)_t$(5-10 membered heteroaryl), —C(O)$NR^{64}$—$(CH_2)_t$($C_3$-$C_{10}$ cycloalkyl), and —C(O)$NR^{64}$—$(CH_2)_t$(4-10 membered heterocycloalkyl), wherein t is an integer from 0 to 4, each $R^{64}$ independently represents H or $C_1$-$C_8$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent 'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

wherein each Y is selected from carbonyl, N, NR$^{65}$, O and S; and R$^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

wherein each W is selected from C(R$^{66}$)$_2$, NR$^{66}$, O and S; and each Y is selected from carbonyl, NR$^{66}$, O and S; and R$^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

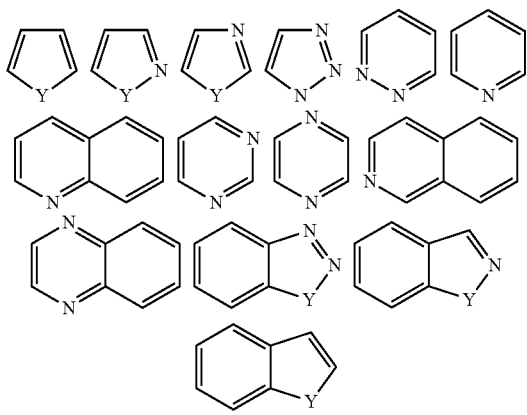

wherein each W is selected from CR$^{67}$, C(R$^{67}$)$_2$, NR$^{67}$, O and S; and each Y is selected from NR$^{67}$, O and S; and R$^{67}$ is independently hydrogen, $C_1$-$C_8$ alkyl, $C_3$-$C_{10}$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —R$^{68}$, —O$^-$, =O, —OR$^{68}$, —SR$^{68}$, —S$^-$, =S, —NR$^{68}$R$^{69}$, =NR$^{68}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{68}$, —OS(O$_2$)O$^-$, —OS(O)$_2$R$^{68}$, —P(O)(O$^-$)$_2$, —P(O)(OR$^{68}$)(O$^-$), —OP(O)(OR$^{68}$)(OR$^{69}$), —C(O)R$^{68}$, —C(S)R$^{68}$, —C(O)OR$^{68}$, —C(O)NR$^{68}$R$^{69}$, —C(O)O$^-$, —C(S)OR$^{68}$, —NR$^{70}$C(O)NR$^{68}$R$^{69}$, —NR$^{70}$C(S)NR$^{68}$R$^{69}$, —NR$^{70}$C(NR$^{70}$)NR$^{68}$R$^{69}$ and —C(NR$^{70}$)NR$^{68}$R$^{69}$;

wherein each R$^{68}$, R$^{69}$, R$^{70}$ and R$^{71}$ are independently:
hydrogen, C$_1$-C$_8$ alkyl, C$_6$-C$_{10}$ aryl, arylalkyl, C$_3$-C$_{10}$ cycloalkyl, 4-10 membered heterocycloalkyl, 5-10 membered heteroaryl, heteroarylalkyl; or C$_1$-C$_8$ alkyl substituted with halo or hydroxy; or C$_6$-C$_{10}$ aryl, 5-10 membered heteroaryl, C$_6$-C$_{10}$ cycloalkyl or 4-10 membered heterocycloalkyl each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from halo, cyano, nitro, trifluoromethyl, trifluoromethoxy, azido, —NR$^{72}$SO$_2$R$^{73}$, —SO$_2$NR$^{73}$R$^{72}$, —C(O)R$^{73}$, —C(O)OR$^{73}$, —OC(O)R$^{73}$, —NR$^{72}$C(O)R$^{73}$, —C(O)NR$^{73}$R$^{72}$, —NR$^{73}$R$^{72}$, —(CR$^{72}$R$^{72}$)$_m$OR$^{72}$, wherein, each R$^{73}$ is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each R" independently represents H or C$_1$-C$_6$alkyl.

'Substituted sulfanyl' refers to the group —SR$^{74}$, wherein R$^{74}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$(C$_3$-C$_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —SR$^{75}$ where R$^{75}$ is a C$_1$-C$_8$ alkyl or group as defined herein. Representative examples include, but are not limited to, methylthio, ethylthio, propylthio and butylthio.

'Substituted Alkylthio' or 'substituted alkylsulfanyl' refers to the group —SR$^{76}$ where R$^{76}$ is a C$_1$-C$_8$ alkyl, substituted with halo, substituted or unsubstituted amino, or hydroxy.

'Cycloalkylthio' or 'Cycloalkylsulfanyl' refers to a radical —SR$^{77}$ where R$^{77}$ is a C$_3$-C$_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —SR$^{78}$ where R$^{78}$ is a C$_3$-C$_{10}$ cycloalkyl, substituted with halo, substituted or unsubstituted amino, or hydroxy.

'Arylthio' or 'Arylsulfanyl' refers to a radical —SR$^{79}$ where R$^{79}$ is a C$_6$-C$_{10}$ aryl group as defined herein.

'Heteroarylthio' or 'Heteroarylsulfanyl' refers to a radical —SR$^{80}$ where R$^{80}$ is a 5-10 membered heteroaryl group as defined herein.

'Substituted sulfinyl' refers to the group —S(O)R$^{81}$, wherein R$^{81}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfinyl' groups are —S(O)—(C$_1$-C$_8$ alkyl) and —S(O)—(C$_3$-C$_{10}$ cycloalkyl), —S(O)—(CH$_2$)$_t$(C$_6$-C$_{10}$ aryl), —S(O)—(CH$_2$)$_t$(5-10 membered heteroaryl), —S(O)—(CH$_2$)$_t$(C$_3$-C$_{10}$ cycloalkyl), and —S(O)—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —S(O)R$^{82}$ where R$^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —S(O)R$^{83}$ where R$^{83}$ is a $C_1$-$C_8$ alkyl group as defined herein. substituted with halo, substituted or unsubstituted amino, or hydroxy.

'Cycloalkylsulfinyl' refers to a radical —S(O)R$^{84}$ where R$^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl. Exemplary 'cycloalkylsulfinyl' groups are S(O)—$C_3$-$C_{10}$ cycloalkyl.

'Substituted cycloalkylsulfinyl' refers to the group —S(O)R$^{85}$ where R$^{85}$ is a $C_3$-$C_{10}$ cycloalkyl, substituted with halo, substituted or unsubstituted amino, or hydroxy.

'Arylsulfinyl' refers to a radical —S(O)R$^{86}$ where R$^{86}$ is a $C_6$-$C_{10}$ aryl group as defined herein.

'Heteroarylsulfinyl' refers to a radical —S(O)R$^{87}$ where R$^{87}$ is a 5-10 membered heteroaryl group as defined herein.

'Substituted sulfonyl' refers to the group —S(O)$_2$R$^{88}$, wherein R$^{88}$ is selected from:
- $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
- $C_1$-$C_8$ alkyl substituted with halo, substituted or unsubstituted amino, or hydroxy; or
- $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —S(O)$_2$—($C_1$-$C_8$ alkyl) and —S(O)$_2$—(C3-C10 cycloalkyl), —S(O)$_2$—(CH$_2$)$_t$($C_6$-$C_{10}$ aryl), —S(O)$_2$—(CH$_2$)$_t$(5-10 membered heteroaryl), —S(O)$_2$—(CH$_2$)$_t$($C_3$-$C_{10}$ cycloalkyl), and —S(O)$_2$—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$R$^{89}$ where R$^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$R$^{90}$ where R$^{90}$ is an $C_1$-$C_8$ alkyl group as defined herein, substituted with halo, substituted or unsubstituted amino, or hydroxy.

'Cycloalkylsulfonyl' refers to a radical —S(O)$_2$R$^{91}$ where R$^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$R$^{92}$ where R$^{92}$ is a $C_3$-$C_{10}$ cycloalkyl, substituted with halo, substituted or unsubstituted amino, or hydroxy.

'Arylsulfonyl' refers to a radical —S(O)$_2$R$^{93}$ where R$^{93}$ is an $C_6$-$C_{10}$ aryl group as defined herein.

'Heteroarylsulfonyl' refers to a radical —S(O)$_2$R$^{94}$ where R$^{94}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$OR$^{95}$, wherein R$^{95}$ is selected from:
- $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
- $C_1$-$C_8$ alkyl substituted with halo, substituted or unsubstituted amino, or hydroxy; or
- $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'Substituted sulfo' or 'sulfonic acid ester' groups are —S(O)$_2$—O—($C_1$-$C_8$ alkyl) and —S(O)$_2$—O—($C_3$-$C_{10}$ cycloalkyl), —S(O)$_2$—O—(CH$_2$)$_t$($C_6$-$C_{10}$ aryl), —S(O)$_2$—O—(CH$_2$)$_t$(5-10 membered heteroaryl), —S(O)$_2$—O—(CH$_2$)$_t$($C_3$-$C_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —NR$^{96}$C(O) NR$^{96}$R$^{96}$ where each R$^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two R$^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C=C)—.

'Ethylene' refers to substituted or unsubstituted —(C—C)—.

'Ethynyl' refers to

'Hydrogen bond donor' group refers to a group containing O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of "substituted" herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)NH$_2$.

'Substituted aminohydroxyphosphoryl' refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group =S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula(e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides a method for preventing, treating or ameliorating in a mammal a disease or condition that is causally related to the aberrant activity of the Wnt signaling pathway in vivo, which comprises administering to the mammal an effective disease-treating or condition-treating amount of a compound according to formula I:

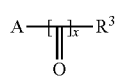

wherein A is $A^1$, $A^2$ or $A^3$;

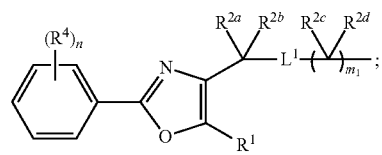

$A^1$ is

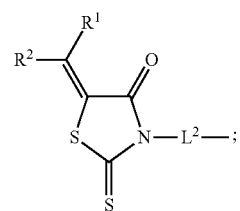

A² is

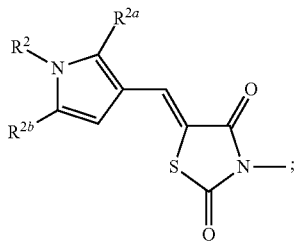

A³ is x is 1, when A is A¹ or A²; or x is 0, when A is A³;

L¹ is S, SO or SO₂;

m1 is 1, 2 or 3; n is 1, 2, 3, 4 or 5;

L² is substituted or unsubstituted $C_1$-$C_7$ alkylene or heteroalkylene;

each $R^1$, $R^{2a}$, $R^{2b}$, $R^{2c}$, and $R^{2d}$ is independently selected from hydrogen, halo, and substituted or unsubstituted $C_1$-$C_6$ alkyl;

$R^2$ is selected from aryl or heteroaryl, unsubstituted or substituted with one or more $R^4$;

$R^3$ is hydroxy, alkoxy, substituted or unsubstituted amino or cycloheteroalkyl; or when A is A³, $R^3$ is $R^5$;

each $R^4$ and $R^{5a}$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and $R^5$ is selected from aryl or heteroaryl, unsubstituted or substituted with one or more $R^{5a}$; or a pharmaceutically acceptable salt, solvate or prodrug thereof;

and stereoisomers, isotopic variants and tautomers thereof.

In one particular embodiment, with respect to compounds of formula I, A¹ is

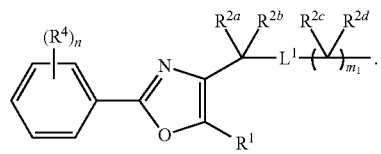

In one particular embodiment, with respect to compounds of formula I, A² is

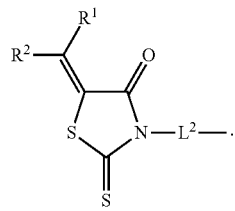

In one particular embodiment, with respect to compounds of formula I, A³ is

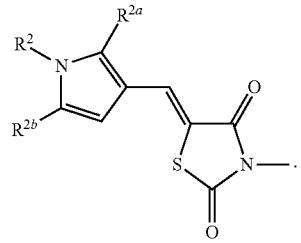

In one particular embodiment, with respect to compounds of formula I, the compound is according to formula IIa:

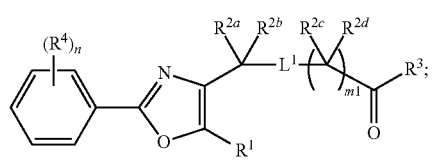

IIa and wherein $L^1$, m1, n, $R^1$, $R^{2a}$, $R^{2b}$, $R^{2c}$, $R^{2d}$, $R^2$, $R^3$, and $R^4$ are as described for formula I.

In one particular embodiment, with respect to compounds of formula I, the compound is according to formula IIb:

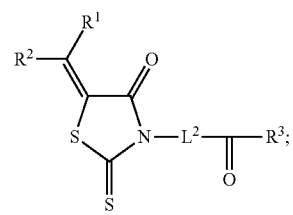

IIb and wherein $L^2$, $R^1$, $R^2$, $R^3$, and $R^4$ are as described for formula I.

In one particular embodiment, with respect to compounds of formula I, the compound is according to formula IIc:

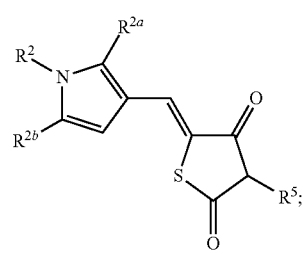

IIc and wherein $R^{2a}$, $R^{2b}$, $R^2$, $R^4$, and $R^5$ are as described for formula.

In one particular embodiment, with respect to compounds of formula IIa; $L^1$ is S.

In one particular embodiment, with respect to compounds of formula IIa; $L^1$ is SO or $SO_2$.

In one particular embodiment, with respect to compounds of formula IIa or IIc; each of $R^{2a}$ and $R^{2b}$ is H.

In one particular embodiment, with respect to compounds of formula IIa or IIc; one of $R^{2a}$ and $R^{2b}$ is independently Me and the other is H.

In one particular embodiment, with respect to compounds of formula Ia or IIc; each of $R^{2a}$ and $R^{2b}$ is Me.

In one particular embodiment with respect to compounds of formula IIa; the subscript m1 is 1 or 2; and each of $R^{2c}$ and $R^{2d}$ is H.

In one particular embodiment, with respect to compounds of formula IIa; the subscript m1 is 1 or 2; and each of $R^{2b}$ and $R^{2d}$ is independently Me and the other is H.

In one particular embodiment, with respect to compounds of formula IIa; the subscript m1 is 1 or 2; and each of $R^{2c}$ and $R^{2d}$ is Me.

In one particular embodiment, with respect to compounds of formula IIa; $L^1$ is S; the subscript m1 is 1; and each of $R^{2a}$, $R^{2b}$, $R^2$ and $R^{2d}$ is H.

In one particular embodiment, with respect to compounds of formula IIb; $L^2$ is —$CH_2$—, —$CH_2$—$CH_2$—, —$CH_2$—$CH_2$—$CH_2$—, or —$CH_2$—$CH_2$—$CH_2$—$CH_2$—.

In one particular embodiment, with respect to compounds of formula I, the compound is according to formula IIc.

In one particular embodiment, with respect to compounds of formula IIb or IIc, $R^2$ is phenyl, unsubstituted or substituted with one or more $R^4$.

In one particular embodiment, with respect to compounds of formula IIb or IIc, $R^2$ is heteroaryl, unsubstituted or substituted with one or more $R^4$.

In one particular embodiment, with respect to compounds of formula IIb or IIc, $R^2$ is pyridyl, furanyl, thiophenyl, or pyrrolidinyl, unsubstituted or substituted with one or more $R^4$.

In one particular embodiment, with respect to compounds of formula IIc, $R^5$ is phenyl, unsubstituted or substituted with one or more $R^4$.

In one particular embodiment, with respect to compounds of formula IIc, $R^5$ is heteroaryl, unsubstituted or substituted with one or more $R^4$.

In one particular embodiment, with respect to compounds of formula IIc, $R^5$ is pyridyl, furanyl, thiophenyl, or pyrrolidinyl, unsubstituted or substituted with one or more $R^4$.

In one particular embodiment, with respect to compounds of formula IIa or IIb; $R^1$ is H or substituted or unsubstituted $C_1$-$C_6$ alkyl.

In one particular embodiment, with respect to compounds of formula IIa or Iib; $R^1$ is halo.

In one particular embodiment, with respect to compounds of formula IIa or IIb; $R^1$ is Me.

In one particular embodiment, with respect to compounds of formula IIa or IIb; $R^3$ is OH.

In one particular embodiment, with respect to compounds of formula IIa or IIb; $R^3$ is alkoxy.

In one particular embodiment, with respect to compounds of formula IIa or IIb; $R^3$ is substituted or unsubstituted amino.

In one particular embodiment, with respect to compounds of formula IIa or IIb; $R^3$ is $NR^{3a}R^{3b}$; and each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ join together to form a cycloheteroalkyl heteroaryl ring.

In one particular embodiment, with respect to compounds of formula I, the compound is according to formulae IIIa, IIIb, IIIc, IIId, IIIe, or IIIf:

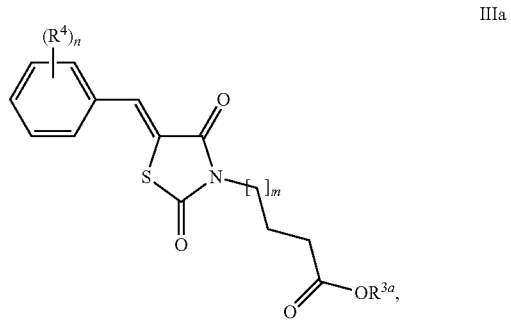

IIIa

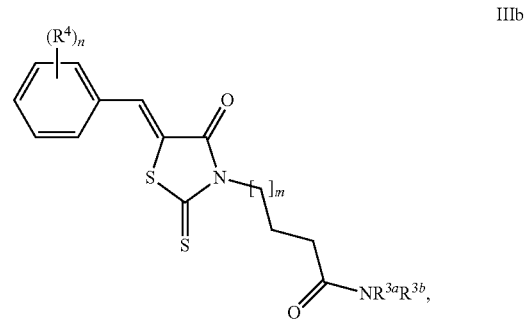

IIIb

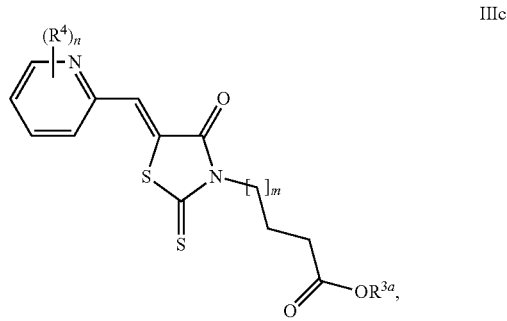

IIIc

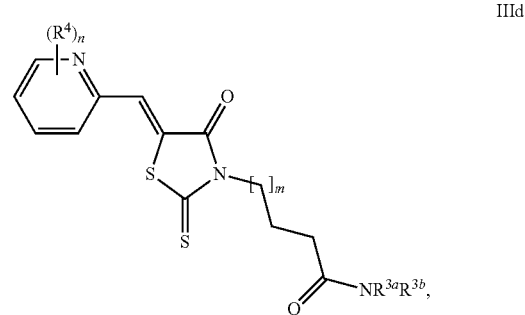

IIId

-continued

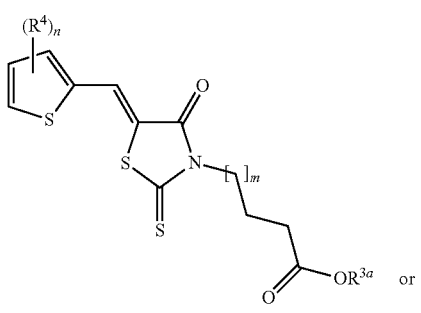
IIIe

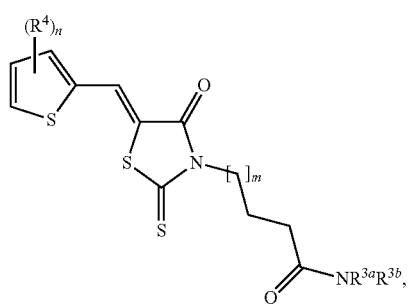
IIIf wherein n and R⁴ are as described for formula I; $R^{3a}$ and $R^{3b}$ are as described above; and m is 0 or 1.

In one particular embodiment, with respect to compounds of formula I, the compound is according to formula IVa, IVb, or IVc:

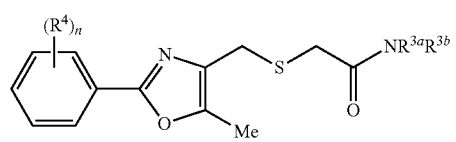
IVa

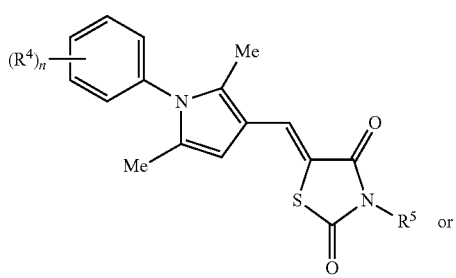
IVb

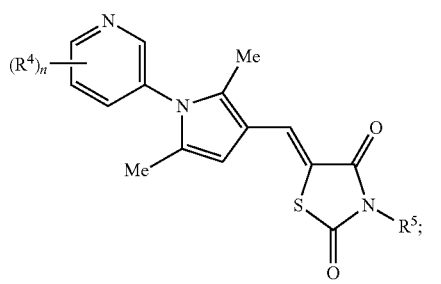
IVc wherein n, R⁴, and R⁵ as described for formula I; and $R^{3a}$ and $R^{3b}$ as described above.

In one particular embodiment, with respect to compounds of formula IIa-IVc, each of R⁴ is H.

In one particular embodiment, with respect to compounds of formula IIa-IVc, n, when present, is 1; and R⁴ is alkyl, alkoxy, haloalkyl, or halo.

In one particular embodiment, with respect to compounds of formula IIa-IVc, n, when present, is 1 or 2; and R⁴ is Me, Et, i-Pr, OMe, OEt, O-i-Pr, Cl, or F.

In one particular embodiment, with respect to compounds of formula IIa-IVc, n, when present, is 1 or 2; and R⁴ is Me, OMe, SMe, or Et.

In one particular embodiment, with respect to compounds of formula I, the compound is according to formulae Va, Vb, Vc, Vd, Ve or Vf:

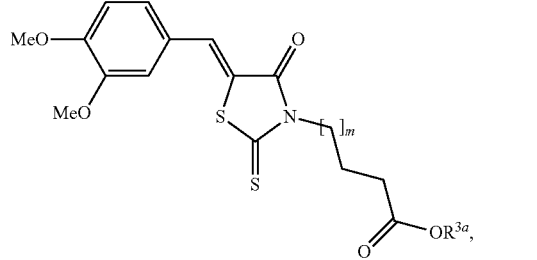
Va

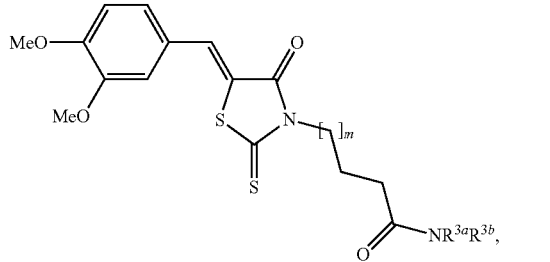
Vb

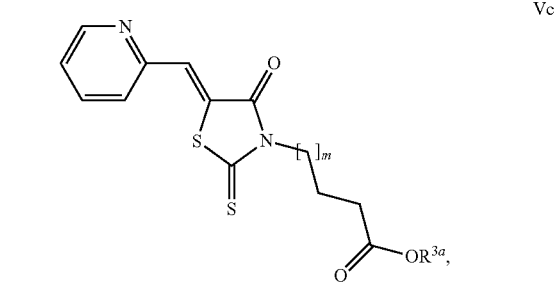
Vc

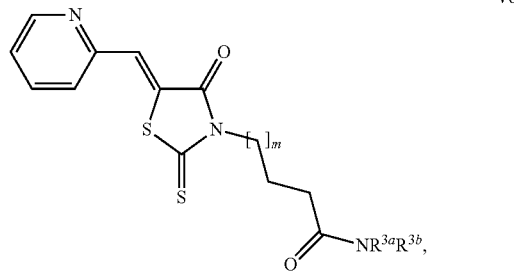
Vd

-continued

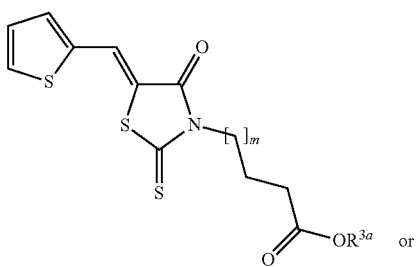

Ve or

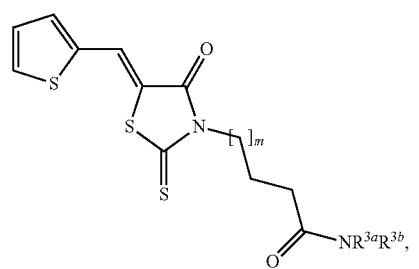

Vf wherein $R^{3a}$ and $R^{3b}$ are as described above; and m is 0 or 1.

In one particular embodiment, with respect to compounds of formula IIIb, IIId, IIIf, IVa, Vb, Vd, or Vf, $R^{3a}$ is H.

In one particular embodiment, with respect to compounds of formula IIIb, IIId, IIIf, IVa, Vb, Vd, or Vf, $R^{3a}$ is substituted or unsubstituted alkyl.

In one particular embodiment, with respect to compounds of formula IIIb, IIId, IIIf, IVa, Vb, Vd, or Vf, $R^{3a}$ is substituted or unsubstituted benzyl.

In one particular embodiment, with respect to compounds of formula IIIb, IIId, IIIf, IVa, Vb, Vd, or Vf, $R^{3a}$ is substituted or unsubstituted phenethyl.

In one particular embodiment, with respect to compounds of formula IIIb, IIId, IIIf, IVa, Vb, Vd, or Vf, $R^{3a}$ is substituted or unsubstituted cycloalkyl.

In one particular embodiment, with respect to compounds of formula IIIb, IIId, IIIf, IVa, Vb, Vd, or Vf, $R^{3a}$ is cyclopropyl.

In one particular embodiment, with respect to compounds of formula IIIb, IIId, IIIf, IVa, Vb, Vd, or Vf; $R^{3b}$ is substituted or unsubstituted heteroaryl.

In one particular embodiment, with respect to compounds of formula IIIb, IIId, IIIf, IVa, Vb, Vd, or Vf; $R^{3b}$ is substituted or unsubstituted heterocycloalkyl.

In one particular embodiment, with respect to compounds of formula I, the compound is according to formula IIIb, IIId, IIIf, IVa, Vb, Vd, or Vf; and each of $R^{3a}$ and $R^{3b}$ is H.

In one particular embodiment, with respect to compounds of formula IIIb, IIId, IIIf, IVa, Vb, Vd, or Vf; one of $R^{3a}$ and $R^{3b}$ is substituted or unsubstituted alkyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted benzyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted phenethyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cycloalkyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cyclopropyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cyclopentyl or cyclobutyl and the other is H.

In one particular embodiment, with respect to compounds of formula IIIb, IIId, IIIf, IVa, Vb, Vd, or Vf; $R^{3a}$ and $R^{3b}$ join together to form a cycloheteroalkyl heteroaryl ring.

In one particular embodiment, with respect to compounds of formula IIIb, IIId, IIIf, IVa, Vb, Vd, or Vf; $NR^{3a}R^{3b}$ is:

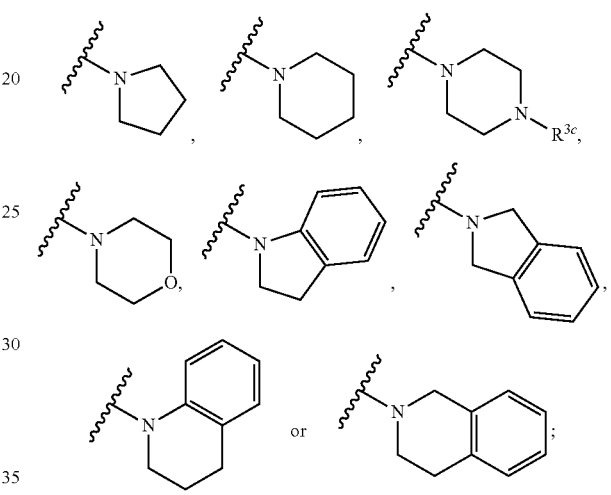

and wherein $R^{3c}$ is H or alkyl.

In one particular embodiment, with respect to compounds of formula I, the compound is according to formula VIa, VIb, or VIc:

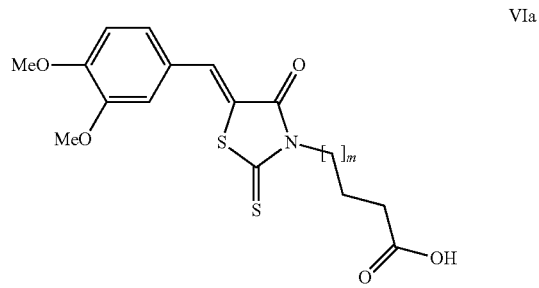

VIa

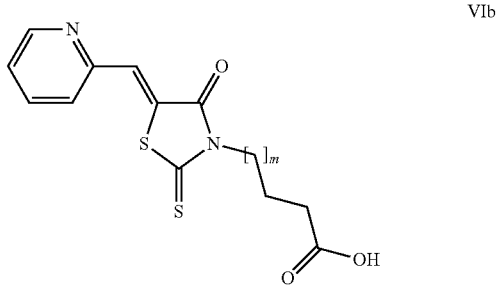

VIb

-continued

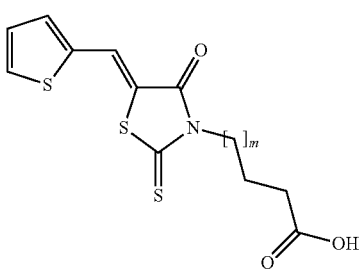
VIc and m is 0 or 1.

In one particular embodiment, with respect to compounds of formula IIIa-VIc, m, when present, is 0.

In one particular embodiment, with respect to compounds of formula IIIa-VIc, m, when present, is 1.

In one particular embodiment, with respect to compounds of formula IIIa-VIc, the compound is according to formula VIIa, VIIb, VIIc or VIId:

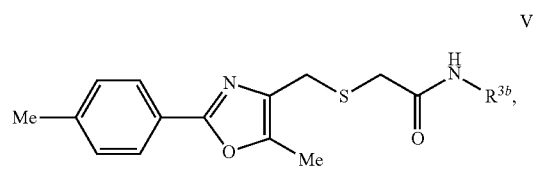
VIIa

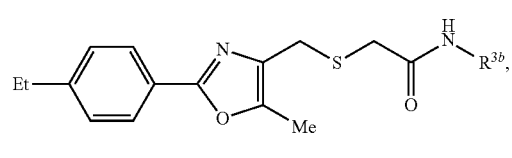
VIIb

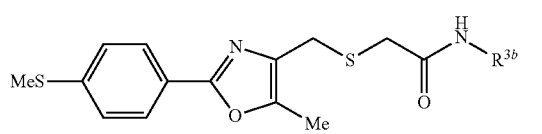
VIIc

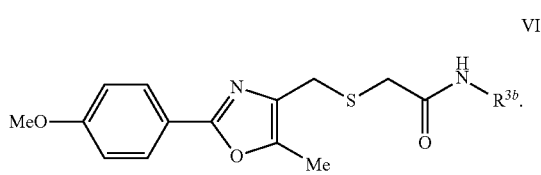
VIId wherein $R^{3b}$ is as described above.

In one particular embodiment, with respect to compounds of formula VIIa, VIIb, VIIc or VIId; $R^{3b}$ is substituted or unsubstituted cycloalkyl, phenyl, benzyl, or phenethyl.

In one particular embodiment, with respect to compounds of formula VIIa, VIIb, VIIc or VIId; $R^{3b}$ is substituted or unsubstituted heteroaryl, or heterocycloalkyl.

In one particular embodiment, with respect to compounds of formula I, the compound is according to formula VIIIa, VIIIb, VIIIc, or VIIId:

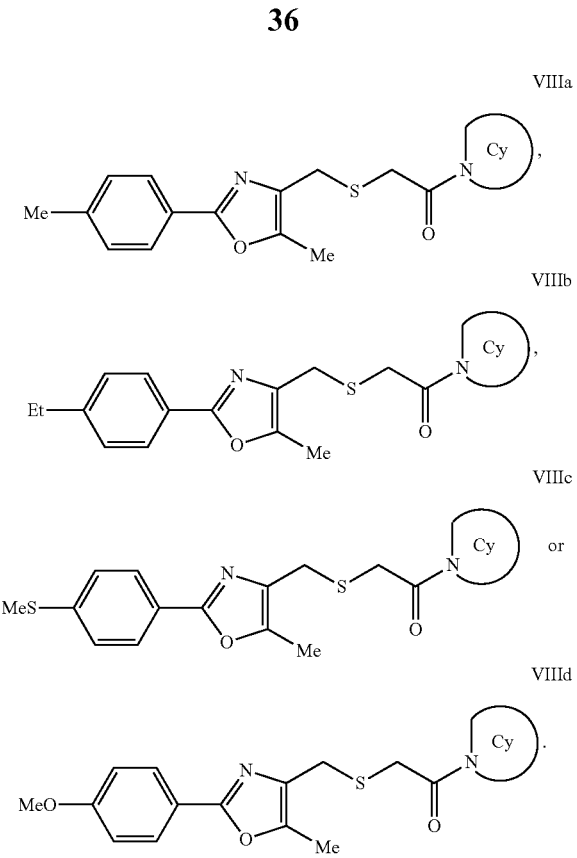

wherein Cy is

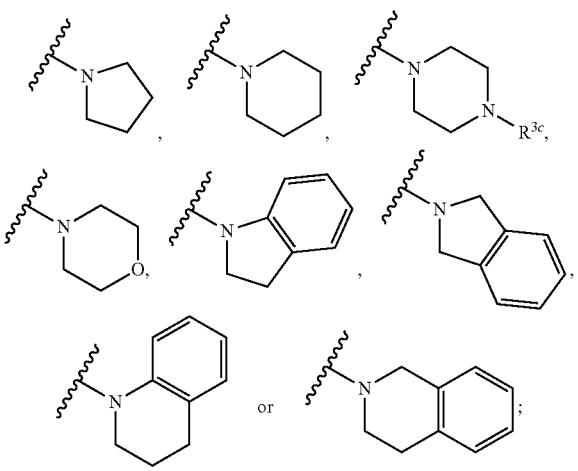

and wherein $R^{3c}$ is H or alkyl.

In one particular embodiment, with respect to compounds of formula I, the compound is according to formula IXa, IXb, IXc or IXd:

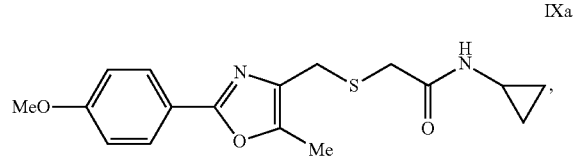
IXa

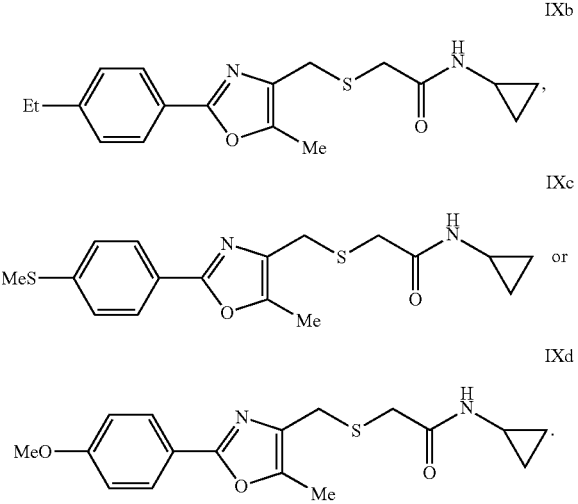

In one particular embodiment, with respect to compounds of formula I, the compound is according to formula Xa, Xb, Xc or Xd:

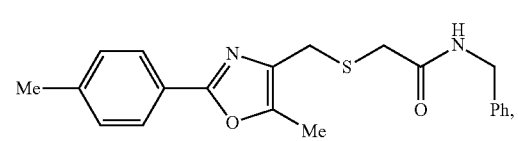

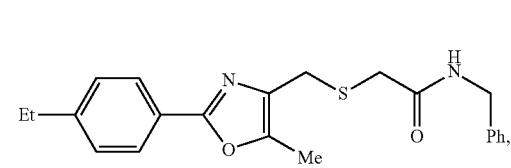

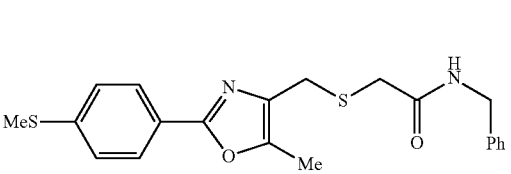

 or

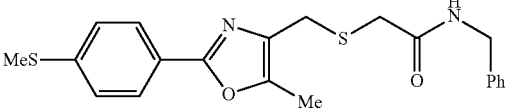

In one particular embodiment, with respect to compounds of formula I, the compound is according to formula XIa, XIb, XIc or XId:

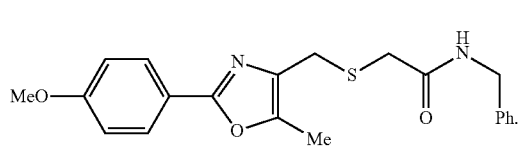

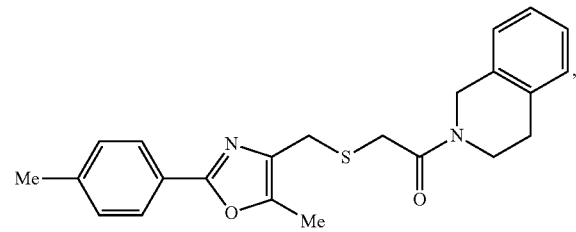

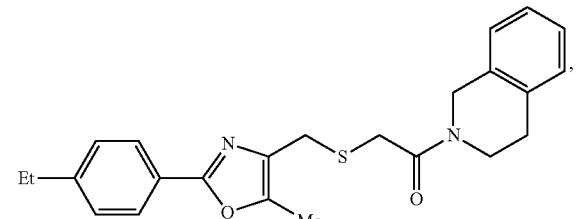

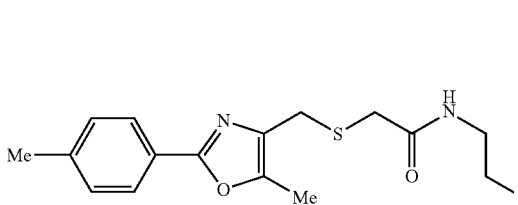

In one particular embodiment, with respect to compounds of formula I, the compound is according to formula XIIa, XIIb, XIIc or XIId:

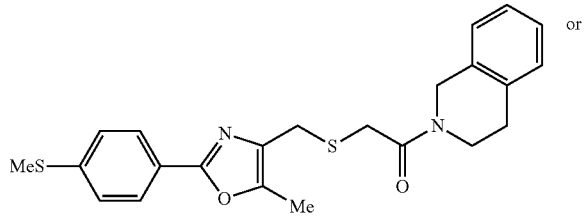

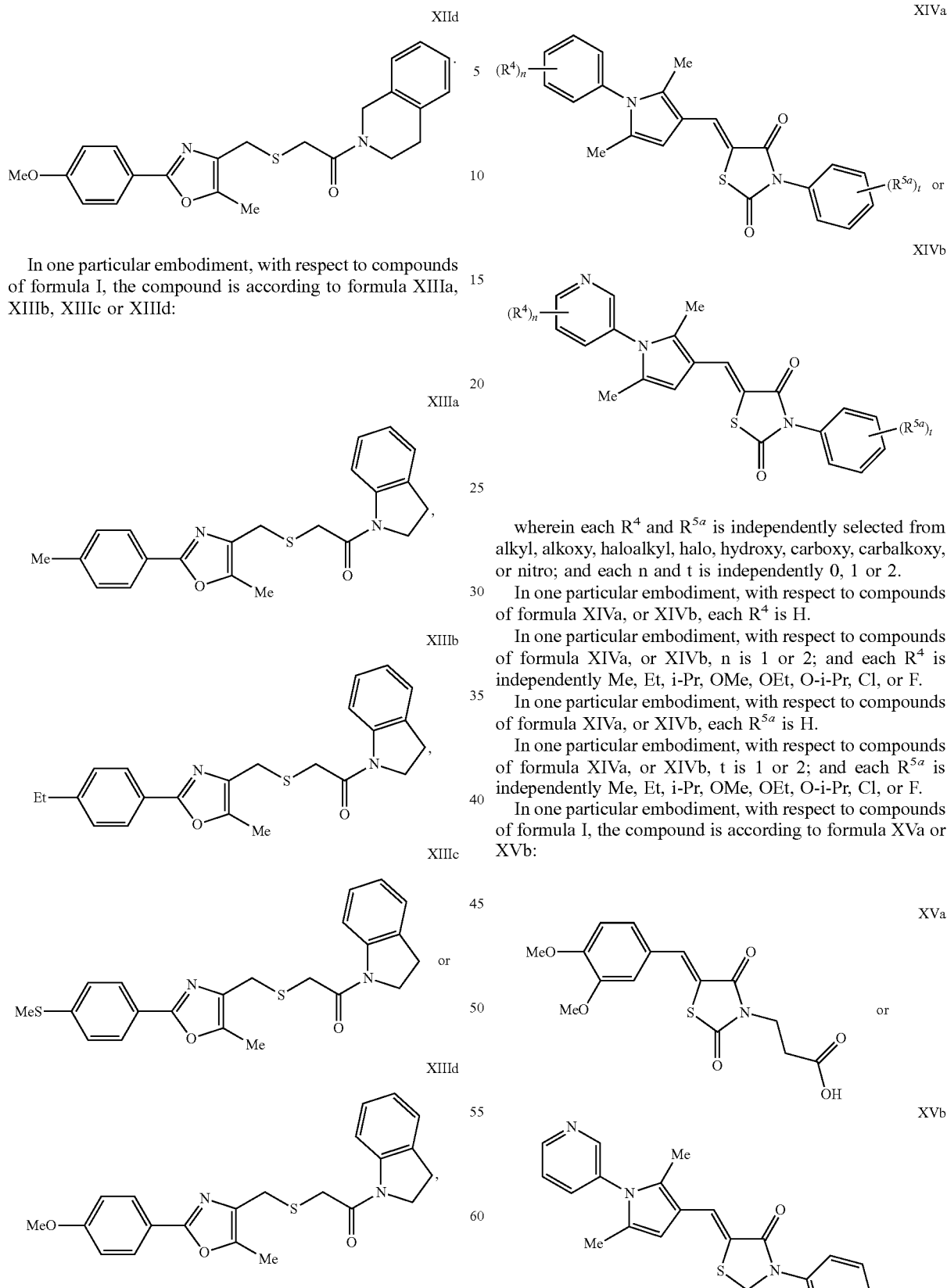

In one particular embodiment, with respect to compounds of formula I, the compound is according to formula XIIIa, XIIIb, XIIIc or XIIId:

In one particular embodiment, with respect to compounds of formula I, the compound is according to formula XIVa, or XIVb:

wherein each $R^4$ and $R^{5a}$ is independently selected from alkyl, alkoxy, haloalkyl, halo, hydroxy, carboxy, carbalkoxy, or nitro; and each n and t is independently 0, 1 or 2.

In one particular embodiment, with respect to compounds of formula XIVa, or XIVb, each $R^4$ is H.

In one particular embodiment, with respect to compounds of formula XIVa, or XIVb, n is 1 or 2; and each $R^4$ is independently Me, Et, i-Pr, OMe, OEt, O-i-Pr, Cl, or F.

In one particular embodiment, with respect to compounds of formula XIVa, or XIVb, each $R^{5a}$ is H.

In one particular embodiment, with respect to compounds of formula XIVa, or XIVb, t is 1 or 2; and each $R^{5a}$ is independently Me, Et, i-Pr, OMe, OEt, O-i-Pr, Cl, or F.

In one particular embodiment, with respect to compounds of formula I, the compound is according to formula XVa or XVb:

In one particular embodiment, with respect to compounds of formula I, the compound is selected from Table 1.

In one particular embodiment, with respect to compounds of formula I, the compound is selected from Table 2.

In one particular embodiment, with respect to compounds of formula I, the compound is selected from Table 3.

In one particular embodiment, with respect to compounds of formula I, the compound is selected from Table 4.

In one particular embodiment, with respect to compounds of formula I, the compound is selected from Table 5.

In one particular embodiment, with respect to compounds of formula I, the compound is selected from Table 6.

In one particular embodiment, with respect to compounds of formula I, the compound is selected from Table 7.

In one particular embodiment, with respect to compounds of formula I, the compound is selected from Table 8.

In one particular embodiment, with respect to compounds of formula I, the compound is selected from Table 9.

In one particular embodiment, with respect to compounds of formula I, the compound is selected from Table 10.

In one particular embodiment, with respect to compounds of formula I, the compound is selected from Table 11.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color would then be diluted with water and added with stirring. Sufficient water is then added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention may be dissolved or suspended in a buffered sterile saline injectable aqueous medium to a concentration of approximately 5 mg/ml.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the Wnt/wg signaling pathway. Accordingly, the compounds and pharmaceutical compositions of this invention find use as therapeutics for preventing and/or treating a variety of cancers and hyperproliferative conditions in mammals, including humans. Thus, and as stated earlier, the present invention includes within its scope, and extends to, the recited methods of treatment, as well as to the compounds for use in such methods, and for the preparation of medicaments useful for such methods.

In a method of treatment aspect, this invention provides a method of treating a mammal susceptible to or afflicted with a condition associated with cancer and/or a hyperproliferative disorder, which method comprises administering an effective amount of one or more of the pharmaceutical compositions just described.

In yet another method of treatment aspect, this invention provides a method of treating a mammal susceptible to or afflicted with a condition that gives rise to increased cellular proliferation or a transformed phenotype, or that relates to dysregulation of Wnt/wg signaling. The present oxazoles and thiazoles have use as anti-proliferative agents that reduce proliferative levels (potentially to normal levels for a particular cell type), and/or anti-transformed phenotype agents that restore, at least in part, normal phenotypic properties of a particular cell type. Accordingly, the present oxazoles and thiazoles have use for the treatment of cancers and hyperproliferative disorders relating to aberrant Wnt/wg signaling.

In additional method of treatment aspects, this invention provides methods of treating a mammal susceptible to or afflicted with a cancer causally related or attributable to aberrant activity of the Wnt/wg signaling pathway. Such cancers include, without limitation, those of the liver, colon, rectum, breast and skin. Such methods comprise administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as psoriasis, the regimen for treatment usually stretches over many months or years so oral dosing is preferred for patient convenience and tolerance. Psoriasis, for example, has been linked to Wnt signaling. Several basic and clinical studies using patient samples revealed an increase in nuclear β-catenin staining in many psoriatic samples. It has been suggested that a sustained low-level increase in Wnt/β-catenin signaling could be responsible for skin psoriatic lesions. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a hyperproliferative condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following schemes are presented with details as to the preparation of representative compounds that have been listed hereinabove. The compounds of the invention may be prepared from known or commercially available starting materials and reagents by one skilled in the art of organic synthesis.

Representative Scheme 1

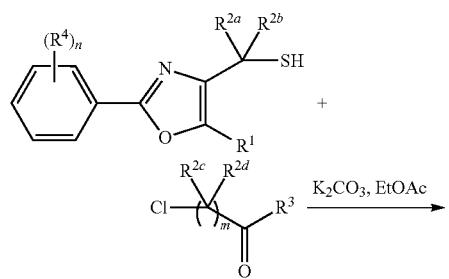

-continued

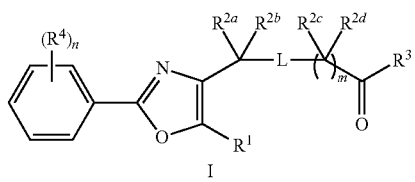

Representative Scheme 2

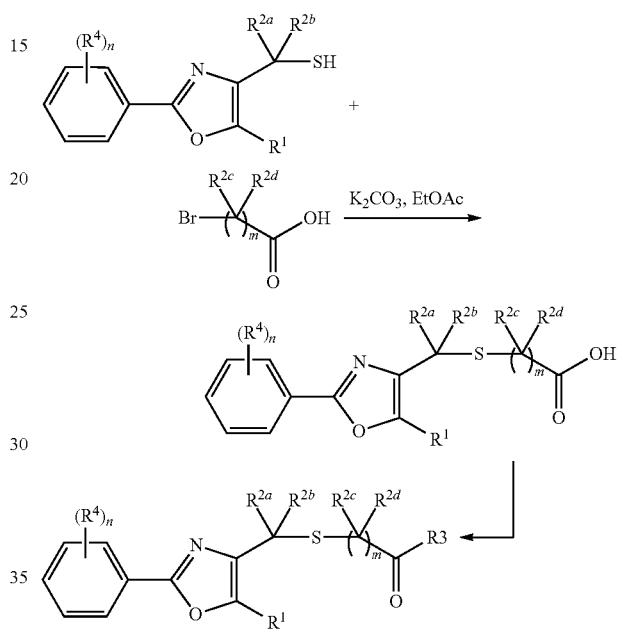

Representative Scheme 3

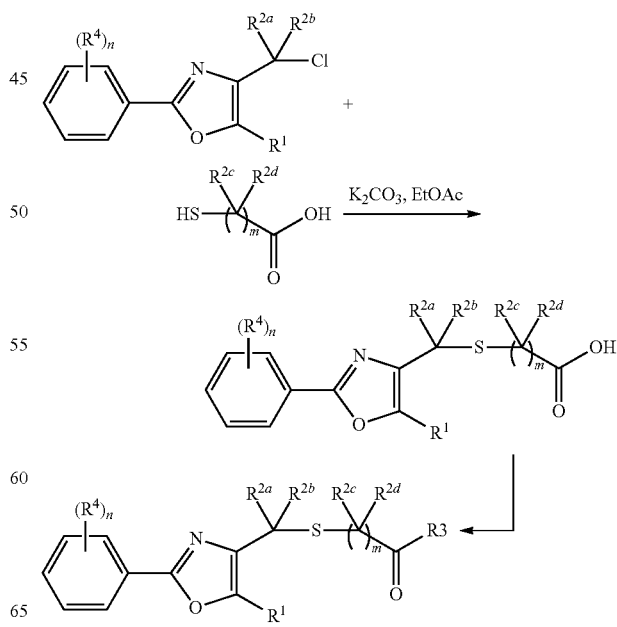

Example 1

Protocols/Methods for In Vitro Testing of Candidate Compounds

The present inventors employed a novel methodology that integrates a "sensitized" chemical genetic high-throughput screen (HTS) with RNA-interference (RNAi) screening technology in order to identify specific small molecule inhibitors of the Wnt pathway in *Drosophila* cells. As described herein, *Drosophila* Clone 8 cell-based assay systems developed by the present inventors to investigate the Wnt/wg pathway [DasGupta et al. Science 308, 826-33 (2005)] were used in a small molecule chemical genetic screen to identify specific inhibitors of the pathway. These cell-based assays, which are described in detail below, utilize a Wnt-responsive luciferase reporter dTF12, the activity of which can be determined using immunofluorescence-based visual detection means. The present inventors used the small-molecule library available from the Institute of Chemistry and Cellular Biology (ICCB-Longwood) at Harvard Medical School, Boston, for the screen.

More particularly, the method for testing and identifying compounds useful in the present invention begins with the activation of the signaling pathway by the introduction of dsRNAs specific for Axin, which is the scaffold protein that negatively regulates β-cat by promoting its GSK-3β-mediated degradation. The resultant activation of the Wnt signaling pathway is then detected by assessing the activity of the Wnt-responsive luciferase reporter gene in the cell-based assay system. Thereafter, candidate compounds are added to the cell-based assay system to assess their effect on the strongly induced Wg-reporter-gene (TOPFlash) activity that results from the dsRNA-mediated knockdown of Axin. This protocol significantly increases the specificity of the small-molecule inhibitors for CRT and serves to identify molecules that regulate Wnt signaling activity downstream of the Axin-mediated degradation complex. Although not wishing to be bound by theory, the prediction is that the candidate compounds act on the "activated" or stable pool of β-cat and potentially prevent its interaction with known components of the transcriptional-activator complex (such as pangolin (pan)/dTcf, pygopus (pygo), legless (lgs) or Bc19, p300/CBP), or other proteins that may function to regulate the activity of stabilized cytosolic β-cat.

Methods and Materials

Primary Small Molecule Screen for the Wingless Signaling Pathway in *Drosophila* Clone 8 Cells Day 1 (PM):
Set up transfection with Wg-reporter (dTF12), Normalization vector (PolIII-RL) and dsRNA against DAxin (dsRNA is specific towards *Drosophila* Axin and lacks any predicted off-targets).
1. Add 40,000 *Drosophila* Clone 8 cells (in 40 µL) in 384-well plate (white solid bottom, Corning Costar) using the multidrop.
2. Add 204 of Transfection mix in each well of a 384-well plate (Corning Costar) using the multidrop.

Transfection Mix:
TOP12x-Luc (DNA)=25 ng (0.25 µL, of DNA @ 0.1 µg/µL)
PolIII-RLuc (DNA)=25 ng (0.25 µL of DNA @ 0.1 µg/µL)
dsRNA to DAxin=100 ng (5 µL of dsRNA @ 20 ng/µL)
Buffer EC=13.5 µL
Enhancer=0.8 µL,
Effectene=0.25 µL
Total volume=20 µL Incubate at 25° C. for 4 days to ensure complete knockdown of Axin.

Day 5 (PM):
Add small molecule library (Cybio Robot). Incubate 18 hrs.

Day 6 (AM):
Assay luminescence from the samples using the "Dual-Glo" luciferase kit (Promega Inc.).
Specifically, aspirate supernatant and add 204 media+20 µL luciferase buffer using the multidrop. Read Firefly Luciferase activity on the En Vision (Perkin Elmer plate reader). Add 20 µL of Stop&Glo using the multidrop. Read Renilla luciferase activity on the En Vision (Perkin Elmer plate reader).

Epistasis Analysis:
Epistasis Analysis was conducted in a 96 well format following the protocol as described for the Primary Screen (above), except that, 80,000 Clone 8 cells were used per well. Small Molecule Compounds were used at a final concentration of 2.5 ng/ul.

Reporter Assay in Mammalian HEK 293 cells:
HEK 293 cells were transfected with 50 ng each of the Wnt-responsive STF16 luciferase reporter and pCMV-RL normalization reporter using the Lipofectamine LTX (Invitrogen Inc.) in a 96 well plate format.

Transfection Mix Per well
STF16-FLuc (DNA): 50 ng (0.54 of DNA @ 0.1 µg/µL)
CMV-RLuc (DNA): 50 ng (0.5 µL of DNA @ 0.1 µg/µL)
Lipofectamine-LTX: 0.25 µL
Serum Free Medium: 20 µL Cells were cultured in DMEM/10% FBS at 37° C. for 2 days following which, they were induced with Wnt3a conditioned media for 1 day and then treated with small molecule compounds to a final concentration of 2.5 ng/µL for approximately 18 hours. Luciferase reporter activity was then measured using the Dual-Glo system (Promega Inc.) on the Envision Plate Reader. Normalized luciferase activity in response to treatment with candidate small molecule compounds was compared to that obtained from cells treated with DMSO.

C57mg transformation Assay: The transformation assay was carried out in a 96 well format. C57 mg cells were cultured in DMEM/10% FBS supplemented with purified Wnt3a protein (R&D Systems) to a final concentration of 100 ng/µl. Small molecule compounds dissolved in DMSO were added to a final concentration of 10 ng/µl and 0.01% DMSO. Following incubation at 37° C. for 5 days, cells were fixed with 4% Formaldehyde in 1×PBS at RT for 30 min and washed subsequently with 1×PBS at room temperature (RT) for 5 minutes (×3). Cells were then permeabilized in Blocking buffer (0.1% Triton-X/1×PBS/5% Normal Goat Serum) at RT for 20 min, subsequent to which, cells were incubated with anti-β-cat at RT for 1 hour (diluted to 1:1000 in blocking buffer). Subsequently, cells were washed with 1×PBS at RT for 10 minutes (×3) and then incubated with secondary antibody and Alexa-Fluor 488 conjugated phalloidin in Blocking buffer at RT for 1 hour. Following a brief wash in 1×PBS, cells were imaged in PBS buffer using the Array-Scan imaging system.

Molecular validation of C57 mg transformation assay was performed by qPCR analysis of the Wnt-target gene, WISP1. First strand cDNA was prepared from C57 mg cells treated as above using Cells-to-cDNA kit (Ambion, Inc.) as directed by the manufacturer. Equal amounts of cDNA were used for qPCR analysis using primers specific for WISP1 and GAPDH (the endogenous control). Comparison of amplification kinetics of WISP1 from samples treated with compounds to those treated with DMSO (ddCt method) was used to study changes in Wnt-directed transcriptional activity in response to treatment with candidate small molecule compounds.

Unless otherwise indicated, all experiments described herein that call for supplemental Wnt3a utilize Wnt3a conditioned media prepared by harvesting media from L-cells stably transfected with a Wnt3a coding construct (available from ATCC #CRL-2647). The cells are cultured in DMEM containing 10% fetal bovine serum (FBS). The medium, harvested from adherent cells cultured to about 80% confluency over 4 days, is purified through a 0.2 μm filter and stored at 4° C. over several months without an appreciable loss in activity [Willert et al. Nature 423, 448-52 (2003)].

Results

The Wnt signaling pathway was induced by the introduction of dsRNAs specific for Axin into Clone 8 cells comprising the Wg-responsive luciferase reporter-gene (dTF12). As described herein, Axin is a scaffold protein that negatively regulates Arm/β-cat by promoting its degradation. Thereafter, a selected set of a small molecule library was added to the Clone 8 cell-based assay system to assess the effect of individual compounds on (Axin dsRNA-mediated) activated CRT by monitoring the activity of the Wg-responsive luciferase reporter-gene (dTF12). The primary screen identified molecules that have a statistically significant effect on the activity of the dTF12-luciferase reporter gene, wherein a minimum of a 2.5-fold change in reporter activity was considered "significant" as a cut-off for hit-picking compounds for secondary screens. As shown in FIG. 1, addition of these compounds to the cells strongly repressed dTF12-reporter activity (>70-90%). Six of the strongest inhibitors are identified herein and, as indicated, share significant structural similarities suggesting that they constitute a family of compounds (i.e., a subset of oxazoles and thiazoles) that regulate a common aspect of the Wnt-pathway activity by potentially binding to the same target protein.

Figure 2:
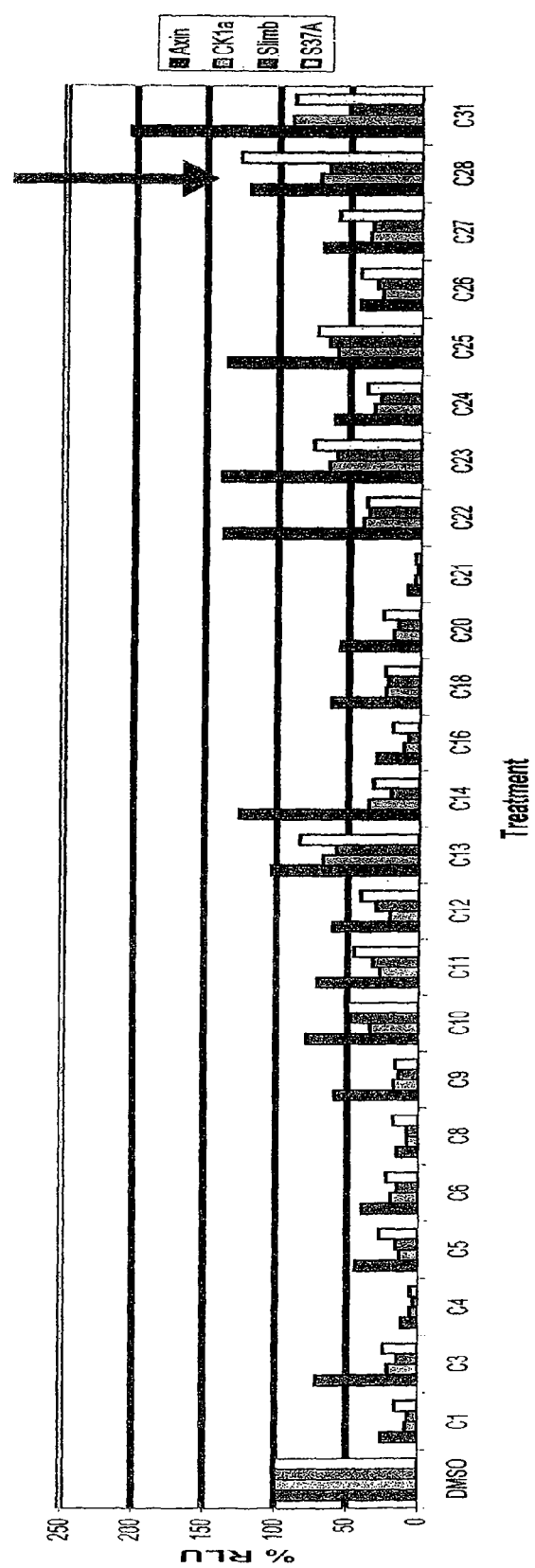
FIG. 2 shows a bar graph depicting the results of genetic epistasis analyses.

Epistatic Analyses:

Small molecule inhibitors identified in the primary screen may modulate Wnt signaling by affecting intermolecular interactions at any point downstream of Axin in the signaling cascade. Given that the oncogenic character of β-cat and therefore the Wnt pathway itself is caused by aberrant CRT (Park et al. Cancer Res 59, 4257-60 (1999); Lin et al. Proc Natl Acad Sci USA 97, 4262-6 (2000), a major focus of the present invention is to study those compounds which affect Wnt-responsiveness by regulating the transcriptional complex involved in CRT. The use of dsRNAs targeted to specific components of the Wnt pathway elucidates the level at which the compounds exert their inhibitory effect on the Wnt/Wg signaling pathway. This objective can be achieved by activating the Wnt pathway in Clone 8 cells using dsRNAs targeting other known negative regulators of the Wnt pathway, such as Slimb/βTrCP and SkpA, and assaying the effect of the compounds on the dTF12 reporter activity in these cells. Each of the aforementioned biomolecules functions to negatively regulate Wnt signaling downstream of Axin, so these analyses further delineate the stage in the Wnt pathway wherein the compound in question exerts its effect. The results of this experimental approach are presented in FIG. 2.

Figure 3:
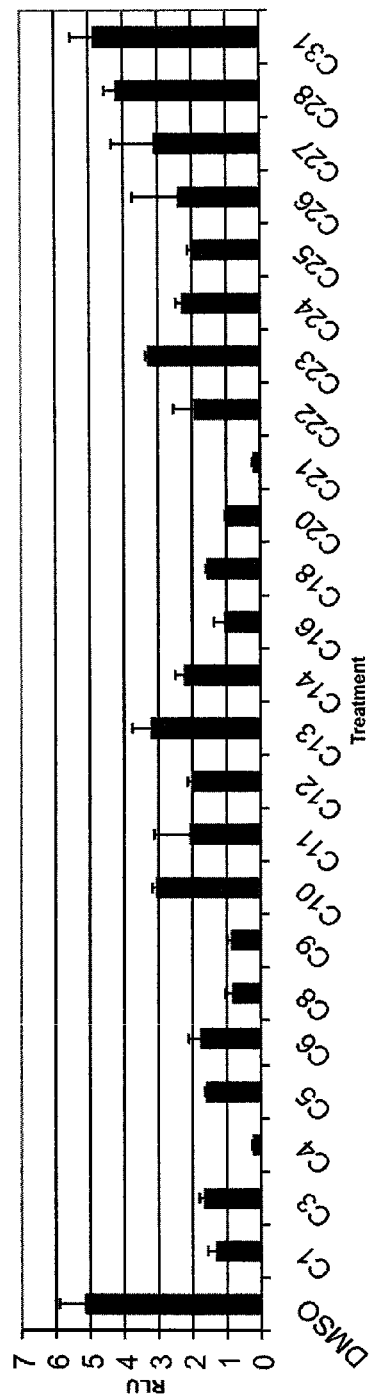
FIG. 3 shows a bar graph depicting the activity of candidate inhibitors on S37A β-catenin mediated TOP12-LF in Clone 8 cells.

To gain further evidence that the compounds exert their inhibitory effect in the nucleus, they have been tested in Clone 8 cells transfected with a construct coding for a degradation resistant form of β-cat, S37A β-cat [Orford et al. J Biol Chem 272, 24735-8 (1997)]. This mutant form of β-cat bears a Serine to Alanine mutation, thus rendering it refractory to GSK3β mediated phosphorylation and hence proteosome degradation. An inhibitory effect of the compounds on the activity of S37A β-cat thus provides further proof that the compounds exert their effect on Wnt responsiveness at the level of CRT. The concentration of the compounds for all of the above assays is kept constant at 2.5 ng/μl, which is the same as that used for the primary screen. As shown in FIG. 3, most of the compounds exert an inhibitory effect on Wnt signaling on the transcriptional level. Data depicted in FIG. 3 show that a majority of the compounds inhibit S37A-mediated reporter activity, thus lending further support to the notion that these putative inhibitors do indeed function by abrogating the activity of stabilized β-cat in the nucleus.

Figure 6:
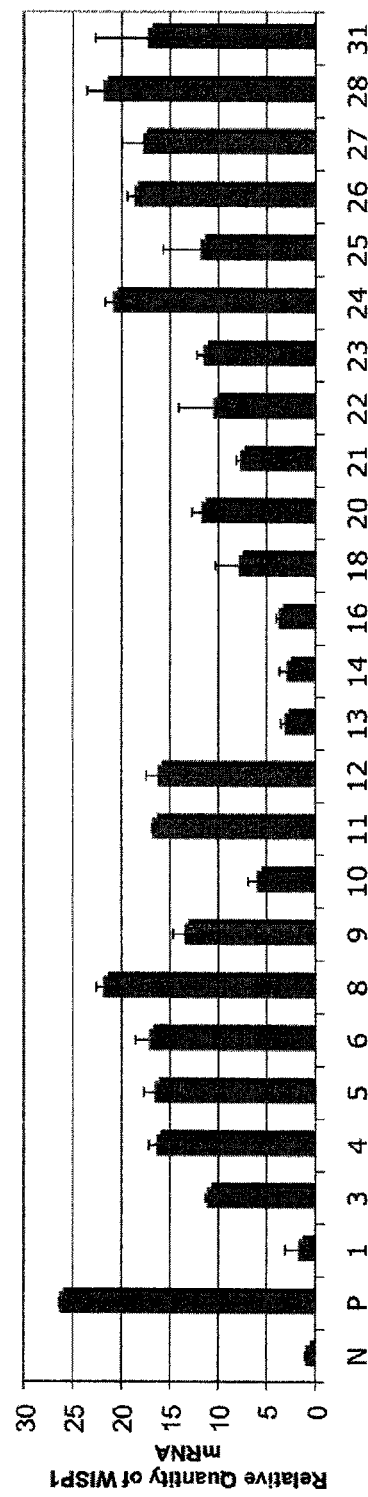
FIG. 6 shows a bar graph of quantitative analyses of Wnt3a transformed C57 mg cell phenotypes and rescue thereof by inhibitory compounds.

Reproducibility of Inhibitory Effect of Small Molecules in Mammalian Cells:

In order to confirm and corroborate the activity of CRT inhibitor compounds in a mammalian context, the present inventors have tested a subset of the inhibitors identified in the context of established mammalian cell lines. To this end, the present inventors have optimized culture conditions for screening for Wnt signaling modulators in mammalian HEK 293 cells in a 96-well plate format. Briefly, HEK 293 cells were transfected with pSTF16-LF along with the normalization reporter, pCMV-RL and the effect of the compounds on reporter activity in such cells was determined by quantifying the luminescence from the luciferase reporter gene as described in Dasgupta et al. [supra (2005)]. As shown in FIG. 6, the present inventors have been able to recapitulate the inhibitory effect of several candidate inhibitors in these cells using the Wnt responsive luciferase reporter, STF16-LF.

In that Wnt signaling has been shown to have a profound influence on both cell fate and cell proliferation in various developmental and pathogenic contexts [Clevers. Cell 127, 469-80 (2006)], the present inventors have begun to investigate the activity of a subset of the CRT inhibitors identified in the primary screen in the context of other available Wnt responsive cell lines. Such cell lines can be used to ascertain further the inhibitory activity of the putative small molecule inhibitors in a phenotypic context. Such Wnt responsive cell-specific phenotypes include an assessment of transformation of the C57 mg mammary epithelial cell line, neural differentiation capacity of G-Olig2 ES cells, E-cadherin expression in the HT-29 colon cancer cell line, and Wnt induced invasive capacity of the MCF-7 breast adenocarcinoma cell line.

The C57 mg cell line, which was isolated from mouse mammary epithelial tissue [Wong et al. Mol Cell Biol 14, 6278-86 (1994)], has previously been shown to undergo transformation when cultured in Wnt-conditioned media. Transformation of the cell line is evidenced by pronounced changes in morphology, typified by formation of chord-like bundles of cells or foci-forming colonies that break off and float in the media [Wong et al. supra, 1994]. This Wnt responsive phenotype provides a mammalian assay in which to evaluate the inhibitory effect of the small molecule inhibitors identified in the primary screen. Briefly, cells are cultured in Wnt3a conditioned media in the presence or absence of a small molecule inhibitor and morphological analysis conducted using automated microscopy.

The present inventors have established a phenotypic assay using the Wnt-responsive C57 mg mouse mammary epithelial cell line to ascertain the validity of the inhibitory compounds identified in the primary screen. Specifically, addition of Wnt3a conditioned media or purified Wnt3a protein results in cellular transformation, manifested by a pronounced change from an epithelial-cell like morphology to those resembling spindle shaped cells with chord like bundles. Addition of candidate small molecule compounds to such cells in the presence of Wnt3a results in significant inhibition of the transformation phenotype. The Array-Scan imagining system (Cellomics Inc.) is used to image such phenotypic changes in a 96-well plate format so as to gain a quantitative estimate of the degree of the inhibitory effect of the compounds on Wnt3a induced transformation in C57 mg cells. Quantitative analysis of the transformation phenotype is measured by the degree of actin fiber alignment (defined as anisotropy), which is expressed as the standard deviation (SD) of the angles projected by the actin fibers relative to the normal; low SD numbers reflect an increase in Wnt-responsive transformation. This approach allows for objective inferences on the cellular effects of the candidate inhibitors. See FIG. 5.

Figure 4:
FIG. 4 shows a bar graph representation of the effect of several inhibitory compounds in mammalian HEK-293 cells.
Figure 5:
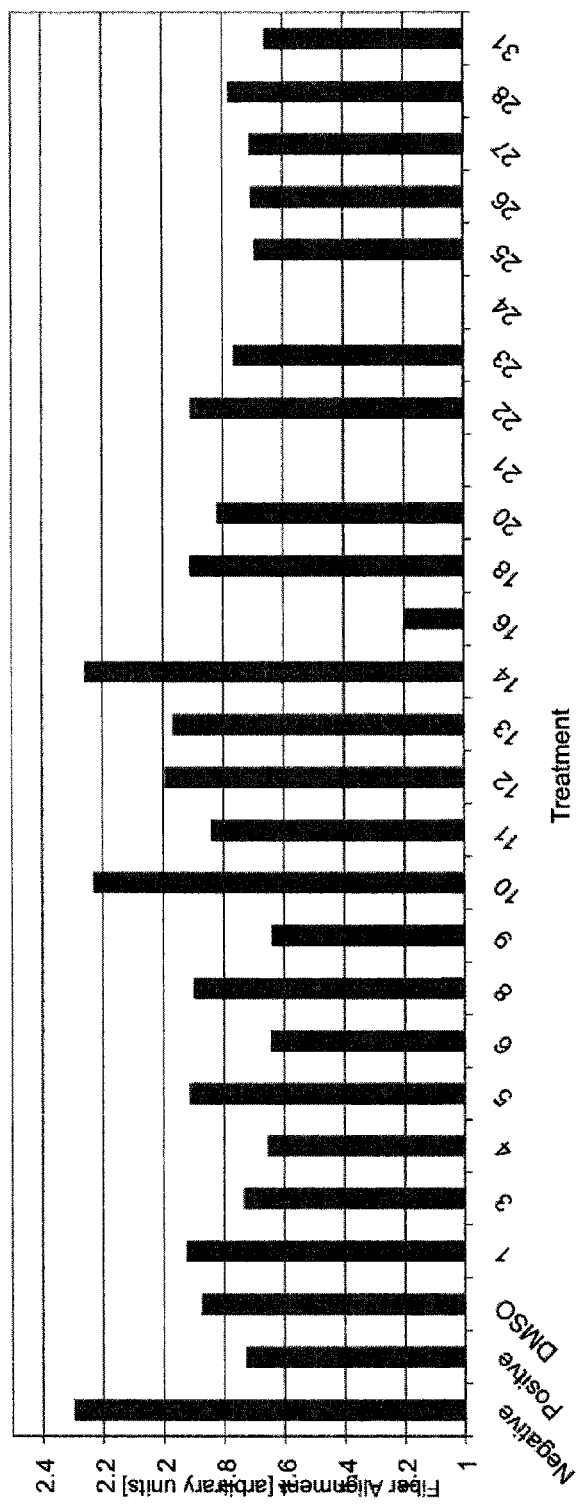
FIG. 5 shows photomicrographs of Wnt3a transformed C57 mg cell phenotypes and rescue thereof by inhibitory compounds.

As depicted in FIG. 5, compounds 10 and 14 show a significant inhibition of Wnt3a induced C57 mg transformation, whereas compounds 1, 5, 8, 11, 12, 13, 18 and 22 show a partial reduction in the degree of transformation. It should be noted that the degree of inhibitory effect of the compounds on Wnt-induced phenotypes may vary with different cellular types. For example, compounds 10 and 14 are poor inhibitors of TOP12-LF activity in HEK-293 cells (see FIG. 4), and yet seem to be potent inhibitors of Wnt3a-induced transformation in C57 mg cells. This could perhaps be due to their effect on the interaction of β-cat with different transcriptional co-factors in the nucleus that drive transcription of different targets. However to further validate the efficacy of candidate compounds in inhibiting Wnt-induced C57 mg transformation, the present inventors monitored changes in the expression of WISP1 mRNA by qRT-PCR. WISP1 is the key β-catenin target responsible for C57 mg transformation in response to Wnt signaling [Xu et al. Genes Dev. 14, 585-95 (2000)]. Reduction in the level of WISP1 mRNA correlates highly with the observed phenotypic rescue in response to Wnt exposure (FIG. 6).

The HT-29 colon cancer cell line has been shown to undergo β-cat/TCF dependent Epithelial Mesenchymal Transition (EMT) which can be monitored by changes in both morphology and downregulation of E-cadherin expression levels and upregulation of vimentin [Yang et al. Cell 127, 139-55 (2006)]. The HT-29 cell line, therefore, provides a model system for analysis of the candidate small molecule inhibitors in the context of a transformed colon cancer cell. Accordingly, the present inventors will treat HT-29 cells with candidate small molecules and assay E-cadherin and vimentin levels by western blotting as well as immunochemistry using commercially available antibodies. Furthermore, morphological analysis by compound differential contrast (DIC) microscopy will also be used to determine the effect of the compounds in inhibiting β-cat dependent EMT.

The MCF-7 breast cancer cell line exhibits a pronounced invasive capacity in response to Wnt signaling [Yook et al. Nat Cell Biol 8, 1398-406 (2006)]. To utilize this cell line to assess the activity of Wnt inhibitor compounds identified, MCF-7 cells can be transduced with recombinant retroviral vectors coding for Wnt3a or β-cat-S33Y, a constitutively active form of β-cat [as described in Yook et al. supra, (2006)]. The retroviral vectors will be prepared from pPGS-β-cateninS33Y- or pPGS-Wnt3a-transfected 293 packaging cells. MCF-7 cells transduced with these retroviral vectors can be loaded onto the upper chamber of Matrigel (prepared in serum-free DMEM culture media) containing Transwells, which are subsequently cultured in complete media with inhibitory compounds or DMSO. The cultures will be incubated at 37° C. in a humidified chamber for 24-72 hrs. Following incubation of the cell-loaded Matrigel, non-invasive cells are scraped off and the invaded cells counted by simple light microscopy by fixing and staining with Trypan Blue [Valster et al. Methods 37, 208-15 (2005)]. Results derived from this assay will provide insights into the use of compounds as inhibitors of the metastatic potential of malignant cells in general and malignant breast cancer cells in particular.

G-Olig2 ES cells (available from ATCC) contain a GFP insertion in the gene for Olig 2, a neural lineage specific transcription factor. Neural differentiation, therefore, results in the upregulation of GFP-positive cells. Neural differentiation of G-Olig2 ES cells can be induced by treating these cells with synthetic Retinoic Acid (RA) following the appearance of Embryoid bodies in culture. It has previously been shown that Wnt signaling inhibits neural differentiation of ES cells [Bouhon et al. Brain Res Bull 68, 62-75 (2005)]. To assay the inhibitory effect of the candidate compounds, the present inventors will culture the above ES cells in Wnt3a conditioned media containing RA and individual compounds and determine the number of GFP positive cells by Flow Cytometry. The inhibitory effect on Wnt signaling will be reflected by a reduction in the number of GFP positive differentiated cells in cultures treated with DMSO+RA as compared to those treated with compound+RA.

Although the present Example is directed to screening in the context of an "activated" Wnt pathway, it will be appreciated that other components of the pathway that promote Wnt signaling can be targeted for RNAi mediated ablation and the result of such an approach would be an "inhibited" Wnt pathway. In either event, the cellular milieu of an "activated" or an "inhibited" Wnt pathway can be used as a genetic background in which to perform small molecule/compound chemical screens directed to the identification of small molecules/compounds such as those of the present invention, that modulate the activity of a specific component of a signaling pathway.

Example 2

Protocols/Methods for In Vitro and In Vivo Testing

Preliminary in vivo tests to assay the efficacy of the compounds will be performed in the zebrafish, *Danio rerio*, wherein increased Wnt signaling during zebrafish embryonic development results in axial specification defects and loss of anterior fates. This is commonly manifested by loss of or reduced eye-structures. To test the effectiveness of the compounds in inhibiting Wnt-signaling in a whole organismal context, one-cell embryos will be injected with synthetic Wnt8 mRNA and cultured in the presence of DMSO or individual compounds. Inhibitory activity of the compounds will be assayed by quantifying the penetrance of the Wnt8 induced phenotype.

Upon successful in vivo validation of the compounds in an animal model system, their efficacy will be further tested in the clinically relevant mouse model system, viz. the APC$_{min}$ mouse. Loss of APC function results in an increase in the level of signaling competent β-catenin, which has been shown to be the causative factor in the induction of colon cancer in the above mouse model. Such mice will be administered candidate compounds and assayed for the regression of tumors resulting from increased Wnt signaling in the APC$_{min}$ mouse. Standardized protocols for tail-vein and/or tissue injections will be used.

Example 3

The colon carcinoma cell line, HCT-116 offers a pathologically-relevant system to examine the effects of candidate Wnt-inhibitors. HCT-116 cells bear a deletion of the S45 residue in β-cat, making it refractory to phosphorylation and degradation, thereby resulting in constitutive CRT. Wnt targets such as CycD1 and c-myc are thus overexpressed in this cell-type.

Figure 7:
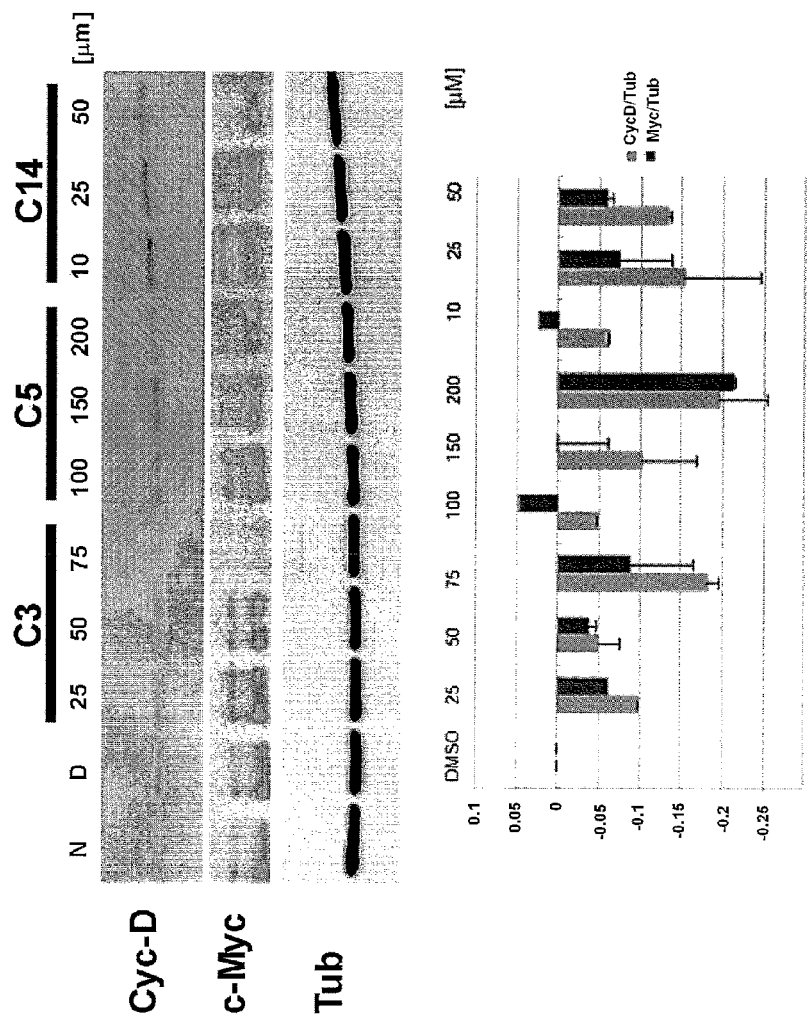
FIG. 7 shows Inhibition of Wnt-target accumulation in HCT116 cells.
Figure 8:
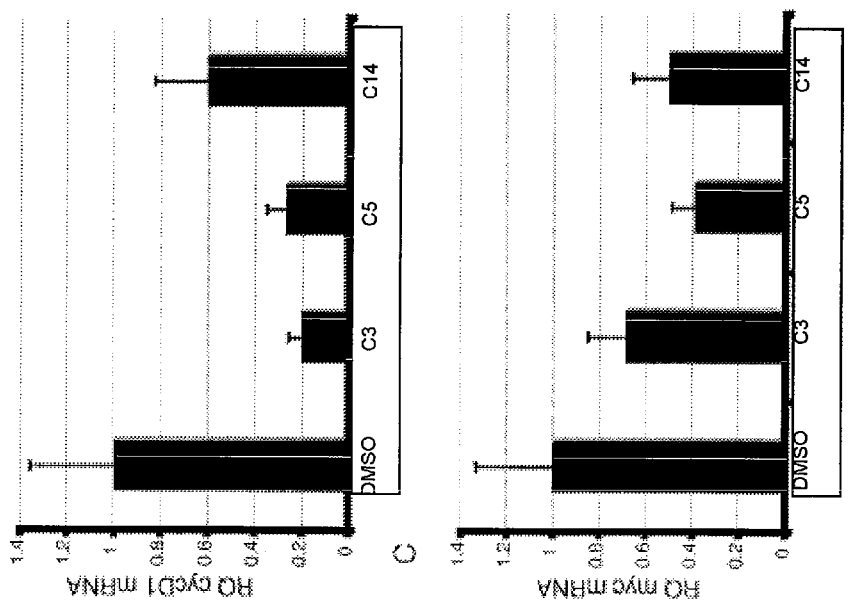
FIG. 8 shows Transcription Inhibition of Wnt-targets in HCT116 cells.
Figure 9:
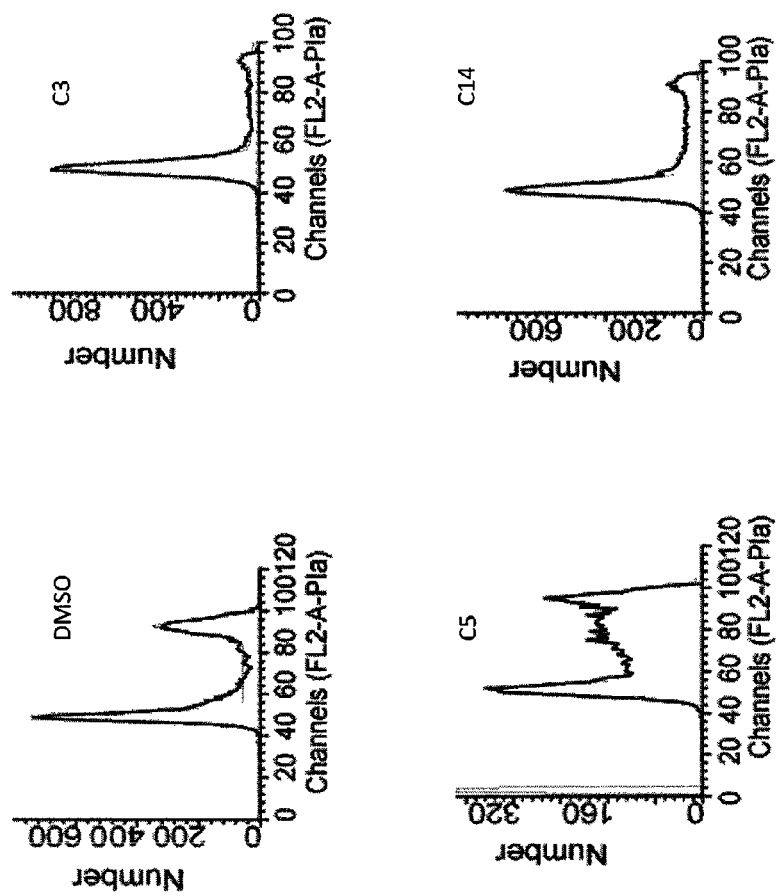
FIG. 9 shows C3 & C14 cause G0/G1 arrest.
Figure 10:
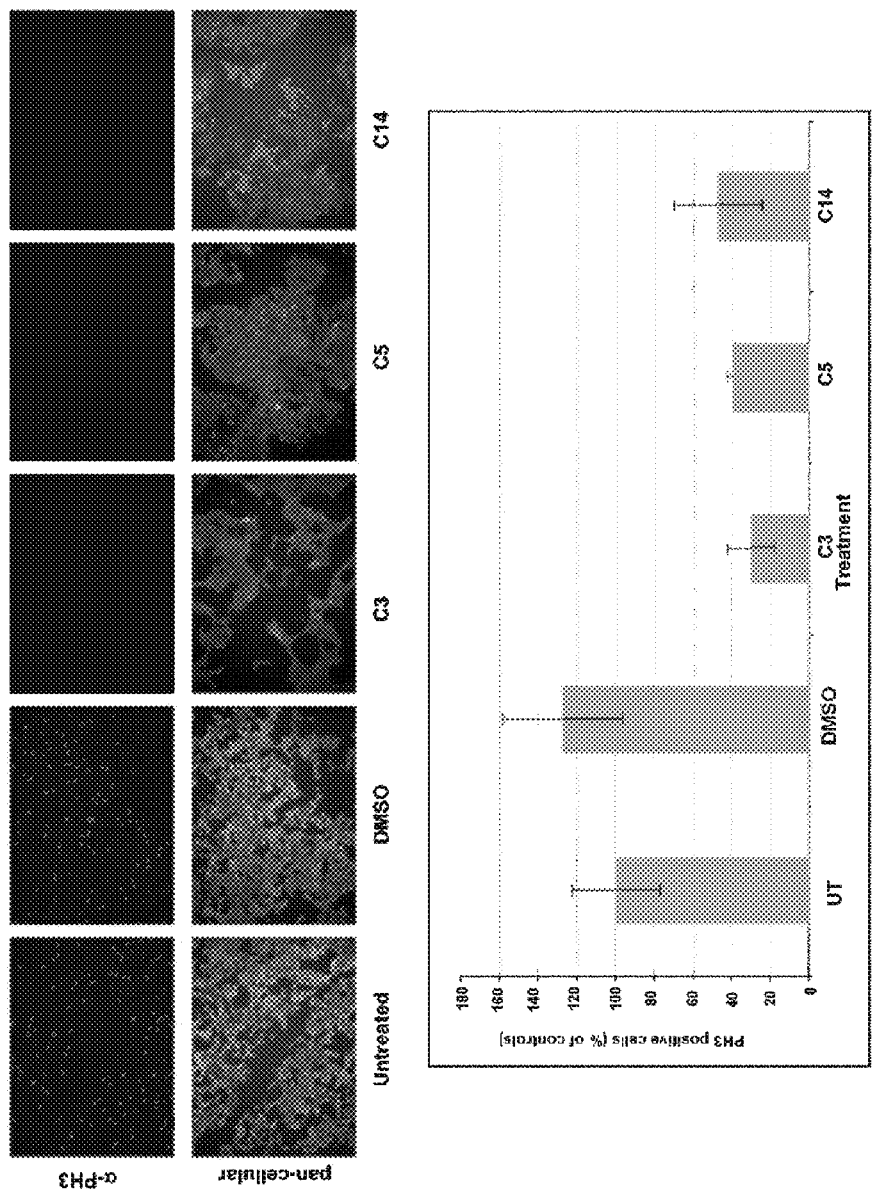
FIG. 10 shows Quantification of -αPH3 staining in compound treated HCT116 cells.

In order to test the inhibitory effect of candidate compounds on the transcription of endogenous Wnt/β-cat target genes in HCT116 cells, lysates were prepared from cells that were either treated with candidate small molecules or DMSO control. As shown in FIG. 7, the protein levels of CycD1 and c-myc were markedly reduced upon the addition of increasing concentrations of candidate compounds. qRT-PCR assays for the CycD1 and c-myc locus confirmed that the changes in their protein level reflected a change in their mRNA transcription (FIG. 8), further corroborating the effect of the candidate small molecules at the level of modulating CRT. Taken together, our analyses suggest a common theme of CRT-inhibition by these candidate compounds in a wide variety of Wnt-responsive heterologous cell types, thus making them ideal lead compounds for drug development for Wnt/CRT-related human disease. Finally, as predicted for the inhibition of target genes involved in cell cycle and cell proliferation, flow cytometry analyses of HCT116 cells treated with candidate compounds showed a G0/G1 arrest of the cell cycle (FIG. 9). Cell cycle arrest of compound treated HCT116 cells was further confirmed by the reduced number of phosphorylated Histone3 (PH3) positive cells, when cultured in the presence of candidate compounds (FIG. 10).

C3: Oxazole
C5: Thiazole

Example 4

Additional Protocols

HCT116 cells were obtained from ATCC (CCL-247) and cultured in McCoy's 5A medium supplemented with 10% Fetal Bovine Serum (FBS) at 37° C. with 5% $CO_2$. Target accumulation validations were performed by qPCR following treatment with the lead compounds. Briefly, cells were treated specified concentrations of compounds for 1 day, and lysed in 50 μl of Cell Lysis Buffer (Ambion #AM8723) at 75° C./10'. First-strand cDNA was prepared using High-Capacity Reverse Transcription Kit (Applied Biosystems #4368814) as per manufacturer's instructions. Real-time qPCR was carried out for CycD1, c-Myc and GAPDH2 (endogenous control) using pre-validated gene-specific primer pairs from Qiagen and the SYBr green PCR master mix from Applied Biosystems. Data analysis was performed using the MxPro-Mx3005P system from Stratagene using the ddCt method.

Flow Cytometry analysis was performed on HCT116 cells treated with candidate compounds for 16 hrs per standard protocols. Briefly, compound treated cells were harvested and washed in 1×PBS followed by fixation in 70% Ethanol at 4° C. for 16 hrs. Cells were then washed in 1×PBS and treated with RNAse at 37° C. for 30'. Following extensive washes in 1×PBS, cellular DNA was stained with 500 ug/ml of Propidium Iodide at room temperature for 10'. Cells were washed again in 1×PBS and analysed by flow cytometry on a FACScalibur machine (Beckson Dickinson) at the NYU flow cytometry core facility.

Example 5

Exemplary Compounds of the Invention

The following compounds, as exemplified in Tables 1-10, have been purchased, or can be purchased, or can be prepared according to the synthetic schemes described herein, or can be prepared according to the synthetic methods known to one skilled in the art.

TABLE 1

Oxazole amides ($R^3$ = NH-benzyl)

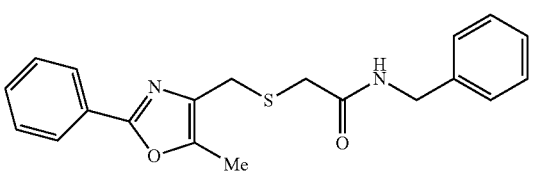

| ID | Structure | MW |
|---|---|---|
| IIa-1 | 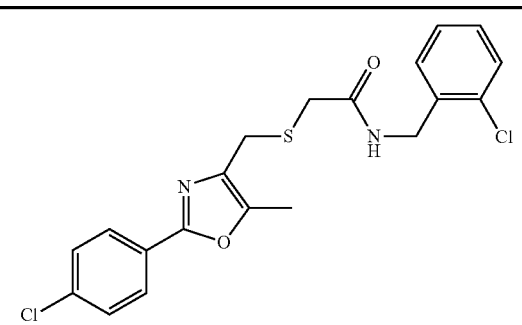 | 421.35 |

TABLE 1-continued
Oxazole amides (R³ = NH-benzyl)
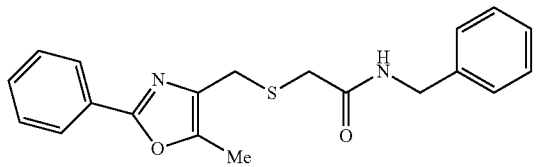 [SMILES: Cc1oc(-c2ccccc2)nc1CSCC(=O)NCc1ccccc1]
| ID | Structure | MW |
| --- | --- | --- |
| IIa-2 | 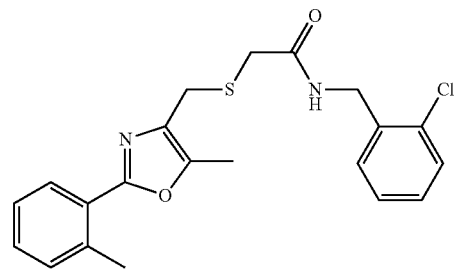 [SMILES: Cc1ccccc1-c1nc(CSCC(=O)NCc2ccccc2Cl)c(C)o1] | 400.93 |
| IIa-3 | 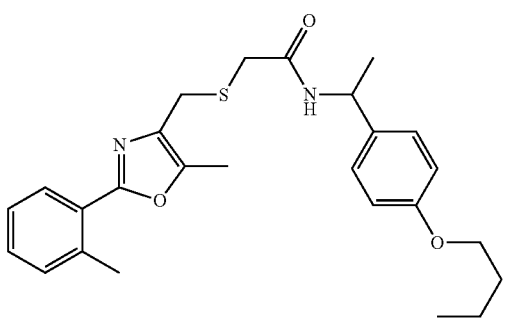 [SMILES: CCCCOc1ccc(C(C)NC(=O)CSCc2nc(-c3ccccc3C)oc2C)cc1] | 452.62 |
| IIa-4 | 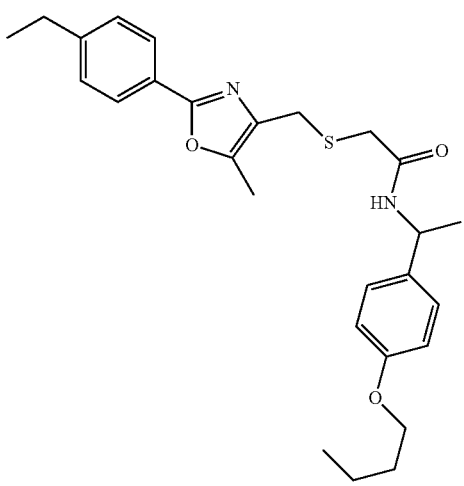 [SMILES: CCCCOc1ccc(C(C)NC(=O)CSCc2nc(-c3ccc(CC)cc3)oc2C)cc1] | 466.65 |

TABLE 1-continued
Oxazole amides (R³ = NH-benzyl)
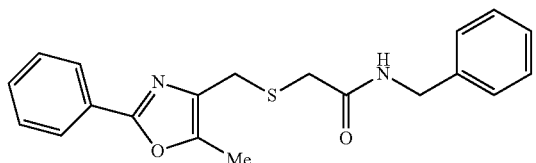
| ID | Structure | MW |
| --- | --- | --- |
| IIa-5 | 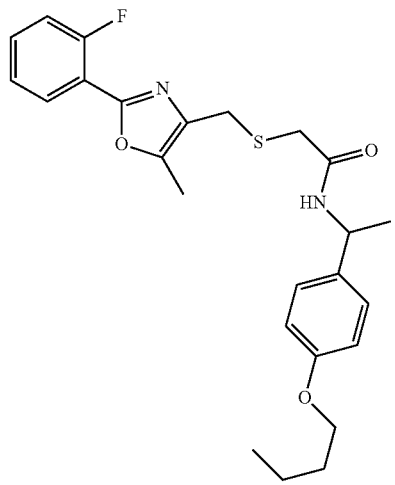 [SMILES: CCCCOc1ccc(C(C)NC(=O)CSCc2nc(-c3ccccc3F)oc2C)cc1] | 456.58 |
| IIa-6 | 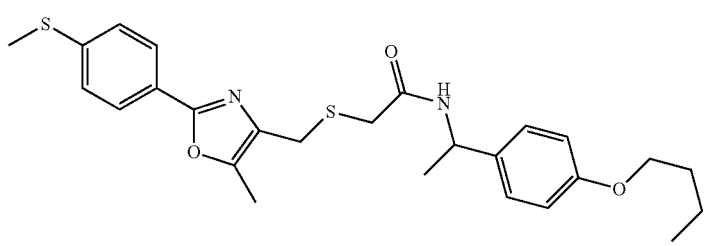 [SMILES: CCCCOc1ccc(C(C)NC(=O)CSCc2nc(-c3ccc(SC)cc3)oc2C)cc1] | 484.68 |
| IIa-7 | 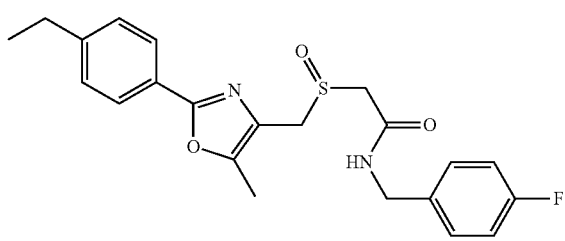 [SMILES: CCc1ccc(-c2nc(CS(=O)CC(=O)NCc3ccc(F)cc3)c(C)o2)cc1] | 414.50 |
| IIa-8 | 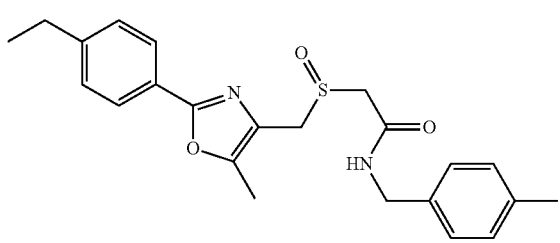 [SMILES: CCc1ccc(-c2nc(CS(=O)CC(=O)NCc3ccc(C)cc3)c(C)o2)cc1] | 410.54 |

TABLE 1-continued
Oxazole amides (R³ = NH-benzyl)
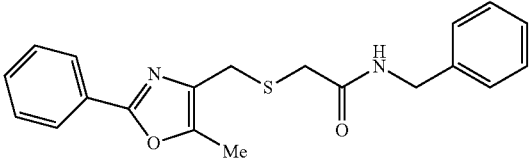
| ID | Structure | MW |
|---|---|---|
| IIa-9 | 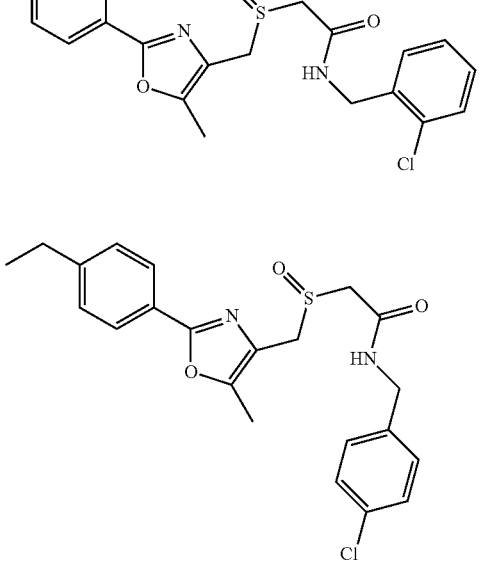 | 430.96 |
| IIa-10 | 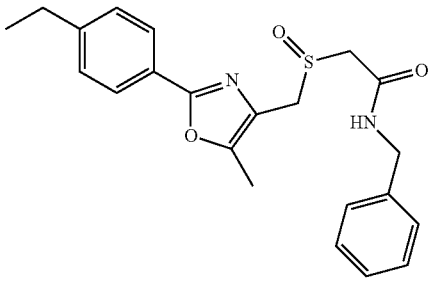 | 430.96 |
| IIa-11 | 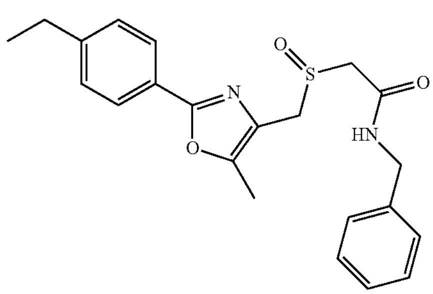 [SMILES: CCc1ccc(-c2nc(CS(=O)CC(=O)NCc3ccccc3)c(C)o2)cc1] | 396.51 |
| IIa-12 | 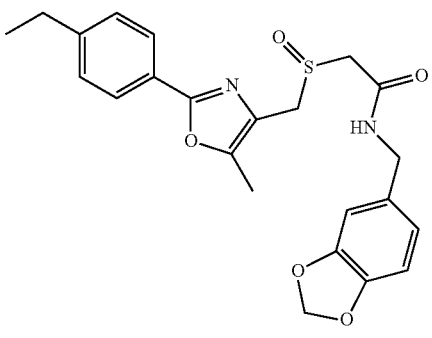 [SMILES: CCc1ccc(-c2nc(CS(=O)CC(=O)NCc3ccc4c(c3)OCO4)c(C)o2)cc1] | 440.52 |

TABLE 1-continued
Oxazole amides (R³ = NH-benzyl)
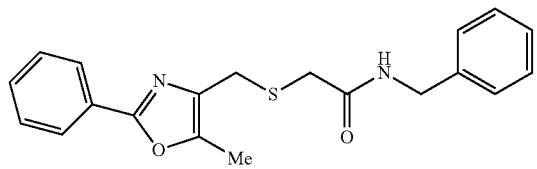
| ID | Structure | MW |
|---|---|---|
| IIa-13 | | 468.62 |
| IIa-14 | | 414.50 |
| IIa-15 | | 396.51 |

TABLE 1-continued
Oxazole amides (R³ = NH-benzyl)
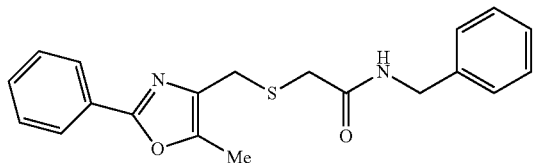
| ID | Structure | MW |
|---|---|---|
| IIa-16 | 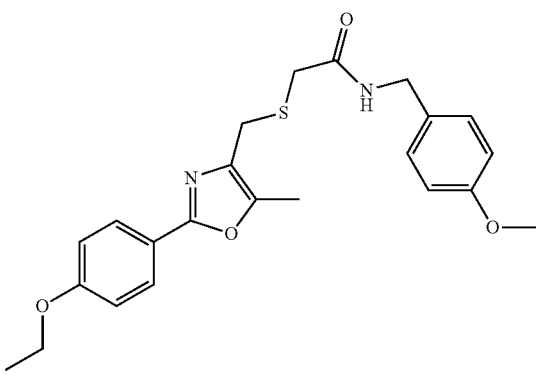 [SMILES: CCOc1ccc(-c2nc(CSCC(=O)NCc3ccc(OC)cc3)c(C)o2)cc1] | 426.54 |
| IIa-17 | 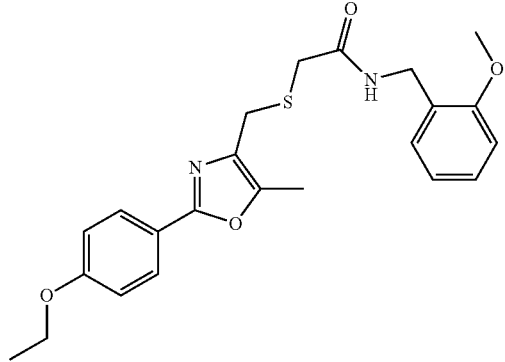 [SMILES: CCOc1ccc(-c2nc(CSCC(=O)NCc3ccccc3OC)c(C)o2)cc1] | 426.54 |
| IIa-18 | 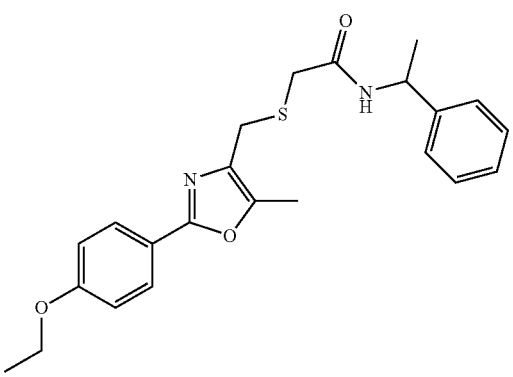 [SMILES: CCOc1ccc(-c2nc(CSCC(=O)NC(C)c3ccccc3)c(C)o2)cc1] | 410.54 |

TABLE 1-continued
Oxazole amides (R³ = NH-benzyl)
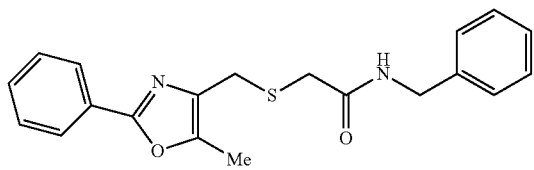
| ID | Structure | MW |
|---|---|---|
| IIa-19 | 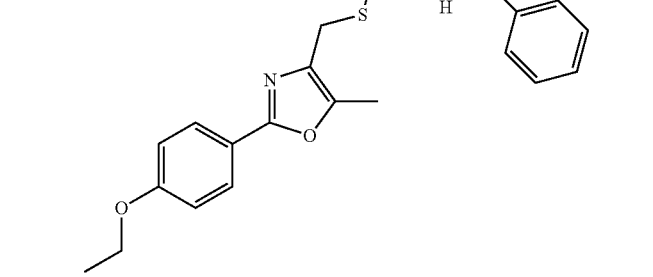 | 436.58 |
| IIa-20 | 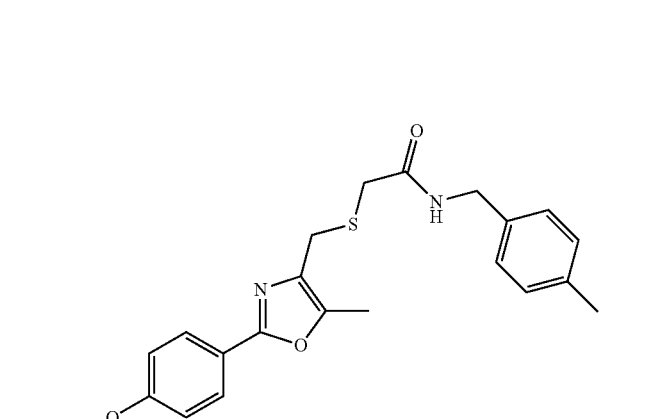 | 410.54 |
| IIa-21 | 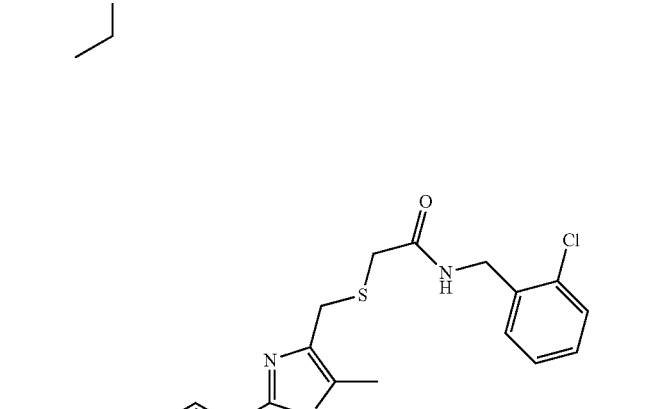 | 430.96 |

TABLE 1-continued
Oxazole amides (R³ = NH-benzyl)
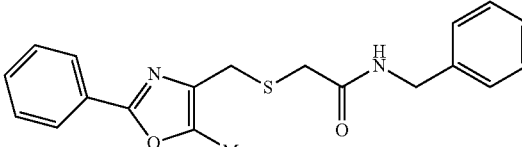
| ID | Structure | MW |
|---|---|---|
| IIa-22 | 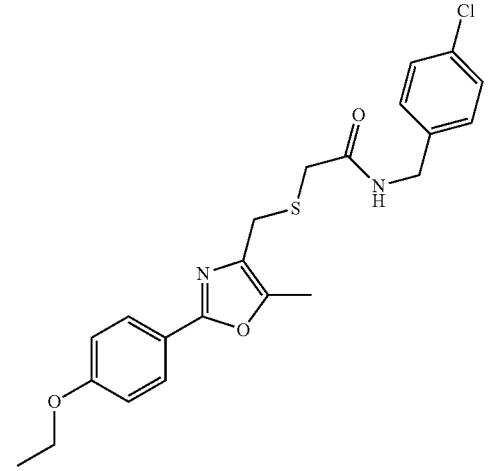 [SMILES: CCOc1ccc(-c2nc(CSCC(=O)NCc3ccc(Cl)cc3)c(C)o2)cc1] | 430.96 |
| IIa-23 | | 382.49 |
| IIa-24 | 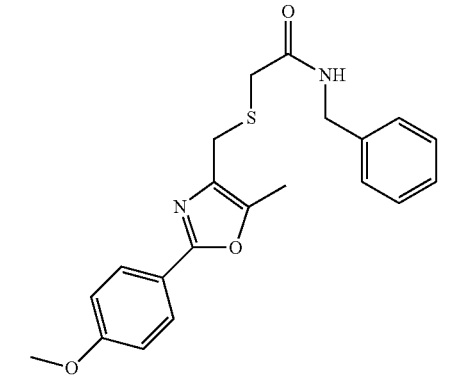 [SMILES: COc1ccc(-c2nc(CSCC(=O)NCc3ccccc3)c(C)o2)cc1] | 416.93 |

TABLE 1-continued

Oxazole amides (R³ = NH-benzyl)

| ID | Structure | MW |
|---|---|---|
| IIa-25 | | 412.51 |
| IIa-26 | | 396.51 |
| IIa-27 | | 426.50 |

TABLE 1-continued

Oxazole amides (R³ = NH-benzyl)

| ID | Structure | MW |
|---|---|---|
| IIa-28 | 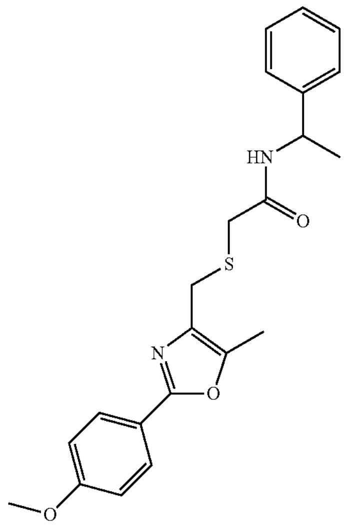 [SMILES: COc1ccc(-c2nc(CSCC(=O)NC(C)c3ccccc3)c(C)o2)cc1] | 396.51 |
| IIa-29 | 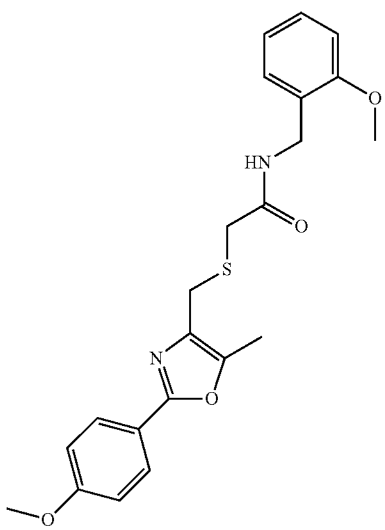 | 412.51 |
| IIa-30 | 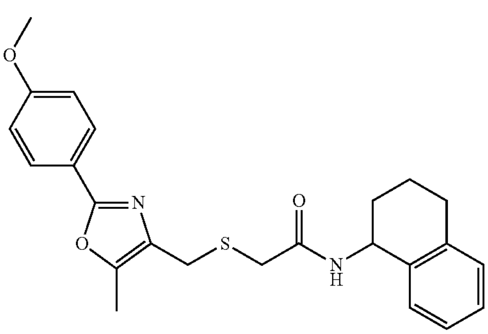 [SMILES: COc1ccc(-c2nc(CSCC(=O)NC3CCCc4ccccc43)c(C)o2)cc1] | 422.55 |

TABLE 1-continued
Oxazole amides (R³ = NH-benzyl)
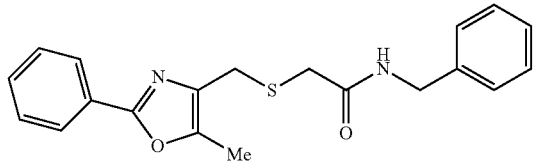
| ID | Structure | MW |
|---|---|---|
| IIa-31 | 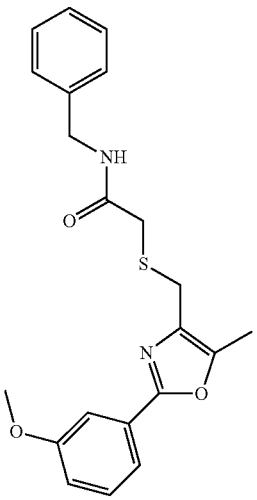 | 382.49 |
| IIa-32 | 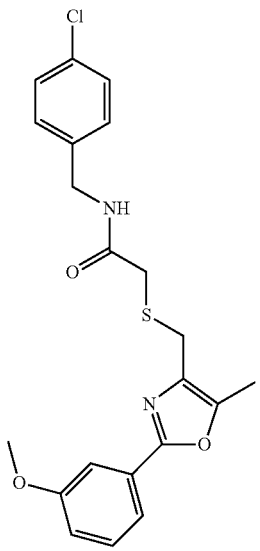 | 416.93 |

TABLE 1-continued

Oxazole amides (R³ = NH-benzyl)

| ID | Structure | MW |
|---|---|---|
| IIa-33 | | 396.51 |
| IIa-34 | | 412.51 |

TABLE 1-continued
Oxazole amides (R³ = NH-benzyl)
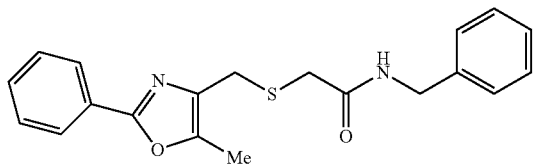
| ID | Structure | MW |
| --- | --- | --- |
| IIa-35 | 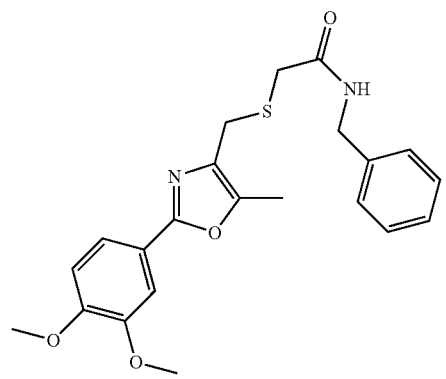 [SMILES: COc1ccc(-c2nc(CSCC(=O)NCc3ccccc3)c(C)o2)cc1OC] | 412.51 |
| IIa-36 | 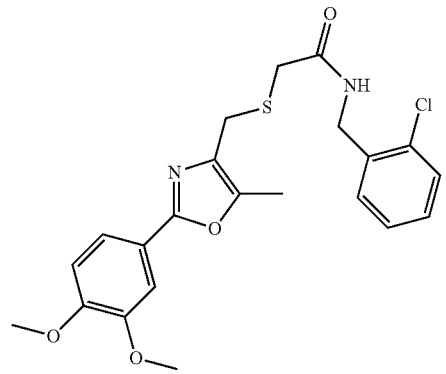 [SMILES: COc1ccc(-c2nc(CSCC(=O)NCc3ccccc3Cl)c(C)o2)cc1OC] | 446.96 |
| IIa-37 | 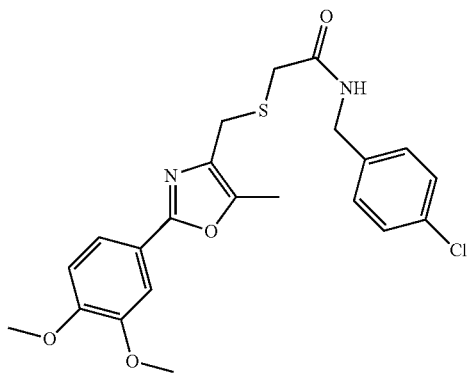 [SMILES: COc1ccc(-c2nc(CSCC(=O)NCc3ccc(Cl)cc3)c(C)o2)cc1OC] | 446.96 |

TABLE 1-continued

Oxazole amides (R³ = NH-benzyl)

| ID | Structure | MW |
|---|---|---|
| IIa-38 | | 442.54 |
| IIa-39 | | 456.52 |
| IIa-40 | | 426.54 |

TABLE 1-continued

Oxazole amides (R³ = NH-benzyl)

| ID | Structure | MW |
|---|---|---|
| IIa-41 | | 442.54 |
| IIa-42 | | 430.50 |
| IIa-43 | | 452.58 |

TABLE 1-continued
Oxazole amides (R³ = NH-benzyl)
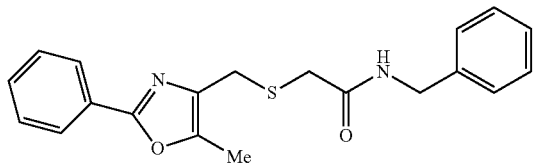
| ID | Structure | MW |
|---|---|---|
| IIa-44 | 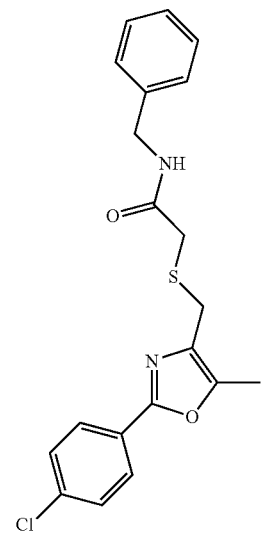 [SMILES: Cc1oc(-c2ccc(Cl)cc2)nc1CSCC(=O)NCc1ccccc1] | 386.90 |
| IIa-45 | 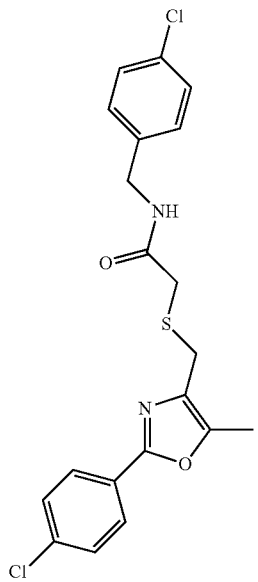 [SMILES: Cc1oc(-c2ccc(Cl)cc2)nc1CSCC(=O)NCc1ccc(Cl)cc1] | 421.35 |

TABLE 1-continued
Oxazole amides (R³ = NH-benzyl)
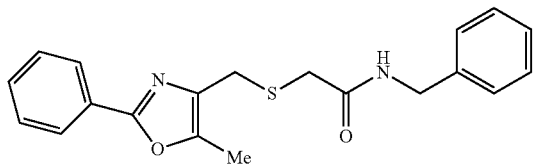
| ID | Structure | MW |
|---|---|---|
| IIa-46 | 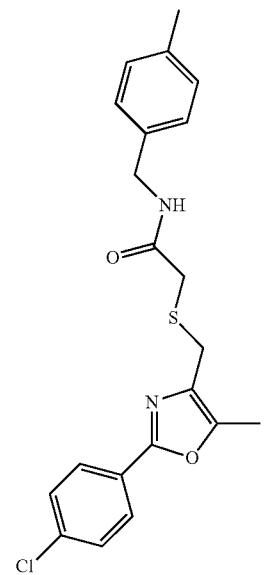 [SMILES: Cc1ccc(CNC(=O)CSCc2nc(-c3ccc(Cl)cc3)oc2C)cc1] | 400.93 |
| IIa-47 | 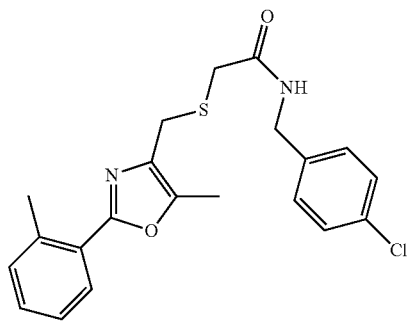 [SMILES: Cc1ccccc1-c1nc(CSCC(=O)NCc2ccc(Cl)cc2)c(C)o1] | 400.93 |
| IIa-48 | 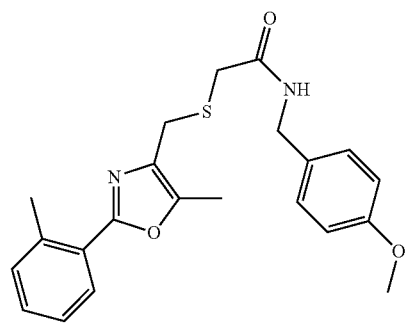 [SMILES: COc1ccc(CNC(=O)CSCc2nc(-c3ccccc3C)oc2C)cc1] | 396.51 |

TABLE 1-continued
Oxazole amides (R³ = NH-benzyl)
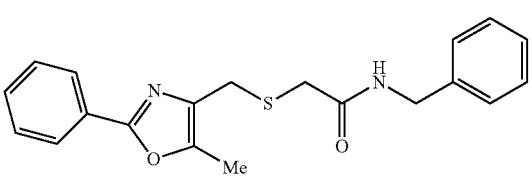
| ID | Structure | MW |
|---|---|---|
| IIa-49 | 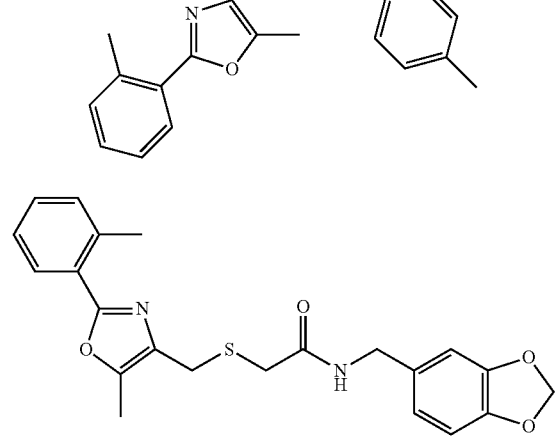 | 380.51 |
| IIa-50 | 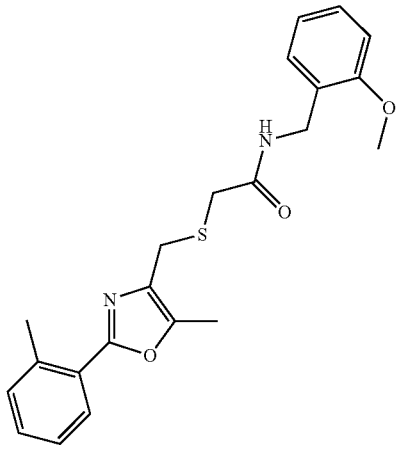 [SMILES: COc1ccccc1CNC(=O)CSCc1nc(-c2ccccc2C)oc1C] | 410.50 |
| IIa-51 | 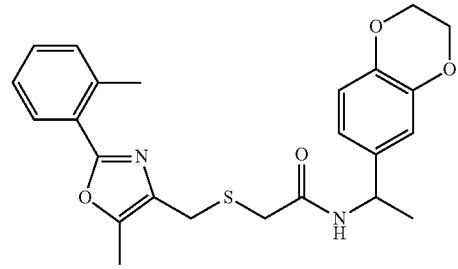 [SMILES: Cc1ccccc1-c1nc(CSCC(=O)NC(C)c2ccc3c(c2)OCCO3)c(C)o1] | 396.51 |
| IIa-52 | 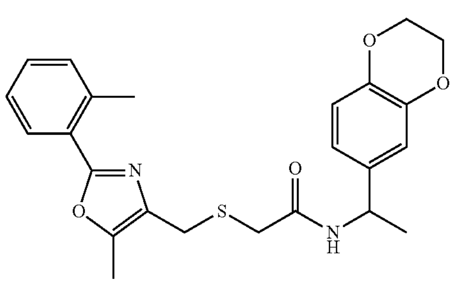 | 438.55 |

TABLE 1-continued

Oxazole amides (R³ = NH-benzyl)

| ID | Structure | MW |
|---|---|---|
| IIa-53 | | 421.35 |
| IIa-54 | | 400.93 |
| IIa-55 | | 430.91 |
| IIa-56 | | 416.93 |

TABLE 1-continued
Oxazole amides (R³ = NH-benzyl)
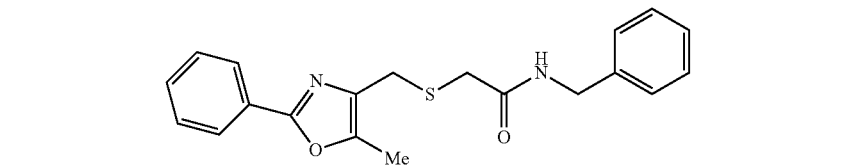
| ID | Structure | MW |
|---|---|---|
| IIa-57 | 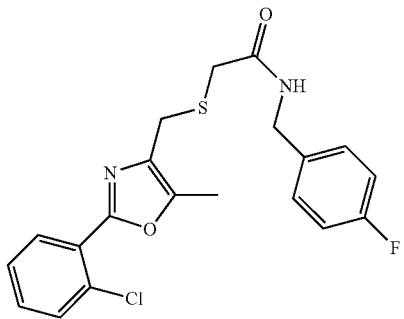 [SMILES: Cc1oc(-c2ccccc2Cl)nc1CSCC(=O)NCc1ccc(F)cc1] | 404.89 |
| IIa-58 | 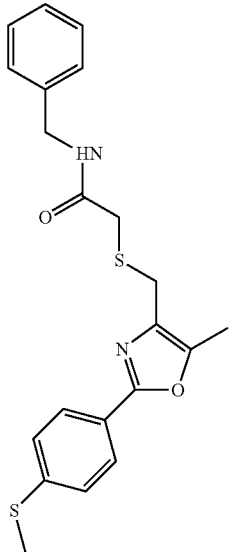 [SMILES: CSc1ccc(-c2nc(CSCC(=O)NCc3ccccc3)c(C)o2)cc1] | 398.55 |

TABLE 1-continued
Oxazole amides (R³ = NH-benzyl)
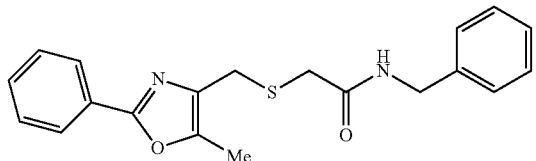
| ID | Structure | MW |
|---|---|---|
| IIa-59 | | 432.99 |
| IIa-60 | | 432.99 |

TABLE 1-continued
Oxazole amides (R³ = NH-benzyl)
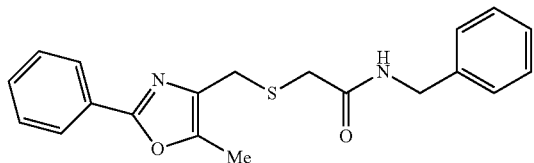
| ID | Structure | MW |
| --- | --- | --- |
| IIa-61 | 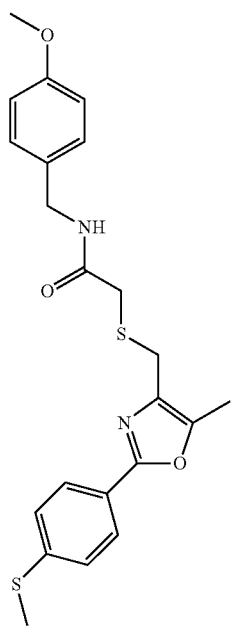 [SMILES: COc1ccc(CNC(=O)CSCc2nc(-c3ccc(SC)cc3)oc2C)cc1] | 428.58 |
| IIa-62 | 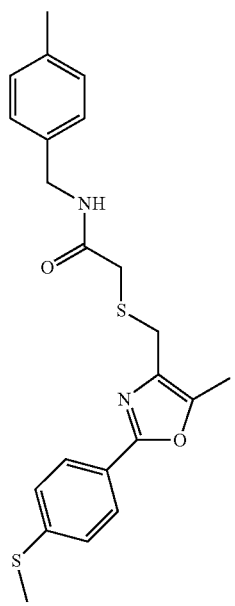 [SMILES: CSc1ccc(-c2nc(CSCC(=O)NCc3ccc(C)cc3)c(C)o2)cc1] | 412.58 |

TABLE 1-continued
Oxazole amides (R³ = NH-benzyl)
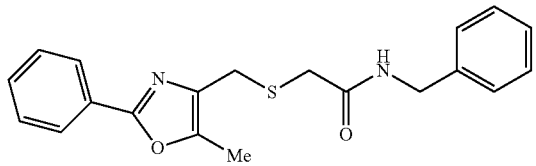
| ID | Structure | MW |
| --- | --- | --- |
| IIa-63 | 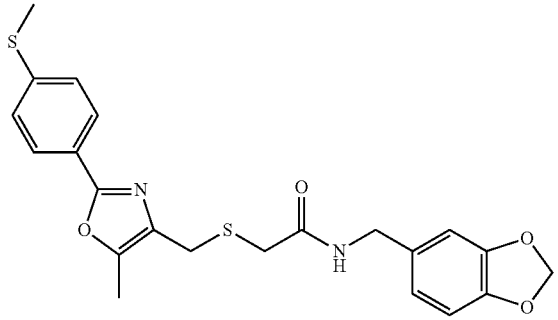 [SMILES: CSc1ccc(-c2nc(CSCC(=O)NCc3ccc4c(c3)OCO4)c(C)o2)cc1] | 442.56 |
| IIa-64 | 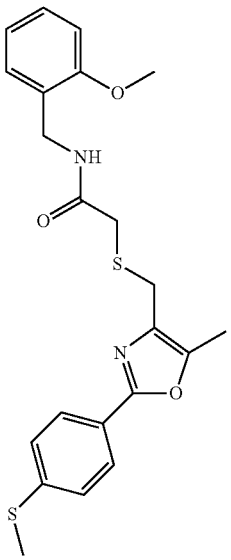 [SMILES: COc1ccccc1CNC(=O)CSCc1nc(-c2ccc(SC)cc2)oc1C] | 428.58 |
| IIa-65 | 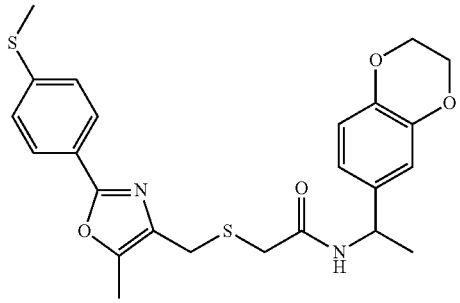 [SMILES: CSc1ccc(-c2nc(CSCC(=O)NC(C)c3ccc4c(c3)OCCO4)c(C)o2)cc1] | 470.61 |

TABLE 1-continued
Oxazole amides (R³ = NH-benzyl)
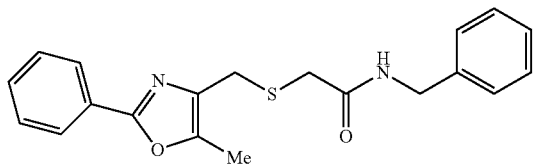
| ID | Structure | MW |
|---|---|---|
| IIa-66 | | 380.51 |
| IIa-67 | | 414.96 |
| IIa-68 | | 414.96 |

TABLE 1-continued

Oxazole amides (R³ = NH-benzyl)

| ID | Structure | MW |
|---|---|---|
| IIa-69 | 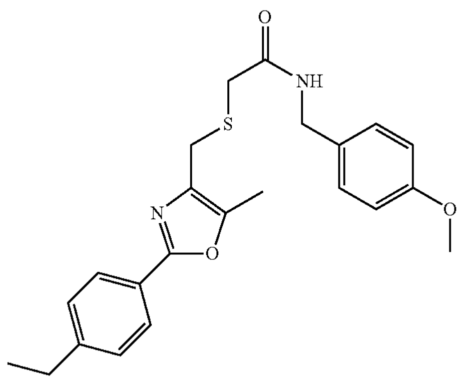 [SMILES: CCc1ccc(-c2nc(CSCC(=O)NCc3ccc(OC)cc3)c(C)o2)cc1] | 410.54 |
| IIa-70 | 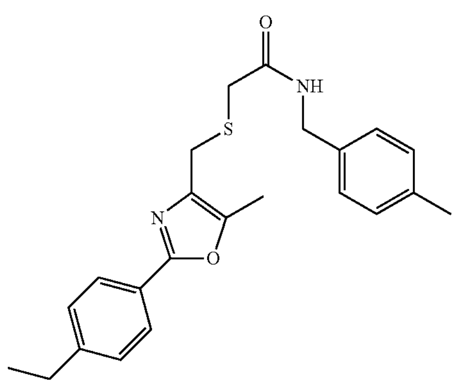 [SMILES: CCc1ccc(-c2nc(CSCC(=O)NCc3ccc(C)cc3)c(C)o2)cc1] | 394.54 |
| IIa-71 | 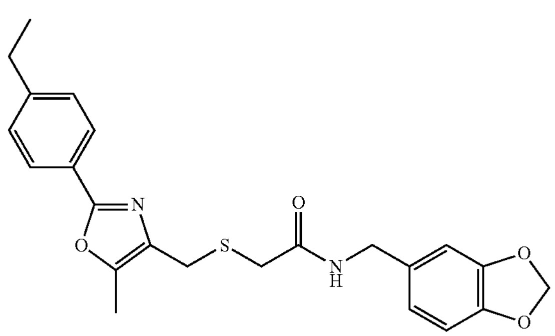 [SMILES: CCc1ccc(-c2nc(CSCC(=O)NCc3ccc4c(c3)OCO4)c(C)o2)cc1] | 424.52 |

TABLE 1-continued
Oxazole amides (R³ = NH-benzyl)
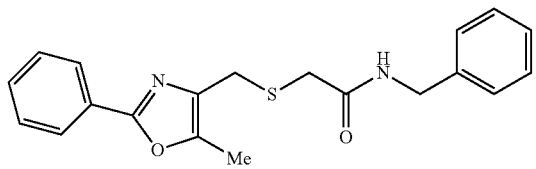
| ID | Structure | MW |
|---|---|---|
| IIa-72 | 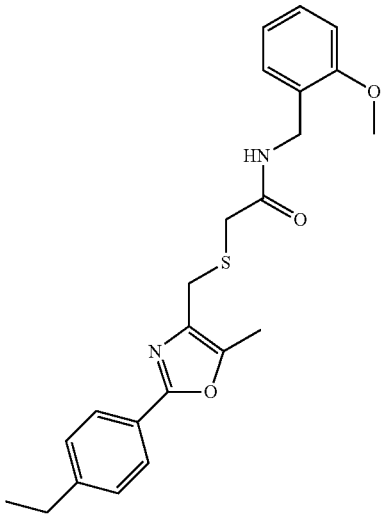 [SMILES: CCc1ccc(-c2nc(CSCC(=O)NCc3ccccc3OC)c(C)o2)cc1] | 410.54 |
| IIa-73 | 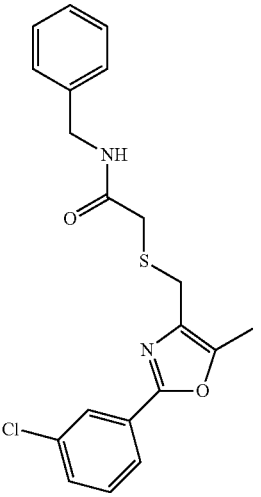 [SMILES: Cc1oc(-c2cccc(Cl)c2)nc1CSCC(=O)NCc1ccccc1] | 386.90 |

TABLE 1-continued
Oxazole amides (R³ = NH-benzyl)
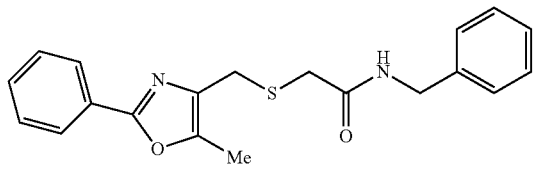
| ID | Structure | MW |
|---|---|---|
| IIa-74 | | 421.35 |
| IIa-75 | | 421.35 |

TABLE 1-continued
Oxazole amides (R³ = NH-benzyl)
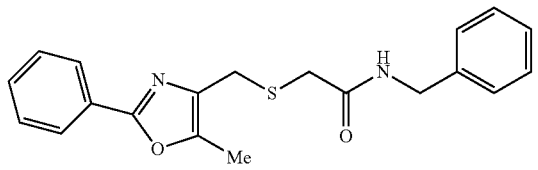
| ID | Structure | MW |
|---|---|---|
| IIa-76 | 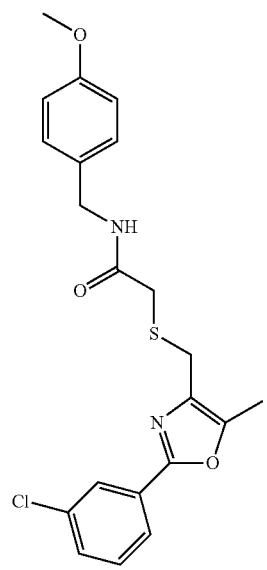 | 416.93 |
| IIa-77 | 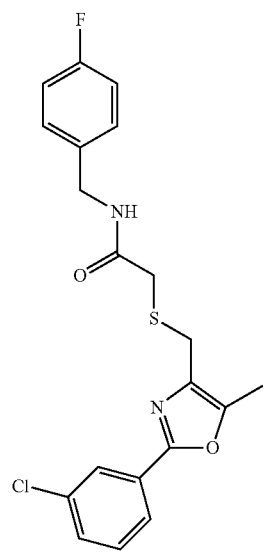 [SMILES: Cc1oc(-c2cccc(Cl)c2)nc1CSCC(=O)NCc1ccc(Cl)cc1] | 404.89 |

TABLE 1-continued
Oxazole amides (R³ = NH-benzyl)
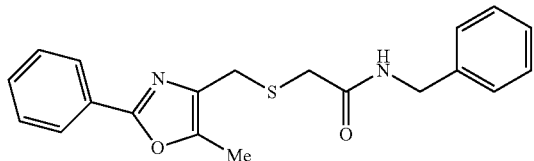
| ID | Structure | MW |
| --- | --- | --- |
| IIa-78 | 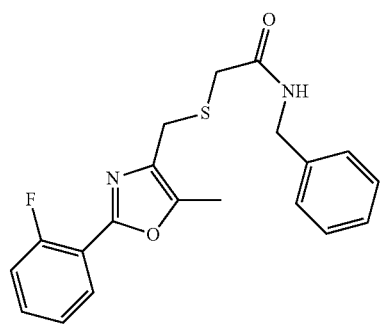 [SMILES: Cc1oc(-c2ccccc2F)nc1CSCC(=O)NCc1ccccc1] | 370.45 |
| IIa-79 | 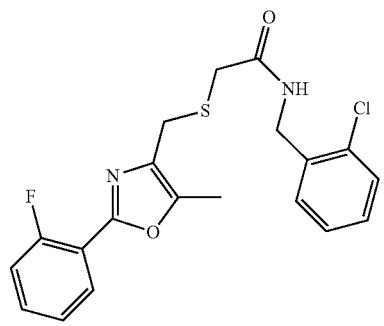 [SMILES: Cc1oc(-c2ccccc2F)nc1CSCC(=O)NCc1ccccc1Cl] | 404.89 |
| IIa-80 | 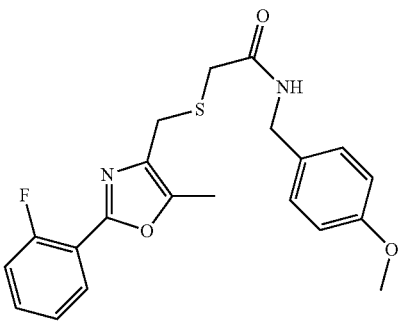 [SMILES: COc1ccc(CNC(=O)CSCc2nc(-c3ccccc3F)oc2C)cc1] | 400.48 |
| IIa-81 | 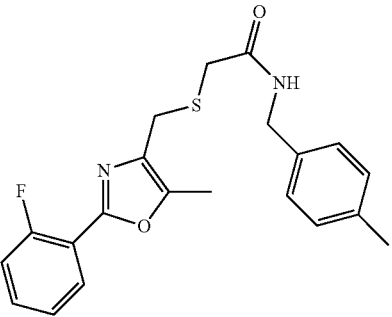 [SMILES: Cc1ccc(CNC(=O)CSCc2nc(-c3ccccc3F)oc2C)cc1] | 384.48 |

TABLE 1-continued

Oxazole amides (R³ = NH-benzyl)

| ID | Structure | MW |
|---|---|---|
| IIa-82 | | 414.46 |
| IIa-83 | | 400.48 |
| IIa-84 | | 366.49 |

TABLE 1-continued

Oxazole amides (R³ = NH-benzyl)

| ID | Structure | MW |
|---|---|---|
| IIa-85 | | 400.93 |
| IIa-86 | | 400.93 |

TABLE 1-continued
Oxazole amides (R³ = NH-benzyl)
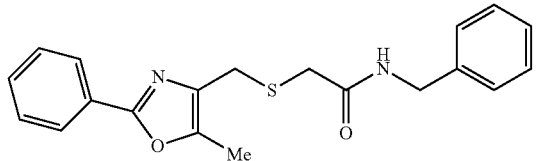
| ID | Structure | MW |
|---|---|---|
| IIa-87 | | 396.51 |
| IIa-88 | | 380.51 |

TABLE 1-continued
Oxazole amides (R³ = NH-benzyl)
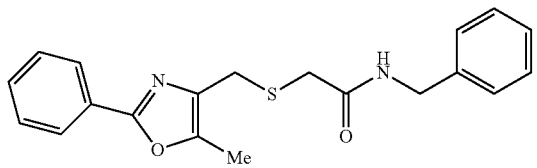
| ID | Structure | MW |
|---|---|---|
| IIa-89 | 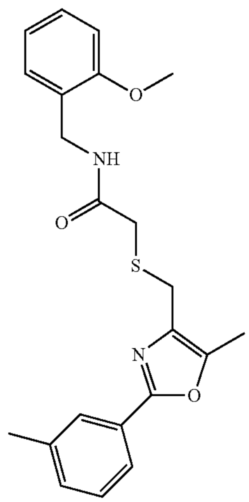 | 396.51 |
| IIa-90 | 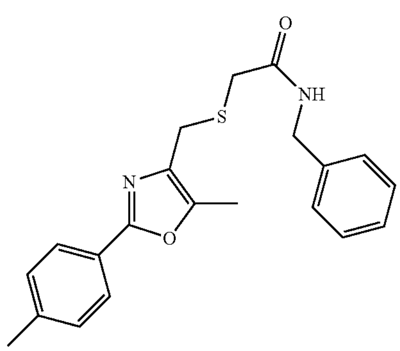 [SMILES: Cc1ccc(-c2nc(CSCC(=O)NCc3ccccc3)c(C)o2)cc1] | 366.49 |
| IIa-91 | 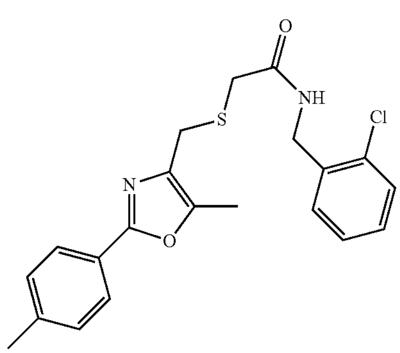 [SMILES: Cc1ccc(-c2nc(CSCC(=O)NCc3ccccc3Cl)c(C)o2)cc1] | 400.93 |

TABLE 1-continued
Oxazole amides (R³ = NH-benzyl)
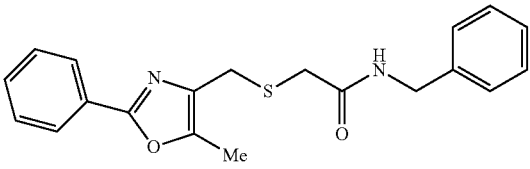
| ID | Structure | MW |
|---|---|---|
| IIa-92 | 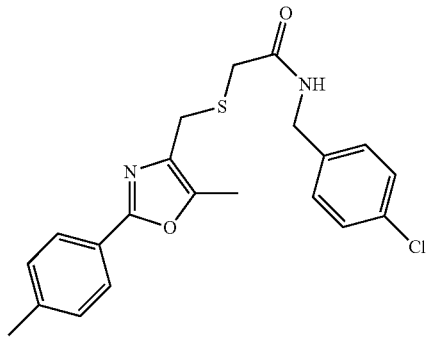 [SMILES: Cc1ccc(-c2nc(CSCC(=O)NCc3ccc(Cl)cc3)c(C)o2)cc1] | 400.93 |
| IIa-93 | 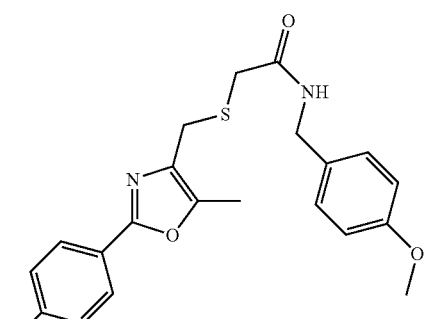 | 396.51 |
| IIa-94 | 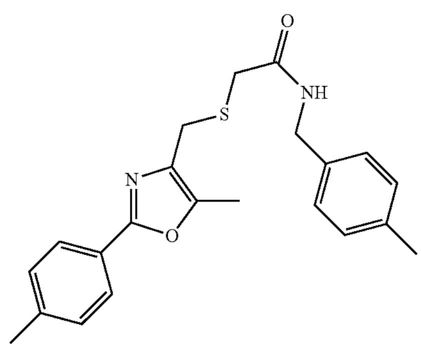 | 380.51 |
| IIa-95 | 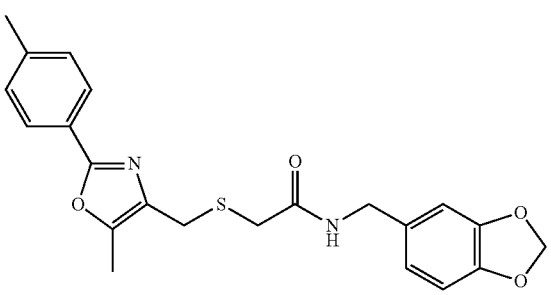 [SMILES: Cc1ccc(-c2nc(CSCC(=O)NCc3ccc4c(c3)OCO4)c(C)o2)cc1] | 410.50 |

TABLE 1-continued

Oxazole amides (R³ = NH-benzyl)

| ID | Structure | MW |
|---|---|---|
| IIa-96 | 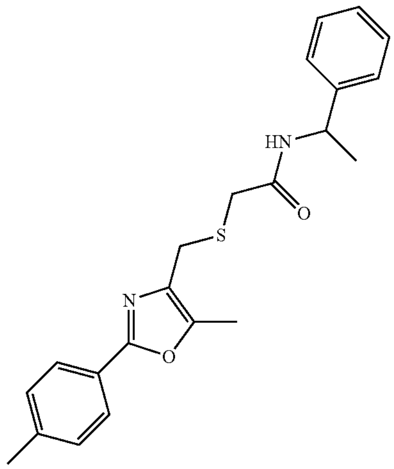 [SMILES: Cc1ccc(-c2nc(CSCC(=O)NC(C)c3ccccc3)c(C)o2)cc1] | 380.51 |
| IIa-97 | 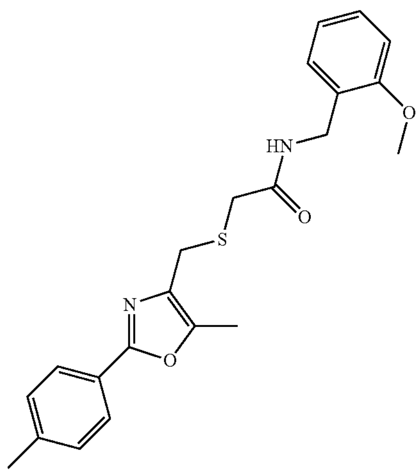 [SMILES: COc1ccccc1CNC(=O)CSCc1nc(-c2ccc(C)cc2)oc1C] | 396.51 |
| IIa-98 | 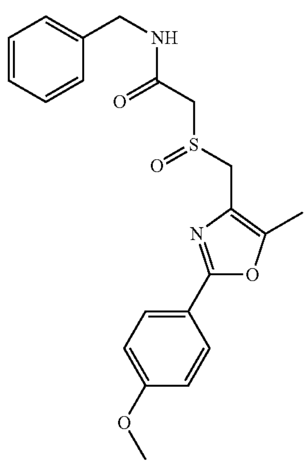 [SMILES: COc1ccc(-c2nc(CS(=O)CC(=O)NCc3ccccc3)c(C)o2)cc1] | 398.48 |

TABLE 1-continued
Oxazole amides (R³ = NH-benzyl)
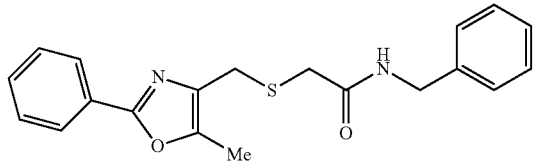
| ID | Structure | MW |
|---|---|---|
| IIa-99 | 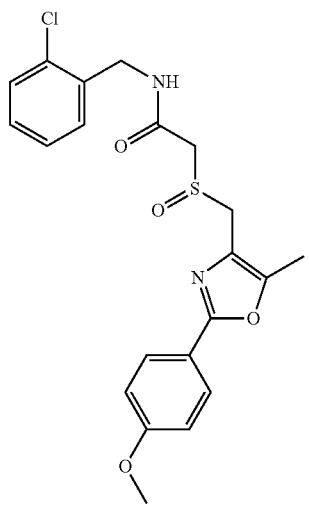 [SMILES: COc1ccc(-c2nc(CS(=O)CC(=O)NCc3ccccc3Cl)c(C)o2)cc1] | 432.93 |
| IIa-100 | 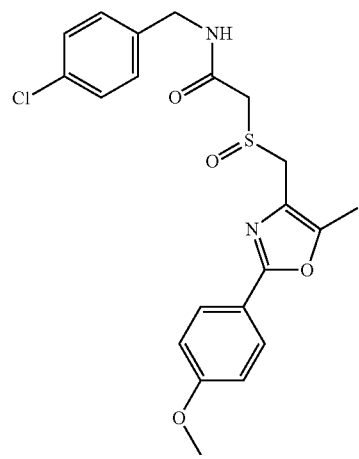 [SMILES: COc1ccc(-c2nc(CS(=O)CC(=O)NCc3ccc(Cl)cc3)c(C)o2)cc1] | 432.93 |

TABLE 1-continued
Oxazole amides (R³ = NH-benzyl)
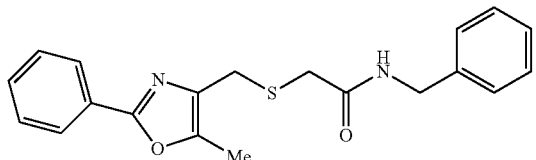
| ID | Structure | MW |
|---|---|---|
| IIa-101 | 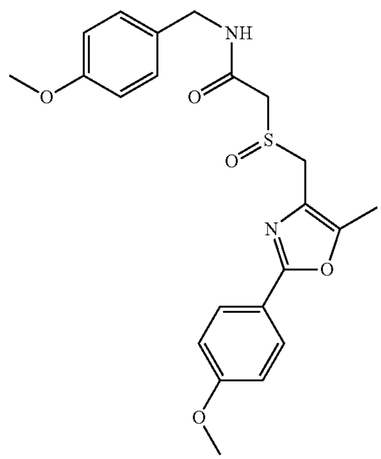 | 428.51 |
| IIa-102 | 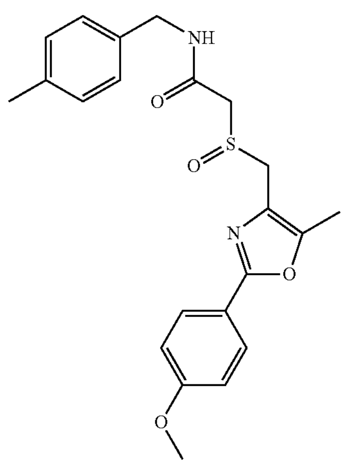 | 412.51 |
| IIa-103 | 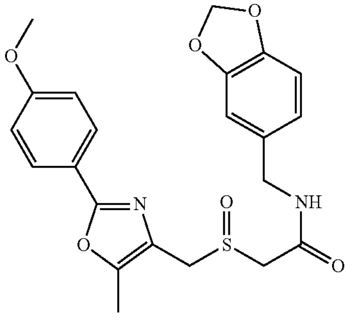 [SMILES: COc1ccc(-c2nc(CS(=O)CC(=O)NCc3ccc4c(c3)OCO4)c(C)o2)cc1] | 442.49 |

TABLE 1-continued
Oxazole amides (R³ = NH-benzyl)
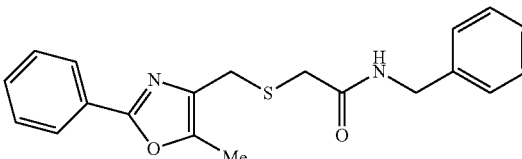
| ID | Structure | MW |
|---|---|---|
| IIa-104 | 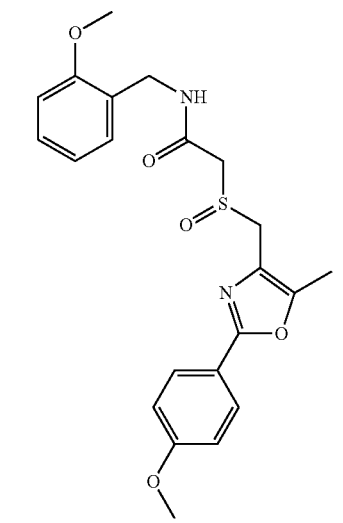 [SMILES: COc1ccc(-c2nc(CS(=O)CC(=O)NCc3ccccc3OC)c(C)o2)cc1] | 428.51 |
| IIa-105 | 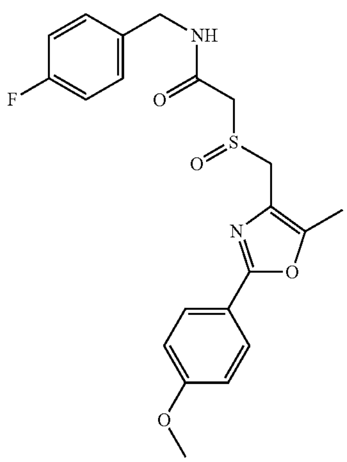 [SMILES: COc1ccc(-c2nc(CS(=O)CC(=O)NCc3ccc(F)cc3)c(C)o2)cc1] | 416.47 |
| IIa-106 | 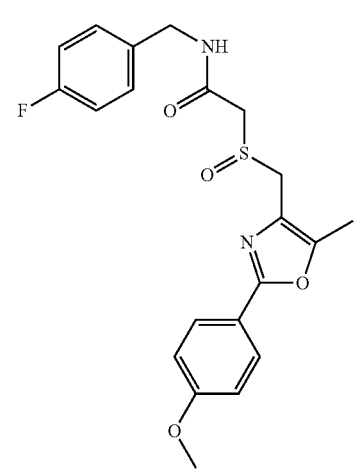 | 437.35 |

TABLE 1-continued
Oxazole amides (R³ = NH-benzyl)
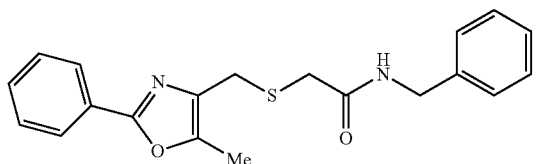
| ID | Structure | MW |
|---|---|---|
| IIa-107 | 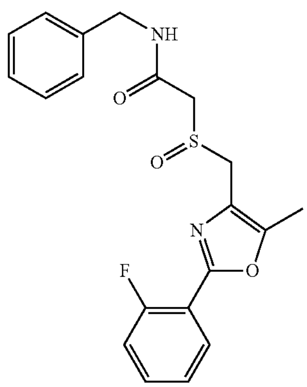 [SMILES: Cc1oc(-c2ccccc2F)nc1CS(=O)CC(=O)NCc1ccccc1] | 386.45 |
| IIa-108 | 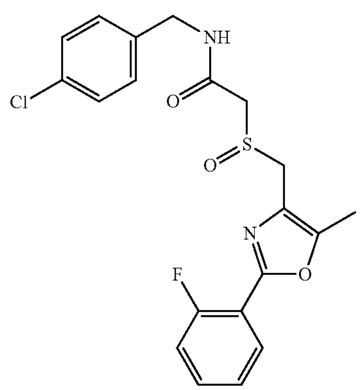 [SMILES: Cc1oc(-c2ccccc2F)nc1CS(=O)CC(=O)NCc1ccc(Cl)cc1] | 420.89 |
| IIa-109 | 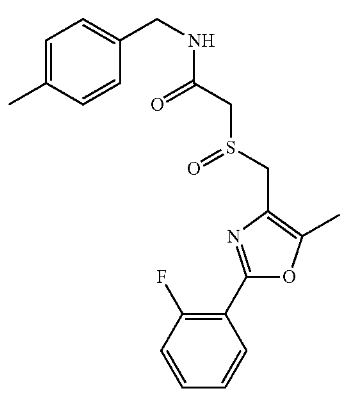 | 400.48 |

TABLE 1-continued
Oxazole amides (R³ = NH-benzyl)
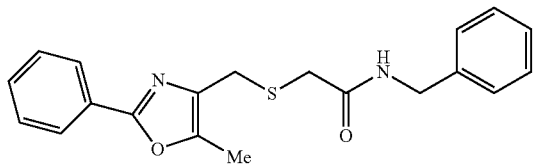
| ID | Structure | MW |
|---|---|---|
| IIa-110 | 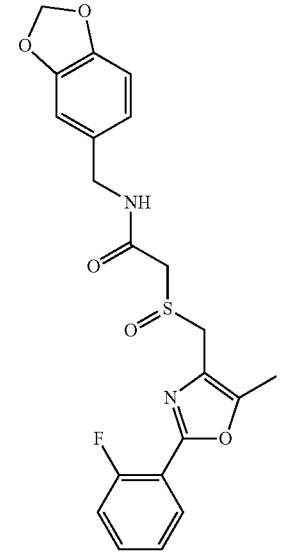 [SMILES: Cc1oc(-c2ccccc2F)nc1CS(=O)CC(=O)NCc1ccc2c(c1)OCO2] | 430.46 |
| IIa-111 | 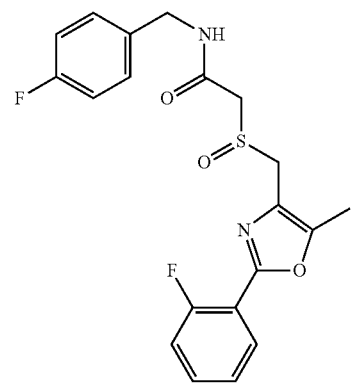 [SMILES: Cc1oc(-c2ccccc2F)nc1CS(=O)CC(=O)NCc1ccc(F)cc1] | 404.44 |
| IIa-112 | 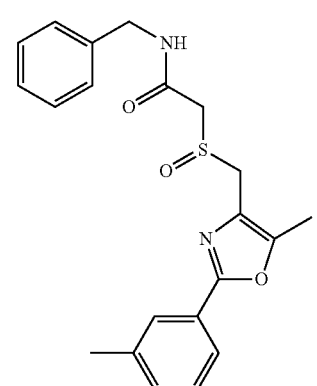 | 382.49 |

TABLE 1-continued
Oxazole amides (R³ = NH-benzyl)
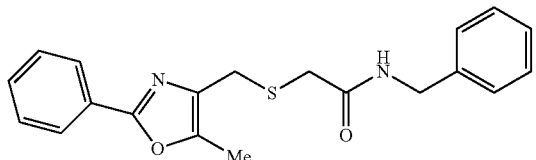
| ID | Structure | MW |
|---|---|---|
| IIa-113 | | 416.93 |
| IIa-114 | | 416.93 |
| IIa-115 | | 412.51 |

TABLE 1-continued
Oxazole amides (R³ = NH-benzyl)
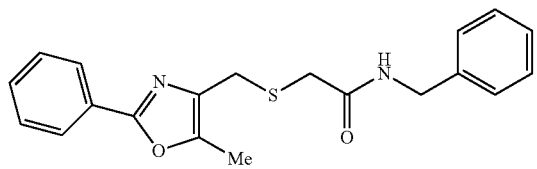
| ID | Structure | MW |
| --- | --- | --- |
| IIa-116 | 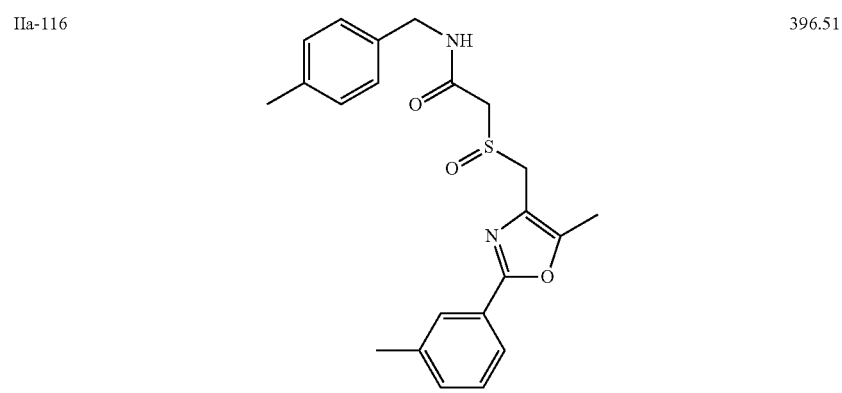 | 396.51 |
| IIa-117 | 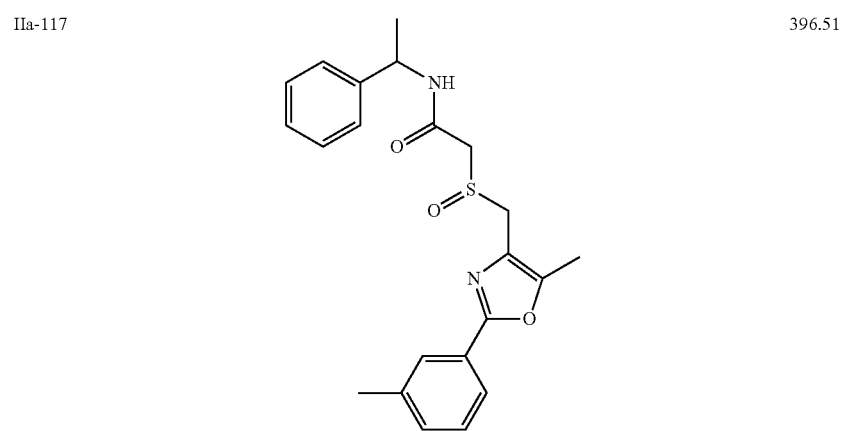 | 396.51 |
| IIa-118 | 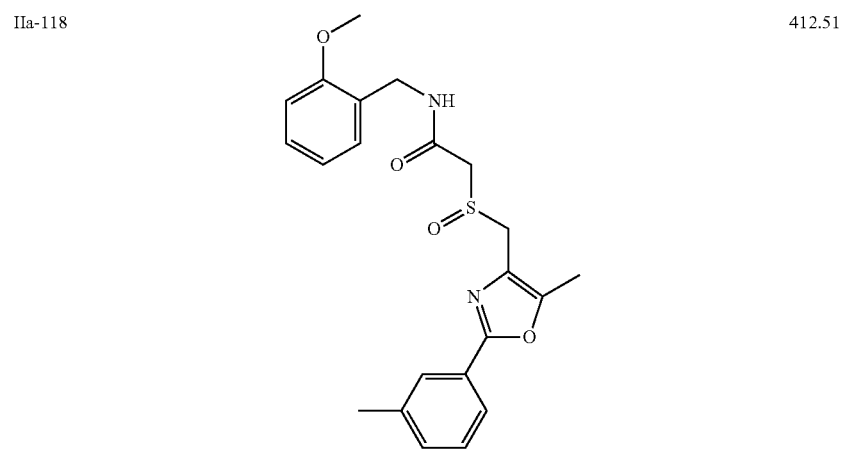 | 412.51 |

TABLE 1-continued
Oxazole amides (R³ = NH-benzyl)
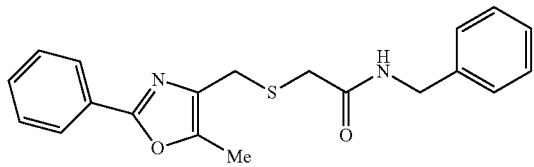
| ID | Structure | MW |
| --- | --- | --- |
| IIa-119 | | 400.48 |
| IIa-120 | | 382.49 |
| IIa-121 | | 416.93 |

TABLE 1-continued
Oxazole amides (R³ = NH-benzyl)
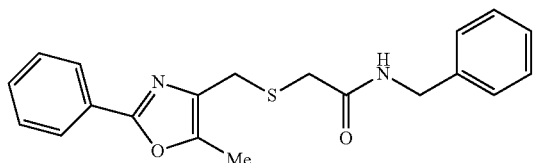
| ID | Structure | MW |
|---|---|---|
| IIa-122 | 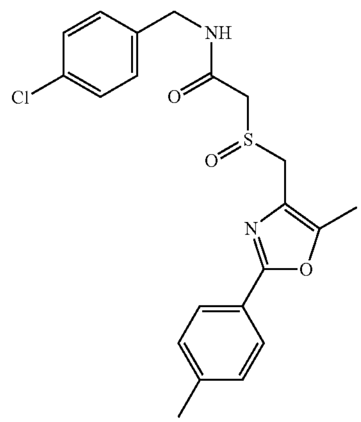 [SMILES: Cc1ccc(-c2nc(CS(=O)CC(=O)NCc3ccc(Cl)cc3)c(C)o2)cc1] | 416.93 |
| IIa-123 | 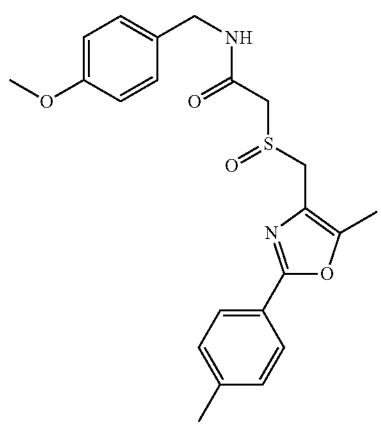 | 412.51 |
| IIa-124 | 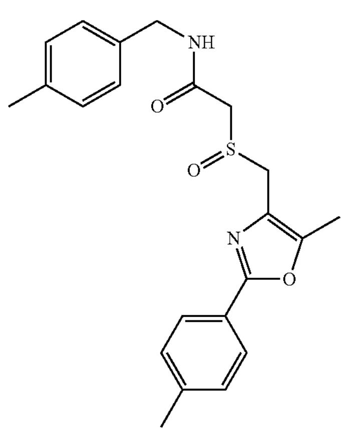 | 396.51 |

TABLE 1-continued
Oxazole amides (R³ = NH-benzyl)
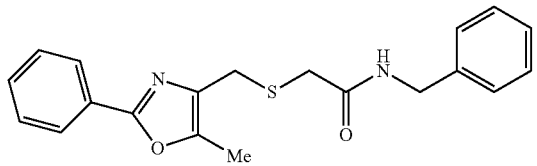
| ID | Structure | MW |
| --- | --- | --- |
| IIa-125 | | 426.50 |
| IIa-126 | | 412.51 |

TABLE 1-continued
Oxazole amides (R³ = NH-benzyl)
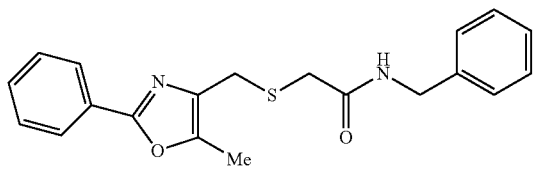
| ID | Structure | MW |
|---|---|---|
| IIa-127 | 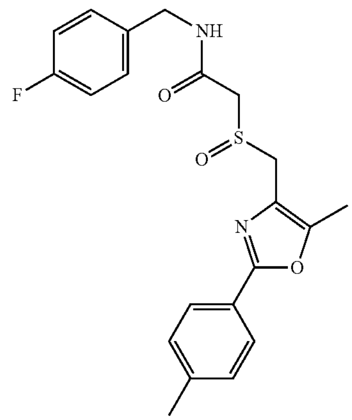 [SMILES: Cc1ccc(-c2nc(CS(=O)CC(=O)NCc3ccc(F)cc3)c(C)o2)cc1] | 400.48 |
| IIa-128 | 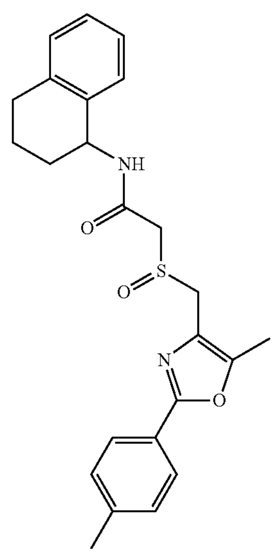 [SMILES: Cc1ccc(-c2nc(CS(=O)CC(=O)NC3CCCc4ccccc43)c(C)o2)cc1] | 422.55 |
| IIa-129 | 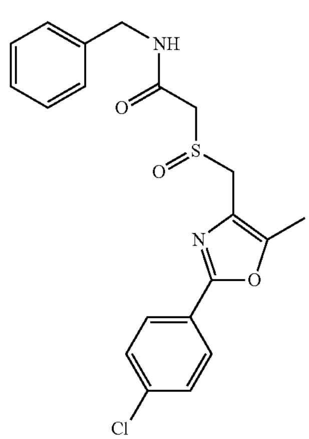 [SMILES: Cc1oc(-c2ccc(Cl)cc2)nc1CS(=O)CC(=O)NCc1ccccc1] | 402.90 |

TABLE 1-continued

Oxazole amides (R³ = NH-benzyl)

| ID | Structure | MW |
|---|---|---|
| IIa-130 | 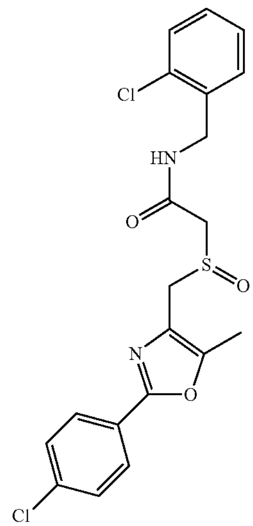 [SMILES: Cc1oc(-c2ccc(Cl)cc2)nc1CS(=O)CC(=O)NCc1ccccc1Cl] | 437.35 |
| IIa-131 | 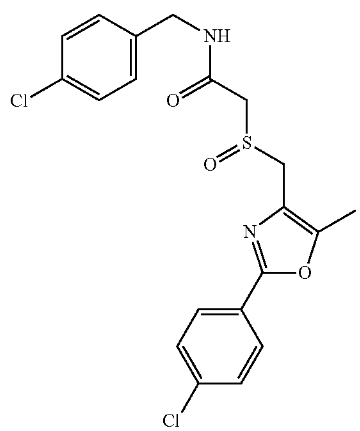 [SMILES: Cc1oc(-c2ccc(Cl)cc2)nc1CS(=O)CC(=O)NCc1ccc(Cl)cc1] | 437.35 |
| IIa-132 | 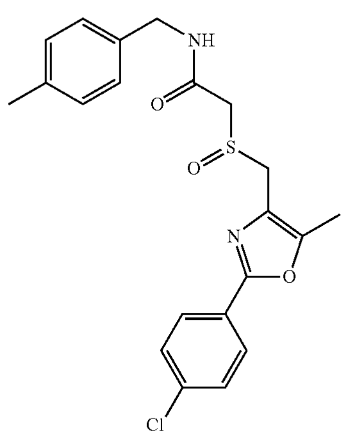 | 416.93 |

TABLE 1-continued
Oxazole amides (R³ = NH-benzyl)
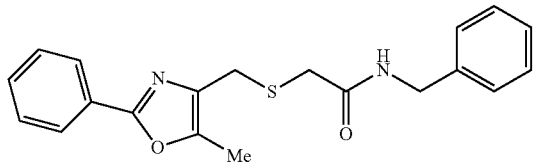
| ID | Structure | MW |
|---|---|---|
| IIa-133 | | 446.91 |
| IIa-134 | | 416.93 |

TABLE 1-continued
Oxazole amides (R³ = NH-benzyl)
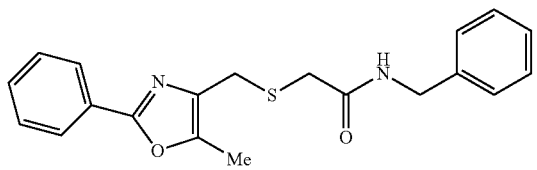
| ID | Structure | MW |
| --- | --- | --- |
| IIa-135 | 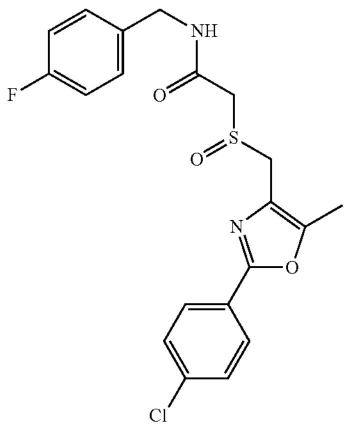 [SMILES: Cc1oc(-c2ccc(Cl)cc2)nc1CS(=O)CC(=O)NCc1ccc(F)cc1] | 420.89 |
| IIa-136 | 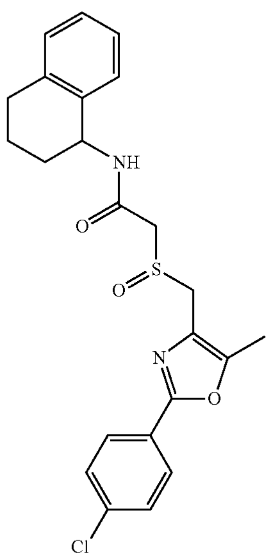 [SMILES: Cc1oc(-c2ccc(Cl)cc2)nc1CS(=O)CC(=O)NC1CCCc2ccccc21] | 442.97 |
| IIa-137 | 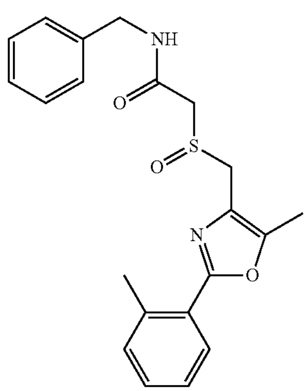 [SMILES: Cc1ccccc1-c1nc(CS(=O)CC(=O)NCc2ccccc2)c(C)o1] | 382.49 |

TABLE 1-continued

Oxazole amides (R³ = NH-benzyl)

| ID | Structure | MW |
|---|---|---|
| IIa-138 | 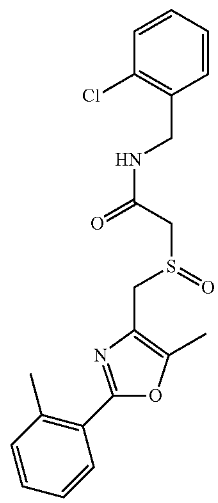 [SMILES: Cc1ccccc1-c1nc(CS(=O)CC(=O)NCc2ccccc2Cl)c(C)o1] | 416.93 |
| IIa-139 | 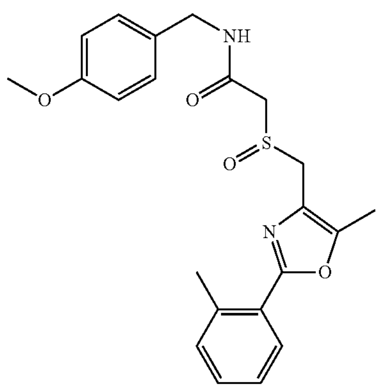 | 412.51 |
| IIa-140 | 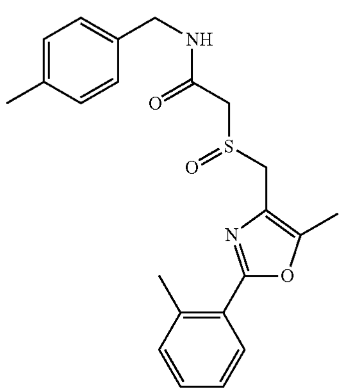 | 396.51 |

TABLE 1-continued

Oxazole amides (R³ = NH-benzyl)

| ID | Structure | MW |
|---|---|---|
| IIa-141 | 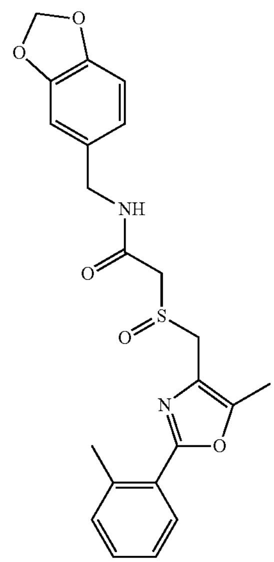 [SMILES: Cc1ccccc1-c1nc(CS(=O)CC(=O)NCc2ccc3c(c2)OCO3)c(C)o1] | 426.50 |
| IIa-142 | 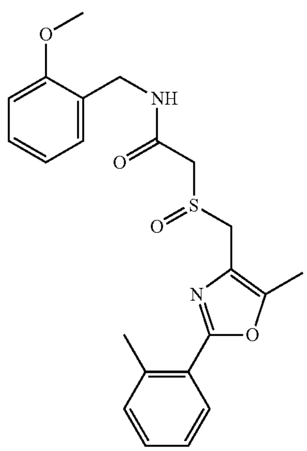 [SMILES: COc1ccccc1CNC(=O)CS(=O)Cc1nc(-c2ccccc2C)oc1C] | 412.51 |
| IIa-143 | 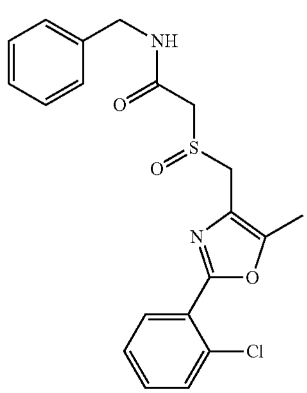 [SMILES: Cc1oc(-c2ccccc2Cl)nc1CS(=O)CC(=O)NCc1ccccc1] | 402.90 |

TABLE 1-continued
Oxazole amides (R³ = NH-benzyl)
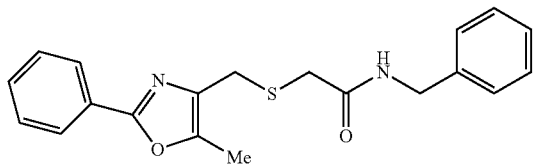
| ID | Structure | MW |
|---|---|---|
| IIa-144 | 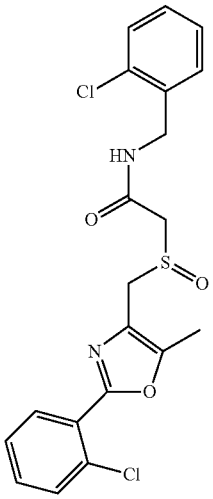 [SMILES: Cc1oc(-c2ccccc2Cl)nc1CS(=O)CC(=O)NCc1ccccc1Cl] | 437.35 |
| IIa-145 | 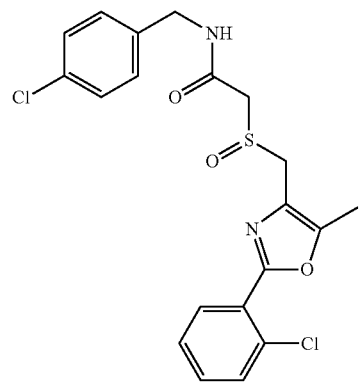 [SMILES: Cc1oc(-c2ccccc2Cl)nc1CS(=O)CC(=O)NCc1ccc(Cl)cc1] | 437.35 |
| IIa-146 | 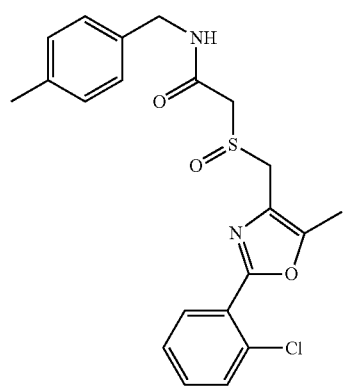 | 416.93 |

TABLE 1-continued
Oxazole amides (R³ = NH-benzyl)
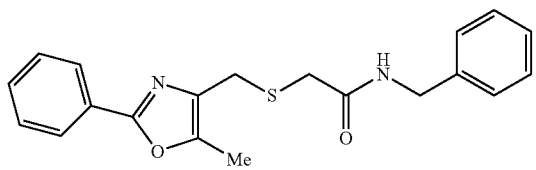
| ID | Structure | MW |
|---|---|---|
| IIa-147 | | 446.91 |
| IIa-148 | | 432.93 |
| IIa-149 | | 420.89 |

TABLE 1-continued

Oxazole amides (R³ = NH-benzyl)

| ID | Structure | MW |
|---|---|---|
| IIa-150 | 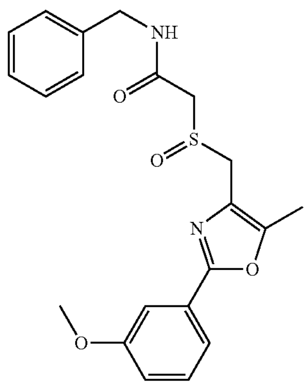 [SMILES: COc1cccc(-c2nc(CS(=O)CC(=O)NCc3ccccc3)c(C)o2)c1] | 398.48 |
| IIa-151 | 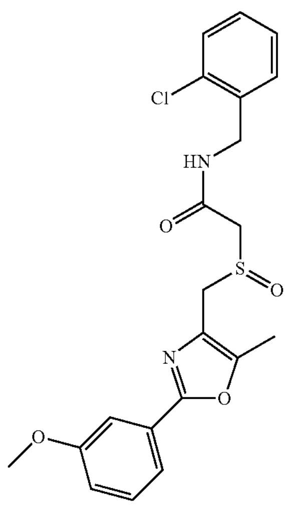 [SMILES: COc1cccc(-c2nc(CS(=O)CC(=O)NCc3ccccc3Cl)c(C)o2)c1] | 432.93 |
| IIa-152 | 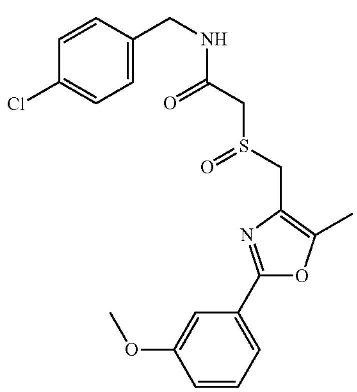 [SMILES: COc1cccc(-c2nc(CS(=O)CC(=O)NCc3ccc(Cl)cc3)c(C)o2)c1] | 432.93 |

TABLE 1-continued

Oxazole amides (R³ = NH-benzyl)

| ID | Structure | MW |
|---|---|---|
| IIa-153 | | 442.49 |
| IIa-154 | | 416.47 |
| IIa-155 | | 428.51 |

TABLE 1-continued
Oxazole amides (R³ = NH-benzyl)
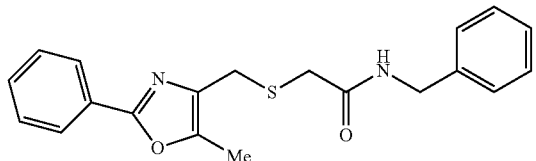
| ID | Structure | MW |
|---|---|---|
| IIa-156 | 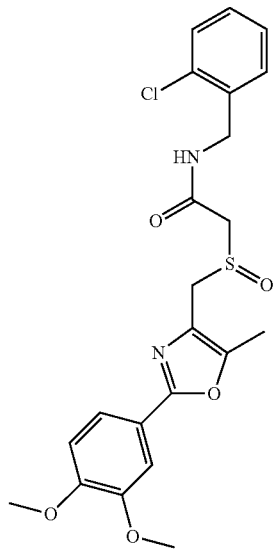 [SMILES: COc1ccc(-c2nc(CS(=O)CC(=O)NCc3ccccc3Cl)c(C)o2)cc1OC] | 462.96 |
| IIa-157 | 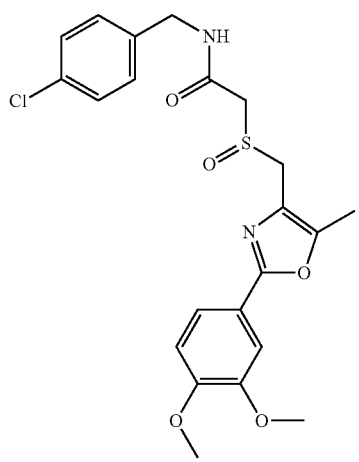 [SMILES: COc1ccc(-c2nc(CS(=O)CC(=O)NCc3ccc(Cl)cc3)c(C)o2)cc1OC] | 462.96 |

TABLE 1-continued
Oxazole amides (R³ = NH-benzyl)
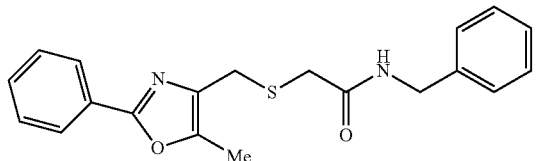
| ID | Structure | MW |
|---|---|---|
| IIa-158 | | 458.54 |
| IIa-159 | | 442.54 |

TABLE 1-continued
Oxazole amides (R³ = NH-benzyl)
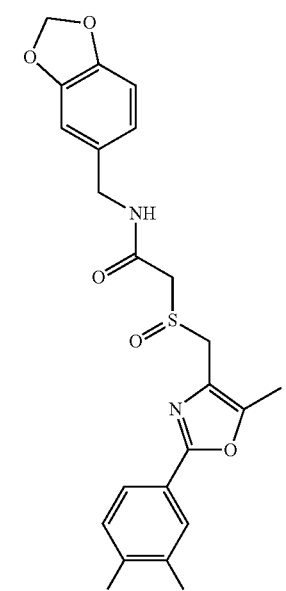
| ID | Structure | MW |
|---|---|---|
| IIa-160 | 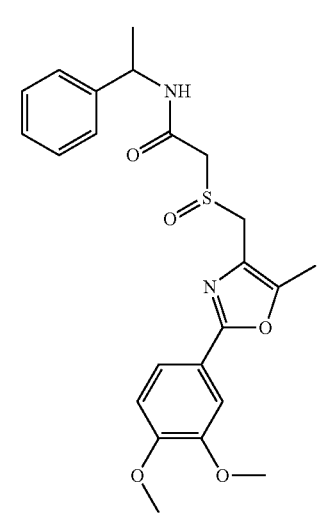 [SMILES: COc1ccc(-c2nc(CS(=O)CC(=O)NC(C)c3ccccc3)c(C)o2)cc1OC] | 472.52 |
| IIa-161 | | 442.54 |

TABLE 1-continued
Oxazole amides (R³ = NH-benzyl)
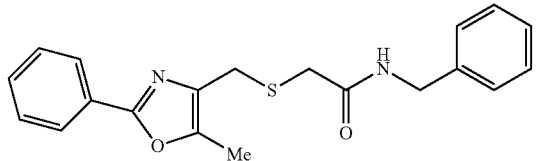
| ID | Structure | MW |
|---|---|---|
| IIa-162 | 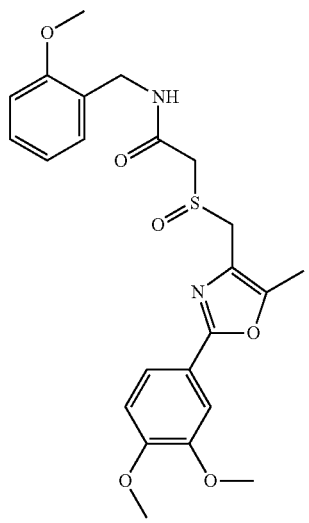 [SMILES: COc1ccccc1CNC(=O)CS(=O)Cc1nc(-c2ccc(OC)c(OC)c2)oc1C] | 458.54 |
| IIa-163 | 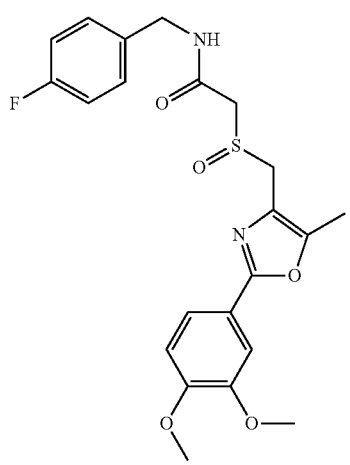 [SMILES: COc1ccc(-c2nc(CS(=O)CC(=O)NCc3ccc(F)cc3)c(C)o2)cc1OC] | 446.50 |

TABLE 1-continued
Oxazole amides (R³ = NH-benzyl)
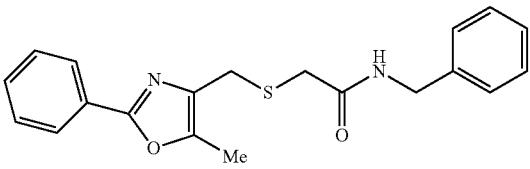
| ID | Structure | MW |
|---|---|---|
| IIa-164 | 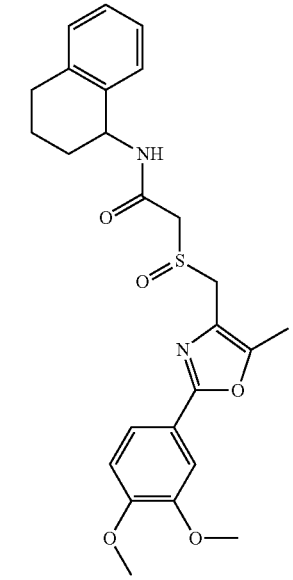 [SMILES: COc1ccc(-c2nc(CS(=O)CC(=O)NC3CCCc4ccccc43)c(C)o2)cc1OC] | 468.58 |
| IIa-165 | 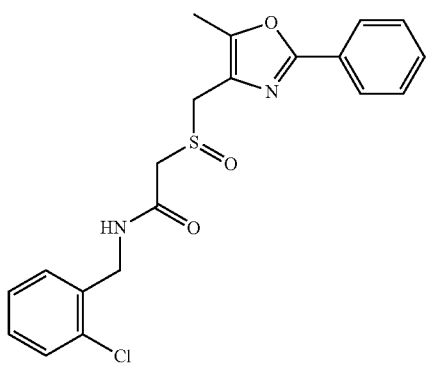 [SMILES: Cc1oc(-c2ccccc2)nc1CS(=O)CC(=O)NCc1ccccc1Cl] | 368.46 |
| IIa-166 | | 402.90 |

TABLE 1-continued
Oxazole amides (R³ = NH-benzyl)
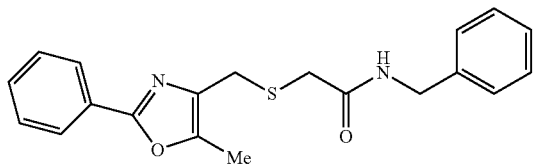
| ID | Structure | MW |
|---|---|---|
| IIa-167 | 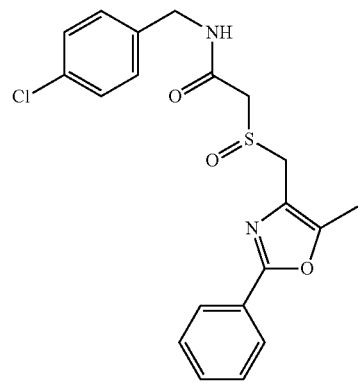 [SMILES: Cc1oc(-c2ccccc2)nc1CS(=O)CC(=O)NCc1ccc(Cl)cc1] | 402.90 |
| IIa-168 | 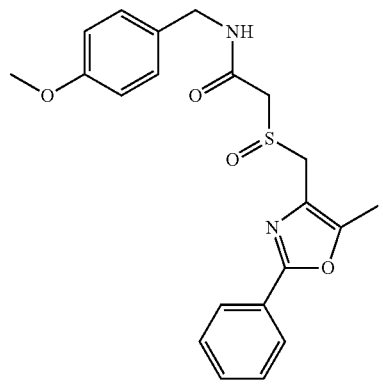 | 398.48 |
| IIa-169 | 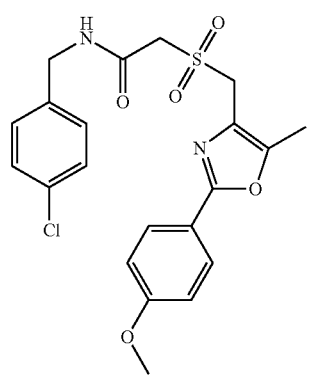 [SMILES: COc1ccc(-c2nc(CS(=O)(=O)CC(=O)NCc3ccc(Cl)cc3)c(C)o2)cc1] | 448.93 |

TABLE 1-continued

Oxazole amides (R³ = NH-benzyl)

| ID | Structure | MW |
|---|---|---|
| IIa-170 | | 432.47 |
| IIa-171 | | 432.93 |
| IIa-172 | | 398.48 |
| IIa-173 | | 432.93 |

TABLE 1-continued
Oxazole amides (R³ = NH-benzyl)
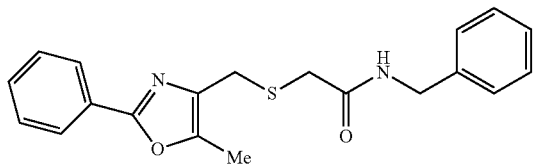
| ID | Structure | MW |
|---|---|---|
| IIa-174 | 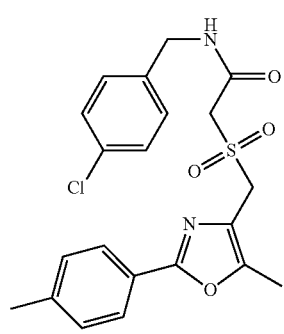 | 432.93 |
| IIa-175 | 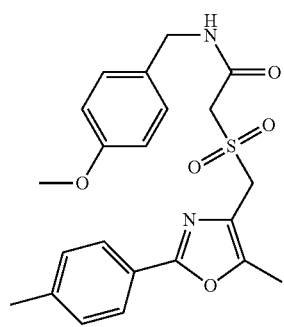 | 428.51 |
| IIa-176 | 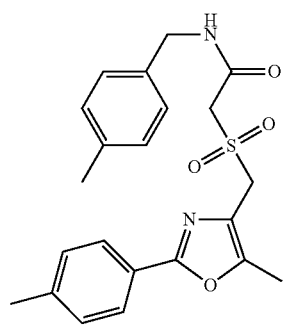 | 412.51 |

TABLE 1-continued
Oxazole amides (R³ = NH-benzyl)
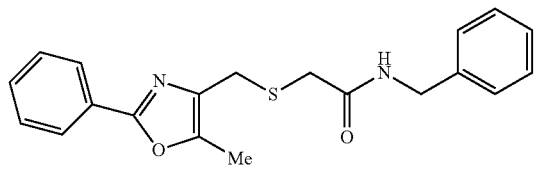
| ID | Structure | MW |
|---|---|---|
| IIa-177 | | 442.49 |
| IIa-178 | | 412.51 |
| IIa-179 | | 438.55 |

TABLE 1-continued
Oxazole amides (R³ = NH-benzyl)
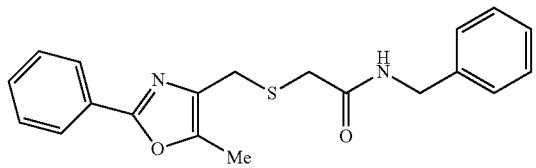
| ID | Structure | MW |
|---|---|---|
| IIa-180 | 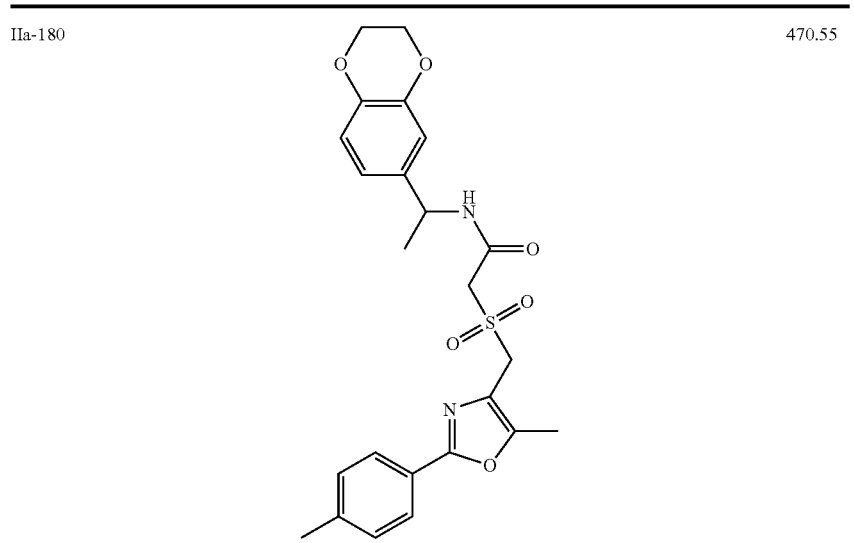 | 470.55 |
| IIa-181 | 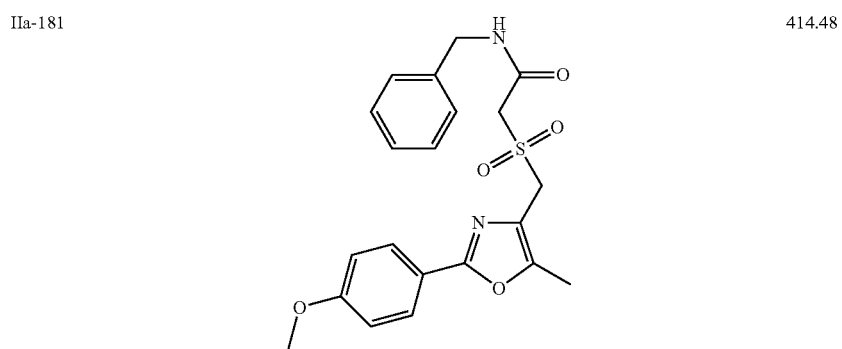 | 414.48 |
| IIa-182 | 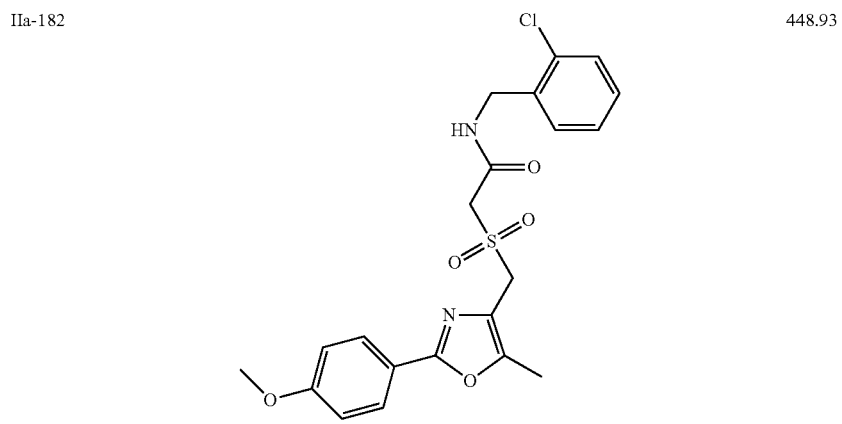 | 448.93 |

TABLE 1-continued
Oxazole amides (R³ = NH-benzyl)
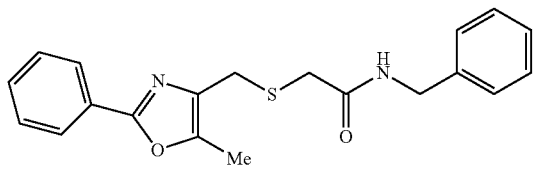
| ID | Structure | MW |
|---|---|---|
| IIa-183 | 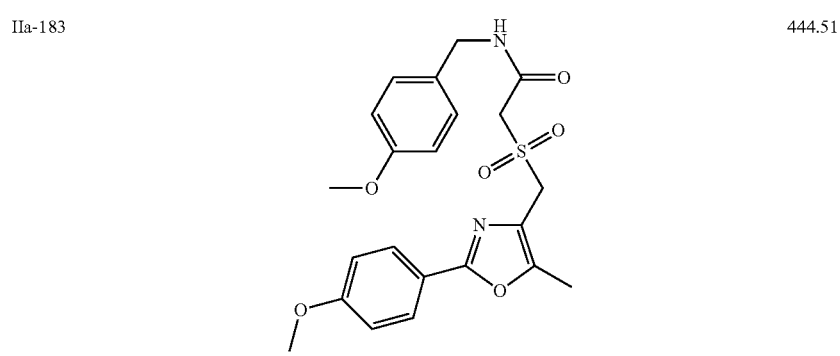 | 444.51 |
| IIa-184 | 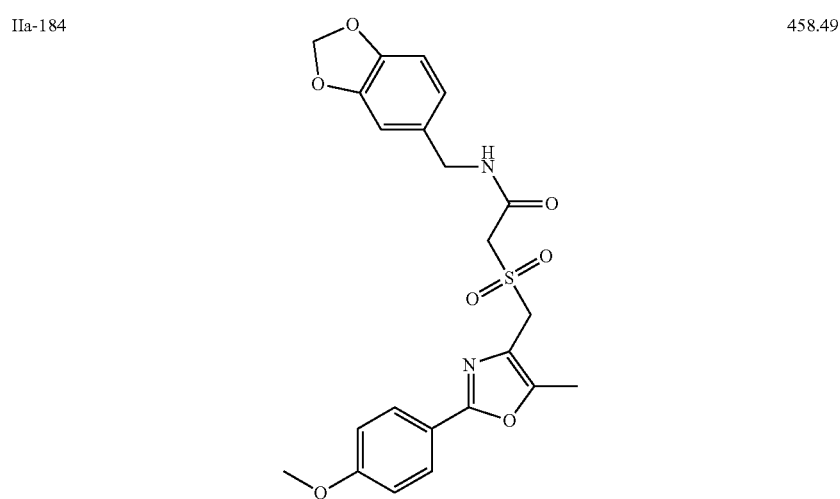 | 458.49 |
| IIa-185 | 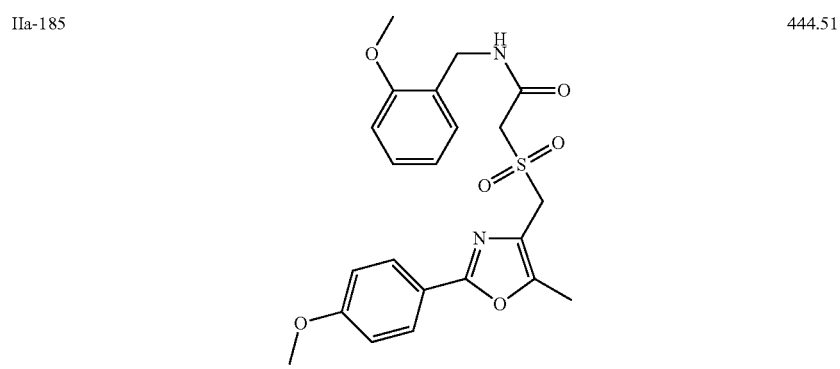 | 444.51 |

TABLE 1-continued
Oxazole amides (R³ = NH-benzyl)
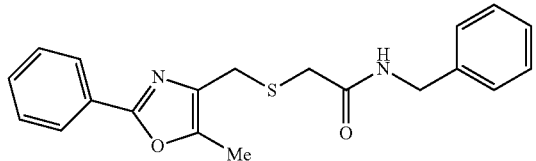
| ID | Structure | MW |
| --- | --- | --- |
| IIa-186 | 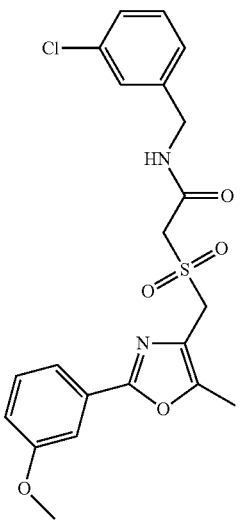 [SMILES: COc1cccc(-c2nc(CS(=O)(=O)CC(=O)NCc3cccc(Cl)c3)c(C)o2)c1] | 448.93 |
| IIa-187 | 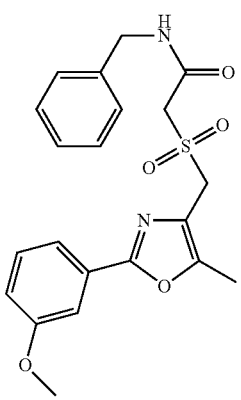 [SMILES: COc1cccc(-c2nc(CS(=O)(=O)CC(=O)NCc3ccccc3)c(C)o2)c1] | 414.48 |

TABLE 1-continued
Oxazole amides (R³ = NH-benzyl)
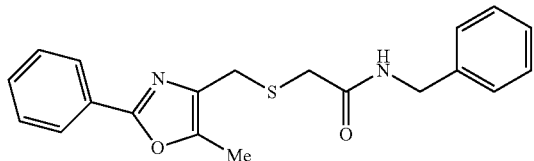
| ID | Structure | MW |
| --- | --- | --- |
| IIa-188 | 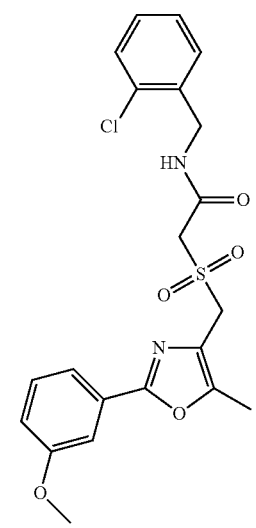 [SMILES: COc1cccc(-c2nc(CS(=O)(=O)CC(=O)NCc3ccccc3Cl)c(C)o2)c1] | 448.93 |
| IIa-189 | 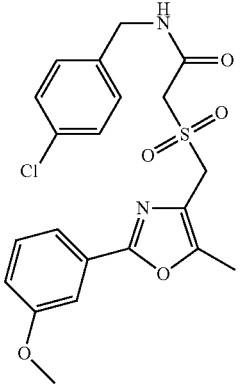 [SMILES: COc1cccc(-c2nc(CS(=O)(=O)CC(=O)NCc3ccc(Cl)cc3)c(C)o2)c1] | 448.93 |
| IIa-190 | 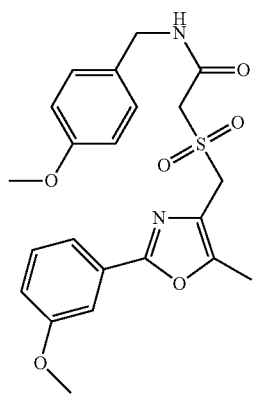 | 444.51 |

TABLE 1-continued

Oxazole amides (R³ = NH-benzyl)

| ID | Structure | MW |
|---|---|---|
| IIa-191 | 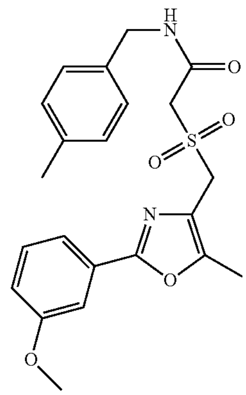 [SMILES: COc1cccc(-c2nc(CS(=O)(=O)CC(=O)NCc3ccc(C)cc3)c(C)o2)c1] | 428.51 |
| IIa-192 | 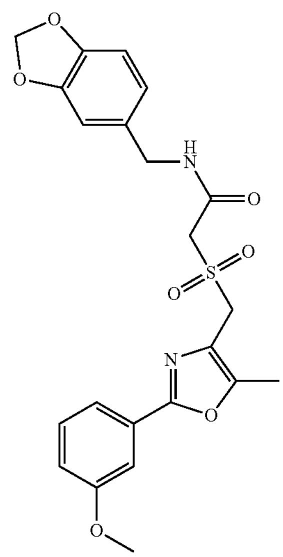 [SMILES: COc1cccc(-c2nc(CS(=O)(=O)CC(=O)NCc3ccc4c(c3)OCO4)c(C)o2)c1] | 458.49 |
| IIa-193 | 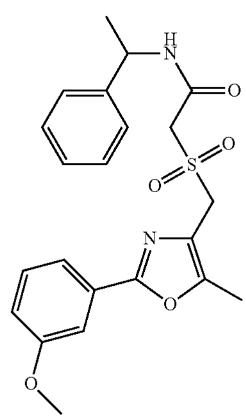 [SMILES: COc1cccc(-c2nc(CS(=O)(=O)CC(=O)NC(C)c3ccccc3)c(C)o2)c1] | 428.51 |

TABLE 1-continued
Oxazole amides (R³ = NH-benzyl)
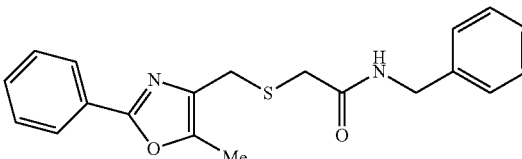
| ID | Structure | MW |
|---|---|---|
| IIa-194 | 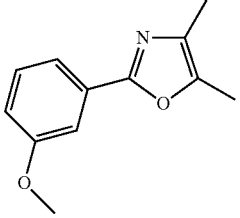 | 444.51 |
| IIa-195 | 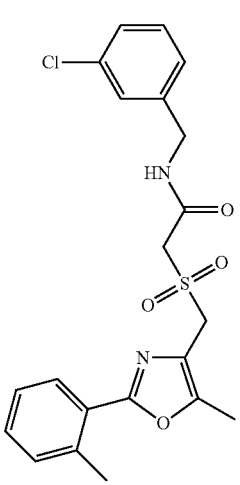 | 454.55 |
| IIa-196 | 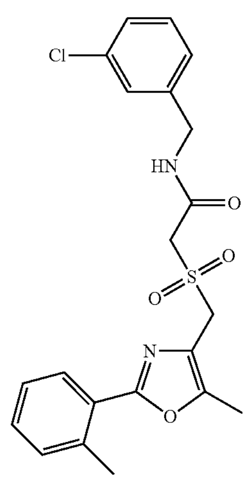 [SMILES: Cc1ccccc1-c1nc(CS(=O)(=O)CC(=O)NCc2cccc(Cl)c2)c(C)o1] | 432.93 |

TABLE 1-continued
Oxazole amides (R³ = NH-benzyl)
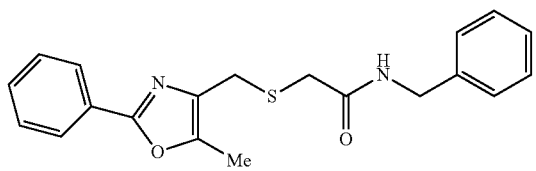
| ID | Structure | MW |
|---|---|---|
| IIa-197 | 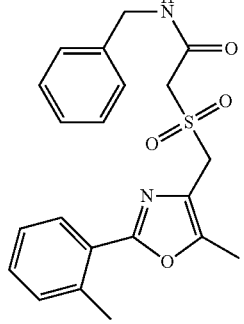 | 398.48 |
| IIa-198 | 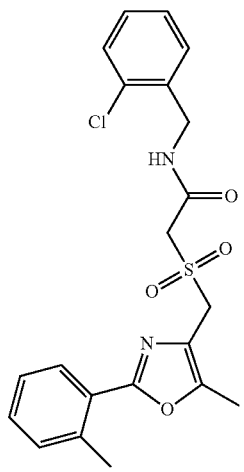 [SMILES: Cc1ccccc1-c1nc(CS(=O)(=O)CC(=O)NCc2ccccc2Cl)c(C)o1] | 432.93 |
| IIa-199 | 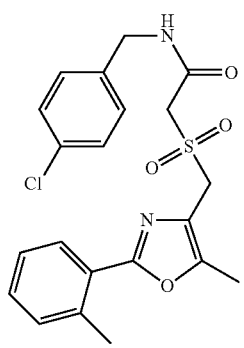 [SMILES: Cc1ccccc1-c1nc(CS(=O)(=O)CC(=O)NCc2ccc(Cl)cc2)c(C)o1] | 432.93 |

TABLE 1-continued
Oxazole amides (R³ = NH-benzyl)
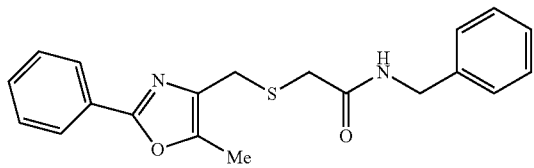
| ID | Structure | MW |
|---|---|---|
| IIa-200 | 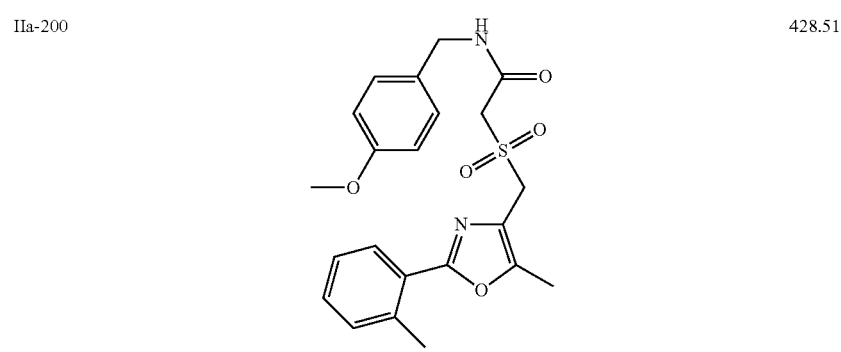 | 428.51 |
| IIa-201 | 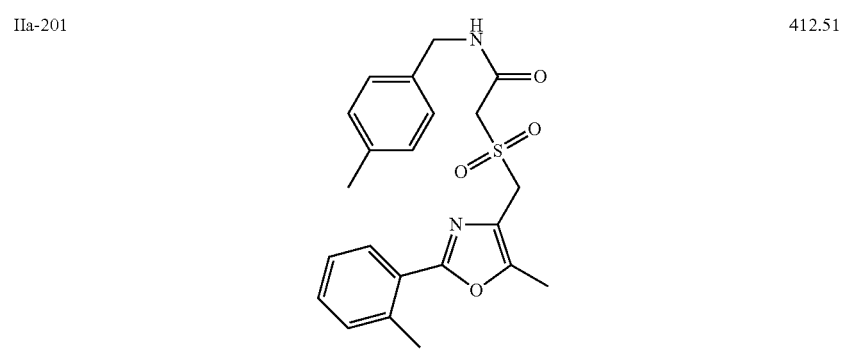 | 412.51 |
| IIa-202 | 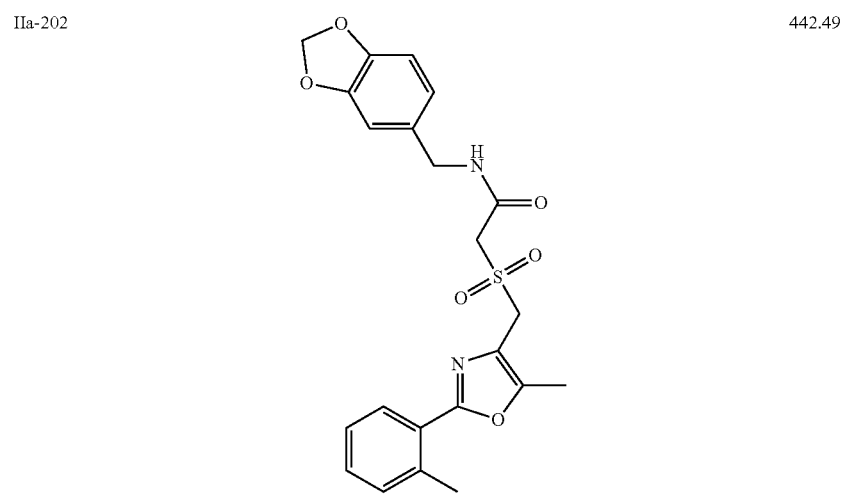 | 442.49 |

TABLE 1-continued
Oxazole amides (R³ = NH-benzyl)
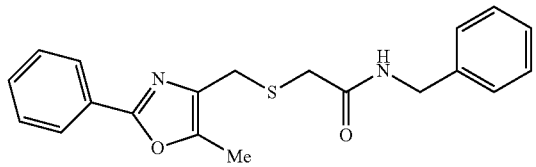
| ID | Structure | MW |
|---|---|---|
| IIa-203 | | 412.51 |
| IIa-204 | | 428.51 |
| IIa-205 | | 416.47 |

TABLE 1-continued

Oxazole amides (R³ = NH-benzyl)

| ID | Structure | MW |
|---|---|---|
| IIa-206 | | 436.89 |
| IIa-207 | | 416.47 |
| IIa-208 | | 418.90 |
| IIa-209 | | 436.89 |

TABLE 1-continued

Oxazole amides (R³ = NH-benzyl)

| ID | Structure | MW |
|---|---|---|
| IIa-210 | 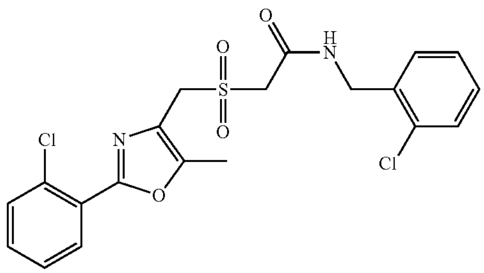 [SMILES: Cc1oc(-c2ccccc2Cl)nc1CS(=O)(=O)CC(=O)NCc1ccccc1Cl] | 453.35 |
| IIa-211 | 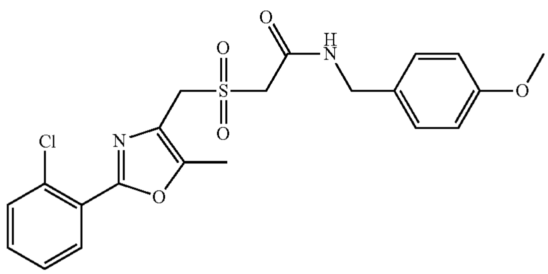 [SMILES: COc1ccc(CNC(=O)CS(=O)(=O)Cc2nc(-c3ccccc3Cl)oc2C)cc1] | 448.93 |
| IIa-212 | 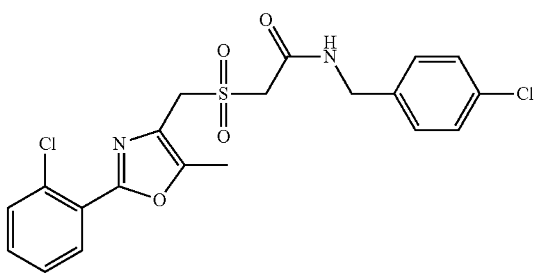 [SMILES: Cc1oc(-c2ccccc2Cl)nc1CS(=O)(=O)CC(=O)NCc1ccc(Cl)cc1] | 453.35 |
| IIa-213 | 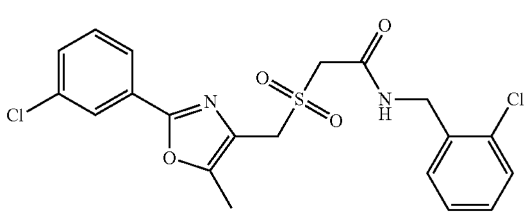 [SMILES: Cc1oc(-c2cccc(Cl)c2)nc1CS(=O)(=O)CC(=O)NCc1ccccc1Cl] | 453.35 |
| IIa-214 | 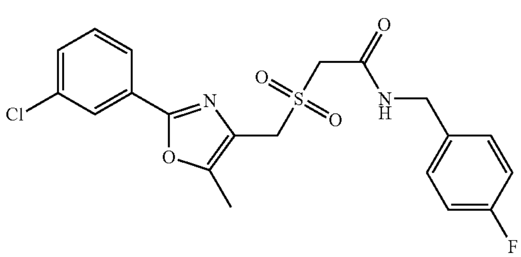 [SMILES: Cc1oc(-c2cccc(Cl)c2)nc1CS(=O)(=O)CC(=O)NCc1ccc(F)cc1] | 436.89 |

TABLE 1-continued

Oxazole amides (R³ = NH-benzyl)

| ID | Structure | MW |
|---|---|---|
| IIa-215 | | 432.93 |
| IIa-216 | | 453.35 |
| IIa-217 | | 448.93 |
| IIa-218 | | 462.91 |
| IIa-219 | | 418.90 |

TABLE 1-continued

Oxazole amides (R³ = NH-benzyl)

| ID | Structure | MW |
|---|---|---|
| IIa-220 | 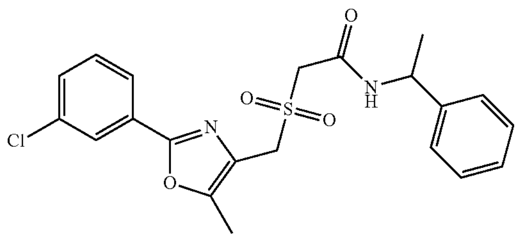 [SMILES: Cc1oc(-c2cccc(Cl)c2)nc1CS(=O)(=O)CC(=O)NC(C)c1ccccc1] | 432.93 |
| IIa-221 | 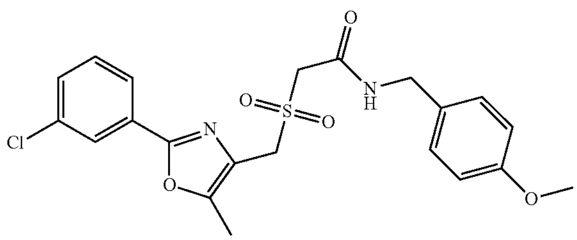 [SMILES: COc1ccc(CNC(=O)CS(=O)(=O)Cc2nc(-c3cccc(Cl)c3)oc2C)cc1] | 448.93 |
| IIa-222 | 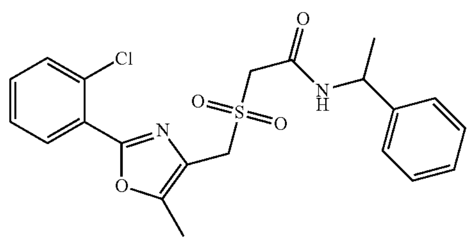 [SMILES: Cc1oc(-c2ccccc2Cl)nc1CS(=O)(=O)CC(=O)NC(C)c1ccccc1] | 432.93 |
| IIa-223 | 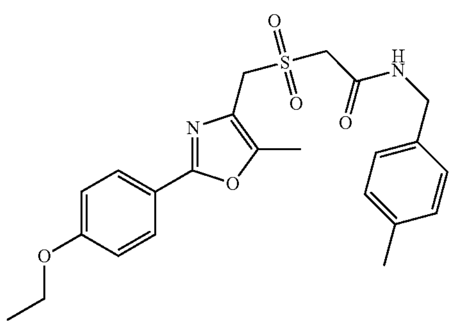 | 442.54 |
| IIa-224 | 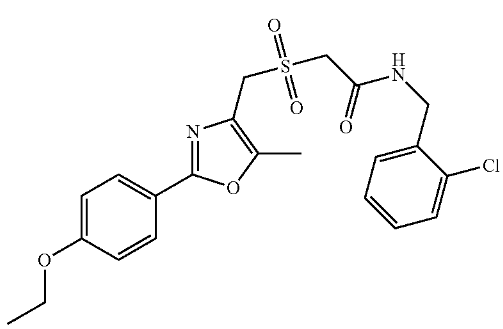 [SMILES: CCOc1ccc(-c2nc(CS(=O)(=O)CC(=O)NCc3ccccc3Cl)c(C)o2)cc1] | 462.96 |

TABLE 1-continued

Oxazole amides (R³ = NH-benzyl)

| ID | Structure | MW |
|---|---|---|
| IIa-225 | | 446.50 |
| IIa-226 | | 458.54 |
| IIa-227 | | 477.38 |
| IIa-228 | | 477.38 |
| IIa-229 | | 412.51 |

TABLE 1-continued

Oxazole amides (R³ = NH-benzyl)

| ID | Structure | MW |
|---|---|---|
| IIa-230 | 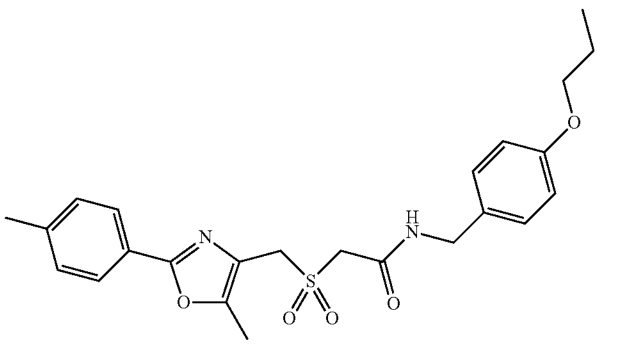 [SMILES: CCCOc1ccc(CNC(=O)CS(=O)(=O)Cc2nc(-c3ccc(C)cc3)oc2C)cc1] | 456.57 |
| IIa-231 | 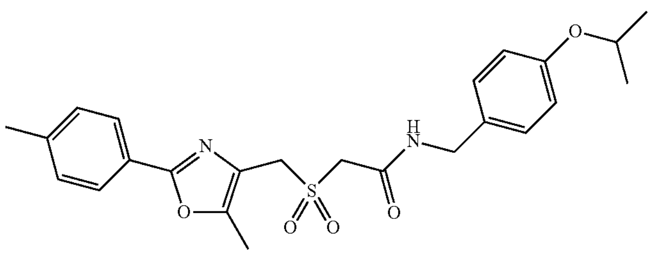 [SMILES: Cc1ccc(-c2nc(CS(=O)(=O)CC(=O)NCc3ccc(OC(C)C)cc3)c(C)o2)cc1] | 456.57 |
| IIa-232 | 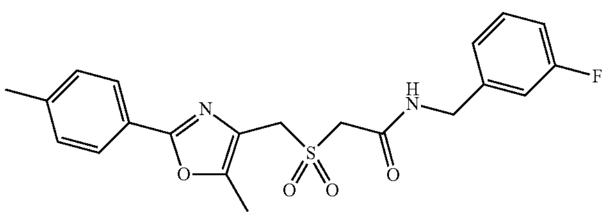 [SMILES: Cc1ccc(-c2nc(CS(=O)(=O)CC(=O)NCc3cccc(F)c3)c(C)o2)cc1] | 416.47 |
| IIa-233 | 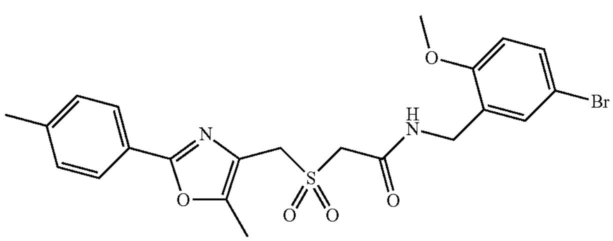 [SMILES: COc1ccc(Br)cc1CNC(=O)CS(=O)(=O)Cc1nc(-c2ccc(C)cc2)oc1C] | 507.41 |
| IIa-234 | 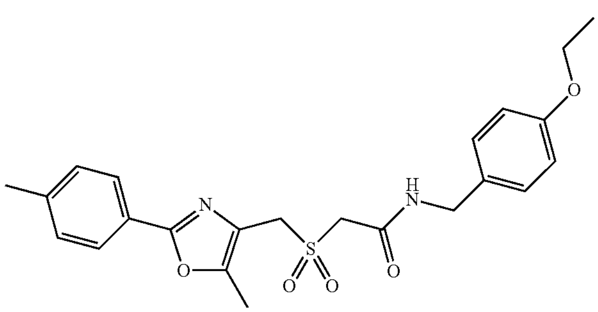 [SMILES: CCOc1ccc(CNC(=O)CS(=O)(=O)Cc2nc(-c3ccc(C)cc3)oc2C)cc1] | 442.54 |

TABLE 1-continued
Oxazole amides (R³ = NH-benzyl)
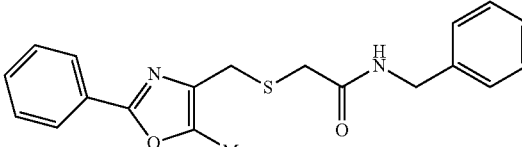
| ID | Structure | MW |
|---|---|---|
| IIa-235 | 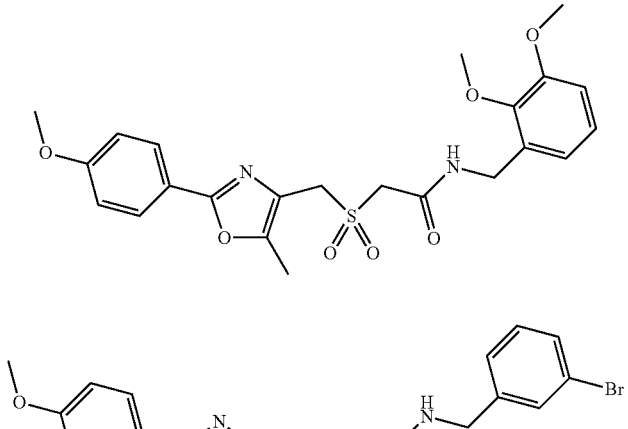 | 474.54 |
| IIa-236 | 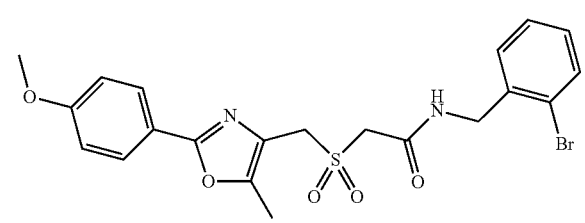 [SMILES: COc1ccc(-c2nc(CS(=O)(=O)CC(=O)NCc3ccccc3Br)c(C)o2)cc1] | 493.38 |
| IIa-237 | 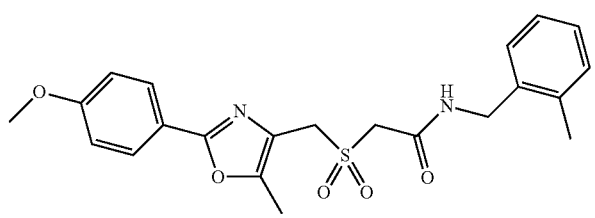 [SMILES: COc1ccc(-c2nc(CS(=O)(=O)CC(=O)NCc3ccccc3C)c(C)o2)cc1] | 493.38 |
| IIa-238 | 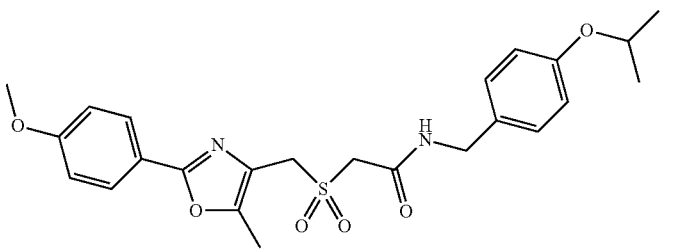 [SMILES: COc1ccc(-c2nc(CS(=O)(=O)CC(=O)NCc3ccc(OC(C)C)cc3)c(C)o2)cc1] | 428.51 |
| IIa-239 | | 472.56 |

TABLE 1-continued

Oxazole amides (R³ = NH-benzyl)

| ID | Structure | MW |
|---|---|---|
| IIa-240 | 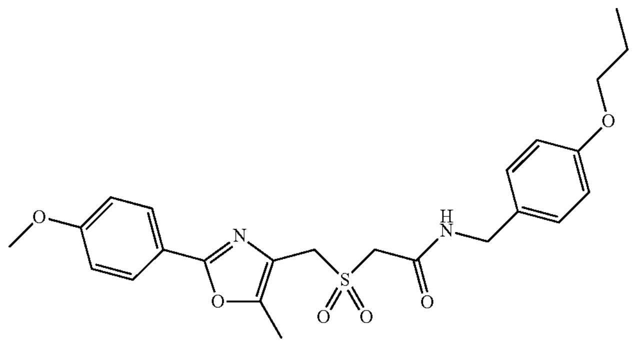 [SMILES: CCCOc1ccc(CNC(=O)CS(=O)(=O)Cc2nc(-c3ccc(OC)cc3)oc2C)cc1] | 472.56 |
| IIa-241 | 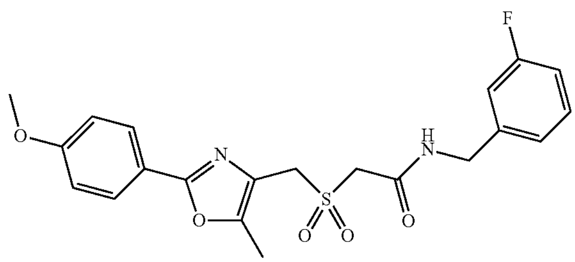 [SMILES: COc1ccc(-c2nc(CS(=O)(=O)CC(=O)NCc3cccc(F)c3)c(C)o2)cc1] | 432.47 |
| IIa-242 | 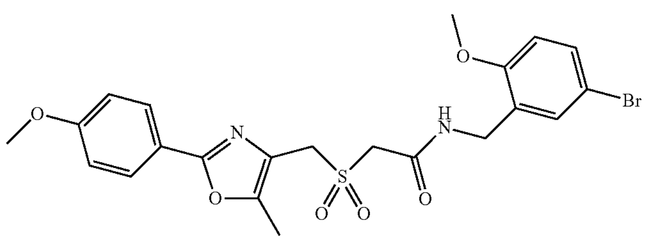 [SMILES: COc1ccc(-c2nc(CS(=O)(=O)CC(=O)NCc3cc(Br)ccc3OC)c(C)o2)cc1] | 523.41 |
| IIa-243 | 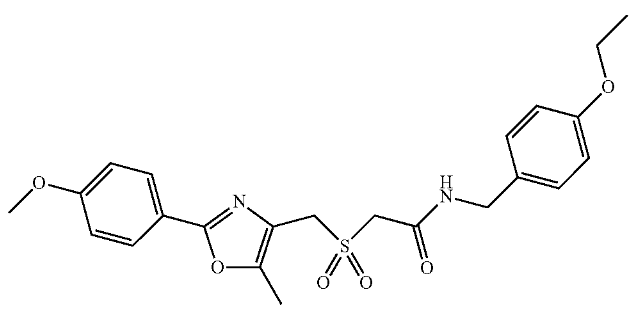 [SMILES: CCOc1ccc(CNC(=O)CS(=O)(=O)Cc2nc(-c3ccc(OC)cc3)oc2C)cc1] | 458.54 |
| IIa-244 | 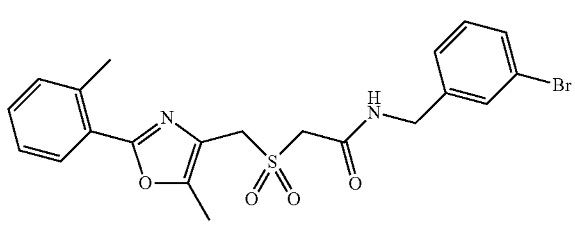 [SMILES: Cc1ccccc1-c1nc(CS(=O)(=O)CC(=O)NCc2cccc(Br)c2)c(C)o1] | 477.38 |

TABLE 1-continued

Oxazole amides (R³ = NH-benzyl)

| ID | Structure | MW |
|---|---|---|
| IIa-245 | | 477.38 |
| IIa-246 | | 442.54 |
| IIa-247 | | 412.51 |
| IIa-248 | | 456.57 |
| IIa-249 | | 456.57 |

TABLE 1-continued

Oxazole amides (R³ = NH-benzyl)

| ID | Structure | MW |
|---|---|---|
| IIa-250 | 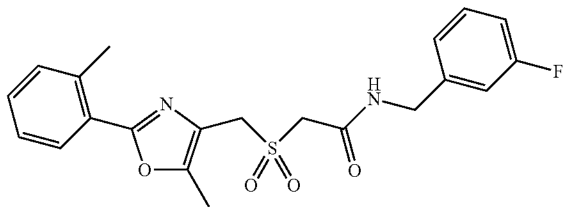 [SMILES: Cc1ccccc1-c1nc(CS(=O)(=O)CC(=O)NCc2cccc(F)c2)c(C)o1] | 416.47 |
| IIa-251 | 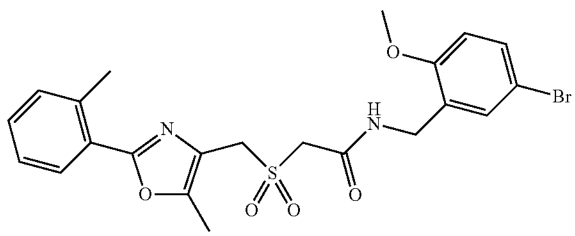 [SMILES: COc1ccc(Br)cc1CNC(=O)CS(=O)(=O)Cc1nc(-c2ccccc2C)oc1C] | 507.41 |
| IIa-252 | 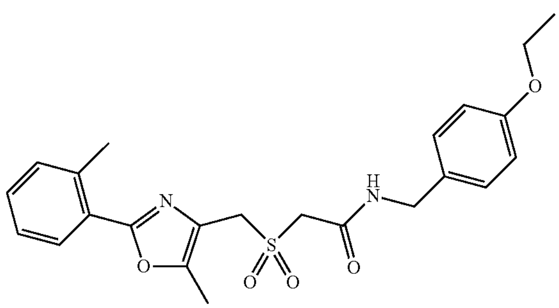 [SMILES: CCOc1ccc(CNC(=O)CS(=O)(=O)Cc2nc(-c3ccccc3C)oc2C)cc1] | 442.54 |
| IIa-253 | 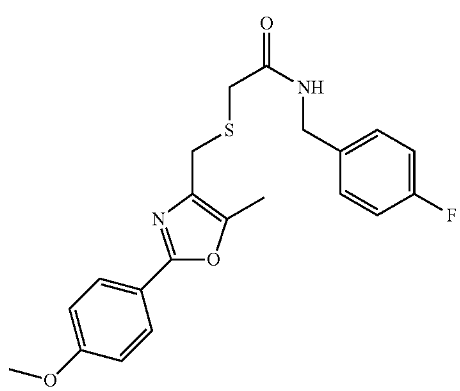 [SMILES: COc1ccc(-c2nc(CSCC(=O)NCc3ccc(F)cc3)c(C)o2)cc1] | 400.48 |

TABLE 1-continued
Oxazole amides (R³ = NH-benzyl)
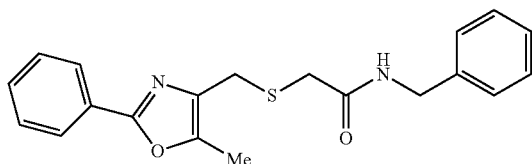
| ID | Structure | MW |
|---|---|---|
| IIa-254 | 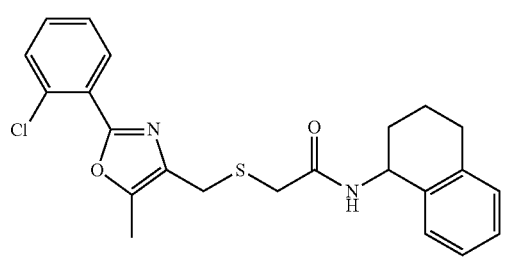 [SMILES: Cc1oc(-c2ccccc2Cl)nc1CSCC(=O)NC1CCCc2ccccc21] | 426.97 |
| IIa-255 | 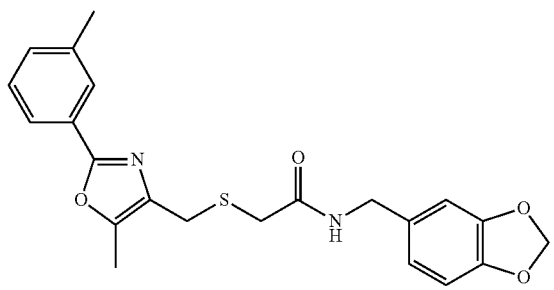 [SMILES: Cc1cccc(-c2nc(CSCC(=O)NCc3ccc4c(c3)OCO4)c(C)o2)c1] | 410.50 |
| IIa-256 | 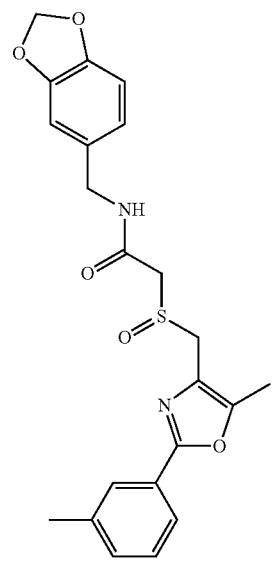 [SMILES: Cc1cccc(-c2nc(CS(=O)CC(=O)NCc3ccc4c(c3)OCO4)c(C)o2)c1] | 426.50 |

TABLE 1-continued
Oxazole amides (R³ = NH-benzyl)
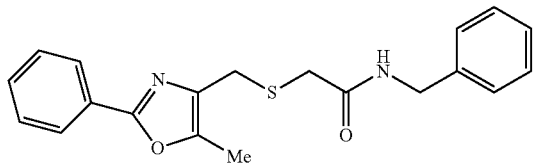
| ID | Structure | MW |
|---|---|---|
| IIa-257 | 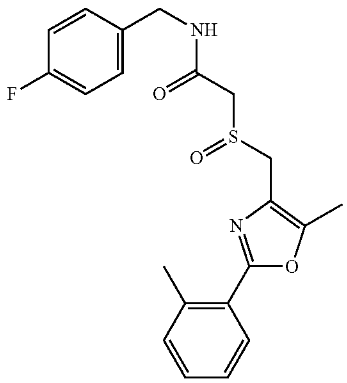 [SMILES: Cc1ccccc1-c1nc(CS(=O)CC(=O)NCc2ccc(F)cc2)c(C)o1] | 400.48 |
| IIa-258 | 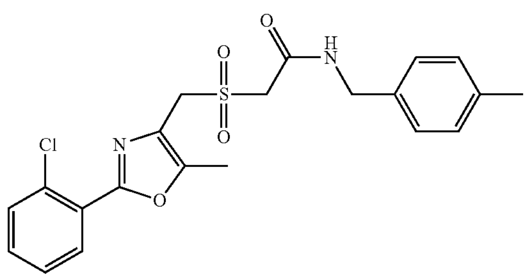 [SMILES: Cc1ccc(CNC(=O)CS(=O)(=O)Cc2nc(-c3ccccc3Cl)oc2C)cc1] | 432.93 |
TABLE 2
Oxazole amides (R³ = NH-phenethyl)
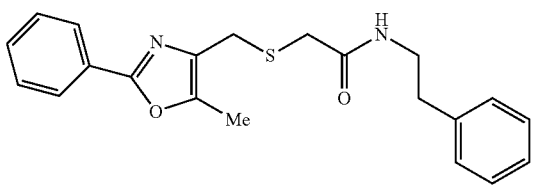
| ID | Structure | MW |
|---|---|---|
| IIa-301 | 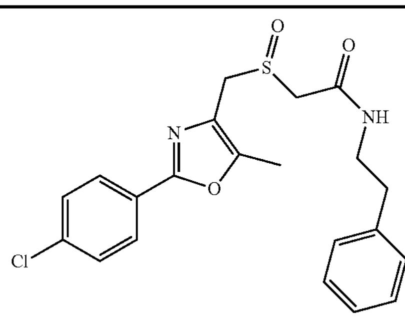 | 416.93 |

TABLE 2-continued

Oxazole amides (R³ = NH-phenethyl)

| ID | Structure | MW |
|---|---|---|
| IIa-302 | | 444.98 |
| IIa-303 | | 424.57 |
| IIa-304 | | 410.54 |
| IIa-305 | | 470.59 |

TABLE 2-continued
Oxazole amides (R³ = NH-phenethyl)
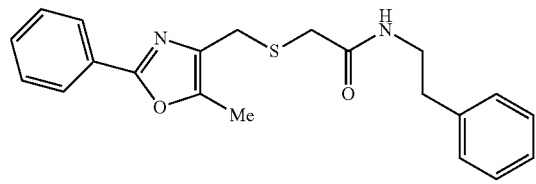 [SMILES: Cc1oc(-c2ccccc2)nc1CSCC(=O)NCCc1ccccc1]
| ID | Structure | MW |
| --- | --- | --- |
| IIa-306 | 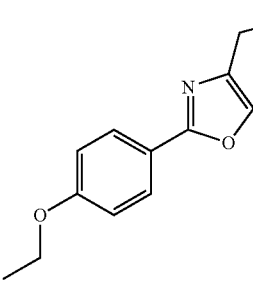 | 410.54 |
| IIa-307 | 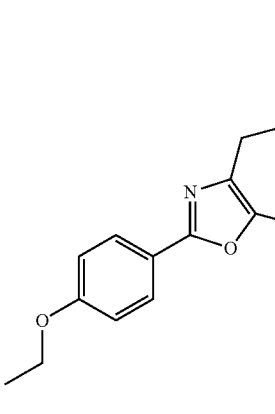 | 424.57 |
| IIa-308 | 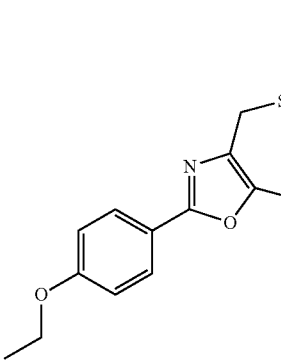 | 444.98 |

TABLE 2-continued
Oxazole amides (R³ = NH-phenethyl)
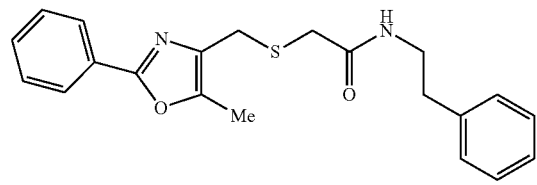
| ID | Structure | MW |
|---|---|---|
| IIa-309 | | 498.65 |
| IIa-310 | | 456.57 |
| IIa-311 | | 442.60 |

TABLE 2-continued

Oxazole amides (R³ = NH-phenethyl)

| ID | Structure | MW |
|---|---|---|
| IIa-312 | 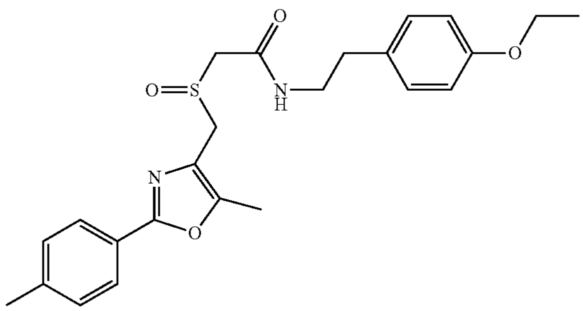 [SMILES: CCOc1ccc(CCNC(=O)CS(=O)Cc2nc(-c3ccc(C)cc3)oc2C)cc1] | 440.57 |
| IIa-313 | 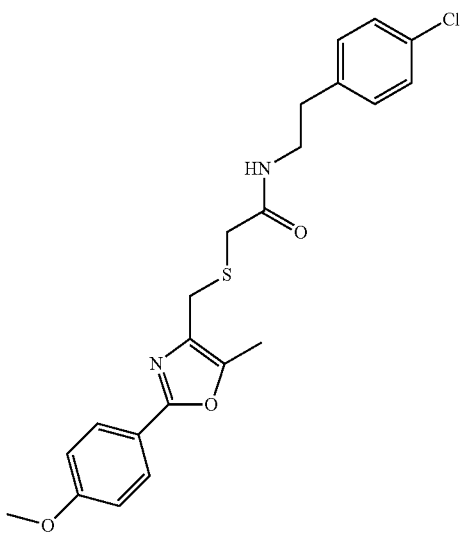 [SMILES: COc1ccc(-c2nc(CSCC(=O)NCCc3ccc(Cl)cc3)c(C)o2)cc1] | 430.96 |
| IIa-314 | 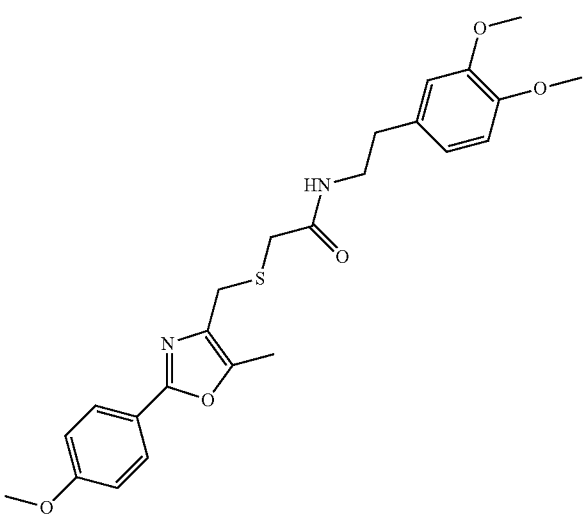 | 456.57 |

TABLE 2-continued
Oxazole amides (R³ = NH-phenethyl)
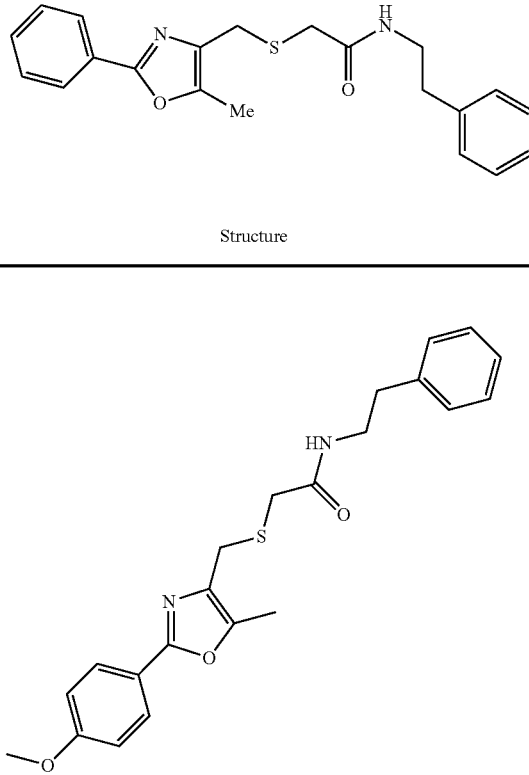
| ID | Structure | MW |
|---|---|---|
| IIa-315 | 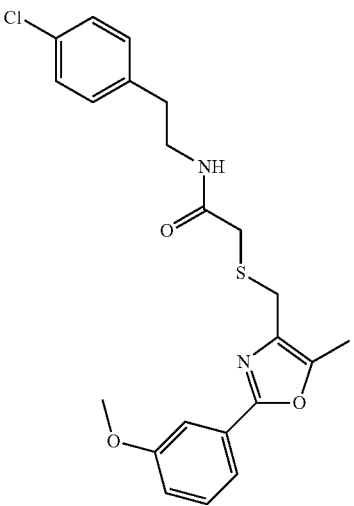 [SMILES: COc1cccc(-c2nc(CSCC(=O)NCCc3ccc(Cl)cc3)c(C)o2)c1] | 396.51 |
| IIa-316 | | 430.96 |

TABLE 2-continued
Oxazole amides (R³ = NH-phenethyl)
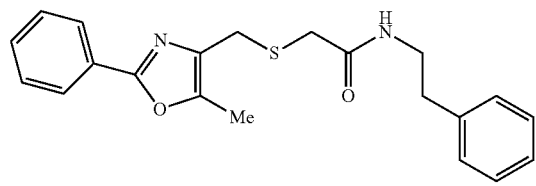
| ID | Structure | MW |
| --- | --- | --- |
| IIa-317 | 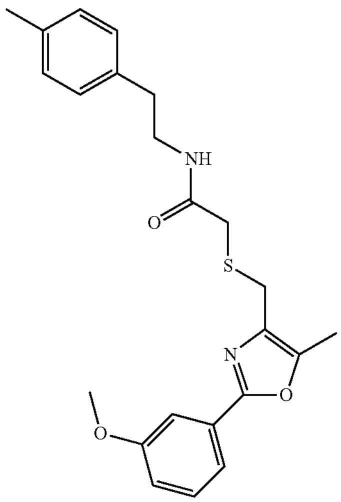 | 410.54 |
| IIa-318 | 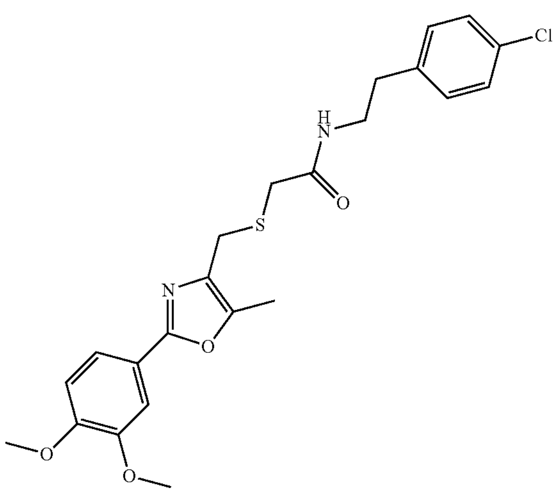 [SMILES: COc1ccc(-c2nc(CSCC(=O)NCCc3ccc(Cl)cc3)c(C)o2)cc1OC] | 460.98 |

TABLE 2-continued
Oxazole amides (R³ = NH-phenethyl)
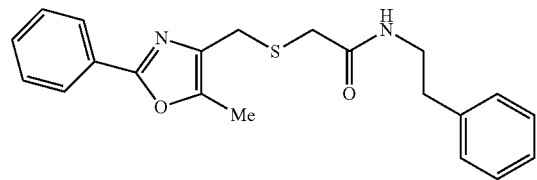
| ID | Structure | MW |
|---|---|---|
| IIa-319 | 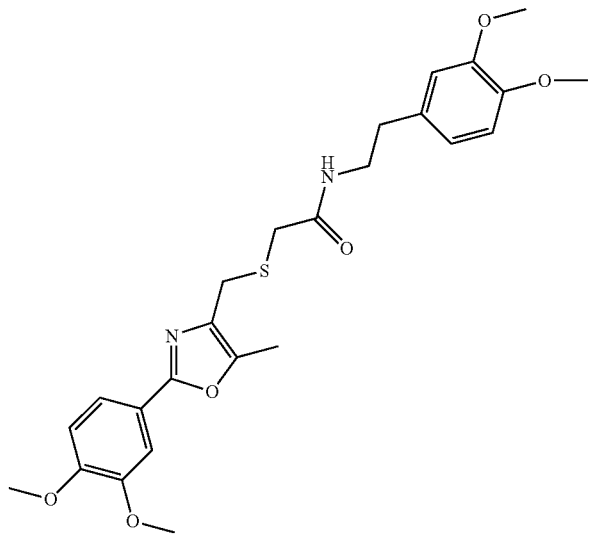 | 486.59 |
| IIa-320 | 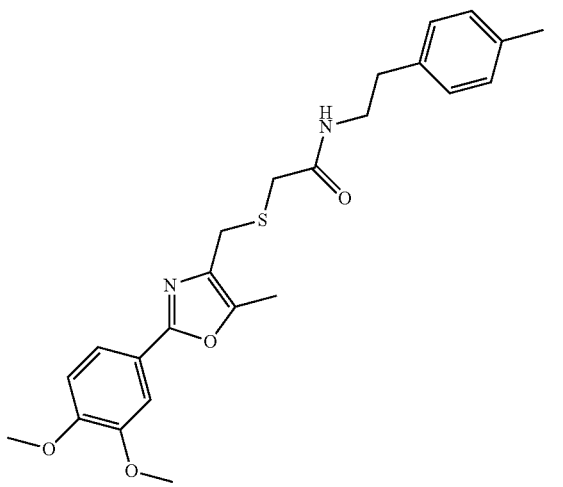 | 440.57 |

TABLE 2-continued
Oxazole amides (R³ = NH-phenethyl)
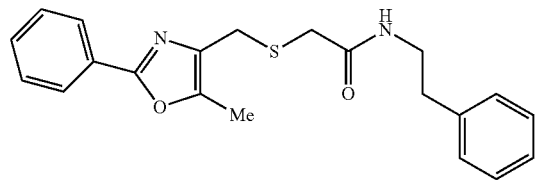
| ID | Structure | MW |
|---|---|---|
| IIa-321 | 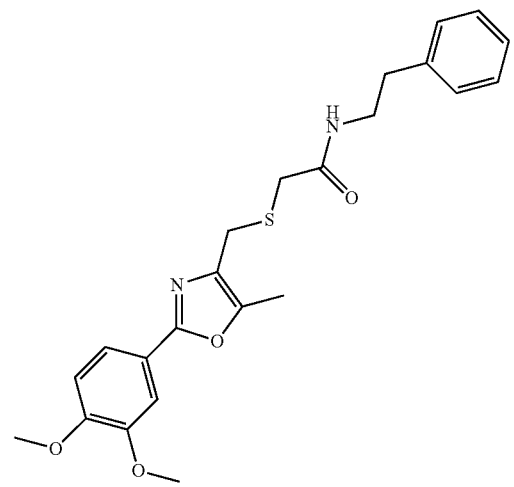 [SMILES: COc1ccc(-c2nc(CSCC(=O)NCCc3ccccc3)c(C)o2)cc1OC] | 426.54 |
| IIa-322 | 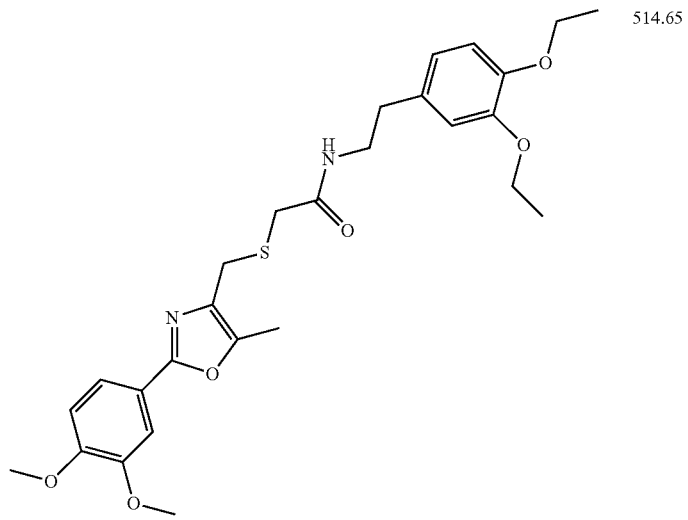 | 514.65 |

TABLE 2-continued
Oxazole amides (R³ = NH-phenethyl)
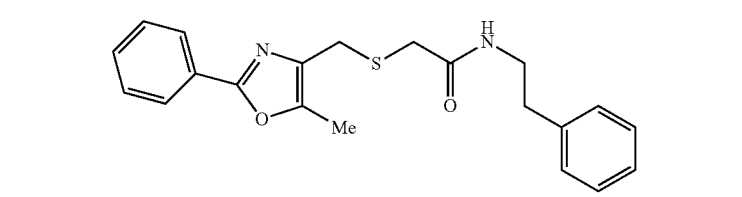
| ID | Structure | MW |
|---|---|---|
| IIa-323 | 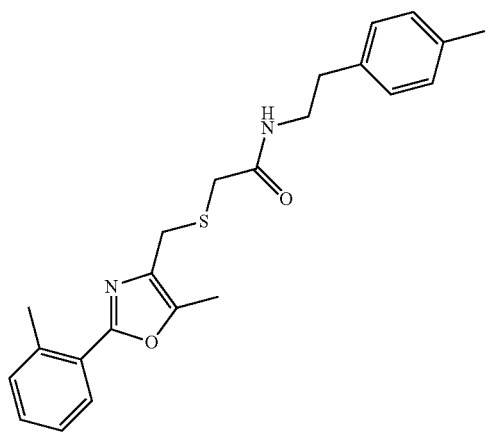 [SMILES: Cc1ccc(CCNC(=O)CSCc2nc(-c3ccccc3C)oc2C)cc1] | 394.54 |
| IIa-324 | 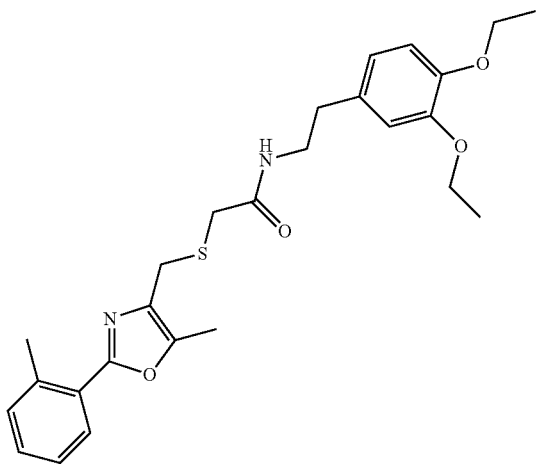 [SMILES: CCOc1ccc(CCNC(=O)CSCc2nc(-c3ccccc3C)oc2C)cc1OCC] | 468.62 |
| IIa-325 | 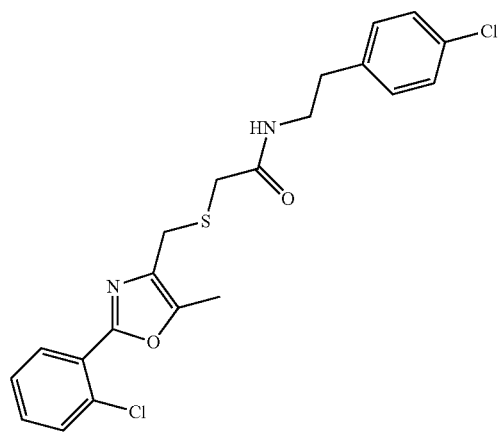 [SMILES: Cc1oc(-c2ccccc2Cl)nc1CSCC(=O)NCCc1ccc(Cl)cc1] | 435.38 |

TABLE 2-continued
Oxazole amides (R³ = NH-phenethyl)
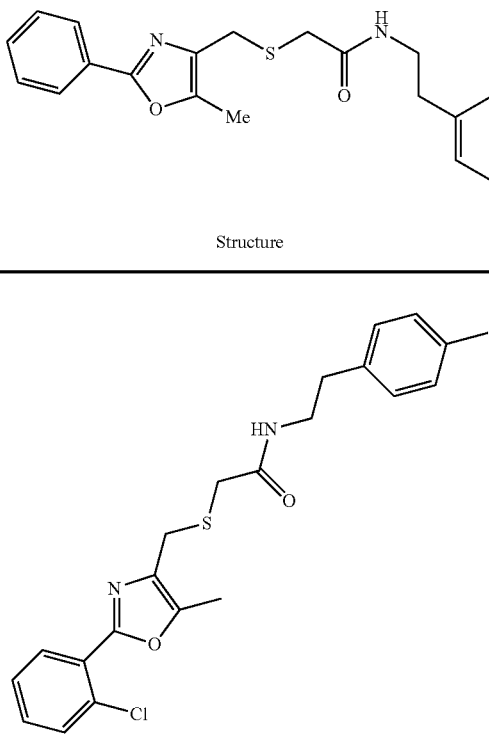
| ID | Structure | MW |
|---|---|---|
| IIa-326 | 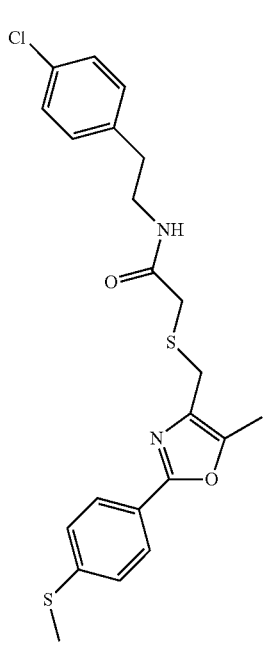 [SMILES: CSc1ccc(-c2nc(CSCC(=O)NCCc3ccc(Cl)cc3)c(C)o2)cc1] | 414.96 |
| IIa-327 | | 447.02 |

TABLE 2-continued
Oxazole amides (R³ = NH-phenethyl)
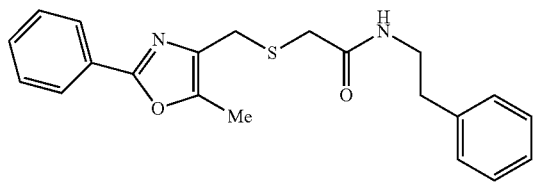
| ID | Structure | MW |
|---|---|---|
| IIa-328 | 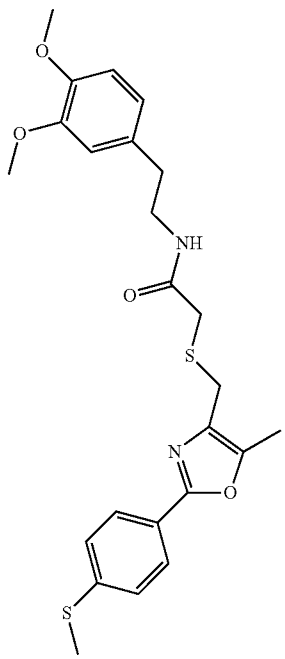 | 472.63 |
| IIa-329 | 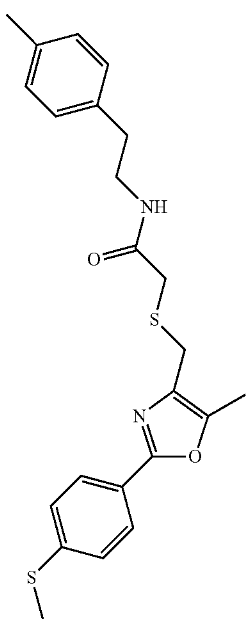 | 426.60 |

TABLE 2-continued
Oxazole amides (R³ = NH-phenethyl)
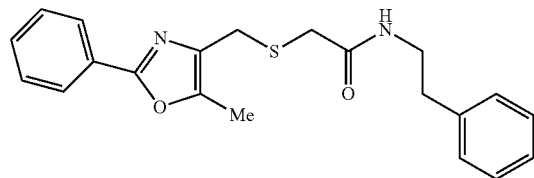
| ID | Structure | MW |
|---|---|---|
| IIa-330 | 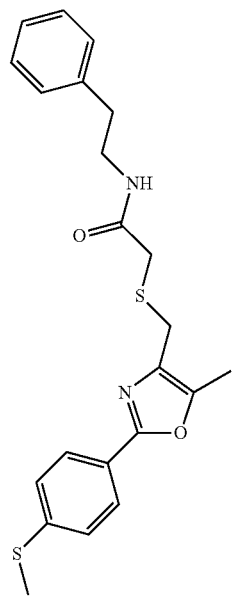 [SMILES: CSc1ccc(-c2nc(CSCC(=O)NCCc3ccccc3)c(C)o2)cc1] | 412.58 |
| IIa-331 | 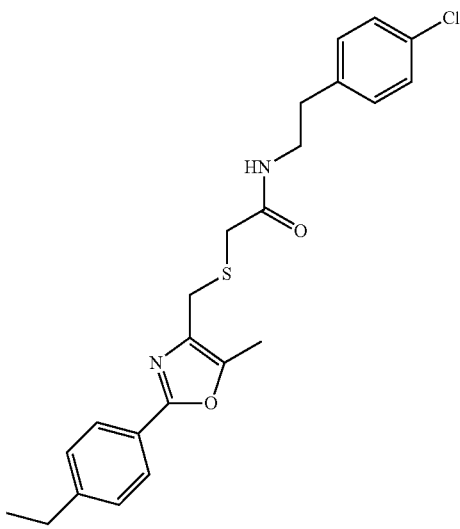 [SMILES: CCc1ccc(-c2nc(CSCC(=O)NCCc3ccc(Cl)cc3)c(C)o2)cc1] | 428.98 |

TABLE 2-continued
Oxazole amides (R³ = NH-phenethyl)
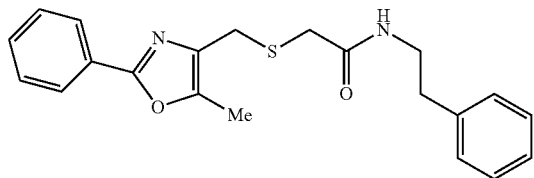
| ID | Structure | MW |
|---|---|---|
| IIa-332 | 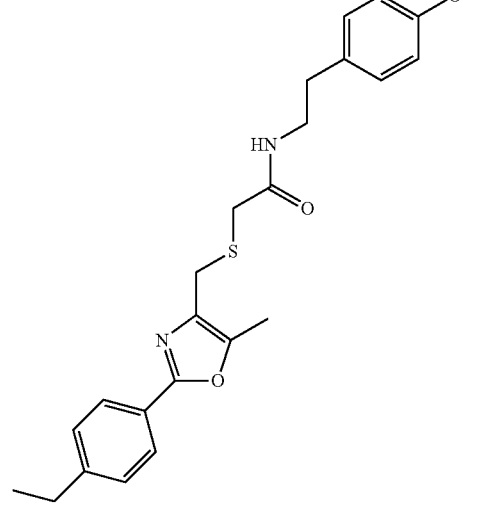 | 454.59 |
| IIa-333 | 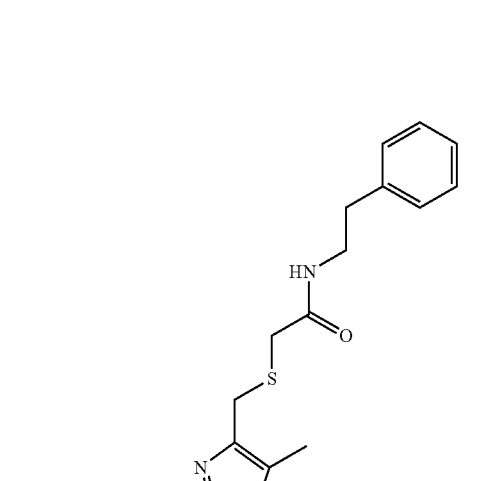 | 394.54 |

TABLE 2-continued
Oxazole amides (R³ = NH-phenethyl)
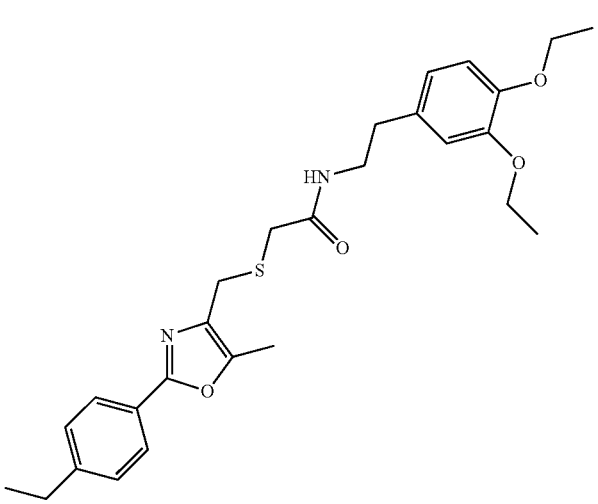 [SMILES: CCOc1ccc(CCNC(=O)CSCc2nc(-c3ccc(CC)cc3)oc2C)cc1OCC]
| ID | Structure | MW |
|---|---|---|
| IIa-334 | 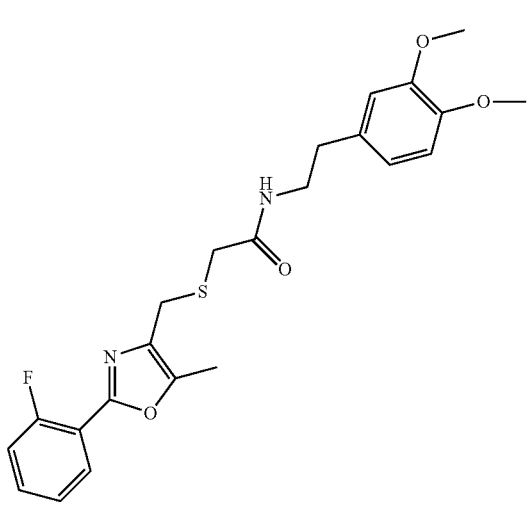 [SMILES: COc1ccc(CCNC(=O)CSCc2nc(-c3ccccc3F)oc2C)cc1OC] | 482.65 |
| IIa-335 | | 444.53 |

TABLE 2-continued
Oxazole amides (R³ = NH-phenethyl)
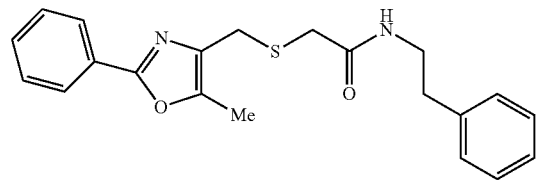
| ID | Structure | MW |
|---|---|---|
| IIa-336 | 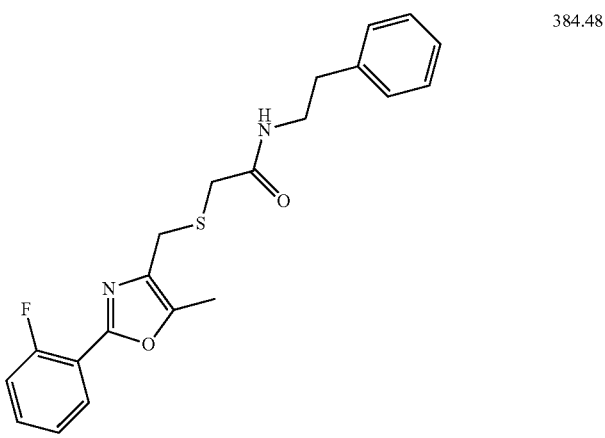 | 384.48 |
| IIa-337 | 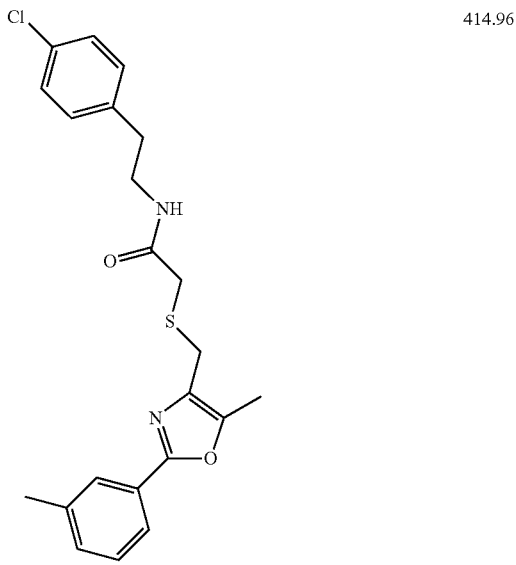 | 414.96 |

TABLE 2-continued
Oxazole amides (R³ = NH-phenethyl)
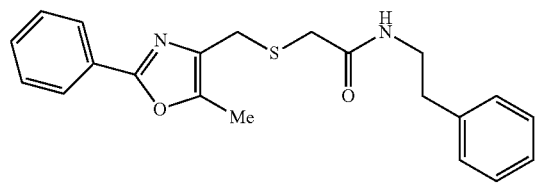
| ID | Structure | MW |
|---|---|---|
| IIa-338 | | 440.57 |
| IIa-339 | | 380.51 |

TABLE 2-continued
Oxazole amides (R³ = NH-phenethyl)
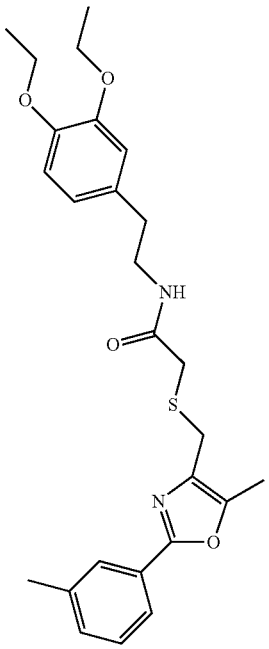 [SMILES: CCOc1ccc(CCNC(=O)CSCc2nc(-c3cccc(C)c3)oc2C)cc1OCC]
| ID | Structure | MW |
|---|---|---|
| IIa-340 | 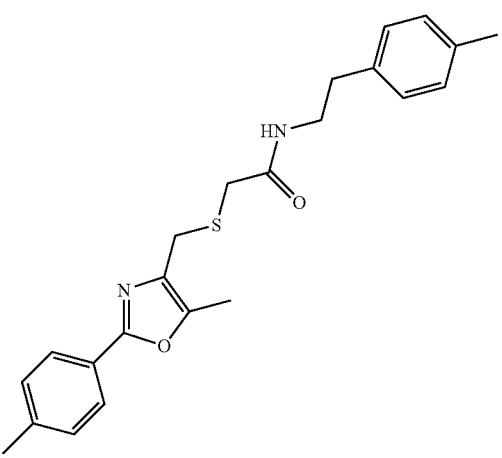 | 468.62 |
| IIa-341 | | 394.54 |

TABLE 2-continued
Oxazole amides (R³ = NH-phenethyl)
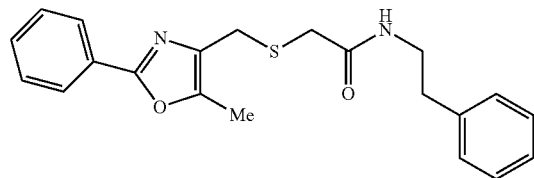
| ID | Structure | MW |
|---|---|---|
| IIa-342 | 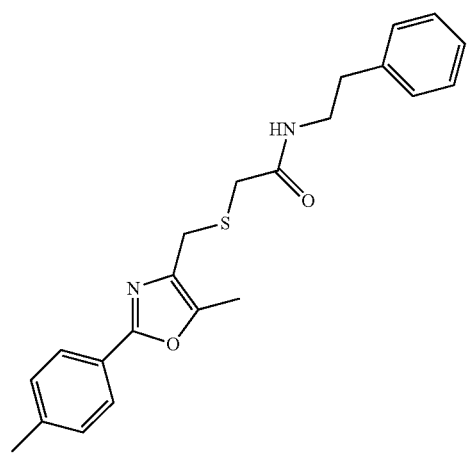 [SMILES: Cc1ccc(-c2nc(CSCC(=O)NCCc3ccccc3)c(C)o2)cc1] | 380.51 |
| IIa-343 | 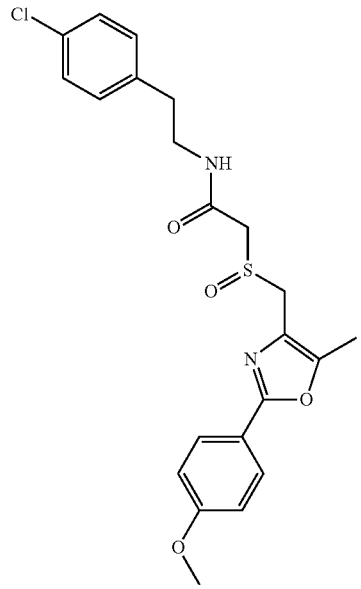 [SMILES: COc1ccc(-c2nc(CS(=O)CC(=O)NCCc3ccc(Cl)cc3)c(C)o2)cc1] | 446.96 |

TABLE 2-continued
Oxazole amides (R³ = NH-phenethyl)
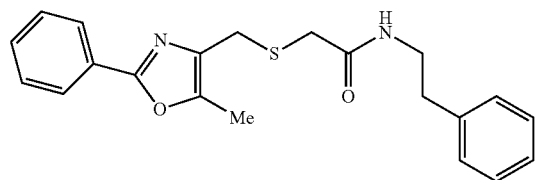
| ID | Structure | MW |
|---|---|---|
| IIa-344 | | 472.56 |
| IIa-345 | | 412.51 |

TABLE 2-continued

Oxazole amides (R³ = NH-phenethyl)

| ID | Structure | MW |
|---|---|---|
| IIa-346 | | 500.62 |
| IIa-347 | | 434.92 |

TABLE 2-continued
Oxazole amides ($R^3$ = NH-phenethyl)
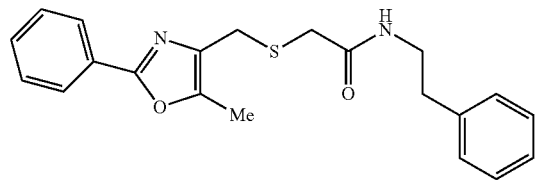
| ID | Structure | MW |
|---|---|---|
| IIa-348 | | 460.53 |
| IIa-349 | | 414.50 |

TABLE 2-continued
Oxazole amides (R³ = NH-phenethyl)
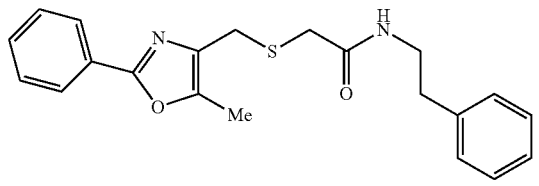
| ID | Structure | MW |
|---|---|---|
| IIa-350 | | 488.58 |
| IIa-351 | | 430.96 |

TABLE 2-continued
Oxazole amides (R³ = NH-phenethyl)
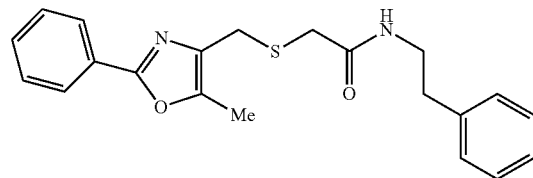
| ID | Structure | MW |
|---|---|---|
| IIa-352 | 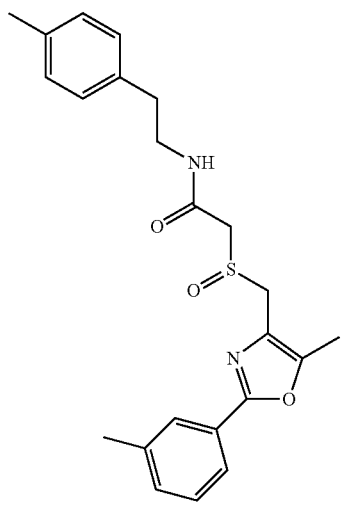 | 410.54 |
| IIa-353 | 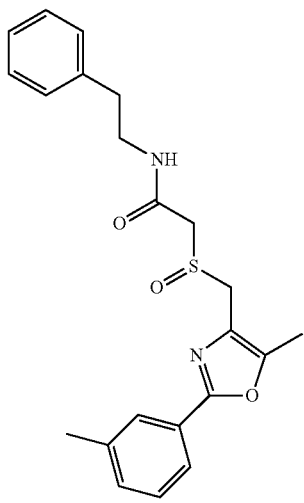 [SMILES: Cc1cccc(-c2nc(CS(=O)CC(=O)NCCc3ccccc3)c(C)o2)c1] | 396.51 |

TABLE 2-continued
Oxazole amides (R³ = NH-phenethyl)
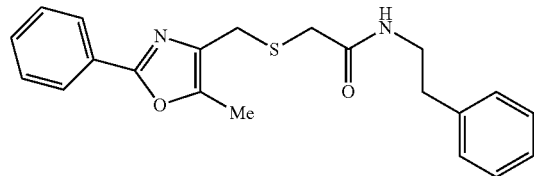
| ID | Structure | MW |
|---|---|---|
| IIa-354 | | 484.62 |
| IIa-355 | | 430.96 |

TABLE 2-continued
Oxazole amides (R³ = NH-phenethyl)

| ID | Structure | MW |
|---|---|---|
| IIa-356 | 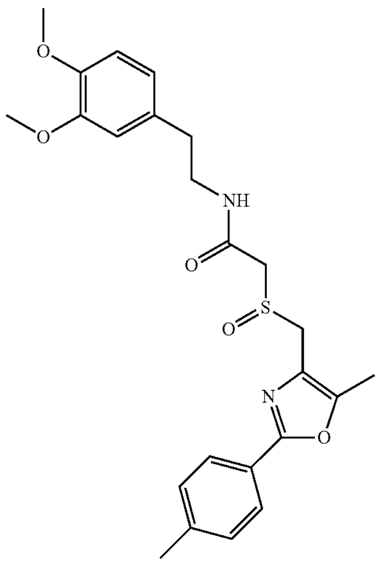 | 456.57 |
| IIa-357 | 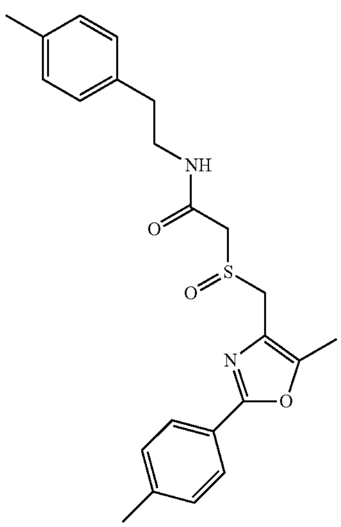 | 410.54 |

TABLE 2-continued
Oxazole amides (R³ = NH-phenethyl)
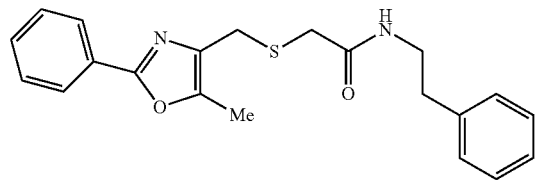
| ID | Structure | MW |
|---|---|---|
| IIa-358 | 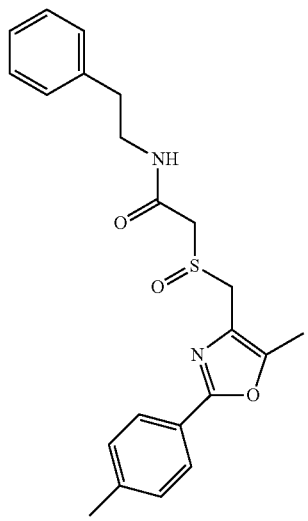 [SMILES: Cc1ccc(-c2nc(CS(=O)CC(=O)NCCc3ccccc3)c(C)o2)cc1] | 396.51 |
| IIa-359 | 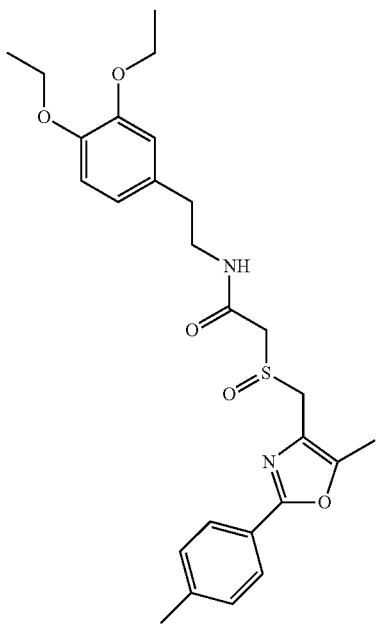 [SMILES: CCOc1ccc(CCNC(=O)CS(=O)Cc2nc(-c3ccc(C)cc3)oc2C)cc1OCC] | 484.62 |

TABLE 2-continued
Oxazole amides (R³ = NH-phenethyl)
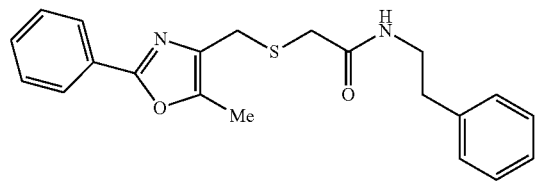
| ID | Structure | MW |
|---|---|---|
| IIa-360 | 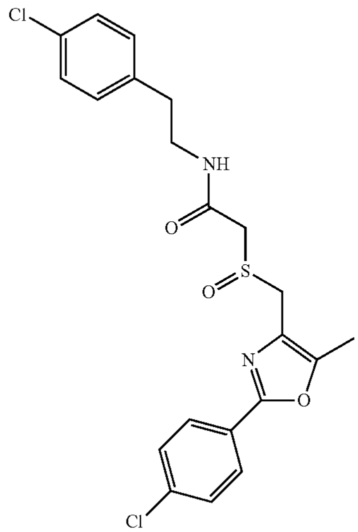 [SMILES: Cc1oc(-c2ccc(Cl)cc2)nc1CS(=O)CC(=O)NCCc1ccc(Cl)cc1] | 451.38 |
| IIa-361 | 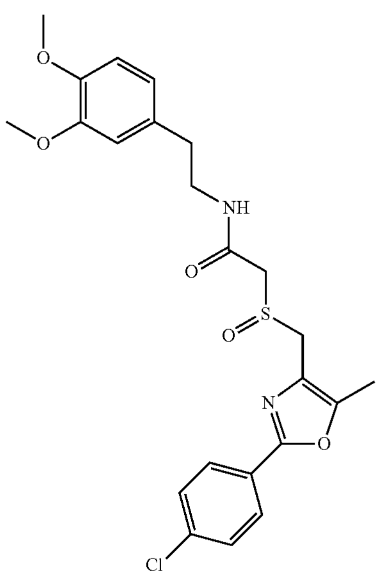 | 476.98 |

TABLE 2-continued
Oxazole amides (R³ = NH-phenethyl)
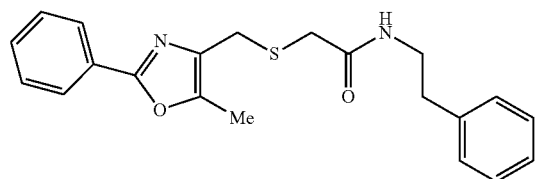
| ID | Structure | MW |
|---|---|---|
| IIa-362 | 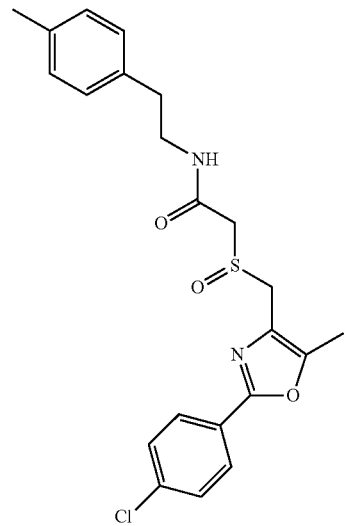 | 430.96 |
| IIa-363 | 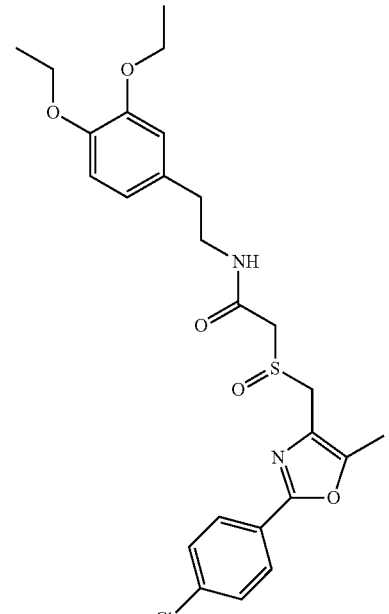 | 505.04 |

TABLE 2-continued
Oxazole amides (R³ = NH-phenethyl)
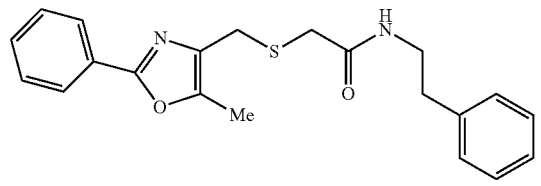
| ID | Structure | MW |
|---|---|---|
| IIa-364 | | 430.96 |
| IIa-365 | | 410.54 |

TABLE 2-continued
Oxazole amides (R³ = NH-phenethyl)
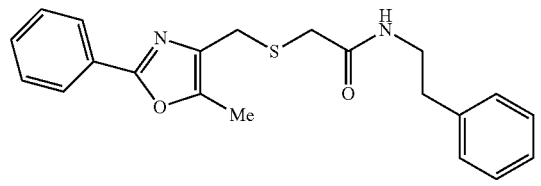
| ID | Structure | MW |
| --- | --- | --- |
| IIa-366 | | 396.51 |
| IIa-367 | | 484.62 |

TABLE 2-continued
Oxazole amides (R³ = NH-phenethyl)
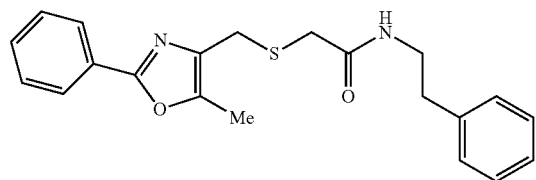
| ID | Structure | MW |
|---|---|---|
| IIa-368 | 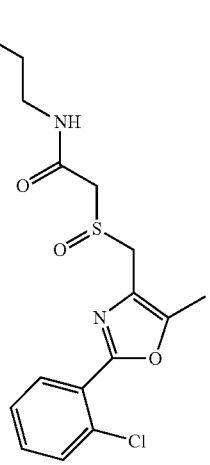 | 451.38 |
| IIa-369 | 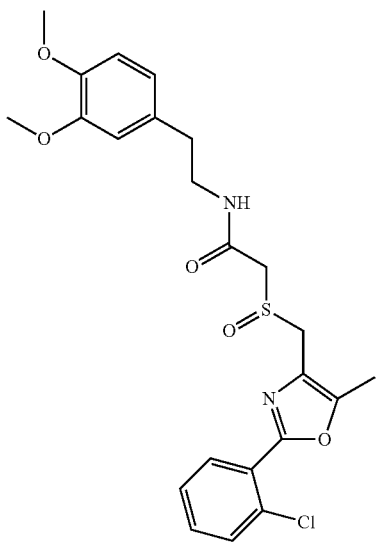 | 476.98 |

TABLE 2-continued
Oxazole amides (R³ = NH-phenethyl)
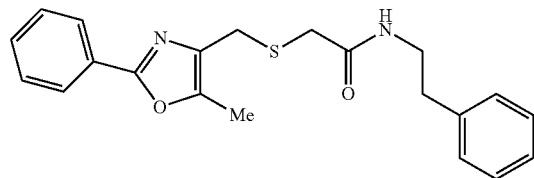
| ID | Structure | MW |
|---|---|---|
| IIa-370 | 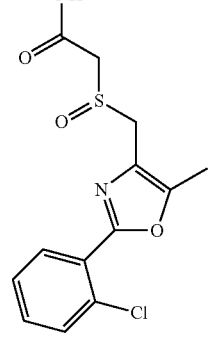 | 430.96 |
| IIa-371 | 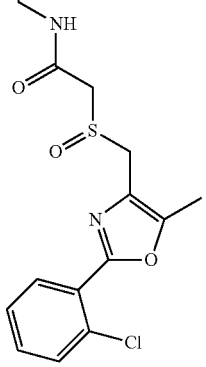 | 416.93 |

TABLE 2-continued
Oxazole amides (R³ = NH-phenethyl)
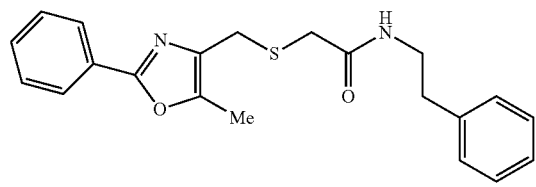
| ID | Structure | MW |
|---|---|---|
| IIa-372 | 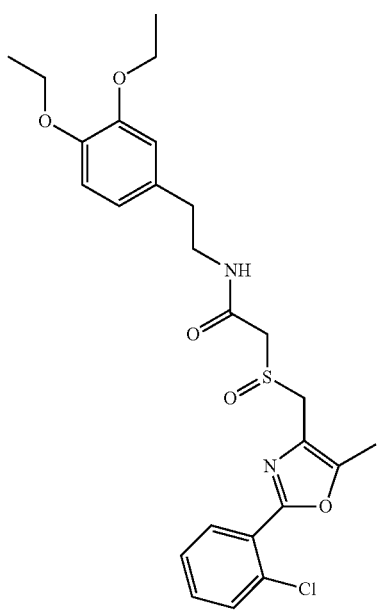 [SMILES: CCOc1ccc(CCNC(=O)CS(=O)Cc2nc(-c3ccccc3Cl)oc2C)cc1OCC] | 505.04 |
| IIa-373 | 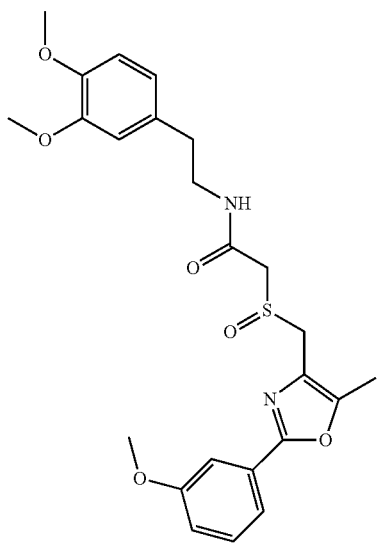 | 472.56 |

TABLE 2-continued
Oxazole amides (R³ = NH-phenethyl)
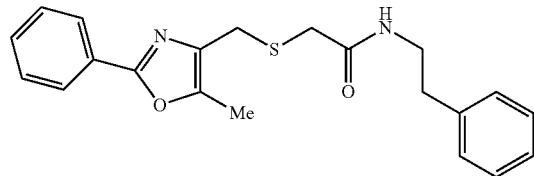
| ID | Structure | MW |
|---|---|---|
| IIa-374 | 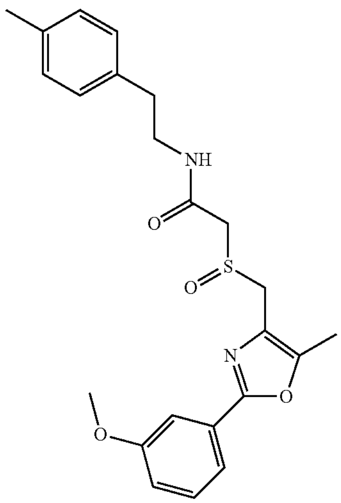 | 426.54 |
| IIa-375 | 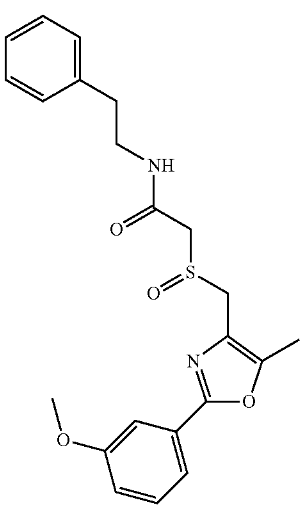 [SMILES: COc1cccc(-c2nc(CS(=O)CC(=O)NCCc3ccccc3)c(C)o2)c1] | 412.51 |

TABLE 2-continued
Oxazole amides (R³ = NH-phenethyl)
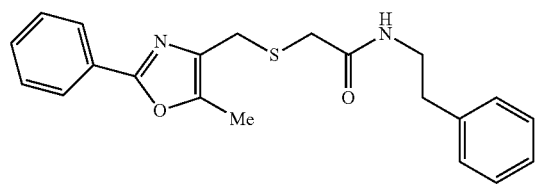
| ID | Structure | MW |
|---|---|---|
| IIa-376 | 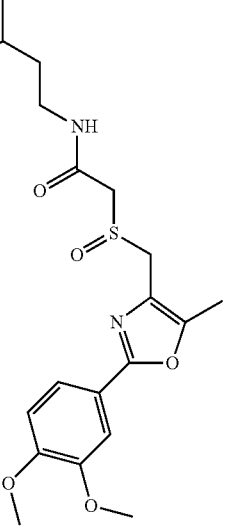 | 476.98 |
| IIa-377 | 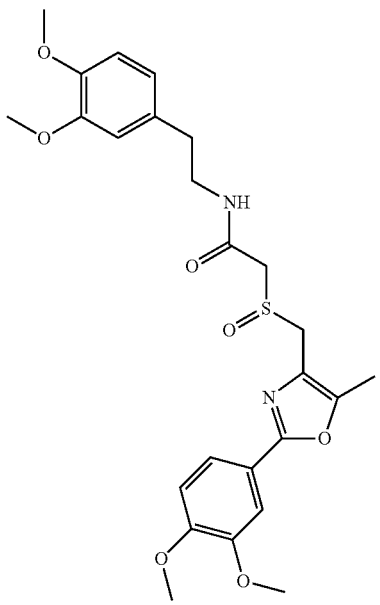 | 502.59 |

TABLE 2-continued
Oxazole amides (R³ = NH-phenethyl)
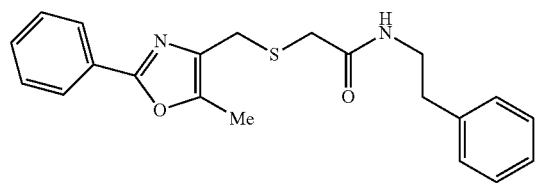
| ID | Structure | MW |
|---|---|---|
| IIa-378 | 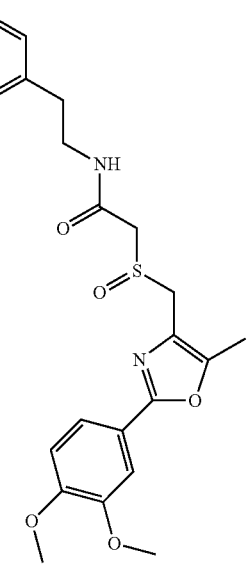 | 456.57 |
| IIa-379 | 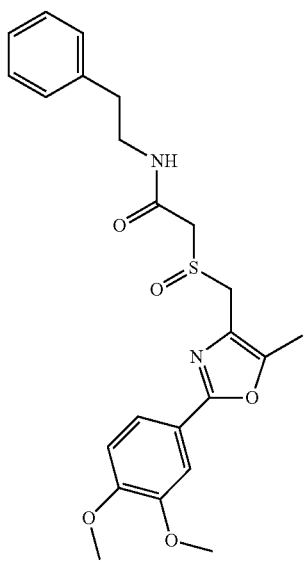 [SMILES: COc1ccc(-c2nc(CS(=O)CC(=O)NCCc3ccccc3)c(C)o2)cc1OC] | 442.54 |

TABLE 2-continued
Oxazole amides (R³ = NH-phenethyl)
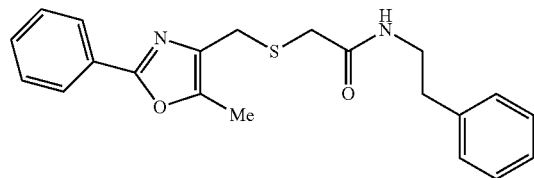
| ID | Structure | MW |
| --- | --- | --- |
| IIa-380 | 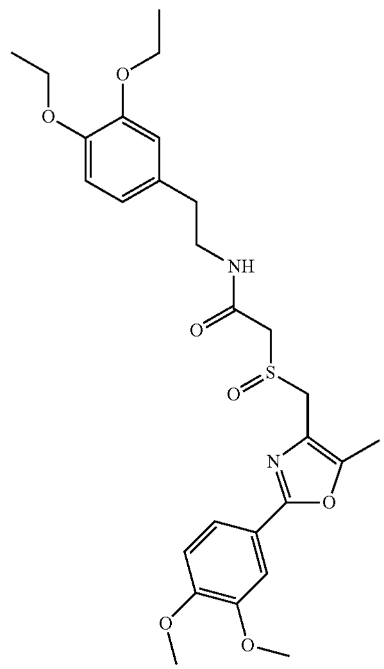 [SMILES: CCOc1ccc(CCNC(=O)CS(=O)Cc2nc(-c3ccc(OC)c(OC)c3)oc2C)cc1OCC] | 530.65 |
| IIa-381 | 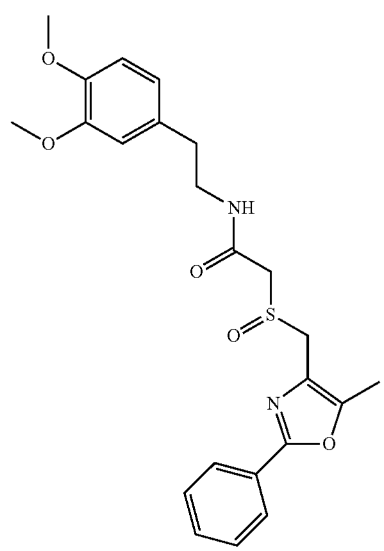 | 442.54 |

TABLE 2-continued
Oxazole amides (R³ = NH-phenethyl)
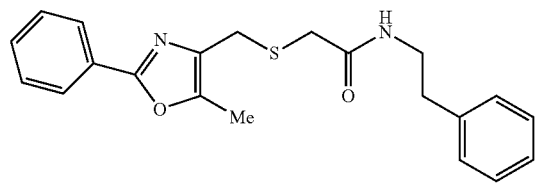
| ID | Structure | MW |
|---|---|---|
| IIa-382 | 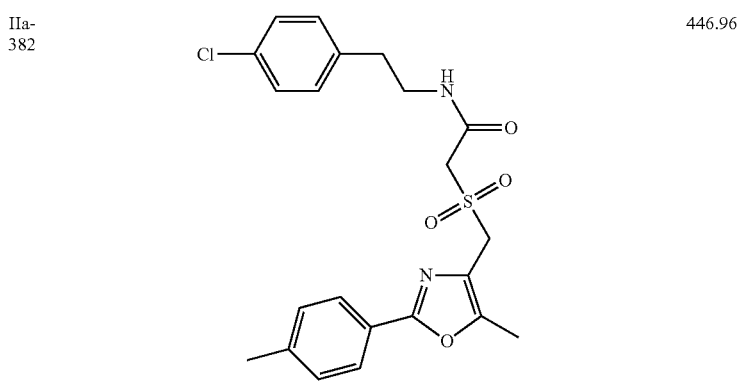 | 446.96 |
| IIa-383 | 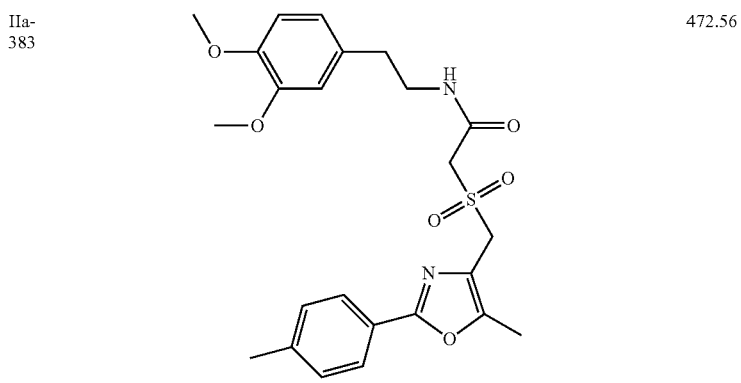 | 472.56 |
| IIa-384 | 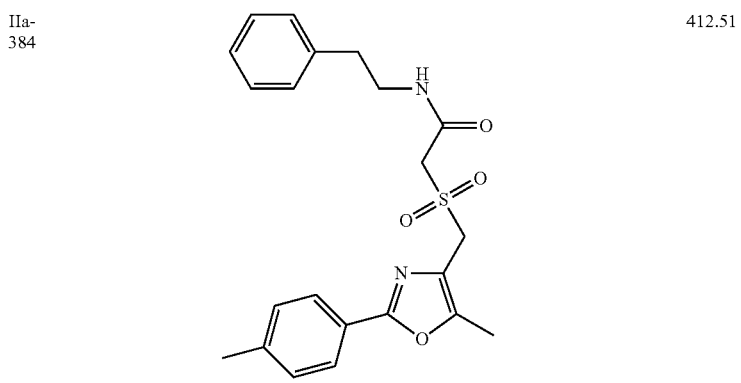 | 412.51 |

TABLE 2-continued
Oxazole amides (R³ = NH-phenethyl)
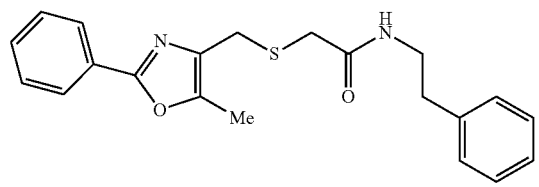
| ID | Structure | MW |
|---|---|---|
| IIa-385 | 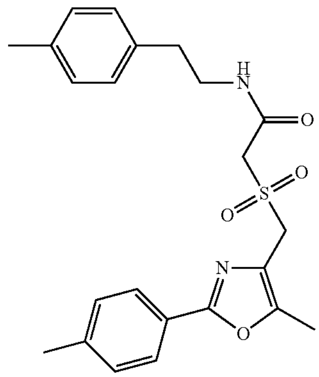 | 426.54 |
| IIa-386 | 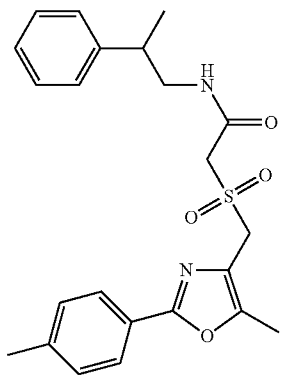 | 426.54 |
| IIa-387 | 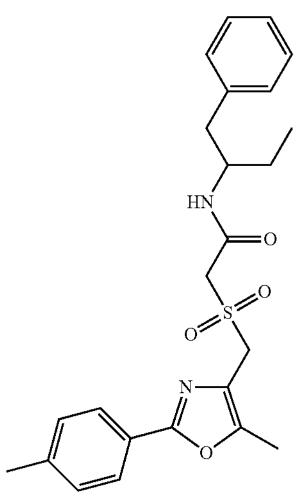 [SMILES: CCC(Cc1ccccc1)NC(=O)CS(=O)(=O)Cc1nc(-c2ccc(C)cc2)oc1C] | 440.57 |

TABLE 2-continued
Oxazole amides (R³ = NH-phenethyl)
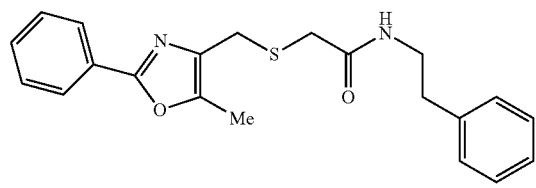
| ID | Structure | MW |
|---|---|---|
| IIa-388 | 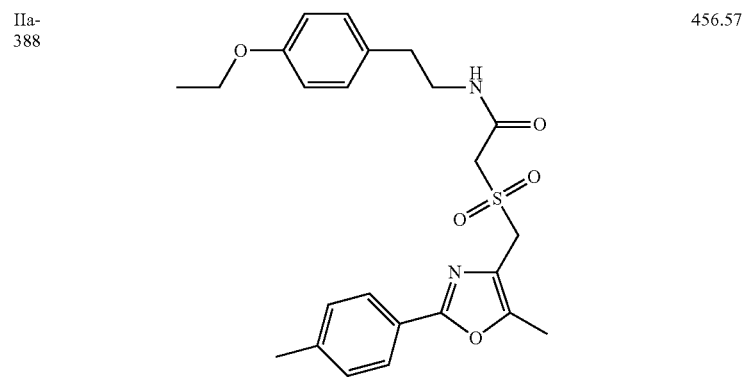 | 456.57 |
| IIa-389 |  | 472.56 |
| IIa-390 |  | 458.60 |

TABLE 2-continued
Oxazole amides (R³ = NH-phenethyl)
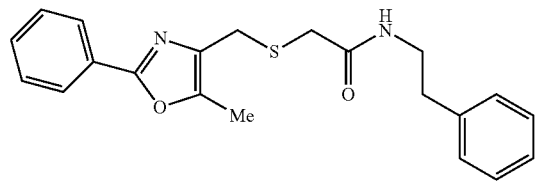
| ID | Structure | MW |
|---|---|---|
| IIa-391 | 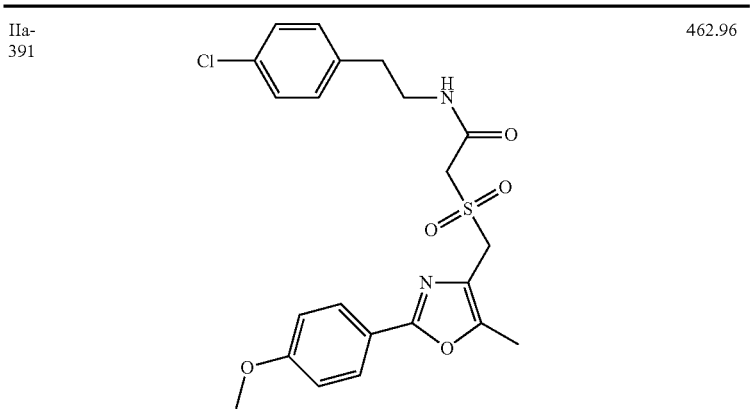 | 462.96 |
| IIa-392 | 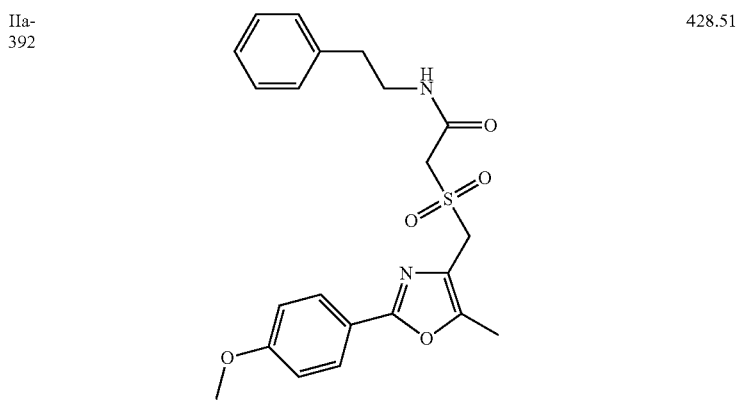 | 428.51 |
| IIa-393 | 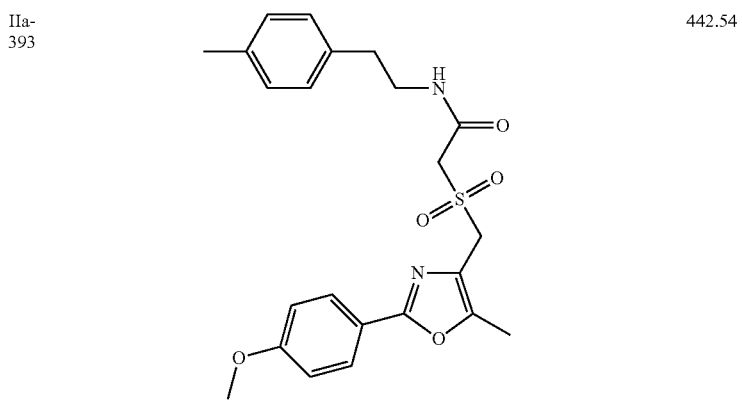 | 442.54 |

TABLE 2-continued
Oxazole amides (R³ = NH-phenethyl)
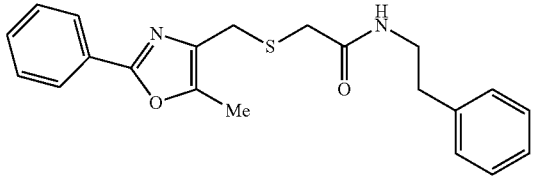
| ID | Structure | MW |
|---|---|---|
| IIa-394 | 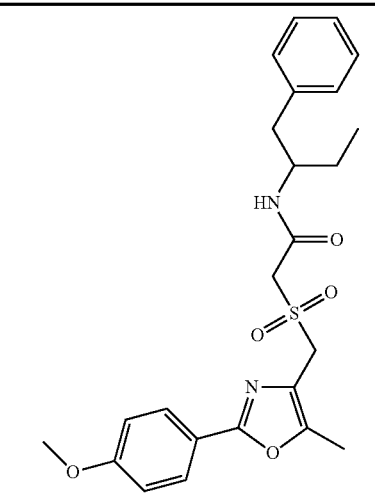 | 456.57 |
| IIa-395 | 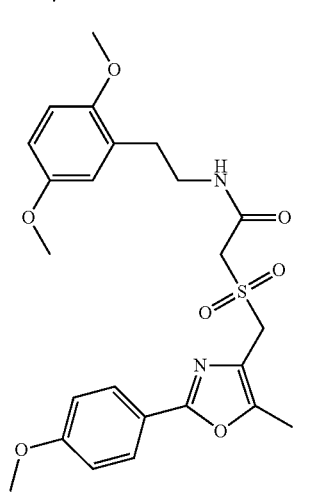 | 472.56 |
| IIa-396 | 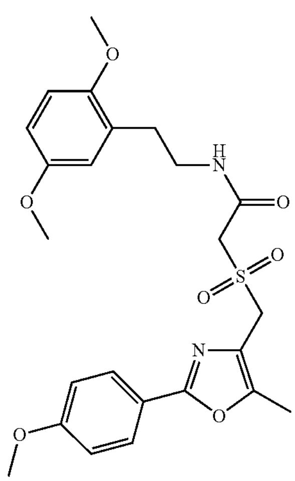 | 488.56 |

TABLE 2-continued
Oxazole amides (R³ = NH-phenethyl)
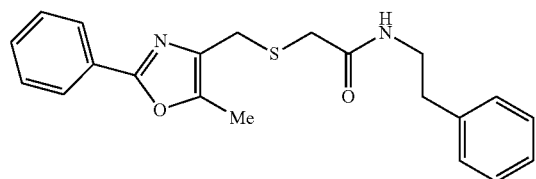
| ID | Structure | MW |
|---|---|---|
| IIa-397 | | 474.60 |
| IIa-398 | | 462.96 |
| IIa-399 | | 488.56 |

TABLE 2-continued
Oxazole amides (R³ = NH-phenethyl)
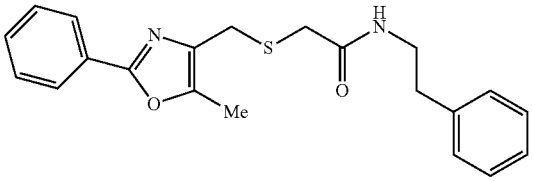
| ID | Structure | MW |
|---|---|---|
| IIa-400 | 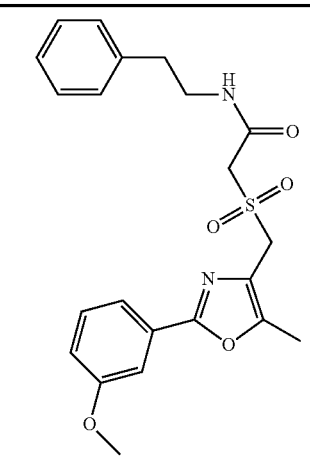 | 428.51 |
| IIa-401 | 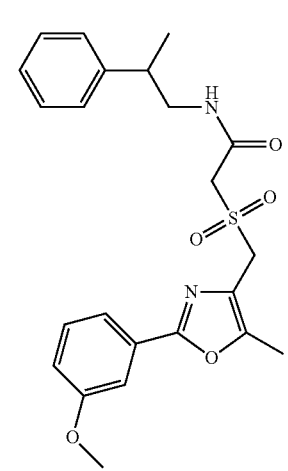 | 442.54 |
| IIa-402 | 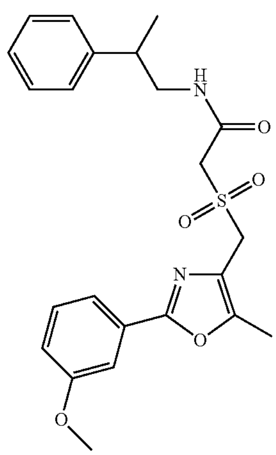 [SMILES: COc1cccc(-c2nc(CS(=O)(=O)CC(=O)NCC(C)c3ccccc3)c(C)o2)c1] | 442.54 |

TABLE 2-continued
Oxazole amides (R³ = NH-phenethyl)
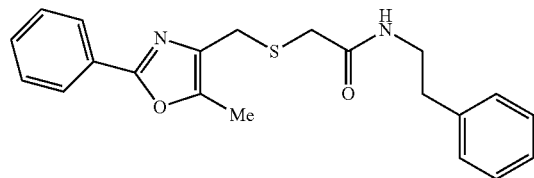
| ID | Structure | MW |
|---|---|---|
| IIa-403 | 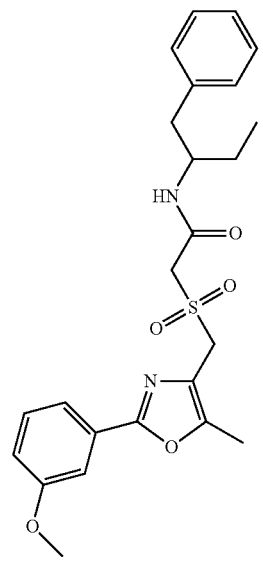 [SMILES: CCC(Cc1ccccc1)NC(=O)CS(=O)(=O)Cc1nc(-c2cccc(OC)c2)oc1C] | 456.57 |
| IIa-404 | 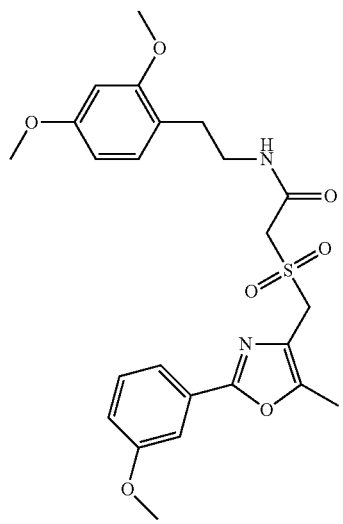 | 488.56 |

TABLE 2-continued

Oxazole amides (R³ = NH-phenethyl)

| ID | Structure | MW |
|---|---|---|
| IIa-405 | 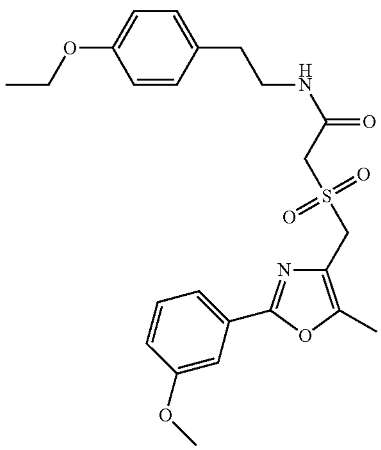 [SMILES: CCOc1ccc(CCNC(=O)CS(=O)(=O)Cc2nc(-c3cccc(OC)c3)oc2C)cc1] | 472.56 |
| IIa-406 | 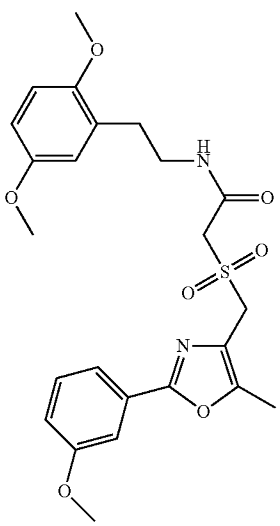 [SMILES: COc1cccc(-c2nc(CS(=O)(=O)CC(=O)NCCc3cc(OC)ccc3OC)c(C)o2)c1] | 488.56 |
| IIa-407 | 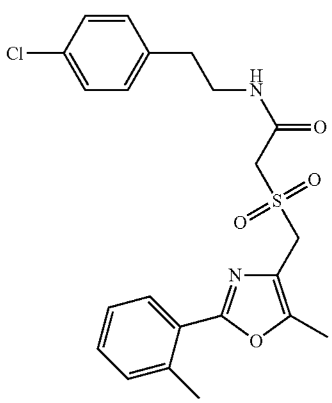 [SMILES: Cc1ccccc1-c1nc(CS(=O)(=O)CC(=O)NCCc2ccc(Cl)cc2)c(C)o1] | 446.96 |

TABLE 2-continued
Oxazole amides (R³ = NH-phenethyl)
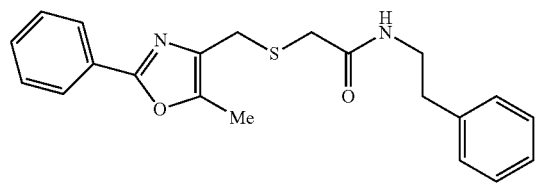
| ID | Structure | MW |
|---|---|---|
| IIa-408 | 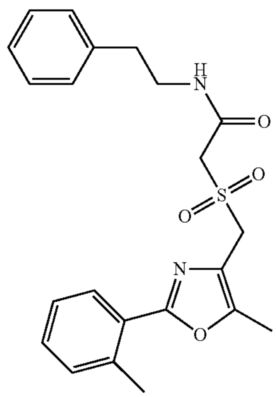 [SMILES: Cc1ccccc1-c1nc(CS(=O)(=O)CC(=O)NCCc2ccccc2)c(C)o1] | 412.51 |
| IIa-409 | 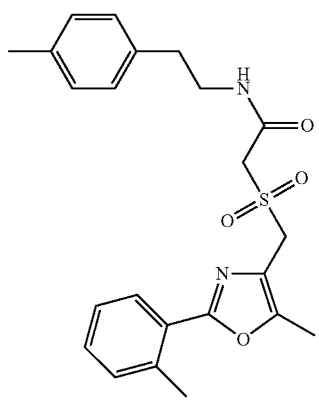 | 426.54 |
| IIa-410 | 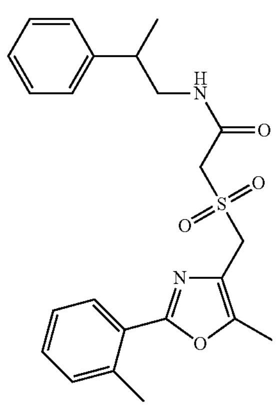 [SMILES: Cc1ccccc1-c1nc(CS(=O)(=O)CC(=O)NCC(C)c2ccccc2)c(C)o1] | 426.54 |

TABLE 2-continued

Oxazole amides (R³ = NH-phenethyl)

| ID | Structure | MW |
|---|---|---|
| IIa-411 | | 440.57 |
| IIa-412 | | 456.57 |
| IIa-413 | | 472.56 |

TABLE 2-continued
Oxazole amides (R³ = NH-phenethyl)
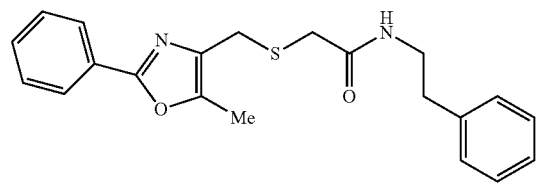
| ID | Structure | MW |
| --- | --- | --- |
| IIa-414 | 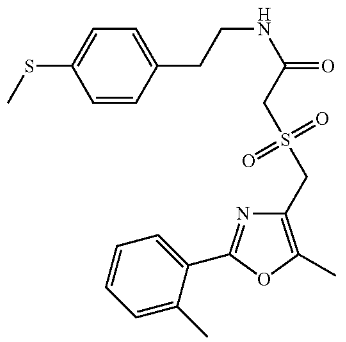 | 458.60 |
| IIa-415 | 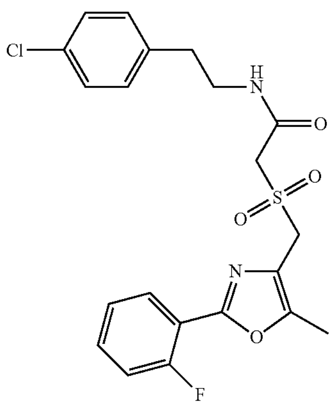 [SMILES: Cc1oc(-c2ccccc2F)nc1CS(=O)(=O)CC(=O)NCCc1ccc(Cl)cc1] | 450.92 |
| IIa-416 | 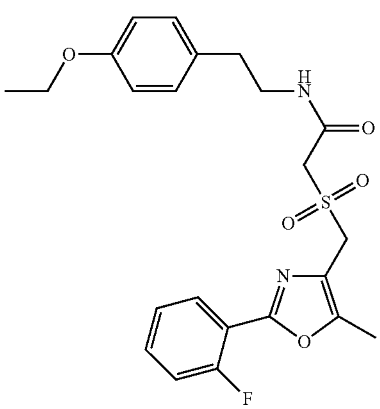 [SMILES: CCOc1ccc(CCNC(=O)CS(=O)(=O)Cc2nc(-c3ccccc3F)oc2C)cc1] | 460.53 |

TABLE 2-continued
Oxazole amides (R³ = NH-phenethyl)
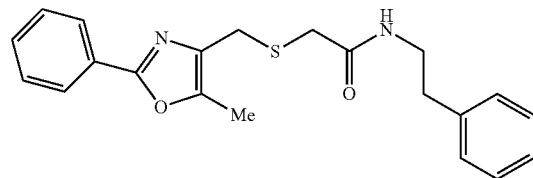
| ID | Structure | MW |
|---|---|---|
| IIa-417 | | 462.57 |
| IIa-418 | | 476.98 |
| IIa-419 | | 432.93 |
| IIa-420 | | 467.37 |

TABLE 2-continued

Oxazole amides (R³ = NH-phenethyl)

| ID | Structure | MW |
|---|---|---|
| IIa-421 | 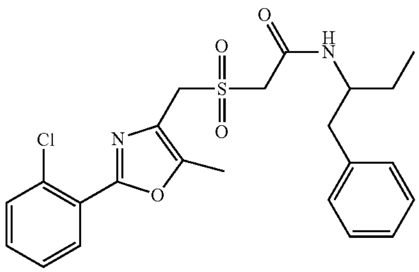 [SMILES: CCC(Cc1ccccc1)NC(=O)CS(=O)(=O)Cc1nc(-c2ccccc2Cl)oc1C] | 460.98 |
| IIa-422 | 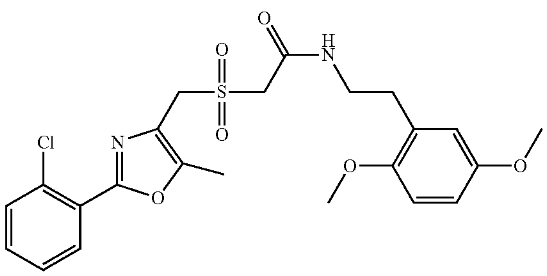 [SMILES: COc1ccc(OC)c(CCNC(=O)CS(=O)(=O)Cc2nc(-c3ccccc3Cl)oc2C)c1] | 492.98 |
| IIa-423 | 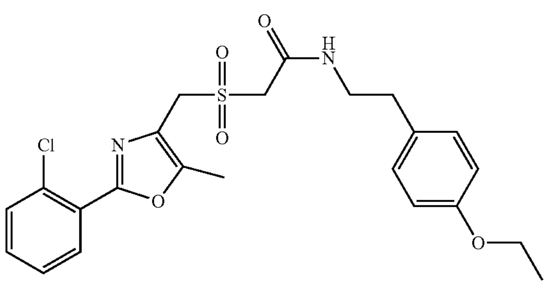 [SMILES: CCOc1ccc(CCNC(=O)CS(=O)(=O)Cc2nc(-c3ccccc3Cl)oc2C)cc1] | 476.98 |
| IIa-424 | 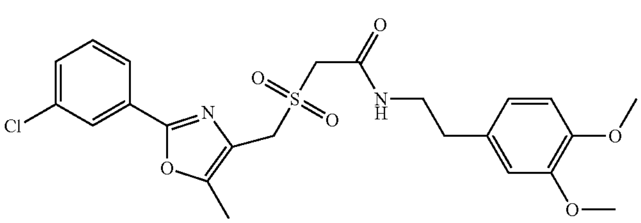 [SMILES: COc1ccc(CCNC(=O)CS(=O)(=O)Cc2nc(-c3cccc(Cl)c3)oc2C)cc1OC] | 492.98 |
| IIa-425 | 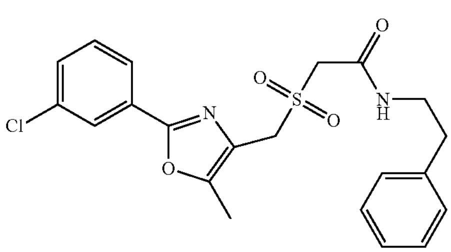 [SMILES: Cc1oc(-c2cccc(Cl)c2)nc1CS(=O)(=O)CC(=O)NCCc1ccccc1] | 432.93 |

TABLE 2-continued
Oxazole amides ($R^3$ = NH-phenethyl)
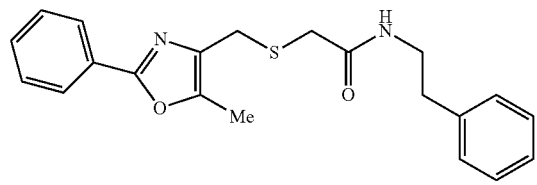
| ID | Structure | MW |
|---|---|---|
| IIa-426 | 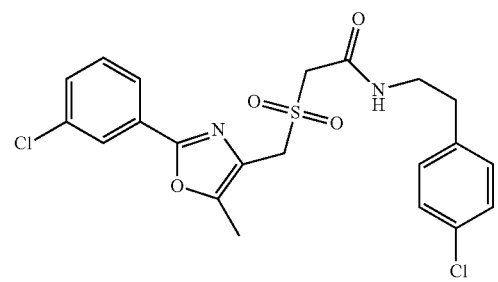 [SMILES: Cc1oc(-c2cccc(Cl)c2)nc1CS(=O)(=O)CC(=O)NCCc1ccc(Cl)cc1] | 467.37 |
| IIa-427 | 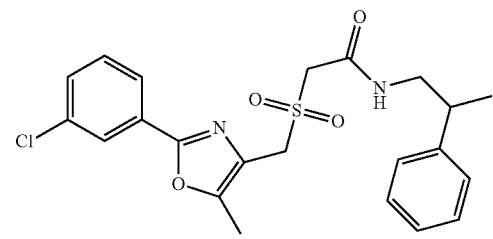 [SMILES: Cc1oc(-c2cccc(Cl)c2)nc1CS(=O)(=O)CC(=O)NCC(C)c1ccccc1] | 446.96 |
| IIa-428 | 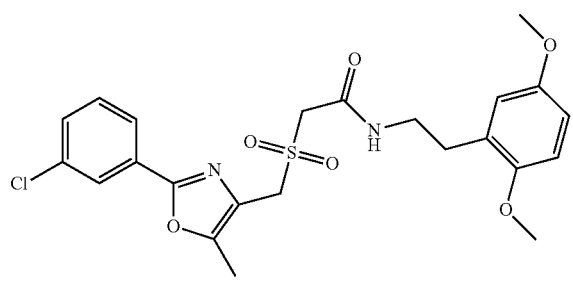 [SMILES: COc1ccc(OC)c(CCNC(=O)CS(=O)(=O)Cc2nc(-c3cccc(Cl)c3)oc2C)c1] | 492.98 |
| IIa-429 | 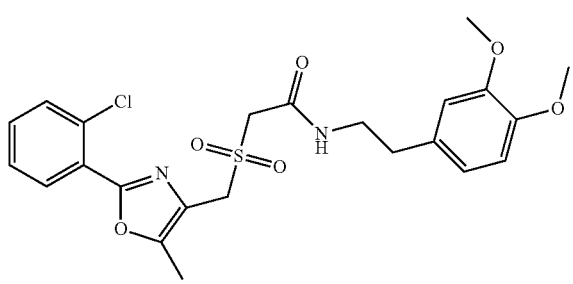 [SMILES: COc1ccc(CCNC(=O)CS(=O)(=O)Cc2nc(-c3ccccc3Cl)oc2C)cc1OC] | 492.98 |

TABLE 3

Oxazole amides (R³ = NH-Phenyl)

| ID | Structure | MW |
|---|---|---|
| IIa-501 | | 443.48 |
| IIa-502 | | 461.38 |
| IIa-503 | | 396.51 |
| IIa-504 | | 456.57 |
| IIa-505 | | 404.44 |

TABLE 3-continued

Oxazole amides (R³ = NH-Phenyl)

| ID | Structure | MW |
|---|---|---|
| IIa-506 | | 382.49 |
| IIa-507 | | 440.52 |
| IIa-508 | | 396.51 |
| IIa-509 | | 393.47 |
| IIa-510 | | 413.46 |

TABLE 3-continued
Oxazole amides (R³ = NH-Phenyl)
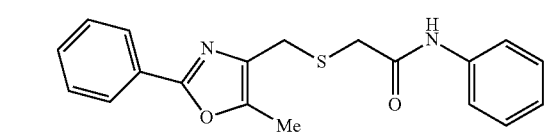 [SMILES: Cc1oc(-c2ccccc2)nc1CSCC(=O)Nc1ccccc1]
| ID | Structure | MW |
|---|---|---|
| IIa-511 | 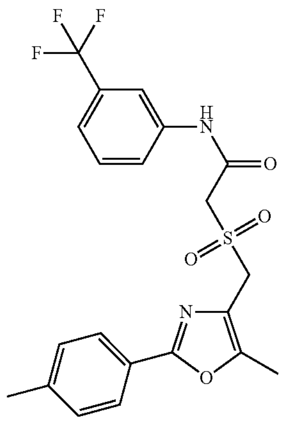 | 452.46 |
| IIa-512 | 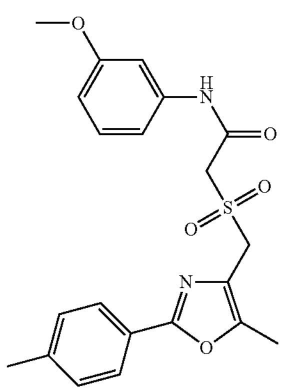 | 414.48 |
| IIa-513 | 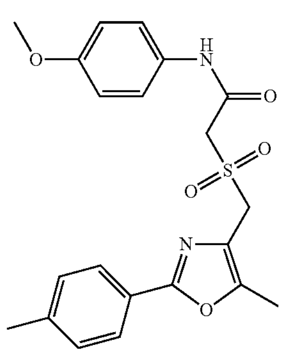 | 414.48 |
TABLE 3-continued
Oxazole amides (R³ = NH-Phenyl)
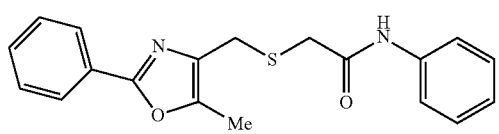
| ID | Structure | MW |
|---|---|---|
| IIa-514 | 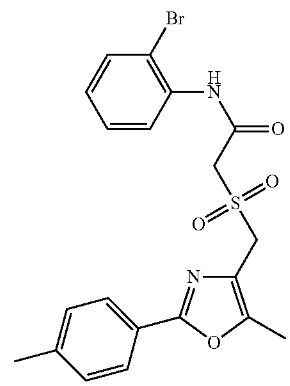 | 463.35 |
| IIa-515 | 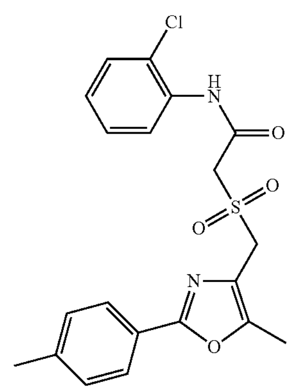 | 418.90 |
| IIa-516 | 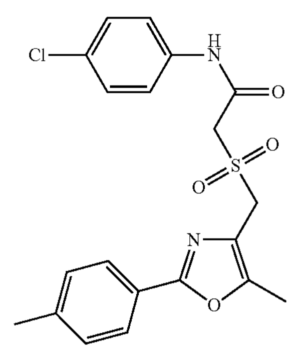 | 418.90 |

TABLE 3-continued

Oxazole amides (R³ = NH-Phenyl)

| ID | Structure | MW |
|---|---|---|
| IIa-517 | 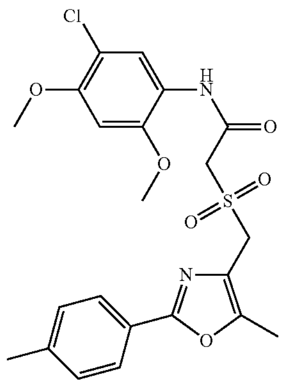 | 478.96 |
| IIa-518 | 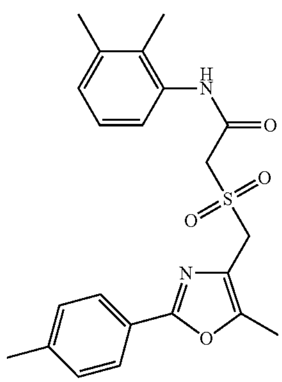 | 412.51 |
| IIa-519 | 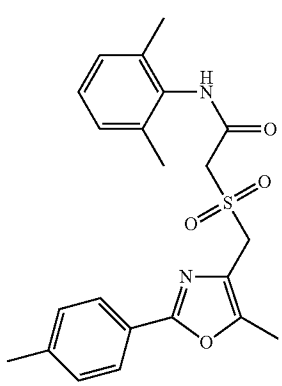 | 412.51 |
| IIa-520 | | 456.52 |
| IIa-521 | | 442.49 |
| IIa-522 | | 428.51 |

TABLE 3-continued

Oxazole amides (R³ = NH-Phenyl)

| ID | Structure | MW |
|---|---|---|
| IIa-523 | 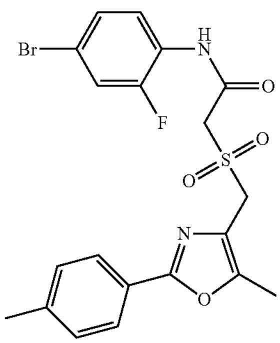 | 481.34 |
| IIa-524 | 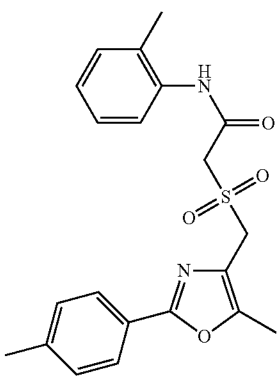 | 398.48 |
| IIa-525 | 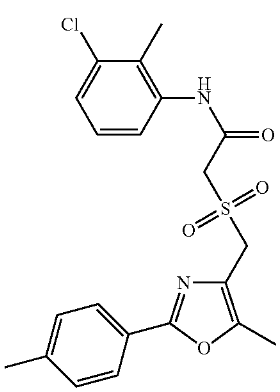 | 432.93 |
| IIa-526 | | 432.93 |
| IIa-527 | | 412.51 |
| IIa-528 | | 412.51 |

TABLE 3-continued

Oxazole amides (R³ = NH-Phenyl)

| ID | Structure | MW |
|---|---|---|
| IIa-529 | 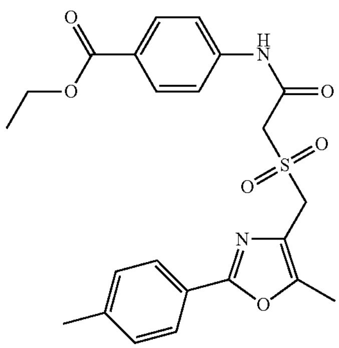 [SMILES: CCOC(=O)c1ccc(NC(=O)CS(=O)(=O)Cc2nc(-c3ccc(C)cc3)oc2C)cc1] | 456.52 |
| IIa-530 | 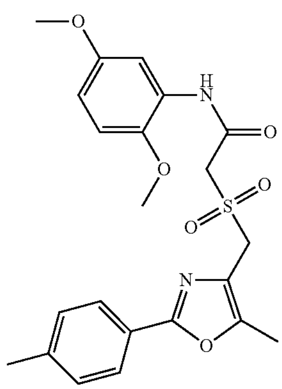 | 444.51 |
| IIa-531 | 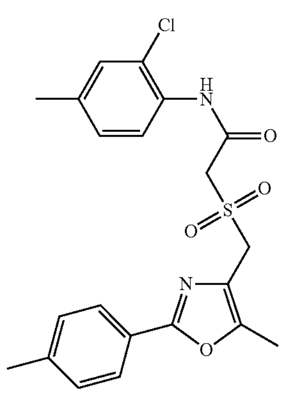 | 432.93 |
| IIa-532 | | 412.51 |
| IIa-533 | | 426.54 |
| IIa-534 | | 420.44 |

TABLE 3-continued
Oxazole amides (R³ = NH-Phenyl)
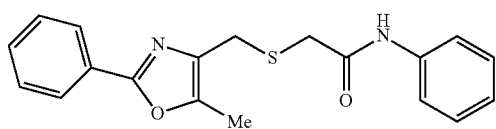
| ID | Structure | MW |
|---|---|---|
| IIa-535 | 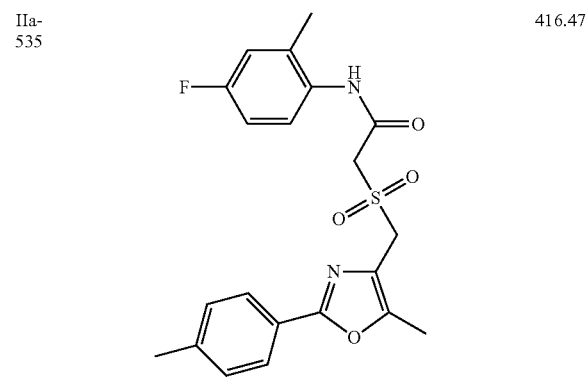 | 416.47 |
| IIa-536 | 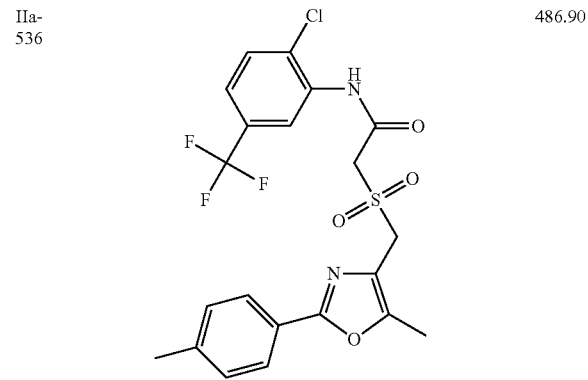 | 486.90 |
| IIa-537 | 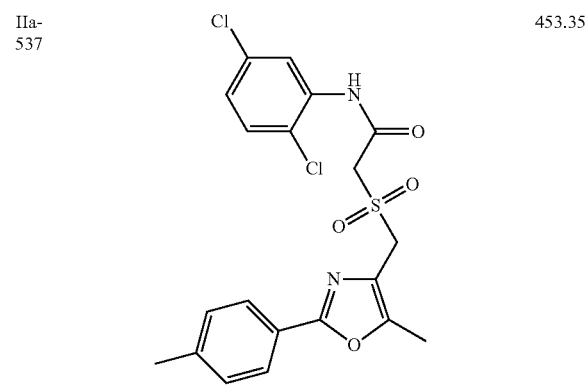 | 453.35 |
TABLE 3-continued
Oxazole amides (R³ = NH-Phenyl)
| ID | Structure | MW |
|---|---|---|
| IIa-538 | 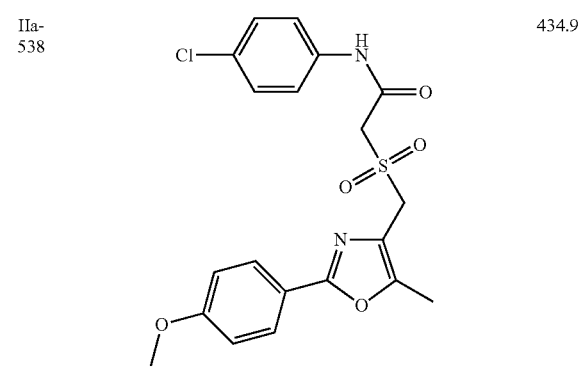 | 434.90 |
| IIa-539 | 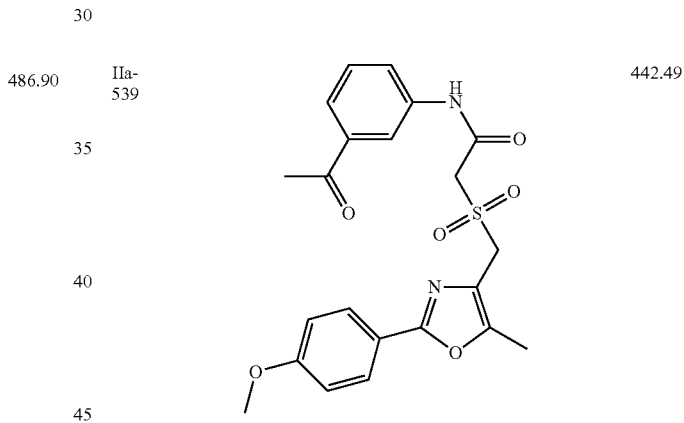 | 442.49 |
| IIa-540 | 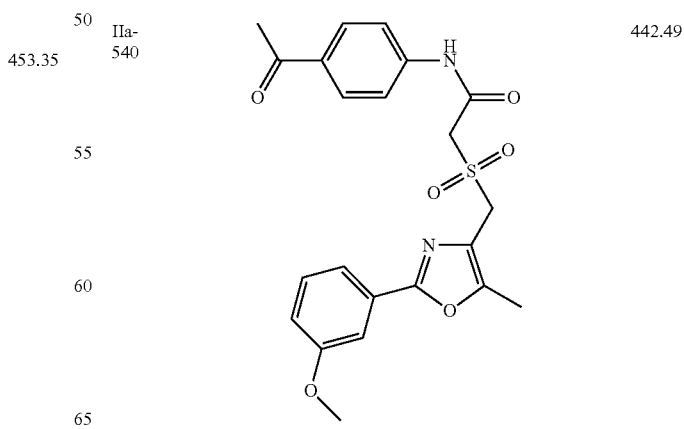 | 442.49 |

TABLE 3-continued

Oxazole amides (R³ = NH-Phenyl)

| ID | Structure | MW |
|---|---|---|
| IIa-541 | 3-(trifluoromethyl)phenyl sulfone derivative | 468.46 |
| IIa-542 | 2-bromophenyl sulfone derivative | 479.35 |
| IIa-543 | 2-chlorophenyl sulfone derivative | 434.90 |
| IIa-544 | 4-chlorophenyl sulfone derivative | 434.90 |
| IIa-545 | 3,5-dichlorophenyl sulfone derivative | 469.35 |
| IIa-546 | 2,4-difluorophenyl sulfone derivative | 436.44 |

TABLE 3-continued

Oxazole amides (R³ = NH-Phenyl)

| ID | Structure | MW |
|---|---|---|
| IIa-547 | 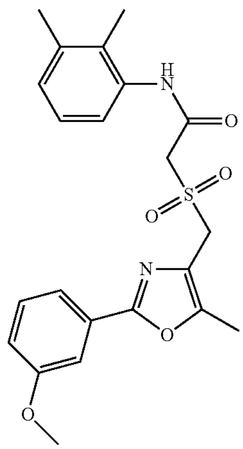 [SMILES: COc1cccc(-c2nc(CS(=O)(=O)CC(=O)Nc3cccc(C)c3C)c(C)o2)c1] | 428.51 |
| IIa-548 | 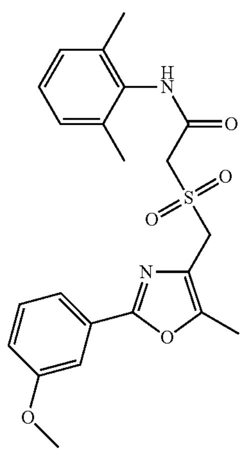 [SMILES: COc1cccc(-c2nc(CS(=O)(=O)CC(=O)Nc3c(C)cccc3C)c(C)o2)c1] | 428.51 |
| IIa-549 | 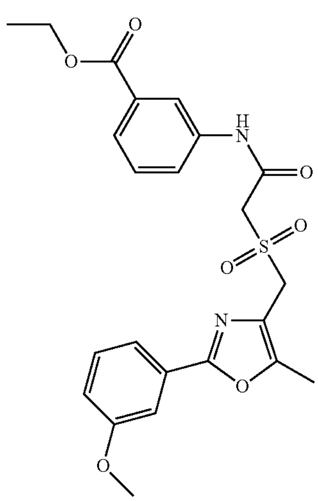 [SMILES: CCOC(=O)c1cccc(NC(=O)CS(=O)(=O)Cc2nc(-c3cccc(OC)c3)oc2C)c1] | 472.52 |
| IIa-550 | | 458.49 |
| IIa-551 | | 497.34 |
| IIa-552 | | 414.48 |

TABLE 3-continued

Oxazole amides (R³ = NH-Phenyl)

| ID | Structure | MW |
|---|---|---|
| IIa-553 | (3-chloro-2-methylphenyl amide; sulfonyl-CH2-oxazole with 2-(3-methoxyphenyl)-5-methyl) | 448.93 |
| IIa-554 | (3-chloro-4-methylphenyl amide; sulfonyl-CH2-oxazole with 2-(3-methoxyphenyl)-5-methyl) | 448.93 |
| IIa-555 | (2,5-dimethylphenyl amide; sulfonyl-CH2-oxazole with 2-(3-methoxyphenyl)-5-methyl) | 428.51 |
| IIa-556 | (2,4-dimethylphenyl amide; sulfonyl-CH2-oxazole with 2-(3-methoxyphenyl)-5-methyl) | 428.51 |
| IIa-557 | (4-ethoxycarbonylphenyl amide; sulfonyl-CH2-oxazole with 2-(3-methoxyphenyl)-5-methyl) | 472.52 |
| IIa-558 | (2,5-dimethoxyphenyl amide; sulfonyl-CH2-oxazole with 2-(3-methoxyphenyl)-5-methyl) | 460.51 |

TABLE 3-continued
Oxazole amides (R³ = NH-Phenyl)
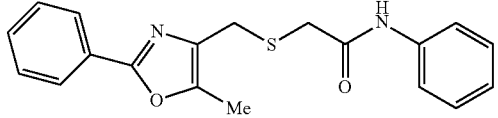
| ID | Structure | MW |
|---|---|---|
| IIa-559 | 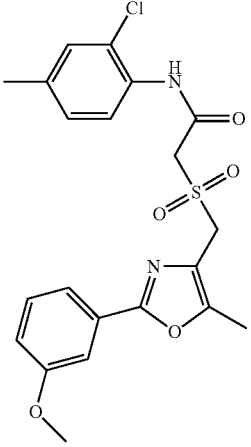 | 448.93 |
| IIa-560 | 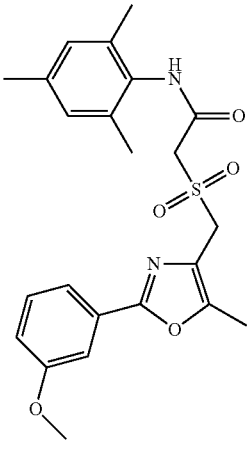 | 442.54 |
| IIa-561 | 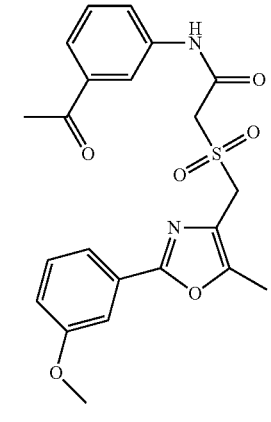 [SMILES: COc1cccc(-c2nc(CS(=O)(=O)CC(=O)Nc3cccc(C(C)=O)c3)c(C)o2)c1] | 428.51 |
TABLE 3-continued
Oxazole amides (R³ = NH-Phenyl)
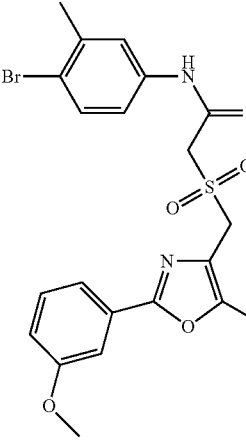
| ID | Structure | MW |
|---|---|---|
| IIa-562 | 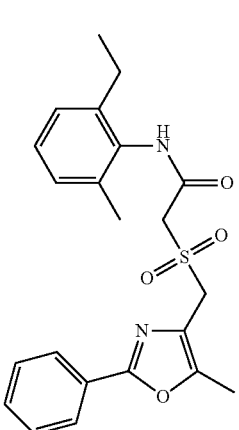 | 442.49 |
| IIa-563 | 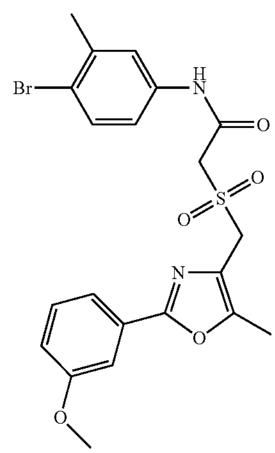 [SMILES: COc1cccc(-c2nc(CS(=O)(=O)CC(=O)Nc3ccc(Br)c(C)c3)c(C)o2)c1] | 493.38 |
| IIa-564 | 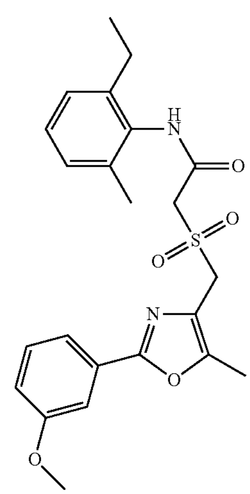 [SMILES: CCc1cccc(C)c1NC(=O)CS(=O)(=O)Cc1nc(-c2cccc(OC)c2)oc1C] | 442.54 |

TABLE 3-continued

Oxazole amides (R³ = NH-Phenyl)

| ID | Structure | MW |
|---|---|---|
| IIa-565 | | 436.44 |
| IIa-566 | | 464.93 |
| IIa-567 | | 432.47 |
| IIa-568 | | 469.35 |
| IIa-569 | | 452.46 |
| IIa-570 | | 418.90 |

TABLE 3-continued

Oxazole amides (R³ = NH-Phenyl)

| ID | Structure | MW |
|---|---|---|
| IIa-571 | 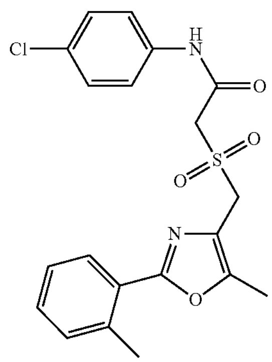 [SMILES: Cc1ccccc1-c1nc(CS(=O)(=O)CC(=O)Nc2ccc(Cl)cc2)c(C)o1] | 418.90 |
| IIa-572 | 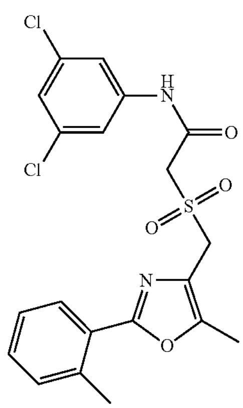 [SMILES: Cc1ccccc1-c1nc(CS(=O)(=O)CC(=O)Nc2cc(Cl)cc(Cl)c2)c(C)o1] | 453.35 |
| IIa-573 | 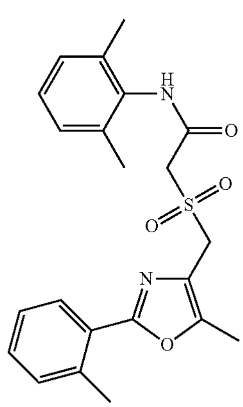 [SMILES: Cc1ccccc1-c1nc(CS(=O)(=O)CC(=O)Nc2c(C)cccc2C)c(C)o1] | 412.51 |
| IIa-574 | | 456.52 |
| IIa-575 | | 481.34 |
| IIa-576 | | 398.48 |

TABLE 3-continued

Oxazole amides (R³ = NH-Phenyl)

| ID | Structure | MW |
|---|---|---|
| IIa-577 | 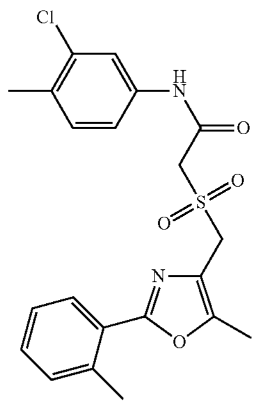 | 432.93 |
| IIa-578 | 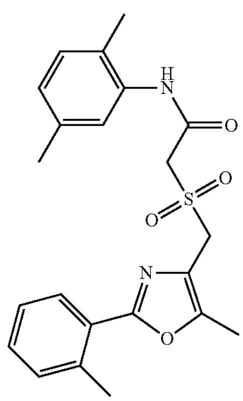 [SMILES: Cc1ccc(C)c(NC(=O)CS(=O)(=O)Cc2nc(-c3ccccc3C)oc2C)c1] | 412.51 |
| IIa-579 | 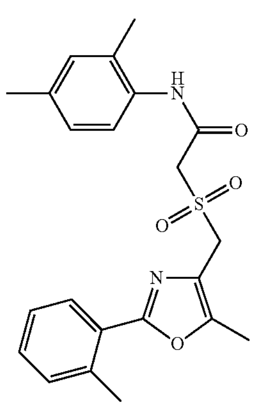 | 412.51 |
| IIa-580 | | 456.52 |
| IIa-581 | | 444.51 |
| IIa-582 | | 432.92 |

TABLE 3-continued

Oxazole amides (R³ = NH-Phenyl)

| ID | Structure | MW |
|---|---|---|
| IIa-583 | | 412.51 |
| IIa-584 | | 420.44 |
| IIa-585 | | 416.47 |
| IIa-586 | 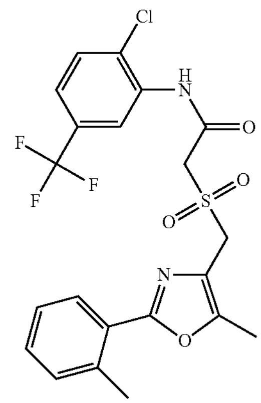 [SMILES: Cc1ccccc1-c1nc(CS(=O)(=O)CC(=O)Nc2cc(C(F)(F)F)ccc2Cl)c(C)o1] | 486.90 |
| IIa-587 | 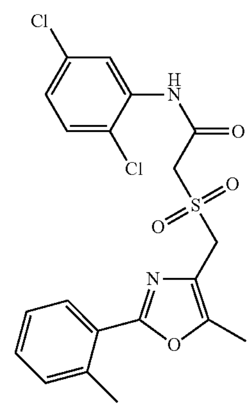 [SMILES: Cc1ccccc1-c1nc(CS(=O)(=O)CC(=O)Nc2cc(Cl)ccc2Cl)c(C)o1] | 453.35 |
| IIa-588 | 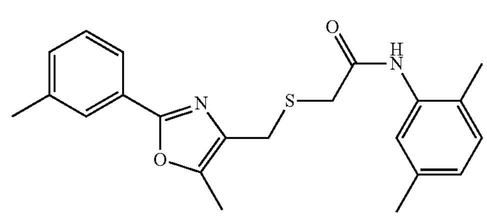 | 380.51 |
| IIa-589 | 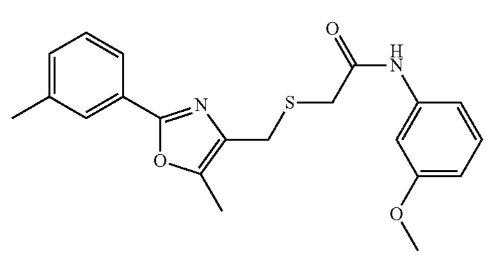 [SMILES: COc1cccc(NC(=O)CSCc2nc(-c3cccc(C)c3)oc2C)c1] | 382.49 |

TABLE 3-continued
Oxazole amides (R³ = NH-Phenyl)
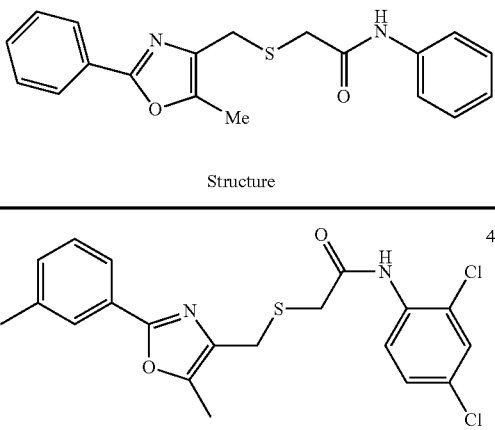
| ID | Structure | MW |
|---|---|---|
| IIa-590 | 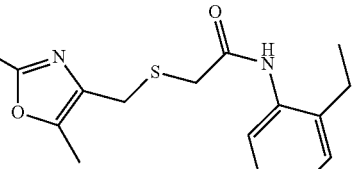 | 421.35 |
| IIa-591 | 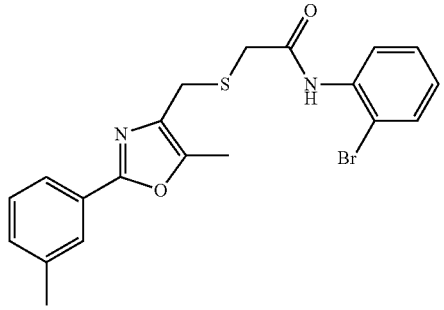 [SMILES: Cc1cccc(-c2nc(CSCC(=O)Nc3ccccc3Br)c(C)o2)c1] | 380.51 |
| IIa-592 | 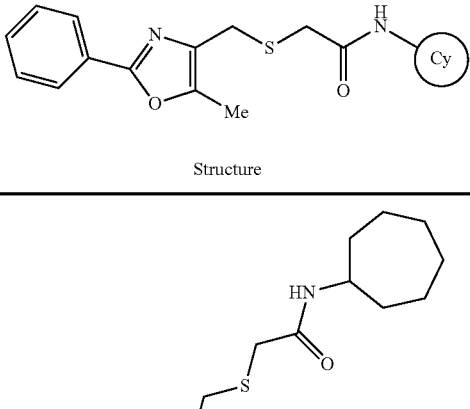 | 431.35 |
TABLE 4
Oxazole amides (R³ = NH-C₃-C₇cycloalkyl)
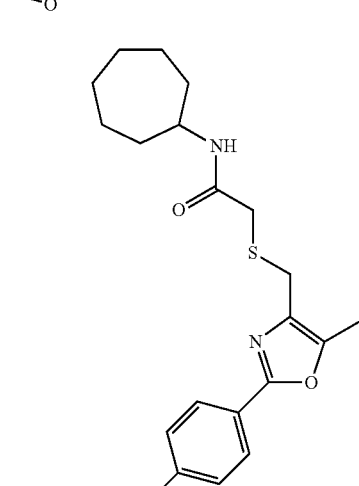
| ID | Structure | MW |
|---|---|---|
| IIa-601 | 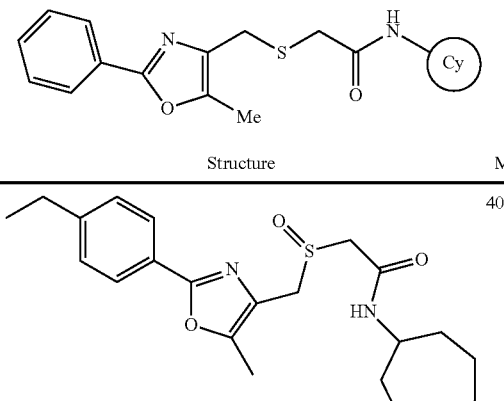 | 402.56 |
TABLE 4-continued
Oxazole amides (R³ = NH-C₃-C₇cycloalkyl)
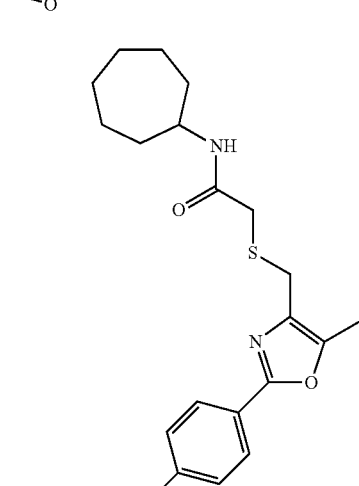
| ID | Structure | MW |
|---|---|---|
| IIa-602 | 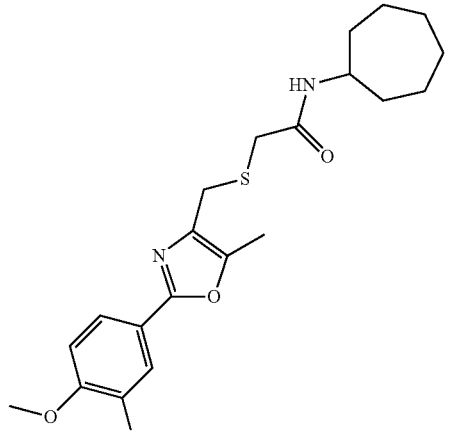 | 388.53 |
| IIa-603 | 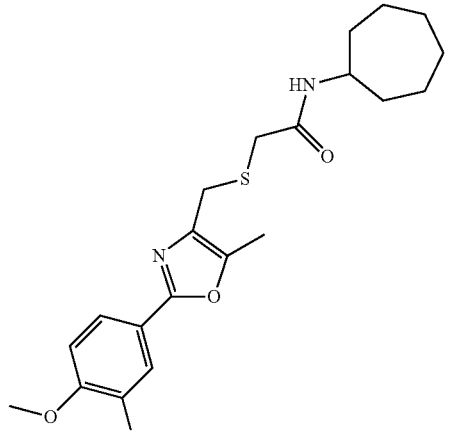 | 388.53 |
| IIa-604 | 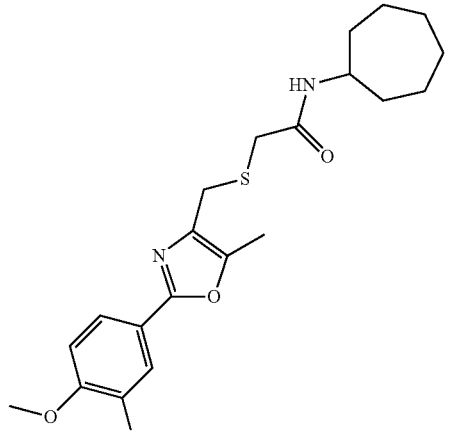 | 418.56 |

TABLE 4-continued

Oxazole amides (R³ = NH-C₃-C₇cycloalkyl)

| ID | Structure | MW |
|---|---|---|
| IIa-605 | | 392.95 |
| IIa-606 | | 372.53 |
| IIa-607 | | 404.60 |
| IIa-608 | | 386.56 |
| IIa-609 | | 392.95 |
| IIa-610 | | 376.50 |

TABLE 4-continued

Oxazole amides (R³ = NH-C₃-C₇cycloalkyl)

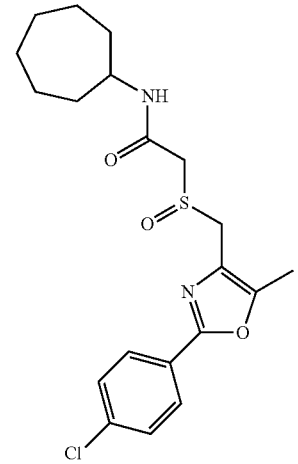 [SMILES: Cc1oc(-c2ccc(Cl)cc2)nc1CS(=O)CC(=O)NC1CCCCCC1]

| ID | Structure | MW |
|---|---|---|
| IIa-611 | cycloheptyl-NH-C(O)-CH₂-S-CH₂-[5-methyl-2-(3-methylphenyl)oxazol-4-yl] | 372.53 |
| IIa-612 | cycloheptyl-NH-C(O)-CH₂-S(O)-CH₂-[5-methyl-2-(4-methoxyphenyl)oxazol-4-yl] | 404.53 |
| IIa-613 | cycloheptyl-NH-C(O)-CH₂-S(O)-CH₂-[5-methyl-2-(3-methylphenyl)oxazol-4-yl] | 388.53 |
| IIa-614 | cycloheptyl-NH-C(O)-CH₂-S(O)-CH₂-[5-methyl-2-(4-chlorophenyl)oxazol-4-yl] | 408.95 |
| IIa-615 | cycloheptyl-NH-C(O)-CH₂-S(O)-CH₂-[5-methyl-2-(2-methylphenyl)oxazol-4-yl] | 388.53 |
| IIa-616 | cycloheptyl-NH-C(O)-CH₂-S(O)-CH₂-[5-methyl-2-phenyloxazol-4-yl] | 374.51 |

TABLE 4-continued

Oxazole amides (R³ = NH-C₃-C₇cycloalkyl)

| ID | Structure | MW |
|---|---|---|
| IIa-617 | 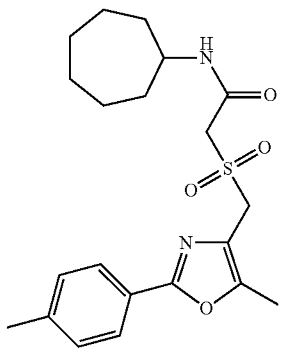 | 404.53 |
| IIa-618 | 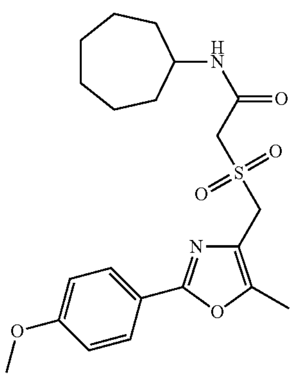 | 420.53 |
| IIa-619 | 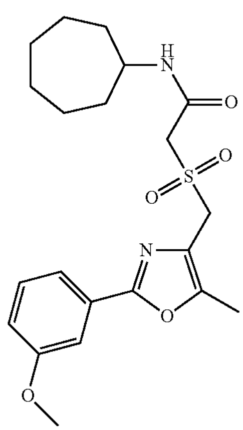 [SMILES: COc1cccc(-c2nc(CS(=O)(=O)CC(=O)NC3CCCCCC3)c(C)o2)c1] | 420.53 |
| IIa-620 | 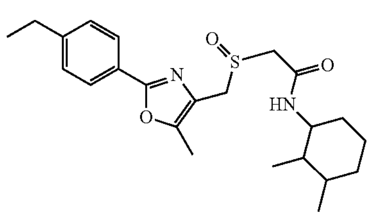 [SMILES: CCc1ccc(-c2nc(CS(=O)CC(=O)NC3CCCC(C)C3C)c(C)o2)cc1] | 416.59 |
| IIa-621 | | 402.56 |
| IIa-622 | | 416.59 |
| IIa-623 | | 402.56 |

TABLE 4-continued
Oxazole amides ($R^3$ = NH-$C_3$-$C_7$cycloalkyl)
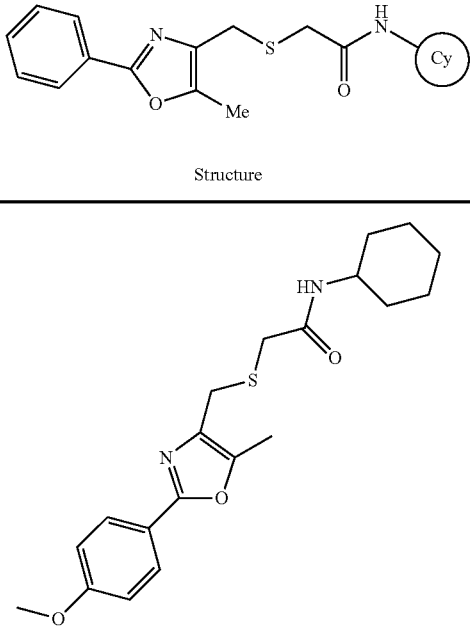
| ID | Structure | MW |
|---|---|---|
| IIa-624 | 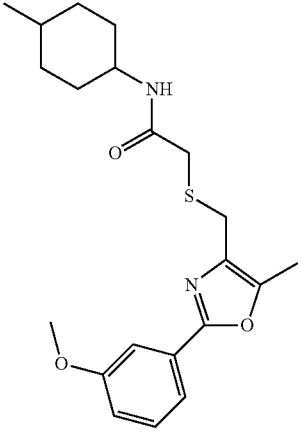 | 374.51 |
| IIa-625 | 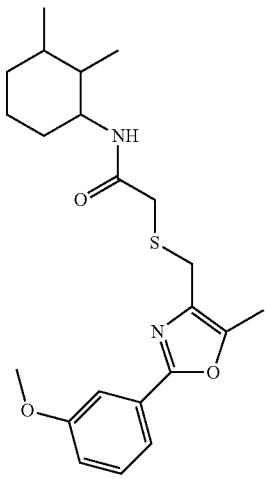 [SMILES: COc1cccc(-c2nc(CSCC(=O)NC3CCCC(C)C3C)c(C)o2)c1] | 388.53 |
| IIa-626 | 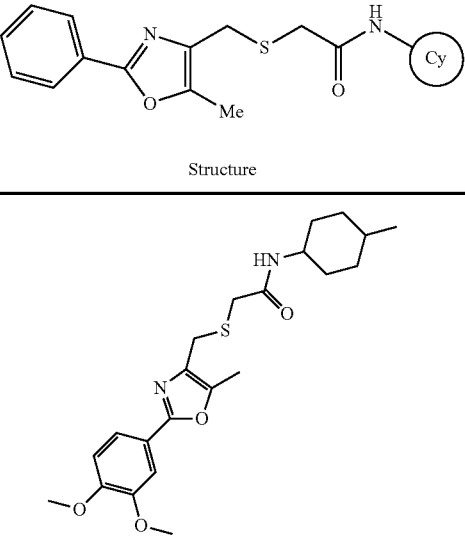 | 402.56 |
TABLE 4-continued
Oxazole amides ($R^3$ = NH-$C_3$-$C_7$cycloalkyl)
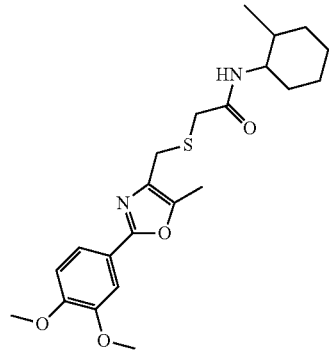
| ID | Structure | MW |
|---|---|---|
| IIa-627 | 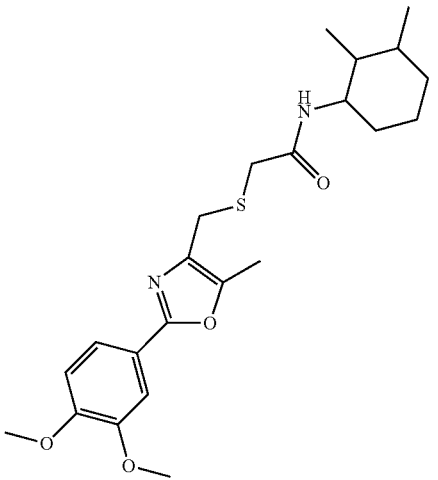 | 418.56 |
| IIa-628 | 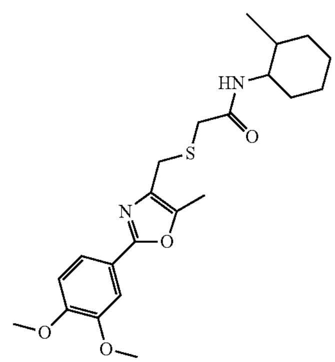 [SMILES: COc1ccc(-c2nc(CSCC(=O)NC3CCCCC3C)c(C)o2)cc1OC] | 418.56 |
| IIa-629 | 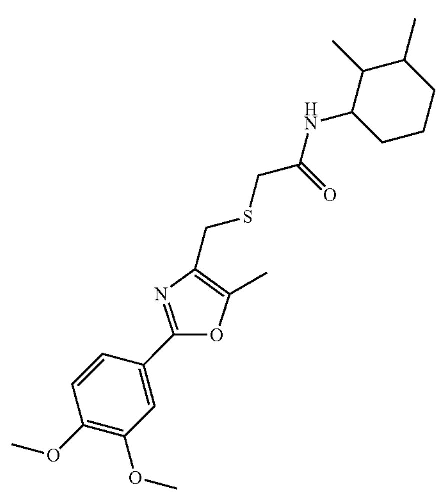 [SMILES: COc1ccc(-c2nc(CSCC(=O)NC3CCCC(C)C3C)c(C)o2)cc1OC] | 432.59 |

TABLE 4-continued

Oxazole amides (R³ = NH-C₃-C₇cycloalkyl)

| ID | Structure | MW |
|---|---|---|
| IIa-630 | 4-chlorophenyl oxazole, 5-Me, CH₂-S-CH₂-C(O)NH-(2,3-dimethylcyclohexyl) | 406.98 |
| IIa-631 | 2-methylphenyl oxazole, 5-Me, CH₂-S-CH₂-C(O)NH-(2,3-dimethylcyclohexyl) | 386.56 |
| IIa-632 | 2-methylphenyl oxazole, 5-Me, CH₂-S-CH₂-C(O)NH-cyclohexyl | 358.51 |
| IIa-633 | 2-chlorophenyl oxazole, 5-Me, CH₂-S-CH₂-C(O)NH-(2-methylcyclohexyl) | 392.95 |
| IIa-634 | 2-chlorophenyl oxazole, 5-Me, CH₂-S-CH₂-C(O)NH-(2,3-dimethylcyclohexyl) | 406.98 |
| IIa-635 | 2-chlorophenyl oxazole, 5-Me, CH₂-S-CH₂-C(O)NH-cyclohexyl | 378.92 |

TABLE 4-continued
Oxazole amides ($R^3$ = NH-$C_3$-$C_7$cycloalkyl)
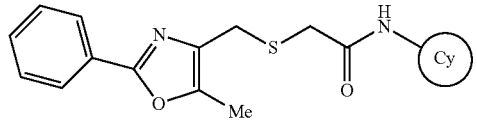
| ID | Structure | MW |
|---|---|---|
| IIa-636 | 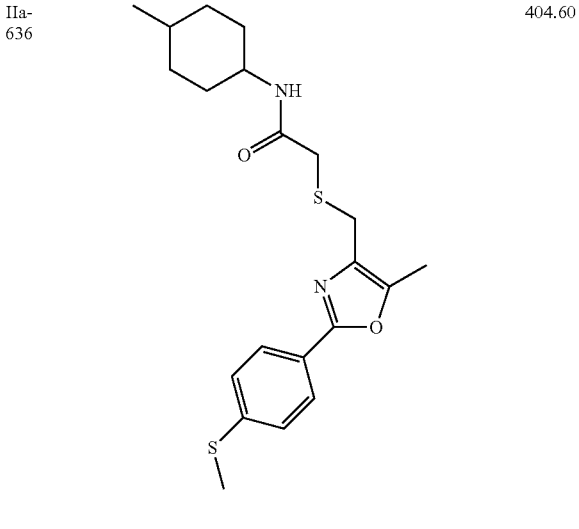 | 404.60 |
| IIa-637 | 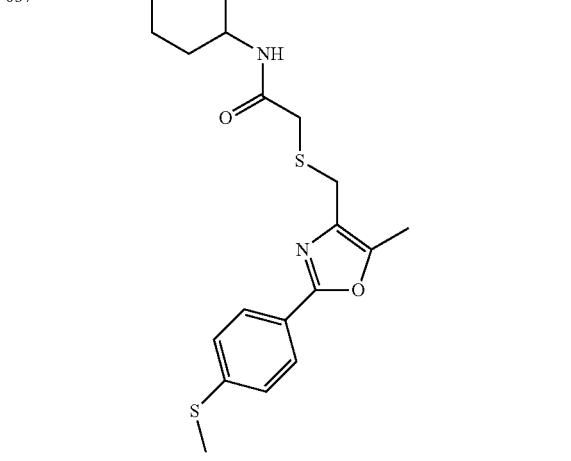 | 404.60 |
TABLE 4-continued
Oxazole amides ($R^3$ = NH-$C_3$-$C_7$cycloalkyl)
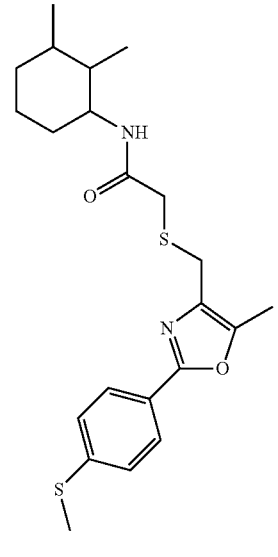 [SMILES: CSc1ccc(-c2nc(CSCC(=O)NC3CCCC(C)C3C)c(C)o2)cc1]
| ID | Structure | MW |
|---|---|---|
| IIa-638 | 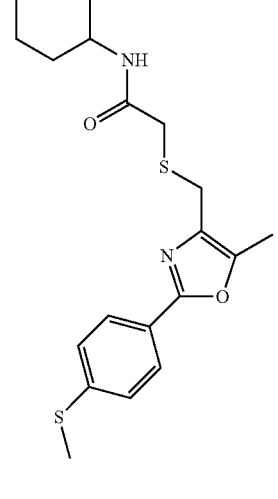 | 418.62 |
| IIa-639 | 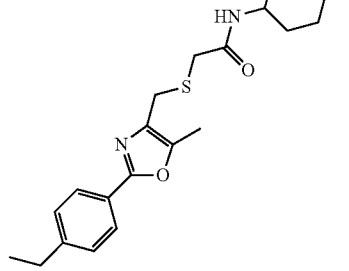 | 390.57 |
| IIa-640 | | 386.56 |

TABLE 4-continued

Oxazole amides ($R^3$ = NH-$C_3$-$C_7$cycloalkyl)

| ID | Structure | MW |
|---|---|---|
| IIa-641 | | 376.50 |
| IIa-642 | | 390.52 |
| IIa-643 | | 362.47 |

TABLE 4-continued

Oxazole amides ($R^3$ = NH-$C_3$-$C_7$cycloalkyl)

| ID | Structure | MW |
|---|---|---|
| IIa-644 | | 372.53 |
| IIa-645 | | 372.53 |

TABLE 4-continued

Oxazole amides (R³ = NH-C₃-C₇cycloalkyl)

| ID | Structure | MW |
|---|---|---|
| IIa-646 | 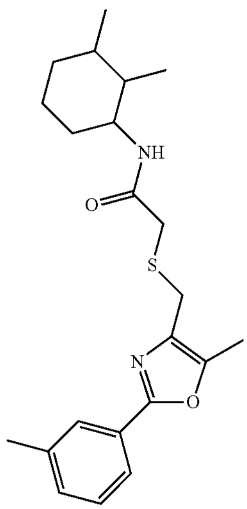 | 386.56 |
| IIa-647 | 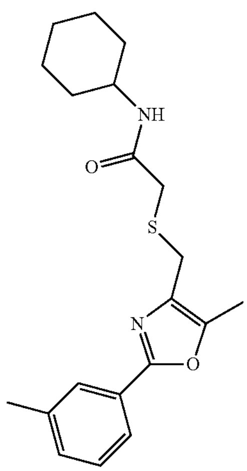 | 358.51 |
| IIa-648 | 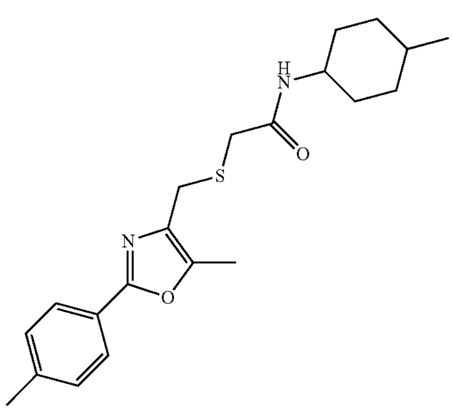 | 372.53 |
| IIa-649 | | 372.53 |
| IIa-650 | | 404.53 |
| IIa-651 | | 418.56 |

TABLE 4-continued

Oxazole amides (R³ = NH-C₃-C₇cycloalkyl)

| ID | Structure | MW |
|---|---|---|
| IIa-652 | 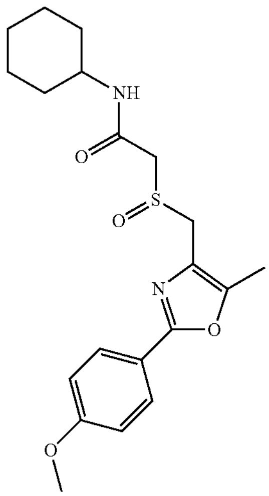 [SMILES: COc1ccc(-c2nc(CS(=O)CC(=O)NC3CCCCC3)c(C)o2)cc1] | 390.51 |
| IIa-653 | 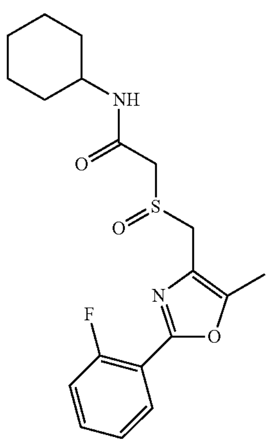 [SMILES: Cc1oc(-c2ccccc2F)nc1CS(=O)CC(=O)NC1CCCCC1] | 378.47 |
| IIa-654 | 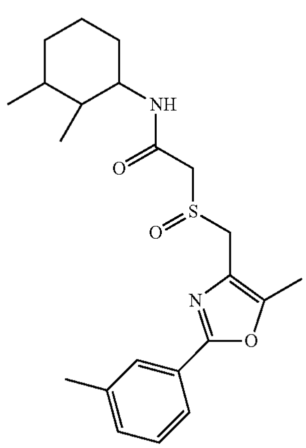 | 402.56 |
| IIa-655 | | 374.51 |
| IIa-656 | | 388.53 |
| IIa-657 | | 402.56 |

TABLE 4-continued

Oxazole amides (R³ = NH-C₃-C₇cycloalkyl)

| ID | Structure | MW |
|---|---|---|
| IIa-658 | 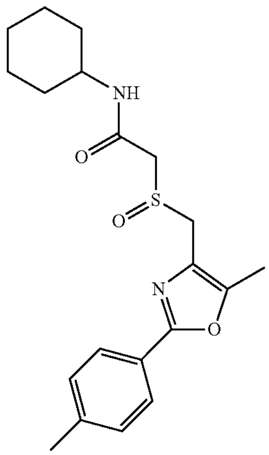 [SMILES: Cc1ccc(-c2nc(CS(=O)CC(=O)NC3CCCCC3)c(C)o2)cc1] | 374.51 |
| IIa-659 | 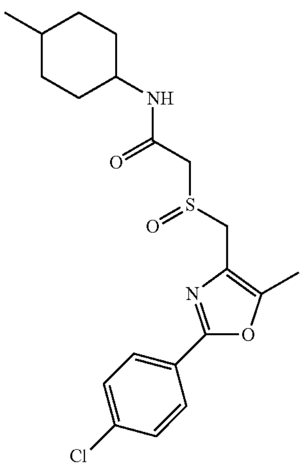 | 408.95 |
| IIa-660 | 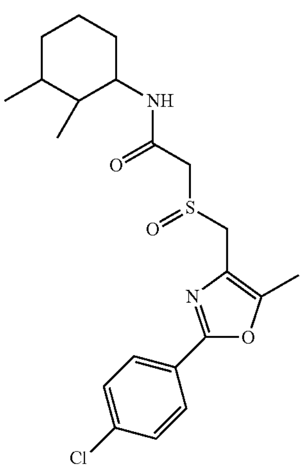 | 422.98 |
| IIa-661 | | 394.92 |
| IIa-662 | | 388.53 |
| IIa-663 | | 402.56 |

TABLE 4-continued

Oxazole amides (R³ = NH-C₃-C₇cycloalkyl)

| ID | Structure | MW |
|---|---|---|
| IIa-664 | 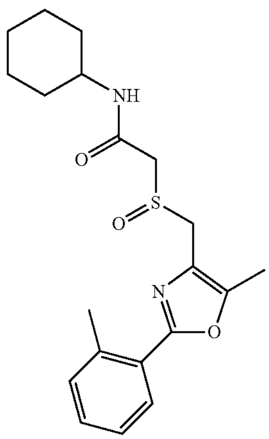 [SMILES: Cc1ccccc1-c1nc(CS(=O)CC(=O)NC2CCCCC2)c(C)o1] | 374.51 |
| IIa-665 | 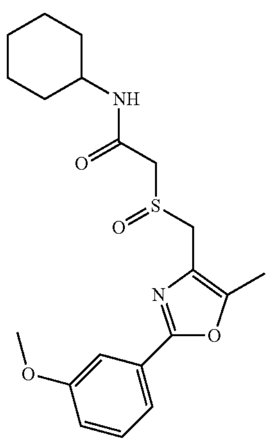 [SMILES: COc1cccc(-c2nc(CS(=O)CC(=O)NC3CCCCC3)c(C)o2)c1] | 390.51 |
| IIa-666 | 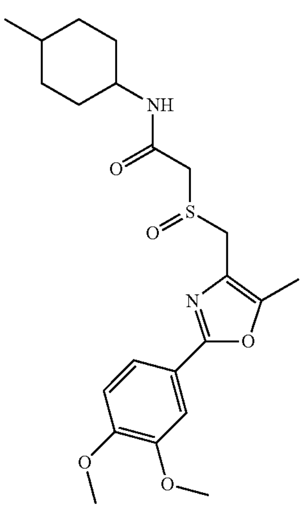 | 434.56 |
| IIa-667 | | 434.56 |
| IIa-668 | | 448.59 |

TABLE 4-continued

Oxazole amides (R³ = NH-C₃-C₇cycloalkyl)

| ID | Structure | MW |
|---|---|---|
| IIa-669 | 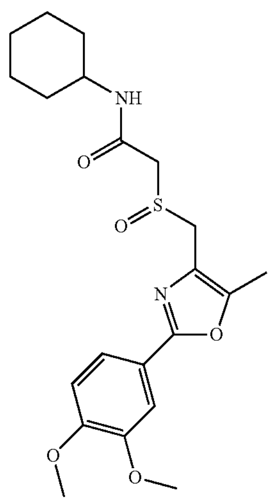 [SMILES: COc1ccc(-c2nc(CS(=O)CC(=O)NC3CCCCC3)c(C)o2)cc1OC] | 420.53 |
| IIa-670 | 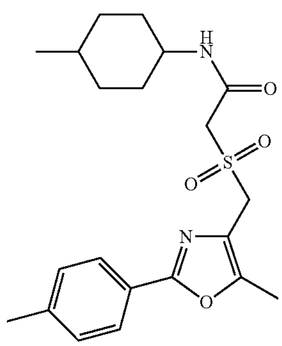 | 404.53 |
| IIa-671 | 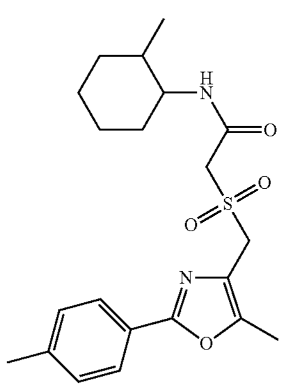 | 404.53 |
| IIa-672 | | 418.56 |
| IIa-673 | | 420.53 |
| IIa-674 | | 420.53 |

TABLE 4-continued

Oxazole amides (R³ = NH-C₃-C₇cycloalkyl)

| ID | Structure | MW |
|---|---|---|
| IIa-675 | 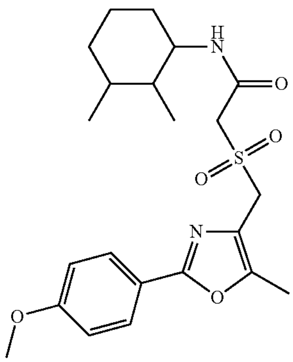 | 434.56 |
| IIa-676 | 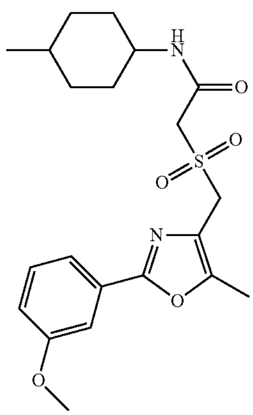 | 420.53 |
| IIa-677 | 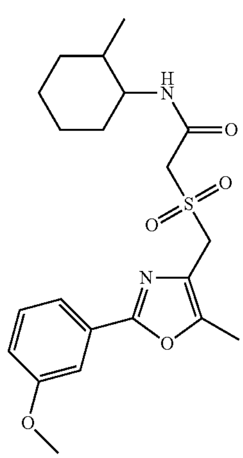 [SMILES: COc1cccc(-c2nc(CS(=O)(=O)CC(=O)NC3CCCCC3C)c(C)o2)c1] | 420.53 |
| IIa-678 | | 434.56 |
| IIa-679 | | 404.53 |
| IIa-680 | | 418.56 |

TABLE 4-continued
Oxazole amides (R³ = NH-C₃-C₇cycloalkyl)
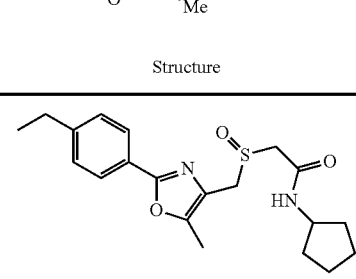
| ID | Structure | MW |
|---|---|---|
| IIa-681 | 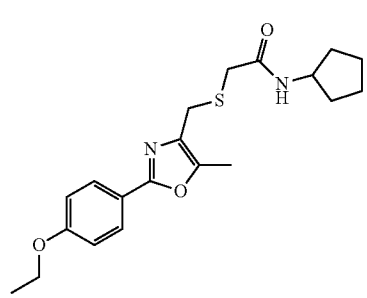 [SMILES: CCOc1ccc(-c2nc(CSCC(=O)NC3CCCC3)c(C)o2)cc1] | 422.52 |
| IIa-682 | 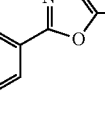 | 424.95 |
| IIa-683 |  | 438.98 |
| IIa-684 | 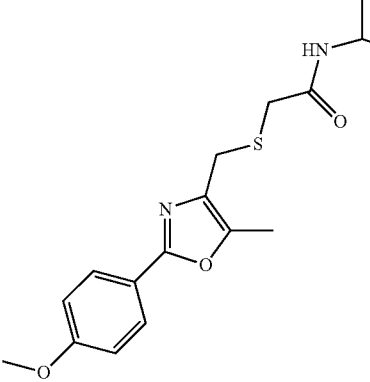 | 424.95 |
| IIa-685 | 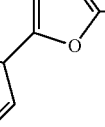 | 438.98 |
TABLE 4-continued
Oxazole amides (R³ = NH-C₃-C₇cycloalkyl)
| ID | Structure | MW |
|---|---|---|
| IIa-686 | 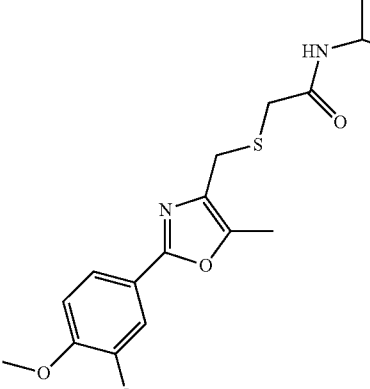 | 374.51 |
| IIa-687 | 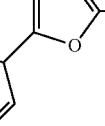 | 374.51 |
| IIa-688 |  | 360.48 |
| IIa-689 | | 390.51 |

TABLE 4-continued

Oxazole amides (R³ = NH-C₃-C₇cycloalkyl)

| ID | Structure | MW |
|---|---|---|
| IIa-690 | 2-(2-chlorophenyl)-5-methyloxazol-4-yl derivative | 364.90 |
| IIa-691 | 2-(4-(methylthio)phenyl)-5-methyloxazol-4-yl derivative | 376.54 |
| IIa-692 | 2-(4-ethylphenyl)-5-methyloxazol-4-yl derivative | 358.51 |
| IIa-693 | 2-(3-chlorophenyl)-5-methyloxazol-4-yl derivative | 364.90 |
| IIa-694 | 2-(2-fluorophenyl)-5-methyloxazol-4-yl derivative | 348.44 |
| IIa-695 | 2-(4-methylphenyl)-5-methyloxazol-4-yl derivative | 344.48 |

TABLE 4-continued

Oxazole amides (R³ = NH-C₃-C₇cycloalkyl)

| ID | Structure | MW |
|---|---|---|
| IIa-696 | (cyclopentyl-NH-C(O)-CH₂-S(O)-CH₂-[5-methyl-2-(4-methoxyphenyl)oxazol-4-yl]) | 376.48 |
| IIa-697 | (cyclopentyl-NH-C(O)-CH₂-S(O)-CH₂-[5-methyl-2-(2-fluorophenyl)oxazol-4-yl]) | 364.44 |
| IIa-698 | (cyclopentyl-NH-C(O)-CH₂-S(O)-CH₂-[5-methyl-2-(3-methylphenyl)oxazol-4-yl]) | 360.48 |
| IIa-699 | (cyclopentyl-NH-C(O)-CH₂-S(O)-CH₂-[5-methyl-2-(4-methylphenyl)oxazol-4-yl]) | 360.48 |
| IIa-700 | (cyclopentyl-NH-C(O)-CH₂-S(O)-CH₂-[5-methyl-2-(4-chlorophenyl)oxazol-4-yl]) | 380.90 |
| IIa-701 | (cyclopentyl-NH-C(O)-CH₂-S(O)-CH₂-[5-methyl-2-(2-methylphenyl)oxazol-4-yl]) | 360.48 |

TABLE 4-continued

Oxazole amides (R³ = NH-C₃-C₇cycloalkyl)

| ID | Structure | MW |
|---|---|---|
| IIa-702 | 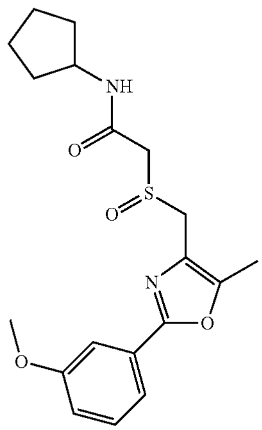 [SMILES: COc1cccc(-c2nc(CS(=O)CC(=O)NC3CCCC3)c(C)o2)c1] | 376.48 |
| IIa-703 | 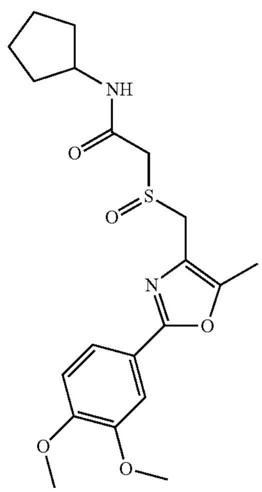 [SMILES: COc1ccc(-c2nc(CS(=O)CC(=O)NC3CCCC3)c(C)o2)cc1OC] | 406.50 |
| IIa-704 | 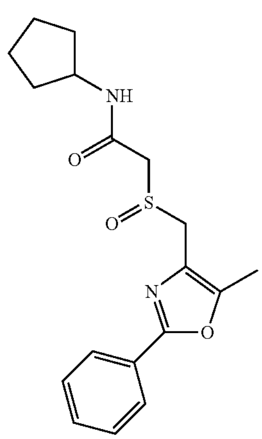 [SMILES: Cc1oc(-c2ccccc2)nc1CS(=O)CC(=O)NC1CCCC1] | 346.45 |
| IIa-705 | 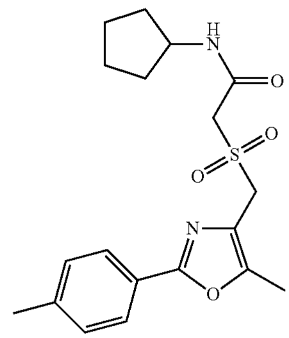 | 376.48 |
| IIa-706 | 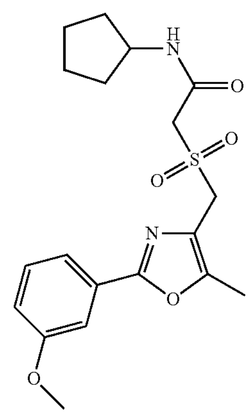 [SMILES: COc1cccc(-c2nc(CS(=O)(=O)CC(=O)NC3CCCC3)c(C)o2)c1] | 392.48 |
| IIa-707 | 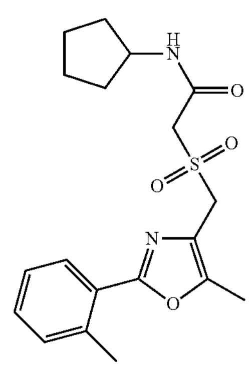 [SMILES: Cc1ccccc1-c1nc(CS(=O)(=O)CC(=O)NC2CCCC2)c(C)o1] | 376.48 |

TABLE 4-continued

Oxazole amides ($R^3$ = NH-$C_3$-$C_7$cycloalkyl)

| ID | Structure | MW |
|---|---|---|
| IIa-708 | 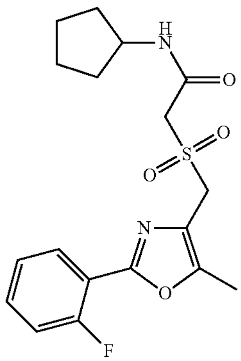 [SMILES: Cc1oc(-c2ccccc2F)nc1CS(=O)(=O)CC(=O)NC1CCCC1] | 380.44 |
| IIa-709 | 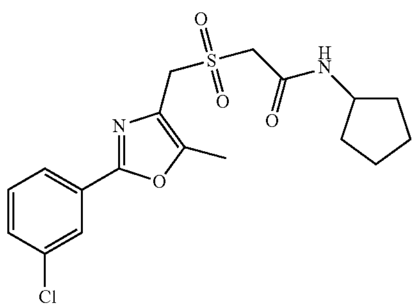 [SMILES: Cc1oc(-c2cccc(Cl)c2)nc1CS(=O)(=O)CC(=O)NC1CCCC1] | 396.90 |
| IIa-710 | 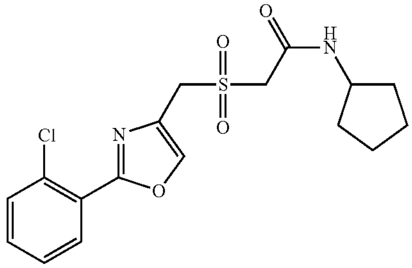 [SMILES: O=C(CS(=O)(=O)Cc1coc(-c2ccccc2Cl)n1)NC1CCCC1] | 396.90 |
| IIa-711 | 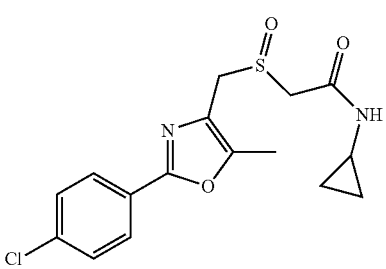 [SMILES: Cc1oc(-c2ccc(Cl)cc2)nc1CS(=O)CC(=O)NC1CC1] | 352.84 |
| IIa-712 | 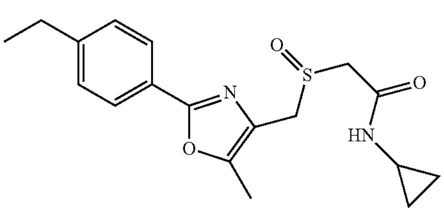 [SMILES: CCc1ccc(-c2nc(CS(=O)CC(=O)NC3CC3)c(C)o2)cc1] | 346.45 |
| IIa-713 | | 346.45 |
| IIa-714 | | 362.45 |
| IIa-715 | | 336.84 |

TABLE 4-continued

Oxazole amides (R³ = NH-C₃-C₇cycloalkyl)

| ID | Structure | MW |
|---|---|---|
| IIa-716 | 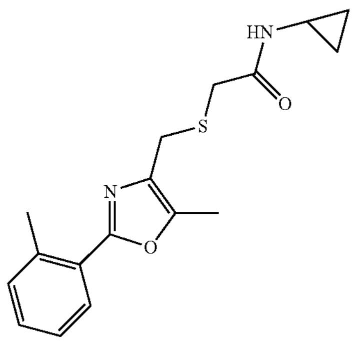 [SMILES: Cc1ccccc1-c1nc(CSCC(=O)NC2CC2)c(C)o1] | 316.43 |
| IIa-717 | 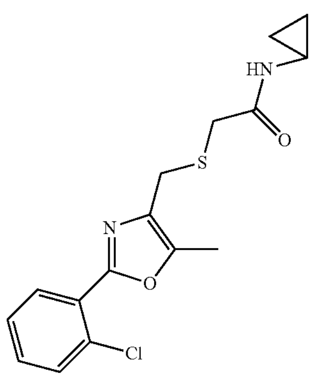 [SMILES: Cc1oc(-c2ccccc2Cl)nc1CSCC(=O)NC1CC1] | 336.84 |
| IIa-718 | 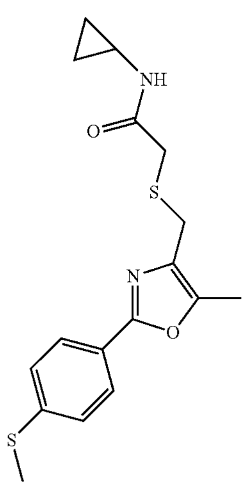 [SMILES: CSc1ccc(-c2nc(CSCC(=O)NC3CC3)c(C)o2)cc1] | 348.49 |
| IIa-719 | | 330.45 |
| IIa-720 | | 320.39 |
| IIa-721 | | 316.43 |

TABLE 4-continued
Oxazole amides (R³ = NH-C₃-C₇cycloalkyl)
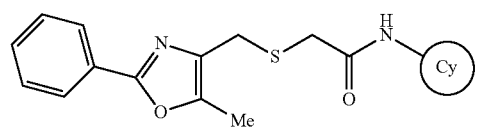
| ID | Structure | MW |
|---|---|---|
| IIa-722 | 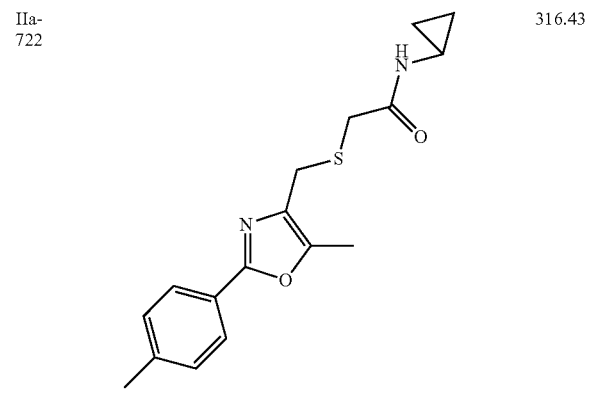 | 316.43 |
| IIa-723 | 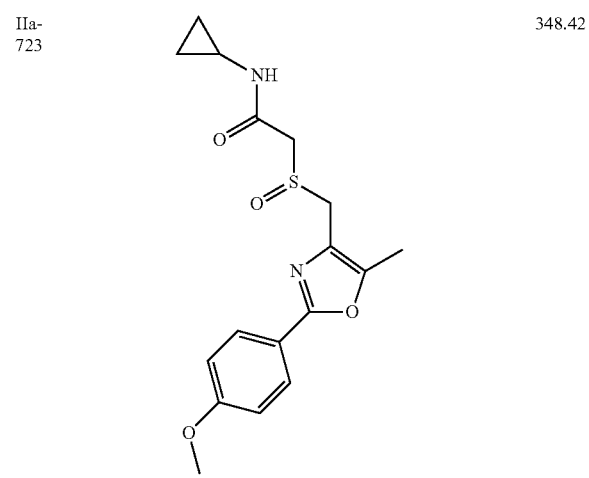 | 348.42 |
| IIa-724 | 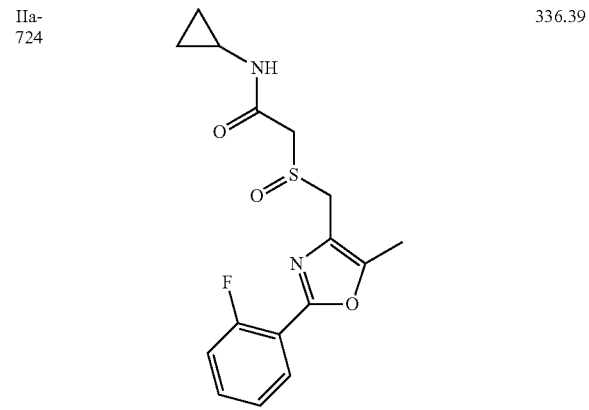 | 336.39 |
TABLE 4-continued
Oxazole amides (R³ = NH-C₃-C₇cycloalkyl)
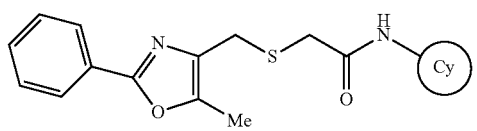
| ID | Structure | MW |
|---|---|---|
| IIa-725 | 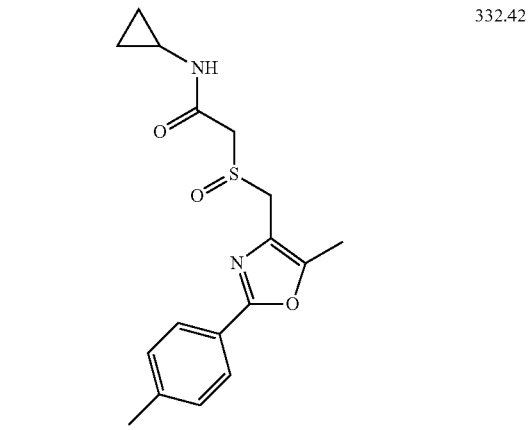 | 332.42 |
| IIa-726 | 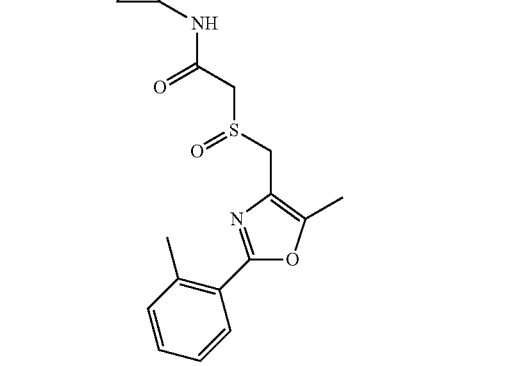 | 332.42 |
| IIa-727 | 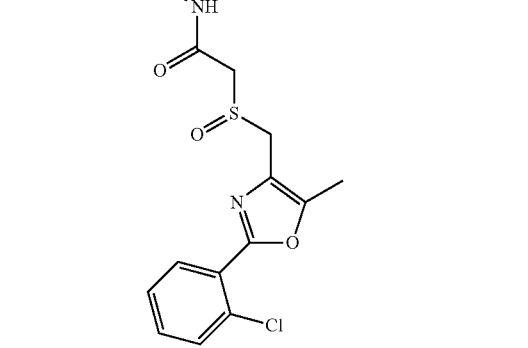 | 352.84 |

TABLE 4-continued

Oxazole amides (R³ = NH-C₃-C₇cycloalkyl)

| ID | Structure | MW |
|---|---|---|
| IIa-728 | 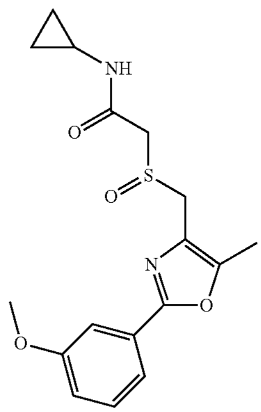 | 348.42 |
| IIa-729 | 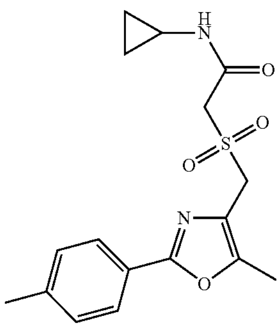 | 348.42 |
| IIa-730 | 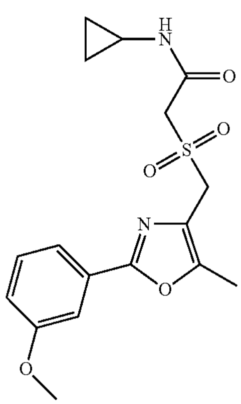 [SMILES: COc1cccc(-c2nc(CS(=O)(=O)CC(=O)NC3CC3)c(C)o2)c1] | 364.42 |
| IIa-731 | | 348.42 |
| IIa-732 | | 368.84 |
| IIa-733 | | 336.84 |

TABLE 5

Oxazole amides ($R^3$ = NH-misc)

| ID | Structure | MW |
|---|---|---|
| IIa-1001 | 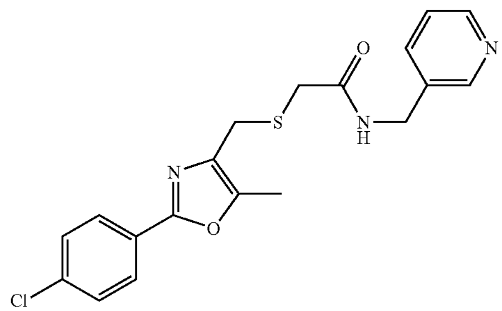 [SMILES: Cc1oc(-c2ccc(Cl)cc2)nc1CSCC(=O)NCc1cccnc1] | 387.89 |
| IIa-1002 | 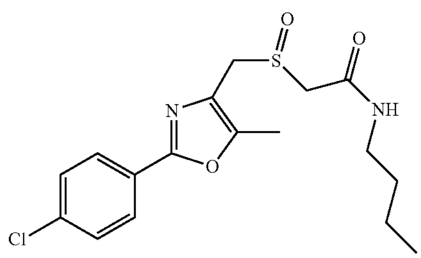 [SMILES: CCCCNC(=O)CS(=O)Cc1nc(-c2ccc(Cl)cc2)oc1C] | 368.89 |
| IIa-1003 | 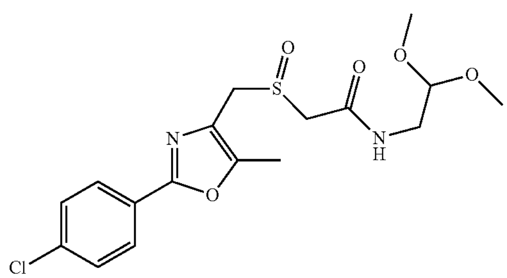 [SMILES: COC(CNC(=O)CS(=O)Cc1nc(-c2ccc(Cl)cc2)oc1C)OC] | 400.88 |
| IIa-1004 | 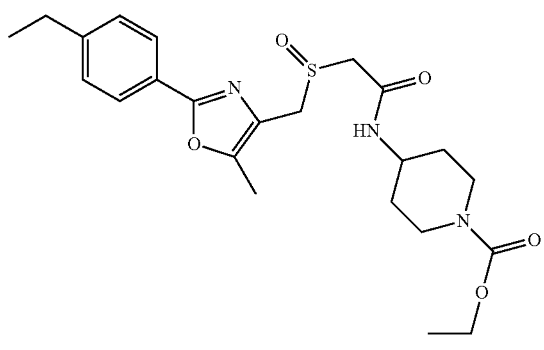 [SMILES: CCOC(=O)N1CCC(NC(=O)CS(=O)Cc2nc(-c3ccc(CC)cc3)oc2C)CC1] | 461.58 |
| IIa-1005 | 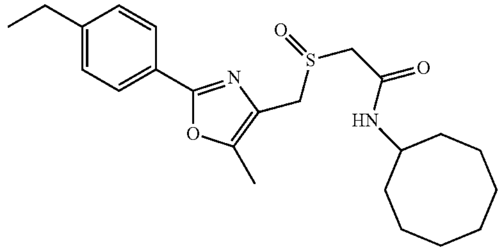 [SMILES: CCc1ccc(-c2nc(CS(=O)CC(=O)NC3CCCCCCC3)c(C)o2)cc1] | 416.59 |

TABLE 5-continued

Oxazole amides (R³ = NH-misc)

| ID | Structure | MW |
|---|---|---|
| IIa-1006 | 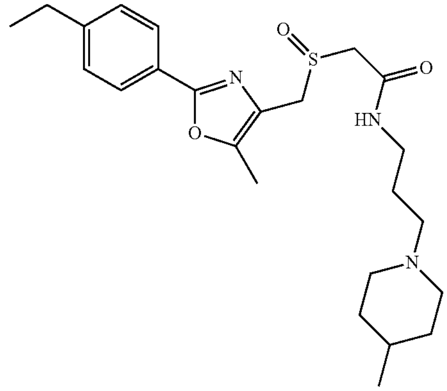 [SMILES: CCc1ccc(-c2nc(CS(=O)CC(=O)NCCCN3CCC(C)CC3)c(C)o2)cc1] | 445.63 |
| IIa-1007 | 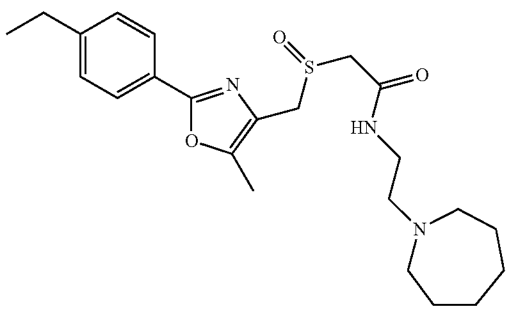 [SMILES: CCc1ccc(-c2nc(CS(=O)CC(=O)NCCN3CCCCCC3)c(C)o2)cc1] | 431.60 |
| IIa-1008 | 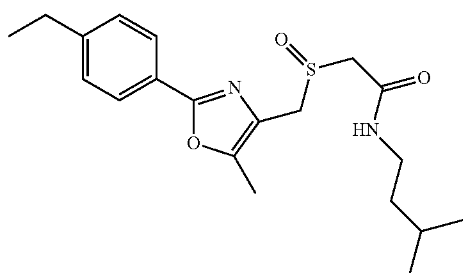 [SMILES: CCc1ccc(-c2nc(CS(=O)CC(=O)NCCC(C)C)c(C)o2)cc1] | 376.52 |
| IIa-1009 | 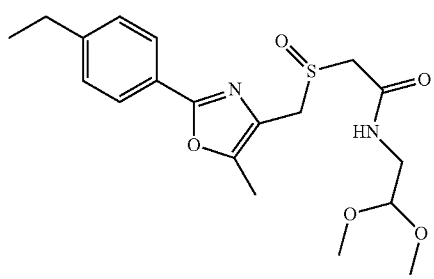 [SMILES: CCc1ccc(-c2nc(CS(=O)CC(=O)NCC(OC)OC)c(C)o2)cc1] | 394.49 |

TABLE 5-continued

Oxazole amides (R³ = NH-misc)

| ID | Structure | MW |
|---|---|---|
| IIa-1010 | 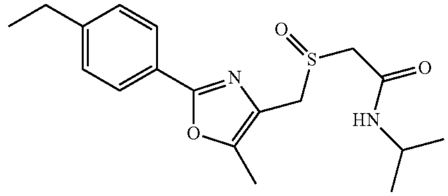 [SMILES: CCc1ccc(-c2nc(CS(=O)CC(=O)NC(C)C)c(C)o2)cc1] | 348.47 |
| IIa-1011 | 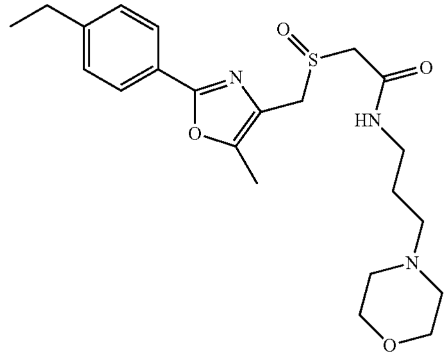 [SMILES: CCc1ccc(-c2nc(CS(=O)CC(=O)NCCCN3CCOCC3)c(C)o2)cc1] | 433.57 |
| IIa-1012 | 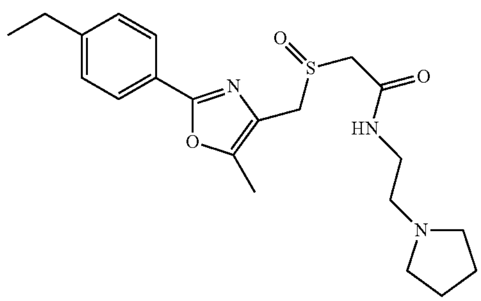 [SMILES: CCc1ccc(-c2nc(CS(=O)CC(=O)NCCN3CCCC3)c(C)o2)cc1] | 403.55 |
| IIa-1013 | 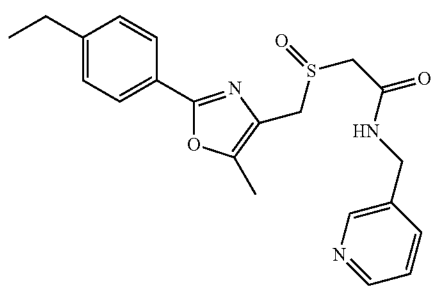 [SMILES: CCc1ccc(-c2nc(CS(=O)CC(=O)NCc3cccnc3)c(C)o2)cc1] | 397.50 |
| IIa-1014 | 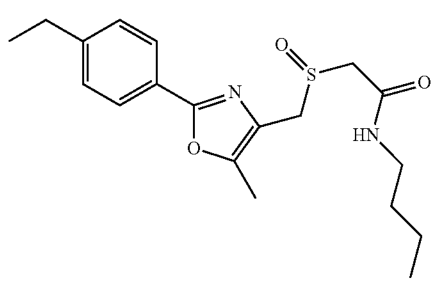 [SMILES: CCCCNC(=O)CS(=O)Cc1nc(-c2ccc(CC)cc2)oc1C] | 362.49 |

TABLE 5-continued

Oxazole amides (R³ = NH-misc)

| ID | Structure | MW |
|---|---|---|
| IIa-1015 | | 378.49 |
| IIa-1016 | | 386.47 |
| IIa-1017 | | 362.49 |
| IIa-1018 | | 434.67 |

TABLE 5-continued

Oxazole amides (R³ = NH-misc)

| ID | Structure | MW |
|---|---|---|
| IIa-1019 | 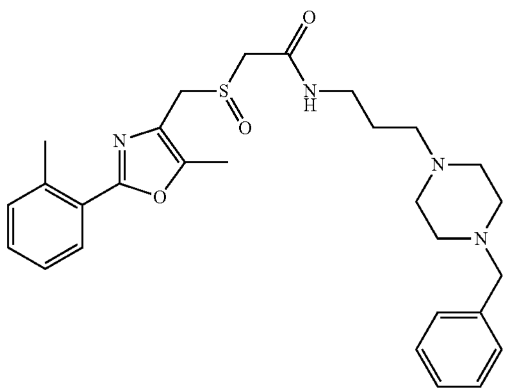 [SMILES: Cc1ccccc1-c1nc(CS(=O)CC(=O)NCCCN2CCN(Cc3ccccc3)CC2)c(C)o1] | 508.69 |
| IIa-1020 | 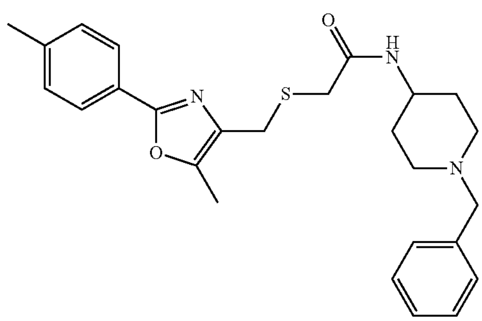 [SMILES: Cc1ccc(-c2nc(CSCC(=O)NC3CCN(Cc4ccccc4)CC3)c(C)o2)cc1] | 449.62 |
| IIa-1021 | 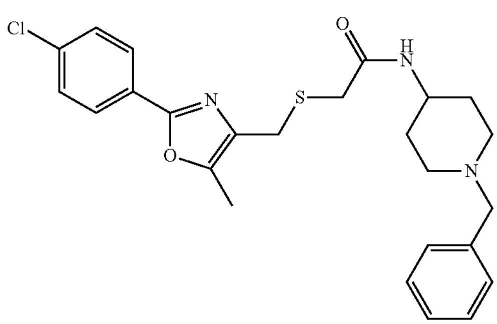 [SMILES: Cc1oc(-c2ccc(Cl)cc2)nc1CSCC(=O)NC1CCN(Cc2ccccc2)CC1] | 470.04 |
| IIa-1022 | 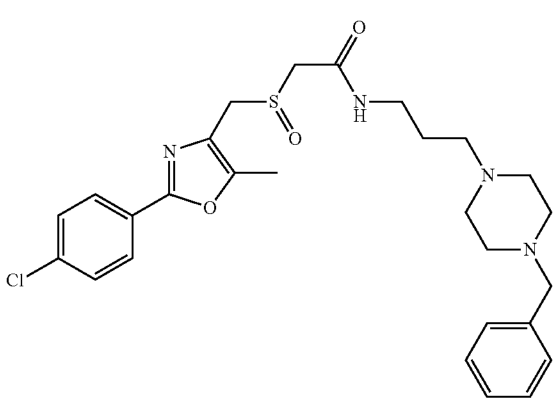 [SMILES: Cc1oc(-c2ccc(Cl)cc2)nc1CS(=O)CC(=O)NCCCN1CCN(Cc2ccccc2)CC1] | 529.11 |

TABLE 5-continued

Oxazole amides (R³ = NH-misc)

| ID | Structure | MW |
|---|---|---|
| IIa-1023 | | 436.64 |
| IIa-1024 | | 462.68 |
| IIa-1025 | | 508.69 |
| IIa-1026 | | 461.58 |

TABLE 5-continued

Oxazole amides (R³ = NH-misc)

| ID | Structure | MW |
|---|---|---|
| IIa-1027 | 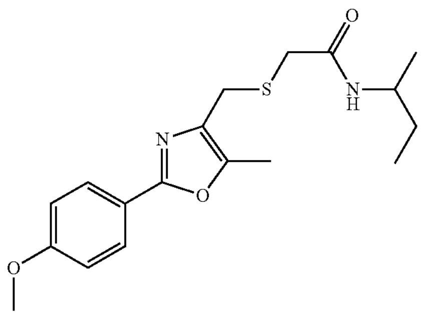 [SMILES: CCC(C)NC(=O)CSCc1nc(-c2ccc(OC)cc2)oc1C] | 362.49 |
| IIa-1028 | 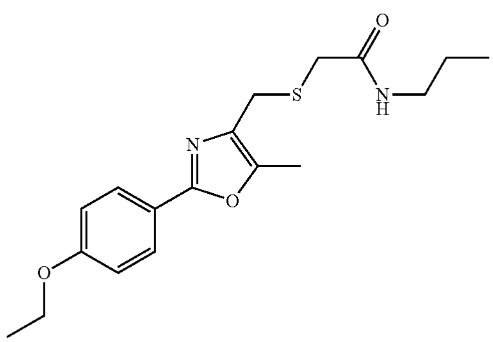 [SMILES: CCCNC(=O)CSCc1nc(-c2ccc(OCC)cc2)oc1C] | 348.47 |
| IIa-1029 | 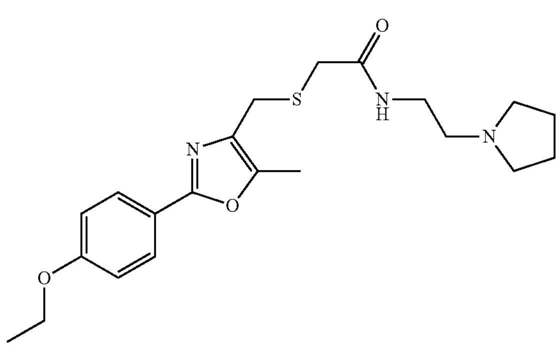 [SMILES: CCOc1ccc(-c2nc(CSCC(=O)NCCN3CCCC3)c(C)o2)cc1] | 403.55 |

TABLE 5-continued

Oxazole amides (R³ = NH-misc)

| ID | Structure | MW |
|---|---|---|
| IIa-1030 | | 529.11 |
| IIa-1031 | | 433.57 |
| IIa-1032 | | 397.50 |

TABLE 5-continued
Oxazole amides (R³ = NH-misc)
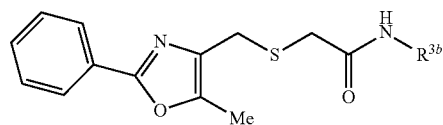
| ID | Structure | MW |
|---|---|---|
| IIa-1033 | | 362.49 |
| IIa-1034 | | 386.47 |
| IIa-1035 | | 406.55 |
| IIa-1036 | | 376.52 |

TABLE 5-continued
Oxazole amides (R³ = NH-misc)
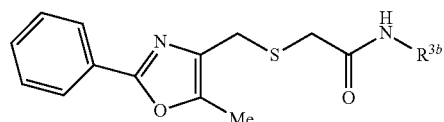
| ID | Structure | MW |
|---|---|---|
| IIa-1037 | 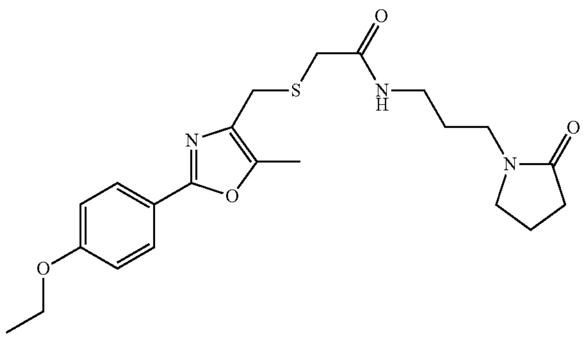 [SMILES: CCOc1ccc(-c2nc(CSCC(=O)NCCCN3CCCC3=O)c(C)o2)cc1] | 431.56 |
| IIa-1038 | 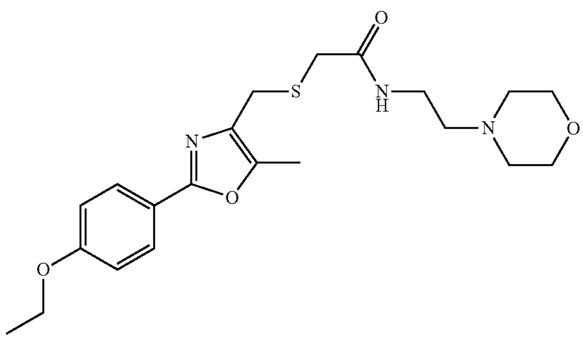 [SMILES: CCOc1ccc(-c2nc(CSCC(=O)NCCN3CCOCC3)c(C)o2)cc1] | 419.55 |
| IIa-1039 | 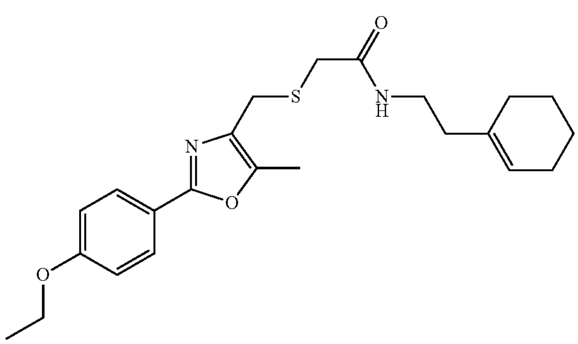 [SMILES: CCOc1ccc(-c2nc(CSCC(=O)NCCC3=CCCCC3)c(C)o2)cc1] | 414.57 |
| IIa-1040 | 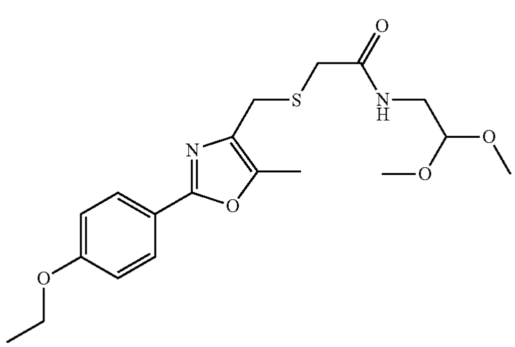 [SMILES: CCOc1ccc(-c2nc(CSCC(=O)NCC(OC)OC)c(C)o2)cc1] | 394.49 |

TABLE 5-continued

Oxazole amides (R³ = NH-misc)

| ID | Structure | MW |
|---|---|---|
| IIa-1041 | | 402.54 |
| IIa-1042 | | 438.59 |
| IIa-1043 | | 422.55 |
| IIa-1044 | | 417.57 |

TABLE 5-continued

Oxazole amides (R³ = NH-misc)

| ID | Structure | MW |
|---|---|---|
| IIa-1045 | | 348.47 |
| IIa-1046 | | 390.51 |
| IIa-1047 | | 508.69 |

TABLE 5-continued

Oxazole amides (R³ = NH-misc)

| ID | Structure | MW |
|---|---|---|
| IIa-1048 | 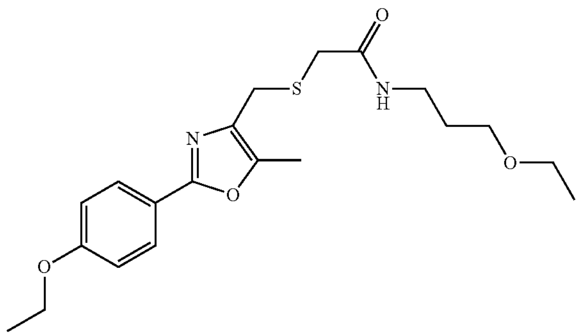 | 392.52 |
| IIa-1049 | 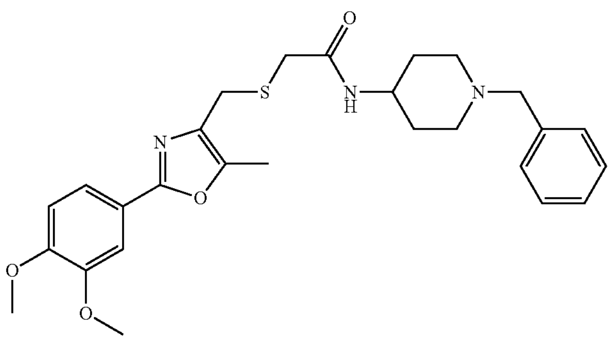 [SMILES: COc1ccc(-c2nc(CSCC(=O)NC3CCN(Cc4ccccc4)CC3)c(C)o2)cc1OC] | 495.65 |
| IIa-1050 | 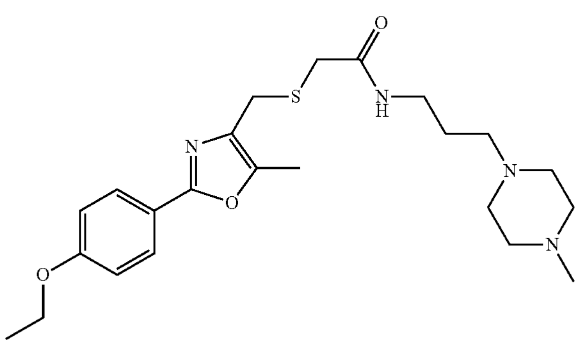 [SMILES: CCOc1ccc(-c2nc(CSCC(=O)NCCCN3CCN(C)CC3)c(C)o2)cc1] | 446.62 |
| IIa-1051 | 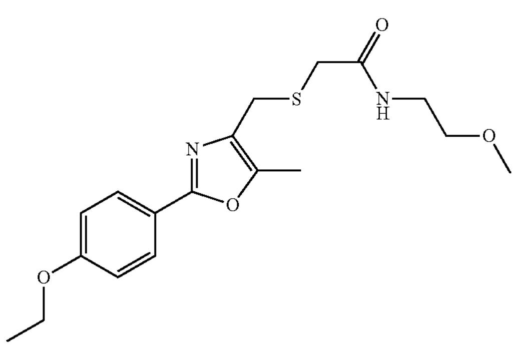 [SMILES: CCOc1ccc(-c2nc(CSCC(=O)NCCOC)c(C)o2)cc1] | 364.47 |

TABLE 5-continued
Oxazole amides (R³ = NH-misc)
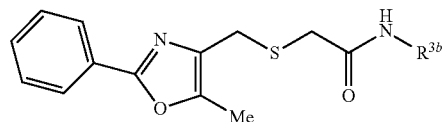
| ID | Structure | MW |
|---|---|---|
| IIa-1052 | 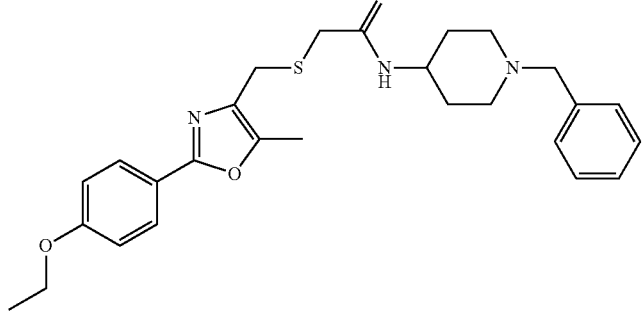 | 479.65 |
| IIa-1053 | 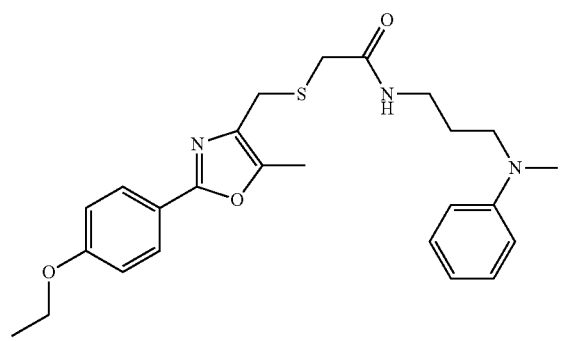 [SMILES: CCOc1ccc(-c2nc(CSCC(=O)NCCCN(C)c3ccccc3)c(C)o2)cc1] | 453.61 |
| IIa-1054 | 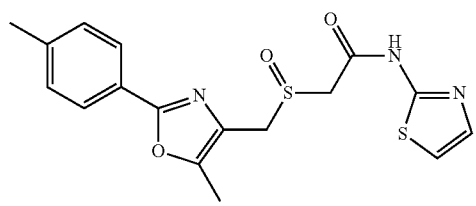 [SMILES: Cc1ccc(-c2nc(CS(=O)CC(=O)Nc3nccs3)c(C)o2)cc1] | 375.47 |
| IIa-1055 | 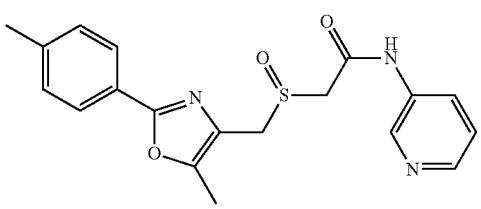 [SMILES: Cc1ccc(-c2nc(CS(=O)CC(=O)Nc3cccnc3)c(C)o2)cc1] | 369.45 |

TABLE 5-continued
Oxazole amides (R³ = NH-misc)
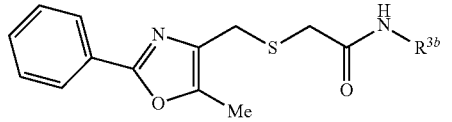
| ID | Structure | MW |
|---|---|---|
| IIa-1056 | 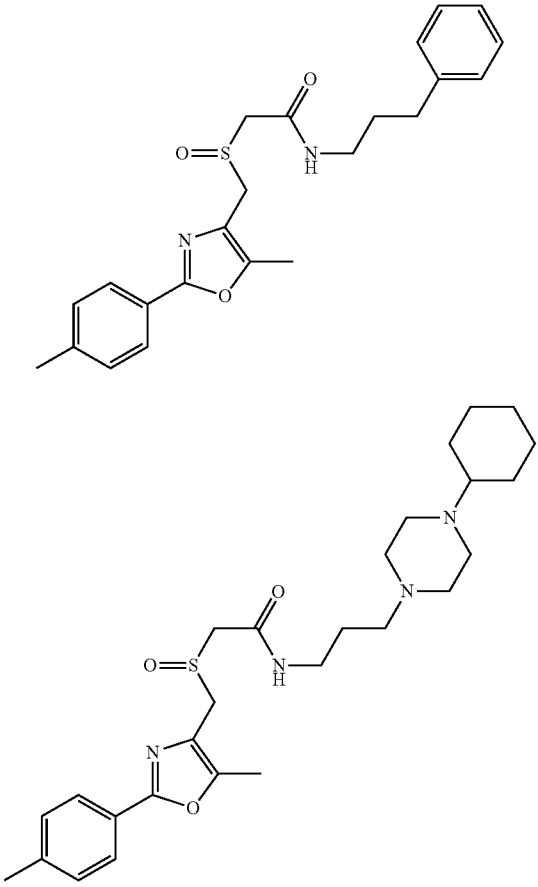 | 410.54 |
| IIa-1057 | | 500.71 |
| IIa-1058 | 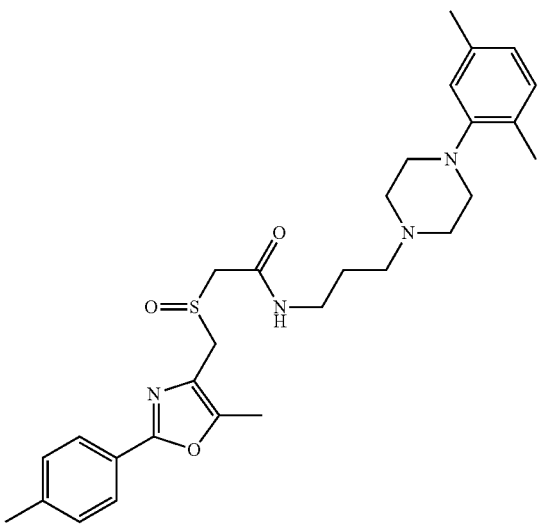 | 522.72 |

TABLE 5-continued

Oxazole amides (R³ = NH-misc)

| ID | Structure | MW |
|---|---|---|
| IIa-1059 | | 447.56 |
| IIa-1060 | | 408.52 |
| IIa-1061 | | 383.47 |

TABLE 5-continued
Oxazole amides (R³ = NH-misc)
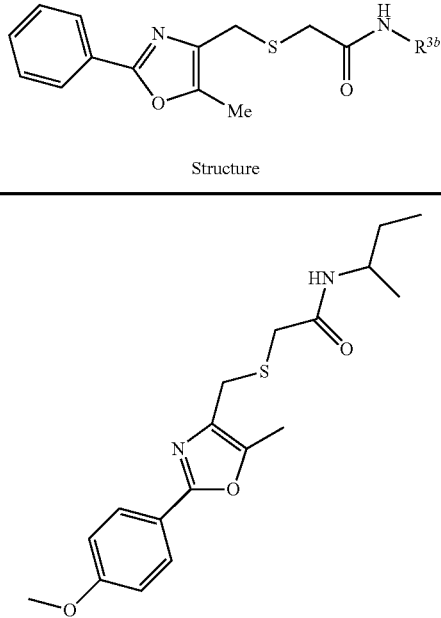
| ID | Structure | MW |
|---|---|---|
| IIa-1062 | 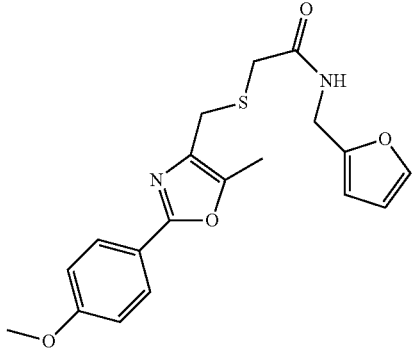 | 348.47 |
| IIa-1063 | 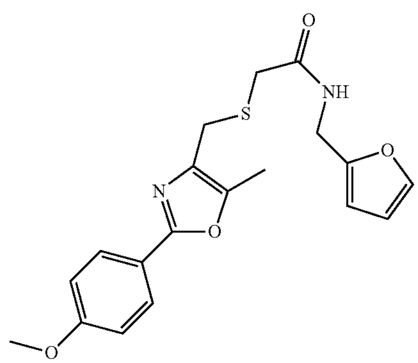 [SMILES: COc1ccc(-c2nc(CSCC(=O)NCc3ccco3)c(C)o2)cc1] | 372.45 |
| IIa-1064 | 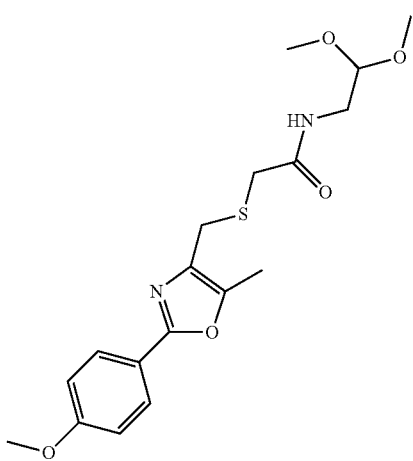 | 380.47 |

TABLE 5-continued

Oxazole amides (R³ = NH-misc)

| ID | Structure | MW |
|---|---|---|
| IIa-1065 | 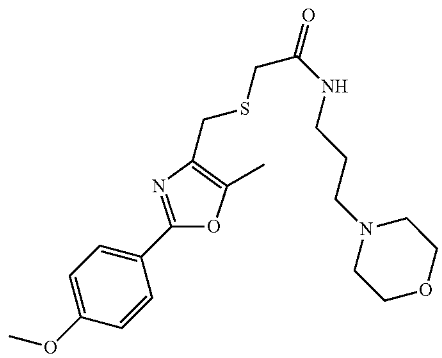 [SMILES: COc1ccc(-c2nc(CSCC(=O)NCCCN3CCOCC3)c(C)o2)cc1] | 419.55 |
| IIa-1066 | 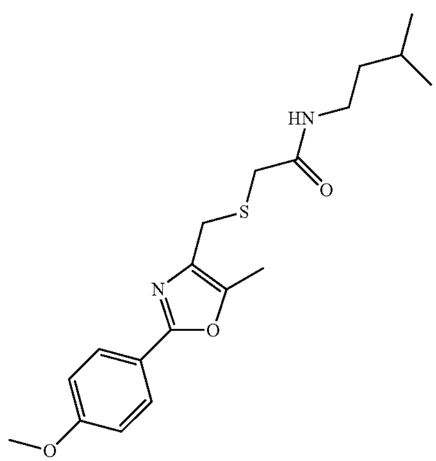 [SMILES: COc1ccc(-c2nc(CSCC(=O)NCCC(C)C)c(C)o2)cc1] | 362.49 |
| IIa-1067 | 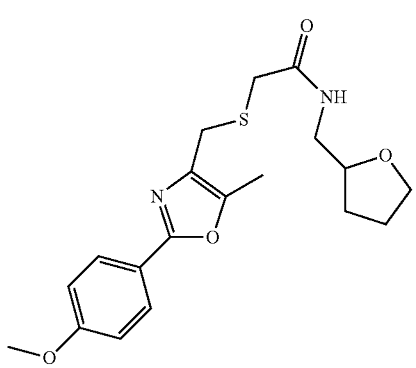 [SMILES: COc1ccc(-c2nc(CSCC(=O)NCC3CCCO3)c(C)o2)cc1] | 376.48 |

TABLE 5-continued

Oxazole amides (R³ = NH-misc)

| ID | Structure | MW |
|---|---|---|
| IIa-1068 | 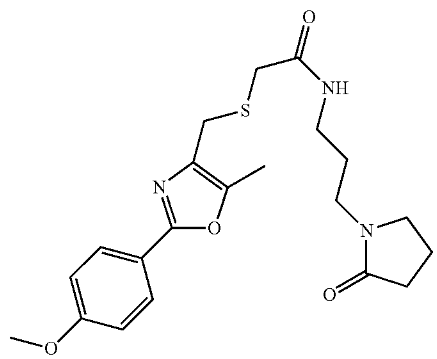 [SMILES: COc1ccc(-c2nc(CSCC(=O)NCCCN3CCCC3=O)c(C)o2)cc1] | 417.53 |
| IIa-1069 | 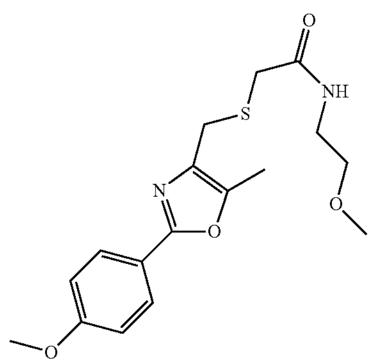 | 350.44 |
| IIa-1070 | 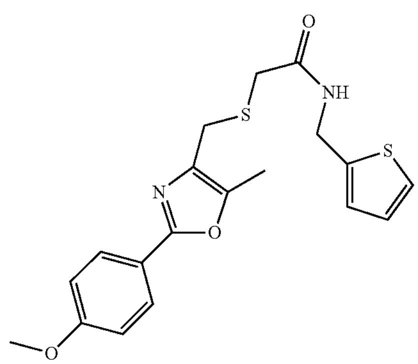 [SMILES: COc1ccc(-c2nc(CSCC(=O)NCc3cccs3)c(C)o2)cc1] | 388.51 |
| IIa-1071 | 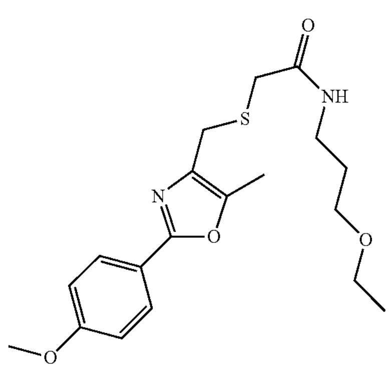 [SMILES: CCOCCCNC(=O)CSCc1nc(-c2ccc(OC)cc2)oc1C] | 378.49 |

TABLE 5-continued

Oxazole amides (R³ = NH-misc)

| ID | Structure | MW |
|---|---|---|
| IIa-1072 | | 400.54 |
| IIa-1073 | | 424.57 |
| IIa-1074 | | 364.47 |

TABLE 5-continued
Oxazole amides (R³ = NH-misc)
| ID | Structure | MW |
|---|---|---|
| IIa-1075 | 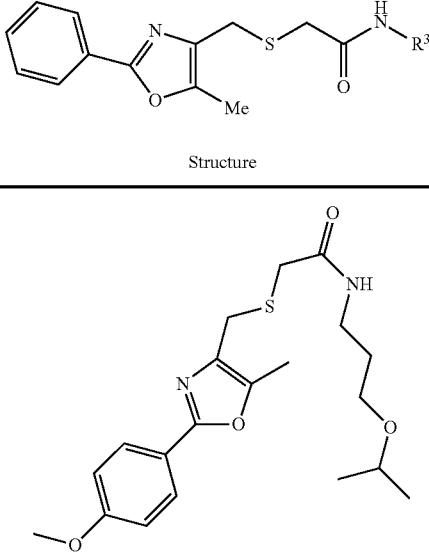 | 392.52 |
| IIa-1076 | 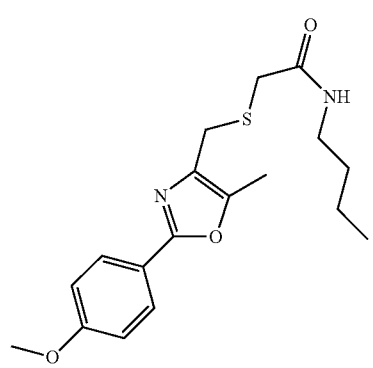 [SMILES: CCCCNC(=O)CSCc1nc(-c2ccc(OC)cc2)oc1C] | 348.47 |
| IIa-1077 | 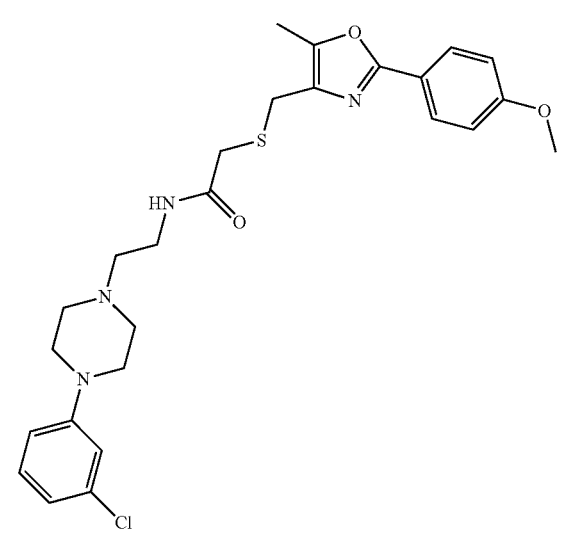 [SMILES: COc1ccc(-c2nc(CSCC(=O)NCCN3CCN(c4cccc(Cl)c4)CC3)c(C)o2)cc1] | 515.08 |

TABLE 5-continued
Oxazole amides (R³ = NH-misc)
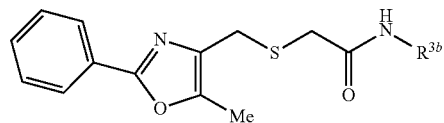
| ID | Structure | MW |
|---|---|---|
| IIa-1078 | 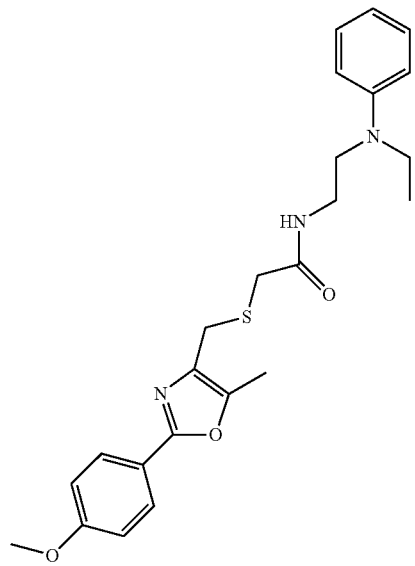 [SMILES: CCN(CCNC(=O)CSCc1nc(-c2ccc(OC)cc2)oc1C)c1ccccc1] | 439.58 |
| IIa-1079 | 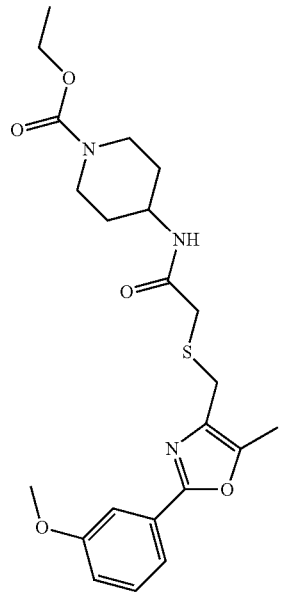 [SMILES: CCOC(=O)N1CCC(NC(=O)CSCc2nc(-c3cccc(OC)c3)oc2C)CC1] | 447.56 |

TABLE 5-continued
Oxazole amides (R³ = NH-misc)
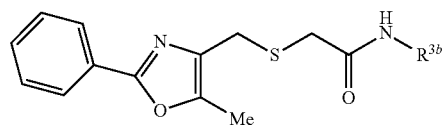
| ID | Structure | MW |
|---|---|---|
| IIa-1080 | | 334.44 |
| IIa-1081 | | 334.44 |
| IIa-1082 | | 376.48 |

TABLE 5-continued

Oxazole amides (R³ = NH-misc)

| ID | Structure | MW |
|---|---|---|
| IIa-1083 | | 378.49 |
| IIa-1084 | | 400.54 |

TABLE 5-continued
Oxazole amides (R³ = NH-misc)
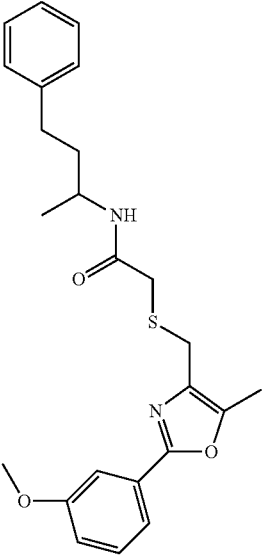
| ID | Structure | MW |
|---|---|---|
| IIa-1085 | 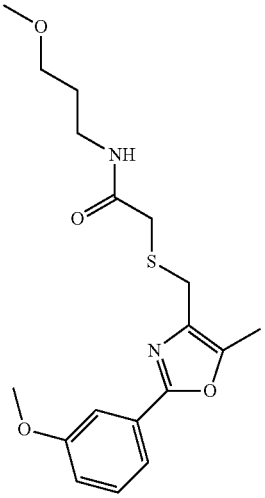 | 424.57 |
| IIa-1086 | | 364.47 |

TABLE 5-continued

Oxazole amides (R³ = NH-misc)

| ID | Structure | MW |
|---|---|---|
| IIa-1087 | | 405.52 |
| IIa-1088 | | 348.47 |

TABLE 5-continued
Oxazole amides (R³ = NH-misc)
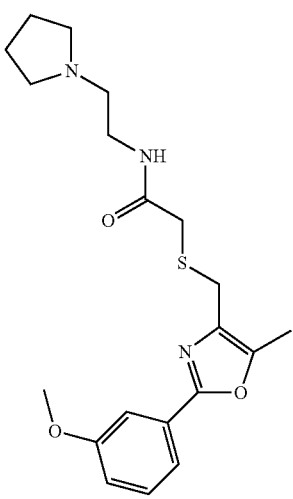 [SMILES: COc1cccc(-c2nc(CSCC(=O)NCCN3CCCC3)c(C)o2)c1]
| ID | Structure | MW |
|---|---|---|
| IIa-1089 | 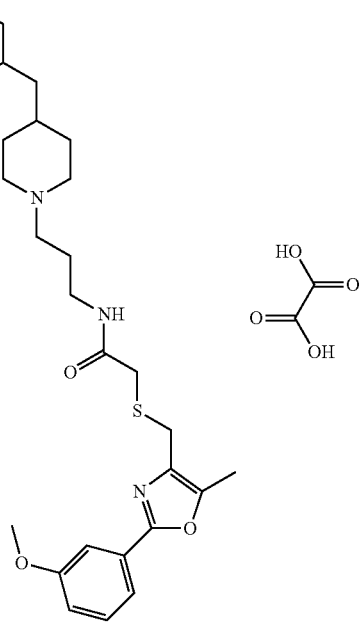 | 389.52 |
| IIa-1090 | | 597.74 |

TABLE 5-continued
Oxazole amides (R³ = NH-misc)
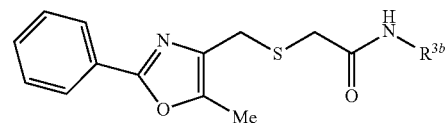
| ID | Structure | MW |
|---|---|---|
| IIa-1091 | 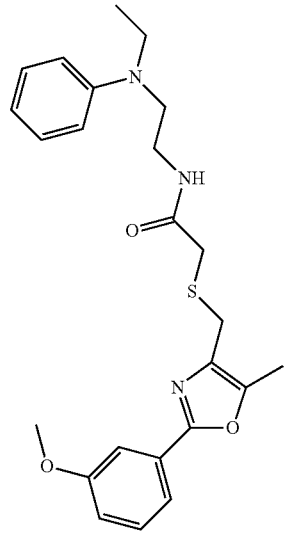 [SMILES: CCN(CCNC(=O)CSCc1nc(-c2cccc(OC)c2)oc1C)c1ccccc1] | 439.58 |
| IIa-1092 | 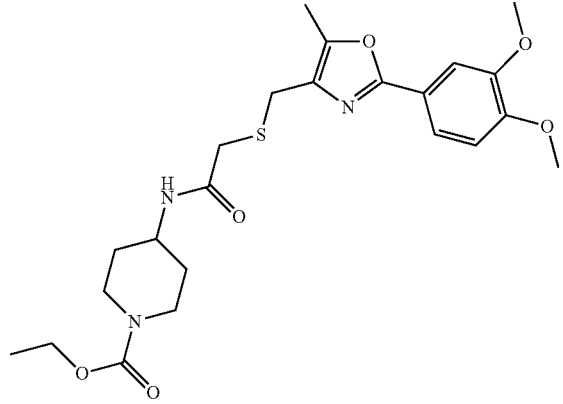 [SMILES: CCOC(=O)N1CCC(NC(=O)CSCc2nc(-c3ccc(OC)c(OC)c3)oc2C)CC1] | 477.58 |
| IIa-1093 | 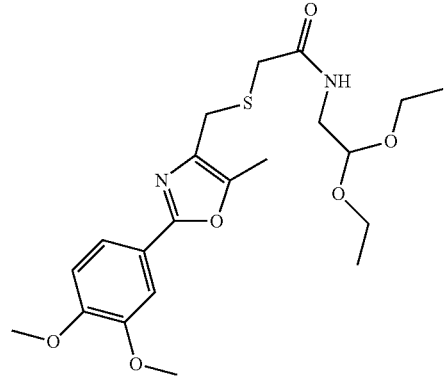 [SMILES: CCOC(CNC(=O)CSCc1nc(-c2ccc(OC)c(OC)c2)oc1C)OCC] | 438.55 |

TABLE 5-continued

Oxazole amides (R³ = NH-misc)

| ID | Structure | MW |
|---|---|---|
| IIa-1094 | | 413.50 |
| IIa-1095 | | 378.49 |
| IIa-1096 | | 364.47 |

TABLE 5-continued
Oxazole amides (R³ = NH-misc)
| ID | Structure | MW |
|---|---|---|
| IIa-1097 | 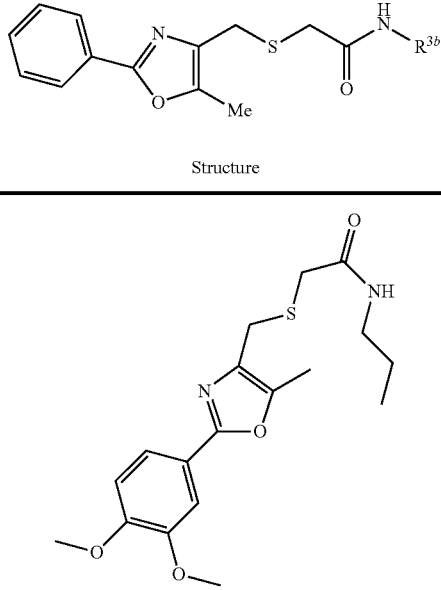 | 364.47 |
| IIa-1098 | 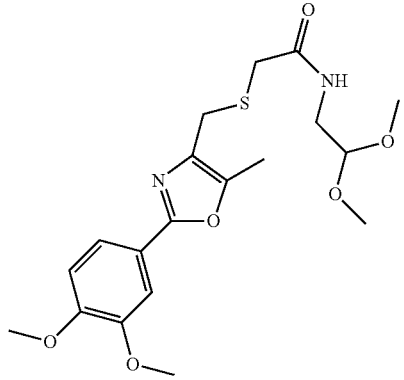 | 410.49 |
| IIa-1099 | 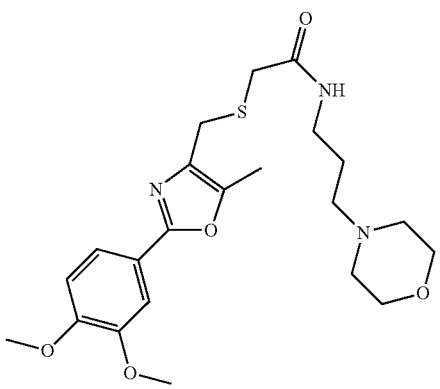 [SMILES: COc1ccc(-c2nc(CSCC(=O)NCCCN3CCOCC3)c(C)o2)cc1OC] | 449.57 |

TABLE 5-continued
Oxazole amides (R³ = NH-misc)
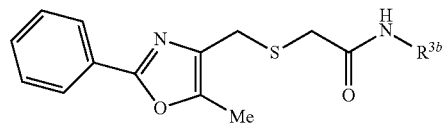
| ID | Structure | MW |
|---|---|---|
| IIa-1100 | 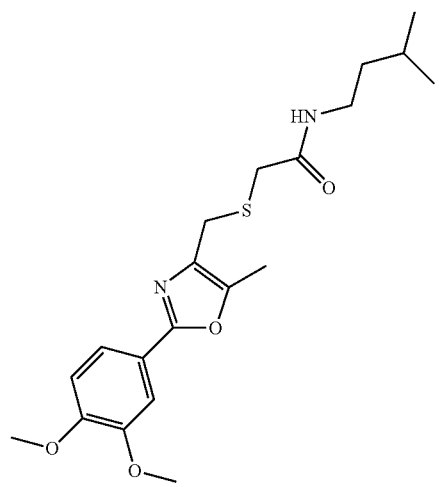 [SMILES: COc1ccc(-c2nc(CSCC(=O)NCCC(C)C)c(C)o2)cc1OC] | 392.52 |
| IIa-1101 | 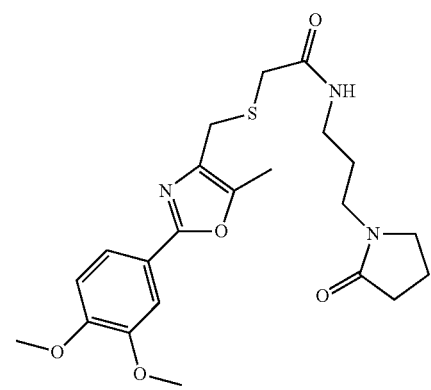 [SMILES: COc1ccc(-c2nc(CSCC(=O)NCCCN3CCCC3=O)c(C)o2)cc1OC] | 447.56 |
| IIa-1102 | 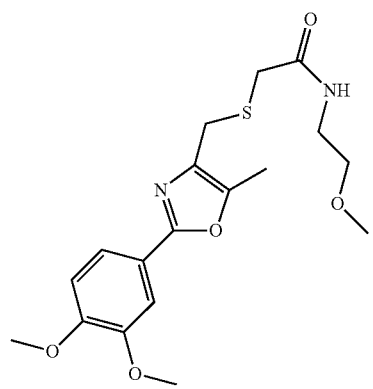 | 380.47 |

TABLE 5-continued
Oxazole amides (R³ = NH-misc)
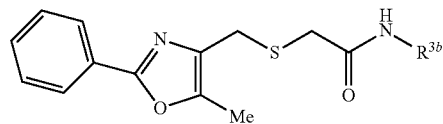
| ID | Structure | MW |
|---|---|---|
| IIa-1103 | | 408.52 |
| IIa-1104 | | 430.57 |
| IIa-1105 | | 394.49 |

TABLE 5-continued

Oxazole amides (R³ = NH-misc)

| ID | Structure | MW |
|---|---|---|
| IIa-1106 | | 435.55 |
| IIa-1107 | | 378.49 |
| IIa-1108 | | 475.66 |

TABLE 5-continued
Oxazole amides (R³ = NH-misc)
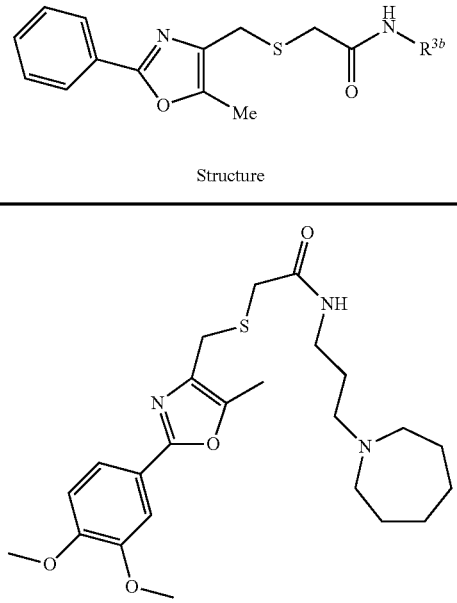
| ID | Structure | MW |
|---|---|---|
| IIa-1109 | 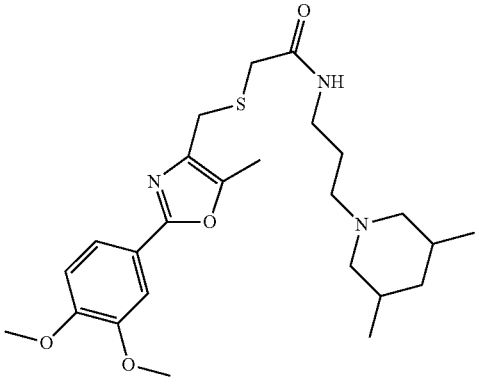 | 461.63 |
| IIa-1110 | 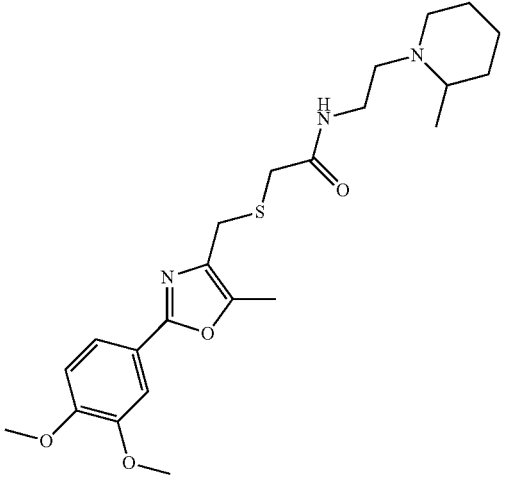 [SMILES: COc1ccc(-c2nc(CSCC(=O)NCCN3CCCCC3C)c(C)o2)cc1OC] | 475.66 |
| IIa-1111 | | 447.60 |

TABLE 5-continued

Oxazole amides (R³ = NH-misc)

| ID | Structure | MW |
|---|---|---|
| IIa-1112 | 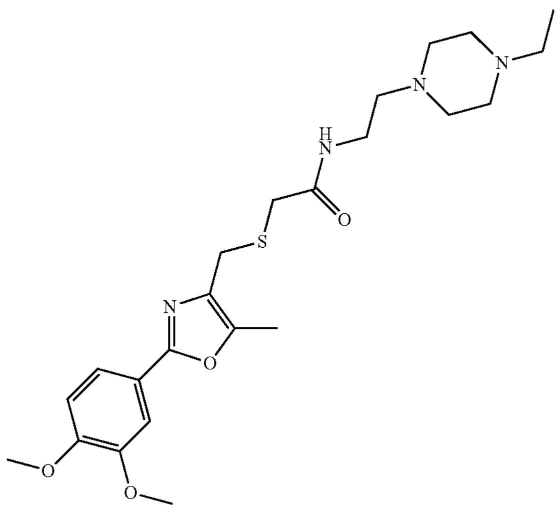 [SMILES: CCN1CCN(CCNC(=O)CSCc2nc(-c3ccc(OC)c(OC)c3)oc2C)CC1] | 462.62 |
| IIa-1113 | 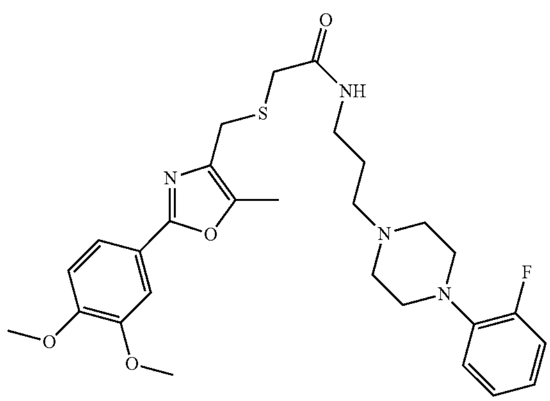 [SMILES: COc1ccc(-c2nc(CSCC(=O)NCCCN3CCN(c4ccccc4F)CC3)c(C)o2)cc1OC] | 542.68 |
| IIa-1114 | 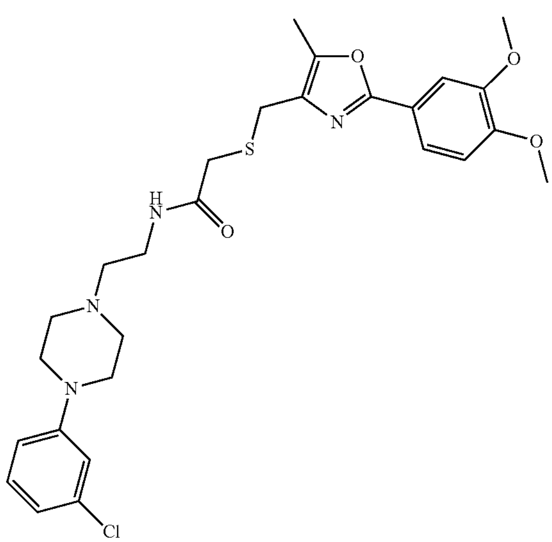 [SMILES: COc1ccc(-c2nc(CSCC(=O)NCCN3CCN(c4cccc(Cl)c4)CC3)c(C)o2)cc1OC] | 545.11 |

TABLE 5-continued
Oxazole amides (R³ = NH-misc)
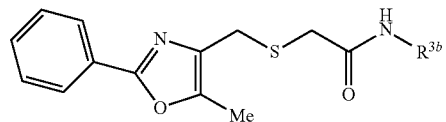
| ID | Structure | MW |
|---|---|---|
| IIa-1115 | 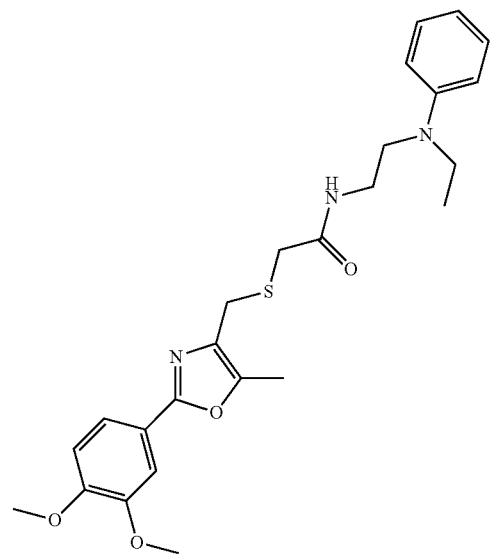 [SMILES: CCN(CCNC(=O)CSCc1nc(-c2ccc(OC)c(OC)c2)oc1C)c1ccccc1] | 469.61 |
| IIa-1116 | 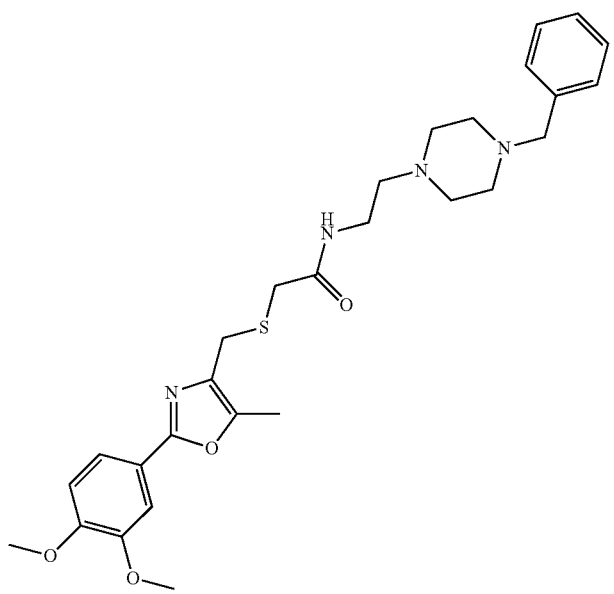 [SMILES: COc1ccc(-c2nc(CSCC(=O)NCCN3CCN(Cc4ccccc4)CC3)c(C)o2)cc1OC] | 524.69 |

TABLE 5-continued
Oxazole amides (R³ = NH-misc)
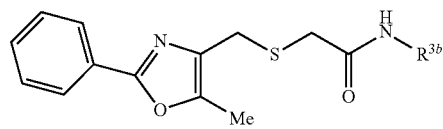
| ID | Structure | MW |
|---|---|---|
| IIa-1117 | 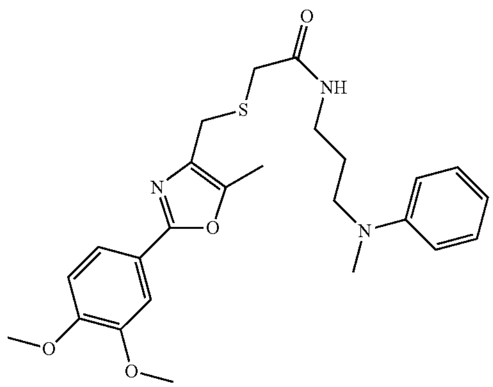 [SMILES: COc1ccc(-c2nc(CSCC(=O)NCCCN(C)c3ccccc3)c(C)o2)cc1OC] | 469.61 |
| IIa-1118 | 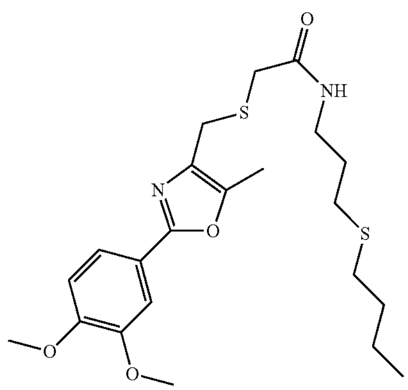 [SMILES: CCCCSCCCNC(=O)CSCc1nc(-c2ccc(OC)c(OC)c2)oc1C] | 452.64 |
| IIa-1119 | 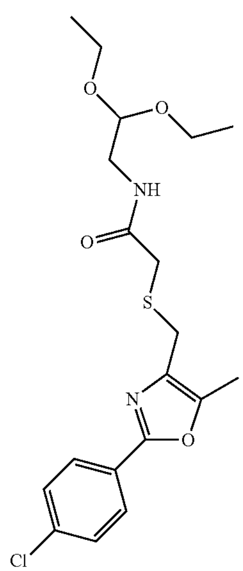 [SMILES: CCOC(CNC(=O)CSCc1nc(-c2ccc(Cl)cc2)oc1C)OCC] | 412.94 |

TABLE 5-continued
Oxazole amides (R³ = NH-misc)
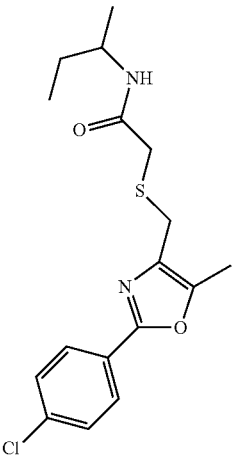 [SMILES: CCC(C)NC(=O)CSCc1nc(-c2ccc(Cl)cc2)oc1C]
| ID | Structure | MW |
|---|---|---|
| IIa-1120 | 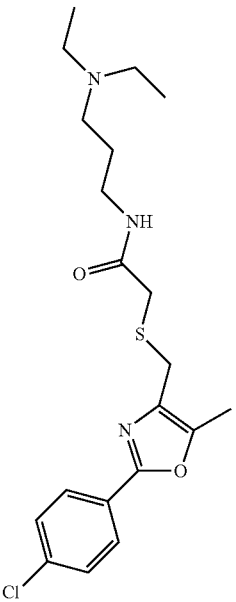 [SMILES: CCN(CC)CCCNC(=O)CSCc1nc(-c2ccc(Cl)cc2)oc1C] | 352.89 |
| IIa-1121 | | 409.98 |

TABLE 5-continued

Oxazole amides (R³ = NH-misc)

| ID | Structure | MW |
|---|---|---|
| IIa-1122 | | 338.86 |
| IIa-1123 | | 338.86 |

TABLE 5-continued
Oxazole amides (R³ = NH-misc)
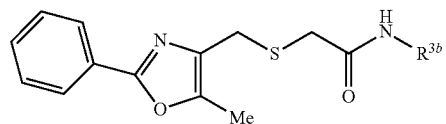
| ID | Structure | MW |
|---|---|---|
| IIa-1124 | 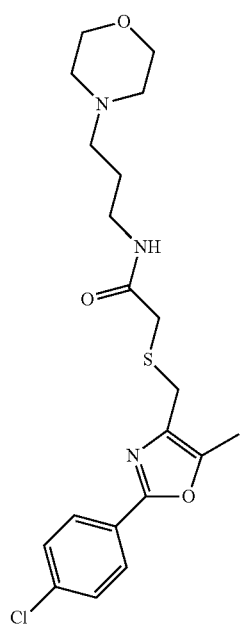 [SMILES: Cc1oc(-c2ccc(Cl)cc2)nc1CSCC(=O)NCCCN1CCOCC1] | 384.88 |
| IIa-1125 | | 423.97 |

TABLE 5-continued
Oxazole amides (R³ = NH-misc)
| ID | Structure | MW |
|---|---|---|
| IIa-1126 | 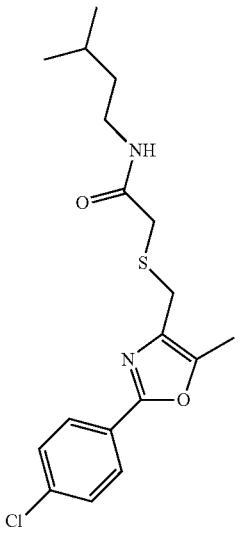 [SMILES: Cc1oc(-c2ccc(Cl)cc2)nc1CSCC(=O)NCCC(C)C] | 366.91 |
| IIa-1127 | 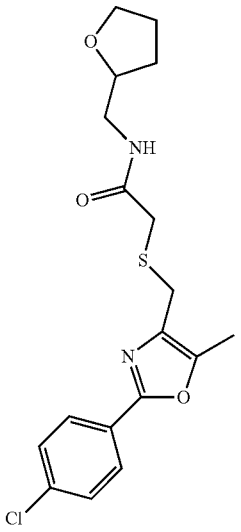 [SMILES: Cc1oc(-c2ccc(Cl)cc2)nc1CSCC(=O)NCC1CCCO1] | 380.90 |

TABLE 5-continued
Oxazole amides (R³ = NH-misc)
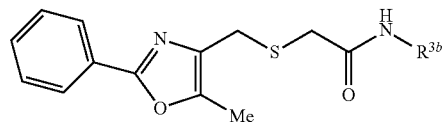
| ID | Structure | MW |
|---|---|---|
| IIa-1128 | | 354.86 |
| IIa-1129 | | 382.91 |

TABLE 5-continued
Oxazole amides (R³ = NH-misc)
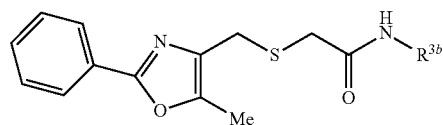
| ID | Structure | MW |
|---|---|---|
| IIa-1130 | 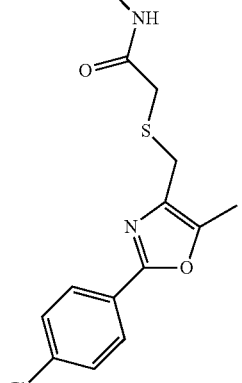 | 368.89 |
| IIa-1131 | 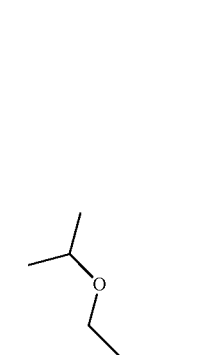 | 396.94 |

TABLE 5-continued
Oxazole amides (R³ = NH-misc)
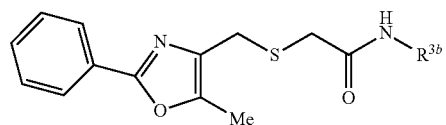
| ID | Structure | MW |
|---|---|---|
| IIa-1132 | 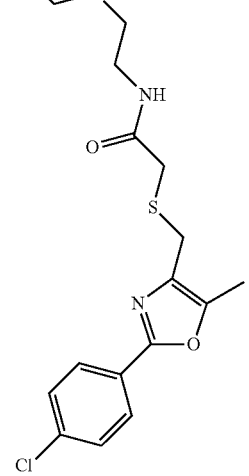 | 409.94 |
| IIa-1133 | 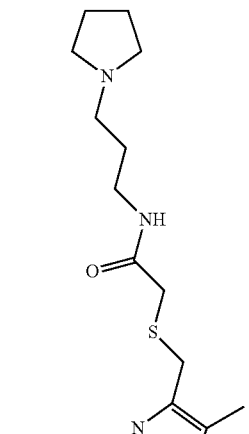 | 407.97 |

TABLE 5-continued
Oxazole amides (R³ = NH-misc)
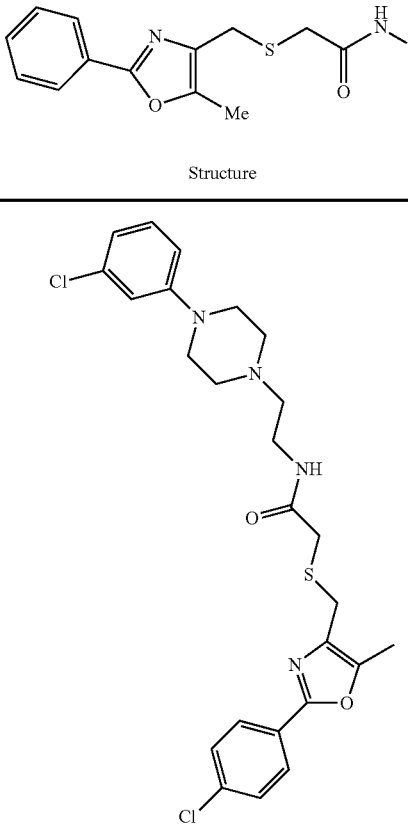
| ID | Structure | MW |
|---|---|---|
| IIa-1134 | 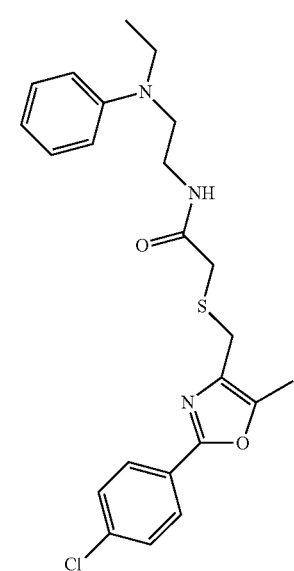 [SMILES: CCN(CCNC(=O)CSCc1nc(-c2ccc(Cl)cc2)oc1C)c1ccccc1] | 519.50 |
| IIa-1135 | | 444.00 |

TABLE 5-continued
Oxazole amides (R³ = NH-misc)
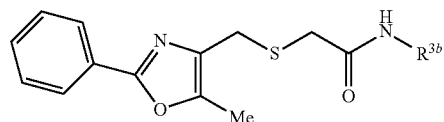
| ID | Structure | MW |
|---|---|---|
| IIa-1136 | 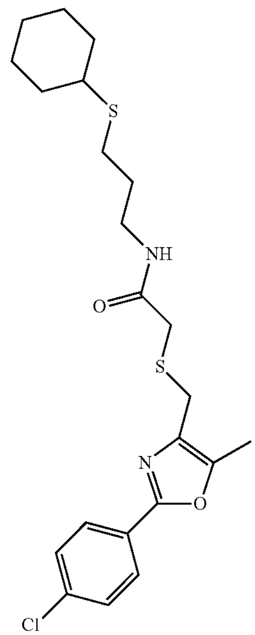 [SMILES: Cc1oc(-c2ccc(Cl)cc2)nc1CSCC(=O)NCCCSC1CCCCC1] | 453.07 |
| IIa-1137 | 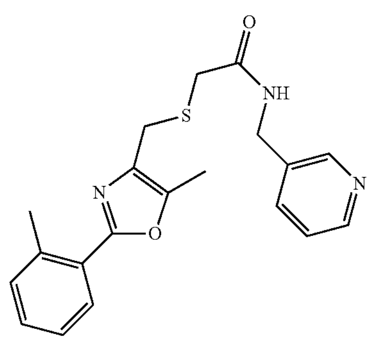 [SMILES: Cc1ccccc1-c1nc(CSCC(=O)NCc2cccnc2)c(C)o1] | 367.47 |
| IIa-1138 | 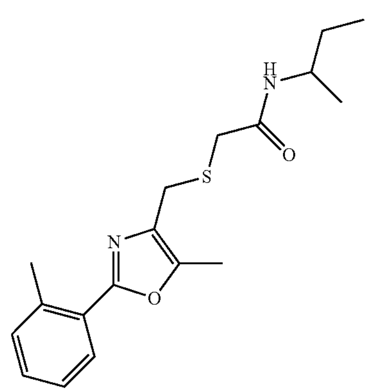 [SMILES: CCC(C)NC(=O)CSCc1nc(-c2ccccc2C)oc1C] | 332.47 |

TABLE 5-continued

Oxazole amides (R³ = NH-misc)

| ID | Structure | MW |
| --- | --- | --- |
| IIa-1139 | | 334.44 |
| IIa-1140 | | 387.55 |
| IIa-1141 | | 372.51 |
| IIa-1142 | | 362.49 |

TABLE 5-continued

Oxazole amides (R³ = NH-misc)

| ID | Structure | MW |
|---|---|---|
| IIa-1143 | | 348.47 |
| IIa-1144 | | 376.52 |
| IIa-1145 | | 373.52 |

TABLE 5-continued
Oxazole amides (R³ = NH-misc)
| ID | Structure | MW |
|---|---|---|
| IIa-1146 | 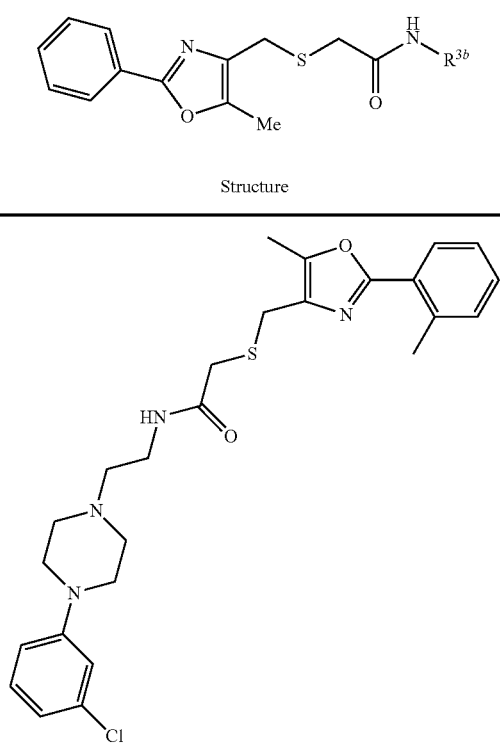 | 499.08 |
| IIa-1147 | 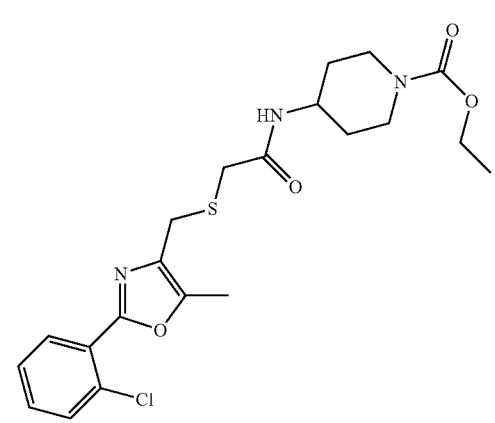 [SMILES: CCOC(=O)N1CCC(NC(=O)CSCc2nc(-c3ccccc3Cl)oc2C)CC1] | 451.98 |
| IIa-1148 | 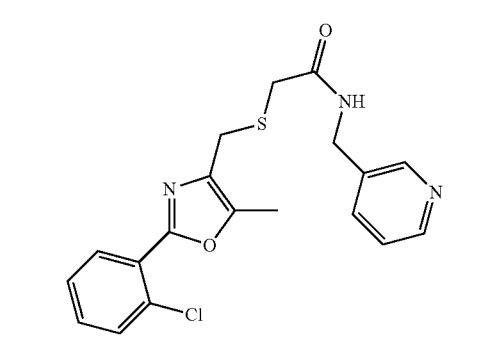 [SMILES: Cc1oc(-c2ccccc2Cl)nc1CSCC(=O)NCc1cccnc1] | 387.89 |

TABLE 5-continued
Oxazole amides (R³ = NH-misc)
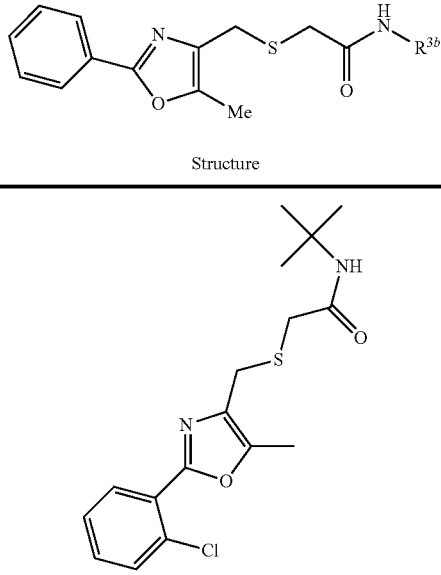
| ID | Structure | MW |
|---|---|---|
| IIa-1149 | 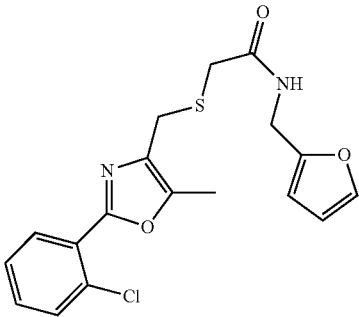 | 352.89 |
| IIa-1150 | 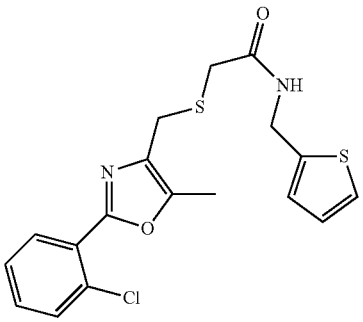 [SMILES: Cc1oc(-c2ccccc2Cl)nc1CSCC(=O)NCc1ccco1] | 376.86 |
| IIa-1151 | 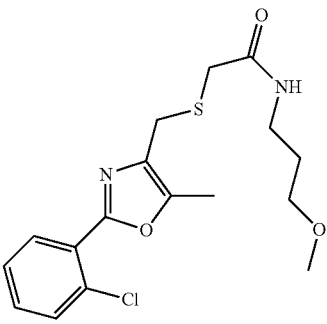 [SMILES: COCCCNC(=O)CSCc1nc(-c2ccccc2Cl)oc1C] | 392.93 |
| IIa-1152 | | 368.89 |

TABLE 5-continued
Oxazole amides (R³ = NH-misc)
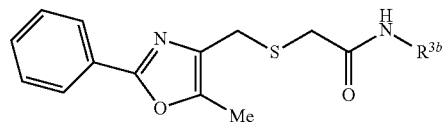
| ID | Structure | MW |
| --- | --- | --- |
| IIa-1153 | | 352.89 |
| IIa-1154 | | 427.03 |
| IIa-1155 | | 463.62 |

TABLE 5-continued
Oxazole amides (R³ = NH-misc)
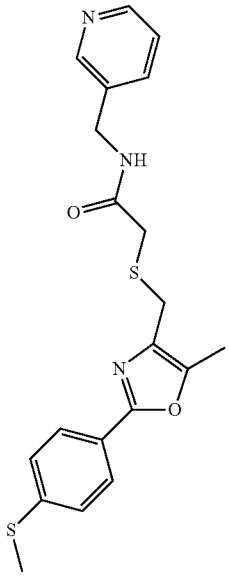 [SMILES: CSc1ccc(-c2nc(CSCC(=O)NCc3cccnc3)c(C)o2)cc1]
| ID | Structure | MW |
|---|---|---|
| IIa-1156 | 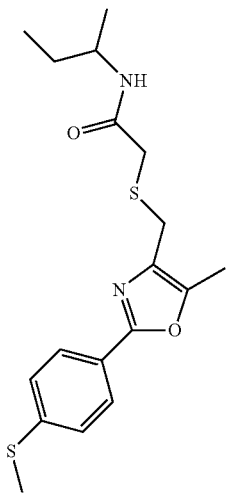 [SMILES: CCC(C)NC(=O)CSCc1nc(-c2ccc(SC)cc2)oc1C] | 399.54 |
| IIa-1157 | | 364.53 |

TABLE 5-continued

Oxazole amides (R³ = NH-misc)

| ID | Structure | MW |
|---|---|---|
| IIa-1158 | | 364.53 |
| IIa-1159 | | 379.55 |

TABLE 5-continued
Oxazole amides (R³ = NH-misc)
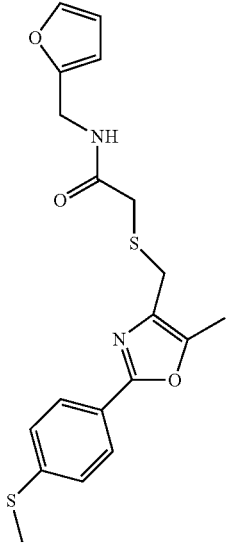 [SMILES: CSc1ccc(-c2nc(CSCC(=O)NCc3ccco3)c(C)o2)cc1]
| ID | Structure | MW |
|---|---|---|
| IIa-1160 | 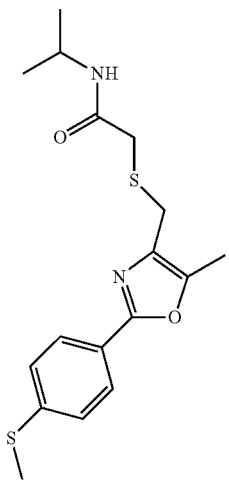 [SMILES: CSc1ccc(-c2nc(CSCC(=O)NC(C)C)c(C)o2)cc1] | 388.51 |
| IIa-1161 | | 350.51 |

TABLE 5-continued

Oxazole amides (R³ = NH-misc)

| ID | Structure | MW |
|---|---|---|
| IIa-1162 | | 350.51 |
| IIa-1163 | | 396.53 |

TABLE 5-continued
Oxazole amides (R³ = NH-misc)
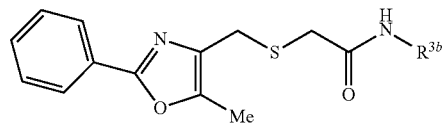
| ID | Structure | MW |
|---|---|---|
| IIa-1164 | | 435.61 |
| IIa-1165 | | 378.56 |

TABLE 5-continued
Oxazole amides (R³ = NH-misc)
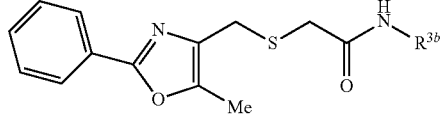
| ID | Structure | MW |
|---|---|---|
| IIa-1166 | 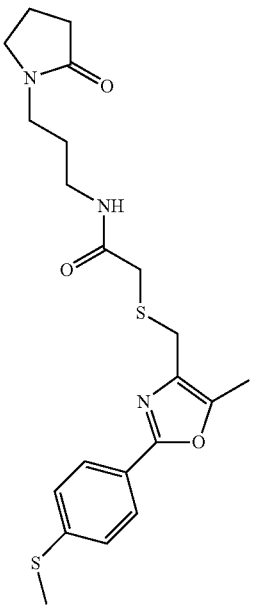 [SMILES: CSc1ccc(-c2nc(CSCC(=O)NCCCN3CCCC3=O)c(C)o2)cc1] | 392.54 |
| IIa-1167 | | 433.60 |

TABLE 5-continued
Oxazole amides (R³ = NH-misc)
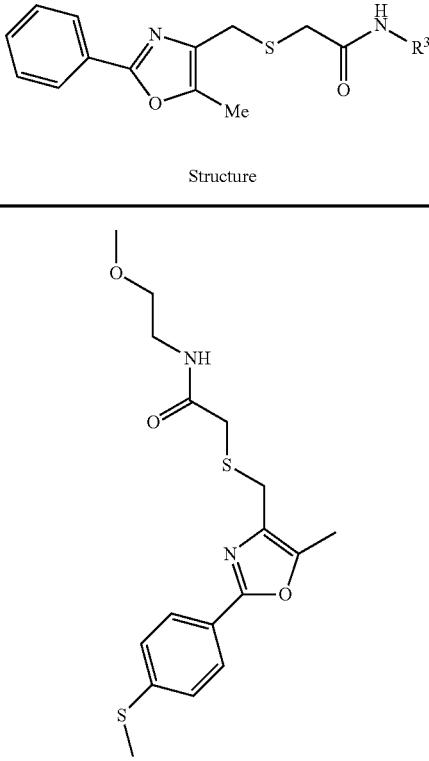
| ID | Structure | MW |
|---|---|---|
| IIa-1168 | 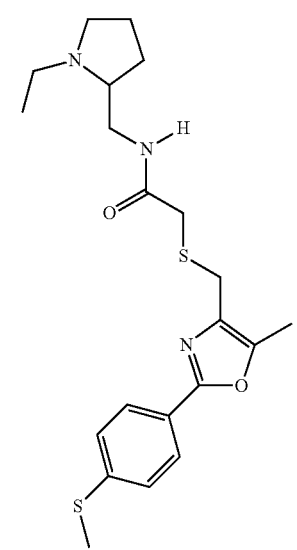 [SMILES: CCN1CCCC1CNC(=O)CSCc1nc(-c2ccc(SC)cc2)oc1C] | 366.50 |
| IIa-1169 | | 419.61 |

TABLE 5-continued
Oxazole amides (R³ = NH-misc)
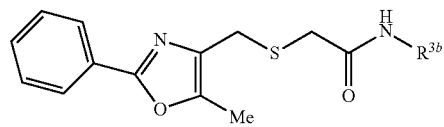
| ID | Structure | MW |
|---|---|---|
| IIa-1170 | 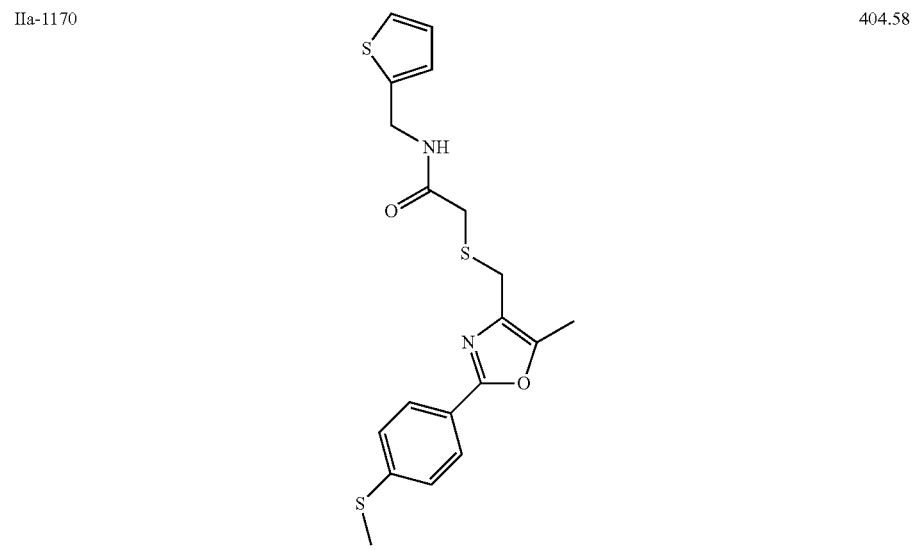 | 404.58 |
| IIa-1171 | 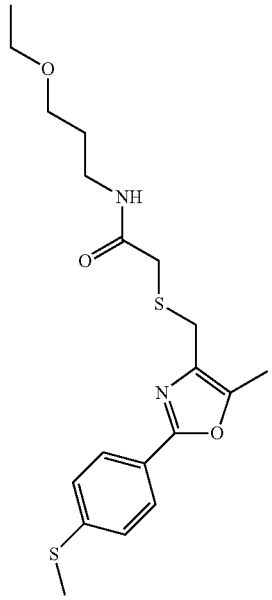 [SMILES: CCOCCCNC(=O)CSCc1nc(-c2ccc(SC)cc2)oc1C] | 394.56 |

TABLE 5-continued
Oxazole amides (R³ = NH-misc)
| ID | Structure | MW |
|---|---|---|
| IIa-1172 | 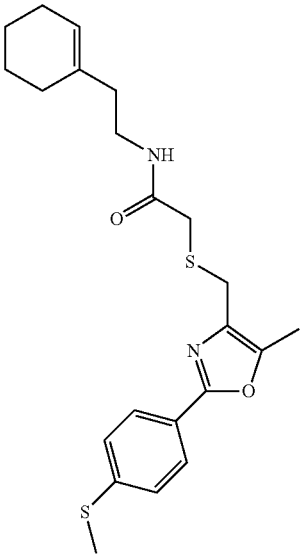 [SMILES: CSc1ccc(-c2nc(CSCC(=O)NCCC3=CCCCC3)c(C)o2)cc1] | 416.61 |
| IIa-1173 | 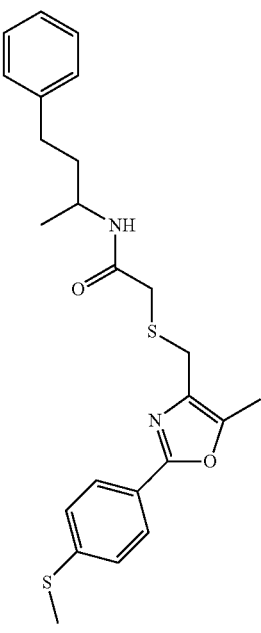 [SMILES: CSc1ccc(-c2nc(CSCC(=O)NC(C)CCc3ccccc3)c(C)o2)cc1] | 440.63 |

TABLE 5-continued
Oxazole amides (R³ = NH-misc)
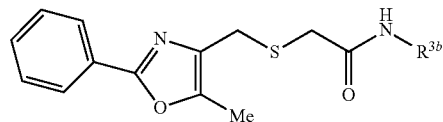
| ID | Structure | MW |
|---|---|---|
| IIa-1174 | | 380.53 |
| IIa-1175 | | 364.53 |

TABLE 5-continued
Oxazole amides (R³ = NH-misc)
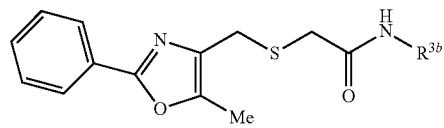
| ID | Structure | MW |
|---|---|---|
| IIa-1176 | | 419.61 |
| IIa-1177 | | 405.59 |

TABLE 5-continued
Oxazole amides (R³ = NH-misc)
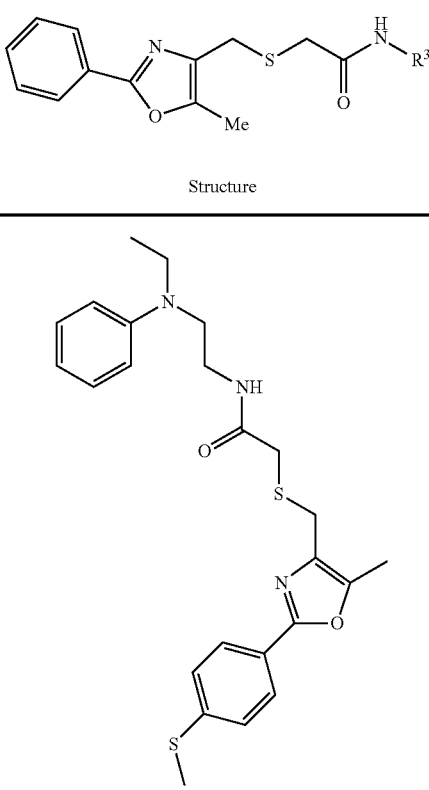
| ID | Structure | MW |
|---|---|---|
| IIa-1178 | 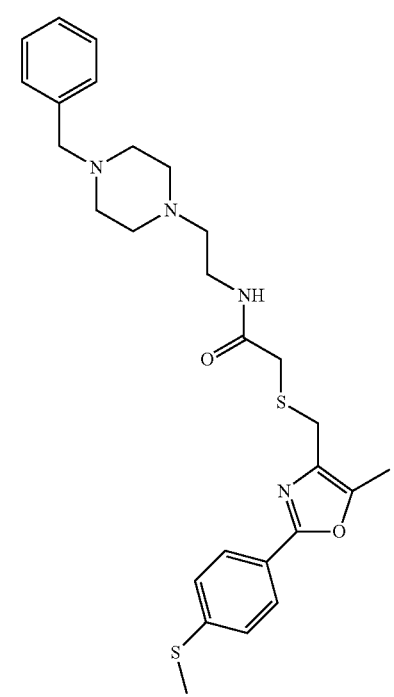 | 455.65 |
| IIa-1179 | 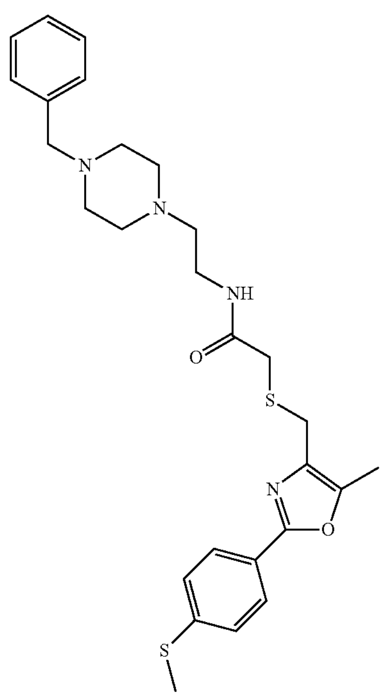 [SMILES: CSc1ccc(-c2nc(CSCC(=O)NCCN3CCN(Cc4ccccc4)CC3)c(C)o2)cc1] | 510.73 |

TABLE 5-continued
Oxazole amides (R³ = NH-misc)
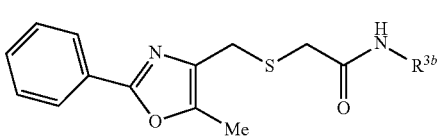
| ID | Structure | MW |
|---|---|---|
| IIa-1180 | 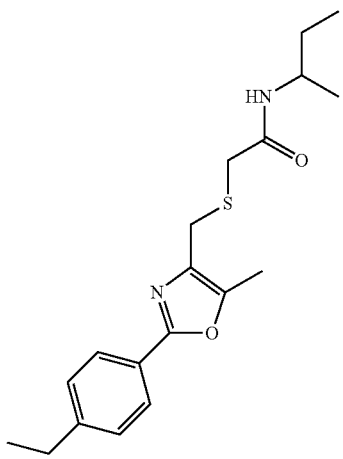 [SMILES: CCc1ccc(-c2nc(CSCC(=O)NC(C)CC)c(C)o2)cc1] | 464.72 |
| IIa-1181 | | 346.50 |

TABLE 5-continued
Oxazole amides (R³ = NH-misc)
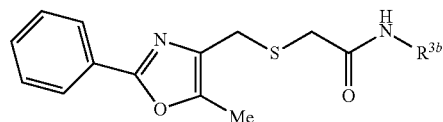
| ID | Structure | MW |
|---|---|---|
| IIa-1182 | | 346.50 |
| IIa-1183 | | 361.51 |
| IIa-1184 | | 370.47 |

TABLE 5-continued
Oxazole amides (R³ = NH-misc)
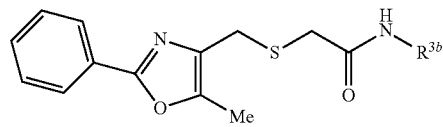
| ID | Structure | MW |
|---|---|---|
| IIa-1185 | | 378.49 |
| IIa-1186 | | 415.56 |
| IIa-1187 | | 386.54 |

TABLE 5-continued
Oxazole amides (R³ = NH-misc)
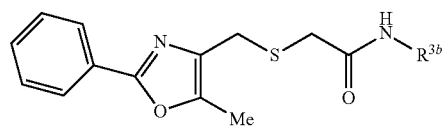
| ID | Structure | MW |
|---|---|---|
| IIa-1188 | 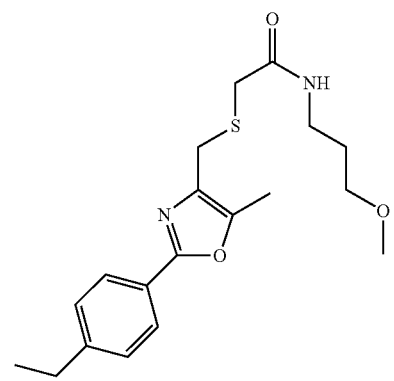 [SMILES: CCc1ccc(-c2nc(CSCC(=O)NCCCOC)c(C)o2)cc1] | 362.49 |
| IIa-1189 | 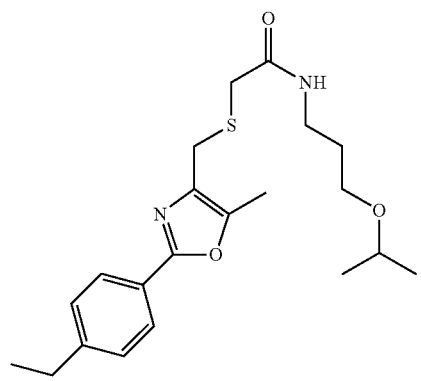 [SMILES: CCc1ccc(-c2nc(CSCC(=O)NCCCOC(C)C)c(C)o2)cc1] | 390.55 |
| IIa-1190 | 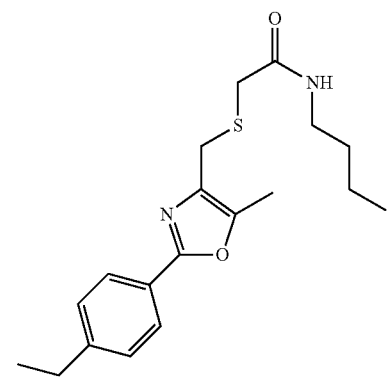 [SMILES: CCCCNC(=O)CSCc1nc(-c2ccc(CC)cc2)oc1C] | 346.50 |

TABLE 5-continued
Oxazole amides (R³ = NH-misc)
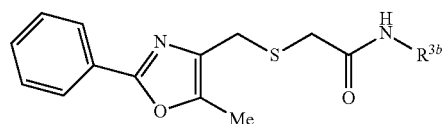
| ID | Structure | MW |
|---|---|---|
| IIa-1191 | | 513.11 |
| IIa-1192 | | 420.64 |
| IIa-1193 | | 446.68 |

TABLE 5-continued
Oxazole amides (R³ = NH-misc)
| ID | Structure | MW |
|---|---|---|
| IIa-1194 | 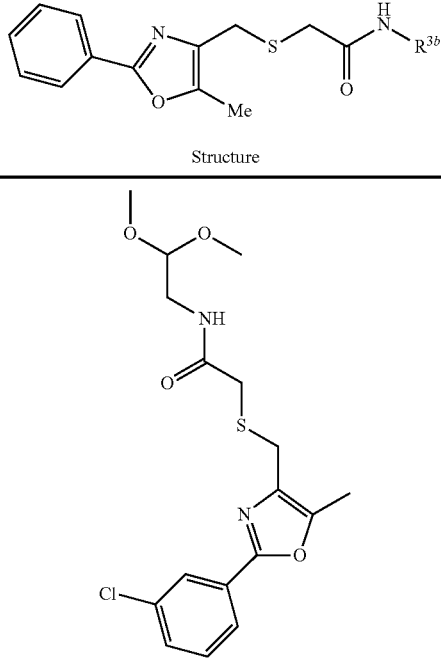 | 384.88 |
| IIa-1195 | 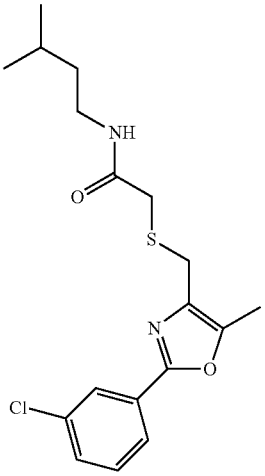 [SMILES: Cc1oc(-c2cccc(Cl)c2)nc1CSCC(=O)NCCC(C)C] | 366.91 |
| IIa-1196 | 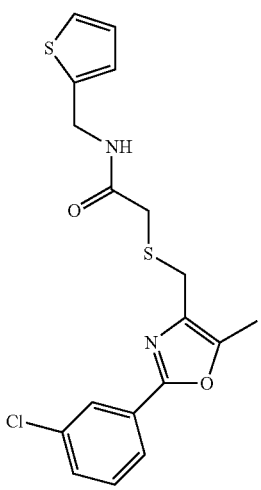 [SMILES: Cc1oc(-c2cccc(Cl)c2)nc1CSCC(=O)NCc1cccs1] | 392.93 |

TABLE 5-continued

Oxazole amides (R³ = NH-misc)

| ID | Structure | MW |
|---|---|---|
| IIa-1197 | 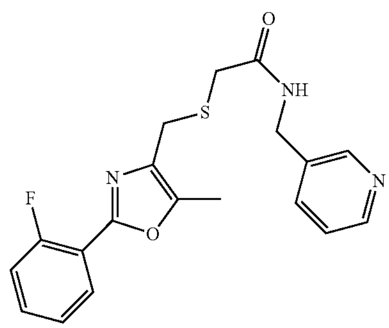 [SMILES: Cc1oc(-c2ccccc2F)nc1CSCC(=O)NCc1cccnc1] | 371.44 |
| IIa-1198 | 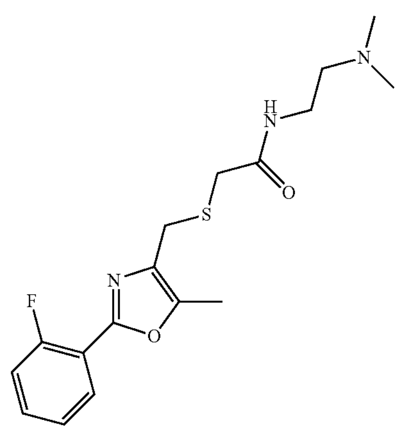 [SMILES: Cc1oc(-c2ccccc2F)nc1CSCC(=O)NCCN(C)C] | 351.45 |
| IIa-1199 | 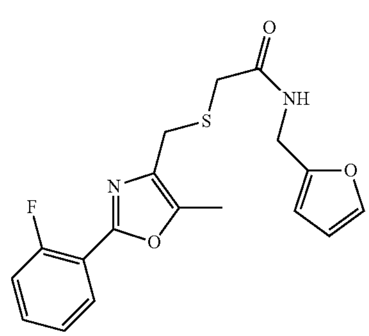 [SMILES: Cc1oc(-c2ccccc2F)nc1CSCC(=O)NCc1ccco1] | 360.41 |

TABLE 5-continued

Oxazole amides (R³ = NH-misc)

| ID | Structure | MW |
|---|---|---|
| IIa-1200 | 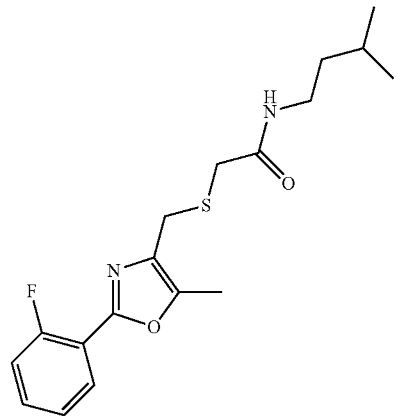 [SMILES: Cc1oc(-c2ccccc2F)nc1CSCC(=O)NCCC(C)C] | 350.46 |
| IIa-1201 | 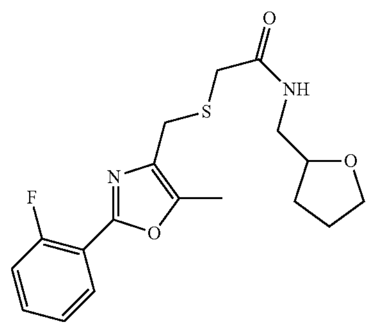 [SMILES: Cc1oc(-c2ccccc2F)nc1CSCC(=O)NCC1CCCO1] | 364.44 |
| IIa-1202 | 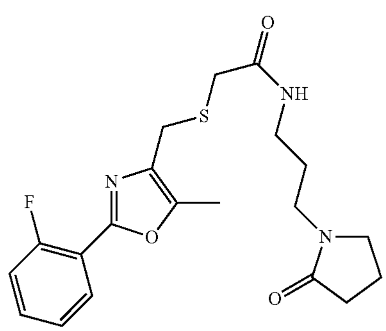 [SMILES: Cc1oc(-c2ccccc2F)nc1CSCC(=O)NCCCN1CCCC1=O] | 405.49 |
| IIa-1203 | 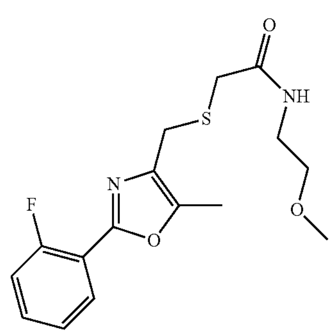 [SMILES: COCCNC(=O)CSCc1nc(-c2ccccc2F)oc1C] | 338.40 |

TABLE 5-continued

Oxazole amides (R³ = NH-misc)

| ID | Structure | MW |
|---|---|---|
| IIa-1204 | | 366.46 |
| IIa-1205 | | 352.43 |
| IIa-1206 | | 377.48 |

TABLE 5-continued

Oxazole amides (R³ = NH-misc)

| ID | Structure | MW |
|---|---|---|
| IIa-1207 | | 410.58 |
| IIa-1208 | | 367.47 |
| IIa-1209 | | 332.47 |

TABLE 5-continued
Oxazole amides (R³ = NH-misc)
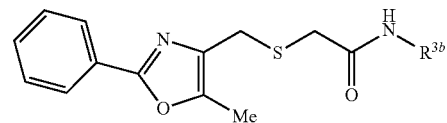
| ID | Structure | MW |
|---|---|---|
| IIa-1210 | | 403.55 |
| IIa-1211 | | 334.44 |

TABLE 5-continued
Oxazole amides (R³ = NH-misc)
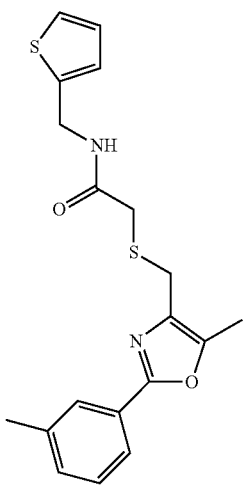
| ID | Structure | MW |
|---|---|---|
| IIa-1212 | 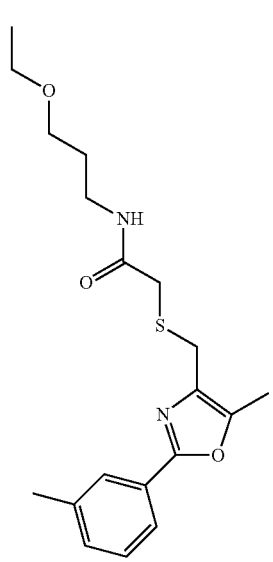 [SMILES: CCOCCCNC(=O)CSCc1nc(-c2cccc(C)c2)oc1C] | 372.51 |
| IIa-1213 | | 362.49 |

TABLE 5-continued
Oxazole amides (R³ = NH-misc)
| ID | Structure | MW |
|---|---|---|
| IIa-1214 | 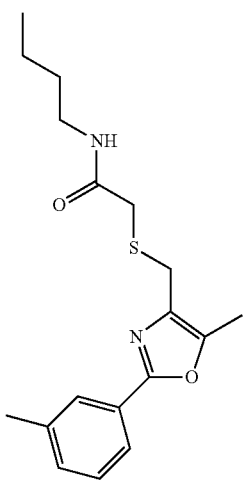 | 332.47 |
| IIa-1215 | 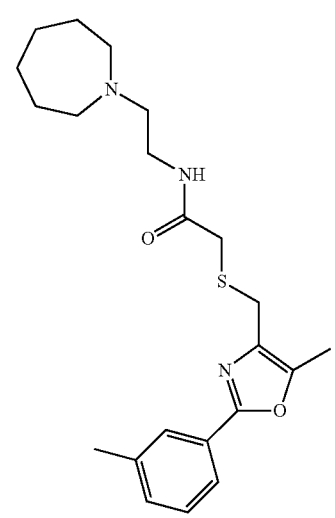 [SMILES: Cc1cccc(-c2nc(CSCC(=O)NCCN3CCCCCC3)c(C)o2)c1] | 401.58 |

TABLE 5-continued
Oxazole amides (R³ = NH-misc)
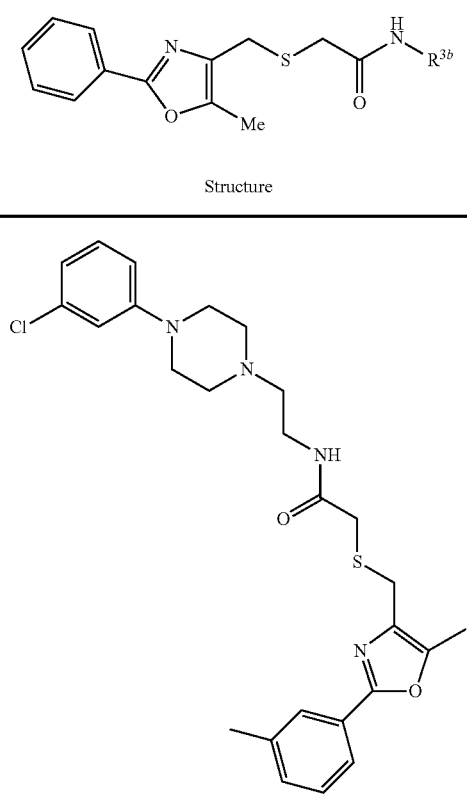
| ID | Structure | MW |
|---|---|---|
| IIa-1216 | 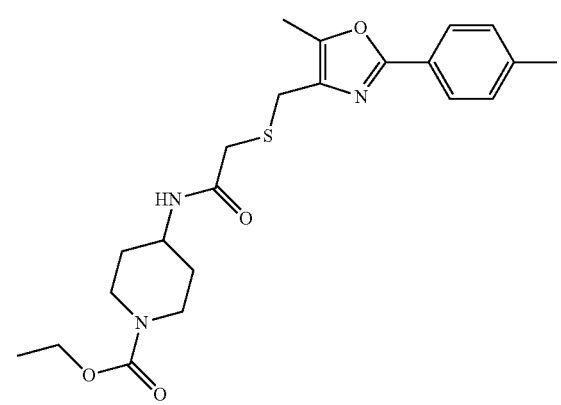 [SMILES: CCOC(=O)N1CCC(NC(=O)CSCc2nc(-c3ccc(C)cc3)oc2C)CC1] | 499.08 |
| IIa-1217 | | 431.56 |
| IIa-1218 | 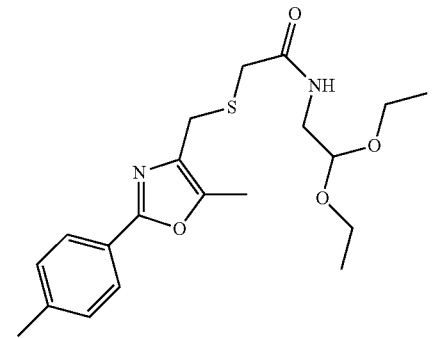 [SMILES: CCOC(CNC(=O)CSCc1nc(-c2ccc(C)cc2)oc1C)OCC] | 392.52 |

TABLE 5-continued

Oxazole amides (R³ = NH-misc)

| ID | Structure | MW |
|---|---|---|
| IIa-1219 | | 367.47 |
| IIa-1220 | | 332.47 |
| IIa-1221 | | 356.45 |

TABLE 5-continued
Oxazole amides (R³ = NH-misc)
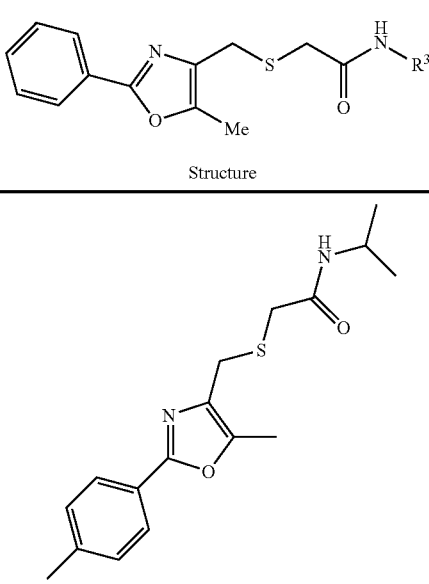
| ID | Structure | MW |
|---|---|---|
| IIa-1222 | 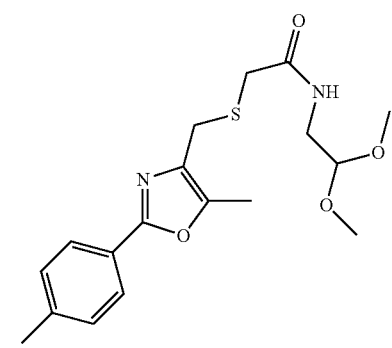 | 318.44 |
| IIa-1223 | 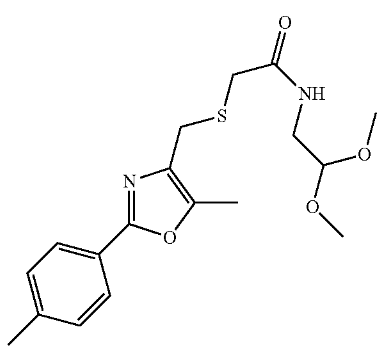 | 364.47 |
| IIa-1224 | 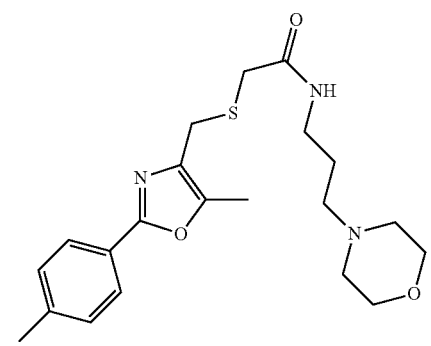 [SMILES: Cc1ccc(-c2nc(CSCC(=O)NCCCN3CCOCC3)c(C)o2)cc1] | 403.55 |

TABLE 5-continued
Oxazole amides (R³ = NH-misc)
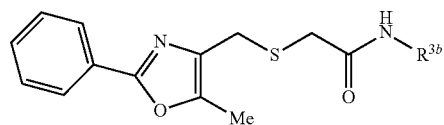
| ID | Structure | MW |
|---|---|---|
| IIa-1225 | 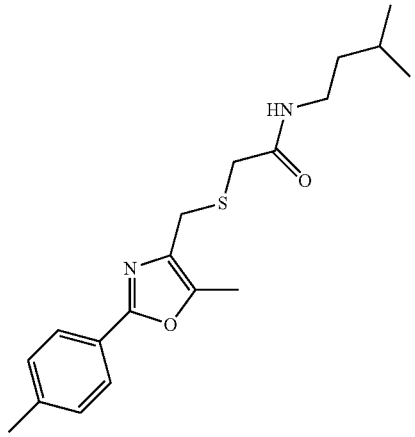 [SMILES: Cc1ccc(-c2nc(CSCC(=O)NCCC(C)C)c(C)o2)cc1] | 346.50 |
| IIa-1226 | 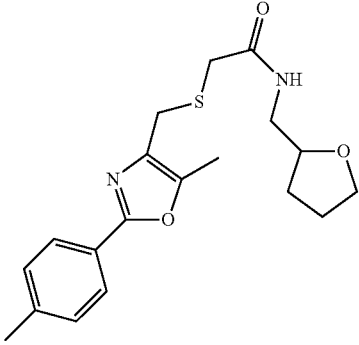 [SMILES: Cc1ccc(-c2nc(CSCC(=O)NCC3CCCO3)c(C)o2)cc1] | 360.48 |
| IIa-1227 | 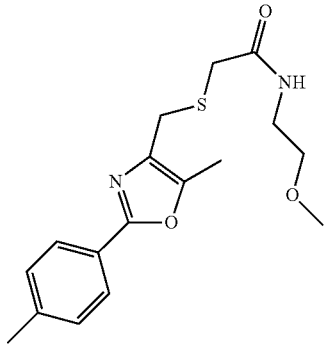 | 334.44 |

TABLE 5-continued
Oxazole amides (R³ = NH-misc)
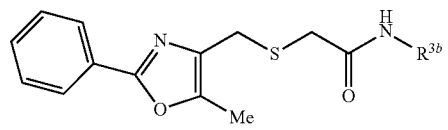
| ID | Structure | MW |
| --- | --- | --- |
| IIa-1228 | | 372.51 |
| IIa-1229 | | 362.49 |
| IIa-1230 | | 408.57 |

TABLE 5-continued
Oxazole amides (R³ = NH-misc)
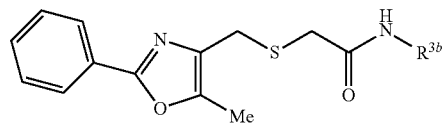
| ID | Structure | MW |
|---|---|---|
| IIa-1231 | | 348.47 |
| IIa-1232 | | 376.52 |
| IIa-1233 | | 389.52 |

TABLE 5-continued
Oxazole amides (R³ = NH-misc)
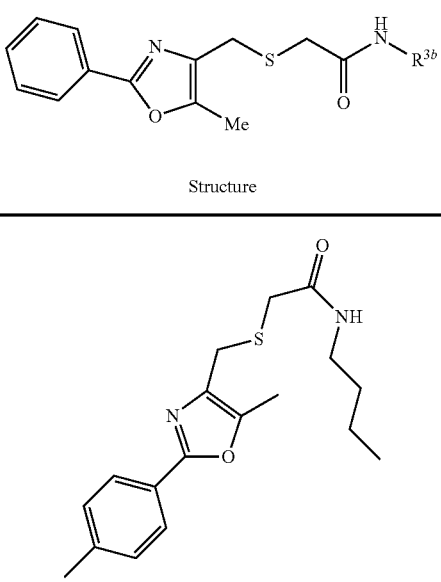
| ID | Structure | MW |
|---|---|---|
| IIa-1234 | 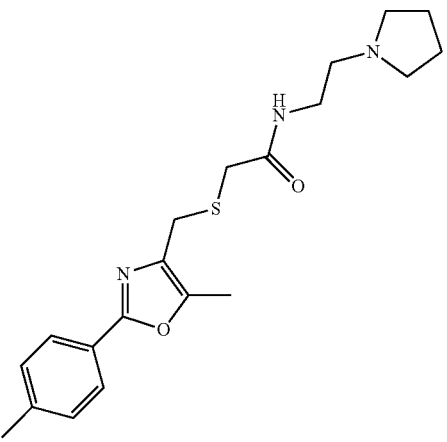 [SMILES: Cc1ccc(-c2nc(CSCC(=O)NCCN3CCCC3)c(C)o2)cc1] | 332.47 |
| IIa-1235 | | 373.52 |
| IIa-1236 | 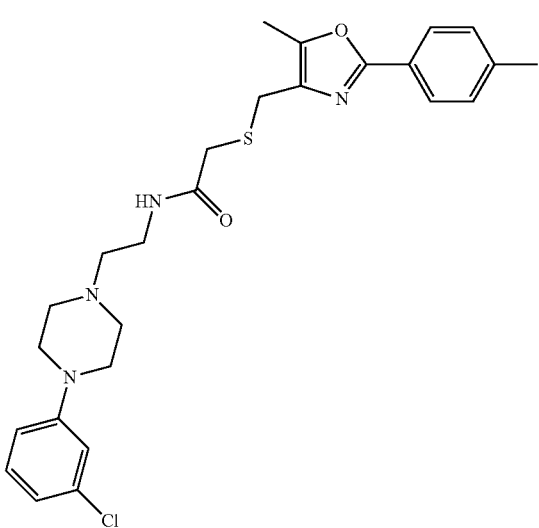 [SMILES: Cc1ccc(-c2nc(CSCC(=O)NCCN3CCN(c4cccc(Cl)c4)CC3)c(C)o2)cc1] | 499.08 |

TABLE 5-continued
Oxazole amides (R³ = NH-misc)
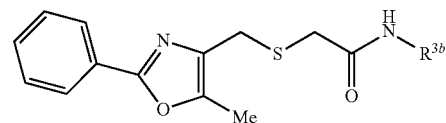
| ID | Structure | MW |
| --- | --- | --- |
| IIa-1237 | | 478.66 |
| IIa-1238 | | 423.58 |
| IIa-1239 | | 432.65 |

TABLE 5-continued
Oxazole amides (R³ = NH-misc)
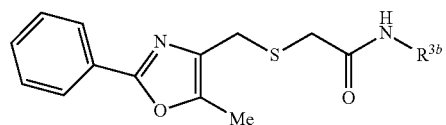
| ID | Structure | MW |
|---|---|---|
| IIa-1240 | | 463.56 |
| IIa-1241 | | 424.52 |

TABLE 5-continued
Oxazole amides (R³ = NH-misc)
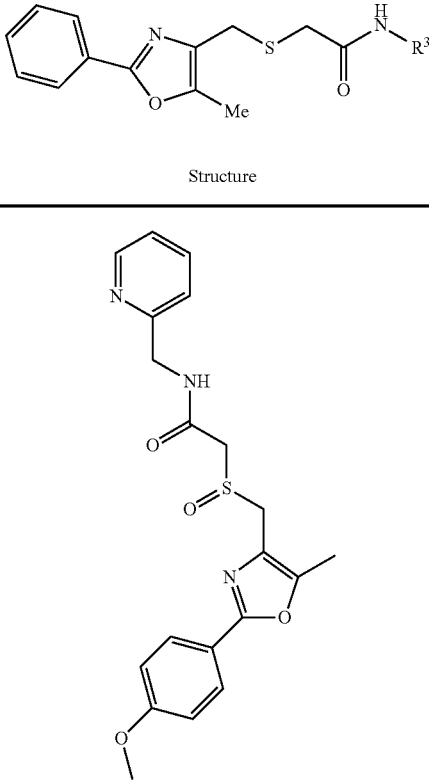
| ID | Structure | MW |
|---|---|---|
| IIa-1242 | 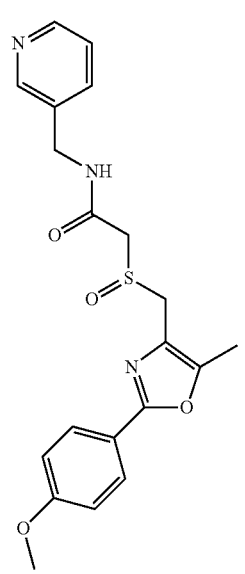 | 399.47 |
| IIa-1243 | 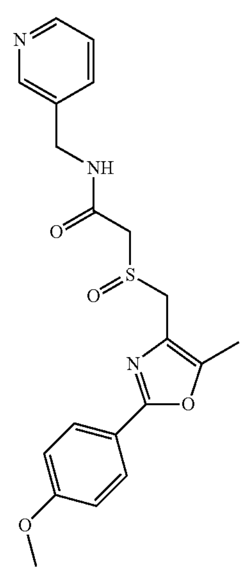 [SMILES: COc1ccc(-c2nc(CS(=O)CC(=O)NCc3cccnc3)c(C)o2)cc1] | 399.47 |

TABLE 5-continued
Oxazole amides (R³ = NH-misc)
| ID | Structure | MW |
|---|---|---|
| IIa-1244 | 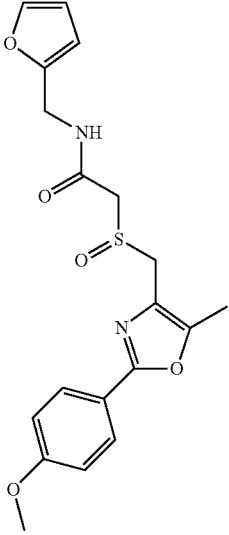 [SMILES: COc1ccc(-c2nc(CS(=O)CC(=O)NCc3ccco3)c(C)o2)cc1] | 388.45 |
| IIa-1245 | 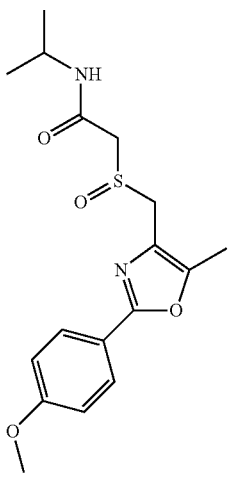 [SMILES: COc1ccc(-c2nc(CS(=O)CC(=O)NC(C)C)c(C)o2)cc1] | 350.44 |

TABLE 5-continued
Oxazole amides (R³ = NH-misc)
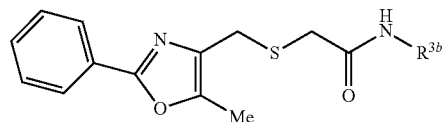
| ID | Structure | MW |
|---|---|---|
| IIa-1246 | 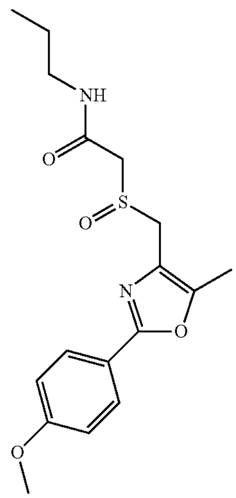 [SMILES: CCCNC(=O)CS(=O)Cc1nc(-c2ccc(OC)cc2)oc1C] | 350.44 |
| IIa-1247 | 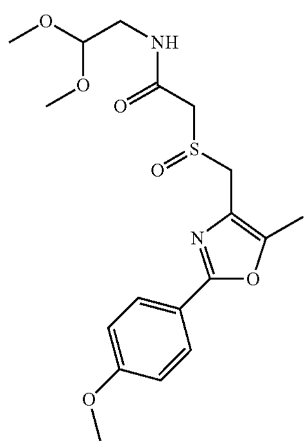 | 396.47 |
| IIa-1248 | 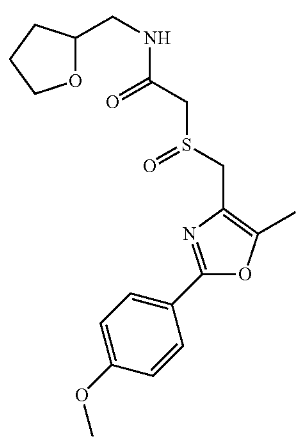 [SMILES: COc1ccc(-c2nc(CS(=O)CC(=O)NCC3CCCO3)c(C)o2)cc1] | 392.48 |

TABLE 5-continued
Oxazole amides (R³ = NH-misc)
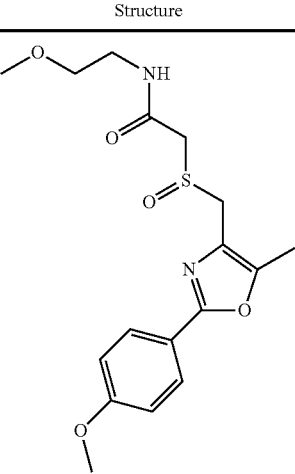
| ID | Structure | MW |
|---|---|---|
| IIa-1249 | 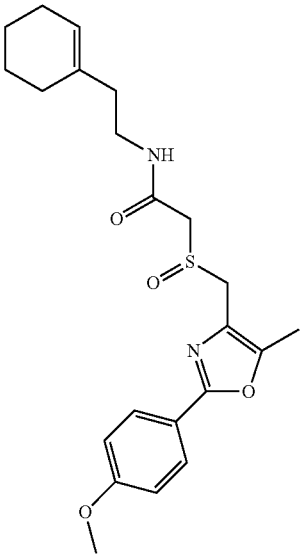 [SMILES: COc1ccc(-c2nc(CS(=O)CC(=O)NCCC3=CCCCC3)c(C)o2)cc1] | 366.44 |
| IIa-1250 | | 416.54 |
| IIa-1251 | 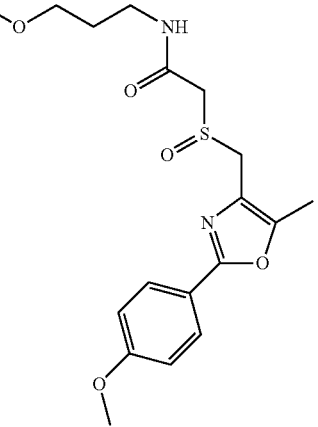 | 380.47 |

TABLE 5-continued
Oxazole amides (R³ = NH-misc)
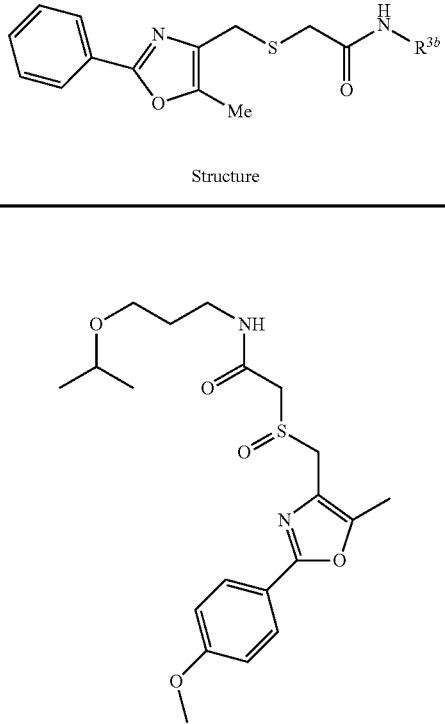
| ID | Structure | MW |
|---|---|---|
| IIa-1252 | 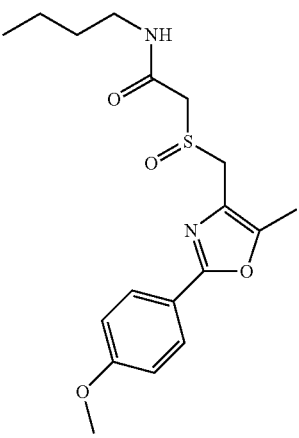 [SMILES: CCCCNC(=O)CS(=O)Cc1nc(-c2ccc(OC)cc2)oc1C] | 408.52 |
| IIa-1253 | | 364.47 |

TABLE 5-continued

Oxazole amides (R³ = NH-misc)

| ID | Structure | MW |
|---|---|---|
| IIa-1254 | | 531.08 |
| IIa-1255 | | 354.86 |
| IIa-1256 | | 384.88 |

TABLE 5-continued

Oxazole amides (R³ = NH-misc)

| ID | Structure | MW |
|---|---|---|
| IIa-1257 | 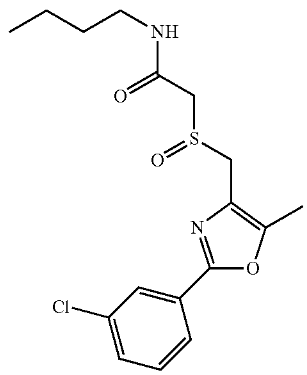 | 368.89 |
| IIa-1258 | 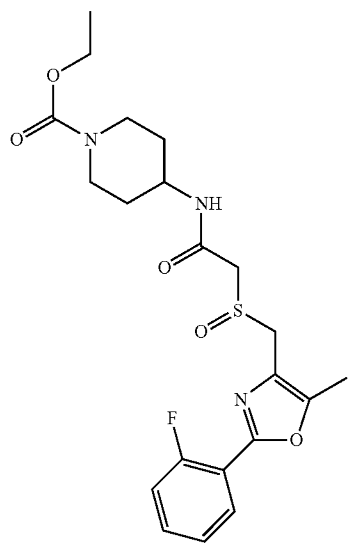 [SMILES: CCOC(=O)N1CCC(NC(=O)CS(=O)Cc2nc(-c3ccccc3F)oc2C)CC1] | 451.52 |
| IIa-1259 | 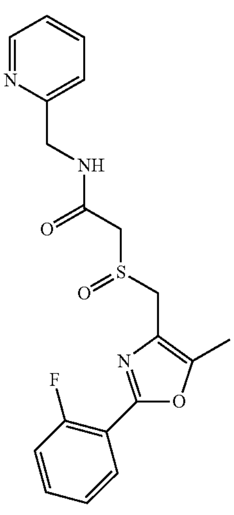 [SMILES: Cc1oc(-c2ccccc2F)nc1CS(=O)CC(=O)NCc1ccccn1] | 387.44 |

TABLE 5-continued
Oxazole amides (R³ = NH-misc)
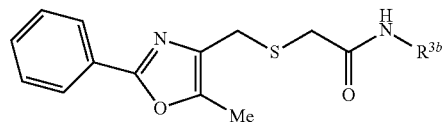
| ID | Structure | MW |
| --- | --- | --- |
| IIa-1260 | 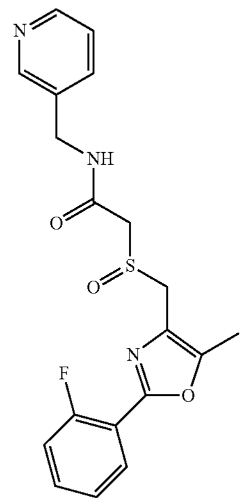 [SMILES: Cc1oc(-c2ccccc2F)nc1CS(=O)CC(=O)NCc1cccnc1] | 387.44 |
| IIa-1261 | 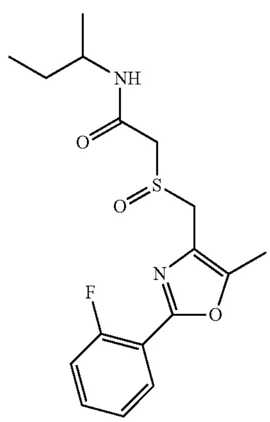 [SMILES: CCC(C)NC(=O)CS(=O)Cc1nc(-c2ccccc2F)oc1C] | 352.43 |
| IIa-1262 | 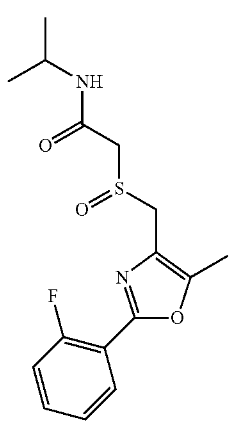 [SMILES: Cc1oc(-c2ccccc2F)nc1CS(=O)CC(=O)NC(C)C] | 338.40 |

TABLE 5-continued
Oxazole amides (R³ = NH-misc)
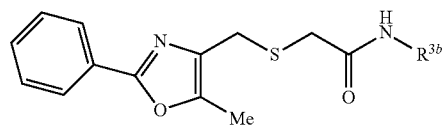
| ID | Structure | MW |
|---|---|---|
| IIa-1263 | 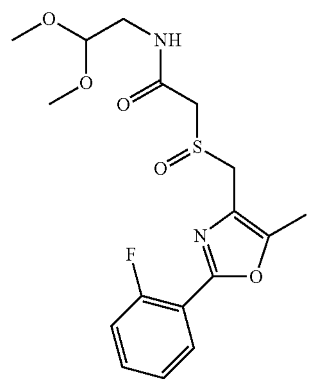 | 384.43 |
| IIa-1264 | 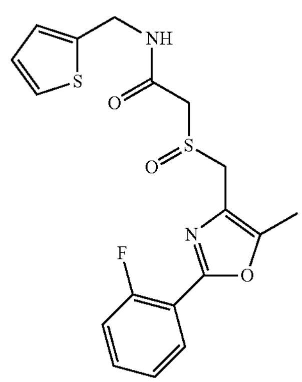 [SMILES: Cc1oc(-c2ccccc2F)nc1CS(=O)CC(=O)NCc1cccs1] | 392.47 |
| IIa-1265 | 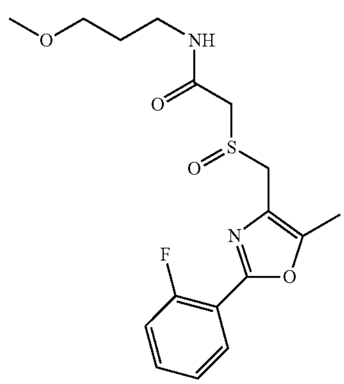 | 368.43 |

TABLE 5-continued
Oxazole amides (R³ = NH-misc)
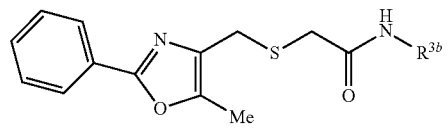
| ID | Structure | MW |
|---|---|---|
| IIa-1266 | | 396.48 |
| IIa-1267 | | 421.54 |
| IIa-1268 | | 383.47 |

TABLE 5-continued
Oxazole amides (R³ = NH-misc)
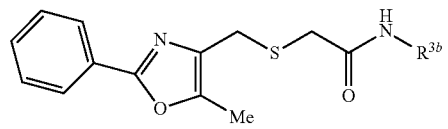
| ID | Structure | MW |
|---|---|---|
| IIa-1269 | | 348.47 |
| IIa-1270 | | 363.48 |
| IIa-1271 | | 372.45 |

TABLE 5-continued
Oxazole amides (R³ = NH-misc)
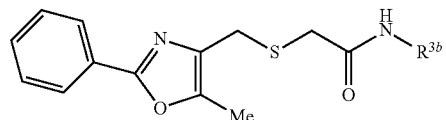
| ID | Structure | MW |
|---|---|---|
| IIa-1272 | | 334.44 |
| IIa-1273 | | 334.44 |
| IIa-1274 | | 380.47 |

TABLE 5-continued
Oxazole amides (R³ = NH-misc)
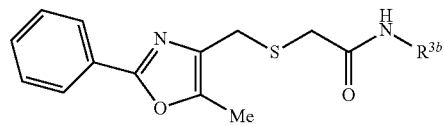
| ID | Structure | MW |
|---|---|---|
| IIa-1275 | 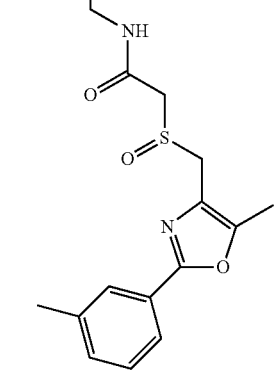 | 362.49 |
| IIa-1276 | 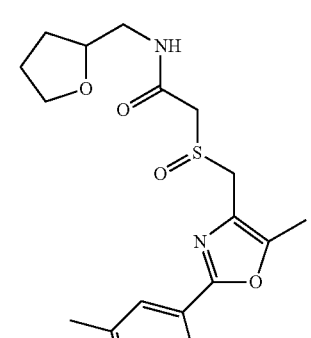 | 376.48 |
| IIa-1277 | 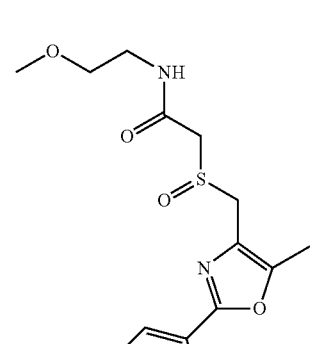 | 350.44 |

TABLE 5-continued
Oxazole amides (R³ = NH-misc)
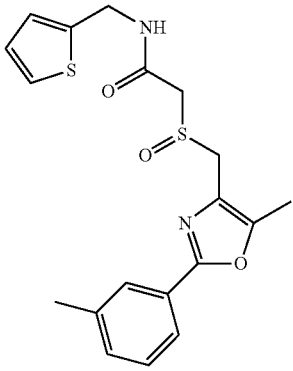 [SMILES: Cc1cccc(-c2nc(CS(=O)CC(=O)NCc3cccs3)c(C)o2)c1]
| ID | Structure | MW |
|---|---|---|
| IIa-1278 | 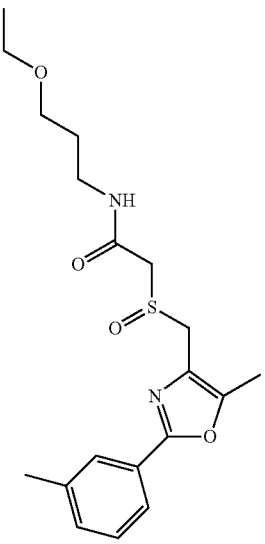 [SMILES: CCOCCCNC(=O)CS(=O)Cc1nc(-c2cccc(C)c2)oc1C] | 388.51 |
| IIa-1279 | | 378.49 |

TABLE 5-continued
Oxazole amides (R³ = NH-misc)
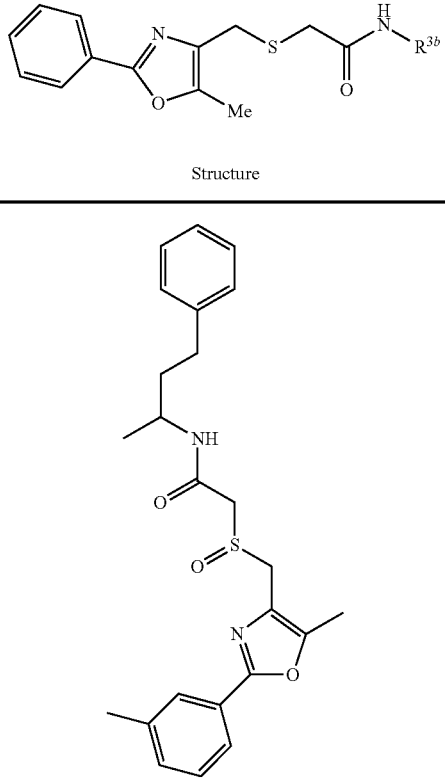
| ID | Structure | MW |
|---|---|---|
| IIa-1280 | 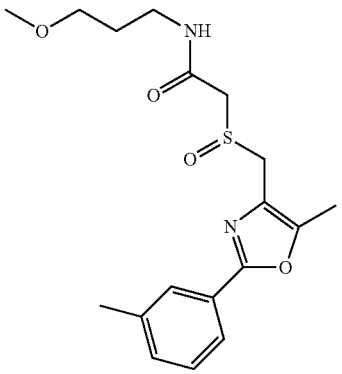 | 424.57 |
| IIa-1281 | | 364.47 |
| IIa-1282 | 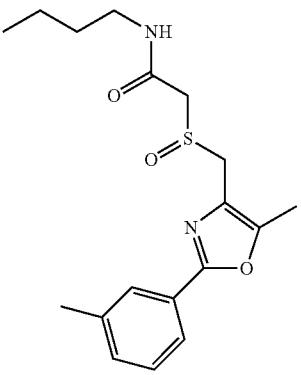 [SMILES: CCCCNC(=O)CS(=O)Cc1nc(-c2cccc(C)c2)oc1C] | 348.47 |

TABLE 5-continued

Oxazole amides (R³ = NH-misc)

| ID | Structure | MW |
|---|---|---|
| IIa-1283 | | 515.08 |
| IIa-1284 | | 467.64 |

TABLE 5-continued
Oxazole amides (R³ = NH-misc)
| ID | Structure | MW |
|---|---|---|
| IIa-1285 | 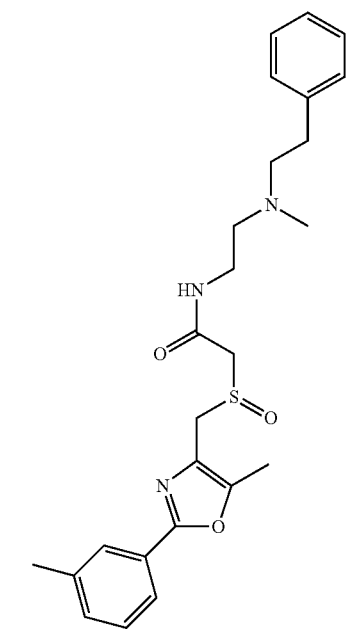 [SMILES: Cc1cccc(-c2nc(CS(=O)CC(=O)NCCN(C)CCc3ccccc3)c(C)o2)c1] | 453.61 |
| IIa-1286 | 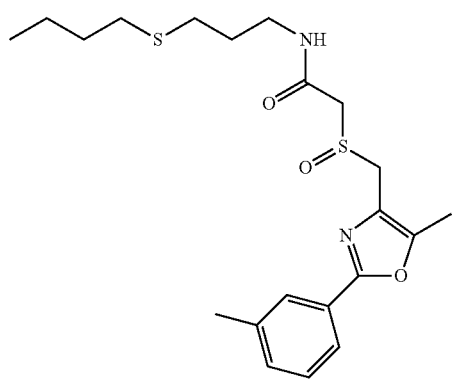 [SMILES: CCCCSCCCNC(=O)CS(=O)Cc1nc(-c2cccc(C)c2)oc1C] | 422.61 |

TABLE 5-continued
Oxazole amides (R³ = NH-misc)
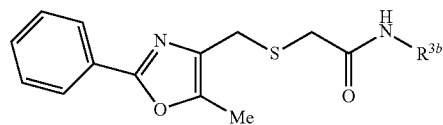
| ID | Structure | MW |
|---|---|---|
| IIa-1287 | 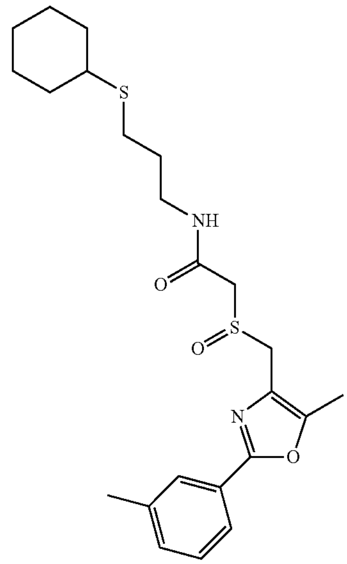 [SMILES: Cc1cccc(-c2nc(CS(=O)CC(=O)NCCCSC3CCCCC3)c(C)o2)c1] | 448.65 |
| IIa-1288 | 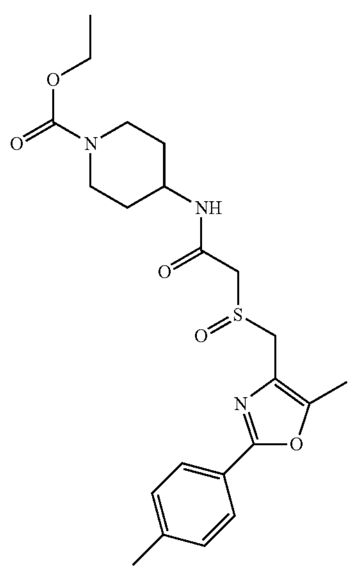 [SMILES: CCOC(=O)N1CCC(NC(=O)CS(=O)Cc2nc(-c3ccc(C)cc3)oc2C)CC1] | 447.56 |

TABLE 5-continued
Oxazole amides (R³ = NH-misc)
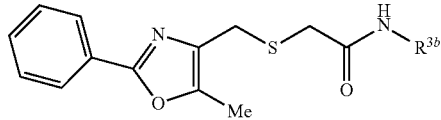
| ID | Structure | MW |
|---|---|---|
| IIa-1289 | 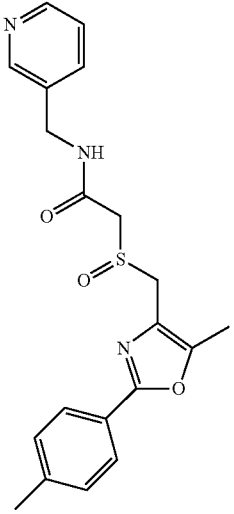 [SMILES: Cc1ccc(-c2nc(CS(=O)CC(=O)NCc3cccnc3)c(C)o2)cc1] | 408.52 |
| IIa-1290 | | 383.47 |

TABLE 5-continued
Oxazole amides (R³ = NH-misc)
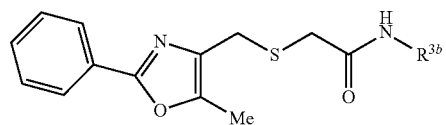
| ID | Structure | MW |
|---|---|---|
| IIa-1291 | | 348.47 |
| IIa-1292 | | 372.45 |
| IIa-1293 | | 334.44 |

TABLE 5-continued

Oxazole amides (R³ = NH-misc)

| ID | Structure | MW |
|---|---|---|
| IIa-1294 | 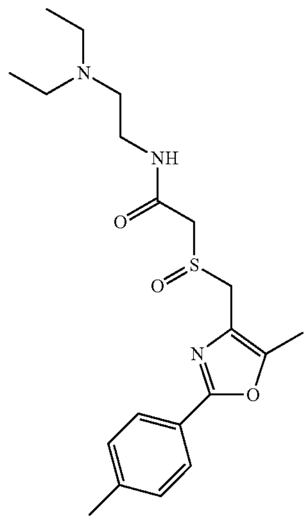 [SMILES: CCN(CC)CCNC(=O)CS(=O)Cc1nc(-c2ccc(C)cc2)oc1C] | 391.54 |
| IIa-1295 | 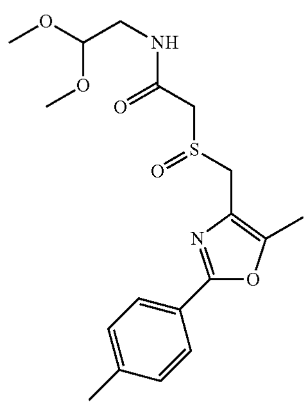 | 380.47 |
| IIa-1296 | 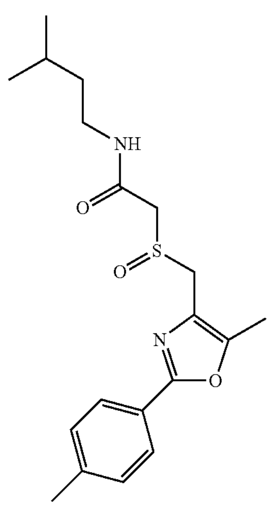 [SMILES: Cc1ccc(-c2nc(CS(=O)CC(=O)NCCC(C)C)c(C)o2)cc1] | 362.49 |

TABLE 5-continued
Oxazole amides (R³ = NH-misc)
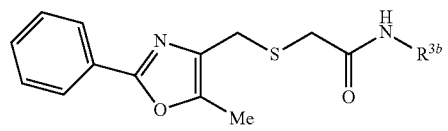
| ID | Structure | MW |
|---|---|---|
| IIa-1297 | | 376.48 |
| IIa-1298 | | 350.44 |
| IIa-1299 | | 388.51 |

TABLE 5-continued
Oxazole amides (R³ = NH-misc)

| ID | Structure | MW |
|---|---|---|
| IIa-1300 | 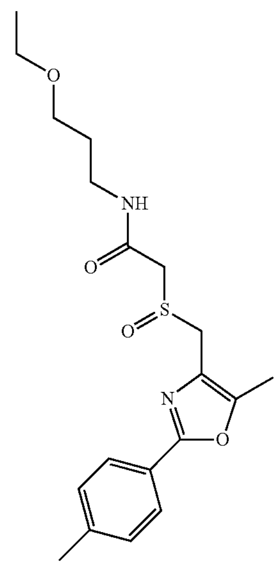 [SMILES: CCOCCCNC(=O)CS(=O)Cc1nc(-c2ccc(C)cc2)oc1C] | 378.49 |
| IIa-1301 | 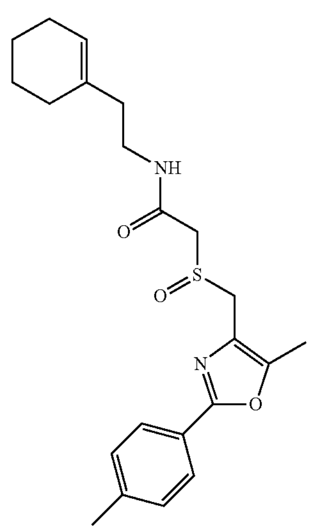 [SMILES: Cc1ccc(-c2nc(CS(=O)CC(=O)NCCC3=CCCCC3)c(C)o2)cc1] | 400.54 |

TABLE 5-continued
Oxazole amides (R³ = NH-misc)
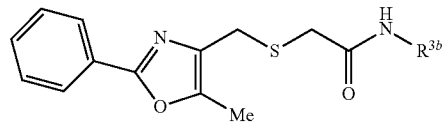
| ID | Structure | MW |
|---|---|---|
| IIa-1302 | 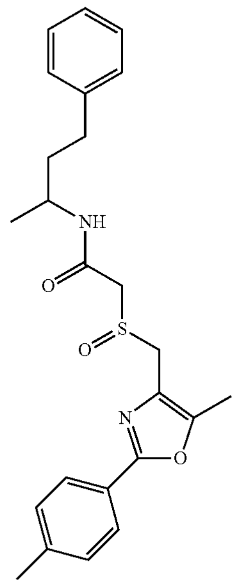 [SMILES: Cc1ccc(-c2nc(CS(=O)CC(=O)NC(C)CCc3ccccc3)c(C)o2)cc1] | 424.57 |
| IIa-1303 | 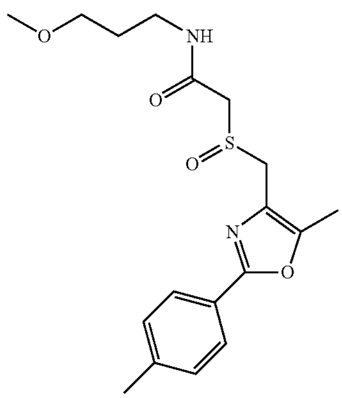 | 364.47 |
| IIa-1304 | 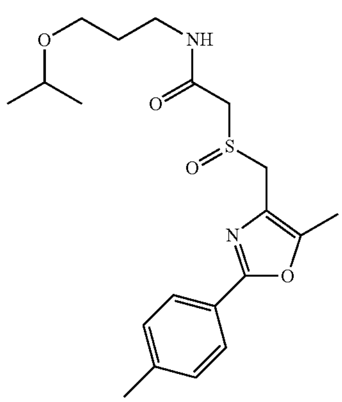 [SMILES: Cc1ccc(-c2nc(CS(=O)CC(=O)NCCCOC(C)C)c(C)o2)cc1] | 392.52 |

TABLE 5-continued
Oxazole amides (R³ = NH-misc)
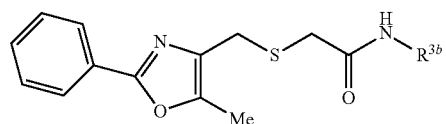
| ID | Structure | MW |
|---|---|---|
| IIa-1305 | | 405.52 |
| IIa-1306 | | 348.47 |
| IIa-1307 | | 431.60 |

TABLE 5-continued
Oxazole amides (R³ = NH-misc)
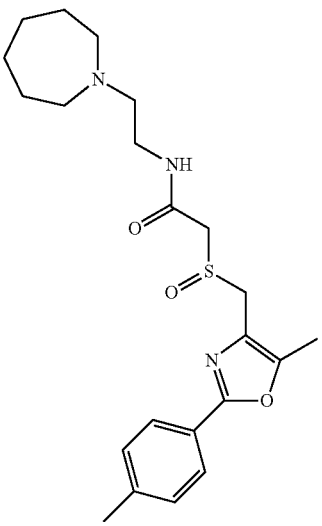 [SMILES: Cc1ccc(-c2nc(CS(=O)CC(=O)NCCN3CCCCCC3)c(C)o2)cc1]
| ID | Structure | MW |
|---|---|---|
| IIa-1308 | 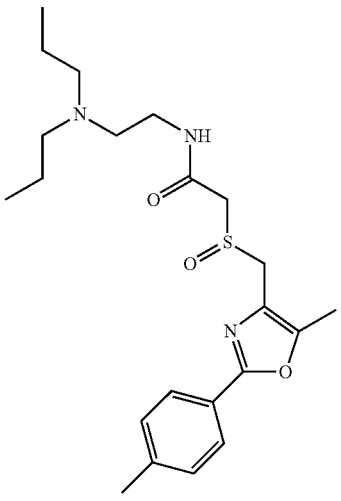 [SMILES: CCCN(CCC)CCNC(=O)CS(=O)Cc1nc(-c2ccc(C)cc2)oc1C] | 417.57 |
| IIa-1309 | | 419.59 |

TABLE 5-continued
Oxazole amides (R³ = NH-misc)
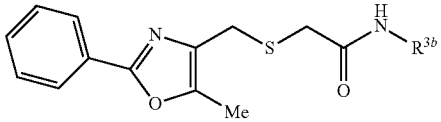
| ID | Structure | MW |
|---|---|---|
| IIa-1310 | 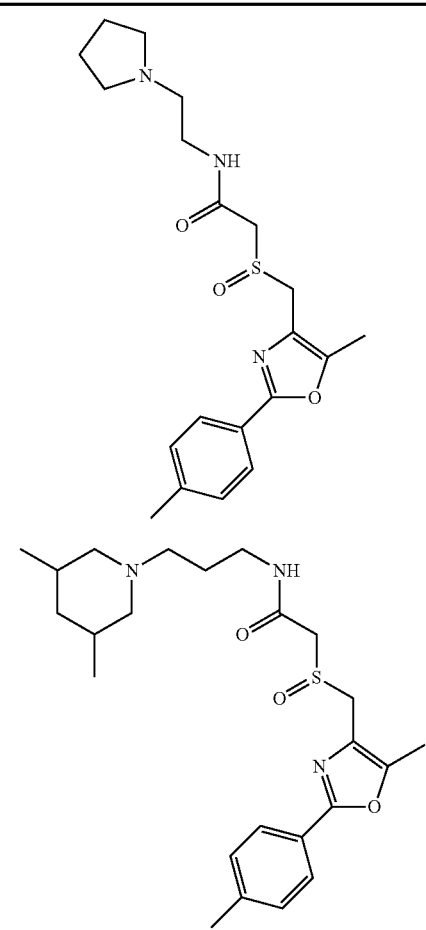 | 389.52 |
| IIa-1311 | | 445.63 |
| IIa-1312 | 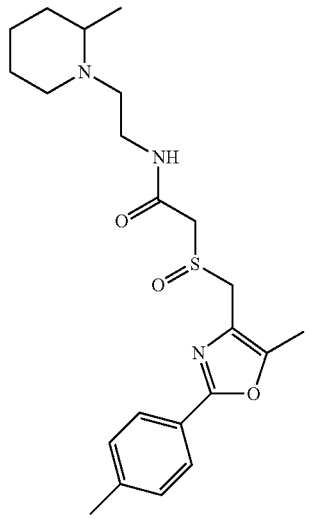 [SMILES: Cc1ccc(-c2nc(CS(=O)CC(=O)NCCN3CCCCC3C)c(C)o2)cc1] | 417.57 |

TABLE 5-continued

Oxazole amides (R³ = NH-misc)

| ID | Structure | MW |
|---|---|---|
| IIa-1313 | 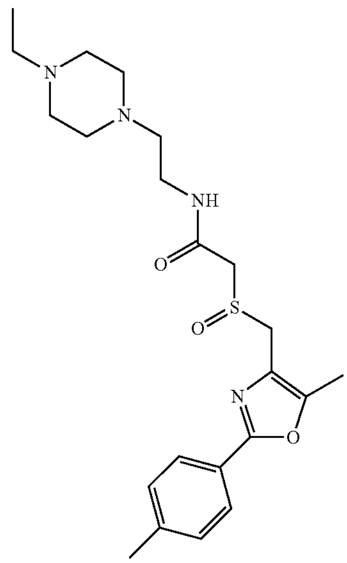 [SMILES: CCN1CCN(CCNC(=O)CS(=O)Cc2nc(-c3ccc(C)cc3)oc2C)CC1] | 432.59 |
| IIa-1314 | 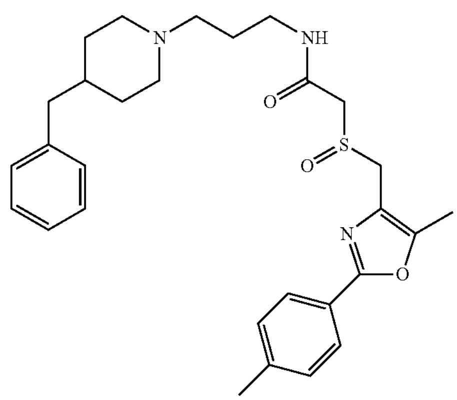 [SMILES: Cc1ccc(-c2nc(CS(=O)CC(=O)NCCCN3CCC(Cc4ccccc4)CC3)c(C)o2)cc1] | 507.70 |
| IIa-1315 | 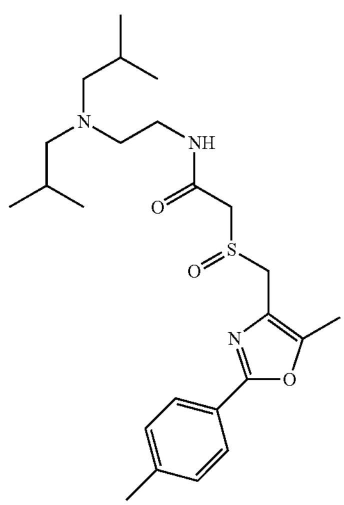 [SMILES: Cc1ccc(-c2nc(CS(=O)CC(=O)NCCN(CC(C)C)CC(C)C)c(C)o2)cc1] | 447.64 |

TABLE 5-continued
Oxazole amides (R³ = NH-misc)
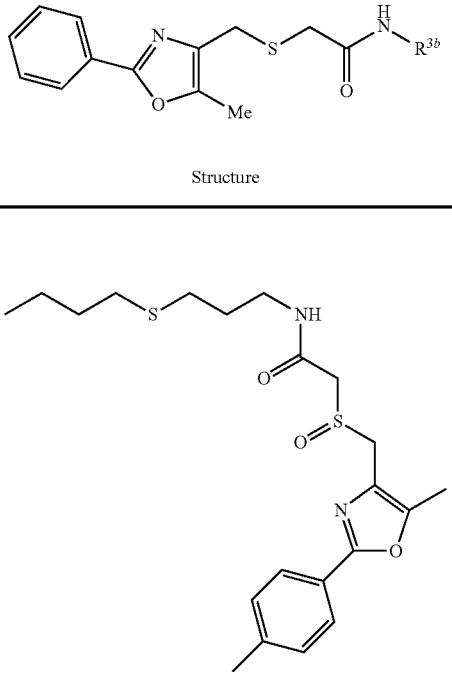
| ID | Structure | MW |
|---|---|---|
| IIa-1316 | 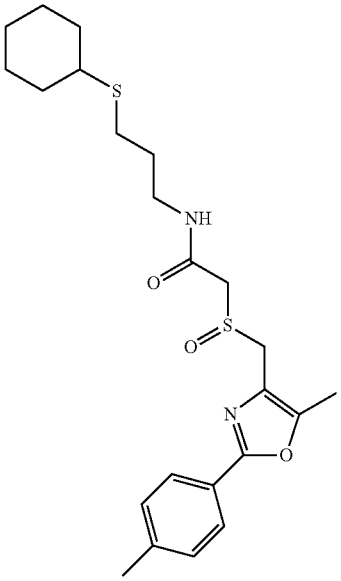 | 422.61 |
| IIa-1317 | 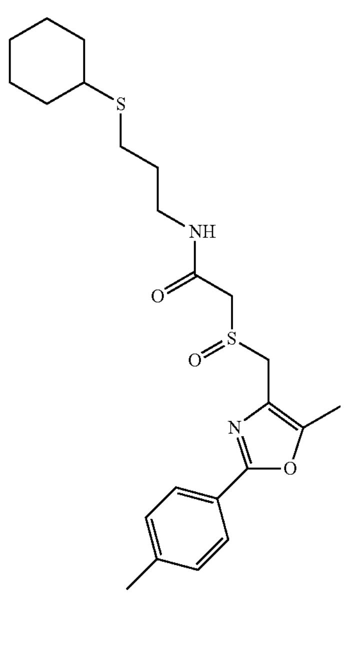 [SMILES: Cc1ccc(-c2nc(CS(=O)CC(=O)NCCCSC3CCCCC3)c(C)o2)cc1] | 448.65 |

TABLE 5-continued

Oxazole amides (R³ = NH-misc)

| ID | Structure | MW |
|---|---|---|
| IIa-1318 | | 467.98 |
| IIa-1319 | | 428.94 |

TABLE 5-continued
Oxazole amides (R³ = NH-misc)
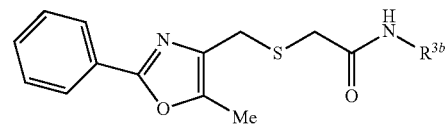
| ID | Structure | MW |
|---|---|---|
| IIa-1320 | | 403.89 |
| IIa-1321 | | 392.86 |

TABLE 5-continued
Oxazole amides (R³ = NH-misc)
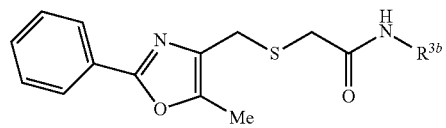
| ID | Structure | MW |
|---|---|---|
| IIa-1322 | | 354.86 |
| IIa-1323 | | 411.95 |
| IIa-1324 | | 439.96 |

TABLE 5-continued
Oxazole amides (R³ = NH-misc)
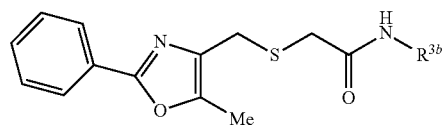
| ID | Structure | MW |
|---|---|---|
| IIa-1325 | | 396.90 |
| IIa-1326 | | 370.86 |
| IIa-1327 | | 408.93 |

TABLE 5-continued
Oxazole amides (R³ = NH-misc)
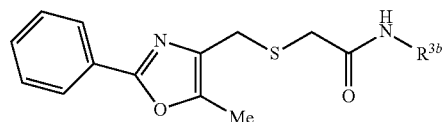
| ID | Structure | MW |
|---|---|---|
| IIa-1328 | 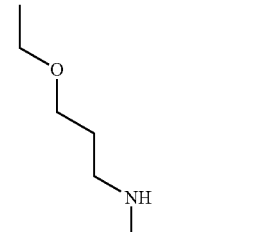 | 398.91 |
| IIa-1329 | 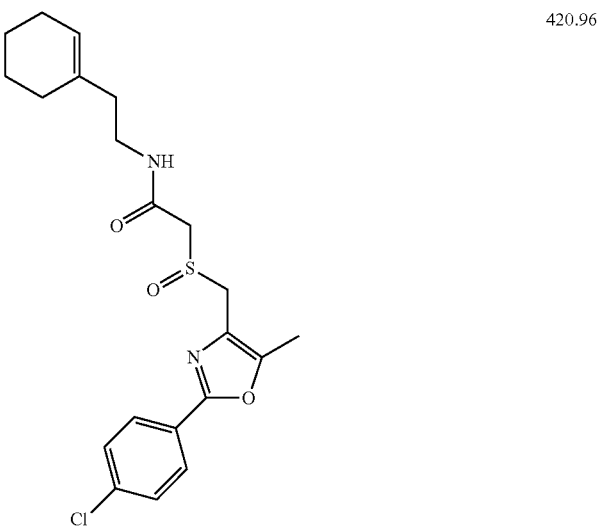 | 420.96 |

TABLE 5-continued

Oxazole amides (R³ = NH-misc)

[Structure: phenyl-oxazole(Me)-CH2-S-CH2-C(=O)-NH-R^{3b}]

| ID | Structure | MW |
|---|---|---|
| IIa-1330 | 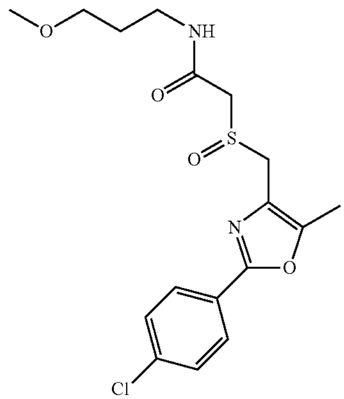 | 384.88 |
| IIa-1331 | 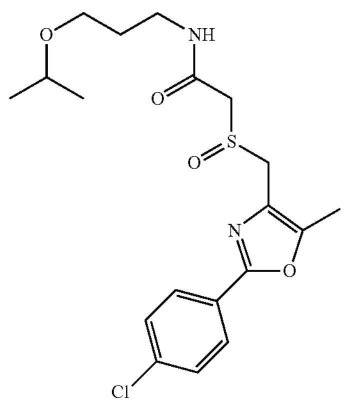 [SMILES: Cc1oc(-c2ccc(Cl)cc2)nc1CS(=O)CC(=O)NCCCOC(C)C] | 412.94 |
| IIa-1332 | 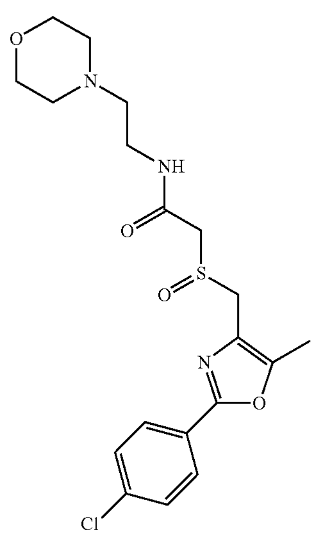 [SMILES: Cc1oc(-c2ccc(Cl)cc2)nc1CS(=O)CC(=O)NCCN1CCOCC1] | 425.94 |

TABLE 5-continued

Oxazole amides (R³ = NH-misc)

| ID | Structure | MW |
|---|---|---|
| IIa-1333 | 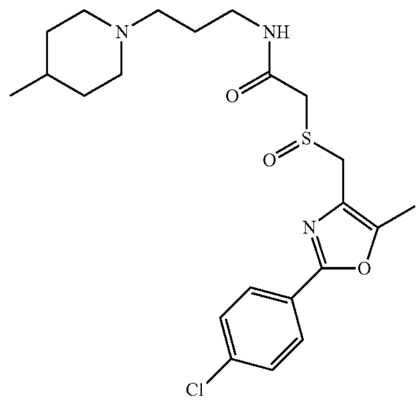 | 452.02 |
| IIa-1334 | 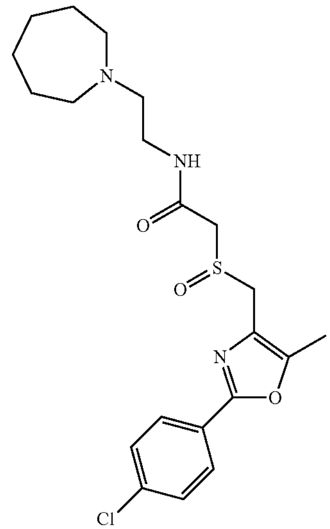 [SMILES: Cc1oc(-c2ccc(Cl)cc2)nc1CS(=O)CC(=O)NCCN1CCCCCC1] | 437.99 |
| IIa-1335 | 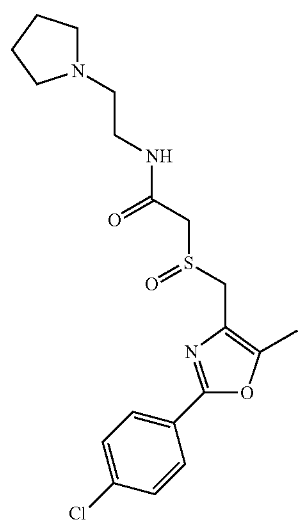 [SMILES: Cc1oc(-c2ccc(Cl)cc2)nc1CS(=O)CC(=O)NCCN1CCCC1] | 409.94 |

TABLE 5-continued

Oxazole amides (R³ = NH-misc)

| ID | Structure | MW |
|---|---|---|
| IIa-1336 | | 466.05 |
| IIa-1337 | | 453.01 |

TABLE 5-continued
Oxazole amides (R³ = NH-misc)
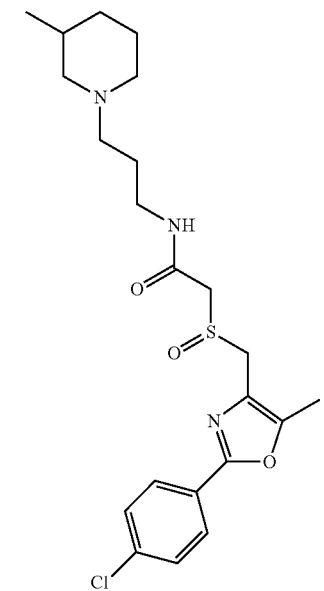
| ID | Structure | MW |
|----|-----------|-----|
| IIa-1338 | 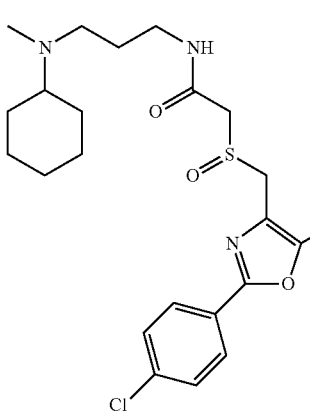 | 452.02 |
| IIa-1339 | | 466.05 |

TABLE 5-continued
Oxazole amides (R³ = NH-misc)
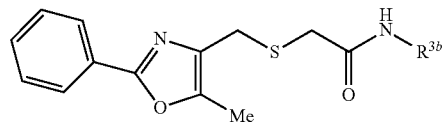
| ID | Structure | MW |
|---|---|---|
| IIa-1340 | | 447.56 |
| IIa-1341 | | 408.52 |

TABLE 5-continued
Oxazole amides (R³ = NH-misc)
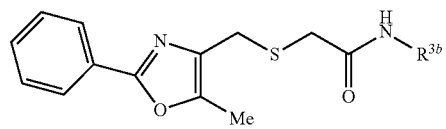
| ID | Structure | MW |
|---|---|---|
| IIa-1342 | | 383.47 |
| IIa-1343 | | 348.47 |
| IIa-1344 | | 334.44 |

TABLE 5-continued
Oxazole amides (R³ = NH-misc)
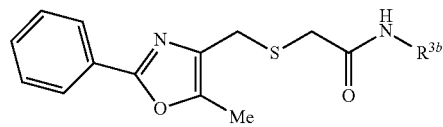
| ID | Structure | MW |
|---|---|---|
| IIa-1345 | | 334.44 |
| IIa-1346 | | 380.47 |
| IIa-1347 | | 419.55 |

TABLE 5-continued
Oxazole amides (R³ = NH-misc)
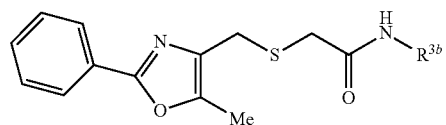
| ID | Structure | MW |
|---|---|---|
| IIa-1348 | | 362.49 |
| IIa-1349 | | 350.44 |
| IIa-1350 | | 388.51 |

TABLE 5-continued
Oxazole amides ($R^3$ = NH-misc)
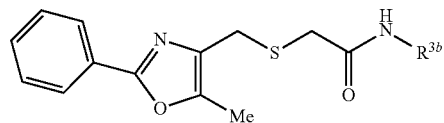
| ID | Structure | MW |
|---|---|---|
| IIa-1351 | | 378.49 |
| IIa-1352 | | 400.54 |

TABLE 5-continued
Oxazole amides (R³ = NH-misc)
| ID | Structure | MW |
|---|---|---|
| IIa-1353 | 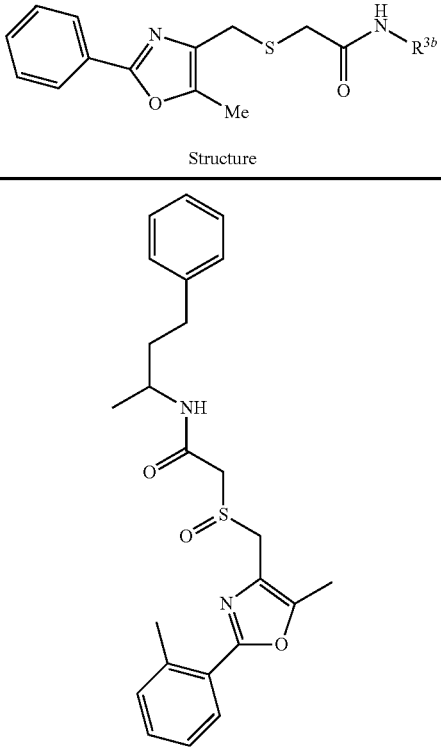 | 424.57 |
| IIa-1354 | 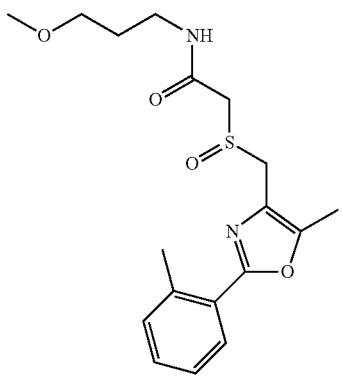 | 364.47 |
| IIa-1355 | 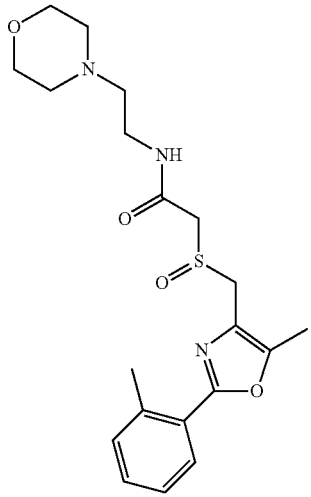 [SMILES: Cc1ccccc1-c1nc(CS(=O)CC(=O)NCCN2CCOCC2)c(C)o1] | 405.52 |

TABLE 5-continued
Oxazole amides (R³ = NH-misc)
| ID | Structure | MW |
|---|---|---|
| IIa-1356 | 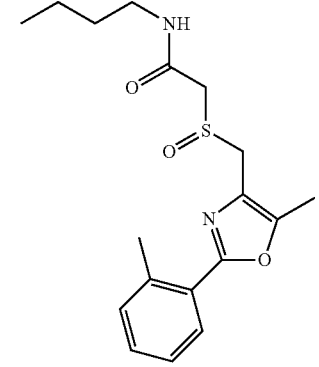 [SMILES: CCCCNC(=O)CS(=O)Cc1nc(-c2ccccc2C)oc1C] | 348.47 |
| IIa-1357 | 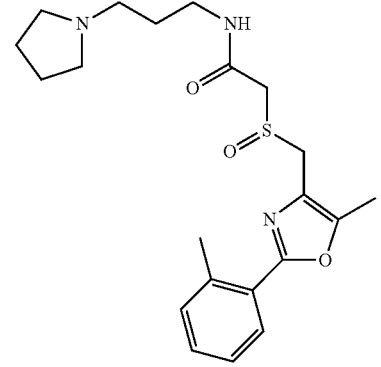 [SMILES: Cc1ccccc1-c1nc(CS(=O)CC(=O)NCCCN2CCCC2)c(C)o1] | 403.55 |
| IIa-1358 | 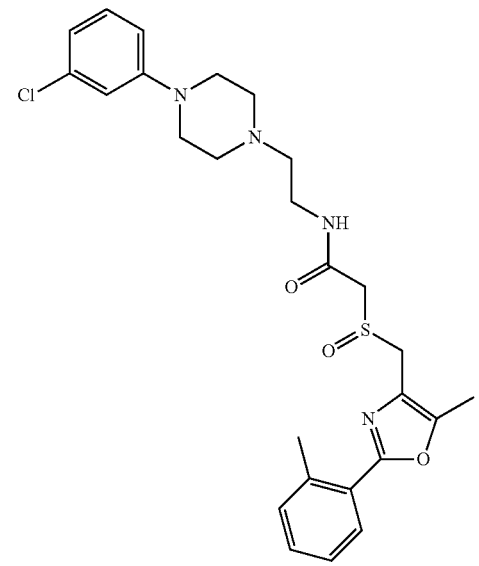 [SMILES: Cc1ccccc1-c1nc(CS(=O)CC(=O)NCCN2CCN(c3cccc(Cl)c3)CC2)c(C)o1] | 515.08 |

TABLE 5-continued

Oxazole amides (R³ = NH-misc)

| ID | Structure | MW |
|---|---|---|
| IIa-1359 | | 494.66 |
| IIa-1360 | | 439.58 |
| IIa-1361 | | 403.89 |

TABLE 5-continued
Oxazole amides (R³ = NH-misc)
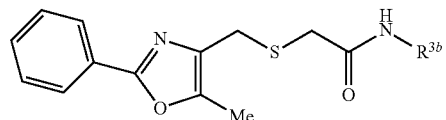
| ID | Structure | MW |
|---|---|---|
| IIa-1362 | 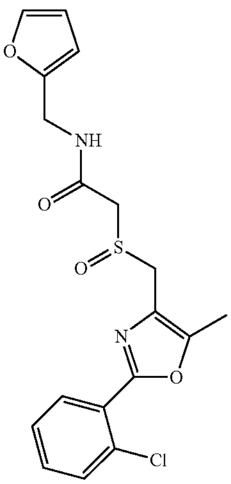 [SMILES: Cc1oc(-c2ccccc2Cl)nc1CS(=O)CC(=O)NCc1ccco1] | 392.86 |
| IIa-1363 | 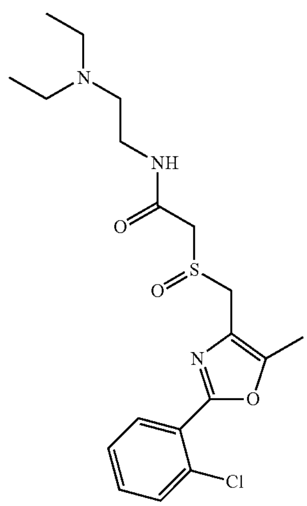 [SMILES: CCN(CC)CCNC(=O)CS(=O)Cc1nc(-c2ccccc2Cl)oc1C] | 411.95 |
| IIa-1364 | 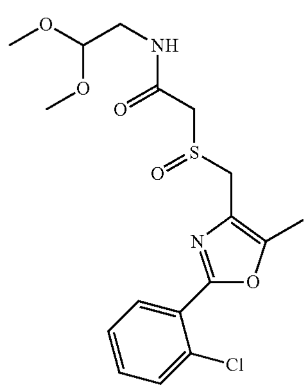 | 400.88 |

TABLE 5-continued
Oxazole amides (R³ = NH-misc)
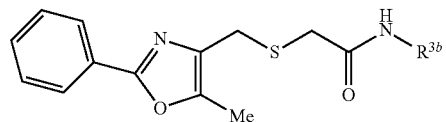
| ID | Structure | MW |
|---|---|---|
| IIa-1365 | 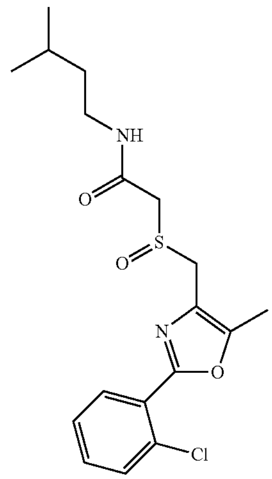 [SMILES: Cc1oc(-c2ccccc2Cl)nc1CS(=O)CC(=O)NCCC(C)C] | 382.91 |
| IIa-1366 | 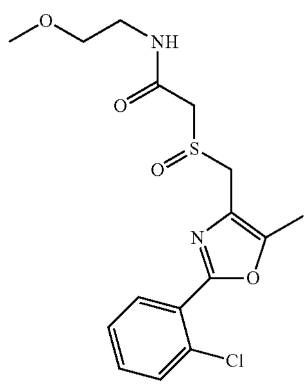 | 370.86 |
| IIa-1367 | 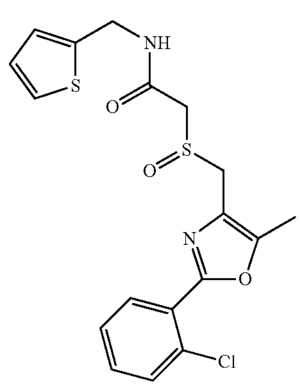 [SMILES: Cc1oc(-c2ccccc2Cl)nc1CS(=O)CC(=O)NCc1cccs1] | 408.93 |

TABLE 5-continued

Oxazole amides (R³ = NH-misc)

| ID | Structure | MW |
|---|---|---|
| IIa-1368 | | 368.89 |
| IIa-1369 | | 466.05 |
| IIa-1370 | | 463.56 |

TABLE 5-continued

Oxazole amides (R³ = NH-misc)

| ID | Structure | MW |
|---|---|---|
| IIa-1371 | 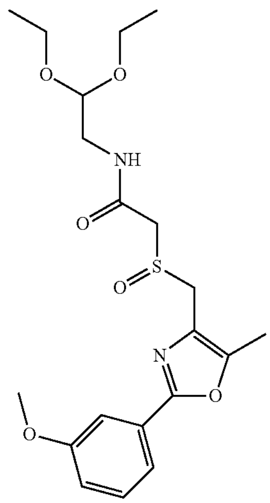 [SMILES: CCOC(CNC(=O)CS(=O)Cc1nc(-c2cccc(OC)c2)oc1C)OCC] | 424.52 |
| IIa-1372 | 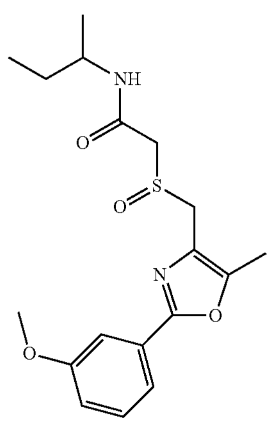 [SMILES: CCC(C)NC(=O)CS(=O)Cc1nc(-c2cccc(OC)c2)oc1C] | 364.47 |
| IIa-1373 | 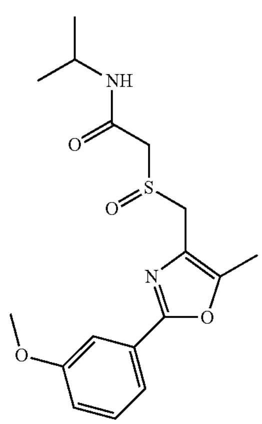 | 350.44 |

TABLE 5-continued
Oxazole amides (R³ = NH-misc)
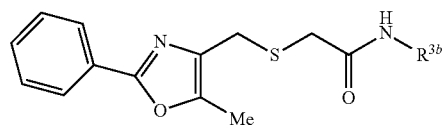
| ID | Structure | MW |
|---|---|---|
| IIa-1374 | 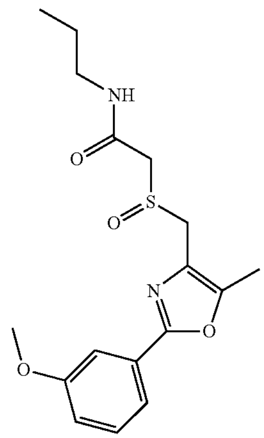 | 350.44 |
| IIa-1375 | 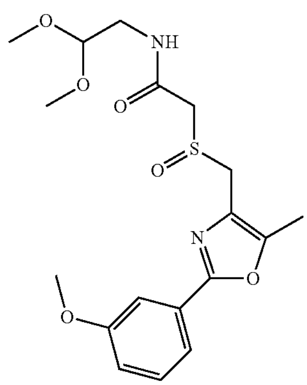 | 396.47 |
| IIa-1376 | 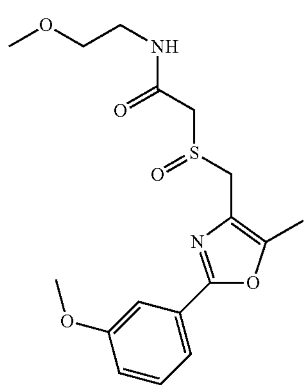 | 366.44 |

TABLE 5-continued

Oxazole amides (R³ = NH-misc)

| ID | Structure | MW |
|---|---|---|
| IIa-1377 | 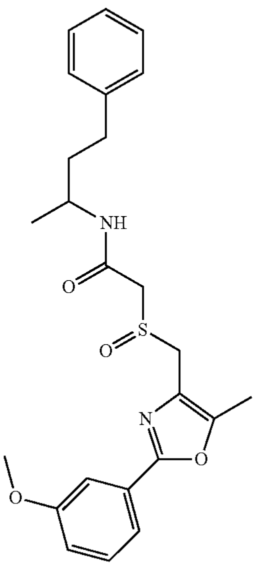 | 440.57 |
| IIa-1378 | 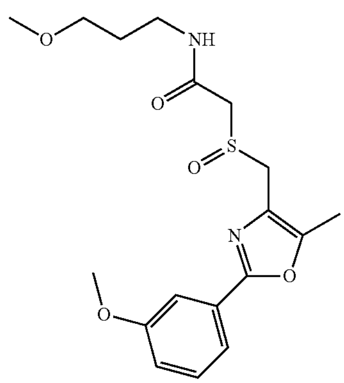 | 380.47 |
| IIa-1379 | 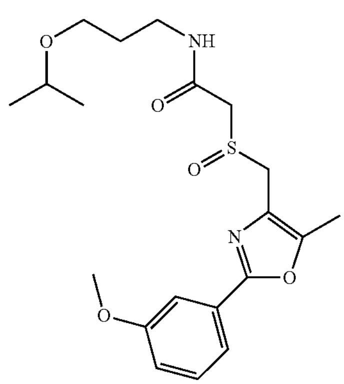 [SMILES: COc1cccc(-c2nc(CS(=O)CC(=O)NCCCOC(C)C)c(C)o2)c1] | 408.52 |

TABLE 5-continued

Oxazole amides (R³ = NH-misc)

| ID | Structure | MW |
|---|---|---|
| IIa-1380 | | 364.47 |
| IIa-1381 | | 493.58 |

TABLE 5-continued
Oxazole amides (R³ = NH-misc)
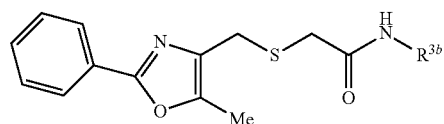
| ID | Structure | MW |
|---|---|---|
| IIa-1382 | 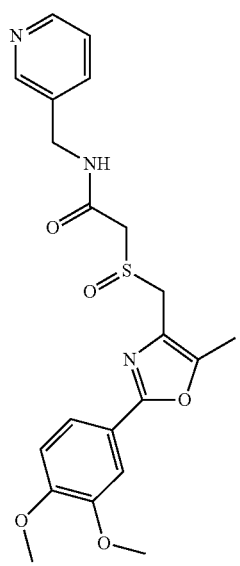 [SMILES: COc1ccc(-c2nc(CS(=O)CC(=O)NCc3cccnc3)c(C)o2)cc1OC] | 454.55 |
| IIa-1383 | | 429.50 |

TABLE 5-continued
Oxazole amides (R³ = NH-misc)
| ID | Structure | MW |
|---|---|---|
| IIa-1384 | 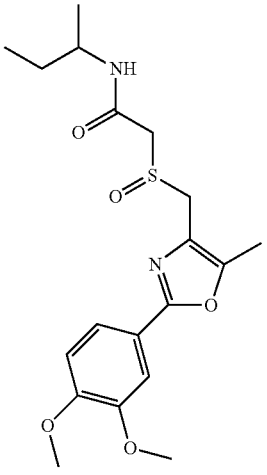 [SMILES: CCC(C)NC(=O)CS(=O)Cc1nc(-c2ccc(OC)c(OC)c2)oc1C] | 394.49 |
| IIa-1385 | 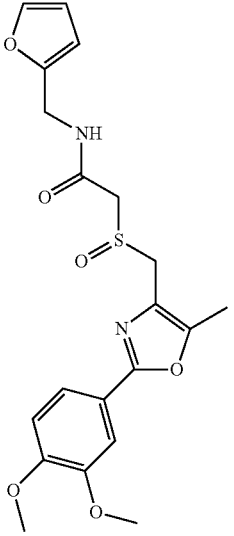 [SMILES: COc1ccc(-c2nc(CS(=O)CC(=O)NCc3ccco3)c(C)o2)cc1OC] | 418.47 |

TABLE 5-continued
Oxazole amides (R³ = NH-misc)
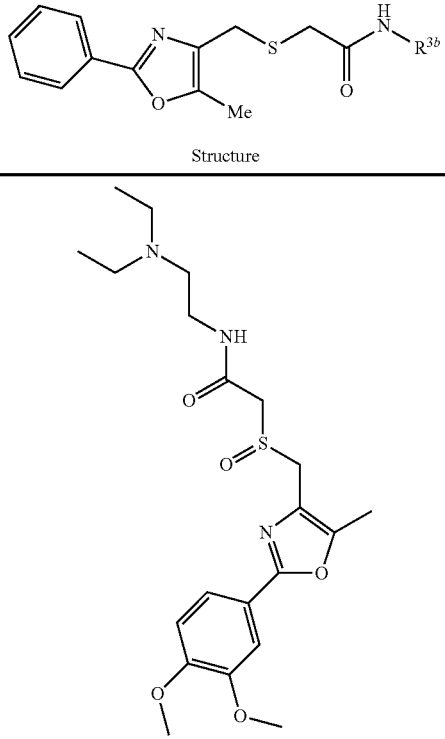
| ID | Structure | MW |
| --- | --- | --- |
| IIa-1386 | 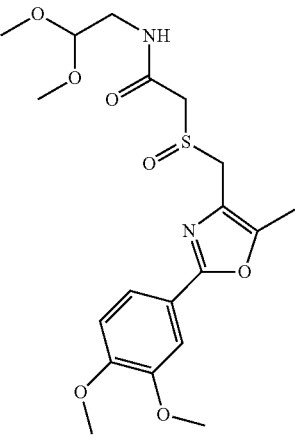 | 437.56 |
| IIa-1387 | | 426.49 |
| IIa-1388 | 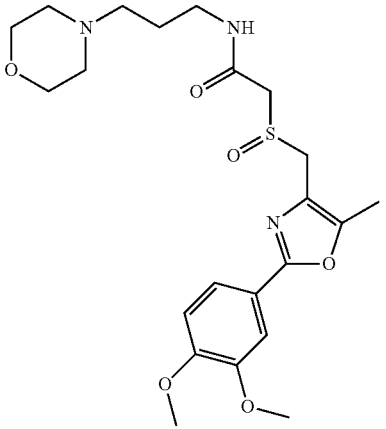 [SMILES: COc1ccc(-c2nc(CS(=O)CC(=O)NCCCN3CCOCC3)c(C)o2)cc1OC] | 465.57 |

TABLE 5-continued

Oxazole amides (R³ = NH-misc)

| ID | Structure | MW |
|---|---|---|
| IIa-1389 | | 408.52 |
| IIa-1390 | | 396.47 |

TABLE 5-continued
Oxazole amides (R³ = NH-misc)
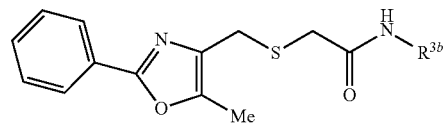
| ID | Structure | MW |
|---|---|---|
| IIa-1391 | 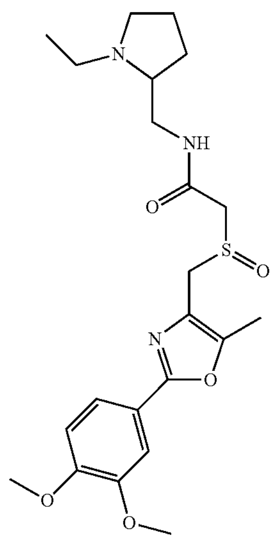 [SMILES: CCN1CCCC1CNC(=O)CS(=O)Cc1nc(-c2ccc(OC)c(OC)c2)oc1C] | 449.57 |
| IIa-1392 | 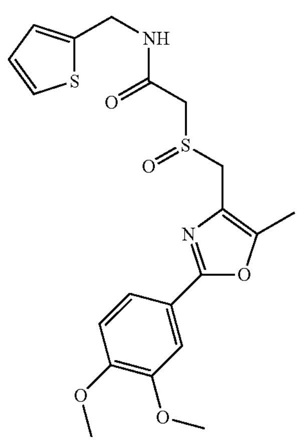 [SMILES: COc1ccc(-c2nc(CS(=O)CC(=O)NCc3cccs3)c(C)o2)cc1OC] | 434.54 |

TABLE 5-continued
Oxazole amides (R³ = NH-misc)
| ID | Structure | MW |
|---|---|---|
| IIa-1393 | 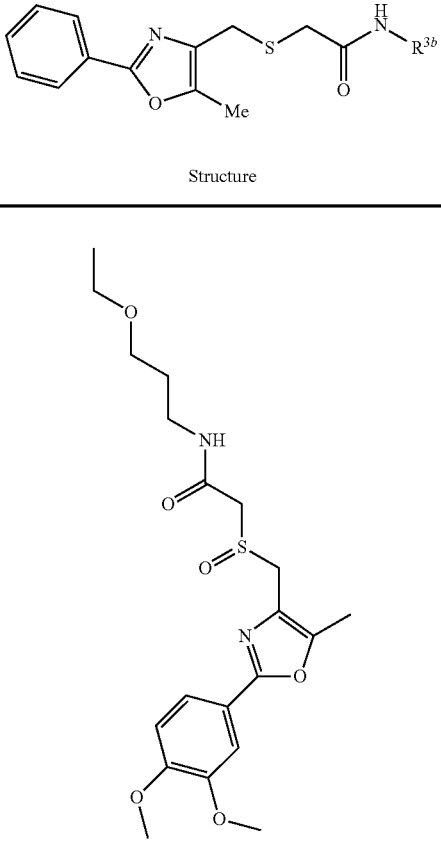 | 424.52 |
| IIa-1394 | 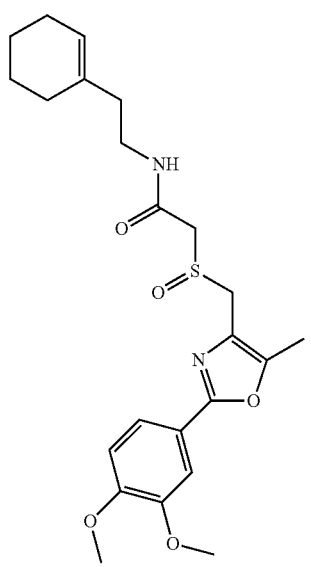 [SMILES: COc1ccc(-c2nc(CS(=O)CC(=O)NCCC3=CCCCC3)c(C)o2)cc1OC] | 446.57 |

TABLE 5-continued

Oxazole amides (R³ = NH-misc)

| ID | Structure | MW |
|---|---|---|
| IIa-1395 | | 470.59 |
| IIa-1396 | | 410.49 |

TABLE 5-continued

Oxazole amides (R³ = NH-misc)

| ID | Structure | MW |
|---|---|---|
| IIa-1397 | | 438.55 |
| IIa-1398 | | 394.49 |
| IIa-1399 | | 491.65 |

TABLE 5-continued
Oxazole amides (R³ = NH-misc)
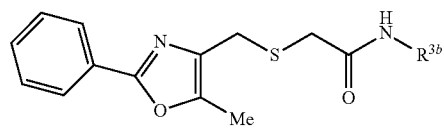
| ID | Structure | MW |
|---|---|---|
| IIa-1400 | | 477.63 |
| IIa-1401 | | 479.64 |
| IIa-1402 | | 449.57 |

TABLE 5-continued
Oxazole amides (R³ = NH-misc)
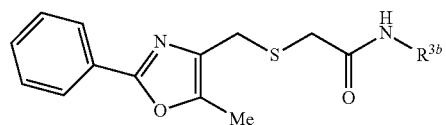
| ID | Structure | MW |
|---|---|---|
| IIa-1403 | | 463.60 |
| IIa-1404 | | 465.62 |

TABLE 5-continued
Oxazole amides (R³ = NH-misc)
| ID | Structure | MW |
|---|---|---|
| IIa-1405 | 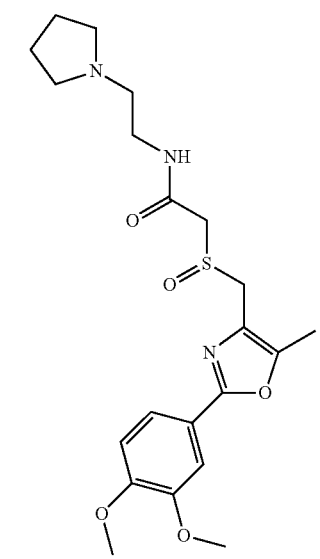 [SMILES: COc1ccc(-c2nc(CS(=O)CC(=O)NCCN3CCCC3)c(C)o2)cc1OC] | 435.55 |
| IIa-1406 | 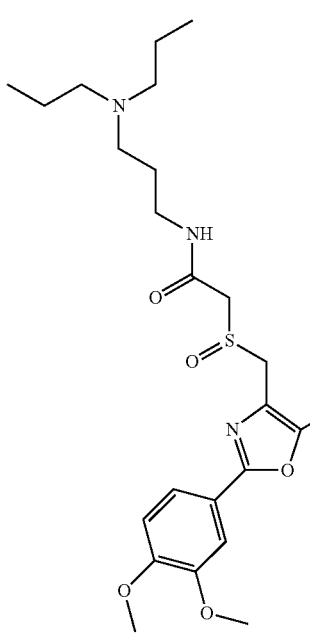 | 479.64 |

TABLE 5-continued
Oxazole amides (R³ = NH-misc)
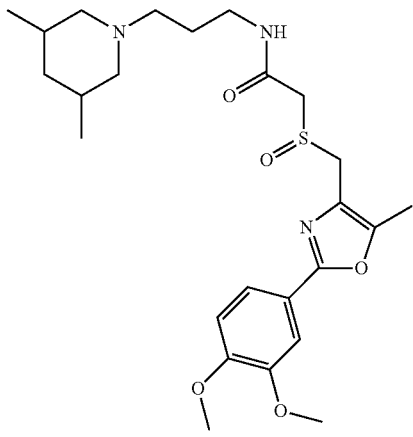
| ID | Structure | MW |
|---|---|---|
| IIa-1407 | 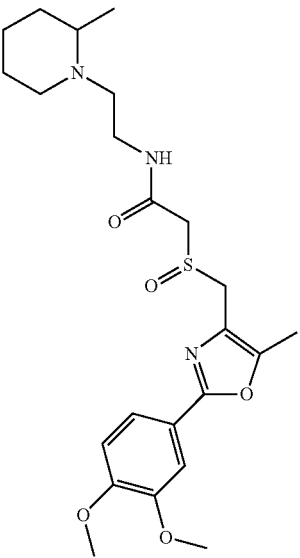 [SMILES: COc1ccc(-c2nc(CS(=O)CC(=O)NCCN3CCCCC3C)c(C)o2)cc1OC] | 491.65 |
| IIa-1408 | | 463.60 |

TABLE 5-continued
Oxazole amides (R³ = NH-misc)
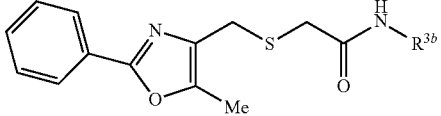
| ID | Structure | MW |
|---|---|---|
| IIa-1409 | 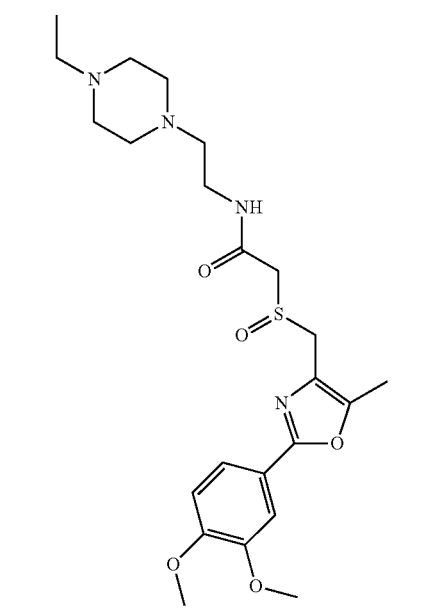 [SMILES: CCN1CCN(CCNC(=O)CS(=O)Cc2nc(-c3ccc(OC)c(OC)c3)oc2C)CC1] | 478.62 |
| IIa-1410 | | 465.62 |

TABLE 5-continued

Oxazole amides (R³ = NH-misc)

| ID | Structure | MW |
|---|---|---|
| IIa-1411 | | 477.63 |
| IIa-1412 | | 553.73 |

TABLE 5-continued

Oxazole amides (R³ = NH-misc)

| ID | Structure | MW |
|---|---|---|
| IIa-1413 | | 507.70 |
| IIa-1414 | | 541.72 |

TABLE 5-continued
Oxazole amides (R³ = NH-misc)
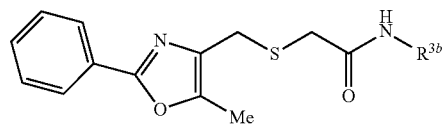
| ID | Structure | MW |
|---|---|---|
| IIa-1415 | 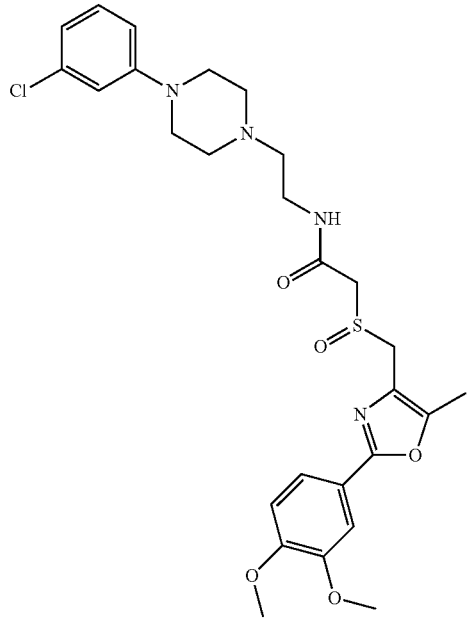 [SMILES: COc1ccc(-c2nc(CS(=O)CC(=O)NCCN3CCN(c4cccc(Cl)c4)CC3)c(C)o2)cc1OC] | 561.10 |
| IIa-1416 | 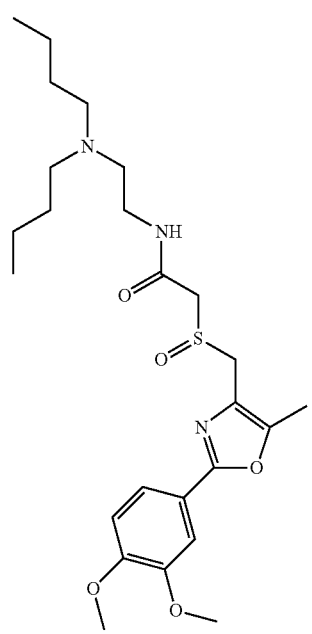 [SMILES: CCCCN(CCCC)CCNC(=O)CS(=O)Cc1nc(-c2ccc(OC)c(OC)c2)oc1C] | 493.67 |

TABLE 5-continued
Oxazole amides (R³ = NH-misc)
| ID | Structure | MW |
|---|---|---|
| IIa-1417 | 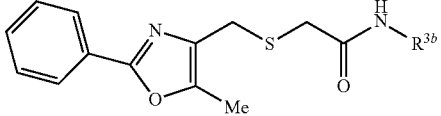 | 485.61 |
| IIa-1418 | 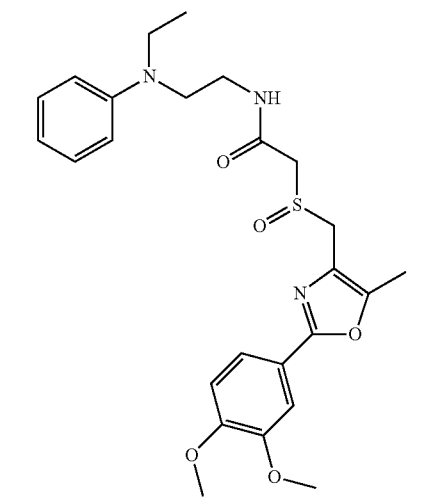 [SMILES: CCN(CCNC(=O)CS(=O)Cc1nc(-c2ccc(OC)c(OC)c2)oc1C)c1ccccc1] | 468.64 |

TABLE 5-continued
Oxazole amides (R³ = NH-misc)
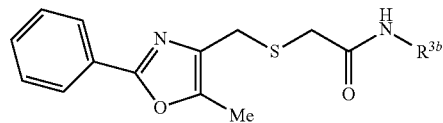
| ID | Structure | MW |
|---|---|---|
| IIa-1419 | | 494.68 |
| IIa-1420 | | 394.49 |

TABLE 5-continued
Oxazole amides (R³ = NH-misc)
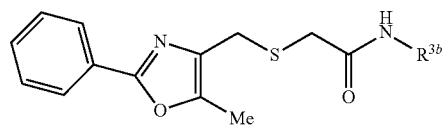
| ID | Structure | MW |
|---|---|---|
| IIa-1421 | 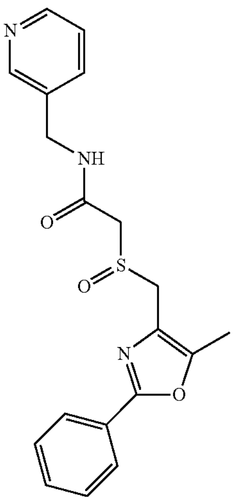 [SMILES: Cc1oc(-c2ccccc2)nc1CS(=O)CC(=O)NCc1cccnc1] | 369.45 |
| IIa-1422 | 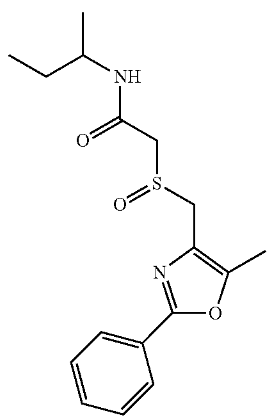 [SMILES: CCC(C)NC(=O)CS(=O)Cc1nc(-c2ccccc2)oc1C] | 334.44 |
| IIa-1423 | 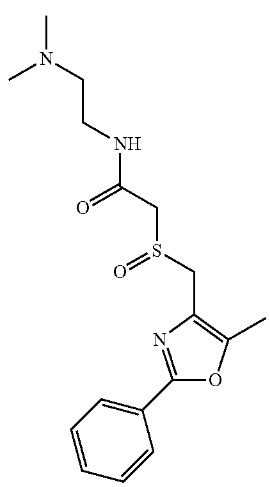 | 349.46 |

TABLE 5-continued

Oxazole amides (R³ = NH-misc)

| ID | Structure | MW |
|---|---|---|
| IIa-1424 | 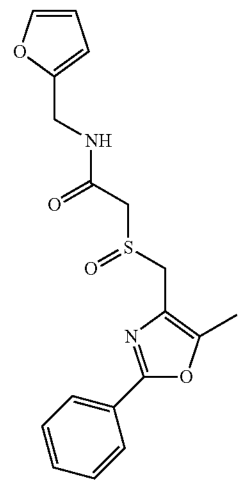 [SMILES: Cc1oc(-c2ccccc2)nc1CS(=O)CC(=O)NCc1ccco1] | 358.42 |
| IIa-1425 | 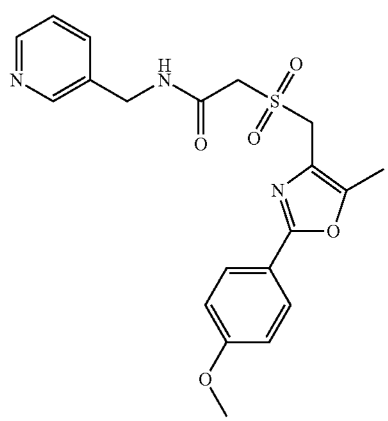 [SMILES: COc1ccc(-c2nc(CS(=O)(=O)CC(=O)NCc3cccnc3)c(C)o2)cc1] | 415.47 |
| IIa-1426 | 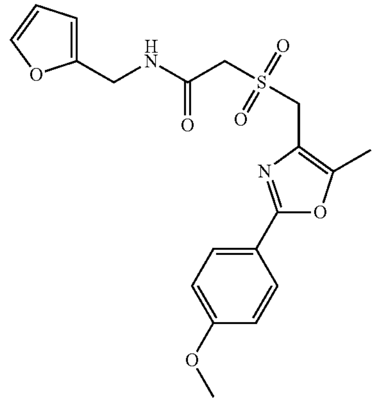 [SMILES: COc1ccc(-c2nc(CS(=O)(=O)CC(=O)NCc3ccco3)c(C)o2)cc1] | 404.45 |

TABLE 5-continued

Oxazole amides (R³ = NH-misc)

| ID | Structure | MW |
|---|---|---|
| IIa-1427 | 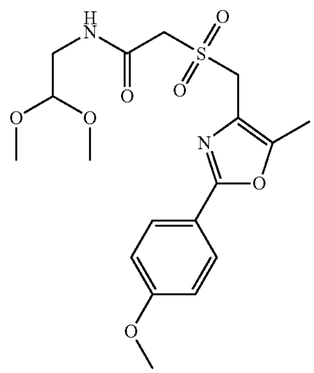 [SMILES: COc1ccc(-c2nc(CS(=O)(=O)CC(=O)NCC(OC)OC)c(C)o2)cc1] | 412.47 |
| IIa-1428 | 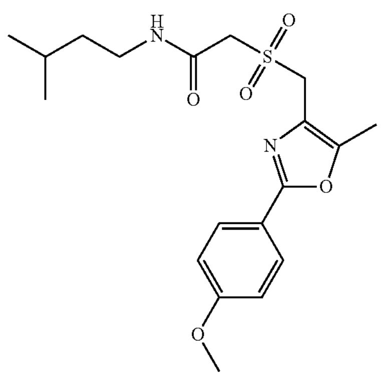 [SMILES: COc1ccc(-c2nc(CS(=O)(=O)CC(=O)NCCC(C)C)c(C)o2)cc1] | 394.49 |
| IIa-1429 | 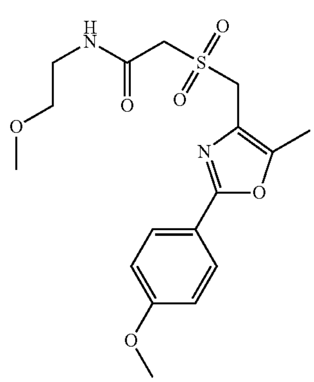 [SMILES: COCCNC(=O)CS(=O)(=O)Cc1nc(-c2ccc(OC)cc2)oc1C] | 382.44 |

TABLE 5-continued
Oxazole amides (R³ = NH-misc)
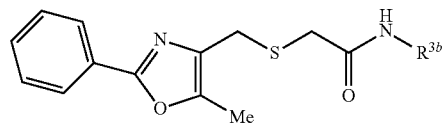
| ID | Structure | MW |
| --- | --- | --- |
| IIa-1430 |  | 432.54 |
| IIa-1431 |  | 396.47 |
| IIa-1432 |  | 380.47 |

TABLE 5-continued
Oxazole amides (R³ = NH-misc)
| ID | Structure | MW |
|---|---|---|
| IIa-1433 | 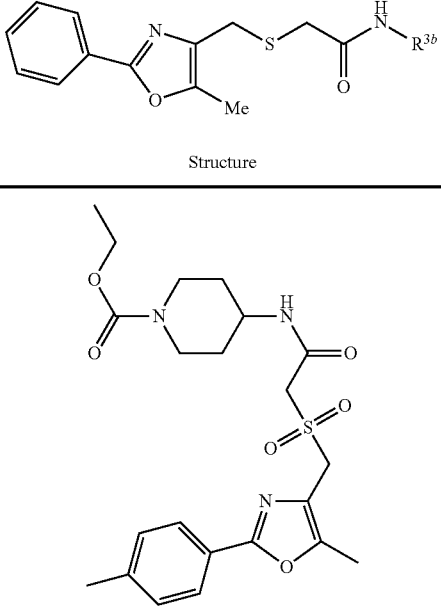 | 463.56 |
| IIa-1434 | 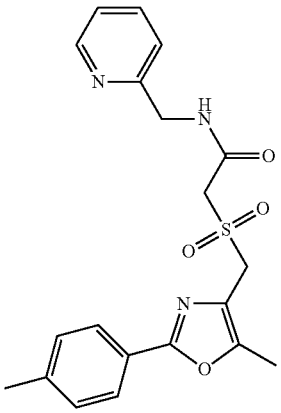 | 399.47 |
| IIa-1435 | 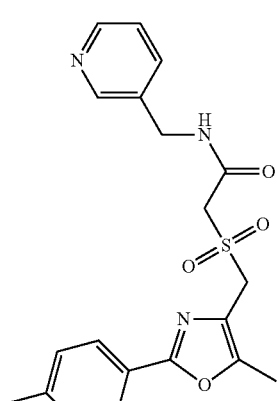 | 399.47 |

TABLE 5-continued
Oxazole amides (R³ = NH-misc)
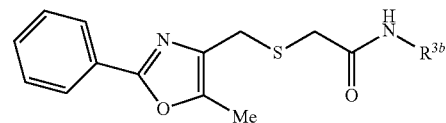
| ID | Structure | MW |
|---|---|---|
| IIa-1436 | 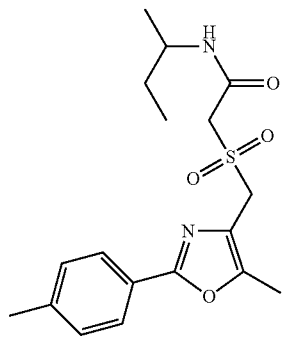 | 364.47 |
| IIa-1437 | 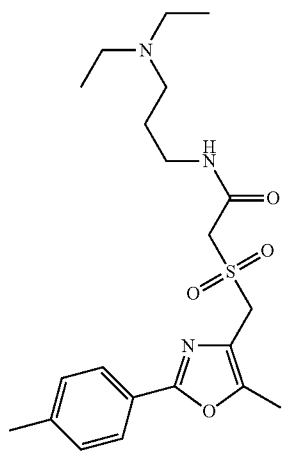 | 421.56 |
| IIa-1438 | 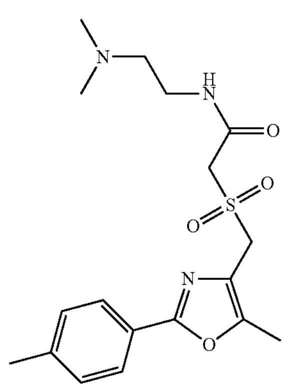 | 379.48 |

TABLE 5-continued
Oxazole amides (R³ = NH-misc)
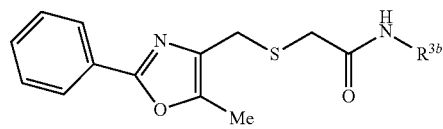
| ID | Structure | MW |
|---|---|---|
| IIa-1439 | | 426.54 |
| IIa-1440 | | 350.44 |
| IIa-1441 | | 435.55 |
| IIa-1442 | | 378.49 |

TABLE 5-continued
Oxazole amides (R³ = NH-misc)
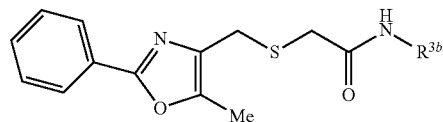
| ID | Structure | MW |
|---|---|---|
| IIa-1443 | 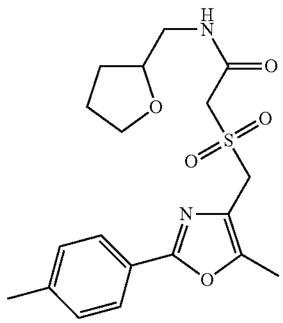 | 392.48 |
| IIa-1444 | 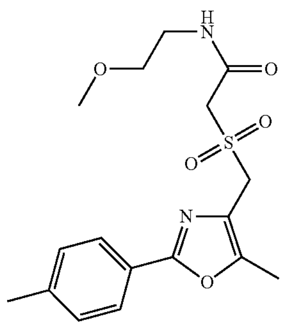 | 366.44 |
| IIa-1445 | 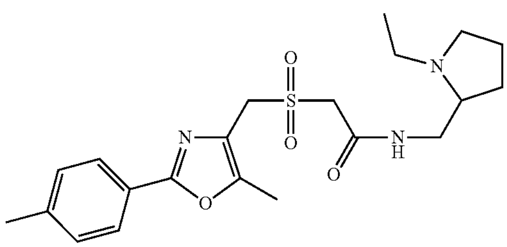 [SMILES: CCN1CCCC1CNC(=O)CS(=O)(=O)Cc1nc(-c2ccc(C)cc2)oc1C] | 419.55 |
| IIa-1446 | 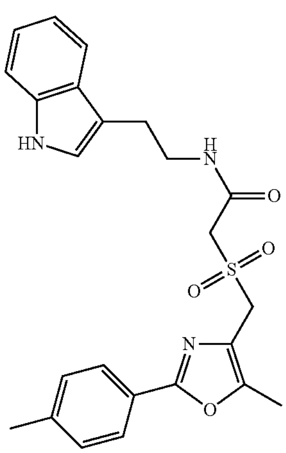 [SMILES: Cc1ccc(-c2nc(CS(=O)(=O)CC(=O)NCCc3c[nH]c4ccccc34)c(C)o2)cc1] | 451.55 |

TABLE 5-continued

Oxazole amides (R³ = NH-misc)

| ID | Structure | MW |
|---|---|---|
| IIa-1447 | | 394.49 |
| IIa-1448 | | 416.54 |
| IIa-1449 | | 440.57 |

TABLE 5-continued

Oxazole amides (R³ = NH-misc)

| ID | Structure | MW |
|---|---|---|
| IIa-1450 | | 380.47 |
| IIa-1451 | | 408.52 |
| IIa-1452 | | 421.52 |

TABLE 5-continued
Oxazole amides (R³ = NH-misc)
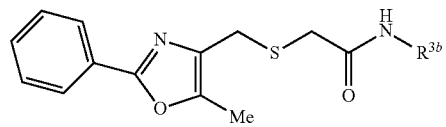
| ID | Structure | MW |
|---|---|---|
| IIa-1453 | | 470.64 |
| IIa-1454 | | 448.59 |
| IIa-1455 | | 469.61 |

TABLE 5-continued
Oxazole amides (R³ = NH-misc)
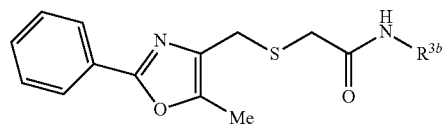
| ID | Structure | MW |
|---|---|---|
| IIa-1456 | | 449.62 |
| IIa-1457 | | 419.55 |
| IIa-1458 | | 435.59 |
| IIa-1459 | | 405.52 |

TABLE 5-continued
Oxazole amides (R³ = NH-misc)
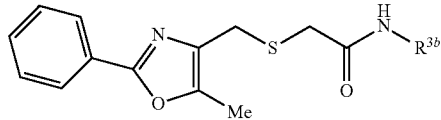
| ID | Structure | MW |
|---|---|---|
| IIa-1460 | 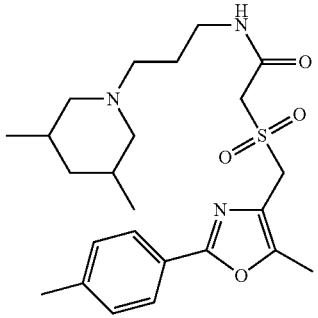 | 461.63 |
| IIa-1461 | 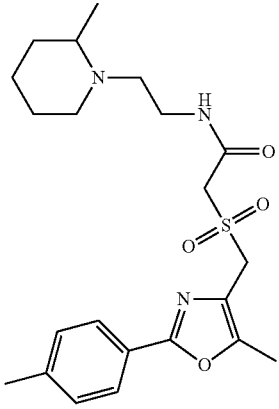 | 462.62 |
| IIa-1462 | 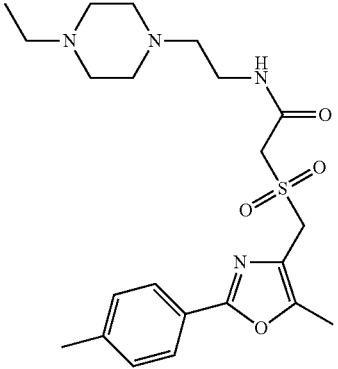 | 433.57 |
| IIa-1463 | 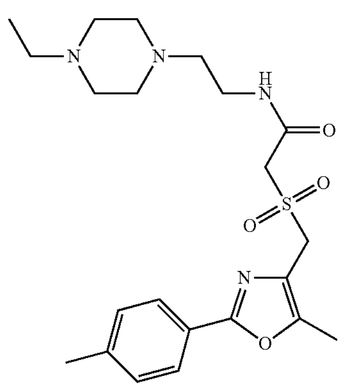 [SMILES: CCN1CCN(CCNC(=O)CS(=O)(=O)Cc2nc(-c3ccc(C)cc3)oc2C)CC1] | 448.59 |

TABLE 5-continued
Oxazole amides (R³ = NH-misc)
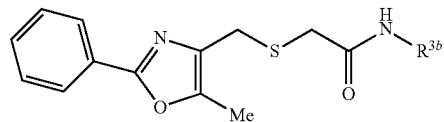
| ID | Structure | MW |
|---|---|---|
| IIa-1464 | | 477.67 |
| IIa-1465 | | 477.67 |

TABLE 5-continued

Oxazole amides (R³ = NH-misc)

| ID | Structure | MW |
|---|---|---|
| IIa-1466 | | 447.60 |
| IIa-1467 | | 463.64 |
| IIa-1468 | | 455.58 |

TABLE 5-continued
Oxazole amides (R³ = NH-misc)
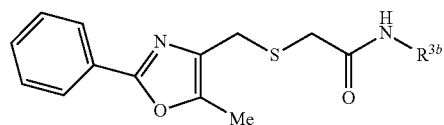
| ID | Structure | MW |
|---|---|---|
| IIa-1469 | | 497.66 |
| IIa-1470 | | 424.59 |
| IIa-1471 | | 464.65 |

TABLE 5-continued

Oxazole amides (R³ = NH-misc)

| ID | Structure | MW |
|---|---|---|
| IIa-1472 | | 489.68 |
| IIa-1473 | | 479.56 |
| IIa-1474 | | 440.52 |

TABLE 5-continued

Oxazole amides (R³ = NH-misc)

| ID | Structure | MW |
|---|---|---|
| IIa-1475 | | 380.47 |
| IIa-1476 | | 395.48 |
| IIa-1477 | | 442.54 |

TABLE 5-continued

Oxazole amides (R³ = NH-misc)

| ID | Structure | MW |
|---|---|---|
| IIa-1478 | 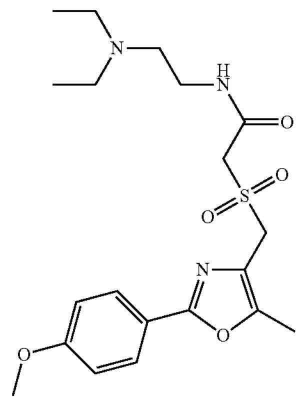 | 423.54 |
| IIa-1479 | 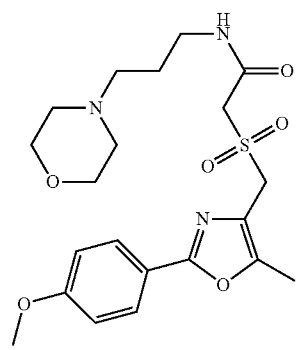 | 451.55 |
| IIa-1480 | 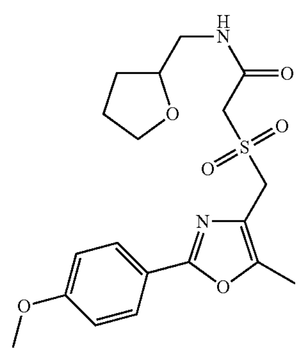 | 408.48 |
| IIa-1481 | 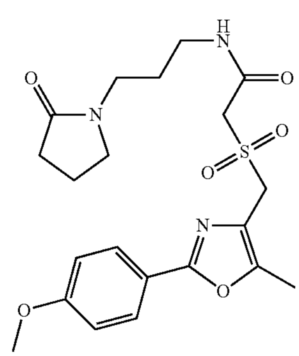 | 449.53 |

TABLE 5-continued

Oxazole amides (R³ = NH-misc)

| ID | Structure | MW |
|---|---|---|
| IIa-1482 | 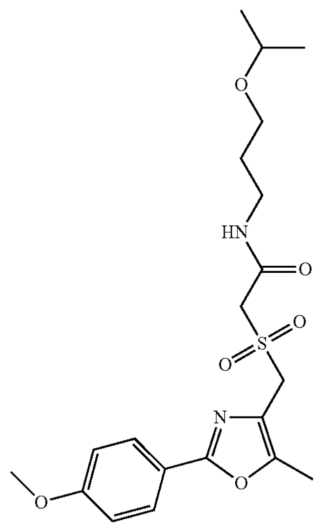 | 424.52 |
| IIa-1483 | 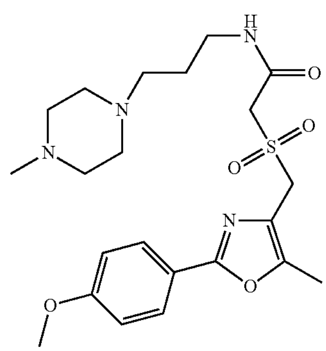 | 464.59 |
| IIa-1484 | 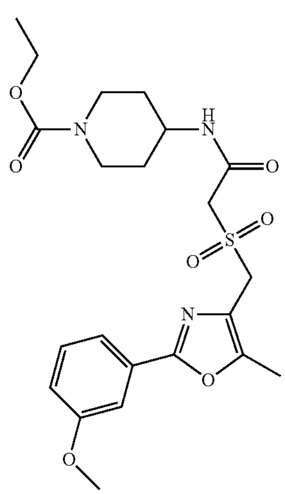 [SMILES: CCOC(=O)N1CCC(NC(=O)CS(=O)(=O)Cc2nc(-c3cccc(OC)c3)oc2C)CC1] | 479.56 |

TABLE 5-continued

Oxazole amides (R³ = NH-misc)

| ID | Structure | MW |
|---|---|---|
| IIa-1485 | | 415.47 |
| IIa-1486 | | 380.47 |
| IIa-1487 | | 437.56 |

TABLE 5-continued
Oxazole amides (R³ = NH-misc)
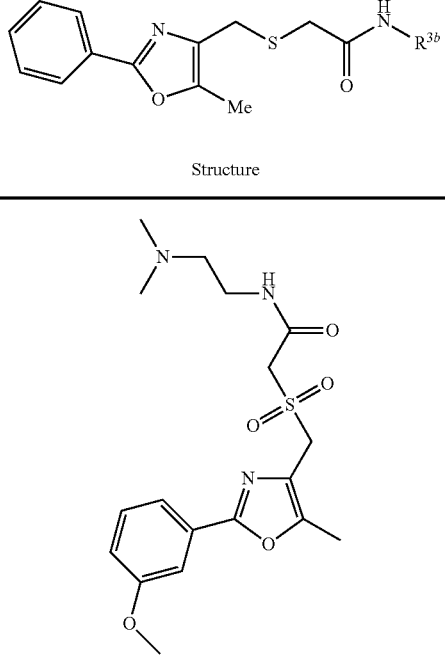
| ID | Structure | MW |
|---|---|---|
| IIa-1488 | 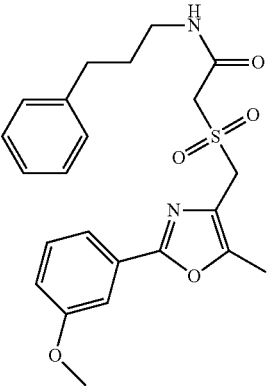 [SMILES: COc1cccc(-c2nc(CS(=O)(=O)CC(=O)NCCCc3ccccc3)c(C)o2)c1] | 395.48 |
| IIa-1489 | 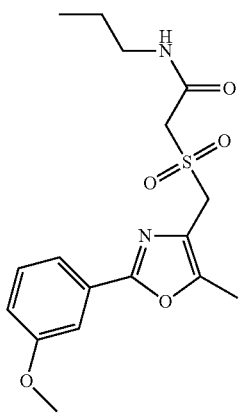 | 442.54 |
| IIa-1490 | 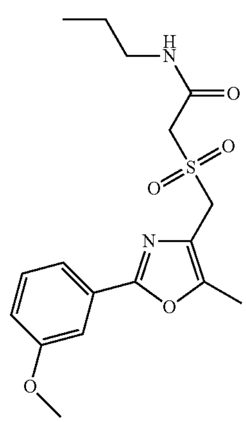 [SMILES: CCCNC(=O)CS(=O)(=O)Cc1nc(-c2cccc(OC)c2)oc1C] | 366.44 |

TABLE 5-continued

Oxazole amides (R³ = NH-misc)

| ID | Structure | MW |
|---|---|---|
| IIa-1491 | 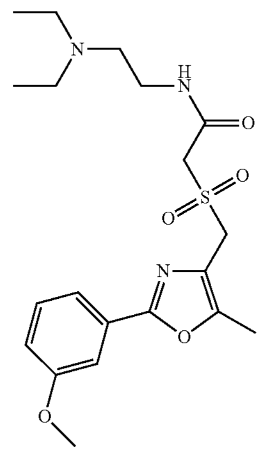 [SMILES: CCN(CC)CCNC(=O)CS(=O)(=O)Cc1nc(-c2cccc(OC)c2)oc1C] | 423.54 |
| IIa-1492 | 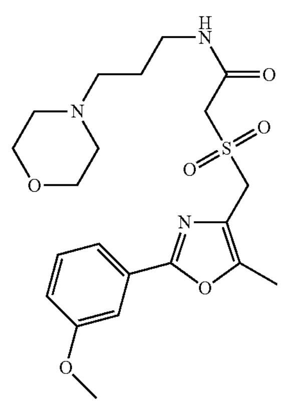 [SMILES: COc1cccc(-c2nc(CS(=O)(=O)CC(=O)NCCCN3CCOCC3)c(C)o2)c1] | 451.55 |
| IIa-1493 | 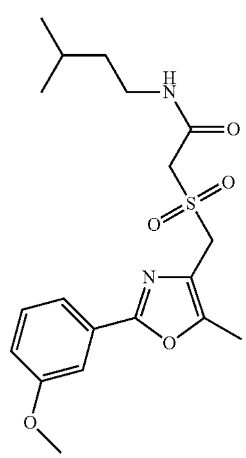 [SMILES: COc1cccc(-c2nc(CS(=O)(=O)CC(=O)NCCC(C)C)c(C)o2)c1] | 394.49 |

TABLE 5-continued
Oxazole amides (R³ = NH-misc)
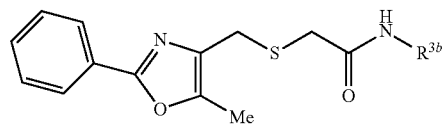
| ID | Structure | MW |
| --- | --- | --- |
| IIa-1494 | 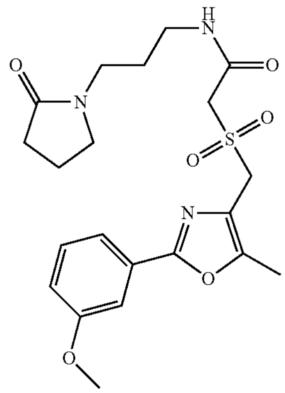 [SMILES: COc1cccc(-c2nc(CS(=O)(=O)CC(=O)NCCCN3CCCC3=O)c(C)o2)c1] | 449.53 |
| IIa-1495 | 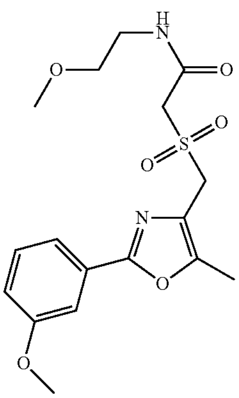 [SMILES: COCCNC(=O)CS(=O)(=O)Cc1nc(-c2cccc(OC)c2)oc1C] | 382.44 |
| IIa-1496 | 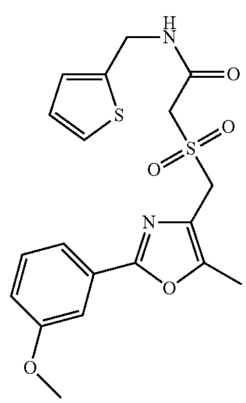 [SMILES: COc1cccc(-c2nc(CS(=O)(=O)CC(=O)NCc3cccs3)c(C)o2)c1] | 420.51 |

TABLE 5-continued

Oxazole amides (R³ = NH-misc)

| ID | Structure | MW |
|---|---|---|
| IIa-1497 | | 410.49 |
| IIa-1498 | | 456.57 |
| IIa-1499 | | 396.47 |

TABLE 5-continued
Oxazole amides (R³ = NH-misc)
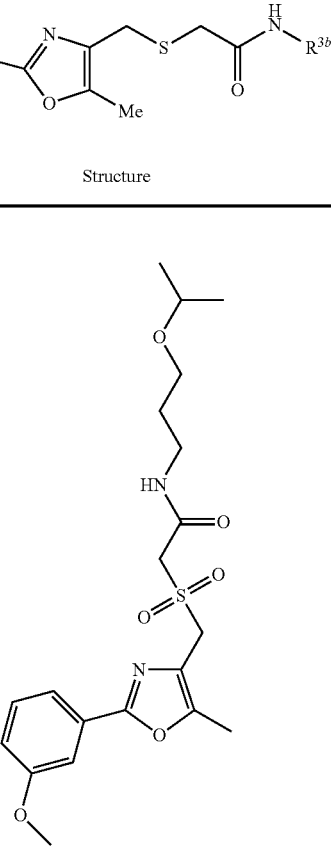
| ID | Structure | MW |
|---|---|---|
| IIa-1500 | 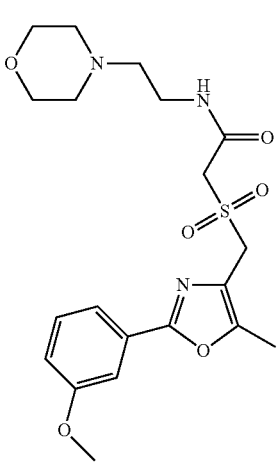 [SMILES: COc1cccc(-c2nc(CS(=O)(=O)CC(=O)NCCN3CCOCC3)c(C)o2)c1] | 424.52 |
| IIa-1501 | | 437.52 |

TABLE 5-continued
Oxazole amides (R³ = NH-misc)
| ID | Structure | MW |
|---|---|---|
| IIa-1502 | 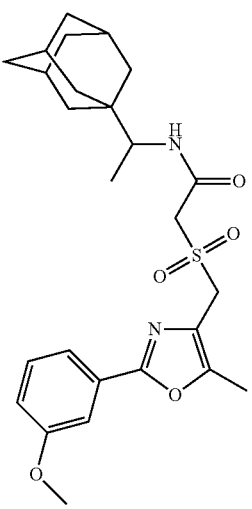 [SMILES: COc1cccc(-c2nc(CS(=O)(=O)CC(=O)NC(C)C34CC5CC(CC(C5)C3)C4)c(C)o2)c1] | 486.64 |
| IIa-1503 | 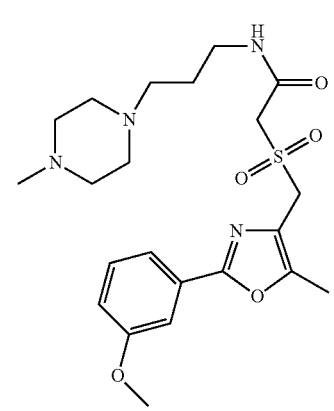 | 464.59 |

TABLE 5-continued
Oxazole amides (R³ = NH-misc)
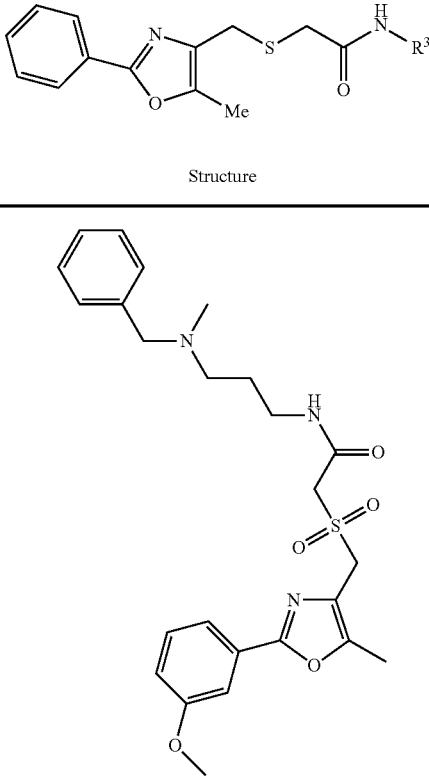
| ID | Structure | MW |
|---|---|---|
| IIa-1504 | 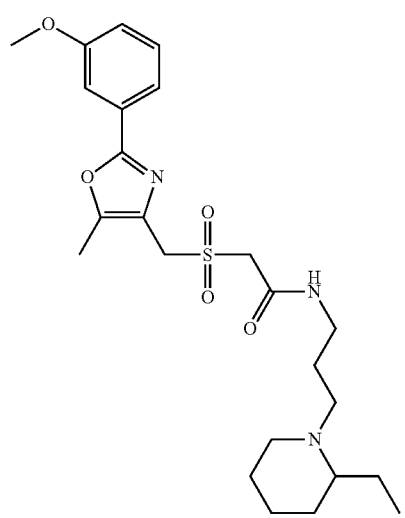 [SMILES: CCC1CCCCN1CCCNC(=O)CS(=O)(=O)Cc1nc(-c2cccc(OC)c2)oc1C] | 485.61 |
| IIa-1505 | | 477.63 |

TABLE 5-continued

Oxazole amides (R³ = NH-misc)

| ID | Structure | MW |
|---|---|---|
| IIa-1506 | | 463.60 |
| IIa-1507 | | 465.62 |
| IIa-1508 | | 449.57 |

TABLE 5-continued

Oxazole amides (R³ = NH-misc)

| ID | Structure | MW |
|---|---|---|
| IIa-1509 | | 451.59 |
| IIa-1510 | | 477.63 |
| IIa-1511 | | 478.62 |

TABLE 5-continued
Oxazole amides (R³ = NH-misc)
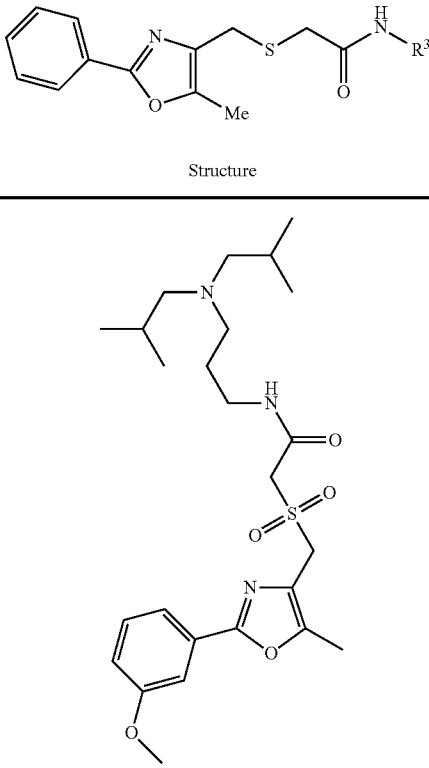
| ID | Structure | MW |
|---|---|---|
| IIa-1512 | 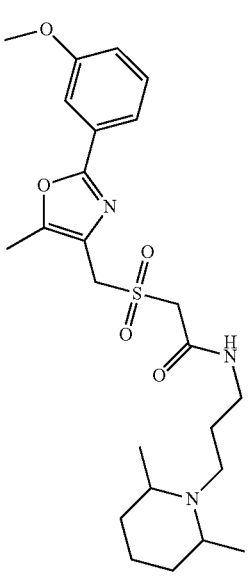 | 493.67 |
| IIa-1513 | | 477.63 |

TABLE 5-continued
Oxazole amides (R³ = NH-misc)
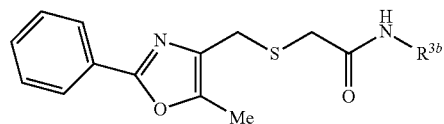
| ID | Structure | MW |
|---|---|---|
| IIa-1514 | | 497.62 |
| IIa-1515 | | 479.64 |

TABLE 5-continued
Oxazole amides (R³ = NH-misc)
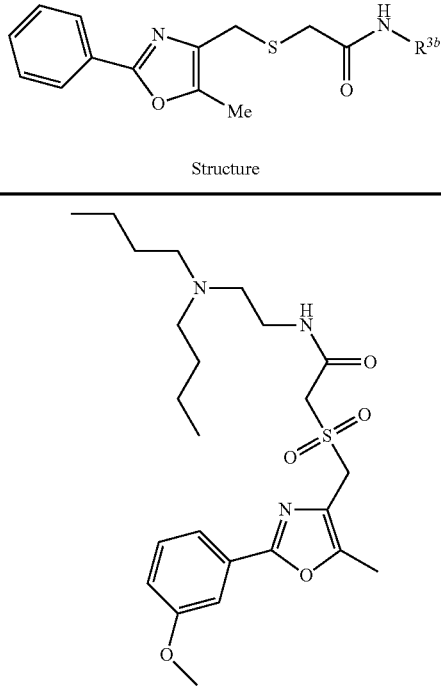
| ID | Structure | MW |
|---|---|---|
| IIa-1516 | 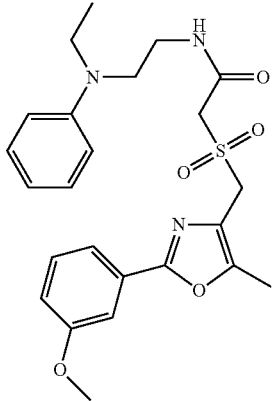 [SMILES: CCN(CCNC(=O)CS(=O)(=O)Cc1nc(-c2cccc(OC)c2)oc1C)c1ccccc1] | 479.64 |
| IIa-1517 | | 471.58 |
| IIa-1518 | 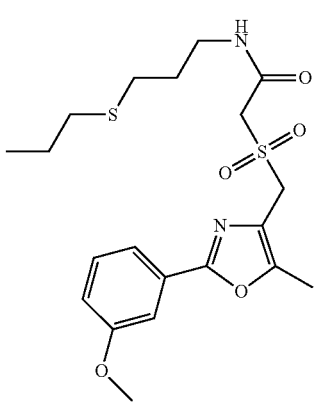 [SMILES: CCCSCCCNC(=O)CS(=O)(=O)Cc1nc(-c2cccc(OC)c2)oc1C] | 440.58 |

TABLE 5-continued

Oxazole amides (R³ = NH-misc)

| ID | Structure | MW |
| --- | --- | --- |
| IIa-1519 | | 480.65 |
| IIa-1520 | | 463.56 |
| IIa-1521 | | 364.47 |

TABLE 5-continued
Oxazole amides (R³ = NH-misc)
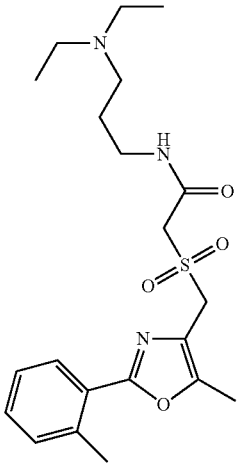 [SMILES: CCN(CC)CCCNC(=O)CS(=O)(=O)Cc1nc(-c2ccccc2C)oc1C]
| ID | Structure | MW |
|---|---|---|
| IIa-1522 | 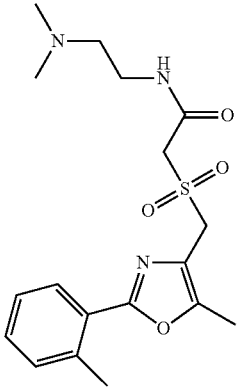 [SMILES: Cc1ccccc1-c1nc(CS(=O)(=O)CC(=O)NCCN(C)C)c(C)o1] | 421.56 |
| IIa-1523 | | 379.48 |
| IIa-1524 | 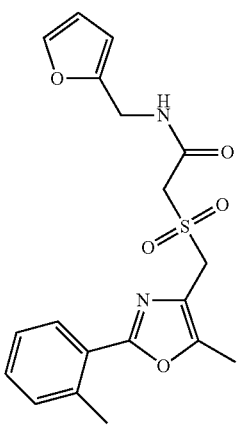 [SMILES: Cc1ccccc1-c1nc(CS(=O)(=O)CC(=O)NCc2ccco2)c(C)o1] | 388.45 |

TABLE 5-continued

Oxazole amides (R³ = NH-misc)

| ID | Structure | MW |
|---|---|---|
| IIa-1525 | | 426.54 |
| IIa-1526 | | 350.44 |
| IIa-1527 | | 407.54 |

TABLE 5-continued

Oxazole amides (R³ = NH-misc)

| ID | Structure | MW |
|---|---|---|
| IIa-1528 | 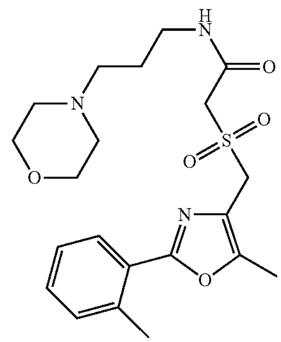 [SMILES: Cc1ccccc1-c1nc(CS(=O)(=O)CC(=O)NCCCN2CCOCC2)c(C)o1] | 435.55 |
| IIa-1529 | 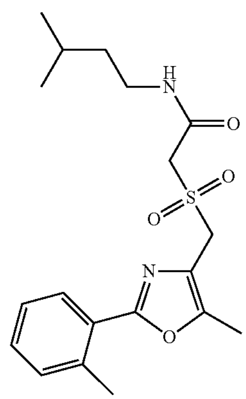 [SMILES: Cc1ccccc1-c1nc(CS(=O)(=O)CC(=O)NCCC(C)C)c(C)o1] | 378.49 |
| IIa-1530 | 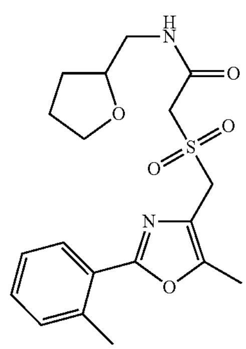 [SMILES: Cc1ccccc1-c1nc(CS(=O)(=O)CC(=O)NCC2CCCO2)c(C)o1] | 392.48 |
| IIa-1531 | 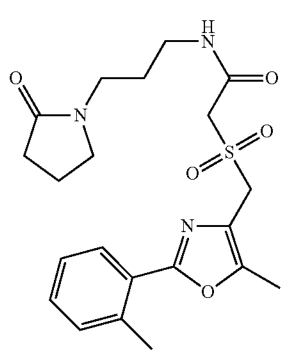 [SMILES: Cc1ccccc1-c1nc(CS(=O)(=O)CC(=O)NCCCN2CCCC2=O)c(C)o1] | 433.53 |

TABLE 5-continued
Oxazole amides (R³ = NH-misc)
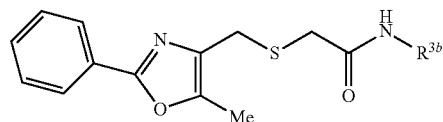
| ID | Structure | MW |
|---|---|---|
| IIa-1532 | 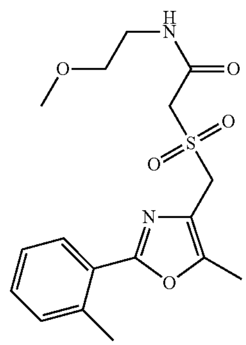 | 366.44 |
| IIa-1533 | 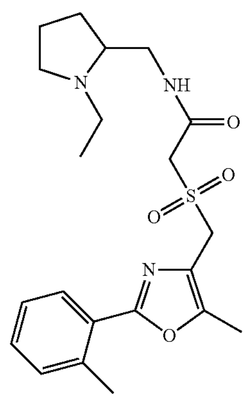 [SMILES: CCN1CCCC1CNC(=O)CS(=O)(=O)Cc1nc(-c2ccccc2C)oc1C] | 419.55 |
| IIa-1534 | 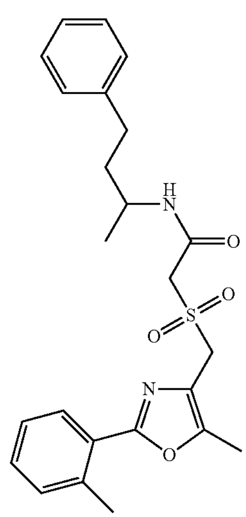 [SMILES: Cc1ccccc1-c1nc(CS(=O)(=O)CC(=O)NC(C)CCc2ccccc2)c(C)o1] | 440.57 |

TABLE 5-continued

Oxazole amides (R³ = NH-misc)

| ID | Structure | MW |
| --- | --- | --- |
| IIa-1535 | 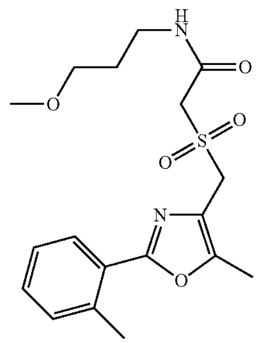 | 380.47 |
| IIa-1536 | 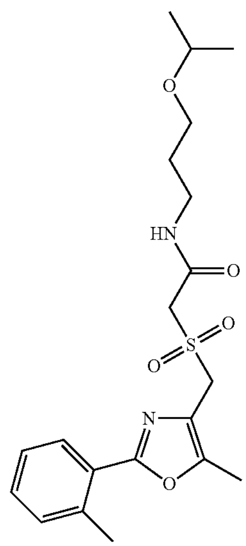 [SMILES: Cc1ccccc1-c1nc(CS(=O)(=O)CC(=O)NCCCOC(C)C)c(C)o1] | 408.52 |
| IIa-1537 | 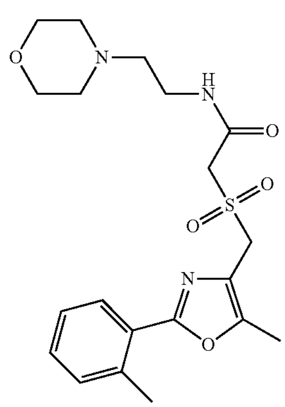 [SMILES: Cc1ccccc1-c1nc(CS(=O)(=O)CC(=O)NCCN2CCOCC2)c(C)o1] | 421.52 |

TABLE 5-continued

Oxazole amides (R³ = NH-misc)

| ID | Structure | MW |
|---|---|---|
| IIa-1538 | | 364.47 |
| IIa-1539 | | 448.59 |
| IIa-1540 | | 419.55 |
| IIa-1541 | | 405.52 |

TABLE 5-continued

Oxazole amides (R³ = NH-misc)

| ID | Structure | MW |
|---|---|---|
| IIa-1542 | 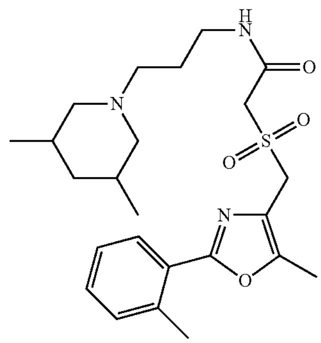 | 461.63 |
| IIa-1543 | 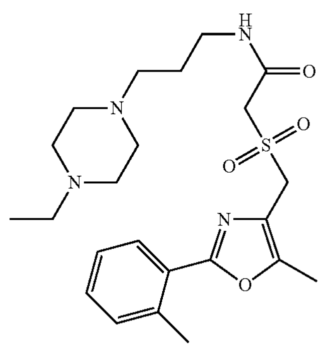 [SMILES: CCN1CCN(CCCNC(=O)CS(=O)(=O)Cc2nc(-c3ccccc3C)oc2C)CC1] | 462.62 |
| IIa-1544 | 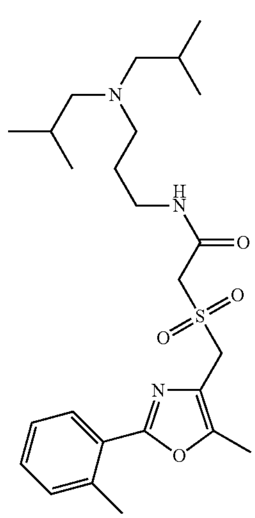 [SMILES: Cc1ccccc1-c1nc(CS(=O)(=O)CC(=O)NCCCN(CC(C)C)CC(C)C)c(C)o1] | 477.67 |

TABLE 5-continued
Oxazole amides (R³ = NH-misc)
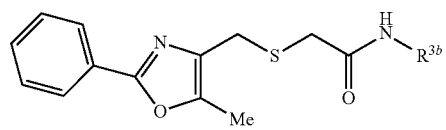
| ID | Structure | MW |
|---|---|---|
| IIa-1545 | | 461.63 |
| IIa-1546 | | 424.59 |
| IIa-1547 | | 383.44 |

TABLE 5-continued
Oxazole amides (R³ = NH-misc)
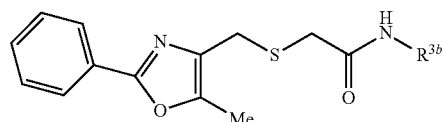
| ID | Structure | MW |
| --- | --- | --- |
| IIa-1548 | | 392.41 |
| IIa-1549 | | 430.50 |
| IIa-1550 | | 400.43 |

TABLE 5-continued
Oxazole amides (R³ = NH-misc)
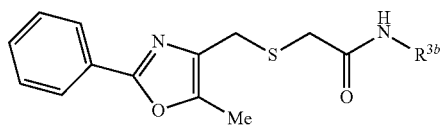
| ID | Structure | MW |
|---|---|---|
| IIa-1551 | | 439.51 |
| IIa-1552 | | 444.53 |
| IIa-1553 | | 452.55 |

TABLE 5-continued

Oxazole amides (R³ = NH-misc)

| ID | Structure | MW |
|---|---|---|
| IIa-1554 | | 439.55 |
| IIa-1555 | | 409.48 |
| IIa-1556 | | 465.59 |

TABLE 5-continued

Oxazole amides (R³ = NH-misc)

| ID | Structure | MW |
|---|---|---|
| IIa-1557 | | 465.59 |
| IIa-1558 | | 485.58 |
| IIa-1559 | | 451.56 |

TABLE 5-continued

Oxazole amides (R³ = NH-misc)

| ID | Structure | MW |
|---|---|---|
| IIa-1560 | | 467.61 |
| IIa-1561 | | 428.55 |
| IIa-1562 | | 468.61 |

TABLE 5-continued
Oxazole amides (R³ = NH-misc)
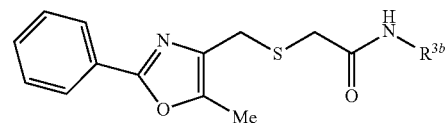
| ID | Structure | MW |
|---|---|---|
| IIa-1563 | 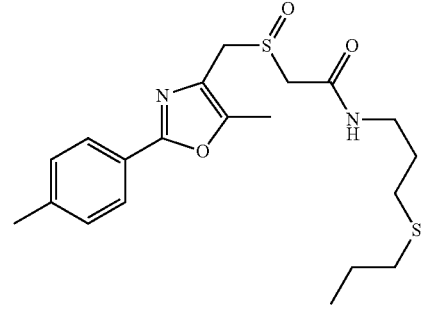 [SMILES: CCCSCCCNC(=O)CS(=O)Cc1nc(-c2ccc(C)cc2)oc1C] | 408.59 |
| IIa-1564 | 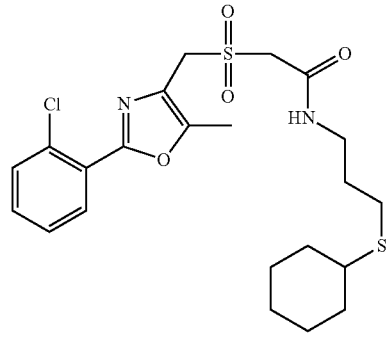 [SMILES: Cc1oc(-c2ccccc2Cl)nc1CS(=O)(=O)CC(=O)NCCCSC1CCCCC1] | 485.07 |
| IIa-1565 | 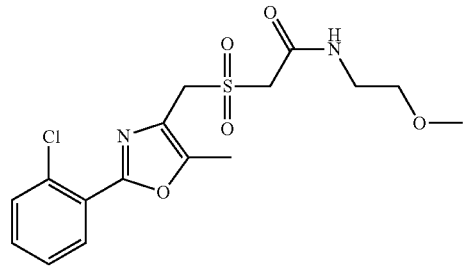 | 386.86 |
| IIa-1566 | 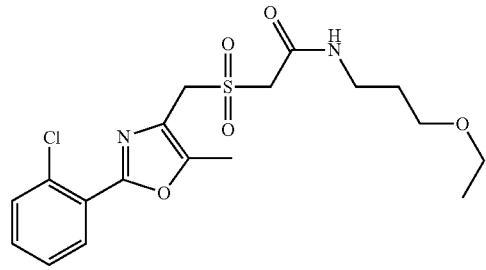 | 414.91 |

TABLE 5-continued
Oxazole amides (R³ = NH-misc)
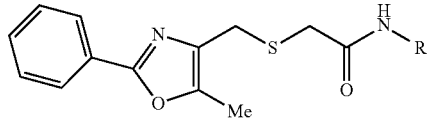
| ID | Structure | MW |
|---|---|---|
| IIa-1567 | 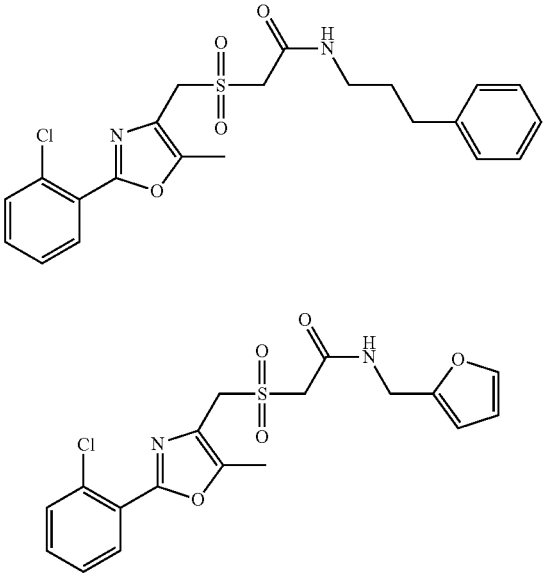 | 446.96 |
| IIa-1568 | 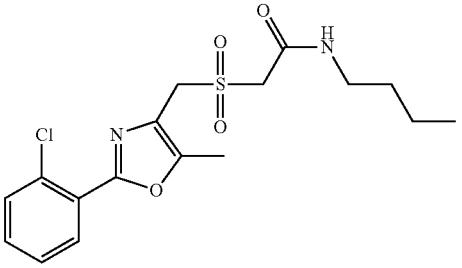 [SMILES: COCCNC(=O)CS(=O)(=O)Cc1nc(-c2ccccc2Cl)oc1C] | 408.86 |
| IIa-1569 | 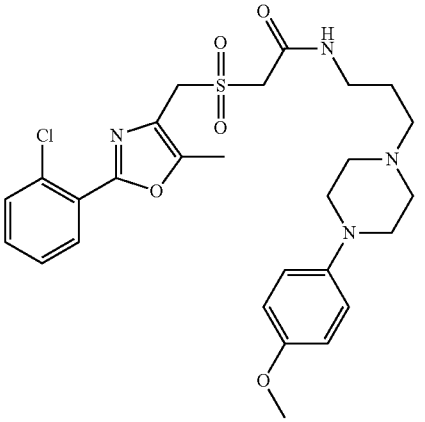 [SMILES: COc1ccc(N2CCN(CCCNC(=O)CS(=O)(=O)Cc3nc(-c4ccccc4Cl)oc3C)CC2)cc1] | 384.88 |
| IIa-1570 | 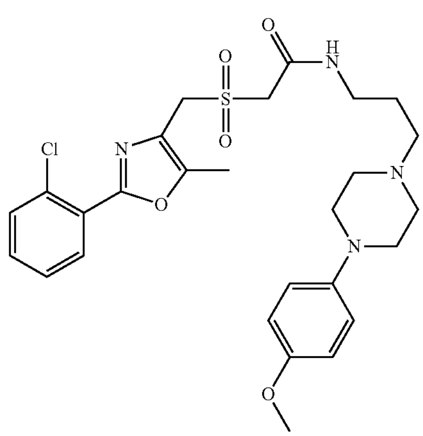 | 561.10 |

TABLE 5-continued

Oxazole amides (R³ = NH-misc)

| ID | Structure | MW |
| --- | --- | --- |
| IIa-1571 | | 400.88 |
| IIa-1572 | | 441.94 |
| IIa-1573 | | 460.98 |
| IIa-1574 | | 483.97 |
| IIa-1575 | | 436.96 |

TABLE 5-continued

Oxazole amides (R³ = NH-misc)

| ID | Structure | MW |
| --- | --- | --- |
| IIa-1576 | 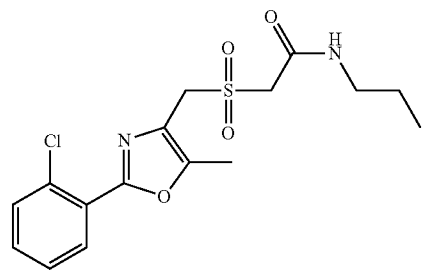 [SMILES: CCCNC(=O)CS(=O)(=O)Cc1nc(-c2ccccc2Cl)oc1C] | 370.86 |
| IIa-1577 | 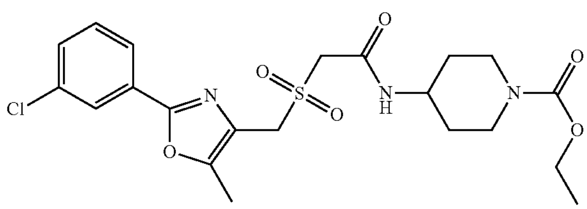 [SMILES: CCOC(=O)N1CCC(NC(=O)CS(=O)(=O)Cc2nc(-c3cccc(Cl)c3)oc2C)CC1] | 483.97 |
| IIa-1578 | 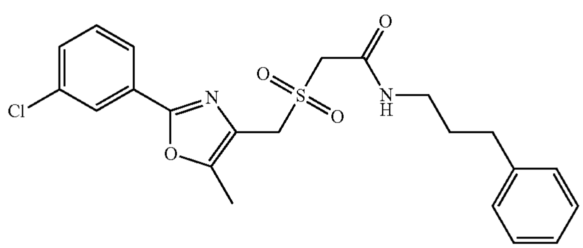 [SMILES: Cc1oc(-c2cccc(Cl)c2)nc1CS(=O)(=O)CC(=O)NCCCc1ccccc1] | 446.96 |
| IIa-1579 | 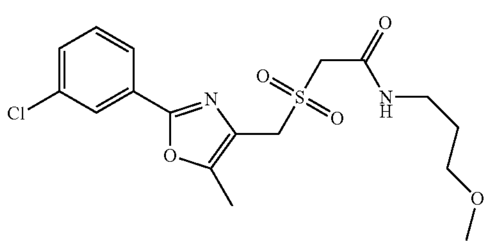 [SMILES: COCCCNC(=O)CS(=O)(=O)Cc1nc(-c2cccc(Cl)c2)oc1C] | 400.88 |
| IIa-1580 | 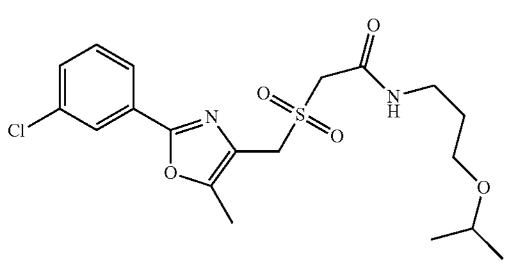 [SMILES: Cc1oc(-c2cccc(Cl)c2)nc1CS(=O)(=O)CC(=O)NCCCOC(C)C] | 428.94 |

TABLE 5-continued

Oxazole amides (R³ = NH-misc)

| ID | Structure | MW |
|---|---|---|
| IIa-1581 | 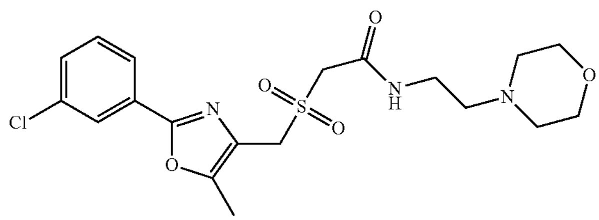 [SMILES: Cc1oc(-c2cccc(Cl)c2)nc1CS(=O)(=O)CC(=O)NCCN1CCOCC1] | 441.94 |
| IIa-1582 | 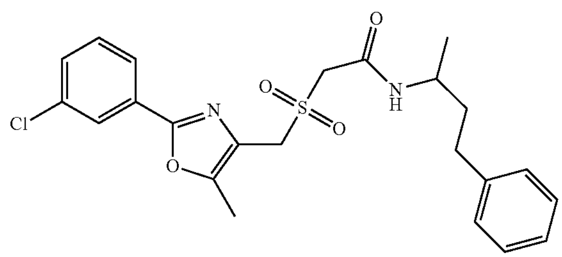 [SMILES: Cc1oc(-c2cccc(Cl)c2)nc1CS(=O)(=O)CC(=O)NC(C)CCc1ccccc1] | 460.98 |
| IIa-1583 | 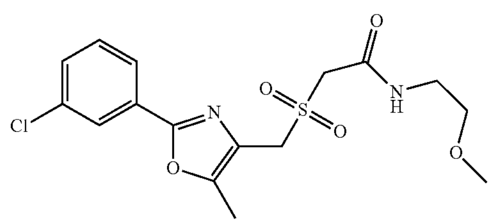 [SMILES: COCCNC(=O)CS(=O)(=O)Cc1nc(-c2cccc(Cl)c2)oc1C] | 386.86 |
| IIa-1584 | 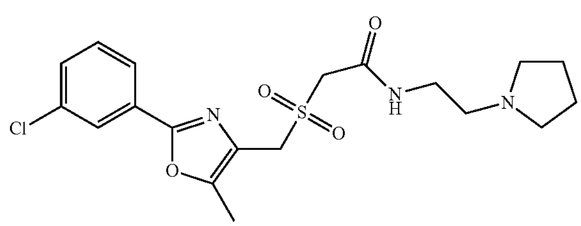 [SMILES: Cc1oc(-c2cccc(Cl)c2)nc1CS(=O)(=O)CC(=O)NCCN1CCCC1] | 425.94 |
| IIa-1585 | 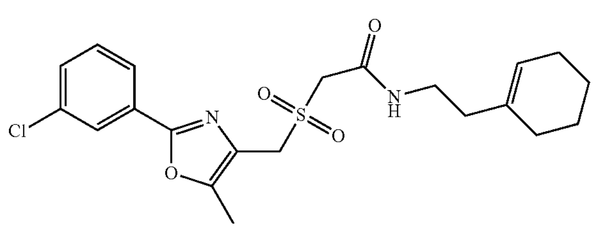 [SMILES: Cc1oc(-c2cccc(Cl)c2)nc1CS(=O)(=O)CC(=O)NCCC1=CCCCC1] | 436.96 |
| IIa-1586 | 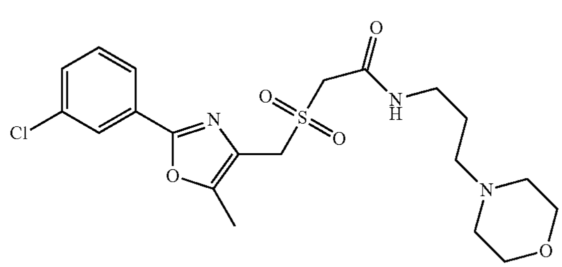 [SMILES: Cc1oc(-c2cccc(Cl)c2)nc1CS(=O)(=O)CC(=O)NCCCN1CCOCC1] | 455.96 |

TABLE 5-continued

Oxazole amides (R³ = NH-misc)

| ID | Structure | MW |
|---|---|---|
| IIa-1587 | 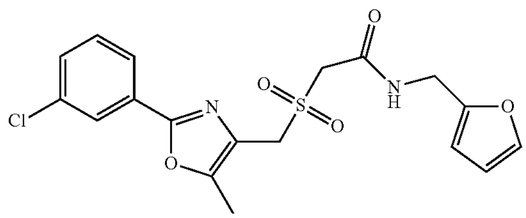 [SMILES: Cc1oc(-c2cccc(Cl)c2)nc1CS(=O)(=O)CC(=O)NCc1ccco1] | 408.86 |
| IIa-1588 | 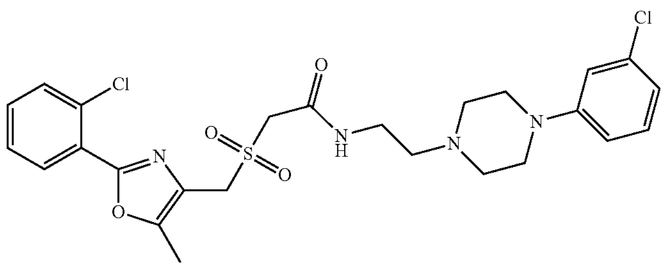 [SMILES: Cc1oc(-c2ccccc2Cl)nc1CS(=O)(=O)CC(=O)NCCN1CCN(c2cccc(Cl)c2)CC1] | 551.50 |
| IIa-1589 | 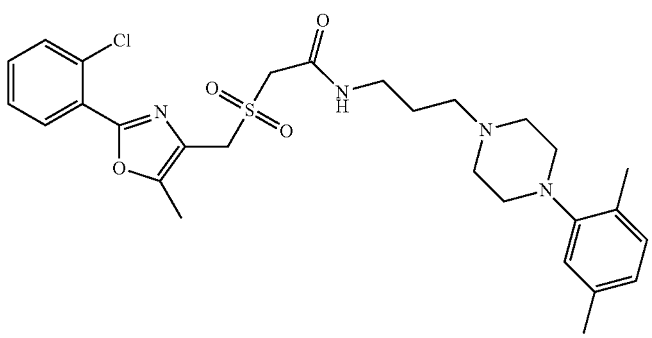 [SMILES: Cc1ccc(C)c(N2CCN(CCCNC(=O)CS(=O)(=O)Cc3nc(-c4ccccc4Cl)oc3C)CC2)c1] | 559.13 |
| IIa-1590 | 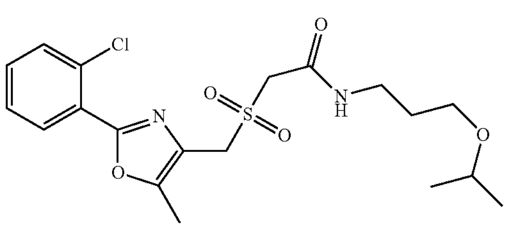 [SMILES: Cc1oc(-c2ccccc2Cl)nc1CS(=O)(=O)CC(=O)NCCCOC(C)C] | 428.94 |

TABLE 5-continued
Oxazole amides (R³ = NH-misc)
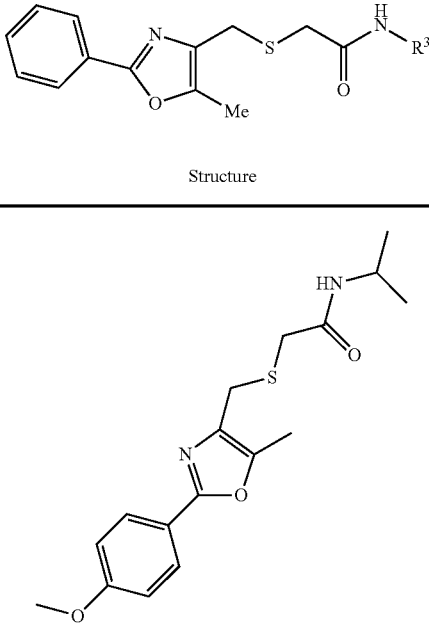
| ID | Structure | MW |
|---|---|---|
| IIa-1591 | 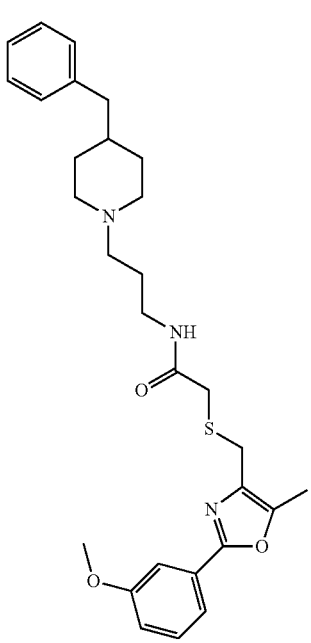 [SMILES: COc1cccc(-c2nc(CSCC(=O)NCCCN3CCC(Cc4ccccc4)CC3)c(C)o2)c1] | 334.44 |
| IIa-1592 | | 507.70 |

TABLE 5-continued
Oxazole amides (R³ = NH-misc)
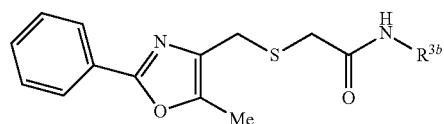
| ID | Structure | MW |
| --- | --- | --- |
| IIa-1593 | | 427.03 |
| IIa-1594 | | 447.56 |

TABLE 5-continued
Oxazole amides (R³ = NH-misc)
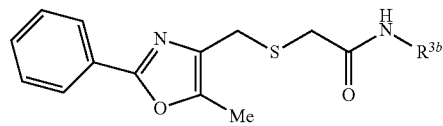
| ID | Structure | MW |
| --- | --- | --- |
| IIa-1595 | 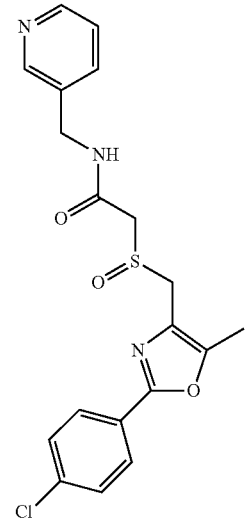 [SMILES: Cc1oc(-c2ccc(Cl)cc2)nc1CS(=O)CC(=O)NCc1cccnc1] | 403.89 |
| IIa-1596 | 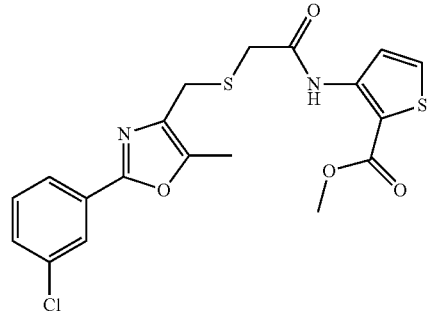 [SMILES: COC(=O)c1sccc1NC(=O)CSCc1nc(-c2cccc(Cl)c2)oc1C] | 436.94 |
| IIa-1597 | 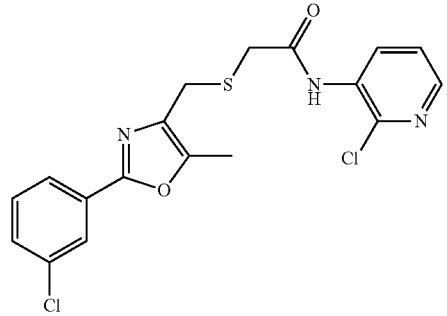 [SMILES: Cc1oc(-c2cccc(Cl)c2)nc1CSCC(=O)Nc1cccnc1Cl] | 408.31 |

US 9,433,611 B2
TABLE 5-continued
Oxazole amides (R³ = NH-misc)
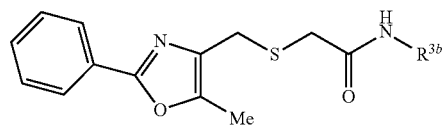
| ID | Structure | MW |
|---|---|---|
| IIa-1598 | | 377.85 |
| IIa-1599 | | 391.85 |
| IIa-1600 | | 361.40 |
| IIa-1601 | | 357.43 |

TABLE 5-continued
Oxazole amides (R³ = NH-misc)
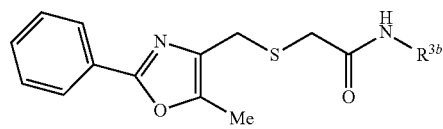
| ID | Structure | MW |
|---|---|---|
| IIa-1602 | | 387.89 |
| IIa-1603 | | 478.04 |
TABLE 6
Oxazole amides (R³ = N-cyclo)
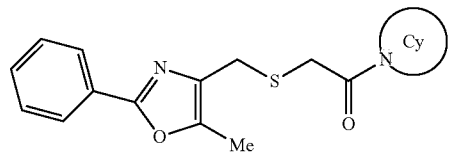 [SMILES: Cc1oc(-c2ccccc2)nc1CSCC(N)=O]
| ID | Structure | MW |
|---|---|---|
| IIa-2001 | | 330.45 |

TABLE 6-continued

Oxazole amides (R³ = N-cyclo)

| ID | Structure | MW |
|---|---|---|
| IIa-2002 | | 387.50 |
| IIa-2003 | | 392.52 |
| IIa-2004 | | 372.53 |
| IIa-2005 | | 437.57 |

TABLE 6-continued
Oxazole amides (R³ = N-cyclo)
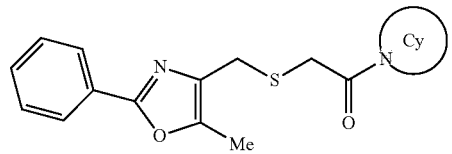
| ID | Structure | MW |
|---|---|---|
| IIa-2006 | 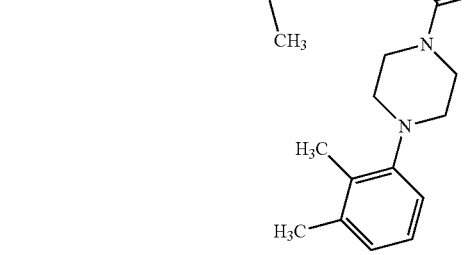 | 463.65 |
| IIa-2007 | 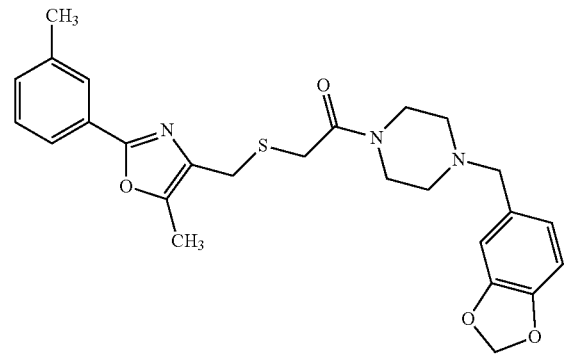 [SMILES: Cc1cccc(-c2nc(CSCC(=O)N3CCN(Cc4ccc5c(c4)OCO5)CC3)c(C)o2)c1] | 479.60 |
| IIa-2008 | 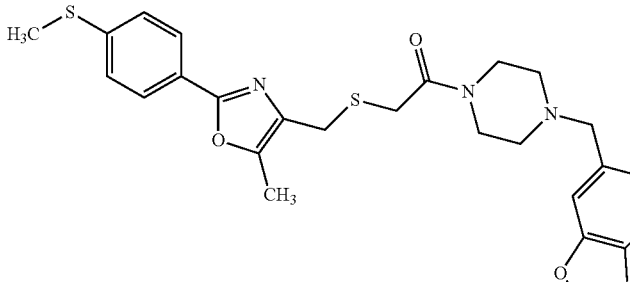 | 511.67 |
| IIa-2009 | 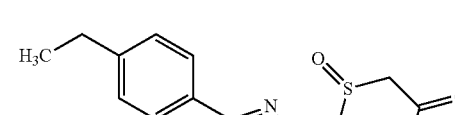 | 376.48 |

TABLE 6-continued
Oxazole amides (R³ = N-cyclo)
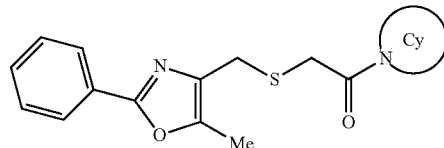
| ID | Structure | MW |
|---|---|---|
| IIa-2010 | | 495.60 |
| IIa-2011 | | 465.62 |
| IIa-2012 | | 449.62 |
| IIa-2013 | | 424.59 |

TABLE 6-continued
Oxazole amides (R³ = N-cyclo)
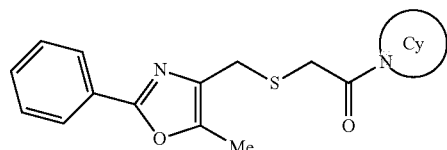
| ID | Structure | MW |
|---|---|---|
| IIa-2014 | 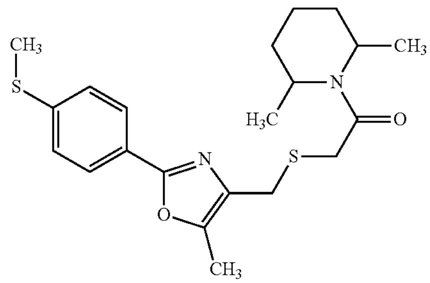 [SMILES: CSc1ccc(-c2nc(CSCC(=O)N3C(C)CCCC3C)c(C)o2)cc1] | 404.60 |
| IIa-2015 | 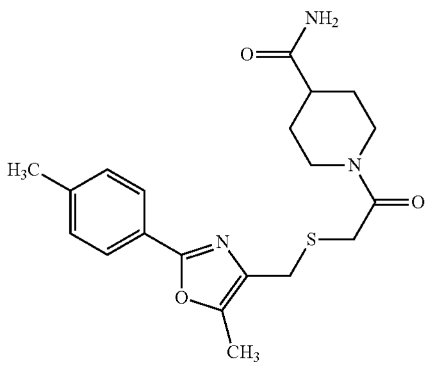 [SMILES: Cc1ccc(-c2nc(CSCC(=O)N3CCC(C(N)=O)CC3)c(C)o2)cc1] | 387.50 |
| IIa-2016 | 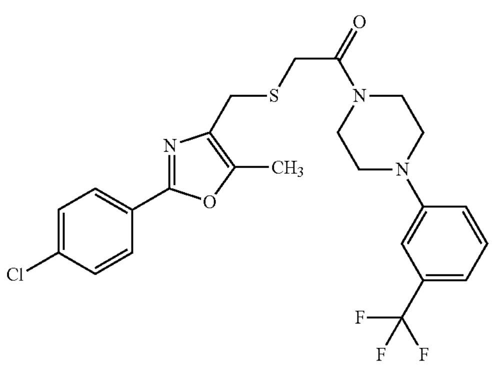 [SMILES: Cc1oc(-c2ccc(Cl)cc2)nc1CSCC(=O)N1CCN(c2cccc(C(F)(F)F)c2)CC1] | 509.98 |
| IIa-2017 | 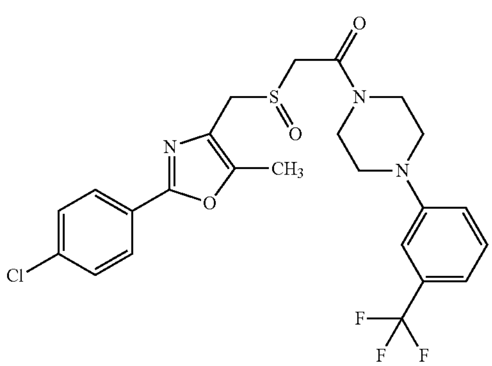 [SMILES: Cc1oc(-c2ccc(Cl)cc2)nc1CS(=O)CC(=O)N1CCN(c2cccc(C(F)(F)F)c2)CC1] | 525.98 |

TABLE 6-continued
Oxazole amides (R³ = N-cyclo)
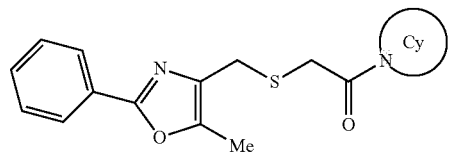
| ID | Structure | MW |
|---|---|---|
| IIa-2018 | | 521.56 |
| IIa-2019 | | 525.98 |
| IIa-2020 | | 505.56 |

TABLE 6-continued
Oxazole amides (R³ = N-cyclo)
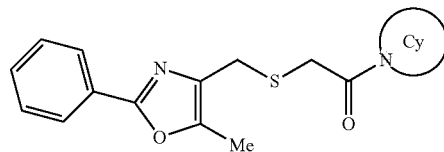
| ID | Structure | MW |
|---|---|---|
| IIa-2021 | 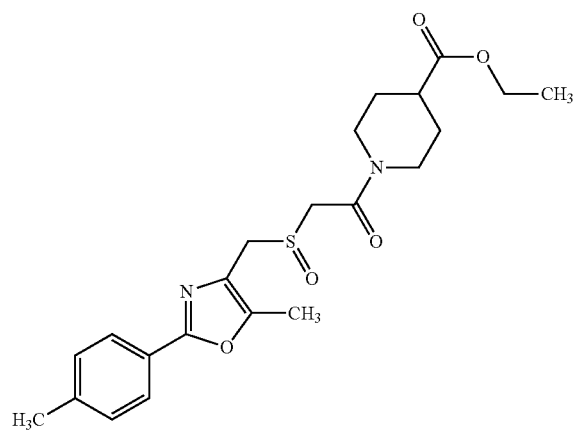 [SMILES: CCOC(=O)C1CCN(C(=O)CS(=O)Cc2nc(-c3ccc(C)cc3)oc2C)CC1] | 432.54 |
| IIa-2022 | 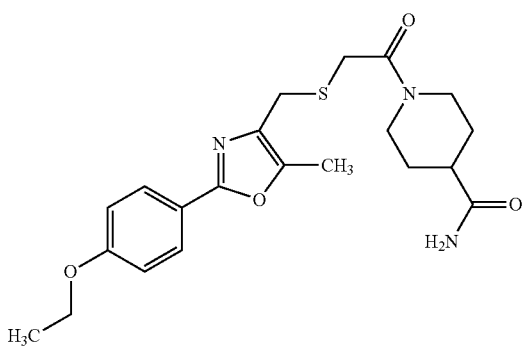 [SMILES: CCOc1ccc(-c2nc(CSCC(=O)N3CCC(C(N)=O)CC3)c(C)o2)cc1] | 417.53 |
| IIa-2023 | 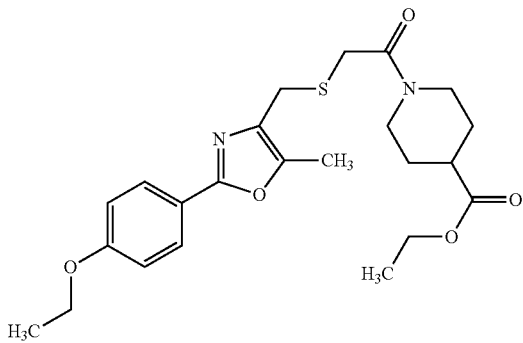 [SMILES: CCOC(=O)C1CCN(C(=O)CSCc2nc(-c3ccc(OCC)cc3)oc2C)CC1] | 446.57 |

TABLE 6-continued

Oxazole amides (R³ = N-cyclo)

| ID | Structure | MW |
|---|---|---|
| IIa-2024 | 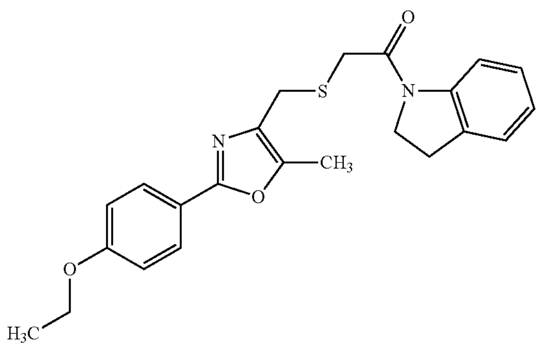 [SMILES: CCOc1ccc(-c2nc(CSCC(=O)N3CCc4ccccc43)c(C)o2)cc1] | 408.52 |
| IIa-2025 | 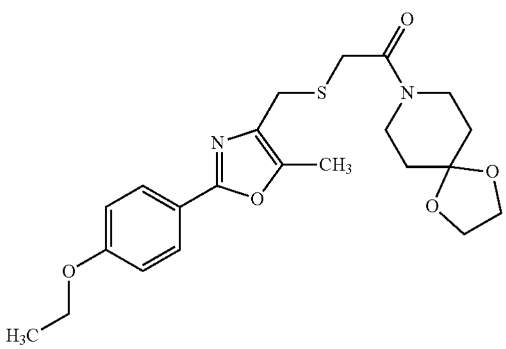 [SMILES: CCOc1ccc(-c2nc(CSCC(=O)N3CCC4(CC3)OCCO4)c(C)o2)cc1] | 432.54 |
| IIa-2026 | 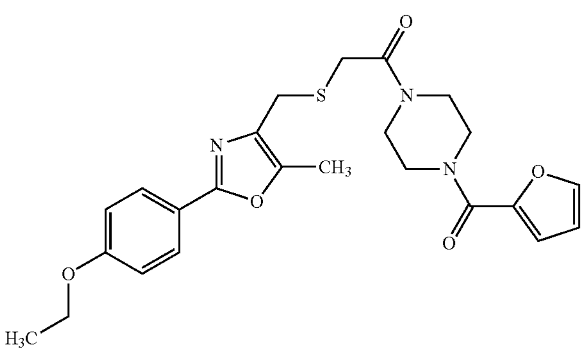 [SMILES: CCOc1ccc(-c2nc(CSCC(=O)N3CCN(C(=O)c4ccco4)CC3)c(C)o2)cc1] | 469.56 |
| IIa-2027 | 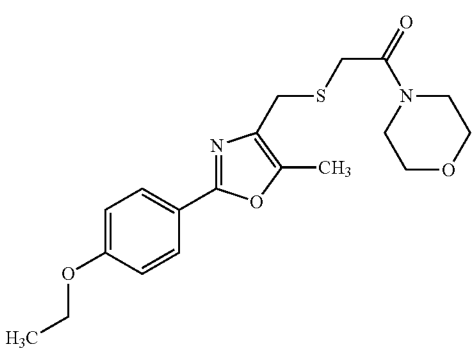 [SMILES: CCOc1ccc(-c2nc(CSCC(=O)N3CCOCC3)c(C)o2)cc1] | 376.48 |

TABLE 6-continued
Oxazole amides (R³ = N-cyclo)
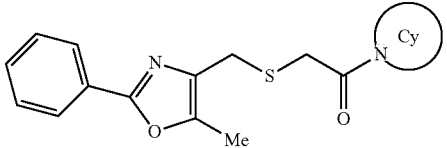
| ID | Structure | MW |
|---|---|---|
| IIa-2028 | 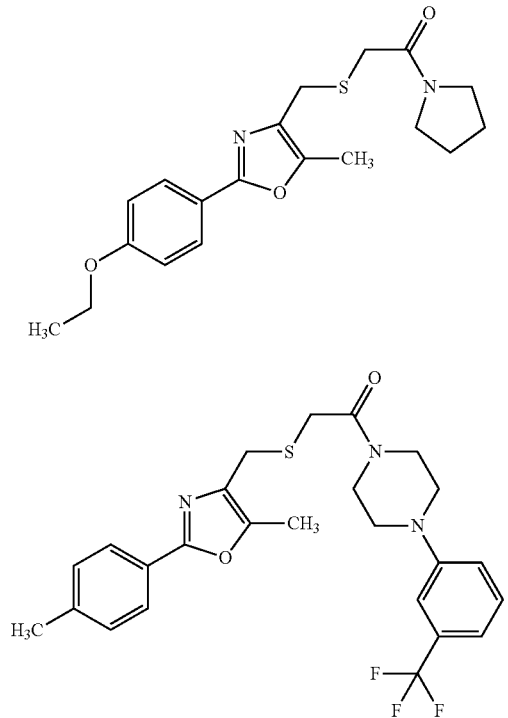 | 360.48 |
| IIa-2029 | 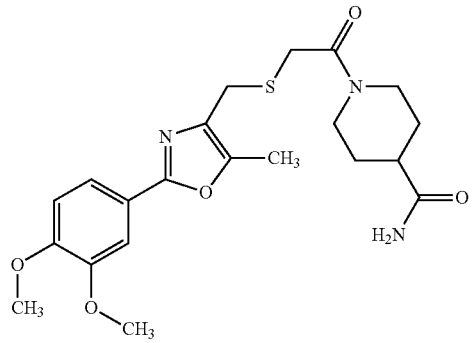 [SMILES: COc1ccc(-c2nc(CSCC(=O)N3CCC(C(N)=O)CC3)c(C)o2)cc1OC] | 489.56 |
| IIa-2030 | 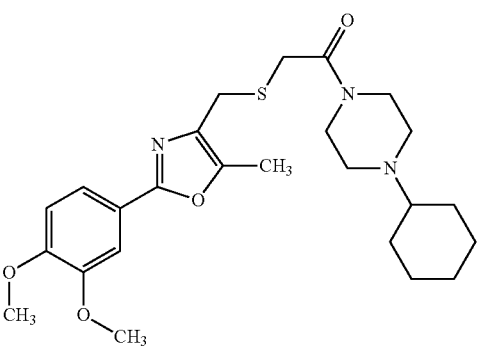 | 433.53 |
| IIa-2031 | 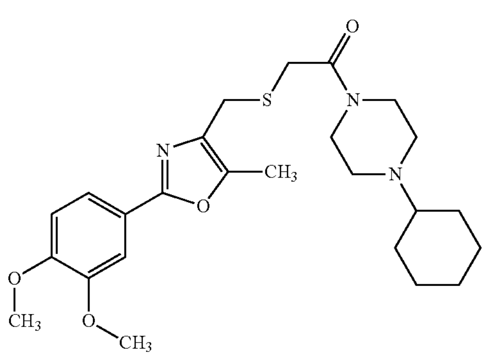 [SMILES: COc1ccc(-c2nc(CSCC(=O)N3CCN(C4CCCCC4)CC3)c(C)o2)cc1OC] | 473.64 |

TABLE 6-continued
Oxazole amides (R³ = N-cyclo)
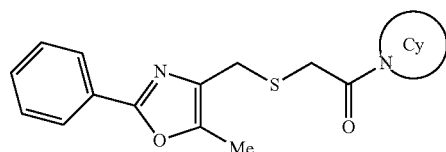
| ID | Structure | MW |
|---|---|---|
| IIa-2032 | | 535.59 |
| IIa-2033 | | 495.65 |
| IIa-2034 | | 472.01 |
| IIa-2035 | | 439.54 |

TABLE 6-continued

Oxazole amides (R³ = N-cyclo)

| ID | Structure | MW |
|---|---|---|
| IIa-2036 | 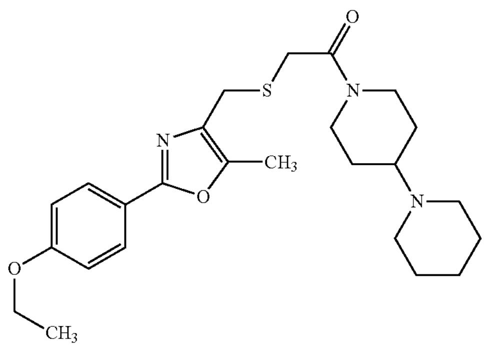 [SMILES: CCOc1ccc(-c2nc(CSCC(=O)N3CCC(N4CCCCC4)CC3)c(C)o2)cc1] | 457.64 |
| IIa-2037 | 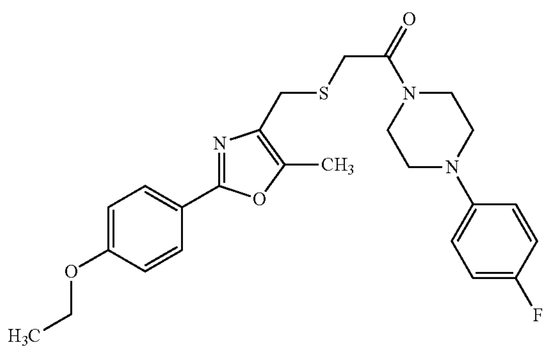 [SMILES: CCOc1ccc(-c2nc(CSCC(=O)N3CCN(c4ccc(F)cc4)CC3)c(C)o2)cc1] | 469.58 |
| IIa-2038 | 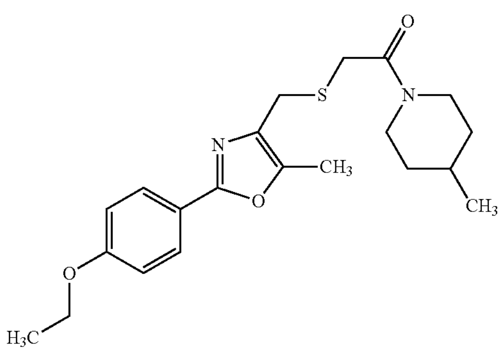 [SMILES: CCOc1ccc(-c2nc(CSCC(=O)N3CCC(C)CC3)c(C)o2)cc1] | 388.53 |
| IIa-2039 | 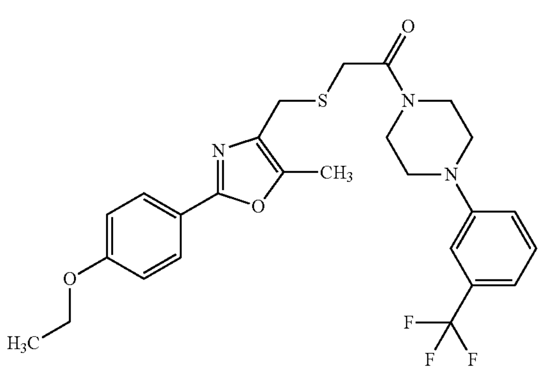 [SMILES: CCOc1ccc(-c2nc(CSCC(=O)N3CCN(c4cccc(C(F)(F)F)c4)CC3)c(C)o2)cc1] | 519.59 |

TABLE 6-continued
Oxazole amides (R³ = N-cyclo)
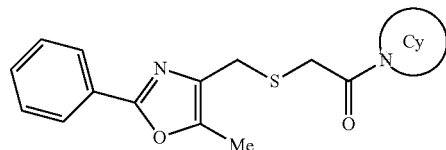
| ID | Structure | MW |
| --- | --- | --- |
| IIa-2040 | 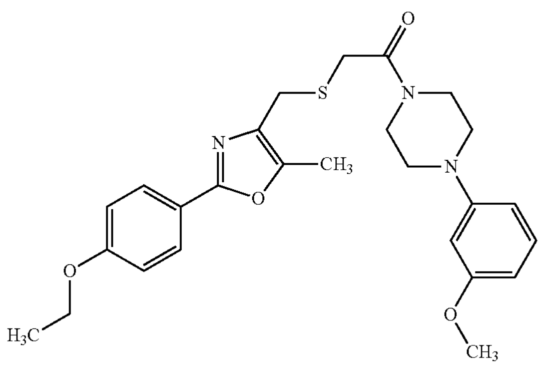 [SMILES: CCOc1ccc(-c2nc(CSCC(=O)N3CCN(c4cccc(OC)c4)CC3)c(C)o2)cc1] | 481.62 |
| IIa-2041 | 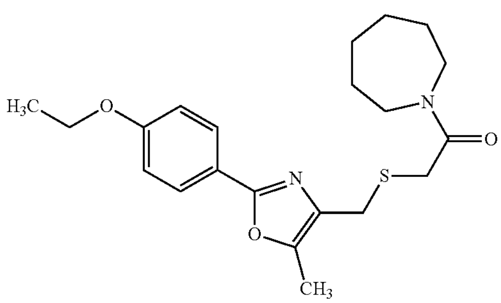 [SMILES: CCOc1ccc(-c2nc(CSCC(=O)N3CCCCCC3)c(C)o2)cc1] | 388.53 |
| IIa-2042 | 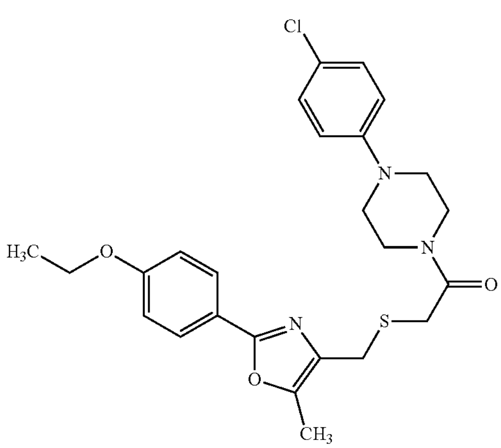 [SMILES: CCOc1ccc(-c2nc(CSCC(=O)N3CCN(c4ccc(Cl)cc4)CC3)c(C)o2)cc1] | 486.04 |

TABLE 6-continued
Oxazole amides (R³ = N-cyclo)
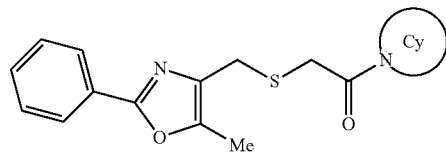
| ID | Structure | MW |
|---|---|---|
| IIa-2043 | | 523.61 |
| IIa-2044 | | 437.57 |
| IIa-2045 | | 346.45 |

TABLE 6-continued
Oxazole amides (R³ = N-cyclo)
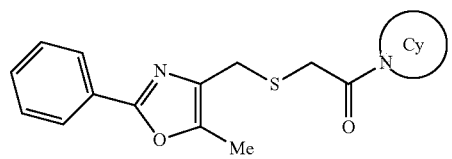
| ID | Structure | MW |
|---|---|---|
| IIa-2046 | 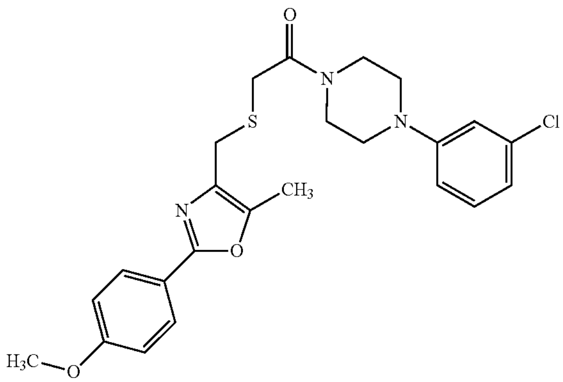 [SMILES: COc1ccc(-c2nc(CSCC(=O)N3CCN(c4cccc(Cl)c4)CC3)c(C)o2)cc1] | 472.01 |
| IIa-2047 | 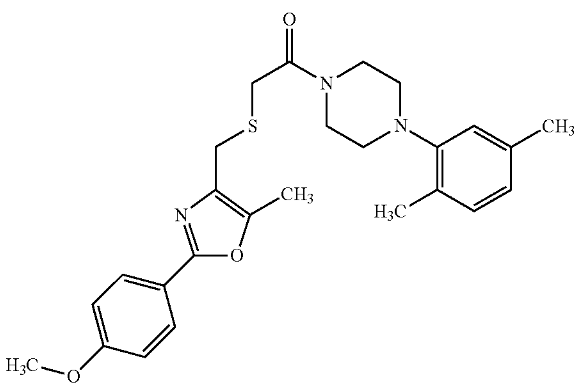 | 465.62 |
| IIa-2048 | 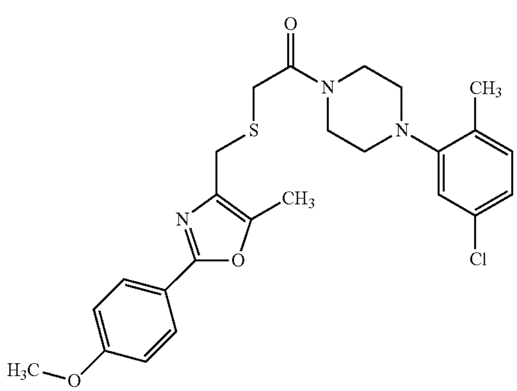 [SMILES: COc1ccc(-c2nc(CSCC(=O)N3CCN(c4cc(Cl)ccc4C)CC3)c(C)o2)cc1] | 486.04 |

TABLE 6-continued
Oxazole amides (R³ = N-cyclo)
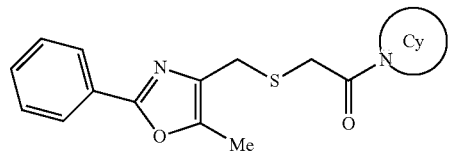
| ID | Structure | MW |
|---|---|---|
| IIa-2049 | | 362.45 |
| IIa-2050 | | 451.59 |
| IIa-2051 | | 455.56 |

TABLE 6-continued
Oxazole amides (R³ = N-cyclo)
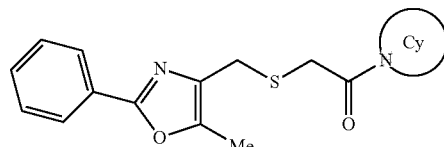
| ID | Structure | MW |
|---|---|---|
| IIa-2052 | 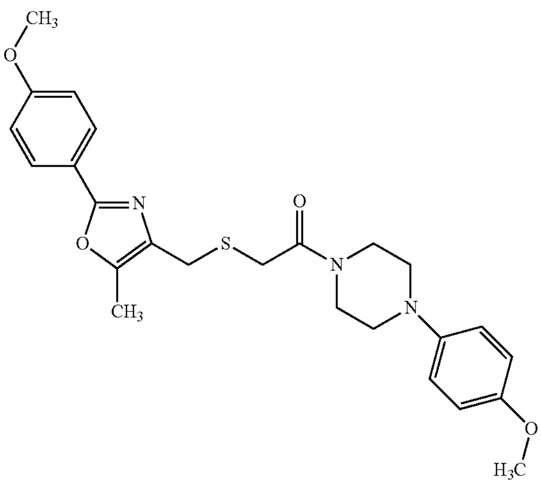 [SMILES: COc1ccc(-c2nc(CSCC(=O)N3CCN(c4ccc(OC)cc4)CC3)c(C)o2)cc1] | 467.59 |
| IIa-2053 | 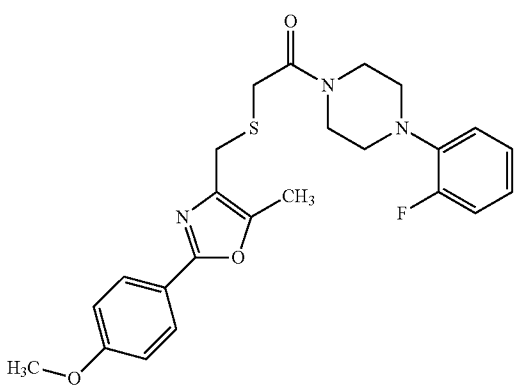 [SMILES: COc1ccc(-c2nc(CSCC(=O)N3CCN(c4ccccc4F)CC3)c(C)o2)cc1] | 455.56 |
| IIa-2054 | 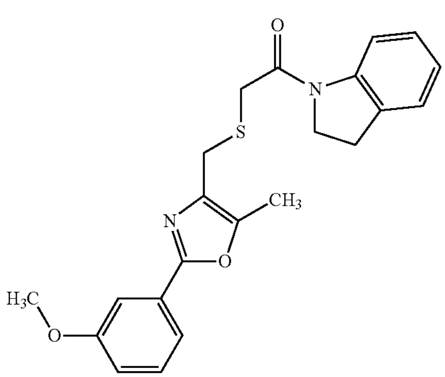 [SMILES: COc1cccc(-c2nc(CSCC(=O)N3CCc4ccccc43)c(C)o2)c1] | 394.50 |

TABLE 6-continued
Oxazole amides (R³ = N-cyclo)
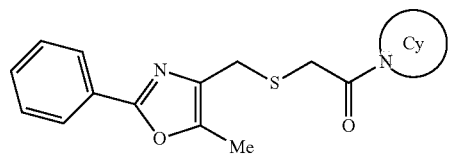
| ID | Structure | MW |
|---|---|---|
| IIa-2055 | 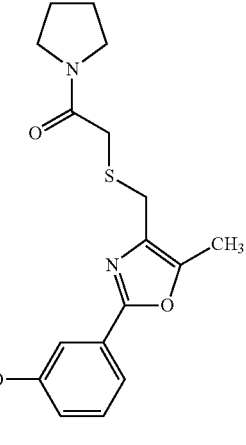 | 346.45 |
| IIa-2056 | 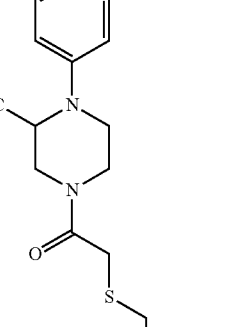 | 465.62 |

TABLE 6-continued
Oxazole amides (R³ = N-cyclo)
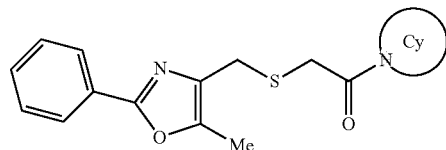
| ID | Structure | MW |
|---|---|---|
| IIa-2057 | | 426.54 |
| IIa-2058 | | 463.56 |
| IIa-2059 | | 424.52 |

TABLE 6-continued
Oxazole amides (R³ = N-cyclo)
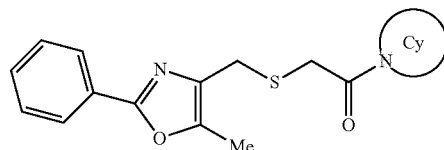
| ID | Structure | MW |
|---|---|---|
| IIa-2060 | | 376.48 |
| IIa-2061 | | 516.06 |
| IIa-2062 | | 438.55 |

TABLE 6-continued
Oxazole amides (R³ = N-cyclo)
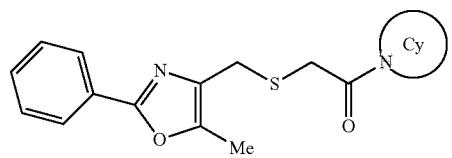
| ID | Structure | MW |
| --- | --- | --- |
| IIa-2063 | 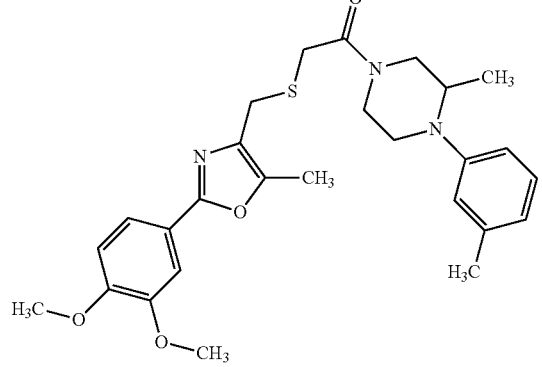 | 495.65 |
| IIa-2064 | 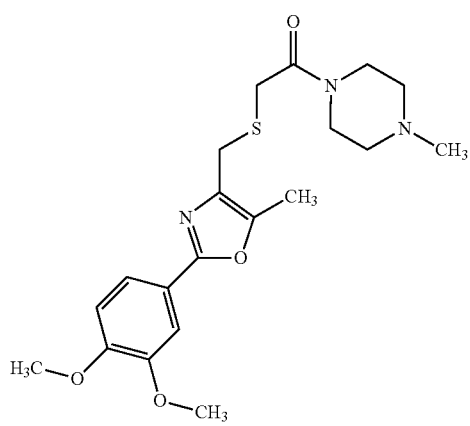 | 405.52 |
| IIa-2065 | 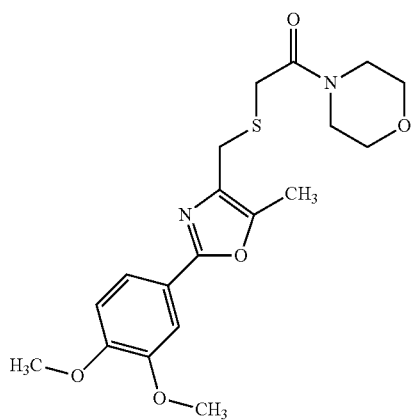 [SMILES: COc1ccc(-c2nc(CSCC(=O)N3CCOCC3)c(C)o2)cc1OC] | 392.48 |

TABLE 6-continued
Oxazole amides (R³ = N-cyclo)
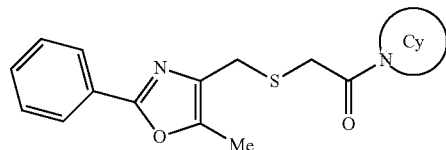
| ID | Structure | MW |
|---|---|---|
| IIa-2066 | 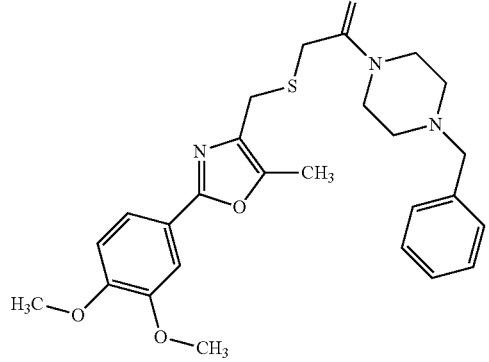 | 480.63 |
| IIa-2067 | 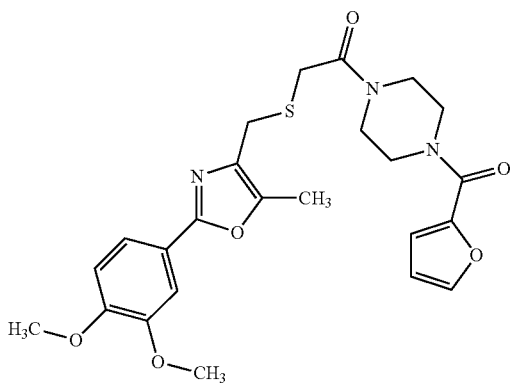 [SMILES: COc1ccc(-c2nc(CSCC(=O)N3CCN(C(=O)c4ccco4)CC3)c(C)o2)cc1OC] | 485.56 |
| IIa-2068 | 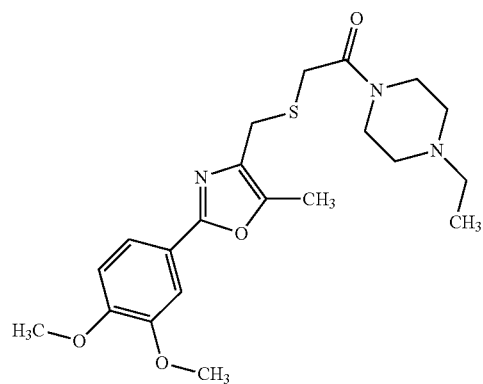 [SMILES: CCN1CCN(C(=O)CSCc2nc(-c3ccc(OC)c(OC)c3)oc2C)CC1] | 419.55 |

TABLE 6-continued
Oxazole amides (R³ = N-cyclo)
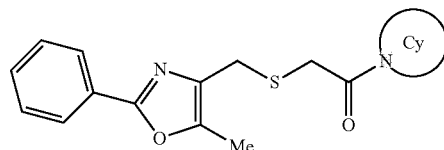
| ID | Structure | MW |
| --- | --- | --- |
| IIa-2069 | 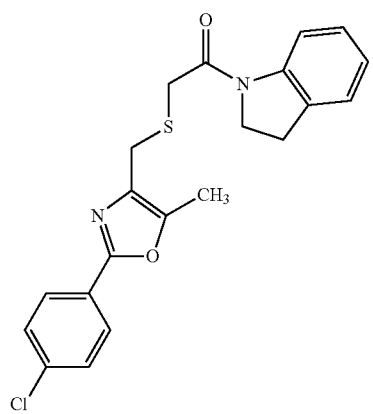 [SMILES: Cc1oc(-c2ccc(Cl)cc2)nc1CSCC(=O)N1CCc2ccccc21] | 398.91 |
| IIa-2070 | 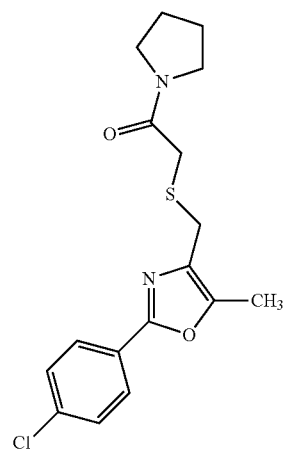 [SMILES: Cc1oc(-c2ccc(Cl)cc2)nc1CSCC(=O)N1CCCC1] | 350.87 |

TABLE 6-continued
Oxazole amides (R³ = N-cyclo)
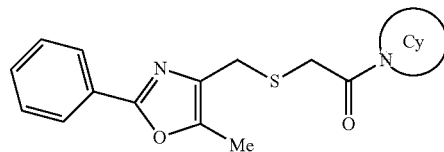
| ID | Structure | MW |
|---|---|---|
| IIa-2071 | | 490.46 |
| IIa-2072 | | 436.96 |

TABLE 6-continued
Oxazole amides (R³ = N-cyclo)
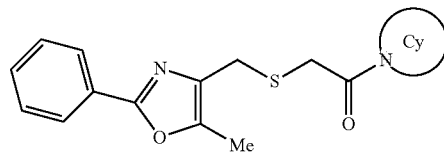
| ID | Structure | MW |
|---|---|---|
| IIa-2073 | 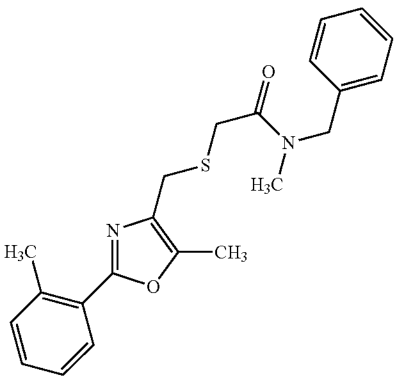 [SMILES: Cc1ccccc1-c1nc(CSCC(=O)N(C)Cc2ccccc2)c(C)o1] | 380.51 |
| IIa-2074 | 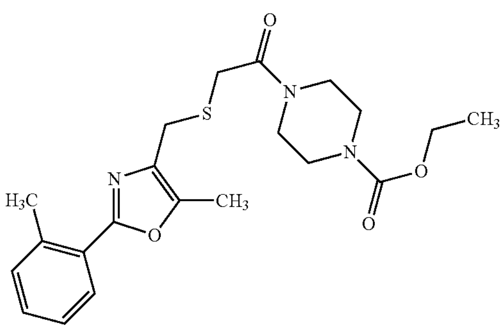 [SMILES: CCOC(=O)N1CCN(C(=O)CSCc2nc(-c3ccccc3C)oc2C)CC1] | 417.53 |
| IIa-2075 | 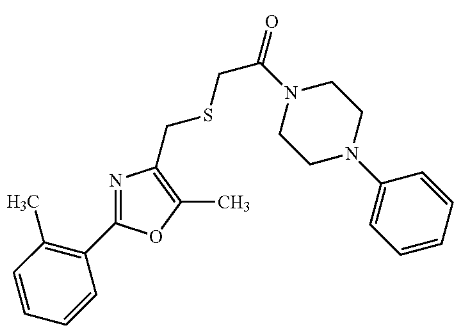 [SMILES: Cc1ccccc1-c1nc(CSCC(=O)N2CCN(c3ccccc3)CC2)c(C)o1] | 421.57 |
| IIa-2076 | 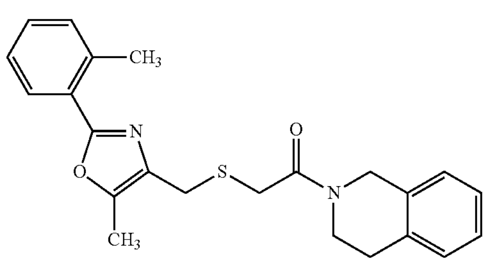 [SMILES: Cc1ccccc1-c1nc(CSCC(=O)N2CCc3ccccc3C2)c(C)o1] | 392.52 |

TABLE 6-continued
Oxazole amides (R³ = N-cyclo)
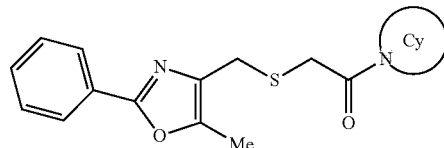
| ID | Structure | MW |
|---|---|---|
| IIa-2077 | | 359.49 |
| IIa-2078 | | 346.45 |
| IIa-2079 | | 435.59 |
| IIa-2080 | | 422.55 |

TABLE 6-continued

Oxazole amides (R³ = N-cyclo)

| ID | Structure | MW |
|---|---|---|
| IIa-2081 | 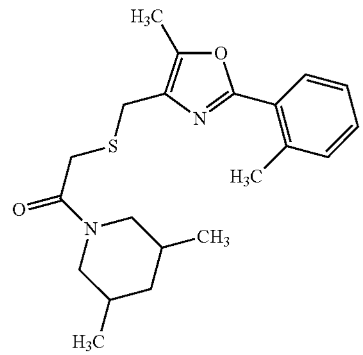 [SMILES: Cc1ccccc1-c1nc(CSCC(=O)N2CC(C)CC(C)C2)c(C)o1] | 372.53 |
| IIa-2082 | 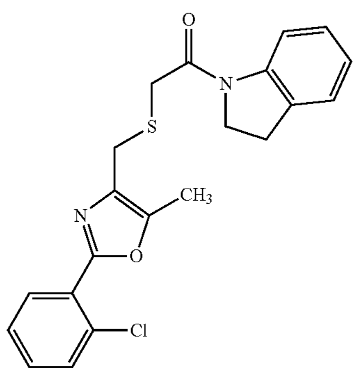 [SMILES: Cc1oc(-c2ccccc2Cl)nc1CSCC(=O)N1CCc2ccccc21] | 398.91 |
| IIa-2083 | 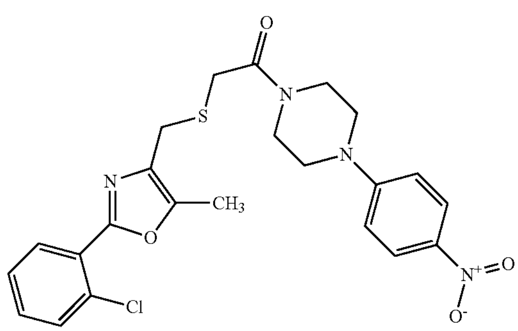 [SMILES: Cc1oc(-c2ccccc2Cl)nc1CSCC(=O)N1CCN(c2ccc([N+](=O)[O-])cc2)CC1] | 486.98 |
| IIa-2084 | 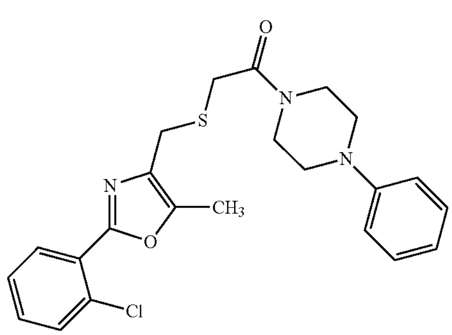 [SMILES: Cc1oc(-c2ccccc2Cl)nc1CSCC(=O)N1CCN(c2ccccc2)CC1] | 441.98 |

TABLE 6-continued
Oxazole amides (R³ = N-cyclo)
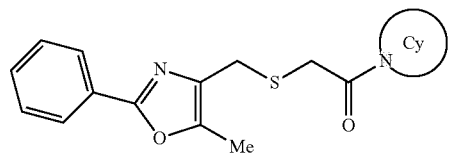
| ID | Structure | MW |
|---|---|---|
| IIa-2085 | | 350.87 |
| IIa-2086 | | 472.01 |
| IIa-2087 | | 412.58 |

TABLE 6-continued
Oxazole amides (R³ = N-cyclo)
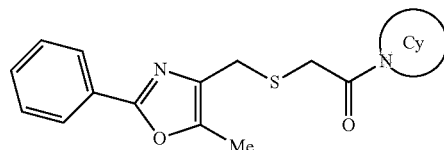
| ID | Structure | MW |
|---|---|---|
| IIa-2088 | | 498.63 |
| IIa-2089 | | 375.51 |

TABLE 6-continued

Oxazole amides (R³ = N-cyclo)

| ID | Structure | MW |
|---|---|---|
| IIa-2090 | | 362.52 |
| IIa-2091 | | 488.07 |

TABLE 6-continued
Oxazole amides (R³ = N-cyclo)
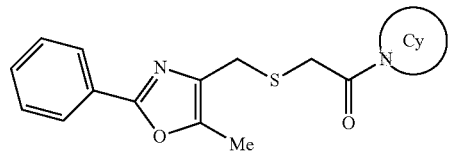
| ID | Structure | MW |
|---|---|---|
| IIa-2092 | | 481.68 |
| IIa-2093 | | 502.10 |

TABLE 6-continued
Oxazole amides (R³ = N-cyclo)
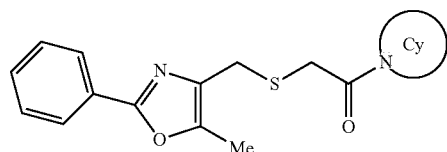
| ID | Structure | MW |
|---|---|---|
| IIa-2094 | 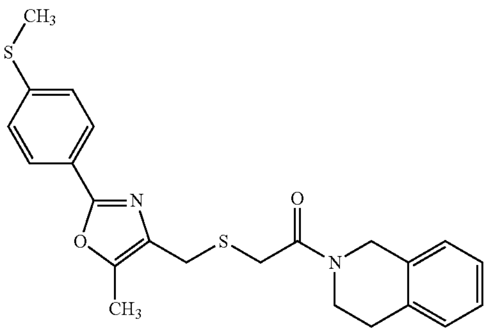 [SMILES: CSc1ccc(-c2nc(CSCC(=O)N3CCc4ccccc4C3)c(C)o2)cc1] | 424.59 |
| IIa-2095 | 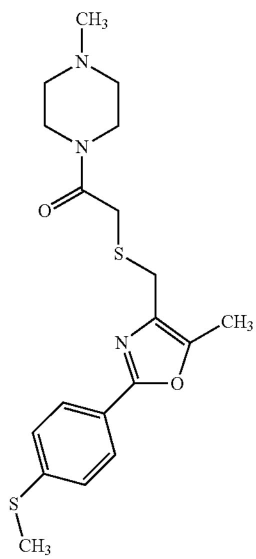 [SMILES: CSc1ccc(-c2nc(CSCC(=O)N3CCN(C)CC3)c(C)o2)cc1] | 391.56 |
| IIa-2096 | 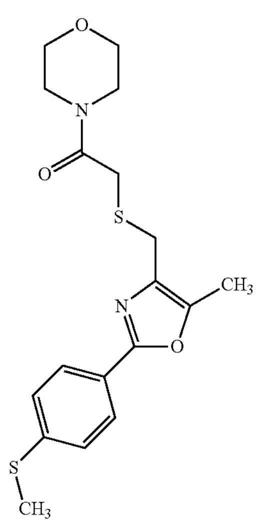 [SMILES: CSc1ccc(-c2nc(CSCC(=O)N3CCOCC3)c(C)o2)cc1] | 378.52 |

TABLE 6-continued
Oxazole amides (R³ = N-cyclo)
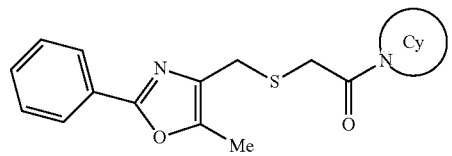
| ID | Structure | MW |
|---|---|---|
| IIa-2097 | | 467.66 |
| IIa-2098 | | 466.67 |

TABLE 6-continued
Oxazole amides (R³ = N-cyclo)
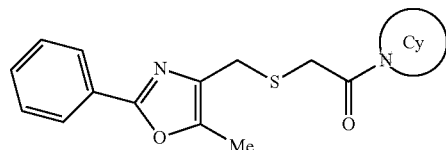
| ID | Structure | MW |
|---|---|---|
| IIa-2099 | 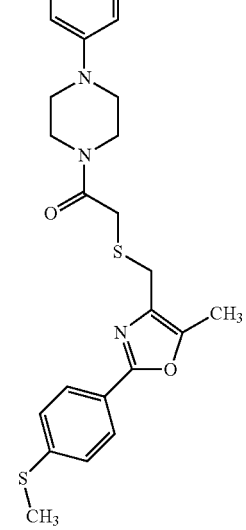 | 471.62 |
| IIa-2100 | 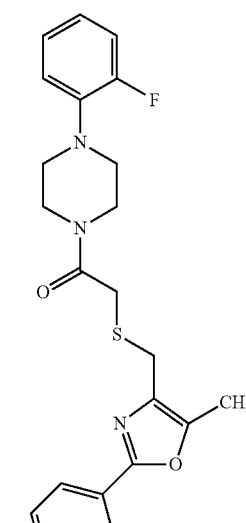 | 471.62 |

TABLE 6-continued
Oxazole amides (R³ = N-cyclo)
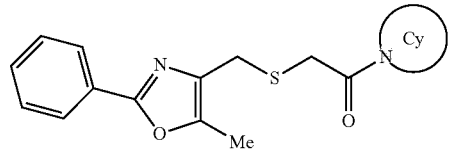
| ID | Structure | MW |
|---|---|---|
| IIa-2101 | 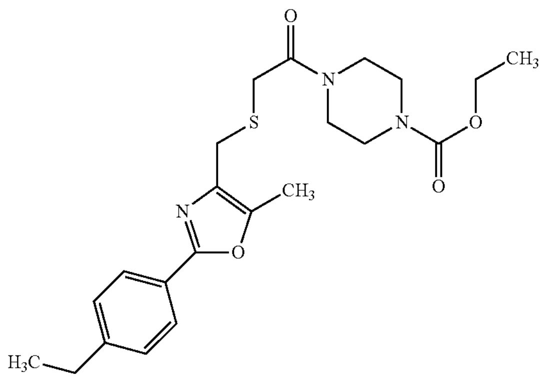 [SMILES: CCOC(=O)N1CCN(C(=O)CSCc2nc(-c3ccc(CC)cc3)oc2C)CC1] | 431.56 |
| IIa-2102 | 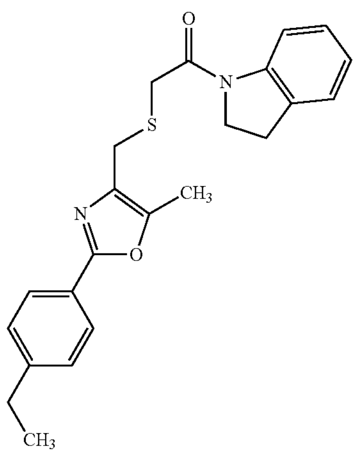 [SMILES: CCc1ccc(-c2nc(CSCC(=O)N3CCc4ccccc43)c(C)o2)cc1] | 392.52 |
| IIa-2103 | 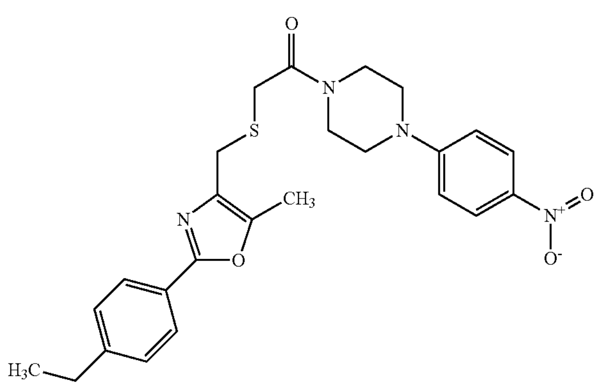 [SMILES: CCc1ccc(-c2nc(CSCC(=O)N3CCN(c4ccc([N+](=O)[O-])cc4)CC3)c(C)o2)cc1] | 480.59 |

TABLE 6-continued
Oxazole amides (R³ = N-cyclo)
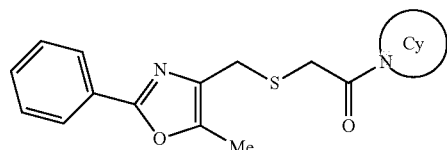
| ID | Structure | MW |
|---|---|---|
| IIa-2104 | | 435.59 |
| IIa-2105 | | 463.65 |
| IIa-2106 | | 484.06 |

TABLE 6-continued
Oxazole amides (R³ = N-cyclo)
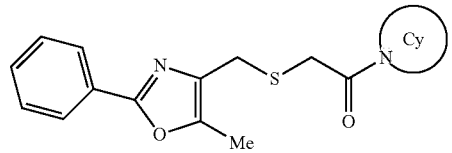
| ID | Structure | MW |
| --- | --- | --- |
| IIa-2107 | | 406.55 |
| IIa-2108 | | 373.52 |
| IIa-2109 | | 360.48 |

TABLE 6-continued
Oxazole amides ($R^3$ = N-cyclo)
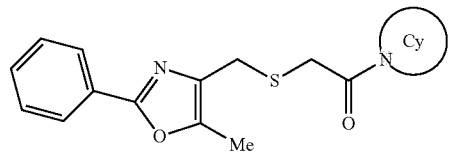
| ID | Structure | MW |
|---|---|---|
| IIa-2110 | 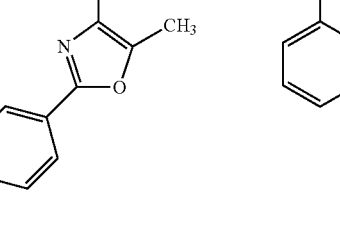 | 449.62 |
| IIa-2111 | 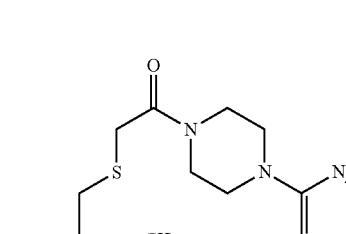 | 436.58 |
| IIa-2112 | 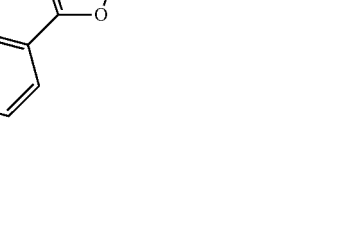 | 453.58 |

TABLE 6-continued
Oxazole amides (R³ = N-cyclo)
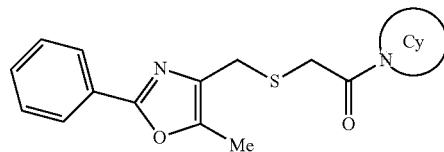
| ID | Structure | MW |
|---|---|---|
| IIa-2113 | | 430.57 |
| IIa-2114 | | 387.55 |
| IIa-2115 | | 350.87 |

TABLE 6-continued
Oxazole amides (R³ = N-cyclo)
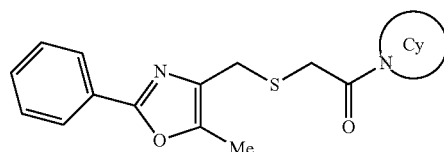
| ID | Structure | MW |
|---|---|---|
| IIa-2116 | 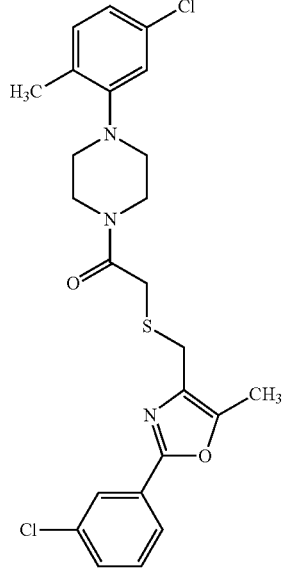 [SMILES: Cc1ccc(Cl)cc1N1CCN(C(=O)CSCc2nc(-c3cccc(Cl)c3)oc2C)CC1] | 490.46 |
| IIa-2117 |  | 459.97 |

TABLE 6-continued
Oxazole amides (R³ = N-cyclo)
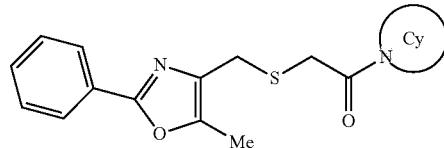
| ID | Structure | MW |
|---|---|---|
| IIa-2118 | 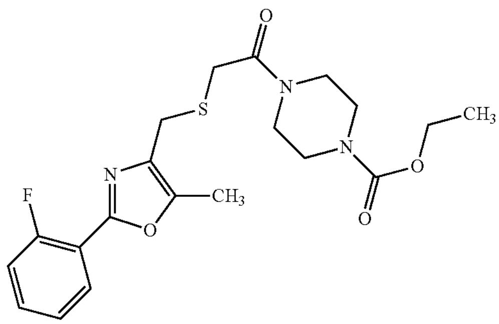 [SMILES: CCOC(=O)N1CCN(C(=O)CSCc2nc(-c3ccccc3F)oc2C)CC1] | 421.49 |
| IIa-2119 | 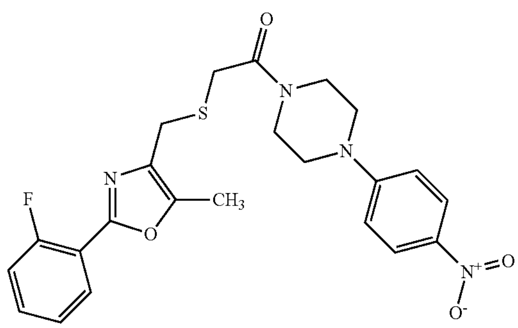 [SMILES: Cc1oc(-c2ccccc2F)nc1CSCC(=O)N1CCN(c2ccc([N+](=O)[O-])cc2)CC1] | 470.53 |
| IIa-2120 | 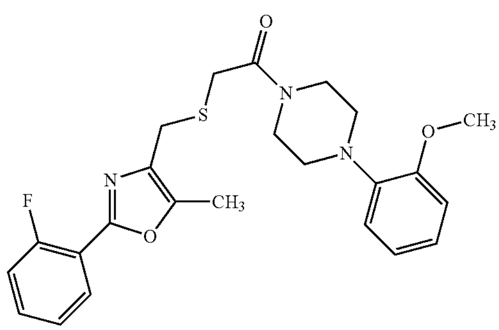 [SMILES: COc1ccccc1N1CCN(C(=O)CSCc2nc(-c3ccccc3F)oc2C)CC1] | 455.56 |
| IIa-2121 | 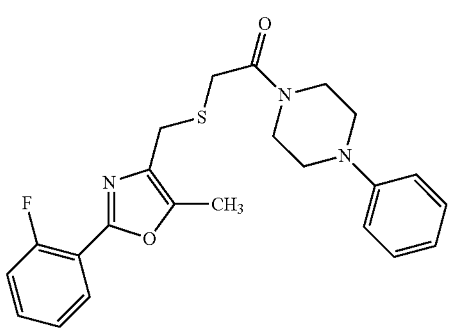 [SMILES: Cc1oc(-c2ccccc2F)nc1CSCC(=O)N1CCN(c2ccccc2)CC1] | 425.53 |

TABLE 6-continued
Oxazole amides (R³ = N-cyclo)
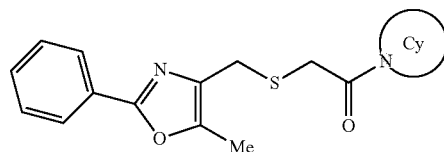
| ID | Structure | MW |
|---|---|---|
| IIa-2122 | | 334.42 |
| IIa-2123 | | 474.00 |
| IIa-2124 | | 443.52 |

TABLE 6-continued
Oxazole amides (R³ = N-cyclo)
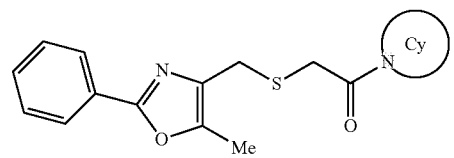
| ID | Structure | MW |
|---|---|---|
| IIa-2125 | | 455.56 |
| IIa-2126 | | 425.53 |

TABLE 6-continued
Oxazole amides (R³ = N-cyclo)
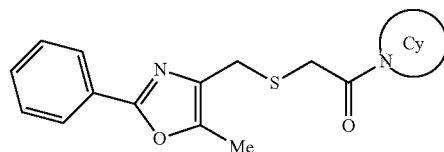
| ID | Structure | MW |
|---|---|---|
| IIa-2127 | | 421.57 |
| IIa-2128 | | 392.52 |
| IIa-2129 | | 359.49 |

TABLE 6-continued
Oxazole amides (R³ = N-cyclo)
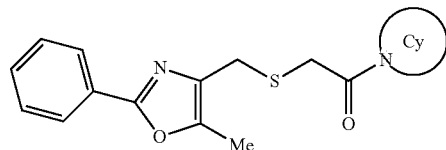
| ID | Structure | MW |
|---|---|---|
| IIa-2130 | | 346.45 |
| IIa-2131 | | 434.61 |

TABLE 6-continued
Oxazole amides (R³ = N-cyclo)
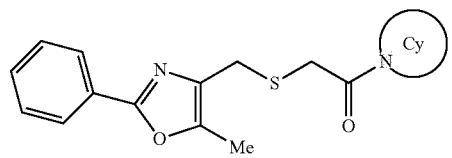
| ID | Structure | MW |
|---|---|---|
| IIa-2132 | | 422.55 |
| IIa-2133 | | 439.56 |

TABLE 6-continued
Oxazole amides (R³ = N-cyclo)
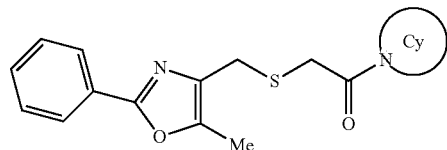
| ID | Structure | MW |
|---|---|---|
| IIa-2134 | 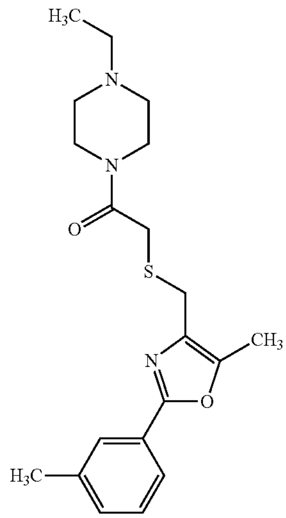 | 373.52 |
| IIa-2135 | 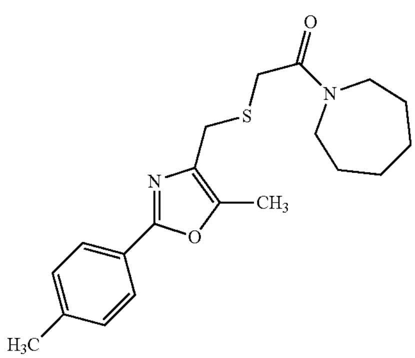 [SMILES: Cc1ccc(-c2nc(CSCC(=O)N3CCCCCC3)c(C)o2)cc1] | 358.51 |
| IIa-2136 | 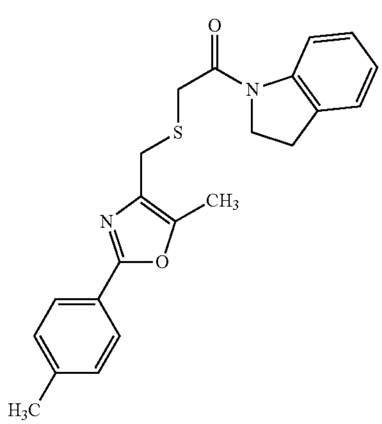 [SMILES: Cc1ccc(-c2nc(CSCC(=O)N3CCc4ccccc43)c(C)o2)cc1] | 378.50 |

TABLE 6-continued
Oxazole amides (R³ = N-cyclo)
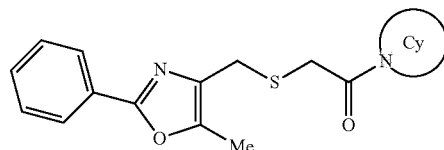
| ID | Structure | MW |
|---|---|---|
| IIa-2137 | | 330.45 |
| IIa-2138 | | 449.62 |
| IIa-2139 | | 346.45 |

TABLE 6-continued
Oxazole amides (R³ = N-cyclo)
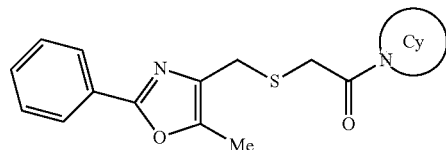
| ID | Structure | MW |
|---|---|---|
| IIa-2140 | | 422.55 |
| IIa-2141 | | 402.52 |
| IIa-2142 | | 439.54 |

TABLE 6-continued
Oxazole amides (R³ = N-cyclo)
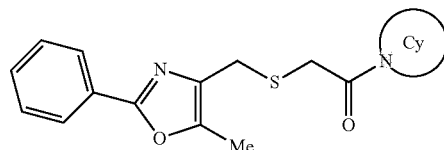
| ID | Structure | MW |
|---|---|---|
| IIa-2143 |  | 392.52 |
| IIa-2144 |  | 449.53 |

TABLE 6-continued
Oxazole amides (R³ = N-cyclo)
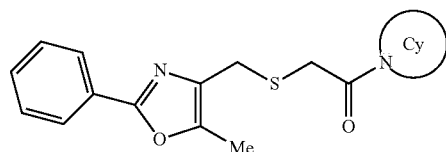
| ID | Structure | MW |
|---|---|---|
| IIa-2145 | | 390.51 |
| IIa-2146 | | 362.45 |

TABLE 6-continued

Oxazole amides (R³ = N-cyclo)

| ID | Structure | MW |
|---|---|---|
| IIa-2147 | | 424.52 |
| IIa-2148 | | 391.49 |

TABLE 6-continued
Oxazole amides (R³ = N-cyclo)
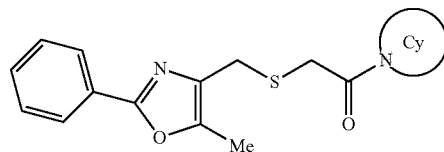
| ID | Structure | MW |
|---|---|---|
| IIa-2149 | | 378.45 |
| IIa-2150 | | 434.52 |

TABLE 6-continued
Oxazole amides (R³ = N-cyclo)
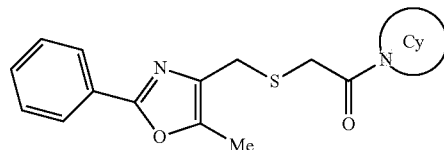
| ID | Structure | MW |
|---|---|---|
| IIa-2151 | | 405.52 |
| IIa-2152 | | 376.48 |

TABLE 6-continued
Oxazole amides (R³ = N-cyclo)
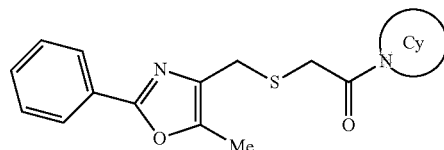
| ID | Structure | MW |
|---|---|---|
| IIa-2153 | | 441.53 |
| IIa-2154 | | 376.52 |

TABLE 6-continued
Oxazole amides (R³ = N-cyclo)
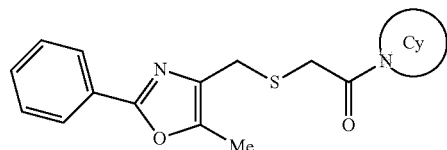
| ID | Structure | MW |
|---|---|---|
| IIa-2155 | | 433.53 |
| IIa-2156 | | 374.51 |

TABLE 6-continued
Oxazole amides (R³ = N-cyclo)
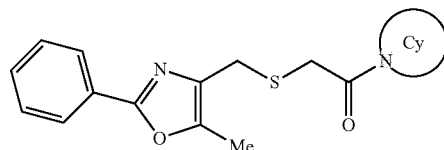
| ID | Structure | MW |
|---|---|---|
| IIa-2157 | 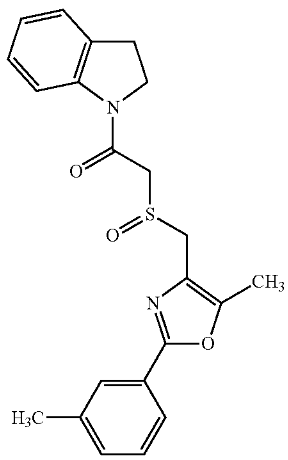 [SMILES: Cc1cccc(-c2nc(CS(=O)CC(=O)N3CCc4ccccc43)c(C)o2)c1] | 394.50 |
| IIa-2158 | 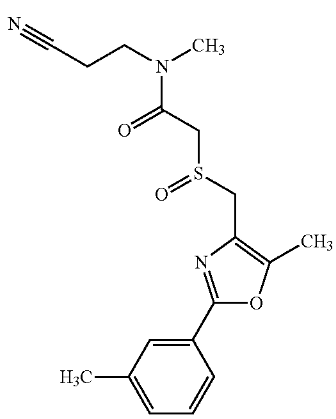 [SMILES: Cc1cccc(-c2nc(CS(=O)CC(=O)N(C)CCC#N)c(C)o2)c1] | 359.45 |

TABLE 6-continued
Oxazole amides (R³ = N-cyclo)
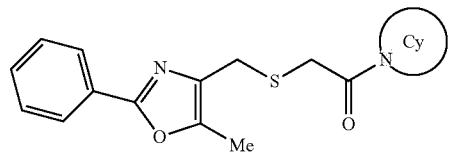
| ID | Structure | MW |
|---|---|---|
| IIa-2159 | | 437.57 |
| IIa-2160 | | 346.45 |

TABLE 6-continued
Oxazole amides (R³ = N-cyclo)
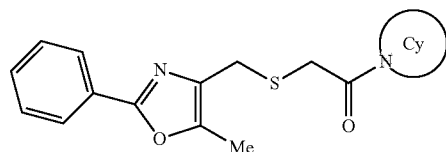
| ID | Structure | MW |
|---|---|---|
| IIa-2161 | 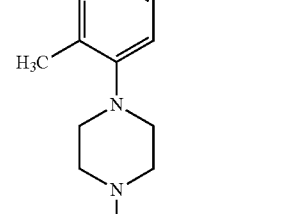 | 486.04 |
| IIa-2162 | 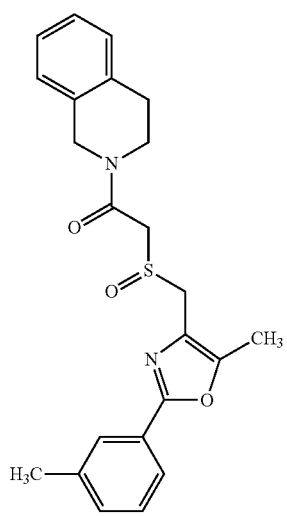 | 408.52 |

TABLE 6-continued
Oxazole amides (R³ = N-cyclo)
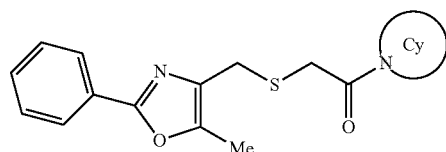
| ID | Structure | MW |
|---|---|---|
| IIa-2163 | | 375.49 |
| IIa-2164 | | 438.55 |
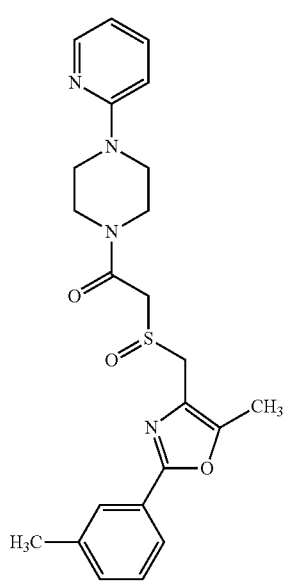

TABLE 6-continued
Oxazole amides (R³ = N-cyclo)
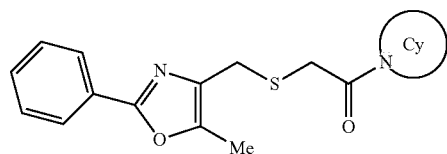
| ID | Structure | MW |
|---|---|---|
| IIa-2165 | 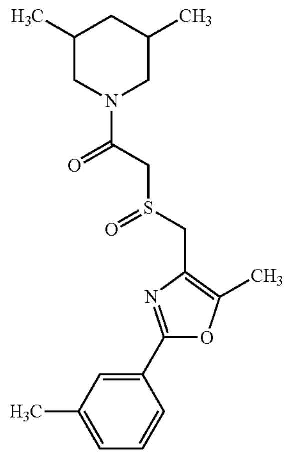 | 388.53 |
| IIa-2166 | 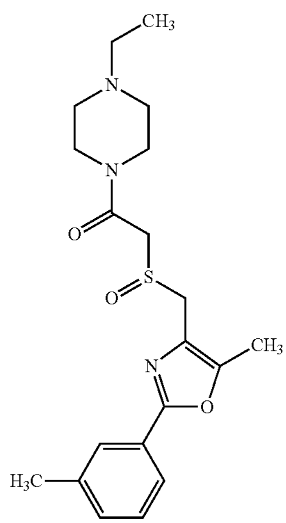 | 389.52 |
| IIa-2167 | 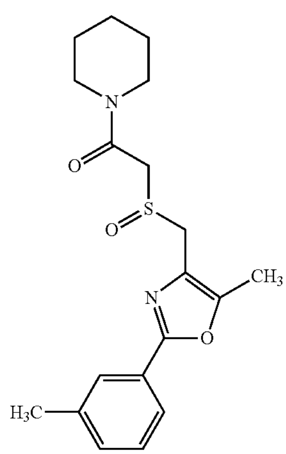 | 360.48 |

TABLE 6-continued

Oxazole amides (R³ = N-cyclo)

| ID | Structure | MW |
|---|---|---|
| IIa-2168 | | 433.53 |
| IIa-2169 | | 437.57 |

TABLE 6-continued
Oxazole amides (R³ = N-cyclo)
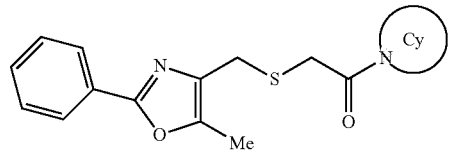
| ID | Structure | MW |
|---|---|---|
| IIa-2170 | 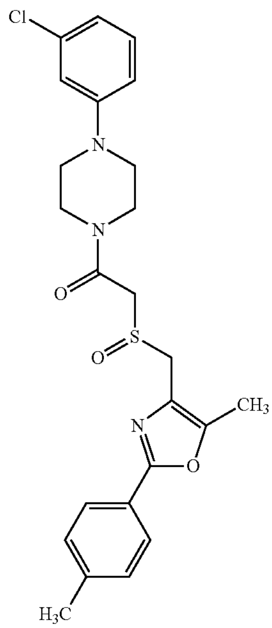 [SMILES: Cc1ccc(-c2nc(CS(=O)CC(=O)N3CCN(c4cccc(Cl)c4)CC3)c(C)o2)cc1] | 472.01 |
| IIa-2171 | 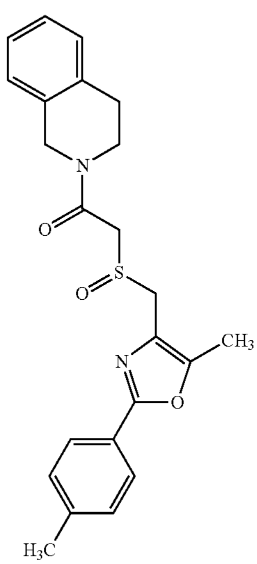 [SMILES: Cc1ccc(-c2nc(CS(=O)CC(=O)N3CCc4ccccc4C3)c(C)o2)cc1] | 408.52 |

TABLE 6-continued

Oxazole amides (R³ = N-cyclo)

| ID | Structure | MW |
|---|---|---|
| IIa-2172 | | 465.62 |
| IIa-2173 | | 362.45 |

TABLE 6-continued
Oxazole amides (R³ = N-cyclo)
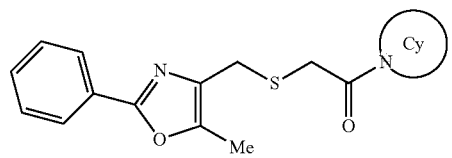
| ID | Structure | MW |
|---|---|---|
| IIa-2174 | | 451.59 |
| IIa-2175 | | 418.52 |

TABLE 6-continued
Oxazole amides (R³ = N-cyclo)
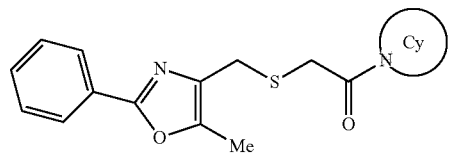
| ID | Structure | MW |
|---|---|---|
| IIa-2176 | | 388.53 |
| IIa-2177 | | 455.56 |

TABLE 6-continued
Oxazole amides (R³ = N-cyclo)
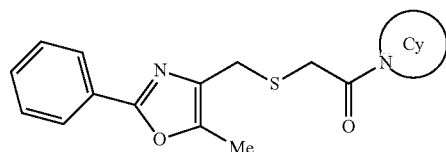
| ID | Structure | MW |
|---|---|---|
| IIa-2178 | 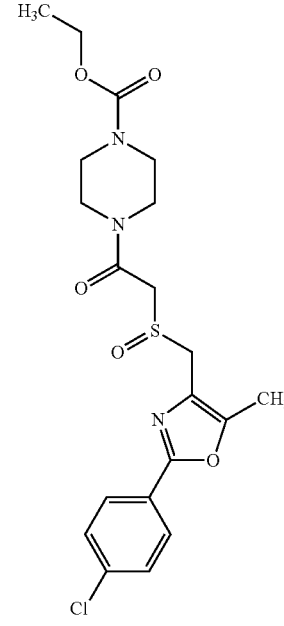 | 453.95 |
| IIa-2179 | 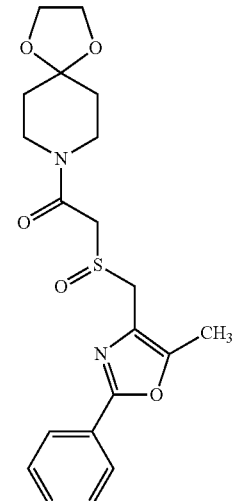 | 438.93 |

TABLE 6-continued
Oxazole amides (R³ = N-cyclo)
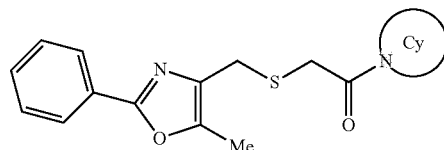
| ID | Structure | MW |
|---|---|---|
| IIa-2180 | 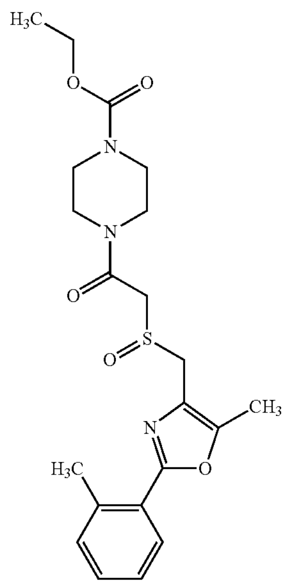 [SMILES: CCOC(=O)N1CCN(C(=O)CS(=O)Cc2nc(-c3ccccc3C)oc2C)CC1] | 433.53 |
| IIa-2181 | 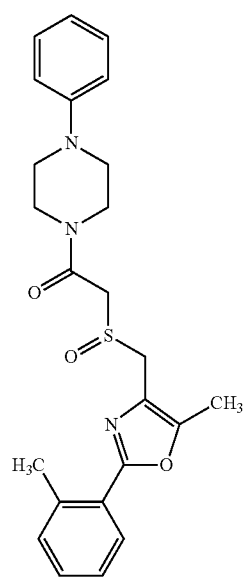 [SMILES: Cc1ccccc1-c1nc(CS(=O)CC(=O)N2CCN(c3ccccc3)CC2)c(C)o1] | 437.57 |

TABLE 6-continued

Oxazole amides (R³ = N-cyclo)

| ID | Structure | MW |
|---|---|---|
| IIa-2182 | | 486.04 |
| IIa-2183 | | 362.45 |

TABLE 6-continued
Oxazole amides (R³ = N-cyclo)
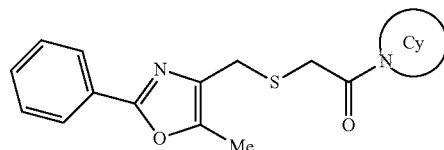
| ID | Structure | MW |
|---|---|---|
| IIa-2184 | | 418.52 |
| IIa-2185 | | 455.54 |

TABLE 6-continued
Oxazole amides (R³ = N-cyclo)
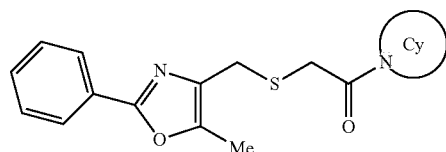
| ID | Structure | MW |
|---|---|---|
| IIa-2186 | | 389.52 |
| IIa-2187 | | 360.48 |
| IIa-2188 | | 394.92 |

TABLE 6-continued
Oxazole amides (R³ = N-cyclo)
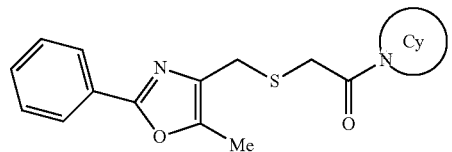
| ID | Structure | MW |
|---|---|---|
| IIa-2189 | 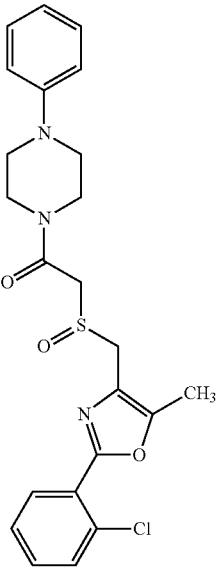 [SMILES: Cc1oc(-c2ccccc2Cl)nc1CS(=O)CC(=O)N1CCN(c2ccccc2)CC1] | 457.98 |
| IIa-2190 | 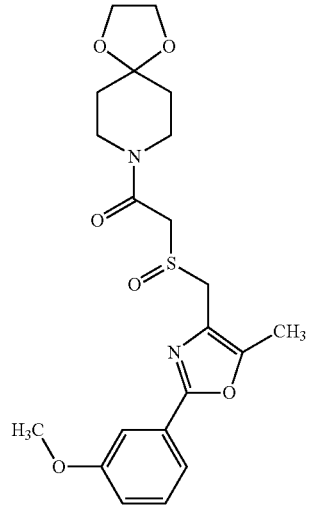 | 434.52 |

TABLE 6-continued
Oxazole amides (R³ = N-cyclo)
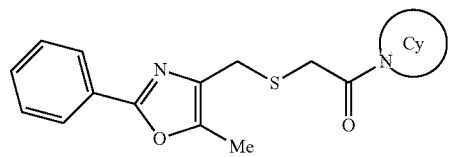
| ID | Structure | MW |
|---|---|---|
| IIa-2191 | 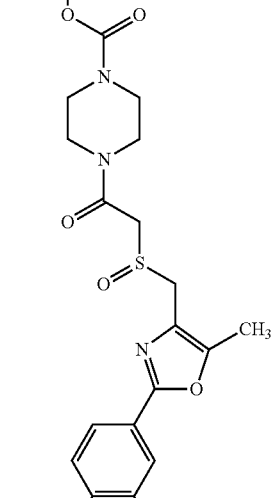 | 479.56 |
| IIa-2192 | 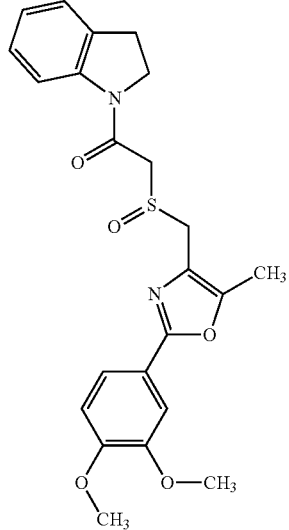 [SMILES: COc1ccc(-c2nc(CS(=O)CC(=O)N3CCc4ccccc43)c(C)o2)cc1OC] | 440.52 |

TABLE 6-continued
Oxazole amides (R³ = N-cyclo)
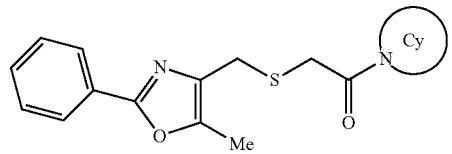
| ID | Structure | MW |
|---|---|---|
| IIa-2193 | 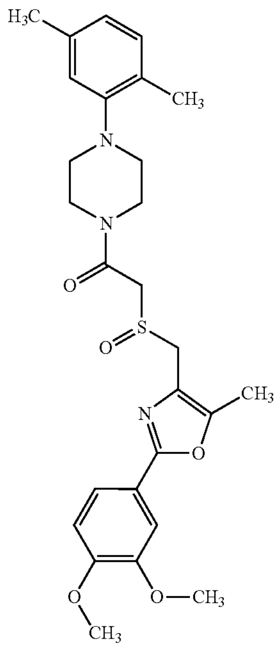 | 511.65 |
| IIa-2194 | 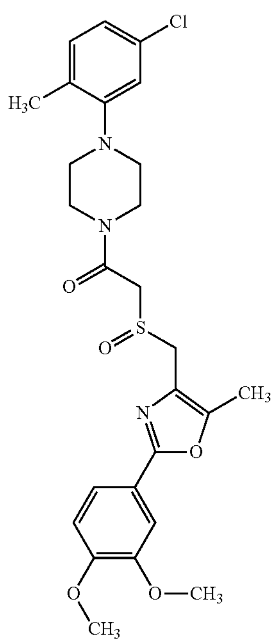 | 532.06 |

TABLE 6-continued
Oxazole amides (R³ = N-cyclo)
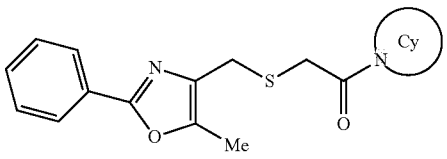
| ID | Structure | MW |
|---|---|---|
| IIa-2195 | 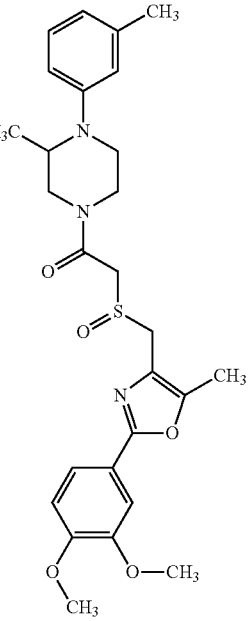 | 511.65 |
| IIa-2196 | 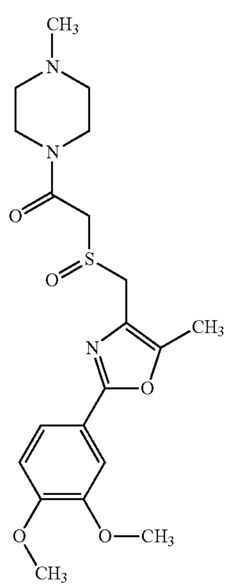 [SMILES: COc1ccc(-c2nc(CS(=O)CC(=O)N3CCN(C)CC3)c(C)o2)cc1OC] | 421.52 |

TABLE 6-continued
Oxazole amides (R³ = N-cyclo)
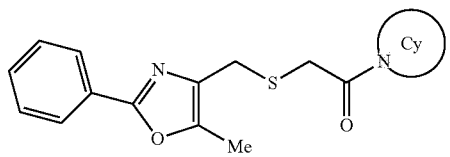
| ID | Structure | MW |
|---|---|---|
| IIa-2197 | | 408.48 |
| IIa-2198 | | 497.62 |

TABLE 6-continued
Oxazole amides (R³ = N-cyclo)
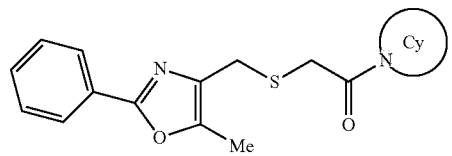
| ID | Structure | MW |
|---|---|---|
| IIa-2199 | 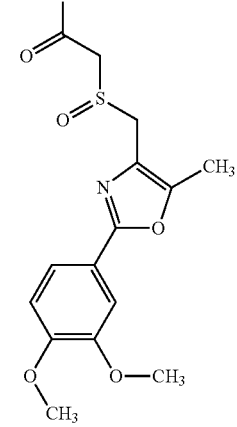 | 435.55 |
| IIa-2200 | 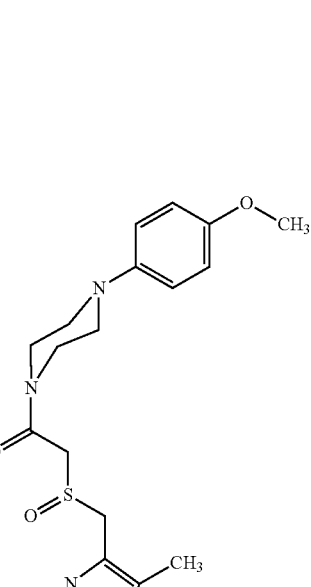 | 513.62 |

TABLE 6-continued
Oxazole amides (R³ = N-cyclo)
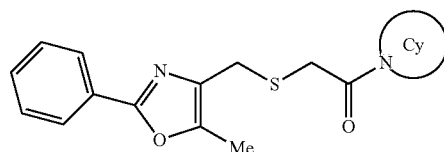
| ID | Structure | MW |
|---|---|---|
| IIa-2201 | | 382.49 |
| IIa-2202 | | 362.49 |
| IIa-2203 | | 380.47 |

TABLE 6-continued
Oxazole amides (R³ = N-cyclo)
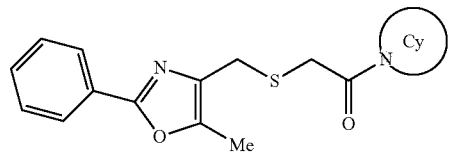
| ID | Structure | MW |
|---|---|---|
| IIa-2204 | | 423.54 |
| IIa-2205 | | 394.50 |

TABLE 6-continued

Oxazole amides (R³ = N-cyclo)

| ID | Structure | MW |
|---|---|---|
| IIa-2206 | 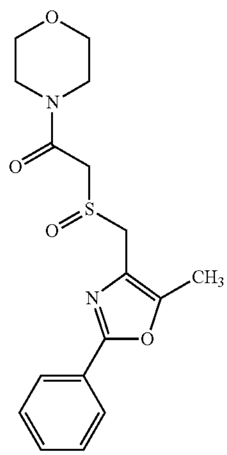 [SMILES: Cc1oc(-c2ccccc2)nc1CS(=O)CC(=O)N1CCOCC1] | 348.42 |
| IIa-2207 | 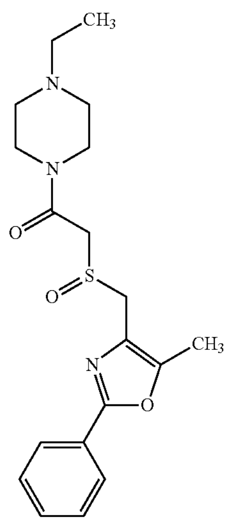 [SMILES: CCN1CCN(C(=O)CS(=O)Cc2nc(-c3ccccc3)oc2C)CC1] | 375.49 |
| IIa-2208 | 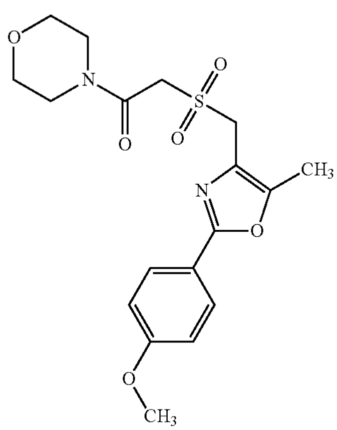 [SMILES: COc1ccc(-c2nc(CS(=O)(=O)CC(=O)N3CCOCC3)c(C)o2)cc1] | 394.45 |

TABLE 6-continued
Oxazole amides (R³ = N-cyclo)
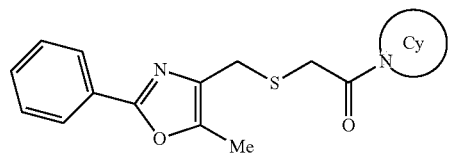
| ID | Structure | MW |
|---|---|---|
| IIa-2209 | | 412.51 |
| IIa-2210 | | 392.52 |
| IIa-2211 | | 449.53 |

TABLE 6-continued
Oxazole amides (R³ = N-cyclo)
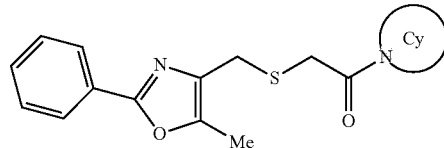
| ID | Structure | MW |
|---|---|---|
| IIa-2212 | 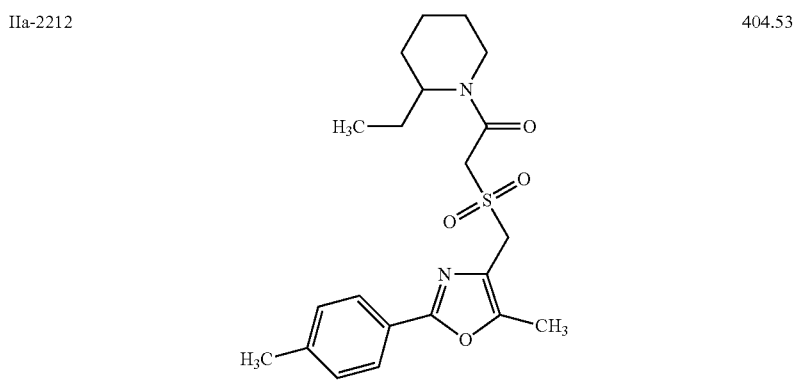 | 404.53 |
| IIa-2213 | 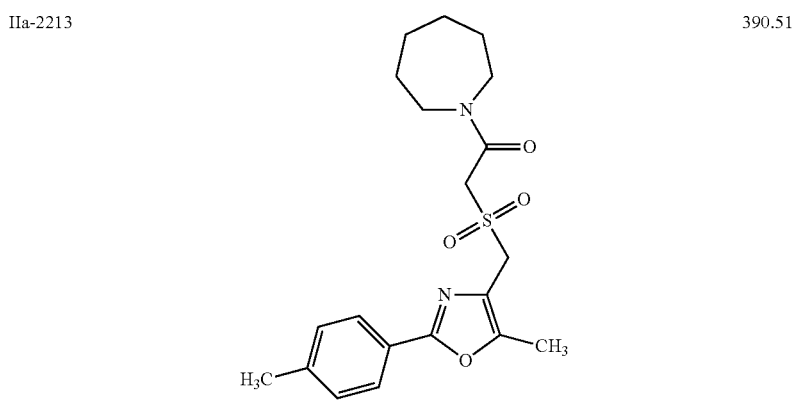 | 390.51 |
| IIa-2214 | 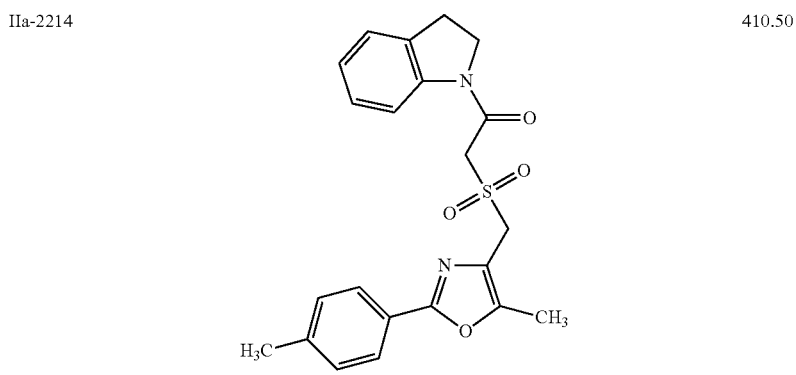 | 410.50 |

TABLE 6-continued
Oxazole amides (R³ = N-cyclo)
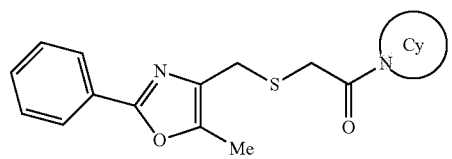
| ID | Structure | MW |
| --- | --- | --- |
| IIa-2215 | 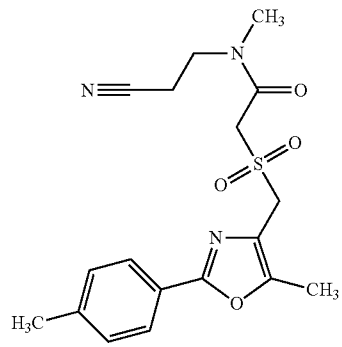 | 375.45 |
| IIa-2216 | 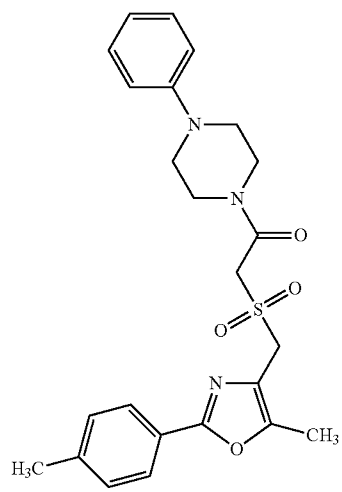 | 453.56 |
| IIa-2217 | 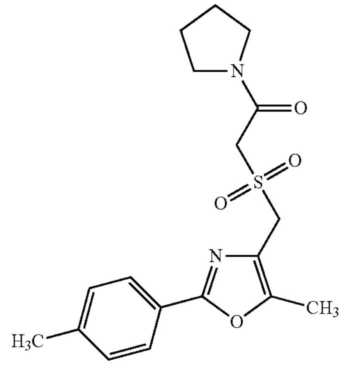 | 362.45 |

TABLE 6-continued
Oxazole amides (R³ = N-cyclo)
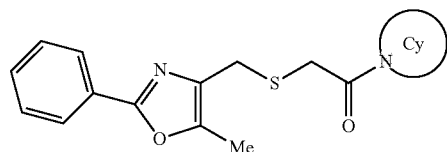
| ID | Structure | MW |
|---|---|---|
| IIa-2218 | 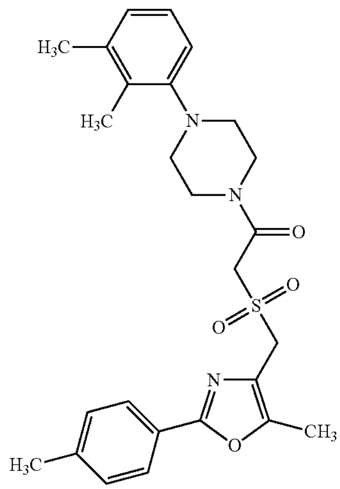 | 481.62 |
| IIa-2219 | 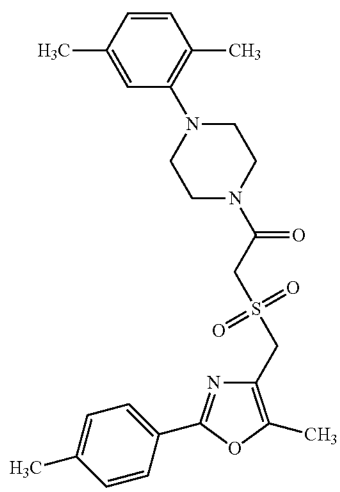 | 481.62 |
| IIa-2220 | 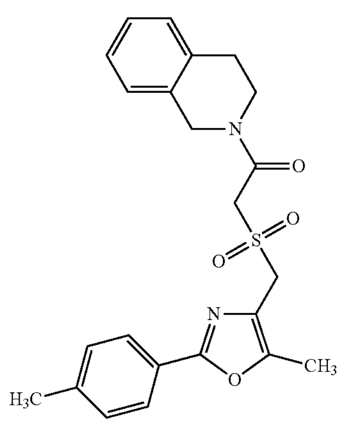 | 424.52 |

TABLE 6-continued
Oxazole amides (R³ = N-cyclo)
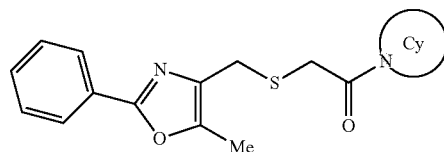
| ID | Structure | MW |
|---|---|---|
| IIa-2221 | | 481.62 |
| IIa-2222 | | 391.49 |
| IIa-2223 | | 378.45 |

TABLE 6-continued

Oxazole amides (R³ = N-cyclo)

| ID | Structure | MW |
| --- | --- | --- |
| IIa-2224 | 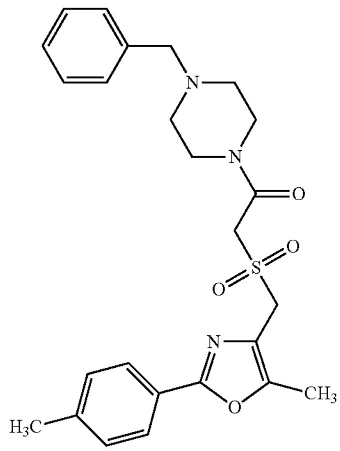 | 467.59 |
| IIa-2225 | 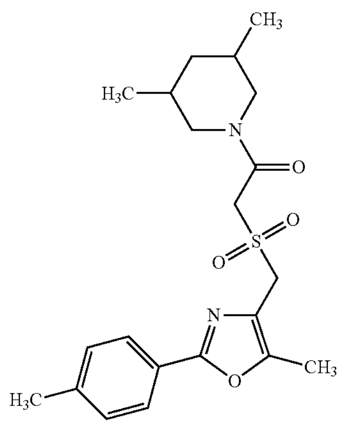 | 404.53 |
| IIa-2226 | 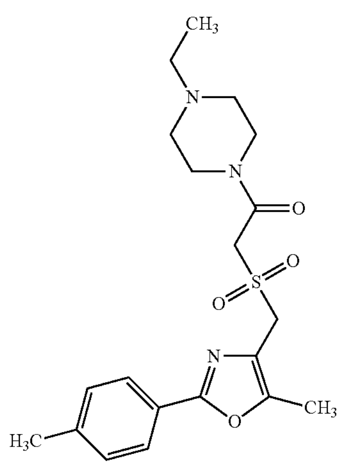 | 405.52 |

TABLE 6-continued
Oxazole amides (R³ = N-cyclo)
| ID | Structure | MW |
|---|---|---|
| IIa-2227 | 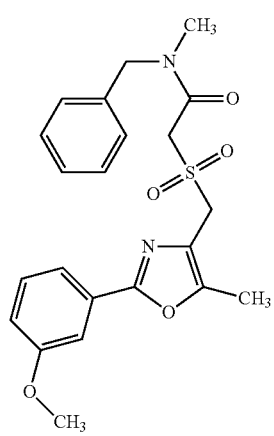 [SMILES: COc1cccc(-c2nc(CS(=O)(=O)CC(=O)N(C)Cc3ccccc3)c(C)o2)c1] | 428.51 |
| IIa-2228 | 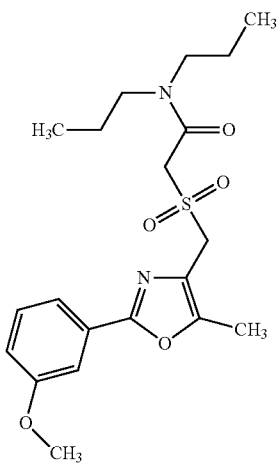 [SMILES: CCCN(CCC)C(=O)CS(=O)(=O)Cc1nc(-c2cccc(OC)c2)oc1C] | 408.52 |

TABLE 6-continued
Oxazole amides (R³ = N-cyclo)
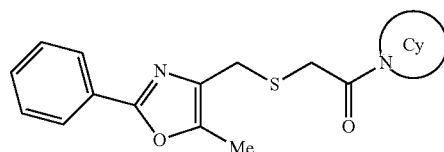
| ID | Structure | MW |
|---|---|---|
| IIa-2229 | | 465.53 |
| IIa-2230 | | 406.50 |

TABLE 6-continued
Oxazole amides (R³ = N-cyclo)
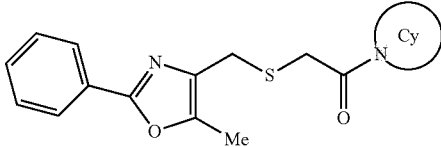
| ID | Structure | MW |
|---|---|---|
| IIa-2231 | 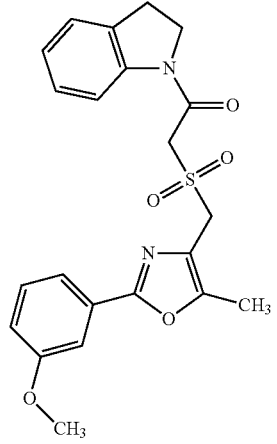 [SMILES: COc1cccc(-c2nc(CS(=O)(=O)CC(=O)N3CCc4ccccc43)c(C)o2)c1] | 426.50 |
| IIa-2232 | | 391.45 |

TABLE 6-continued
Oxazole amides (R³ = N-cyclo)
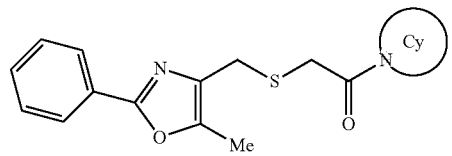
| ID | Structure | MW |
|---|---|---|
| IIa-2233 | 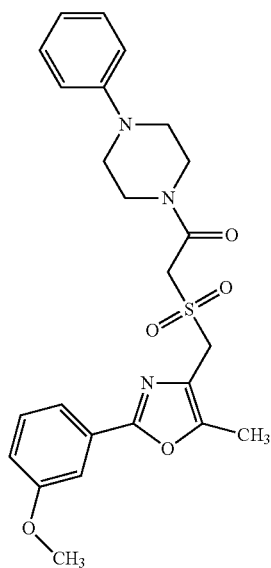 [SMILES: COc1cccc(-c2nc(CS(=O)(=O)CC(=O)N3CCN(c4ccccc4)CC3)c(C)o2)c1] | 469.56 |
| IIa-2234 | 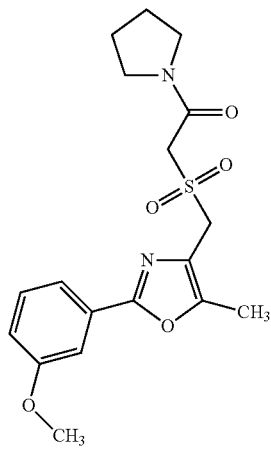 [SMILES: COc1cccc(-c2nc(CS(=O)(=O)CC(=O)N3CCCC3)c(C)o2)c1] | 378.45 |

TABLE 6-continued
Oxazole amides (R³ = N-cyclo)
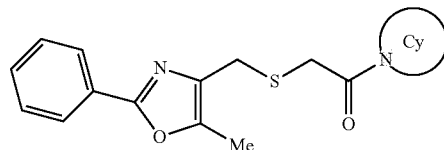
| ID | Structure | MW |
|---|---|---|
| IIa-2235 | 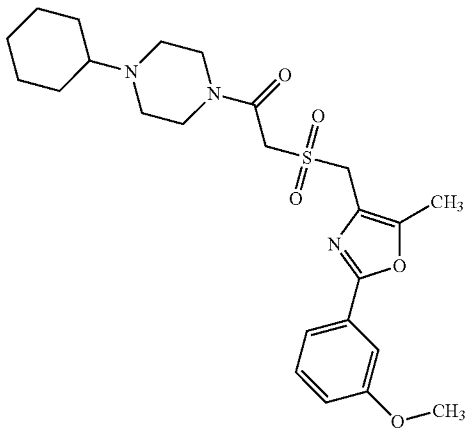 [SMILES: COc1cccc(-c2nc(CS(=O)(=O)CC(=O)N3CCN(C4CCCCC4)CC3)c(C)o2)c1] | 475.61 |
| IIa-2236 | 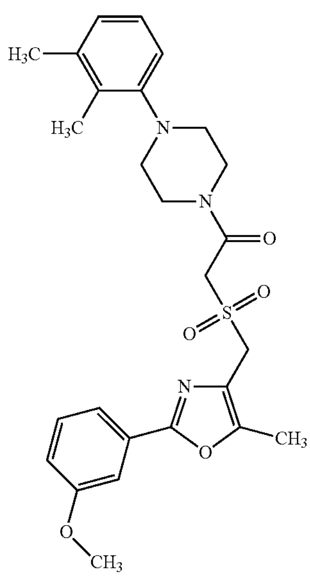 | 497.62 |

TABLE 6-continued
Oxazole amides (R³ = N-cyclo)
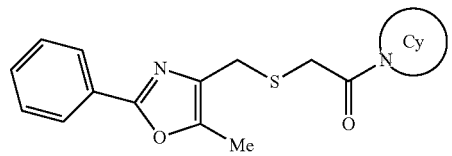
| ID | Structure | MW |
|---|---|---|
| IIa-2237 | 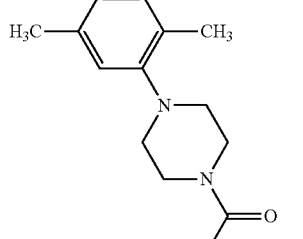 | 497.62 |
| IIa-2238 | 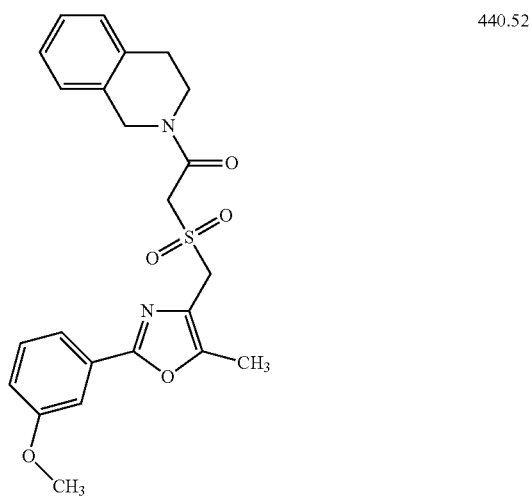 | 440.52 |

TABLE 6-continued
Oxazole amides (R³ = N-cyclo)
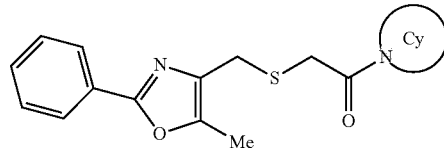
| ID | Structure | MW |
|---|---|---|
| IIa-2239 | 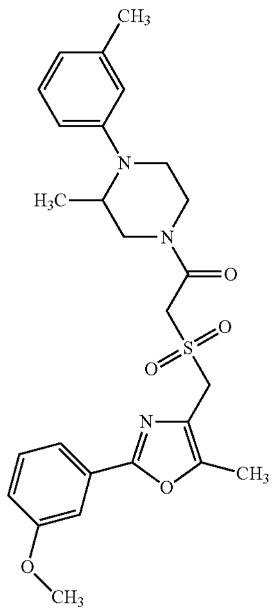 [SMILES: COc1cccc(-c2nc(CS(=O)(=O)CC(=O)N3CCN(c4cccc(C)c4)C(C)C3)c(C)o2)c1] | 497.62 |
| IIa-2240 | 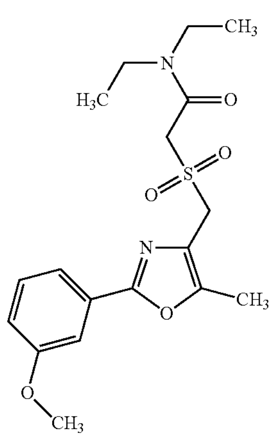 [SMILES: CCN(CC)C(=O)CS(=O)(=O)Cc1nc(-c2cccc(OC)c2)oc1C] | 380.47 |

TABLE 6-continued
Oxazole amides (R³ = N-cyclo)
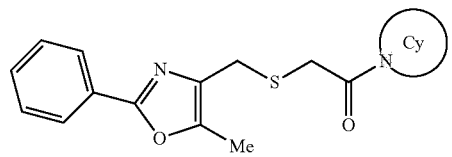
| ID | Structure | MW |
|---|---|---|
| IIa-2241 | | 407.49 |
| IIa-2242 | | 394.45 |

TABLE 6-continued
Oxazole amides (R³ = N-cyclo)
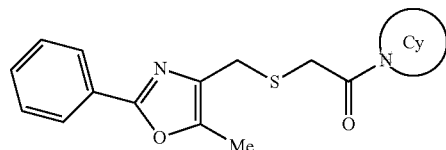
| ID | Structure | MW |
|---|---|---|
| IIa-2243 | 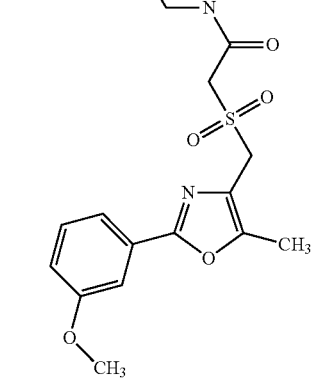 | 483.59 |
| IIa-2244 | 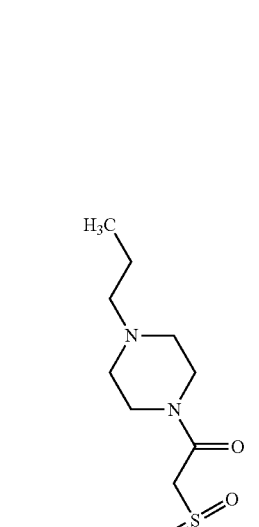 | 435.55 |

TABLE 6-continued
Oxazole amides (R³ = N-cyclo)
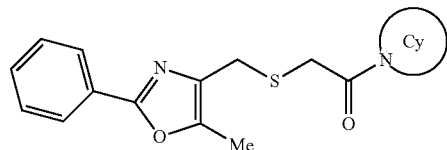
| ID | Structure | MW |
| --- | --- | --- |
| IIa-2245 | 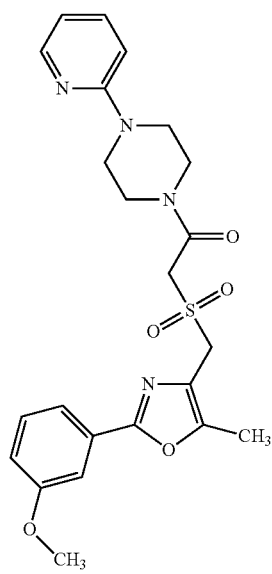 [SMILES: COc1cccc(-c2nc(CS(=O)(=O)CC(=O)N3CCN(c4ccccn4)CC3)c(C)o2)c1] | 470.55 |
| IIa-2246 | 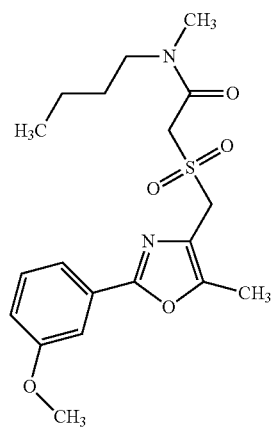 [SMILES: CCCCN(C)C(=O)CS(=O)(=O)Cc1nc(-c2cccc(OC)c2)oc1C] | 394.49 |

TABLE 6-continued
Oxazole amides (R³ = N-cyclo)
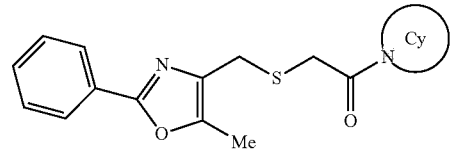
| ID | Structure | MW |
|---|---|---|
| IIa-2247 | 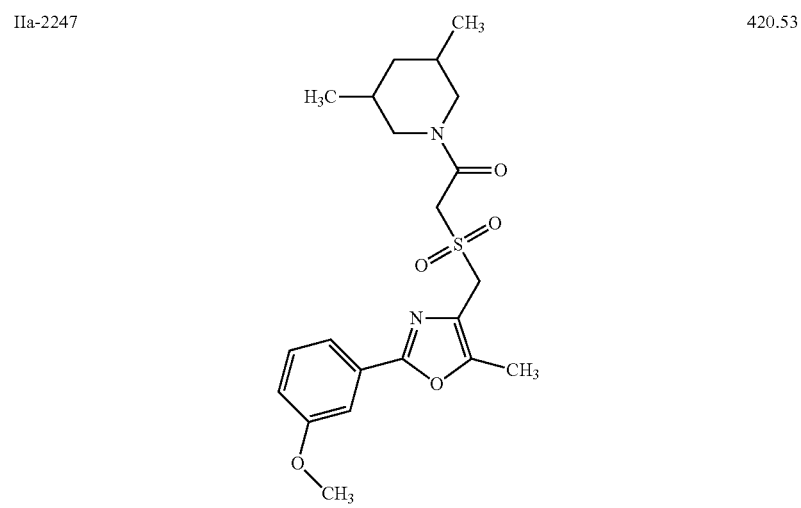 | 420.53 |
| IIa-2248 | 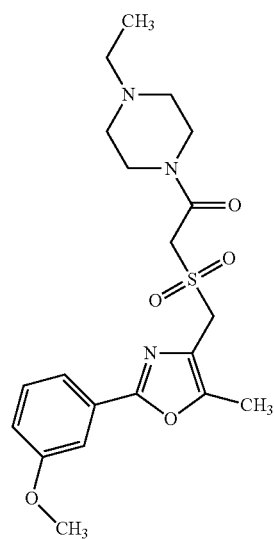 [SMILES: CCN1CCN(C(=O)CS(=O)(=O)Cc2nc(-c3cccc(OC)c3)oc2C)CC1] | 421.52 |

TABLE 6-continued
Oxazole amides (R³ = N-cyclo)
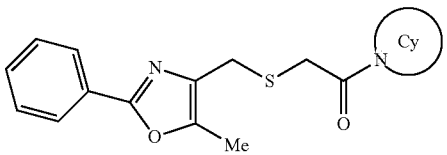
| ID | Structure | MW |
|---|---|---|
| IIa-2249 | 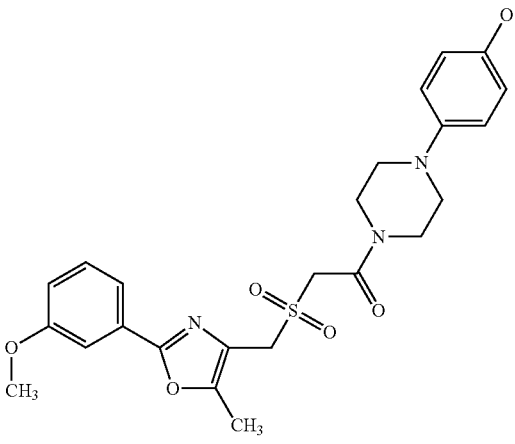 | 499.59 |
| IIa-2250 | | 392.48 |
| IIa-2251 | 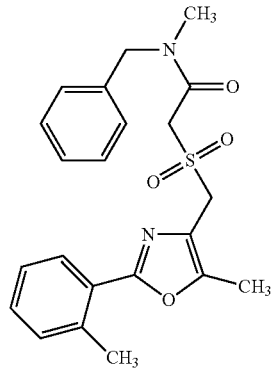 [SMILES: Cc1ccccc1-c1nc(CS(=O)(=O)CC(=O)N(C)Cc2ccccc2)c(C)o1] | 412.51 |

TABLE 6-continued
Oxazole amides (R³ = N-cyclo)
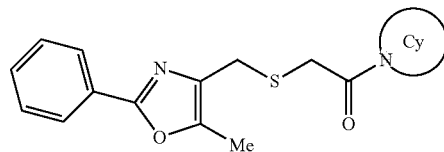
| ID | Structure | MW |
|---|---|---|
| IIa-2252 | 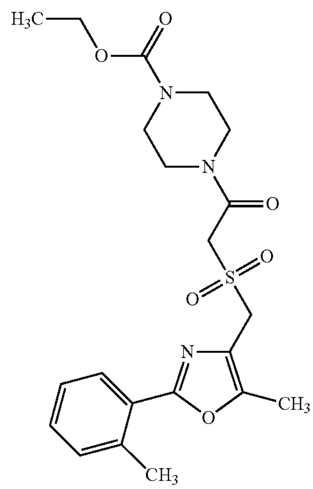 [SMILES: CCOC(=O)N1CCN(C(=O)CS(=O)(=O)Cc2nc(-c3ccccc3C)oc2C)CC1] | 449.53 |
| IIa-2253 | 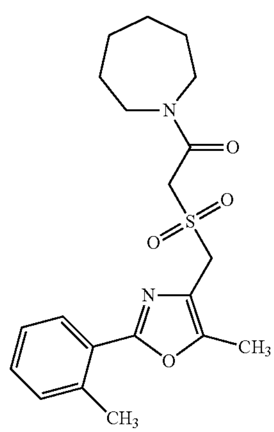 [SMILES: Cc1ccccc1-c1nc(CS(=O)(=O)CC(=O)N2CCCCCC2)c(C)o1] | 390.51 |
| IIa-2254 | 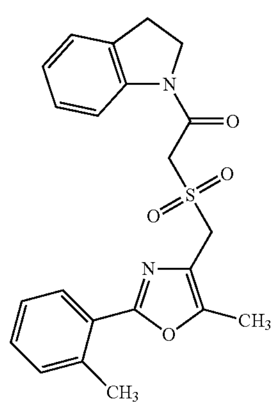 [SMILES: Cc1ccccc1-c1nc(CS(=O)(=O)CC(=O)N2CCc3ccccc32)c(C)o1] | 410.50 |

TABLE 6-continued
Oxazole amides ($R^3$ = N-cyclo)
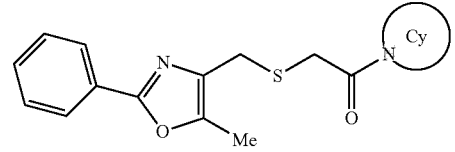
| ID | Structure | MW |
|---|---|---|
| IIa-2255 | 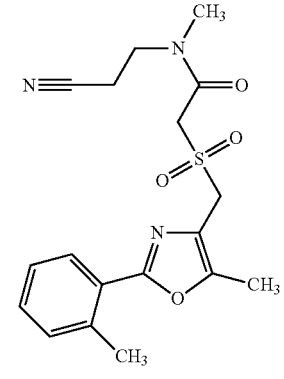 [SMILES: Cc1ccccc1-c1nc(CS(=O)(=O)CC(=O)N(C)CCC#N)c(C)o1] | 375.45 |
| IIa-2256 | 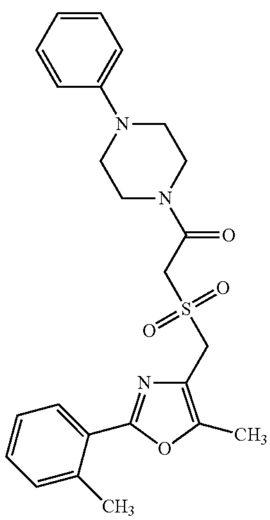 [SMILES: Cc1ccccc1-c1nc(CS(=O)(=O)CC(=O)N2CCN(c3ccccc3)CC2)c(C)o1] | 453.56 |
| IIa-2257 | 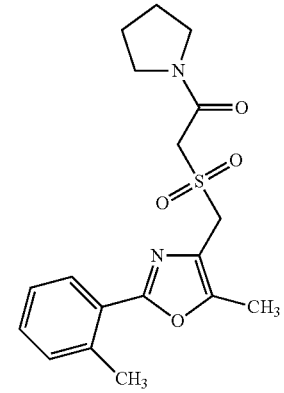 [SMILES: Cc1ccccc1-c1nc(CS(=O)(=O)CC(=O)N2CCCC2)c(C)o1] | 362.45 |

TABLE 6-continued
Oxazole amides (R³ = N-cyclo)
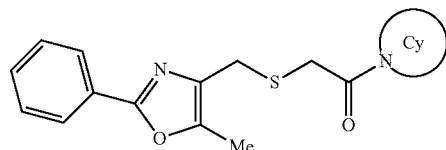
| ID | Structure | MW |
|---|---|---|
| IIa-2258 | | 424.52 |
| IIa-2259 | | 404.53 |

TABLE 6-continued
Oxazole amides (R³ = N-cyclo)
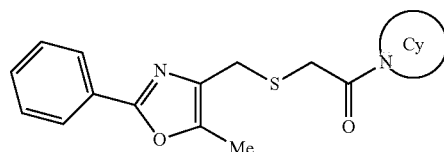
| ID | Structure | MW |
|---|---|---|
| IIa-2260 | | 481.62 |
| IIa-2261 | | 391.49 |
| IIa-2262 | | 378.45 |

TABLE 6-continued
Oxazole amides (R³ = N-cyclo)
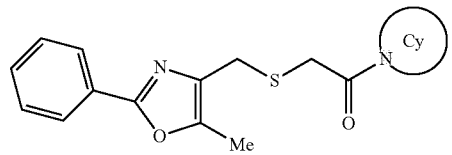
| ID | Structure | MW |
|---|---|---|
| IIa-2263 | 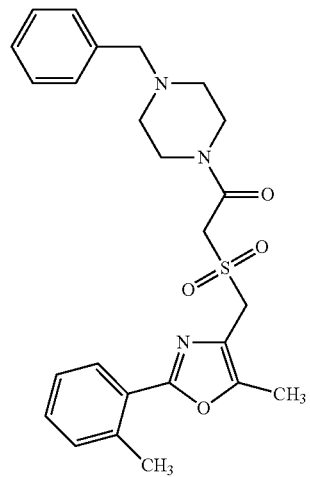 [SMILES: Cc1ccccc1-c1nc(CS(=O)(=O)CC(=O)N2CCN(Cc3ccccc3)CC2)c(C)o1] | 467.59 |
| IIa-2264 | 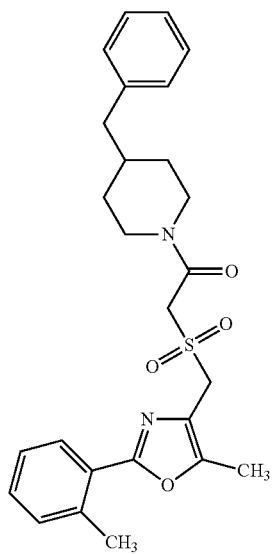 [SMILES: Cc1ccccc1-c1nc(CS(=O)(=O)CC(=O)N2CCC(Cc3ccccc3)CC2)c(C)o1] | 466.60 |

TABLE 6-continued
Oxazole amides (R³ = N-cyclo)
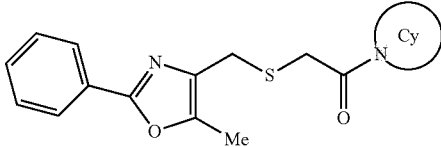
| ID | Structure | MW |
|---|---|---|
| IIa-2265 | 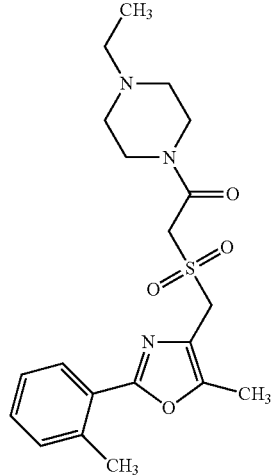 [SMILES: CCN1CCN(C(=O)CS(=O)(=O)Cc2nc(-c3ccccc3C)oc2C)CC1] | 405.52 |
| IIa-2266 | | 376.48 |

TABLE 6-continued
Oxazole amides (R³ = N-cyclo)
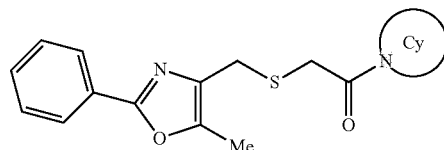
| ID | Structure | MW |
|---|---|---|
| IIa-2267 | | 491.97 |
| IIa-2268 | | 408.50 |

TABLE 6-continued
Oxazole amides (R³ = N-cyclo)
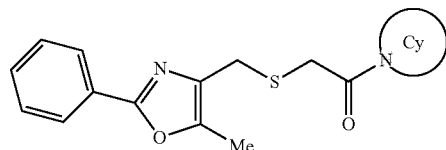
| ID | Structure | MW |
|---|---|---|
| IIa-2269 | 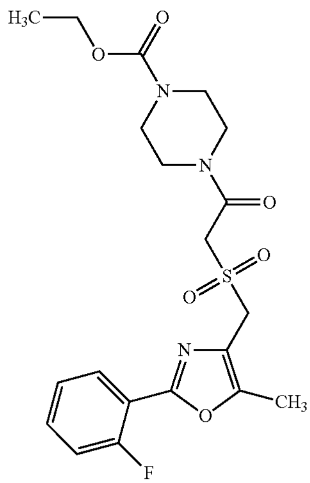 [SMILES: CCOC(=O)N1CCN(C(=O)CS(=O)(=O)Cc2nc(-c3ccccc3F)oc2C)CC1] | 453.49 |
| IIa-2270 | 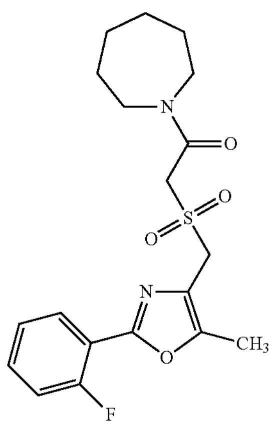 [SMILES: Cc1oc(-c2ccccc2F)nc1CS(=O)(=O)CC(=O)N1CCCCCC1] | 394.47 |
| IIa-2271 | 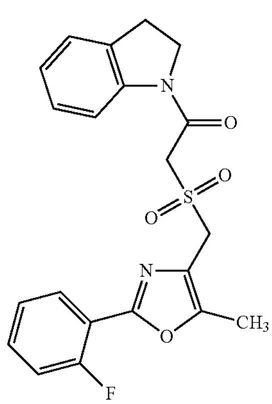 [SMILES: Cc1oc(-c2ccccc2F)nc1CS(=O)(=O)CC(=O)N1CCc2ccccc21] | 414.46 |

TABLE 6-continued
Oxazole amides (R³ = N-cyclo)
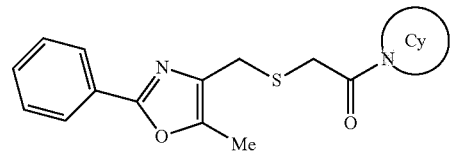
| ID | Structure | MW |
|---|---|---|
| IIa-2272 | | 457.53 |
| IIa-2273 | | 428.49 |

TABLE 6-continued
Oxazole amides (R³ = N-cyclo)
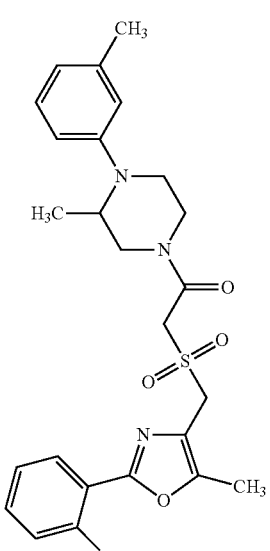
| ID | Structure | MW |
|---|---|---|
| IIa-2274 | 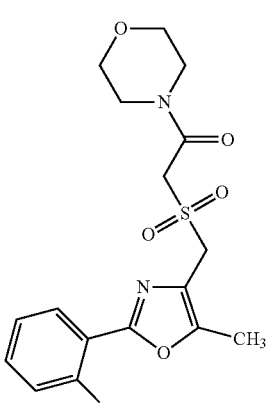 | 485.58 |
| IIa-2275 | | 382.41 |

TABLE 6-continued
Oxazole amides (R³ = N-cyclo)
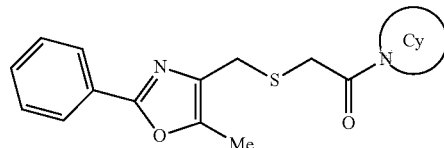
| ID | Structure | MW |
|---|---|---|
| IIa-2276 | 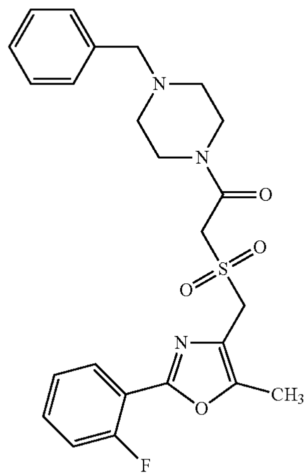 [SMILES: Cc1oc(-c2ccccc2F)nc1CS(=O)(=O)CC(=O)N1CCN(Cc2ccccc2)CC1] | 471.55 |
| IIa-2277 | 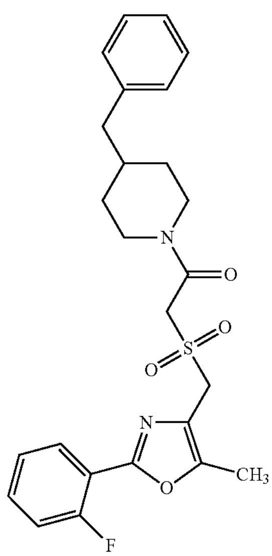 [SMILES: Cc1oc(-c2ccccc2F)nc1CS(=O)(=O)CC(=O)N1CCC(Cc2ccccc2)CC1] | 470.57 |
| IIa-2278 | 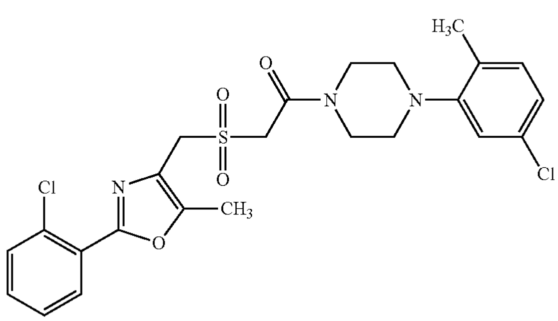 [SMILES: Cc1ccc(Cl)cc1N1CCN(C(=O)CS(=O)(=O)Cc2nc(-c3ccccc3Cl)oc2C)CC1] | 522.45 |

TABLE 6-continued
Oxazole amides (R³ = N-cyclo)
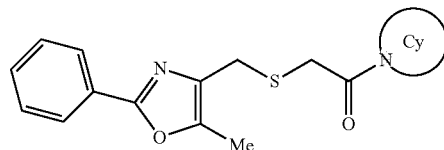
| ID | Structure | MW |
|---|---|---|
| IIa-2279 | 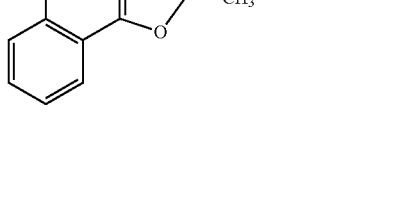 | 430.91 |
| IIa-2280 | 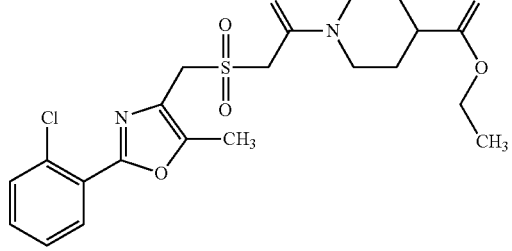 | 468.96 |
| IIa-2281 | 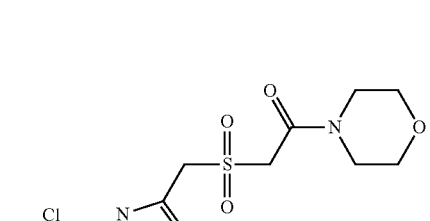 | 398.87 |
| IIa-2282 | 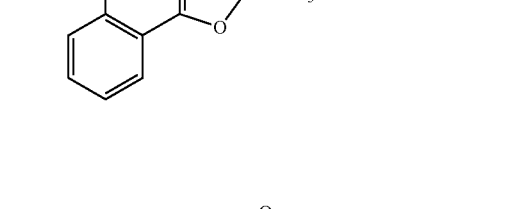 | 480.03 |

TABLE 6-continued
Oxazole amides (R³ = N-cyclo)
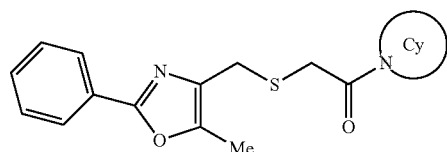
| ID | Structure | MW |
| --- | --- | --- |
| IIa-2283 | | 578.09 |
| IIa-2284 | | 475.52 |
| IIa-2285 | | 506.00 |
| IIa-2286 | | 525.53 |

TABLE 6-continued
Oxazole amides (R³ = N-cyclo)
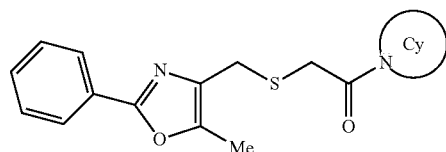
| ID | Structure | MW |
|---|---|---|
| IIa-2287 | 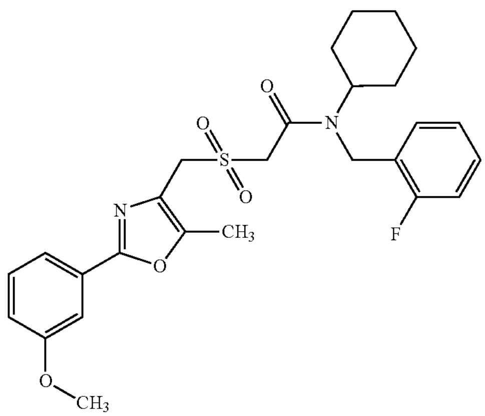 [SMILES: COc1cccc(-c2nc(CS(=O)(=O)CC(=O)N(Cc3ccccc3F)C3CCCCC3)c(C)o2)c1] | 514.62 |
| IIa-2288 | 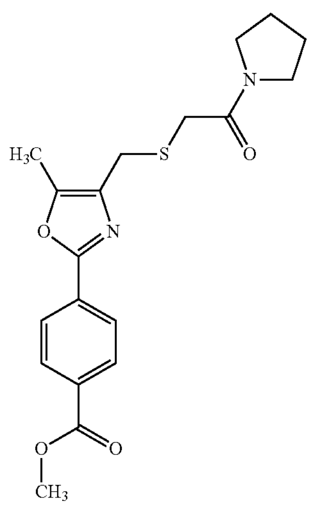 [SMILES: COC(=O)c1ccc(-c2nc(CSCC(=O)N3CCCC3)c(C)o2)cc1] | 374.46 |
| IIa-2289 | 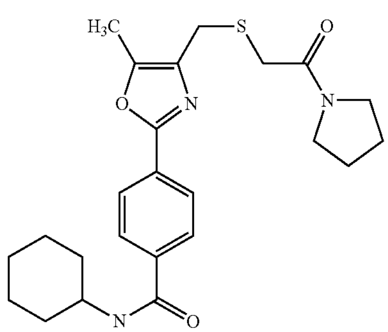 [SMILES: Cc1oc(-c2ccc(C(=O)NC3CCCCC3)cc2)nc1CSCC(=O)N1CCCC1] | 441.60 |

TABLE 6-continued
Oxazole amides (R³ = N-cyclo)
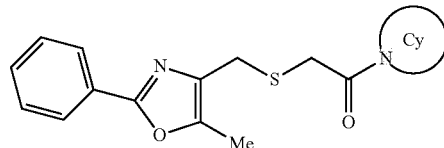
| ID | Structure | MW |
|---|---|---|
| IIa-2290 | 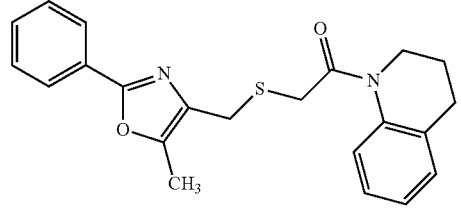 | 392.52 |
| IIa-2291 | 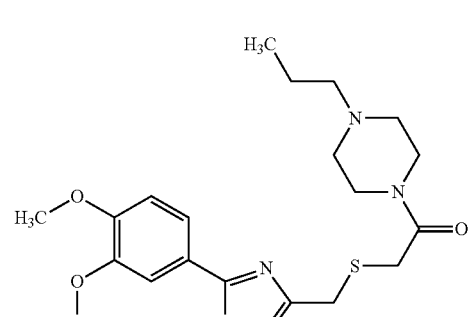 | 433.57 |
TABLE 7
Phenmethylene-Thiazole Alkanoic Acids (R³ = OH)
| ID | Structure | MW |
|---|---|---|
| IIb-1 | 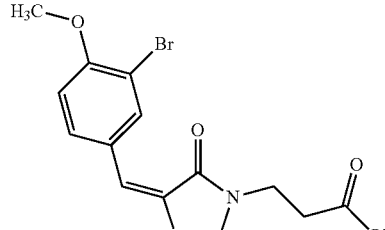 | 402.3 |
| IIb-2 | 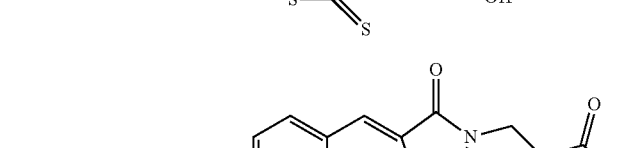 | 409.5 |

TABLE 7-continued
Phenmethylene-Thiazole Alkanoic Acids (R$^3$ = OH)
| ID | Structure | MW |
|---|---|---|
| IIb-3 | 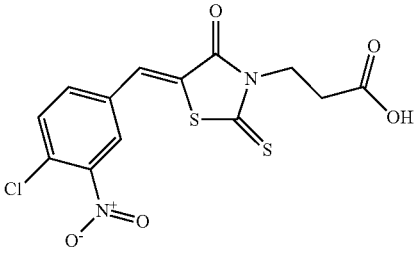 [SMILES: O=C(O)CCN1C(=O)/C(=C/c2ccc(Cl)c([N+](=O)[O-])c2)SC1=S] | 372.8 |
| IIb-4 | 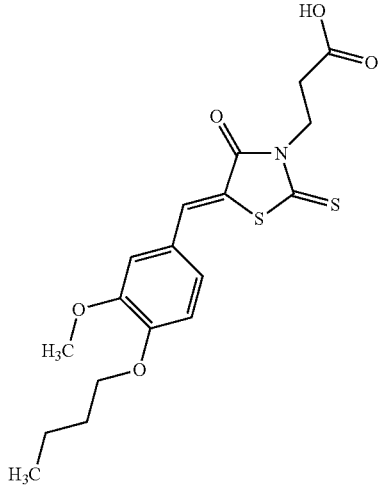 [SMILES: CCCCOc1ccc(/C=C2\SC(=S)N(CCC(=O)O)C2=O)cc1OC] | 395.5 |
| IIb-5 | 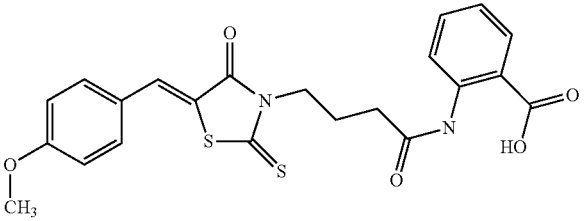 [SMILES: COc1ccc(/C=C2\SC(=S)N(CCCC(=O)Nc3ccccc3C(=O)O)C2=O)cc1] | 456.5 |
| IIb-6 | 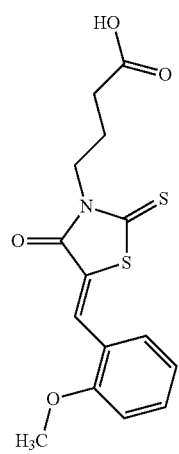 [SMILES: COc1ccccc1/C=C1\SC(=S)N(CCCC(=O)O)C1=O] | 337.4 |

TABLE 7-continued

Phenmethylene-Thiazole Alkanoic Acids (R³ = OH)

| ID | Structure | MW |
|---|---|---|
| IIb-7 | 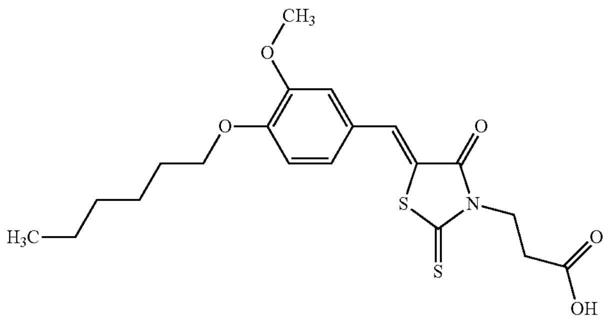 [SMILES: CCCCCCOc1ccc(/C=C2\SC(=S)N(CCC(=O)O)C2=O)cc1OC] | 423.6 |
| IIb-8 | 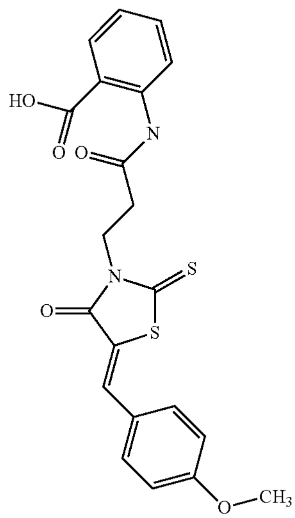 [SMILES: COc1ccc(/C=C2\SC(=S)N(CCC(=O)Nc3ccccc3C(=O)O)C2=O)cc1] | 442.5 |
| IIb-9 | 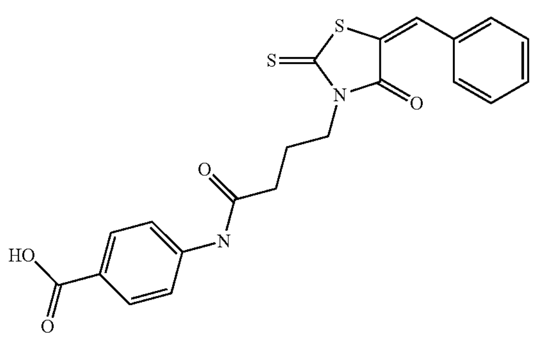 [SMILES: O=C(CCCN1C(=O)/C(=C\c2ccccc2)SC1=S)Nc1ccc(C(=O)O)cc1] | 426.5 |
| IIb-10 | 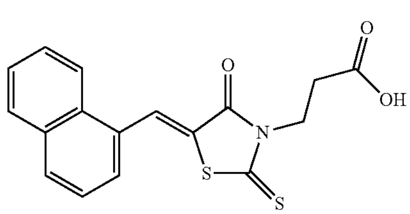 [SMILES: O=C(O)CCN1C(=O)/C(=C/c2cccc3ccccc23)SC1=S] | 343.4 |

TABLE 7-continued

Phenmethylene-Thiazole Alkanoic Acids (R³ = OH)

| ID | Structure | MW |
|---|---|---|
| IIb-11 | 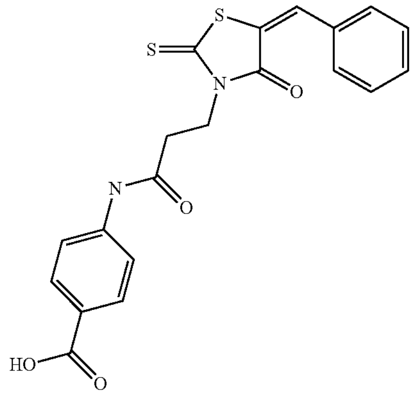 [SMILES: O=C(CCN1C(=O)/C(=C\c2ccccc2)SC1=S)Nc1ccc(C(=O)O)cc1] | 412.5 |
| IIb-12 | 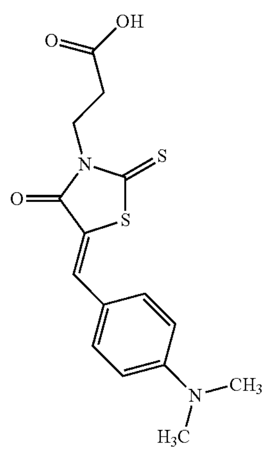 [SMILES: CN(C)c1ccc(/C=C2\SC(=S)N(CCC(=O)O)C2=O)cc1] | 336.4 |
| IIb-13 | 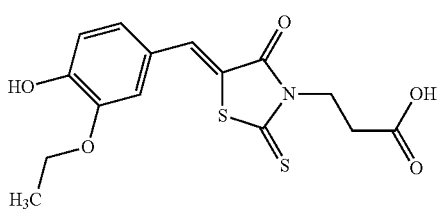 [SMILES: CCOc1cc(/C=C2\SC(=S)N(CCC(=O)O)C2=O)ccc1O] | 353.4 |
| IIb-14 | 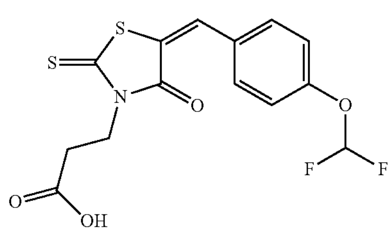 [SMILES: O=C(O)CCN1C(=O)/C(=C\c2ccc(OC(F)F)cc2)SC1=S] | 359.4 |

TABLE 7-continued

Phenmethylene-Thiazole Alkanoic Acids ($R^3$ = OH)

| ID | Structure | MW |
|---|---|---|
| IIb-15 | 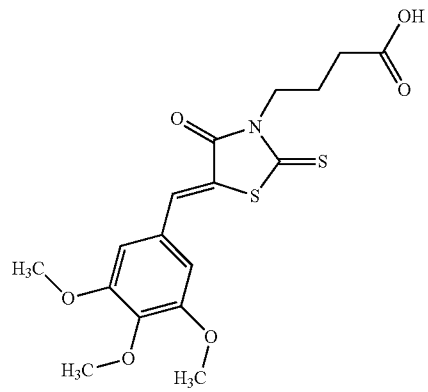 [SMILES: COc1cc(/C=C2\SC(=S)N(CCCC(=O)O)C2=O)cc(OC)c1OC] | 397.5 |
| IIb-16 | 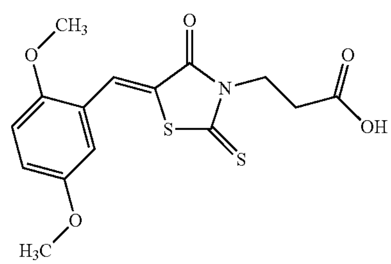 [SMILES: COc1ccc(OC)c(/C=C2\SC(=S)N(CCC(=O)O)C2=O)c1] | 353.4 |
| IIb-17 | 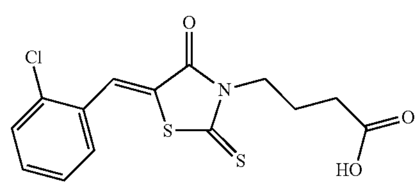 [SMILES: O=C(O)CCCN1C(=O)/C(=C/c2ccccc2Cl)SC1=S] | 341.8 |
| IIb-18 | 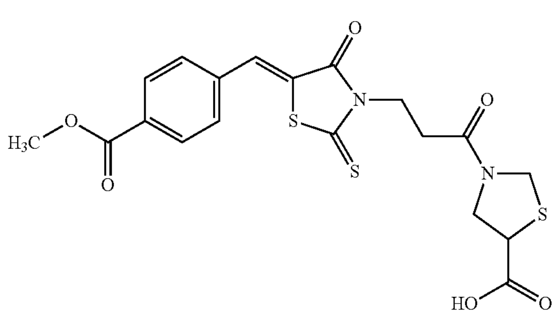 [SMILES: COC(=O)c1ccc(/C=C2\SC(=S)N(CCC(=O)N3CSC(C(=O)O)C3)C2=O)cc1] | 466.6 |

TABLE 7-continued
Phenmethylene-Thiazole Alkanoic Acids (R³ = OH)
| ID | Structure | MW |
|---|---|---|
| IIb-19 | 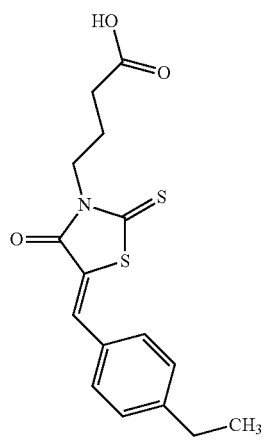 [SMILES: CCc1ccc(/C=C2\SC(=S)N(CCCC(=O)O)C2=O)cc1] | 335.4 |
| IIb-20 | 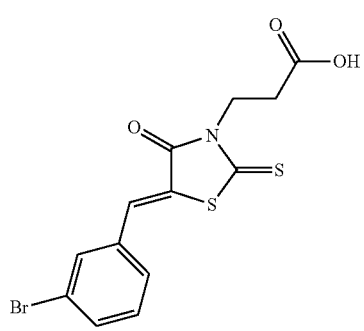 [SMILES: O=C(O)CCN1C(=O)/C(=C/c2cccc(Br)c2)SC1=S] | 372.3 |
| IIb-21 | 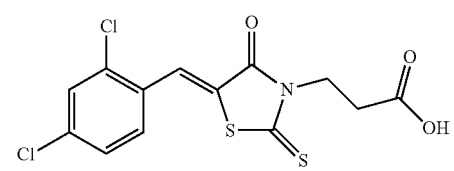 [SMILES: O=C(O)CCN1C(=O)/C(=C/c2ccc(Cl)cc2Cl)SC1=S] | 362.3 |
| IIb-22 | 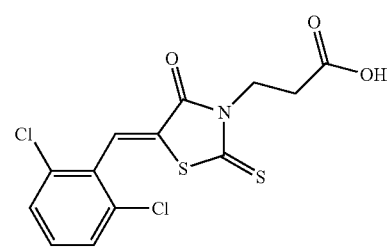 [SMILES: O=C(O)CCN1C(=O)/C(=C/c2c(Cl)cccc2Cl)SC1=S] | 362.3 |
| IIb-23 | 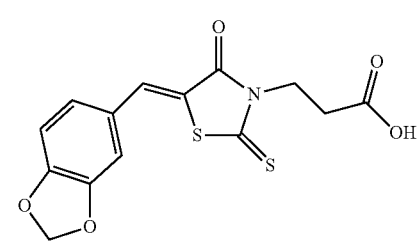 [SMILES: O=C(O)CCN1C(=O)/C(=C/c2ccc3c(c2)OCO3)SC1=S] | 337.4 |

TABLE 7-continued

Phenmethylene-Thiazole Alkanoic Acids ($R^3$ = OH)

| ID | Structure | MW |
|---|---|---|
| IIb-24 | 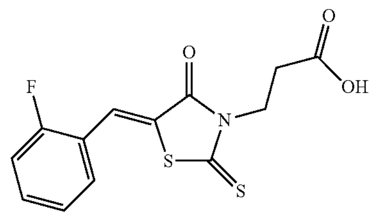 [SMILES: O=C(O)CCN1C(=O)/C(=C/c2ccccc2F)SC1=S] | 311.4 |
| IIb-25 | 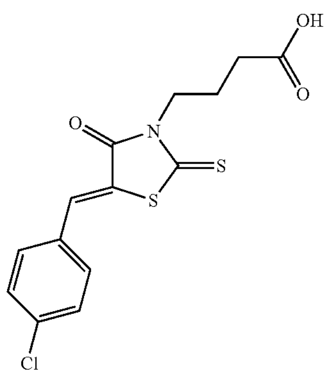 [SMILES: O=C(O)CCCN1C(=O)/C(=C/c2ccc(Cl)cc2)SC1=S] | 341.8 |
| IIb-26 | 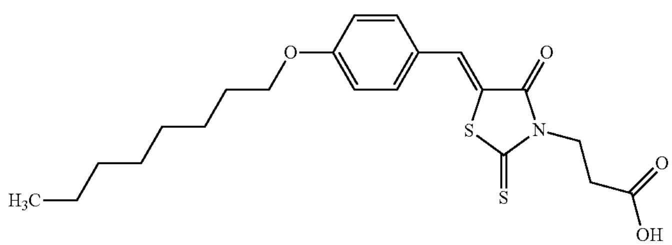 [SMILES: CCCCCCCCOc1ccc(/C=C2\SC(=S)N(CCC(=O)O)C2=O)cc1] | 421.6 |
| IIb-27 | 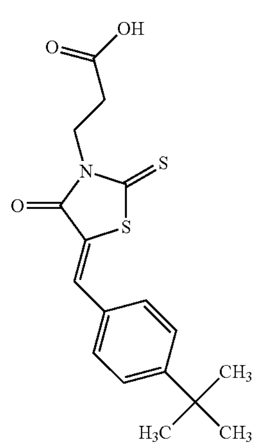 [SMILES: CC(C)(C)c1ccc(/C=C2\SC(=S)N(CCC(=O)O)C2=O)cc1] | 349.5 |

TABLE 7-continued

Phenmethylene-Thiazole Alkanoic Acids ($R^3$ = OH)

| ID | Structure | MW |
|---|---|---|
| IIb-28 | 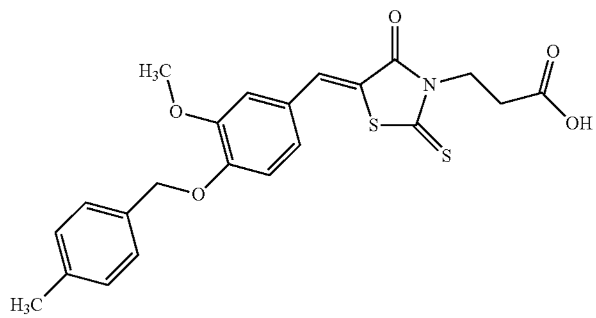 [SMILES: COc1cc(/C=C2\SC(=S)N(CCC(=O)O)C2=O)ccc1OCc1ccc(C)cc1] | 443.5 |
| IIb-29 | 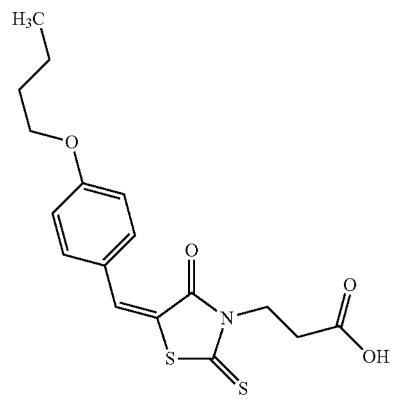 [SMILES: CCCCOc1ccc(/C=C2/SC(=S)N(CCC(=O)O)C2=O)cc1] | 365.5 |
| IIb-30 | 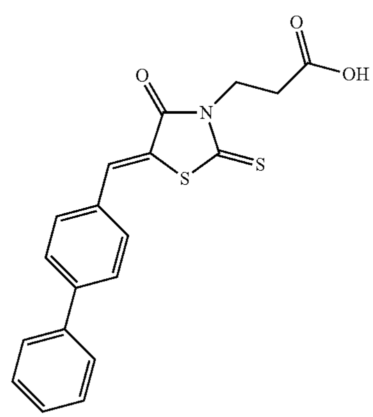 [SMILES: O=C(O)CCN1C(=O)/C(=C/c2ccc(-c3ccccc3)cc2)SC1=S] | 369.5 |
| IIb-31 | 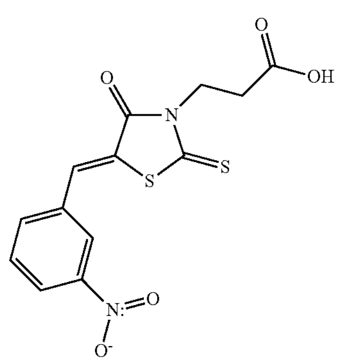 | 338.4 |

TABLE 7-continued

Phenmethylene-Thiazole Alkanoic Acids (R³ = OH)

| ID | Structure | MW |
|---|---|---|
| IIb-32 | 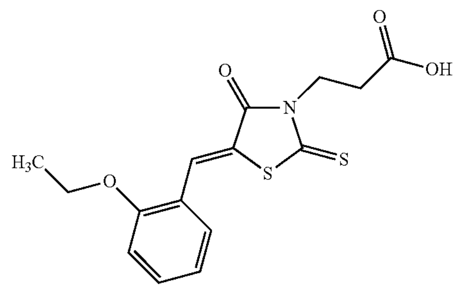 [SMILES: CCOc1ccccc1/C=C1\SC(=S)N(CCC(=O)O)C1=O] | 337.4 |
| IIb-33 | 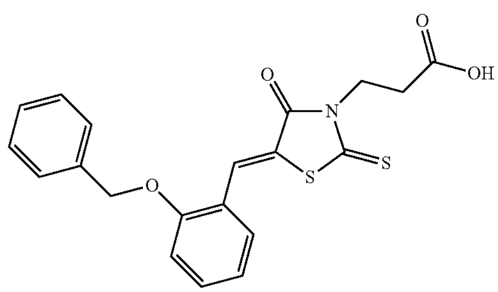 [SMILES: O=C(O)CCN1C(=O)/C(=C/c2ccccc2OCc2ccccc2)SC1=S] | 399.5 |
| IIb-34 | 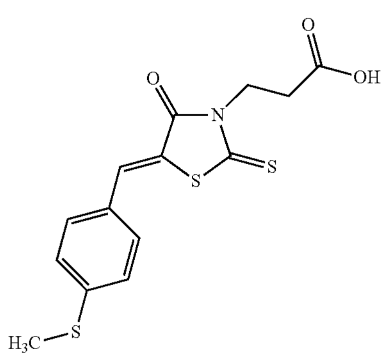 [SMILES: CSc1ccc(/C=C2\SC(=S)N(CCC(=O)O)C2=O)cc1] | 339.5 |
| IIb-35 | 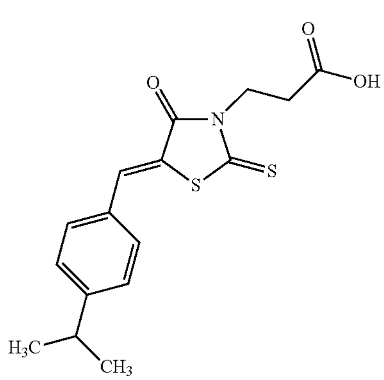 [SMILES: CC(C)c1ccc(/C=C2\SC(=S)N(CCC(=O)O)C2=O)cc1] | 335.4 |

TABLE 7-continued

Phenmethylene-Thiazole Alkanoic Acids ($R^3$ = OH)

| ID | Structure | MW |
|---|---|---|
| IIb-36 | 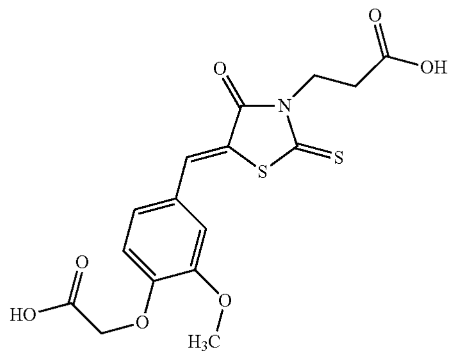 [SMILES: COc1cc(/C=C2\SC(=S)N(CCC(=O)O)C2=O)ccc1OCC(=O)O] | 397.4 |
| IIb-37 | 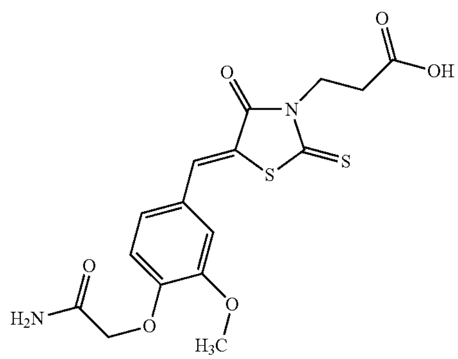 [SMILES: COc1cc(/C=C2\SC(=S)N(CCC(=O)O)C2=O)ccc1OCC(N)=O] | 396.4 |
| IIb-38 | 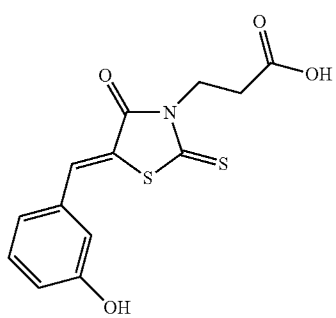 [SMILES: O=C(O)CCN1C(=O)/C(=C/c2cccc(O)c2)SC1=S] | 309.4 |
| IIb-39 | 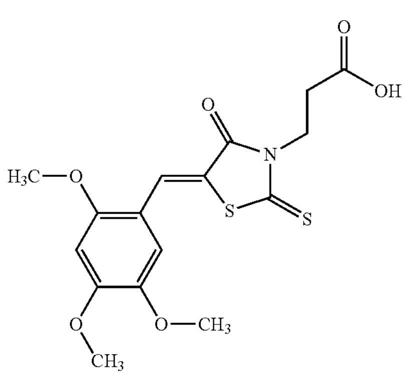 [SMILES: COc1cc(OC)c(OC)cc1/C=C1\SC(=S)N(CCC(=O)O)C1=O] | 383.4 |

TABLE 7-continued

Phenmethylene-Thiazole Alkanoic Acids ($R^3$ = OH)

| ID | Structure | MW |
|---|---|---|
| IIb-40 | 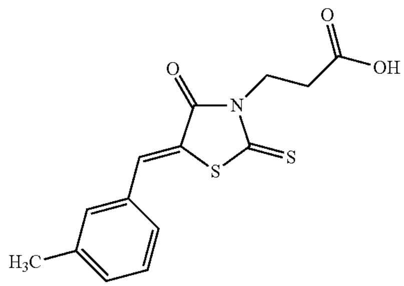 [SMILES: Cc1cccc(/C=C2\SC(=S)N(CCC(=O)O)C2=O)c1] | 307.4 |
| IIb-41 | 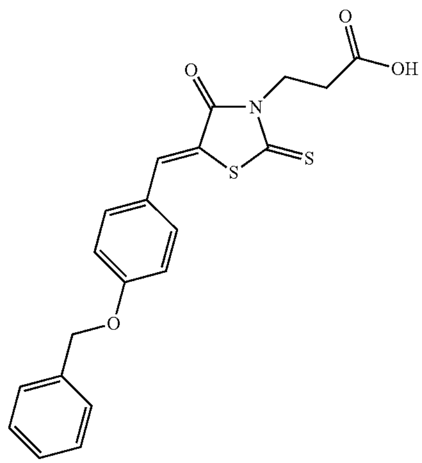 [SMILES: O=C(O)CCN1C(=O)/C(=C/c2ccc(OCc3ccccc3)cc2)SC1=S] | 399.5 |
| IIb-42 | 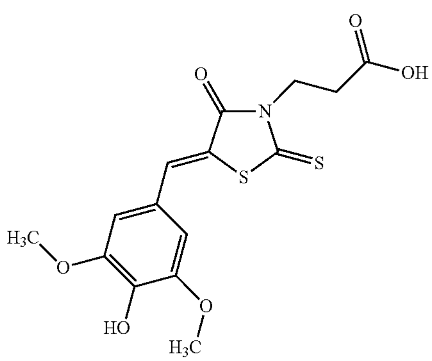 [SMILES: COc1cc(/C=C2\SC(=S)N(CCC(=O)O)C2=O)cc(OC)c1O] | 369.4 |
| IIb-43 | 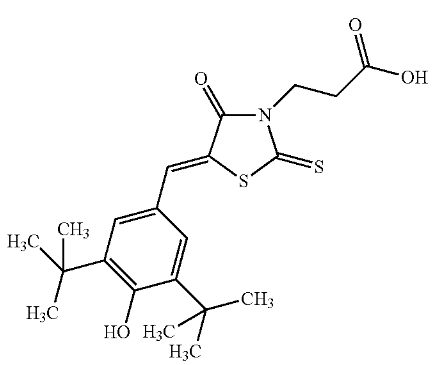 [SMILES: CC(C)(C)c1cc(/C=C2\SC(=S)N(CCC(=O)O)C2=O)cc(C(C)(C)C)c1O] | 421.6 |

TABLE 7-continued
Phenmethylene-Thiazole Alkanoic Acids ($R^3$ = OH)
| ID | Structure | MW |
|---|---|---|
| IIb-44 | 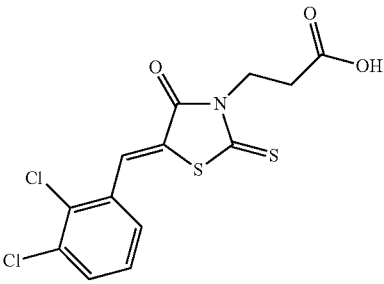 [SMILES: O=C(O)CCN1C(=O)/C(=C/c2cccc(Cl)c2Cl)SC1=S] | 362.3 |
| IIb-45 | 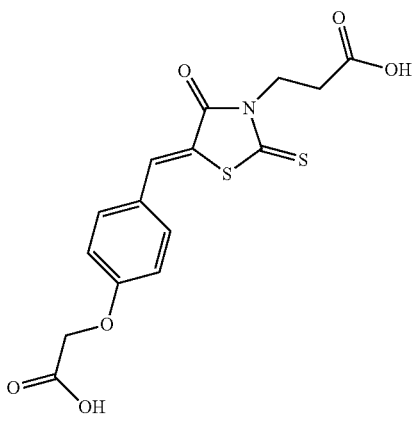 [SMILES: O=C(O)CCN1C(=O)/C(=C/c2ccc(OCC(=O)O)cc2)SC1=S] | 367.4 |
| IIb-46 | 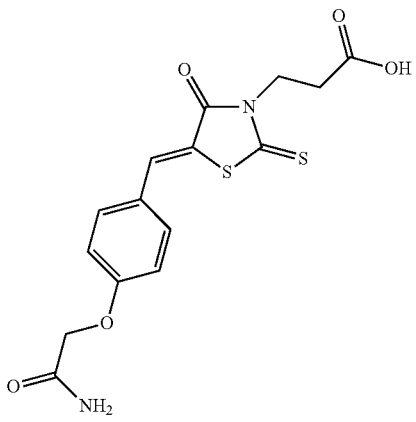 [SMILES: NC(=O)COc1ccc(/C=C2\SC(=S)N(CCC(=O)O)C2=O)cc1] | 366.4 |
| IIb-47 | 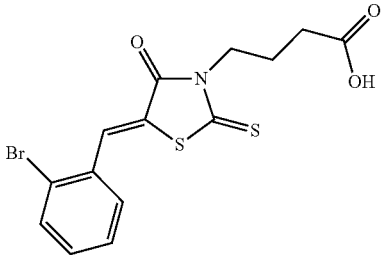 [SMILES: O=C(O)CCCN1C(=O)/C(=C/c2ccccc2Br)SC1=S] | 386.3 |

TABLE 7-continued

Phenmethylene-Thiazole Alkanoic Acids (R³ = OH)

| ID | Structure | MW |
|---|---|---|
| IIb-48 | 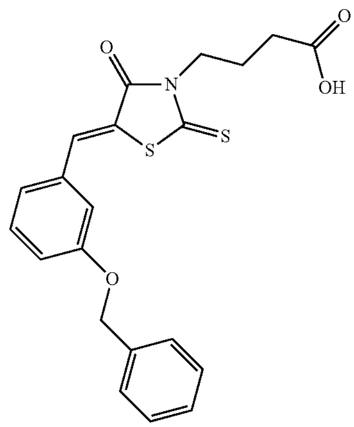 [SMILES: O=C(O)CCCN1C(=O)/C(=C/c2cccc(OCc3ccccc3)c2)SC1=S] | 413.5 |
| IIb-49 | 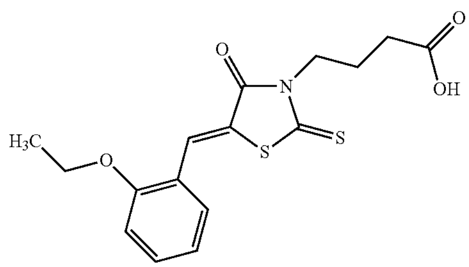 [SMILES: CCOc1ccccc1/C=C1\SC(=S)N(CCCC(=O)O)C1=O] | 351.4 |
| IIb-50 | 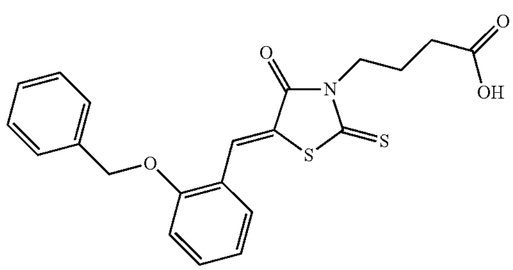 [SMILES: O=C(O)CCCN1C(=O)/C(=C/c2ccccc2OCc2ccccc2)SC1=S] | 413.5 |
| IIb-51 | 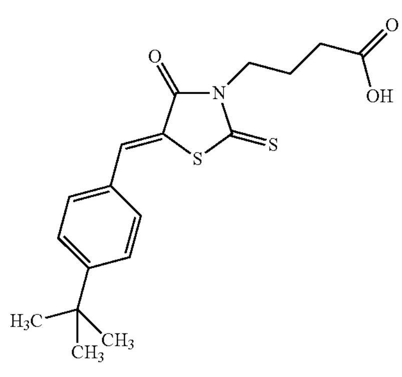 [SMILES: CC(C)(C)c1ccc(/C=C2\SC(=S)N(CCCC(=O)O)C2=O)cc1] | 363.5 |

TABLE 7-continued
Phenmethylene-Thiazole Alkanoic Acids (R³ = OH)
| ID | Structure | MW |
|---|---|---|
| IIb-52 | 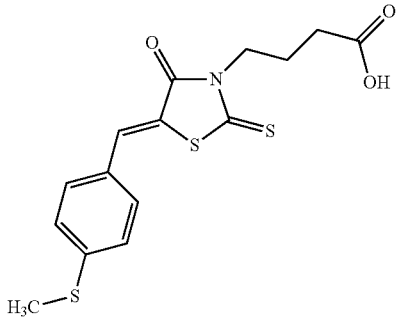 [SMILES: CSc1ccc(/C=C2\SC(=S)N(CCCC(=O)O)C2=O)cc1] | 353.5 |
| IIb-53 | 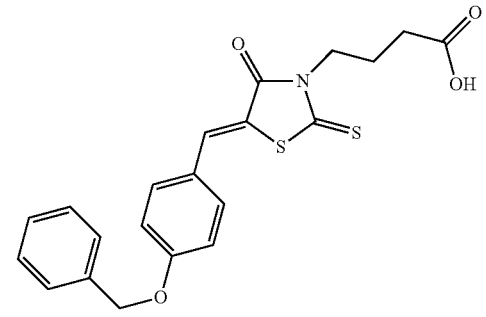 [SMILES: O=C(O)CCCN1C(=O)/C(=C/c2ccc(OCc3ccccc3)cc2)SC1=S] | 413.5 |
| IIb-54 | 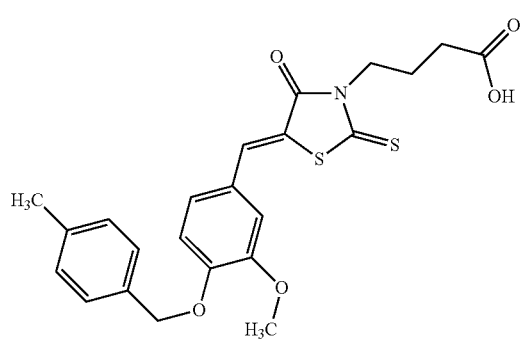 [SMILES: COc1cc(/C=C2\SC(=S)N(CCCC(=O)O)C2=O)ccc1OCc1ccc(C)cc1] | 457.6 |
| IIb-55 | 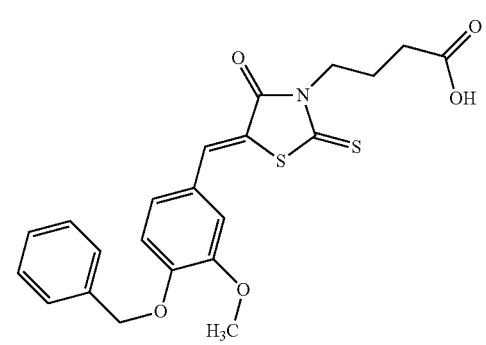 [SMILES: COc1cc(/C=C2\SC(=S)N(CCCC(=O)O)C2=O)ccc1OCc1ccccc1] | 443.5 |

TABLE 7-continued

Phenmethylene-Thiazole Alkanoic Acids (R³ = OH)

| ID | Structure | MW |
|---|---|---|
| IIb-56 | 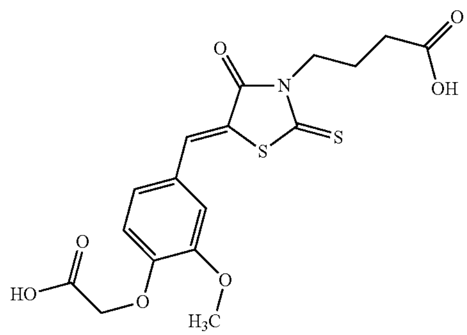 [SMILES: COc1cc(/C=C2\SC(=S)N(CCCC(=O)O)C2=O)ccc1OCC(=O)O] | 411.5 |
| IIb-57 | 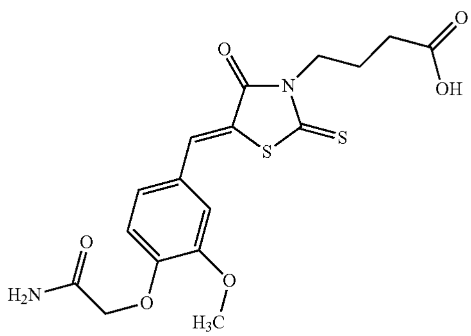 [SMILES: COc1cc(/C=C2\SC(=S)N(CCCC(=O)O)C2=O)ccc1OCC(N)=O] | 410.5 |
| IIb-58 | 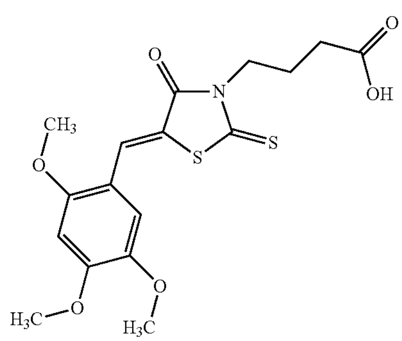 [SMILES: COc1cc(OC)c(OC)cc1/C=C1\SC(=S)N(CCCC(=O)O)C1=O] | 397.5 |
| IIb-59 | 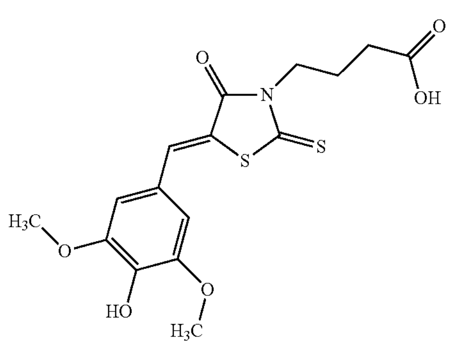 [SMILES: COc1cc(/C=C2\SC(=S)N(CCCC(=O)O)C2=O)cc(OC)c1O] | 383.4 |

TABLE 7-continued
Phenmethylene-Thiazole Alkanoic Acids (R³ = OH)
| ID | Structure | MW |
|---|---|---|
| IIb-60 | 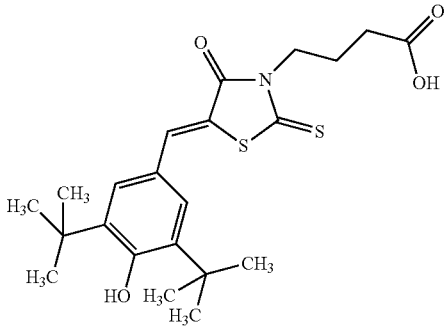 [SMILES: CC(C)(C)c1cc(/C=C2\SC(=S)N(CCCC(=O)O)C2=O)cc(C(C)(C)C)c1O] | 435.6 |
| IIb-61 | 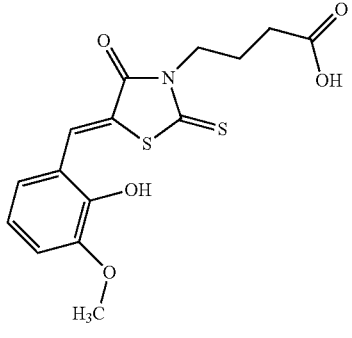 [SMILES: COc1cccc(/C=C2\SC(=S)N(CCCC(=O)O)C2=O)c1O] | 353.4 |
| IIb-62 | 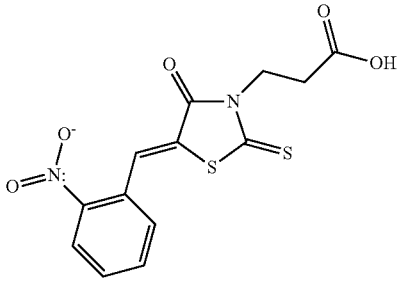 | 338.4 |
| IIb-63 | 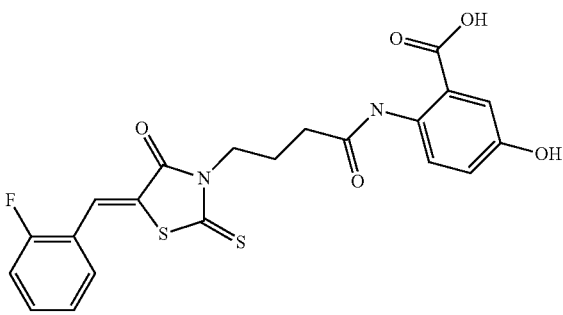 [SMILES: O=C(CCCN1C(=O)/C(=C/c2ccccc2F)SC1=S)Nc1ccc(O)cc1C(=O)O] | 460.5 |
| IIb-64 | 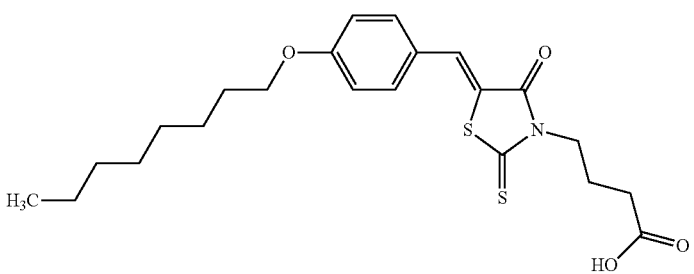 [SMILES: CCCCCCCCOc1ccc(/C=C2\SC(=S)N(CCCC(=O)O)C2=O)cc1] | 435.6 |

TABLE 7-continued

Phenmethylene-Thiazole Alkanoic Acids ($R^3$ = OH)

| ID | Structure | MW |
|---|---|---|
| IIb-65 | 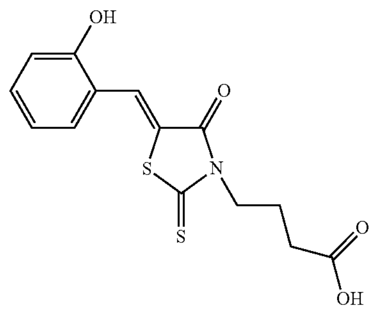 [SMILES: O=C(O)CCCN1C(=O)/C(=C/c2ccccc2O)SC1=S] | 323.4 |
| IIb-66 | 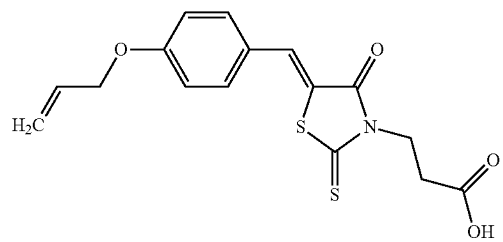 [SMILES: C=CCOc1ccc(/C=C2\SC(=S)N(CCC(=O)O)C2=O)cc1] | 349.4 |
| IIb-67 | 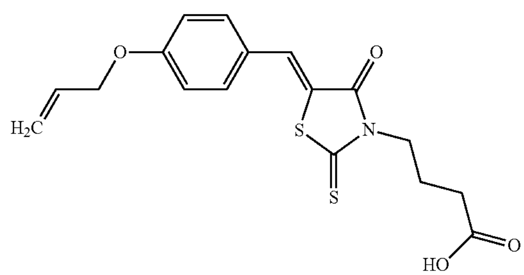 [SMILES: C=CCOc1ccc(/C=C2\SC(=S)N(CCCC(=O)O)C2=O)cc1] | 363.5 |
| IIb-68 | 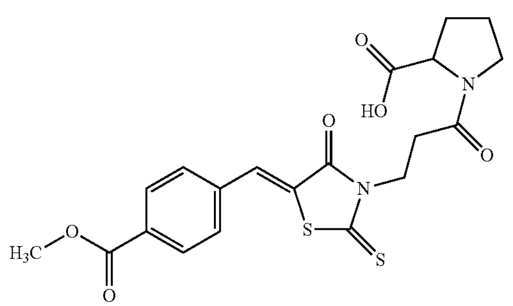 [SMILES: COC(=O)c1ccc(/C=C2\SC(=S)N(CCC(=O)N3CCCC3C(=O)O)C2=O)cc1] | 448.5 |
| IIb-69 | 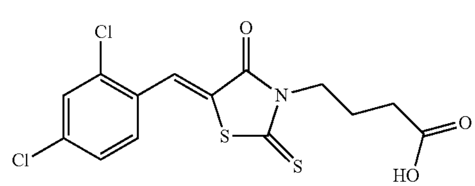 [SMILES: O=C(O)CCCN1C(=O)/C(=C/c2ccc(Cl)cc2Cl)SC1=S] | 376.3 |
| IIb-70 | 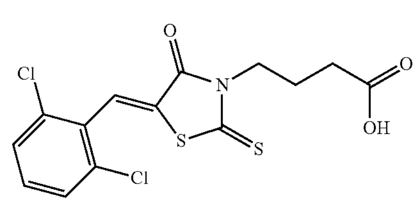 [SMILES: O=C(O)CCCN1C(=O)/C(=C/c2c(Cl)cccc2Cl)SC1=S] | 376.3 |

TABLE 7-continued
Phenmethylene-Thiazole Alkanoic Acids (R³ = OH)
| ID | Structure | MW |
|---|---|---|
| IIb-71 | 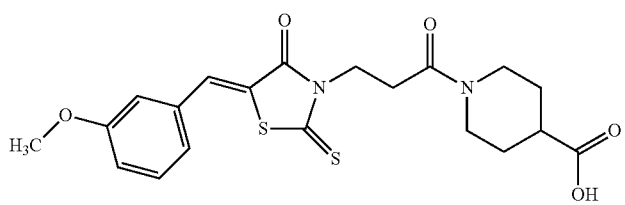 [SMILES: COc1cccc(/C=C2\SC(=S)N(CCC(=O)N3CCC(C(=O)O)CC3)C2=O)c1] | 434.5 |
| IIb-72 | 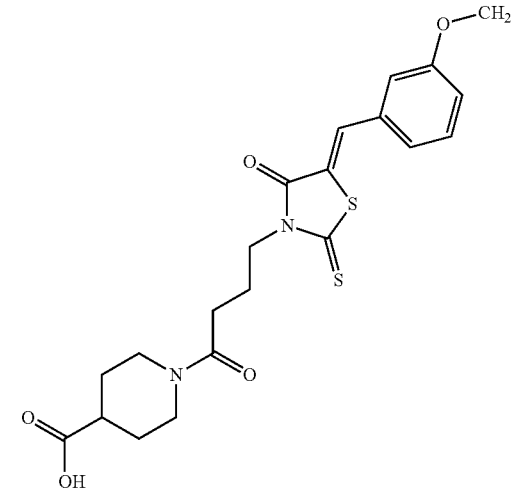 [SMILES: COc1cccc(/C=C2\SC(=S)N(CCCC(=O)N3CCC(C(=O)O)CC3)C2=O)c1] | 448.6 |
| IIb-73 | 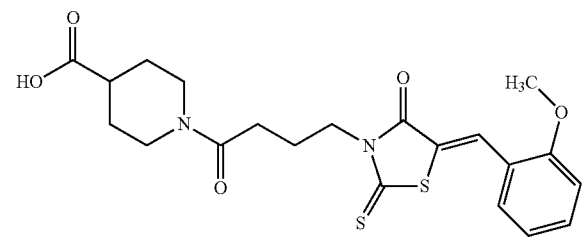 [SMILES: COc1ccccc1/C=C1\SC(=S)N(CCCC(=O)N2CCC(C(=O)O)CC2)C1=O] | 448.6 |
| IIb-74 | 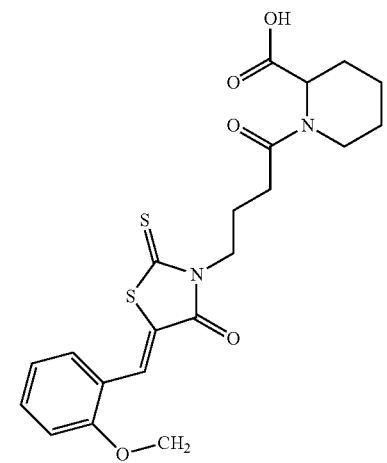 [SMILES: COc1ccccc1/C=C1\SC(=S)N(CCCC(=O)N2CCCCC2C(=O)O)C1=O] | 448.6 |

TABLE 7-continued

Phenmethylene-Thiazole Alkanoic Acids ($R^3$ = OH)

| ID | Structure | MW |
| --- | --- | --- |
| IIb-75 | 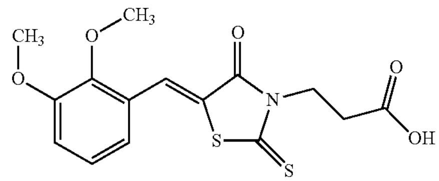 [SMILES: COc1cccc(/C=C2\SC(=S)N(CCC(=O)O)C2=O)c1OC] | 353.4 |
| IIb-76 | 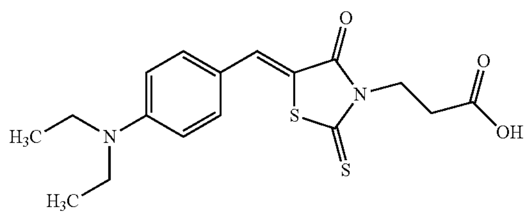 [SMILES: CCN(CC)c1ccc(/C=C2\SC(=S)N(CCC(=O)O)C2=O)cc1] | 364.5 |
| IIb-77 | 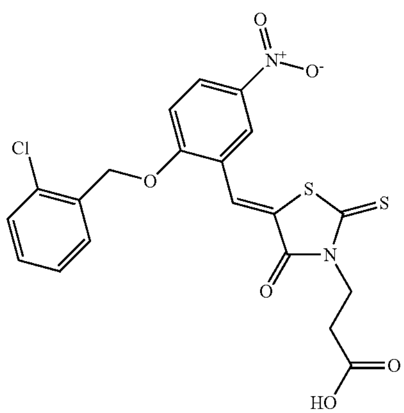 [SMILES: O=C(O)CCN1C(=O)/C(=C/c2cc([N+](=O)[O-])ccc2OCc2ccccc2Cl)SC1=S] | 478.9 |
| IIb-78 | 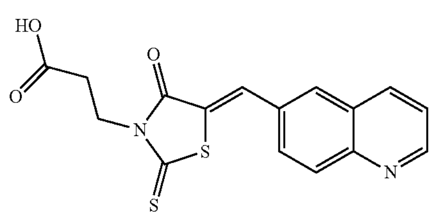 [SMILES: O=C(O)CCN1C(=O)/C(=C/c2ccc3ncccc3c2)SC1=S] | 344.4 |
| IIb-79 | 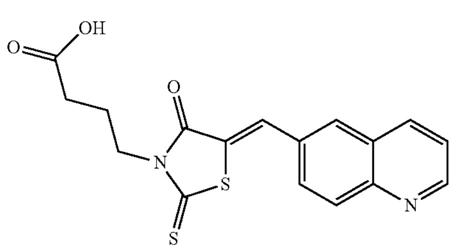 [SMILES: O=C(O)CCCN1C(=O)/C(=C/c2ccc3ncccc3c2)SC1=S] | 358.4 |

TABLE 7-continued
Phenmethylene-Thiazole Alkanoic Acids ($R^3$ = OH)
| ID | Structure | MW |
|---|---|---|
| IIb-80 | 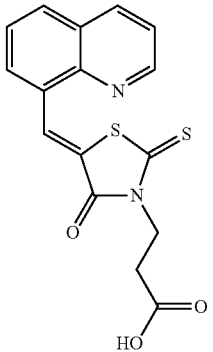 [SMILES: O=C(O)CCN1C(=O)/C(=C/c2cccc3cccnc23)SC1=S] | 344.4 |
| IIb-81 | 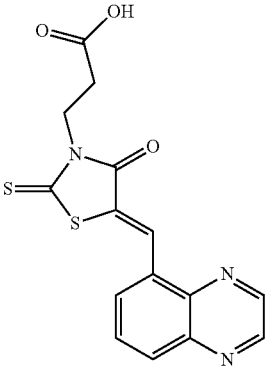 [SMILES: O=C(O)CCN1C(=O)/C(=C/c2cccc3nccnc23)SC1=S] | 345.4 |
| IIb-82 | 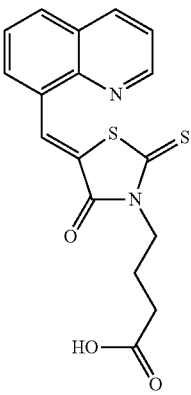 [SMILES: O=C(O)CCCN1C(=O)/C(=C/c2cccc3cccnc23)SC1=S] | 358.4 |
| IIb-83 | 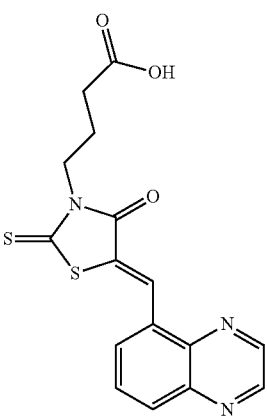 [SMILES: O=C(O)CCCN1C(=O)/C(=C/c2cccc3nccnc23)SC1=S] | 359.4 |

TABLE 7-continued

Phenmethylene-Thiazole Alkanoic Acids ($R^3$ = OH)

| ID | Structure | MW |
|---|---|---|
| IIb-84 | 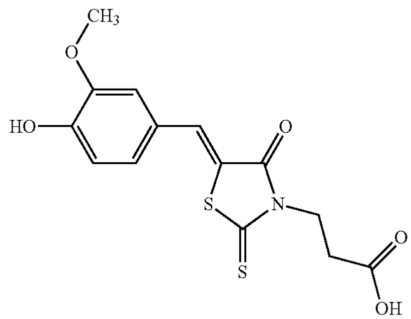 [SMILES: COc1cc(/C=C2\SC(=S)N(CCC(=O)O)C2=O)ccc1O] | 339.4 |
| IIb-85 | 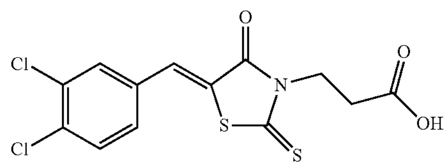 [SMILES: O=C(O)CCN1C(=O)/C(=C/c2ccc(Cl)c(Cl)c2)SC1=S] | 362.3 |
| IIb-86 | 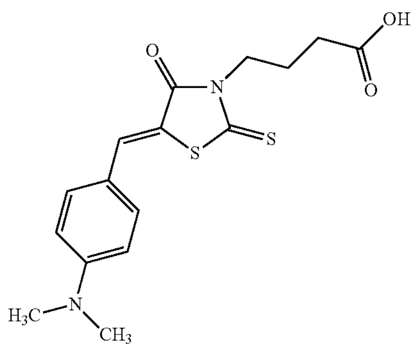 [SMILES: CN(C)c1ccc(/C=C2\SC(=S)N(CCCC(=O)O)C2=O)cc1] | 350.5 |
| IIb-87 | 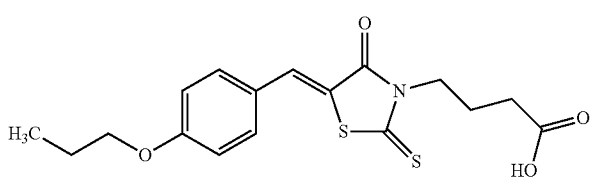 [SMILES: CCCOc1ccc(/C=C2\SC(=S)N(CCCC(=O)O)C2=O)cc1] | 365.5 |
| IIb-88 | 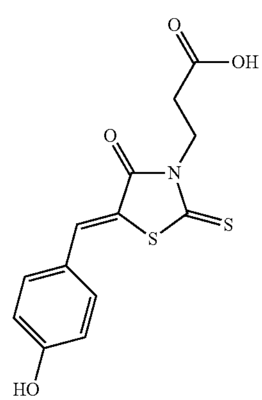 [SMILES: O=C(O)CCN1C(=O)/C(=C/c2ccc(O)cc2)SC1=S] | 309.4 |

TABLE 7-continued

Phenmethylene-Thiazole Alkanoic Acids (R³ = OH)

| ID | Structure | MW |
|---|---|---|
| IIb-89 | 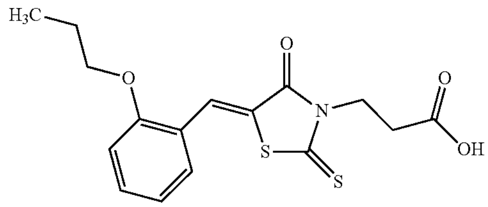 [SMILES: CCCOc1ccccc1/C=C1\SC(=S)N(CCC(=O)O)C1=O] | 351.4 |
| IIb-90 | 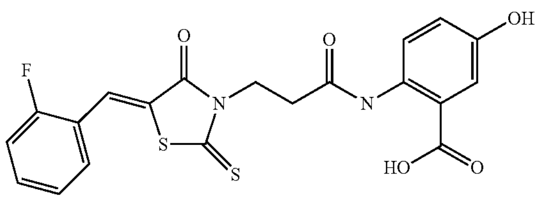 [SMILES: O=C(CCN1C(=O)/C(=C/c2ccccc2F)SC1=S)Nc1ccc(O)cc1C(=O)O] | 446.5 |
| IIb-91 | 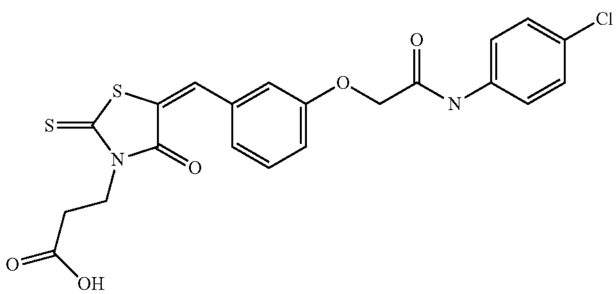 [SMILES: O=C(O)CCN1C(=O)/C(=C\c2cccc(OCC(=O)Nc3ccc(Cl)cc3)c2)SC1=S] | 477.0 |
| IIb-92 | 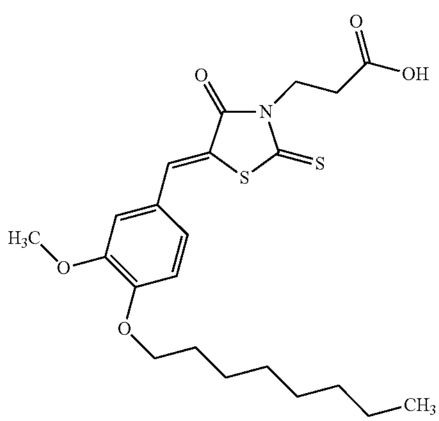 [SMILES: CCCCCCCCOc1ccc(/C=C2\SC(=S)N(CCC(=O)O)C2=O)cc1OC] | 451.6 |
| IIb-93 | 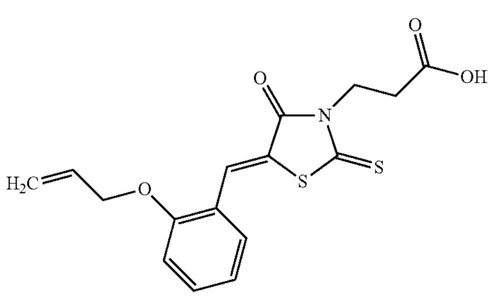 [SMILES: C=CCOc1ccccc1/C=C1\SC(=S)N(CCC(=O)O)C1=O] | 349.4 |

TABLE 7-continued

Phenmethylene-Thiazole Alkanoic Acids (R³ = OH)

| ID | Structure | MW |
|---|---|---|
| IIb-94 | 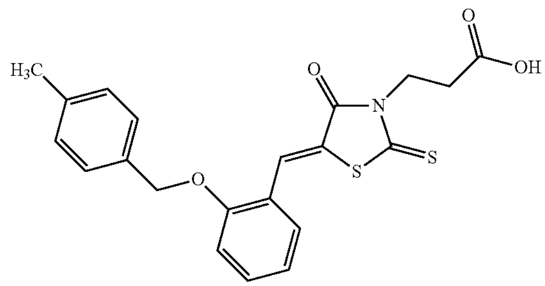 [SMILES: Cc1ccc(COc2ccccc2/C=C2\SC(=S)N(CCC(=O)O)C2=O)cc1] | 413.5 |
| IIb-95 | 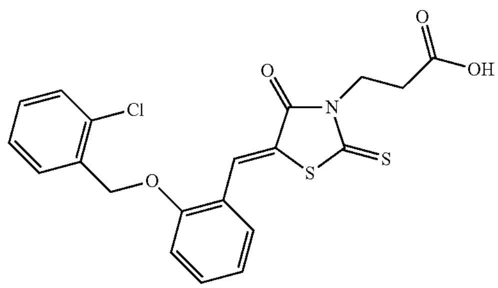 [SMILES: O=C(O)CCN1C(=O)/C(=C/c2ccccc2OCc2ccccc2Cl)SC1=S] | 433.9 |
| IIb-96 | 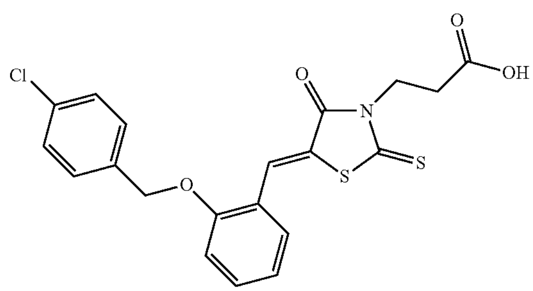 [SMILES: O=C(O)CCN1C(=O)/C(=C/c2ccccc2OCc2ccc(Cl)cc2)SC1=S] | 433.9 |
| IIb-97 | 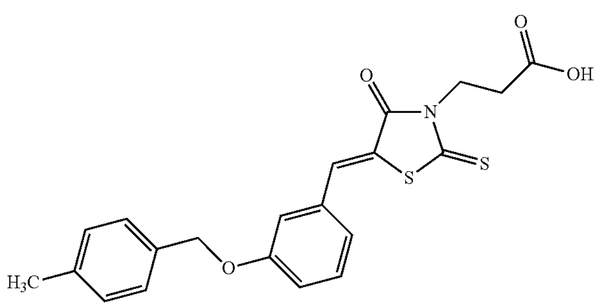 [SMILES: Cc1ccc(COc2cccc(/C=C3\SC(=S)N(CCC(=O)O)C3=O)c2)cc1] | 413.5 |
| IIb-98 | 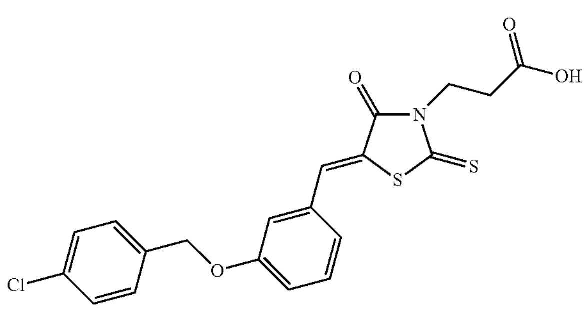 [SMILES: O=C(O)CCN1C(=O)/C(=C/c2cccc(OCc3ccc(Cl)cc3)c2)SC1=S] | 433.9 |

TABLE 7-continued
Phenmethylene-Thiazole Alkanoic Acids ($R^3$ = OH)
| ID | Structure | MW |
|---|---|---|
| IIb-99 | 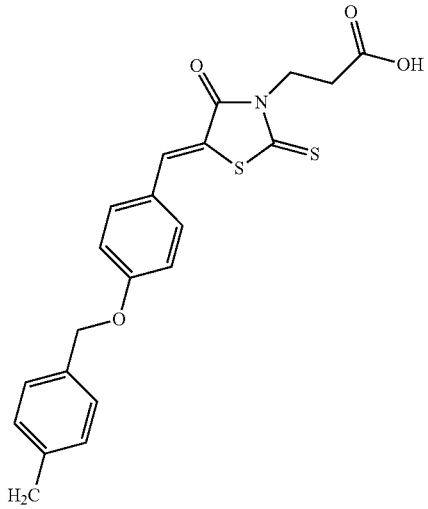 [SMILES: Cc1ccc(COc2ccc(/C=C3\SC(=S)N(CCC(=O)O)C3=O)cc2)cc1] | 413.5 |
| IIb-100 | 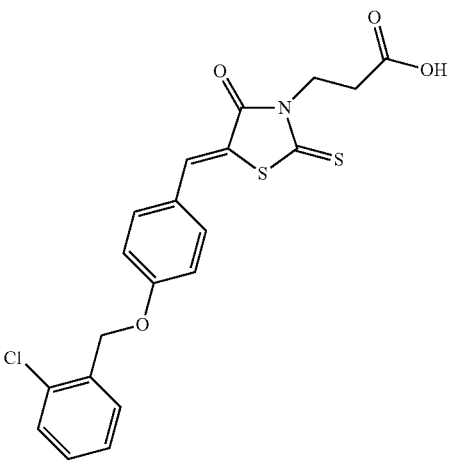 [SMILES: O=C(O)CCN1C(=O)/C(=C/c2ccc(OCc3ccccc3Cl)cc2)SC1=S] | 433.9 |
| IIb-101 | 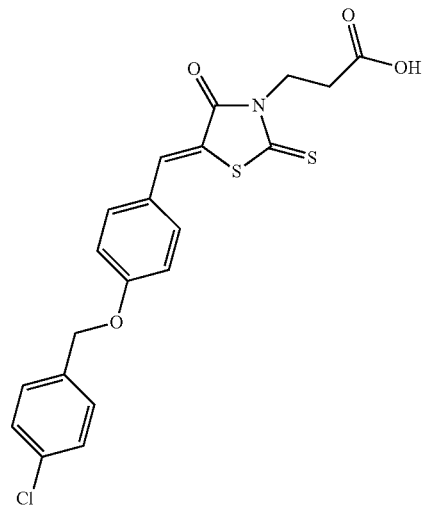 [SMILES: O=C(O)CCN1C(=O)/C(=C/c2ccc(OCc3ccc(Cl)cc3)cc2)SC1=S] | 433.9 |

TABLE 7-continued

Phenmethylene-Thiazole Alkanoic Acids ($R^3$ = OH)

| ID | Structure | MW |
|---|---|---|
| IIb-102 | 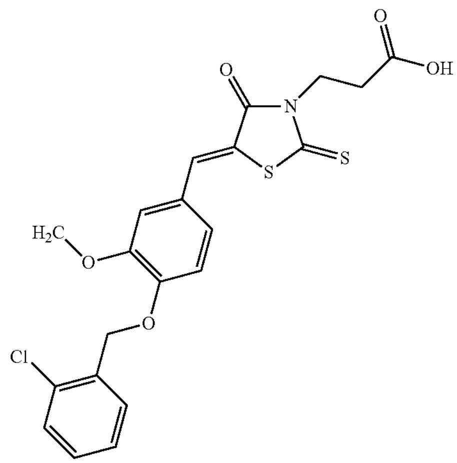 [SMILES: COc1cc(/C=C2\SC(=S)N(CCC(=O)O)C2=O)ccc1OCc1ccccc1Cl] | 464.0 |
| IIb-103 | 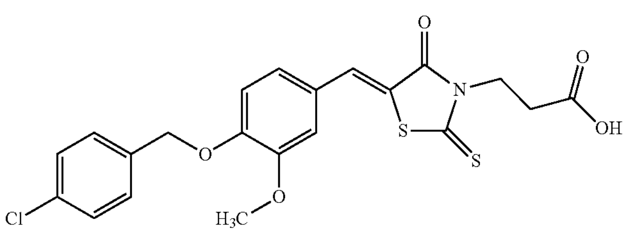 [SMILES: COc1cc(/C=C2\SC(=S)N(CCC(=O)O)C2=O)ccc1OCc1ccc(Cl)cc1] | 464.0 |
| IIb-104 | 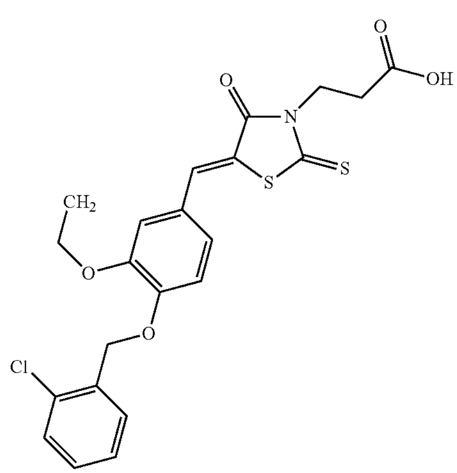 [SMILES: CCOc1cc(/C=C2\SC(=S)N(CCC(=O)O)C2=O)ccc1OCc1ccccc1Cl] | 478.0 |

TABLE 7-continued

Phenmethylene-Thiazole Alkanoic Acids ($R^3$ = OH)

| ID | Structure | MW |
|---|---|---|
| IIb-105 | 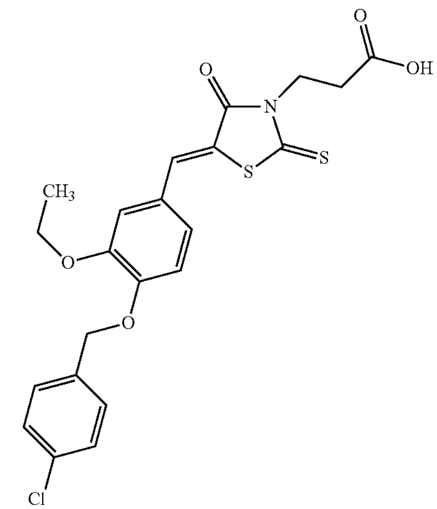 [SMILES: CCOc1cc(/C=C2\SC(=S)N(CCC(=O)O)C2=O)ccc1OCc1ccc(Cl)cc1] | 478.0 |
| IIb-106 | 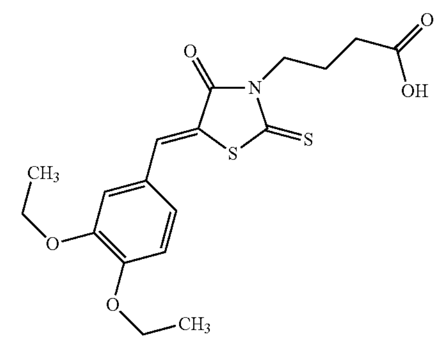 [SMILES: CCOc1ccc(/C=C2\SC(=S)N(CCCC(=O)O)C2=O)cc1OCC] | 395.5 |
| IIb-107 | 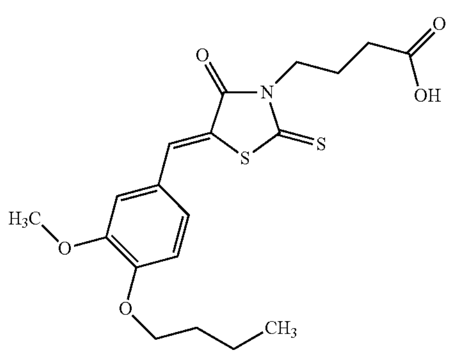 [SMILES: CCCCOc1ccc(/C=C2\SC(=S)N(CCCC(=O)O)C2=O)cc1OC] | 409.5 |
| IIb-108 | 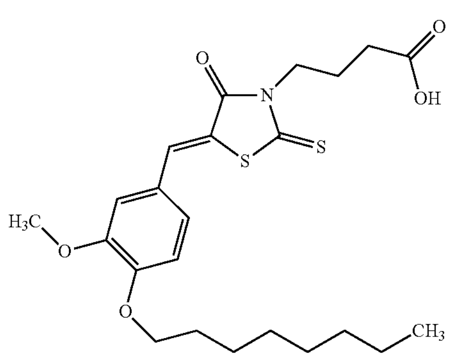 [SMILES: CCCCCCCCOc1ccc(/C=C2\SC(=S)N(CCCC(=O)O)C2=O)cc1OC] | 465.6 |

TABLE 7-continued

Phenmethylene-Thiazole Alkanoic Acids ($R^3$ = OH)

| ID | Structure | MW |
| --- | --- | --- |
| IIb-109 | 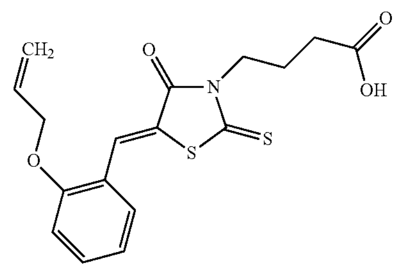 [SMILES: C=CCOc1ccccc1/C=C1\SC(=S)N(CCCC(=O)O)C1=O] | 363.5 |
| IIb-110 | 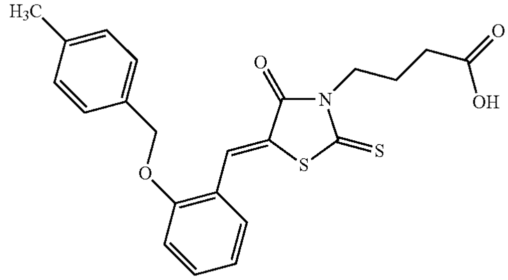 [SMILES: Cc1ccc(COc2ccccc2/C=C2\SC(=S)N(CCCC(=O)O)C2=O)cc1] | 427.5 |
| IIb-111 | 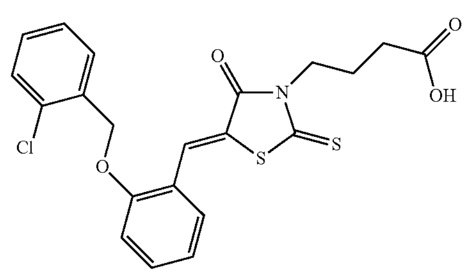 [SMILES: O=C(O)CCCN1C(=O)/C(=C/c2ccccc2OCc2ccccc2Cl)SC1=S] | 448.0 |
| IIb-112 | 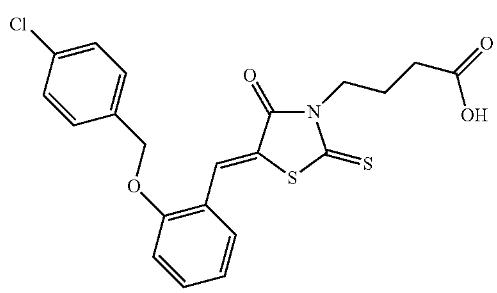 [SMILES: O=C(O)CCCN1C(=O)/C(=C/c2ccccc2OCc2ccc(Cl)cc2)SC1=S] | 448.0 |
| IIb-113 | 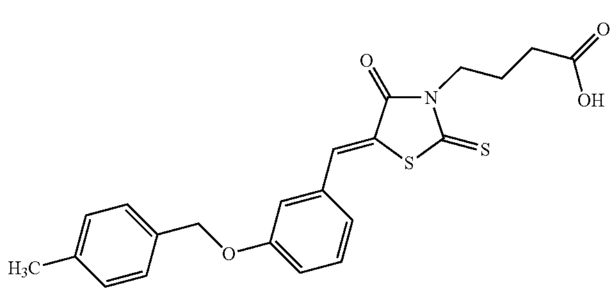 [SMILES: Cc1ccc(COc2cccc(/C=C3\SC(=S)N(CCCC(=O)O)C3=O)c2)cc1] | 427.5 |

TABLE 7-continued
Phenmethylene-Thiazole Alkanoic Acids ($R^3$ = OH)
| ID | Structure | MW |
|---|---|---|
| IIb-114 | 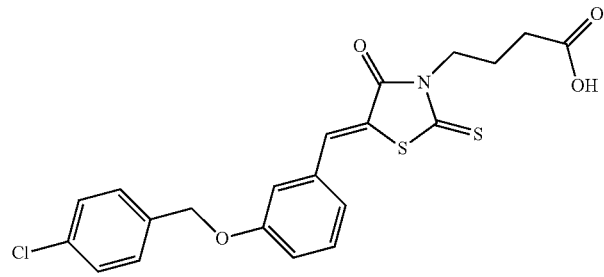 [SMILES: O=C(O)CCCN1C(=O)/C(=C/c2cccc(OCc3ccc(Cl)cc3)c2)SC1=S] | 448.0 |
| IIb-115 | 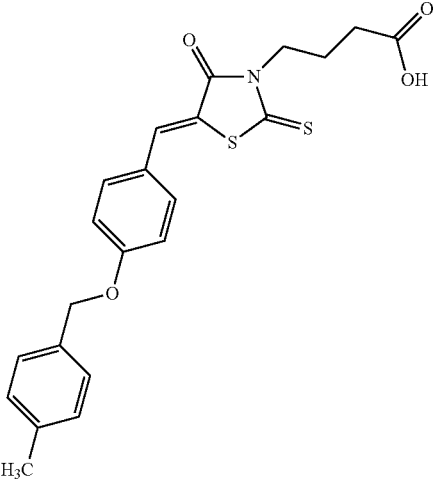 [SMILES: Cc1ccc(COc2ccc(/C=C3\SC(=S)N(CCCC(=O)O)C3=O)cc2)cc1] | 427.5 |
| IIb-116 | 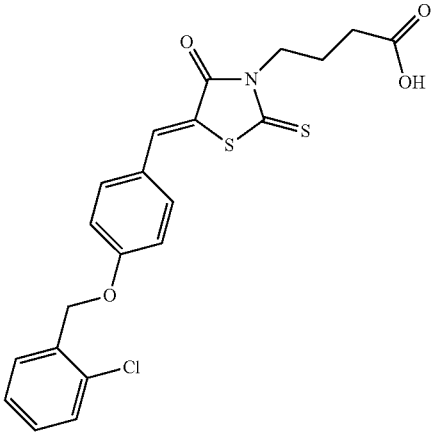 [SMILES: O=C(O)CCCN1C(=O)/C(=C/c2ccc(OCc3ccccc3Cl)cc2)SC1=S] | 448.0 |

TABLE 7-continued

Phenmethylene-Thiazole Alkanoic Acids (R³ = OH)

| ID | Structure | MW |
|---|---|---|
| IIb-117 | 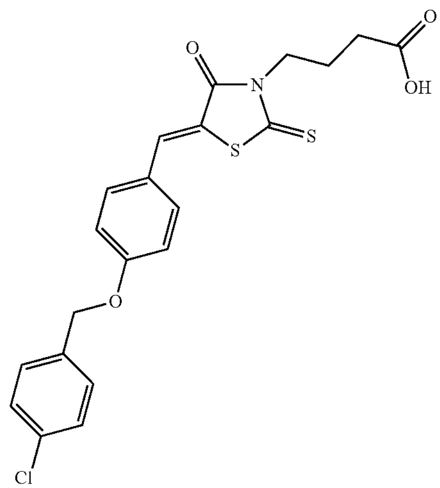 [SMILES: O=C(O)CCCN1C(=O)/C(=C/c2ccc(OCc3ccc(Cl)cc3)cc2)SC1=S] | 448.0 |
| IIb-118 | 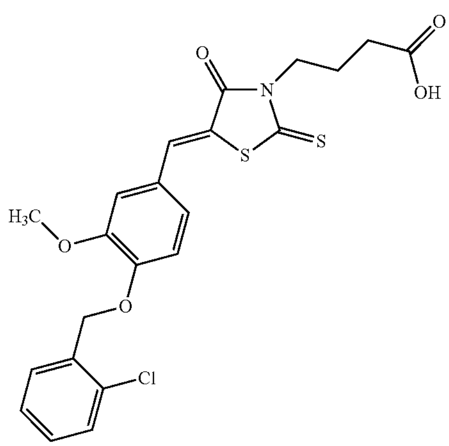 [SMILES: COc1cc(/C=C2\SC(=S)N(CCCC(=O)O)C2=O)ccc1OCc1ccccc1Cl] | 478.0 |
| IIb-119 | 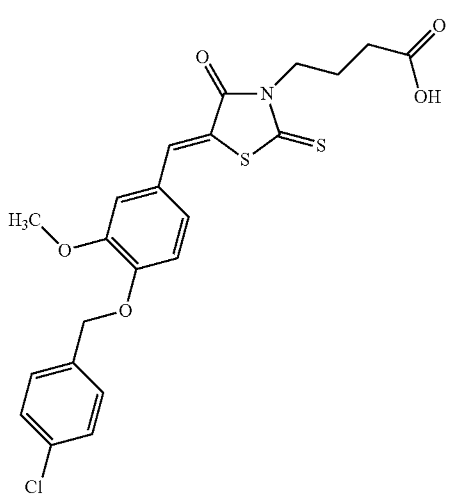 [SMILES: COc1cc(/C=C2\SC(=S)N(CCCC(=O)O)C2=O)ccc1OCc1ccc(Cl)cc1] | 478.0 |

TABLE 7-continued

Phenmethylene-Thiazole Alkanoic Acids (R³ = OH)

| ID | Structure | MW |
|---|---|---|
| IIb-120 | 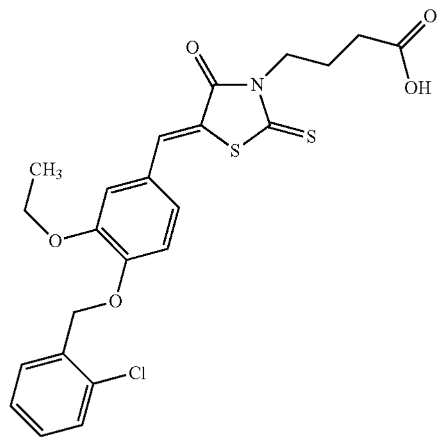 [SMILES: CCOc1cc(/C=C2\SC(=S)N(CCCC(=O)O)C2=O)ccc1OCc1ccccc1Cl] | 492.0 |
| IIb-121 | 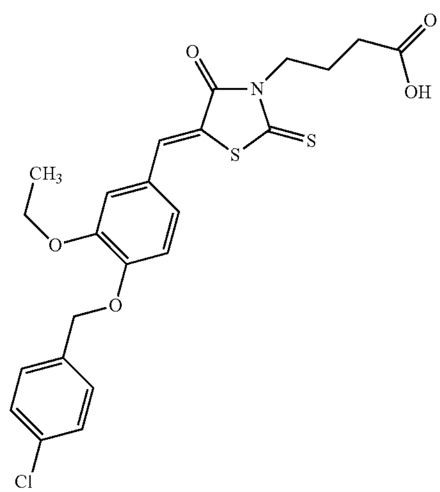 [SMILES: CCOc1cc(/C=C2\SC(=S)N(CCCC(=O)O)C2=O)ccc1OCc1ccc(Cl)cc1] | 492.0 |
| IIb-122 | 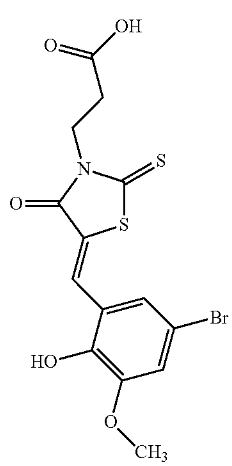 [SMILES: COc1cc(Br)cc(/C=C2\SC(=S)N(CCC(=O)O)C2=O)c1O] | 418.3 |

TABLE 7-continued

Phenmethylene-Thiazole Alkanoic Acids ($R^3$ = OH)

| ID | Structure | MW |
|---|---|---|
| IIb-123 | 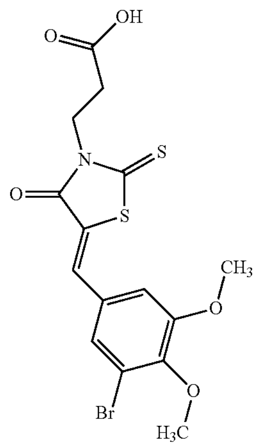 [SMILES: COc1cc(/C=C2\SC(=S)N(CCC(=O)O)C2=O)cc(Br)c1OC] | 432.3 |
| IIb-124 | 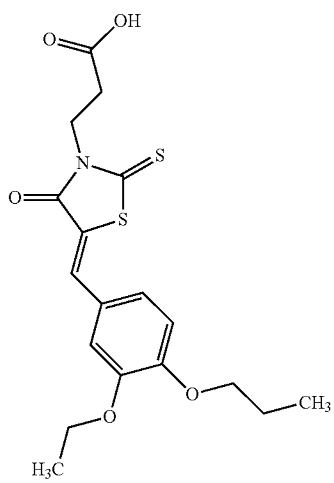 [SMILES: CCCOc1ccc(/C=C2\SC(=S)N(CCC(=O)O)C2=O)cc1OCC] | 395.5 |
| IIb-125 | 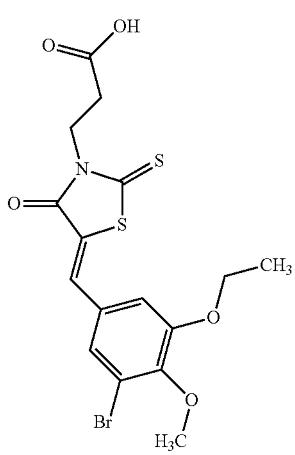 [SMILES: CCOc1cc(/C=C2\SC(=S)N(CCC(=O)O)C2=O)cc(Br)c1OC] | 446.3 |

TABLE 7-continued

Phenmethylene-Thiazole Alkanoic Acids ($R^3$ = OH)

| ID | Structure | MW |
| --- | --- | --- |
| IIb-126 | 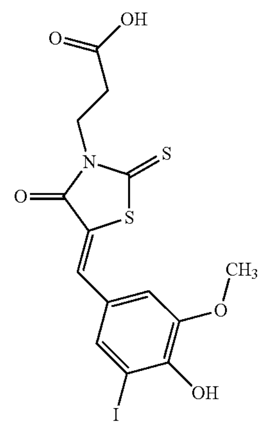 [SMILES: COc1cc(/C=C2\SC(=S)N(CCC(=O)O)C2=O)cc(I)c1O] | 465.3 |
| IIb-127 | 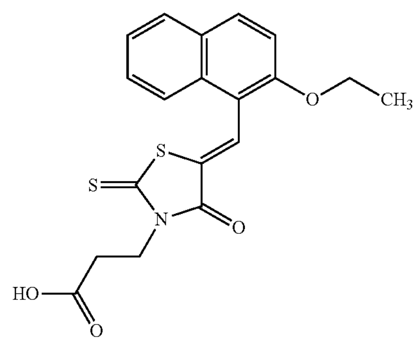 [SMILES: CCOc1ccc2ccccc2c1/C=C1\SC(=S)N(CCC(=O)O)C1=O] | 387.5 |
| IIb-128 | 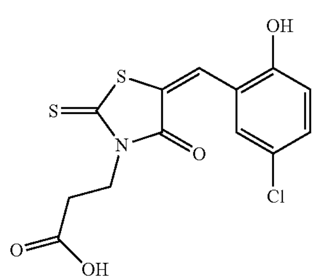 [SMILES: O=C(O)CCN1C(=O)/C(=C\c2cc(Cl)ccc2O)SC1=S] | 343.8 |
| IIb-129 | 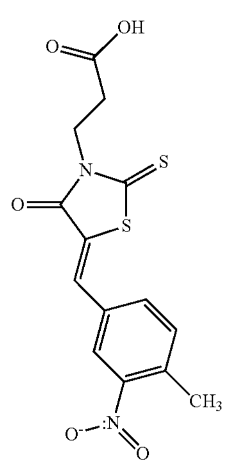 | 352.4 |

TABLE 7-continued

Phenmethylene-Thiazole Alkanoic Acids ($R^3$ = OH)

| ID | Structure | MW |
|---|---|---|
| IIb-130 | 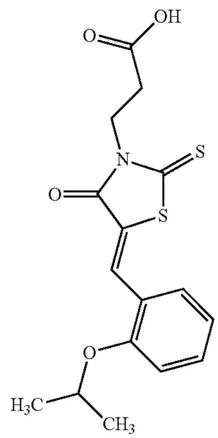 [SMILES: CC(C)Oc1ccccc1/C=C1\SC(=S)N(CCC(=O)O)C1=O] | 351.4 |
| IIb-131 | 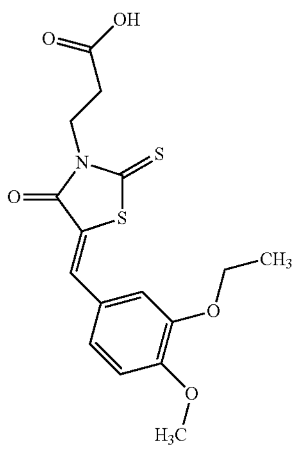 [SMILES: CCOc1cc(/C=C2\SC(=S)N(CCC(=O)O)C2=O)ccc1OC] | 367.4 |
| IIb-132 | 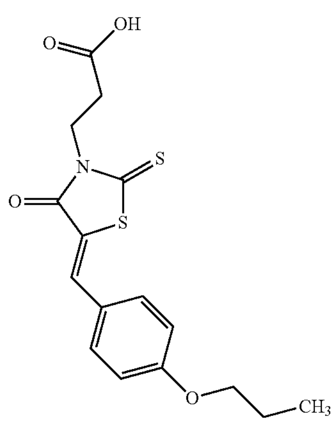 [SMILES: CCCOc1ccc(/C=C2\SC(=S)N(CCC(=O)O)C2=O)cc1] | 351.4 |

TABLE 7-continued

Phenmethylene-Thiazole Alkanoic Acids ($R^3$ = OH)

| ID | Structure | MW |
|---|---|---|
| IIb-133 | 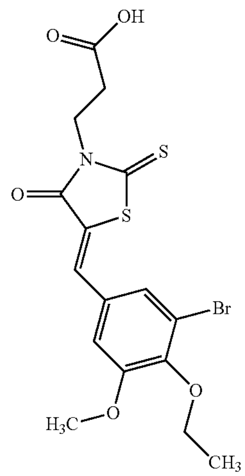 [SMILES: CCOc1c(Br)cc(/C=C2\SC(=S)N(CCC(=O)O)C2=O)cc1OC] | 446.3 |
| IIb-134 | 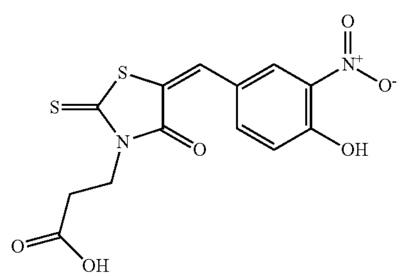 [SMILES: O=C(O)CCN1C(=O)/C(=C\c2ccc(O)c([N+](=O)[O-])c2)SC1=S] | 354.4 |
| IIb-135 | 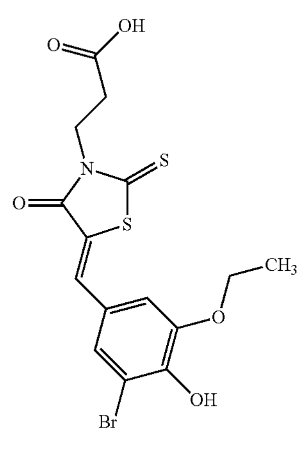 [SMILES: CCOc1cc(/C=C2\SC(=S)N(CCC(=O)O)C2=O)cc(Br)c1O] | 432.3 |

TABLE 7-continued

Phenmethylene-Thiazole Alkanoic Acids ($R^3$ = OH)

| ID | Structure | MW |
|---|---|---|
| IIb-136 | 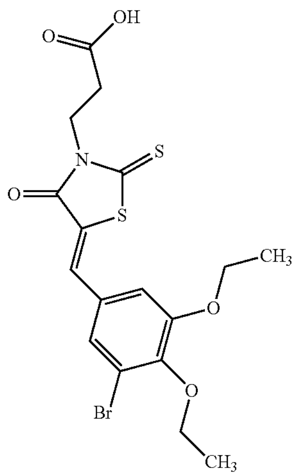 [SMILES: CCOc1cc(/C=C2\SC(=S)N(CCC(=O)O)C2=O)cc(Br)c1OCC] | 460.4 |
| IIb-137 | 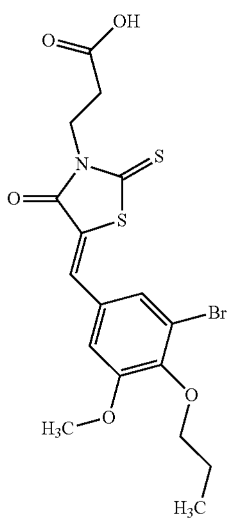 [SMILES: CCCOc1c(Br)cc(/C=C2\SC(=S)N(CCC(=O)O)C2=O)cc1OC] | 460.4 |
| IIb-138 | 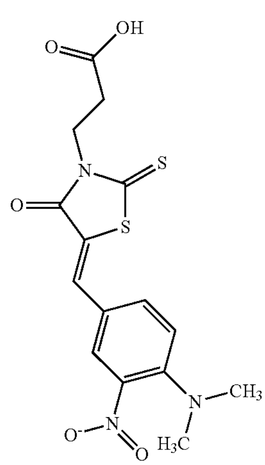 | 381.4 |

TABLE 7-continued

Phenmethylene-Thiazole Alkanoic Acids (R³ = OH)

| ID | Structure | MW |
|---|---|---|
| IIb-139 | 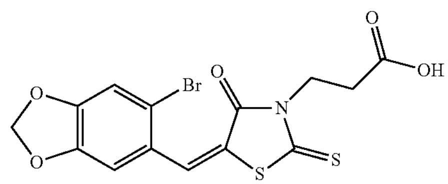 [SMILES: O=C(O)CCN1C(=O)/C(=C\c2cc3c(cc2Br)OCO3)SC1=S] | 416.3 |
| IIb-140 | 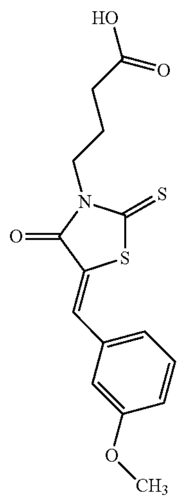 [SMILES: COc1cccc(/C=C2\SC(=S)N(CCCC(=O)O)C2=O)c1] | 337.4 |
| IIb-141 | 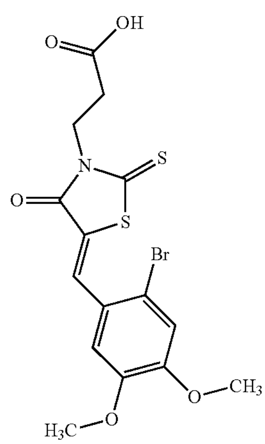 [SMILES: COc1cc(Br)c(/C=C2\SC(=S)N(CCC(=O)O)C2=O)cc1OC] | 432.3 |
| IIb-142 | 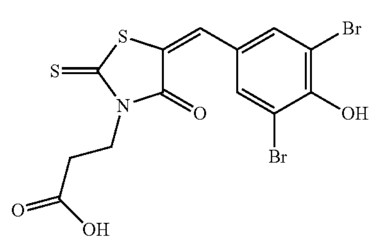 [SMILES: O=C(O)CCN1C(=O)/C(=C\c2cc(Br)c(O)c(Br)c2)SC1=S] | 467.2 |

TABLE 7-continued

Phenmethylene-Thiazole Alkanoic Acids ($R^3$ = OH)

| ID | Structure | MW |
|---|---|---|
| IIb-143 | 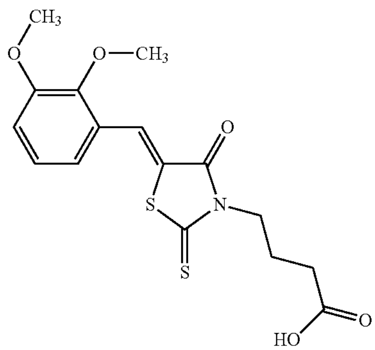 [SMILES: COc1cccc(/C=C2\SC(=S)N(CCCC(=O)O)C2=O)c1OC] | 367.4 |
| IIb-144 | 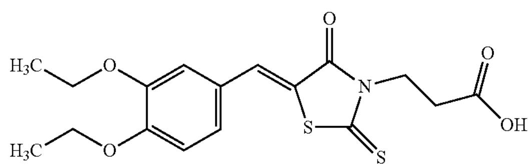 [SMILES: CCOc1ccc(/C=C2\SC(=S)N(CCC(=O)O)C2=O)cc1OCC] | 381.5 |
| IIb-145 | 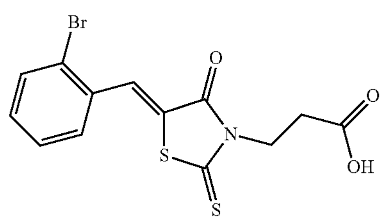 [SMILES: O=C(O)CCN1C(=O)/C(=C/c2ccccc2Br)SC1=S] | 372.3 |
| IIb-146 | 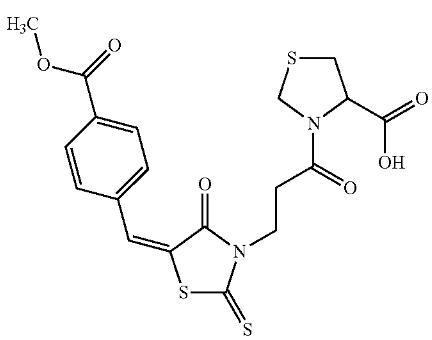 [SMILES: COC(=O)c1ccc(/C=C2/SC(=S)N(CCC(=O)N3CSCC3C(=O)O)C2=O)cc1] | 466.6 |
| IIb-147 | 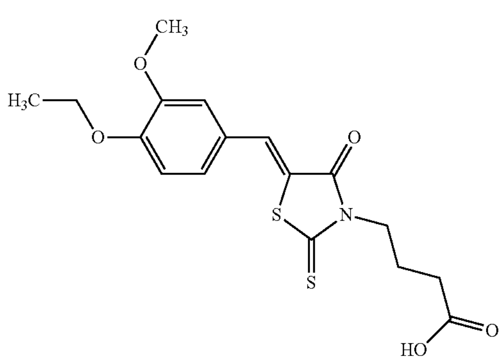 [SMILES: CCOc1ccc(/C=C2\SC(=S)N(CCCC(=O)O)C2=O)cc1OC] | 381.5 |

TABLE 7-continued
Phenmethylene-Thiazole Alkanoic Acids ($R^3$ = OH)
| ID | Structure | MW |
| --- | --- | --- |
| IIb-148 | 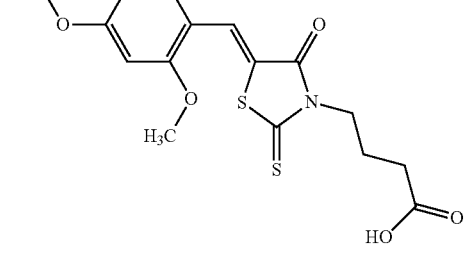 | 367.4 |
| IIb-149 | 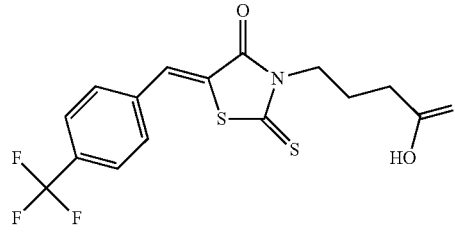 | 375.4 |
| IIb-150 | 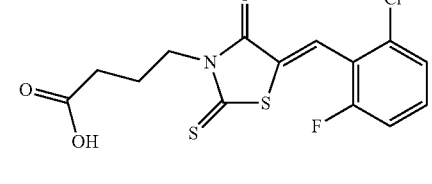 | 359.8 |
| IIb-151 | 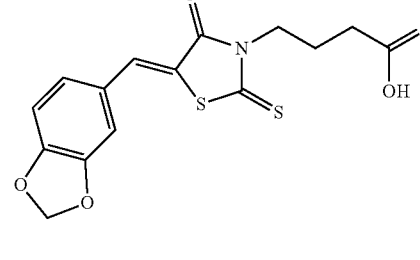 | 351.4 |
| IIb-152 | 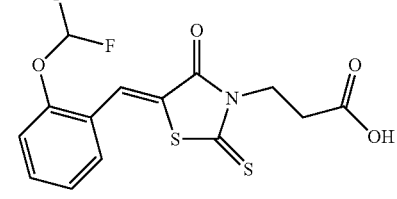 | 359.4 |
| IIb-153 | 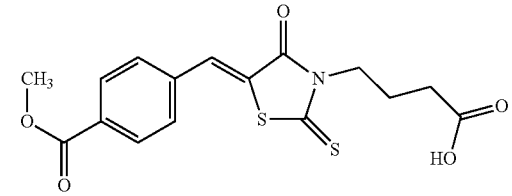 [SMILES: COC(=O)c1ccc(/C=C2\SC(=S)N(CCCC(=O)O)C2=O)cc1] | 365.4 |

TABLE 7-continued

Phenmethylene-Thiazole Alkanoic Acids ($R^3$ = OH)

| ID | Structure | MW |
|---|---|---|
| IIb-154 | 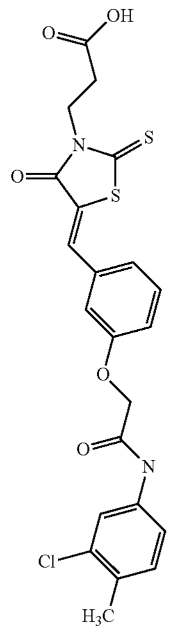 [SMILES: Cc1ccc(NC(=O)COc2cccc(/C=C3\SC(=S)N(CCC(=O)O)C3=O)c2)cc1Cl] | 491.0 |
| IIb-155 | 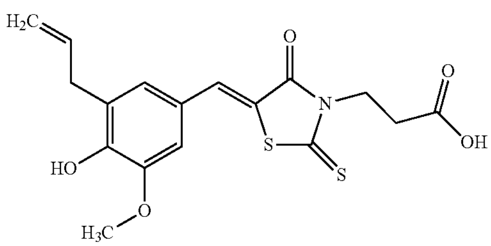 [SMILES: C=CCc1cc(/C=C2\SC(=S)N(CCC(=O)O)C2=O)cc(OC)c1O] | 379.5 |
| IIb-156 | 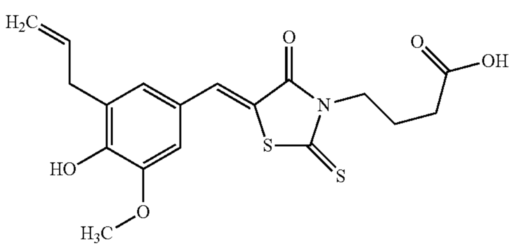 [SMILES: C=CCc1cc(/C=C2\SC(=S)N(CCCC(=O)O)C2=O)cc(OC)c1O] | 393.5 |
| IIb-157 | 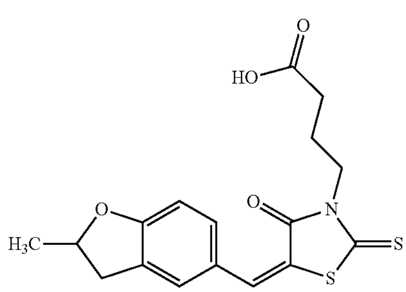 [SMILES: CC1Cc2cc(/C=C3/SC(=S)N(CCCC(=O)O)C3=O)ccc2O1] | 363.5 |

TABLE 7-continued

Phenmethylene-Thiazole Alkanoic Acids ($R^3$ = OH)

| ID | Structure | MW |
|---|---|---|
| IIb-158 | 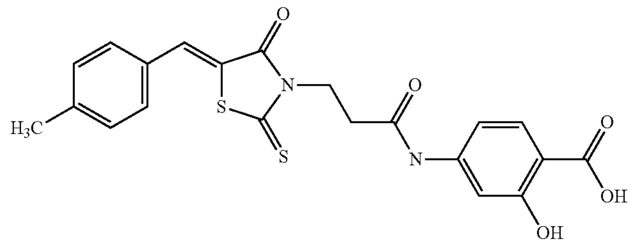 [SMILES: Cc1ccc(/C=C2\SC(=S)N(CCC(=O)Nc3ccc(C(=O)O)c(O)c3)C2=O)cc1] | 442.5 |
| IIb-159 | 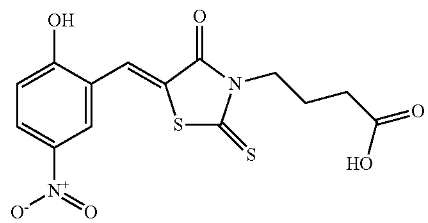 [SMILES: O=C(O)CCCN1C(=O)/C(=C/c2cc([N+](=O)[O-])ccc2O)SC1=S] | 368.4 |
| IIb-160 | 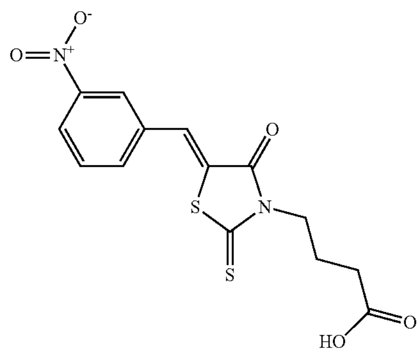 [SMILES: O=C(O)CCCN1C(=O)/C(=C/c2cccc([N+](=O)[O-])c2)SC1=S] | 352.4 |
| IIb-161 | 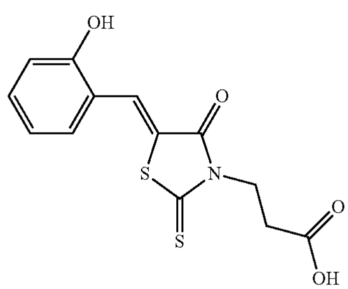 [SMILES: O=C(O)CCN1C(=O)/C(=C/c2ccccc2O)SC1=S] | 309.4 |
| IIb-162 | 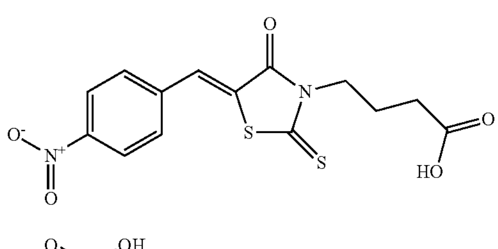 | 352.4 |
| IIb-163 | 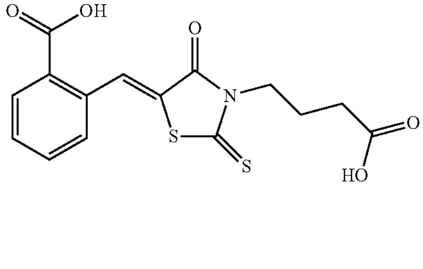 [SMILES: O=C(O)CCCN1C(=O)/C(=C/c2ccccc2C(=O)O)SC1=S] | 351.4 |

TABLE 7-continued

Phenmethylene-Thiazole Alkanoic Acids (R³ = OH)

| ID | Structure | MW |
|---|---|---|
| IIb-164 | 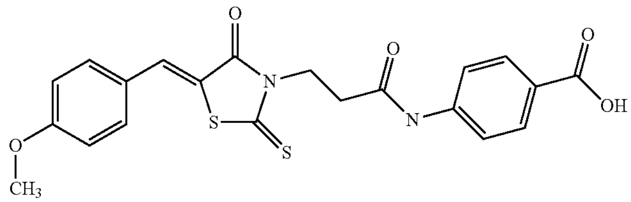 | 442.5 |
| IIb-165 | 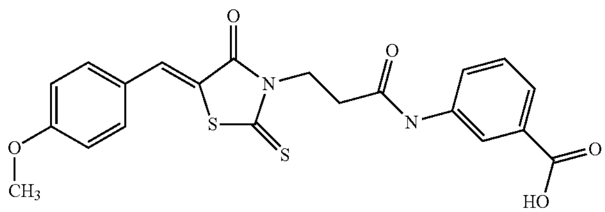 | 442.5 |
| IIb-166 | 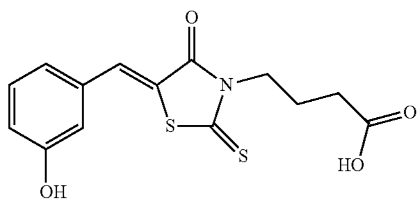 [SMILES: O=C(O)CCCN1C(=O)/C(=C/c2cccc(O)c2)SC1=S] | 323.4 |
| IIb-167 | 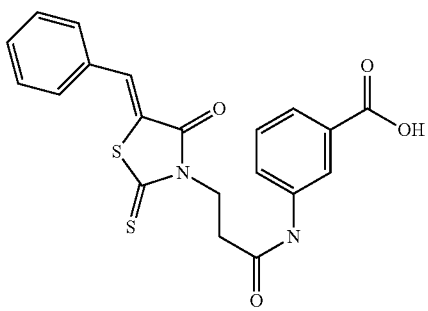 [SMILES: O=C(CCN1C(=O)/C(=C/c2ccccc2)SC1=S)Nc1cccc(C(=O)O)c1] | 412.5 |
| IIb-168 | 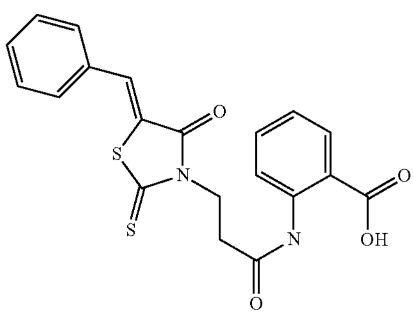 [SMILES: O=C(CCN1C(=O)/C(=C/c2ccccc2)SC1=S)Nc1ccccc1C(=O)O] | 412.5 |
| IIb-169 | 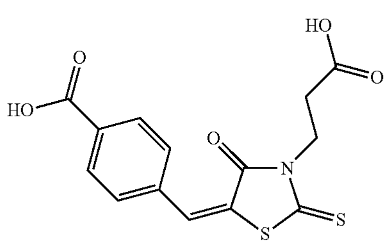 [SMILES: O=C(O)CCN1C(=O)/C(=C\c2ccc(C(=O)O)cc2)SC1=S] | 337.4 |

TABLE 7-continued

Phenmethylene-Thiazole Alkanoic Acids ($R^3$ = OH)

| ID | Structure | MW |
|---|---|---|
| IIb-170 | 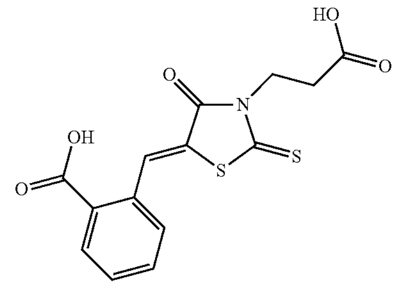 [SMILES: O=C(O)CCN1C(=O)/C(=C/c2ccccc2C(=O)O)SC1=S] | 337.4 |
| IIb-171 | 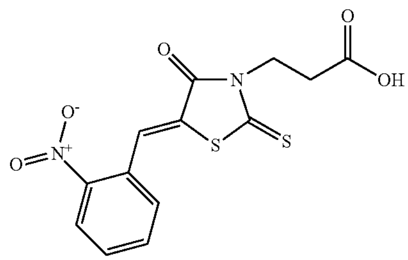 [SMILES: O=C(O)CCN1C(=O)/C(=C/c2ccccc2[N+](=O)[O-])SC1=S] | 338.4 |
| IIb-172 | 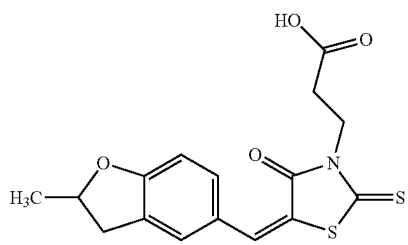 [SMILES: CC1Cc2cc(/C=C3/SC(=S)N(CCC(=O)O)C3=O)ccc2O1] | 349.4 |
| IIb-173 | 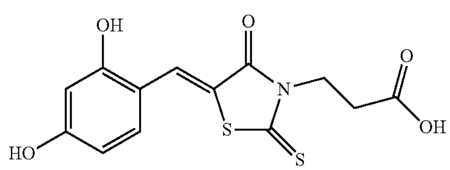 [SMILES: O=C(O)CCN1C(=O)/C(=C/c2ccc(O)cc2O)SC1=S] | 325.4 |
| IIb-174 | 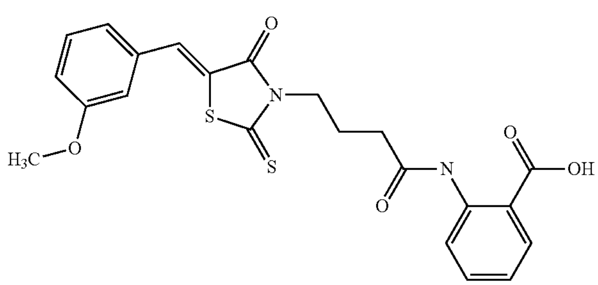 [SMILES: COc1cccc(/C=C2\SC(=S)N(CCCC(=O)Nc3ccccc3C(=O)O)C2=O)c1] | 456.5 |
| IIb-175 | 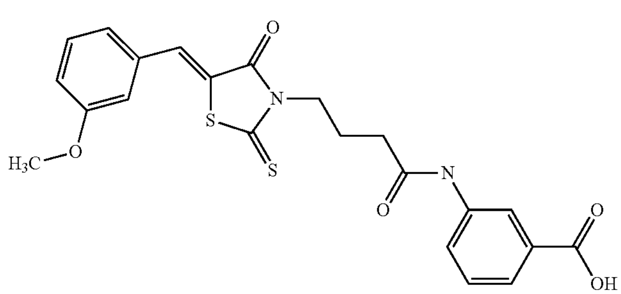 [SMILES: COc1cccc(/C=C2\SC(=S)N(CCCC(=O)Nc3cccc(C(=O)O)c3)C2=O)c1] | 456.5 |

TABLE 7-continued

| | Phenmethylene-Thiazole Alkanoic Acids (R³ = OH) | |
|---|---|---|
| ID | Structure | MW |
| IIb-176 | | 456.5 |
| IIb-177 | | 430.5 |
| IIb-178 | | 430.5 |
| IIb-179 | | 430.5 |
| IIb-180 | | 446.5 |

TABLE 7-continued
Phenmethylene-Thiazole Alkanoic Acids ($R^3$ = OH)
| ID | Structure | MW |
|---|---|---|
| IIb-181 | 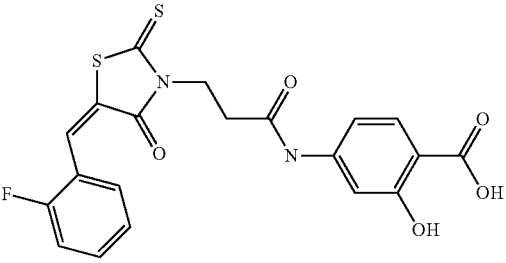 [SMILES: O=C(CCN1C(=O)/C(=C\c2ccccc2F)SC1=S)Nc1ccc(C(=O)O)c(O)c1] | 446.5 |
| IIb-182 | 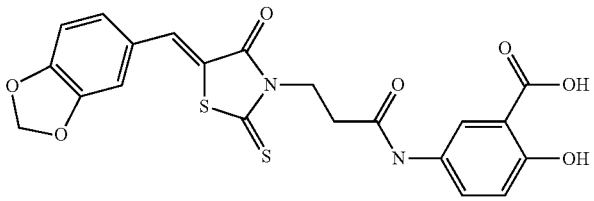 [SMILES: O=C(CCN1C(=O)/C(=C/c2ccc3c(c2)OCO3)SC1=S)Nc1ccc(O)c(C(=O)O)c1] | 472.5 |
| IIb-183 | 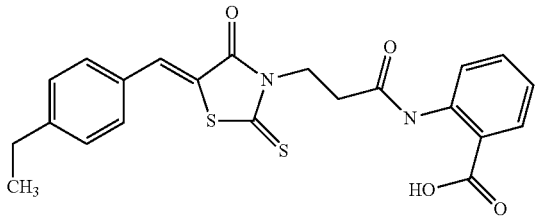 [SMILES: CCc1ccc(/C=C2\SC(=S)N(CCC(=O)Nc3ccccc3C(=O)O)C2=O)cc1] | 440.5 |
| IIb-184 | 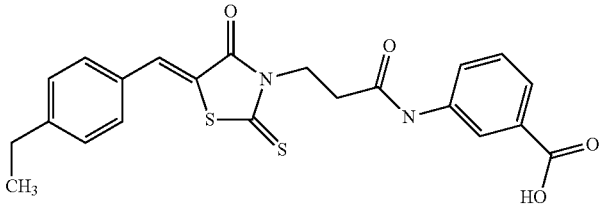 [SMILES: CCc1ccc(/C=C2\SC(=S)N(CCC(=O)Nc3cccc(C(=O)O)c3)C2=O)cc1] | 440.5 |
| IIb-185 | 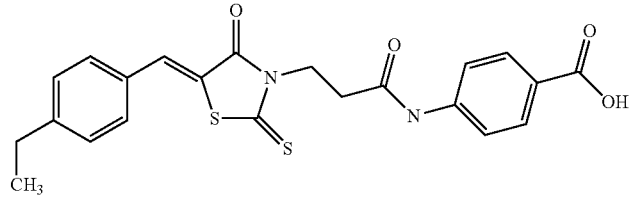 [SMILES: CCc1ccc(/C=C2\SC(=S)N(CCC(=O)Nc3ccc(C(=O)O)cc3)C2=O)cc1] | 440.5 |
| IIb-186 | 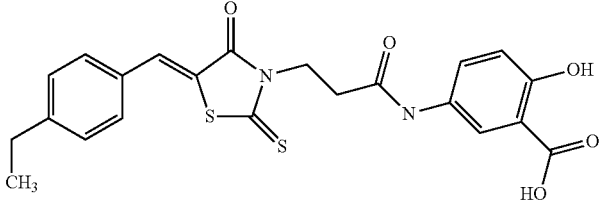 [SMILES: CCc1ccc(/C=C2\SC(=S)N(CCC(=O)Nc3ccc(O)c(C(=O)O)c3)C2=O)cc1] | 456.5 |
| IIb-187 | 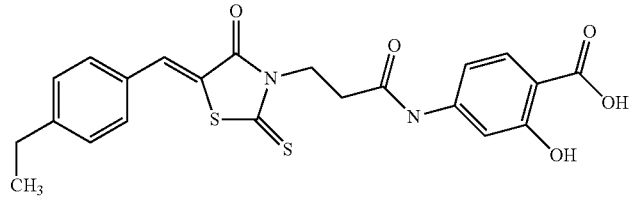 | 456.5 |

TABLE 7-continued
Phenmethylene-Thiazole Alkanoic Acids (R³ = OH)
| ID | Structure | MW |
|---|---|---|
| IIb-188 | 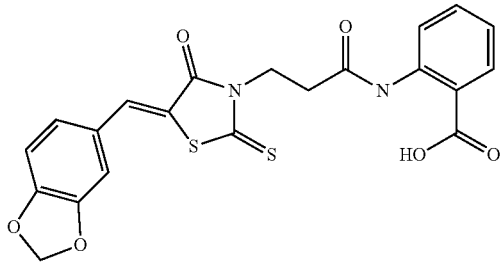 [SMILES: O=C(CCN1C(=O)/C(=C/c2ccc3c(c2)OCO3)SC1=S)Nc1ccccc1C(=O)O] | 456.5 |
| IIb-189 | 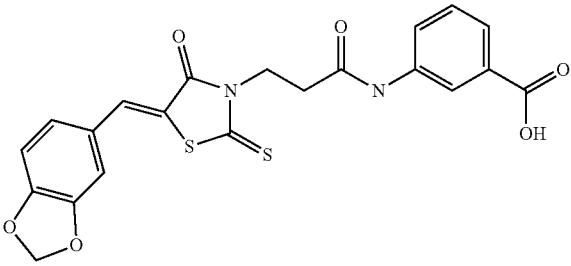 [SMILES: O=C(CCN1C(=O)/C(=C/c2ccc3c(c2)OCO3)SC1=S)Nc1cccc(C(=O)O)c1] | 456.5 |
| IIb-190 | 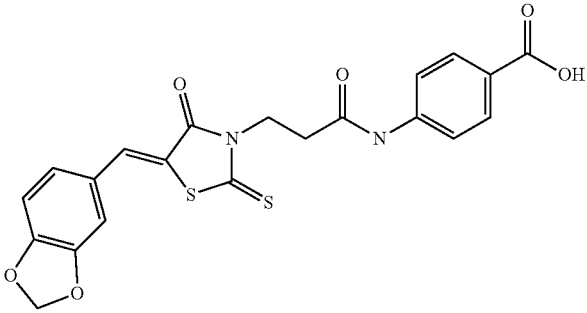 [SMILES: O=C(CCN1C(=O)/C(=C/c2ccc3c(c2)OCO3)SC1=S)Nc1ccc(C(=O)O)cc1] | 456.5 |
| IIb-191 | 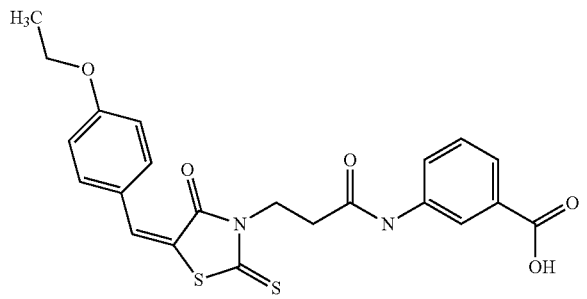 [SMILES: CCOc1ccc(/C=C2/SC(=S)N(CCC(=O)Nc3cccc(C(=O)O)c3)C2=O)cc1] | 456.5 |
| IIb-192 | 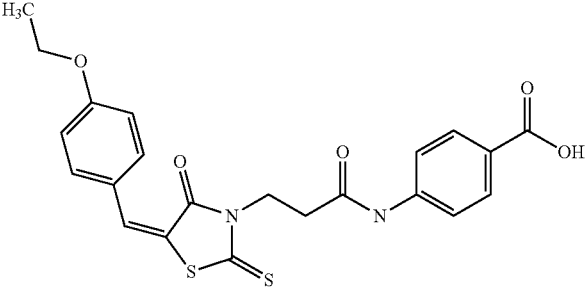 [SMILES: CCOc1ccc(/C=C2/SC(=S)N(CCC(=O)Nc3ccc(C(=O)O)cc3)C2=O)cc1] | 456.5 |

TABLE 7-continued

Phenmethylene-Thiazole Alkanoic Acids ($R^3$ = OH)

| ID | Structure | MW |
|---|---|---|
| IIb-193 | 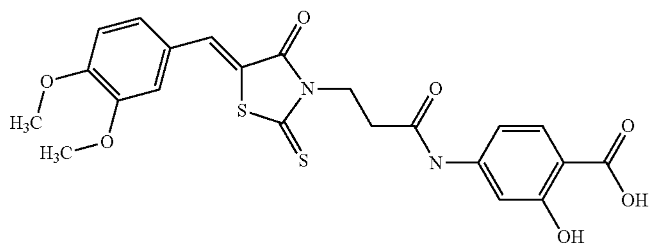 [SMILES: COc1ccc(/C=C2\SC(=S)N(CCC(=O)Nc3ccc(C(=O)O)c(O)c3)C2=O)cc1OC] | 488.5 |
| IIb-194 | 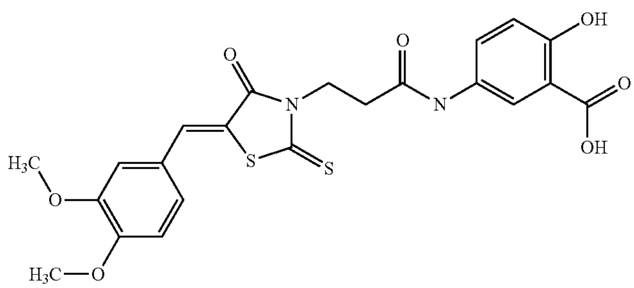 [SMILES: COc1ccc(/C=C2\SC(=S)N(CCC(=O)Nc3ccc(O)c(C(=O)O)c3)C2=O)cc1OC] | 488.5 |
| IIb-195 | 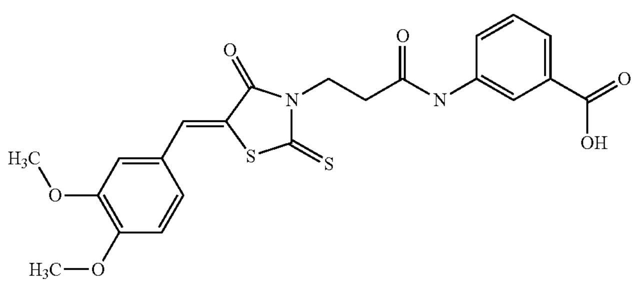 [SMILES: COc1ccc(/C=C2\SC(=S)N(CCC(=O)Nc3cccc(C(=O)O)c3)C2=O)cc1OC] | 472.5 |
| IIb-196 | 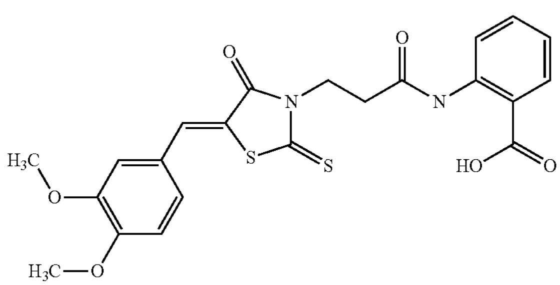 [SMILES: COc1ccc(/C=C2\SC(=S)N(CCC(=O)Nc3ccccc3C(=O)O)C2=O)cc1OC] | 472.5 |
| IIb-197 | 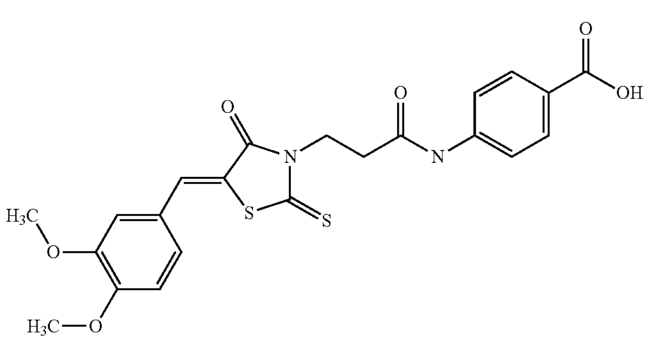 [SMILES: COc1ccc(/C=C2\SC(=S)N(CCC(=O)Nc3ccc(C(=O)O)cc3)C2=O)cc1OC] | 472.5 |

TABLE 7-continued

Phenmethylene-Thiazole Alkanoic Acids ($R^3$ = OH)

| ID | Structure | MW |
|---|---|---|
| IIb-198 | 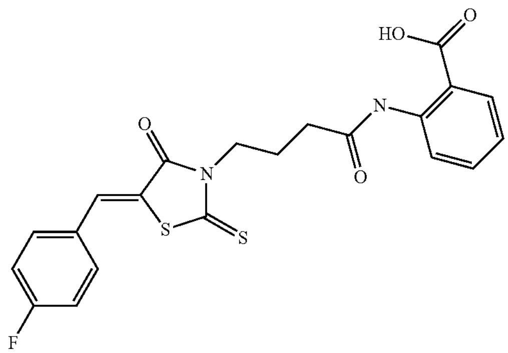 [SMILES: O=C(CCCN1C(=O)/C(=C/c2ccc(F)cc2)SC1=S)Nc1ccccc1C(=O)O] | 444.5 |
| IIb-199 | 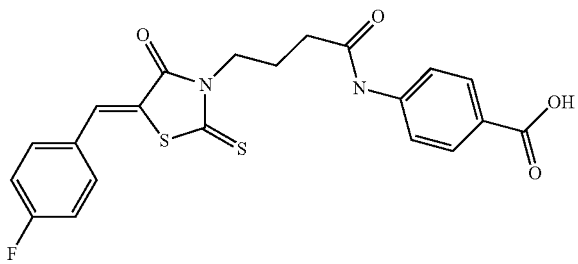 [SMILES: O=C(CCCN1C(=O)/C(=C/c2ccc(F)cc2)SC1=S)Nc1ccc(C(=O)O)cc1] | 444.5 |
| IIb-200 | 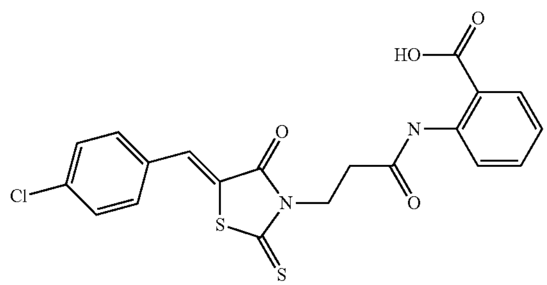 [SMILES: O=C(CCN1C(=O)/C(=C/c2ccc(Cl)cc2)SC1=S)Nc1ccccc1C(=O)O] | 446.9 |
| IIb-201 | 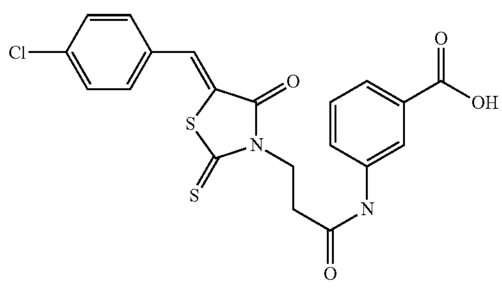 [SMILES: O=C(CCN1C(=O)/C(=C/c2ccc(Cl)cc2)SC1=S)Nc1cccc(C(=O)O)c1] | 446.9 |
| IIb-202 | 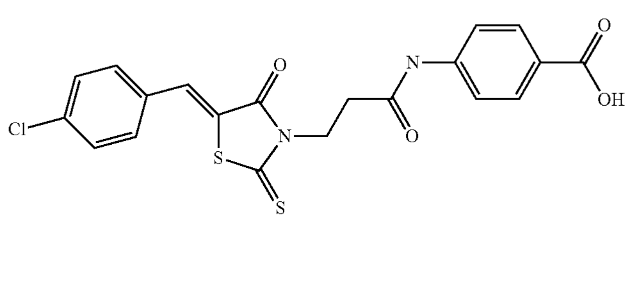 [SMILES: O=C(CCN1C(=O)/C(=C/c2ccc(Cl)cc2)SC1=S)Nc1ccc(C(=O)O)cc1] | 446.9 |

TABLE 7-continued

Phenmethylene-Thiazole Alkanoic Acids (R³ = OH)

| ID | Structure | MW |
|---|---|---|
| IIb-203 | 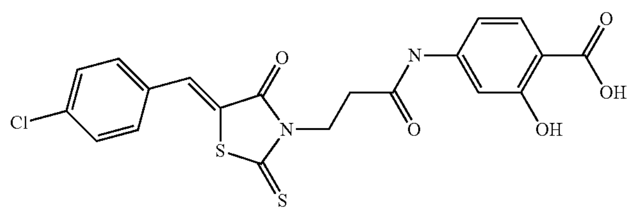 [SMILES: O=C(CCN1C(=O)/C(=C/c2ccc(Cl)cc2)SC1=S)Nc1ccc(C(=O)O)c(O)c1] | 462.9 |
| IIb-204 | 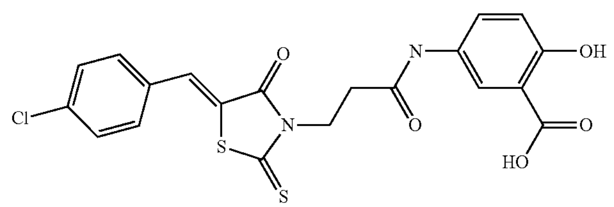 [SMILES: O=C(CCN1C(=O)/C(=C/c2ccc(Cl)cc2)SC1=S)Nc1ccc(O)c(C(=O)O)c1] | 462.9 |
| IIb-205 | 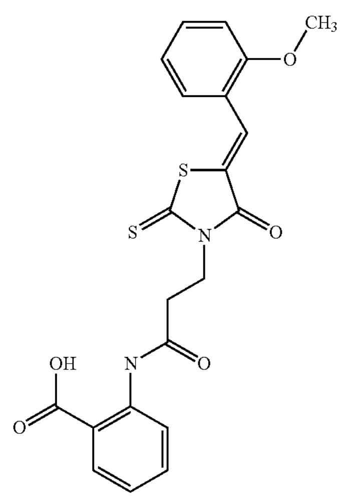 [SMILES: COc1ccccc1/C=C1\SC(=S)N(CCC(=O)Nc2ccccc2C(=O)O)C1=O] | 442.5 |
| IIb-206 | 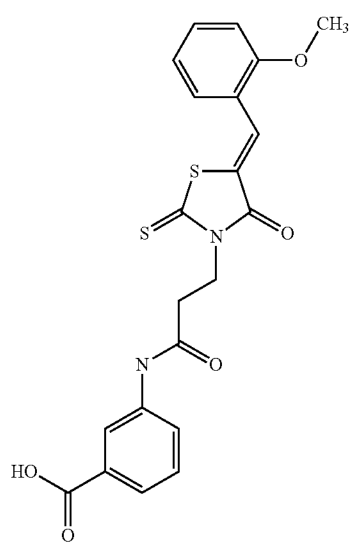 [SMILES: COc1ccccc1/C=C1\SC(=S)N(CCC(=O)Nc2cccc(C(=O)O)c2)C1=O] | 442.5 |

TABLE 7-continued
Phenmethylene-Thiazole Alkanoic Acids ($R^3$ = OH)
| ID | Structure | MW |
|---|---|---|
| IIb-207 | 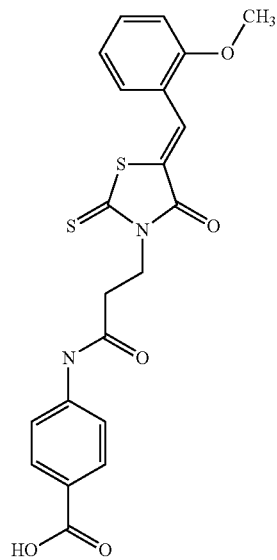 [SMILES: COc1ccccc1/C=C1\SC(=S)N(CCC(=O)Nc2ccc(C(=O)O)cc2)C1=O] | 442.5 |
| IIb-208 | 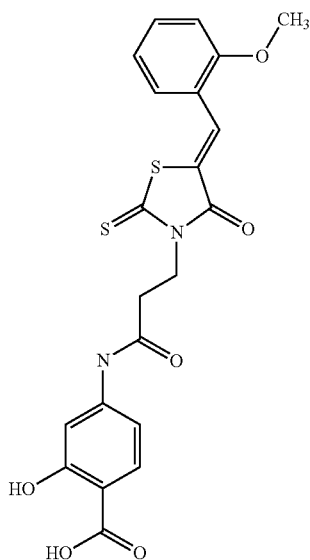 [SMILES: COc1ccccc1/C=C1\SC(=S)N(CCC(=O)Nc2ccc(C(=O)O)c(O)c2)C1=O] | 458.5 |

TABLE 7-continued
Phenmethylene-Thiazole Alkanoic Acids ($R^3$ = OH)
| ID | Structure | MW |
|---|---|---|
| IIb-209 | 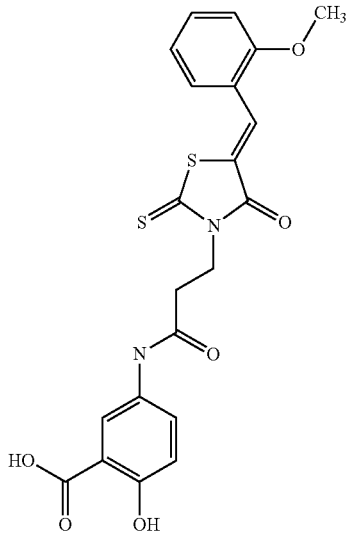 [SMILES: COc1ccccc1/C=C1\SC(=S)N(CCC(=O)Nc2ccc(O)c(C(=O)O)c2)C1=O] | 458.5 |
| IIb-210 | 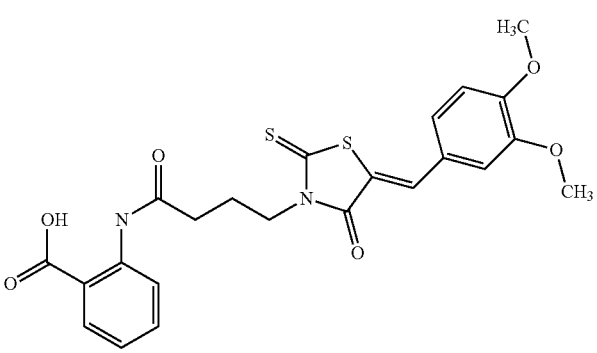 [SMILES: COc1ccc(/C=C2\SC(=S)N(CCCC(=O)Nc3ccccc3C(=O)O)C2=O)cc1OC] | 486.6 |
| IIb-211 | 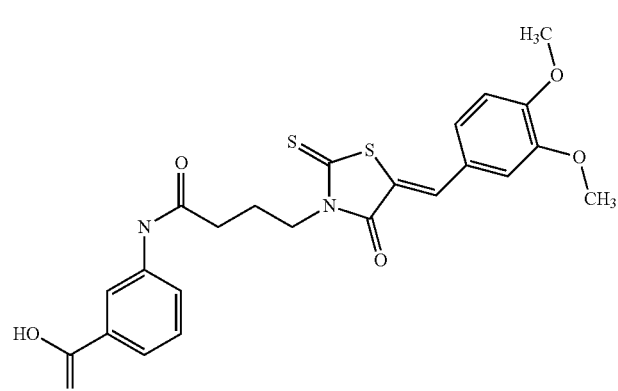 | 486.6 |

TABLE 7-continued

Phenmethylene-Thiazole Alkanoic Acids (R³ = OH)

| ID | Structure | MW |
|---|---|---|
| IIb-212 | 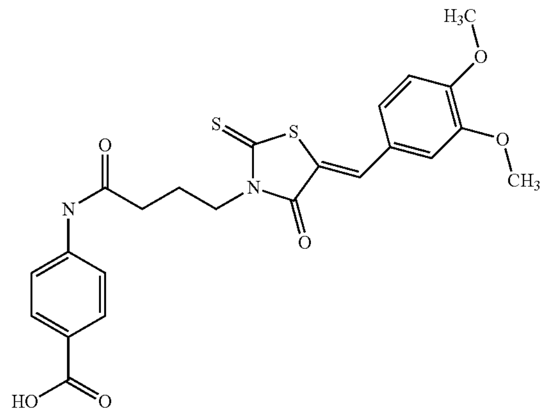 [SMILES: COc1ccc(/C=C2\SC(=S)N(CCCC(=O)Nc3ccc(C(=O)O)cc3)C2=O)cc1OC] | 486.6 |
| IIb-213 | 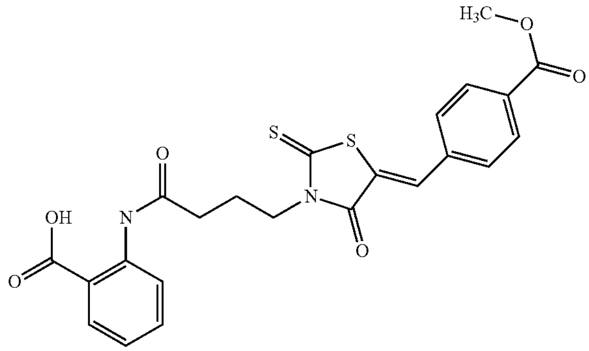 [SMILES: COC(=O)c1ccc(/C=C2\SC(=S)N(CCCC(=O)Nc3ccccc3C(=O)O)C2=O)cc1] | 484.6 |
| IIb-214 | 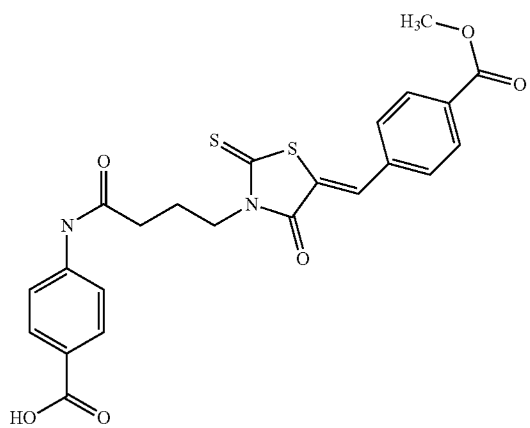 [SMILES: COC(=O)c1ccc(/C=C2\SC(=S)N(CCCC(=O)Nc3ccc(C(=O)O)cc3)C2=O)cc1] | 484.6 |
| IIb-215 | 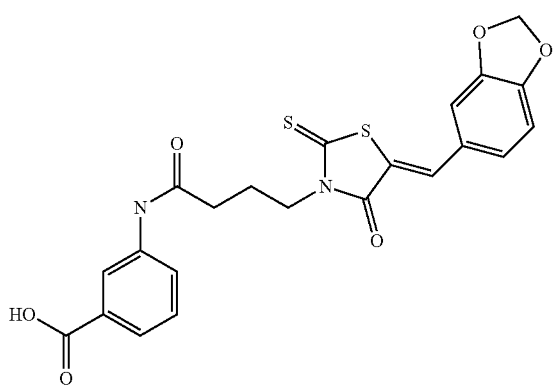 [SMILES: O=C(CCCN1C(=O)/C(=C/c2ccc3c(c2)OCO3)SC1=S)Nc1cccc(C(=O)O)c1] | 470.5 |

TABLE 7-continued

Phenmethylene-Thiazole Alkanoic Acids ($R^3$ = OH)

| ID | Structure | MW |
|---|---|---|
| IIb-216 | 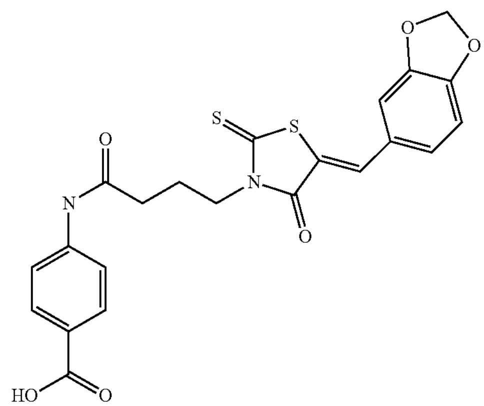 [SMILES: O=C(CCCN1C(=O)/C(=C/c2ccc3c(c2)OCO3)SC1=S)Nc1ccc(C(=O)O)cc1] | 470.5 |
| IIb-217 | 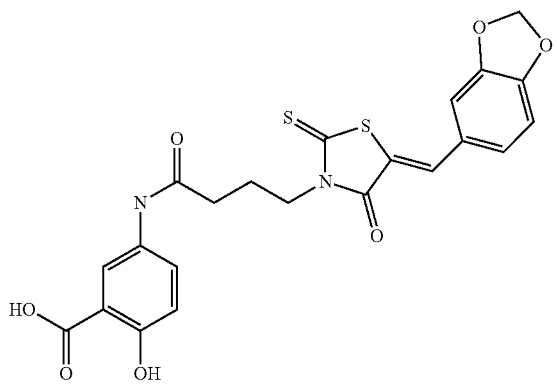 [SMILES: O=C(CCCN1C(=O)/C(=C/c2ccc3c(c2)OCO3)SC1=S)Nc1ccc(O)c(C(=O)O)c1] | 486.5 |
| IIb-218 | 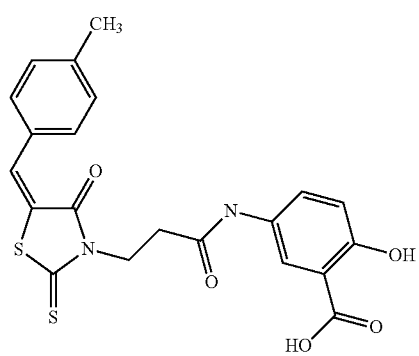 [SMILES: Cc1ccc(/C=C2/SC(=S)N(CCC(=O)Nc3ccc(O)c(C(=O)O)c3)C2=O)cc1] | 442.5 |
| IIb-219 | 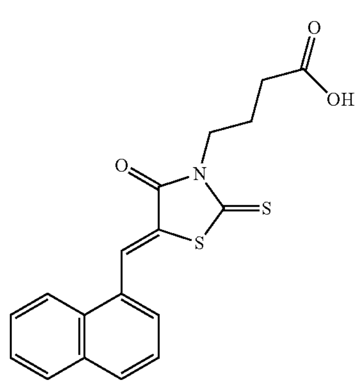 [SMILES: O=C(O)CCCN1C(=O)/C(=C/c2cccc3ccccc23)SC1=S] | 357.5 |

TABLE 7-continued

Phenmethylene-Thiazole Alkanoic Acids ($R^3$ = OH)

| ID | Structure | MW |
|---|---|---|
| IIb-220 | 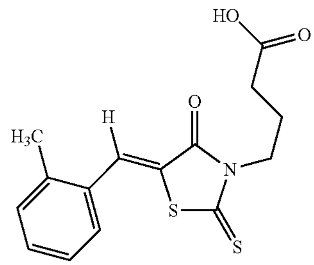 [SMILES: Cc1ccccc1/C=C1\SC(=S)N(CCCC(=O)O)C1=O] | 321.4 |
| IIb-221 | 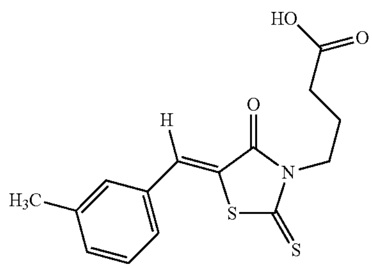 [SMILES: Cc1cccc(/C=C2\SC(=S)N(CCCC(=O)O)C2=O)c1] | 321.4 |
| IIb-222 | 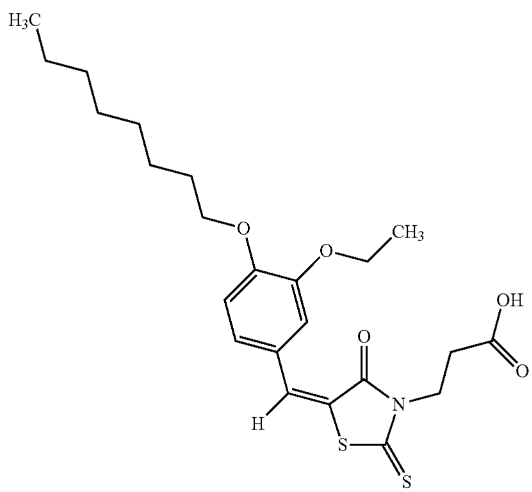 [SMILES: CCCCCCCCOc1ccc(/C=C2/SC(=S)N(CCC(=O)O)C2=O)cc1OCC] | 465.6 |
| IIb-223 | 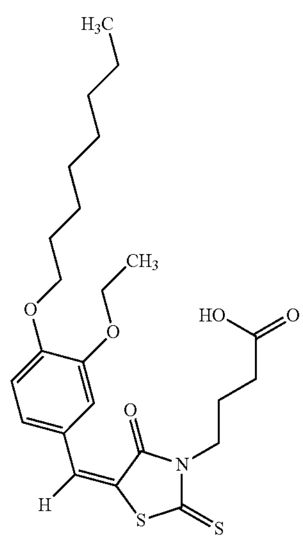 [SMILES: CCCCCCCCOc1ccc(/C=C2/SC(=S)N(CCCC(=O)O)C2=O)cc1OCC] | 479.7 |

TABLE 7-continued

Phenmethylene-Thiazole Alkanoic Acids ($R^3$ = OH)

| ID | Structure | MW |
|---|---|---|
| IIb-224 | 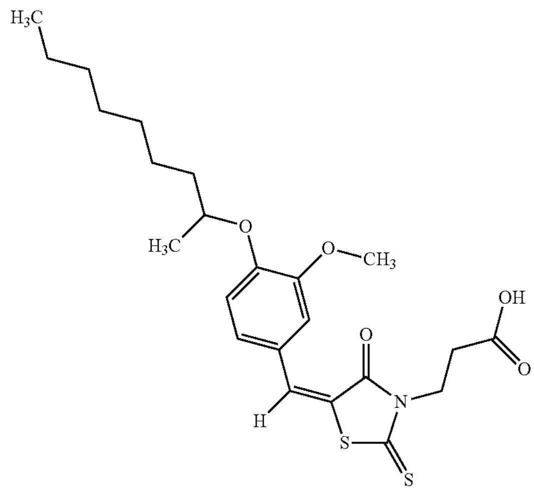 [SMILES: CCCCCCCC(C)Oc1ccc(/C=C2/SC(=S)N(CCC(=O)O)C2=O)cc1OC] | 465.6 |
| IIb-225 | 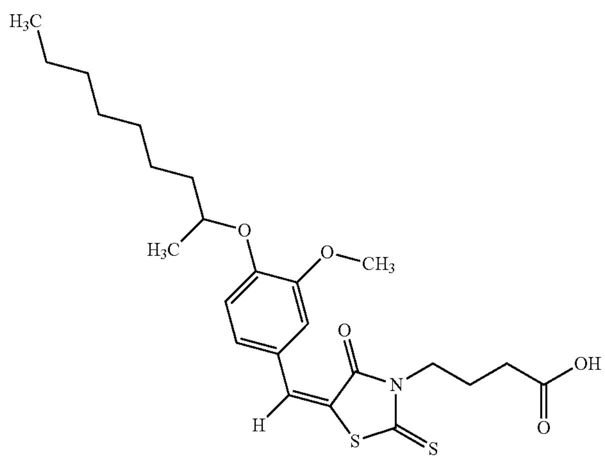 [SMILES: CCCCCCCC(C)Oc1ccc(/C=C2/SC(=S)N(CCCC(=O)O)C2=O)cc1OC] | 479.7 |
| IIb-226 | 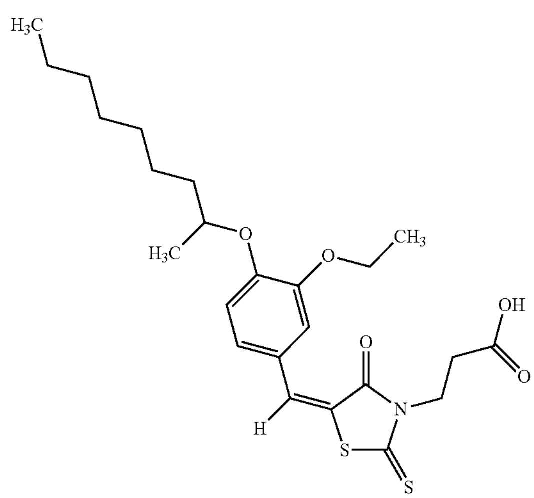 [SMILES: CCCCCCCC(C)Oc1ccc(/C=C2/SC(=S)N(CCC(=O)O)C2=O)cc1OCC] | 479.7 |

TABLE 7-continued
Phenmethylene-Thiazole Alkanoic Acids (R³ = OH)
| ID | Structure | MW |
|---|---|---|
| IIb-227 | 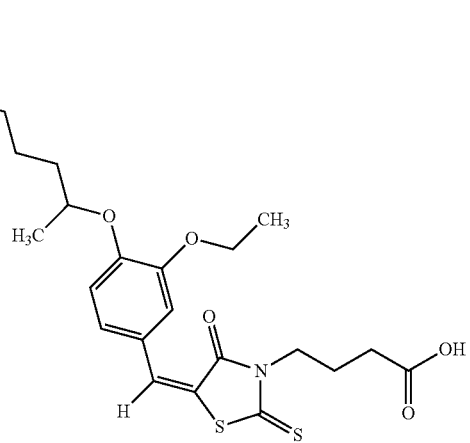 | 493.7 |
| IIb-228 | 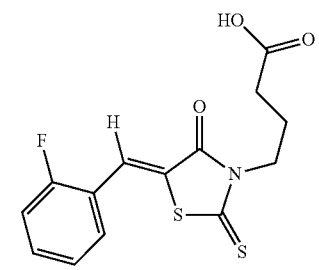 [SMILES: O=C(O)CCCN1C(=O)/C(=C/c2ccccc2F)SC1=S] | 325.4 |
| IIb-229 | 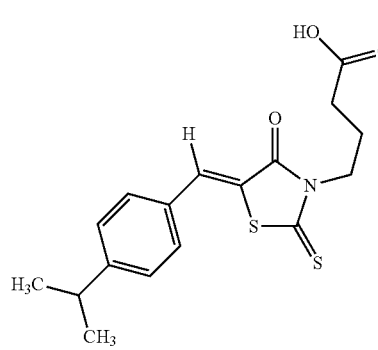 | 349.5 |
| IIb-230 | 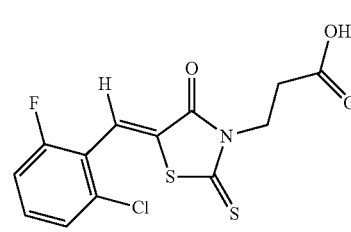 | 345.8 |
| IIb-231 | 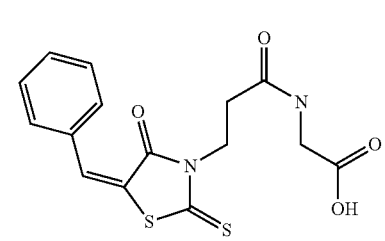 [SMILES: O=C(O)CNC(=O)CCN1C(=O)/C(=C\c2ccccc2)SC1=S] | 350.4 |

TABLE 7-continued
Phenmethylene-Thiazole Alkanoic Acids ($R^3$ = OH)
| ID | Structure | MW |
|---|---|---|
| IIb-232 | 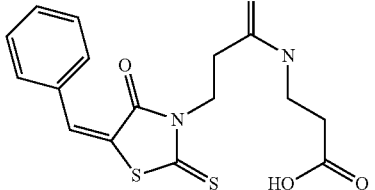 | 364.4 |
| IIb-233 | 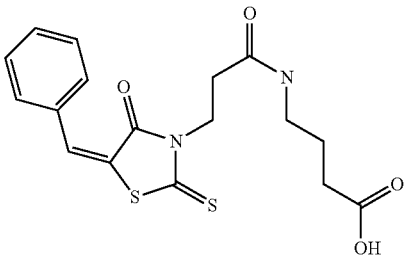 [SMILES: O=C(O)CCCNC(=O)CCN1C(=O)/C(=C\c2ccccc2)SC1=S] | 378.5 |
| IIb-234 | 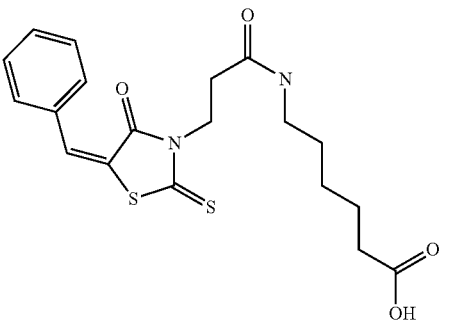 [SMILES: O=C(O)CCCCCNC(=O)CCN1C(=O)/C(=C\c2ccccc2)SC1=S] | 406.5 |
| IIb-235 | 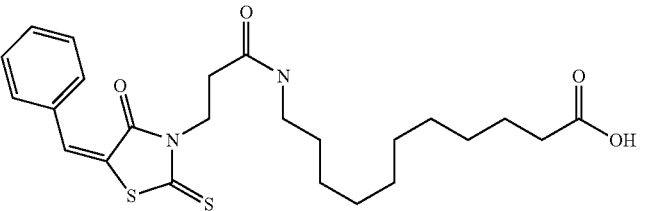 [SMILES: O=C(O)CCCCCCCCCCNC(=O)CCN1C(=O)/C(=C\c2ccccc2)SC1=S] | 476.7 |
| IIb-236 | 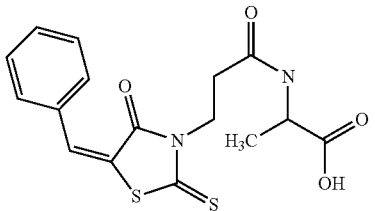 [SMILES: CC(NC(=O)CCN1C(=O)/C(=C\c2ccccc2)SC1=S)C(=O)O] | 364.4 |
| IIb-237 | 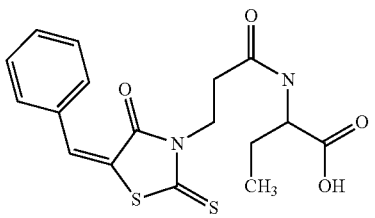 [SMILES: CCC(NC(=O)CCN1C(=O)/C(=C\c2ccccc2)SC1=S)C(=O)O] | 378.5 |

TABLE 7-continued

Phenmethylene-Thiazole Alkanoic Acids ($R^3$ = OH)

| ID | Structure | MW |
|---|---|---|
| IIb-238 | 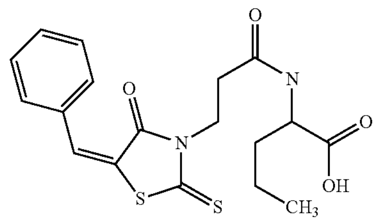 [SMILES: CCCC(NC(=O)CCN1C(=O)/C(=C\c2ccccc2)SC1=S)C(=O)O] | 392.5 |
| IIb-239 | 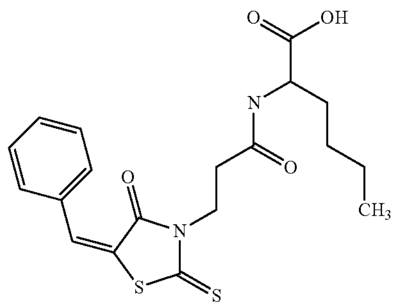 [SMILES: CCCCC(NC(=O)CCN1C(=O)/C(=C\c2ccccc2)SC1=S)C(=O)O] | 406.5 |
| IIb-240 | 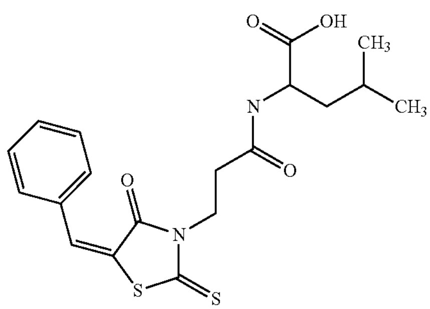 [SMILES: CC(C)CC(NC(=O)CCN1C(=O)/C(=C\c2ccccc2)SC1=S)C(=O)O] | 406.5 |
| IIb-241 | 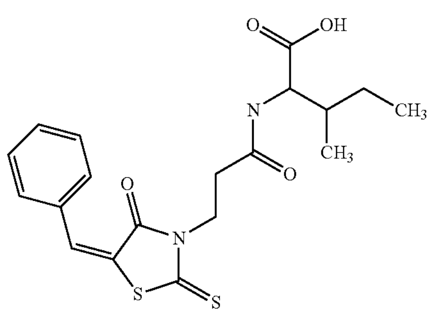 [SMILES: CCC(C)C(NC(=O)CCN1C(=O)/C(=C\c2ccccc2)SC1=S)C(=O)O] | 406.5 |
| IIb-242 | 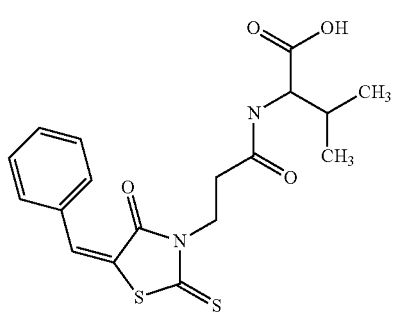 [SMILES: CC(C)C(NC(=O)CCN1C(=O)/C(=C\c2ccccc2)SC1=S)C(=O)O] | 392.5 |

TABLE 7-continued

Phenmethylene-Thiazole Alkanoic Acids ($R^3$ = OH)

| ID | Structure | MW |
|---|---|---|
| IIb-243 | 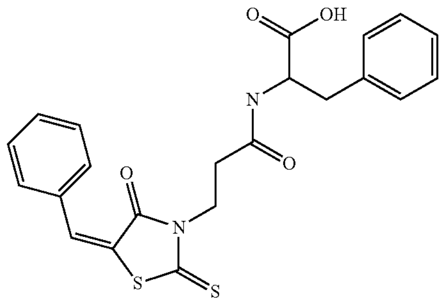 [SMILES: O=C(CCN1C(=O)/C(=C\c2ccccc2)SC1=S)NC(Cc1ccccc1)C(=O)O] | 440.5 |
| IIb-244 | 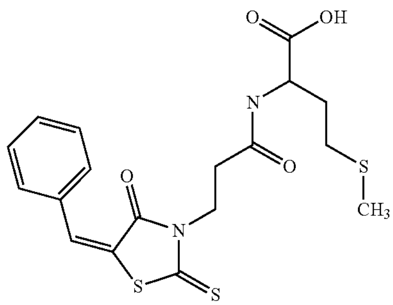 | 424.6 |
| IIb-245 | 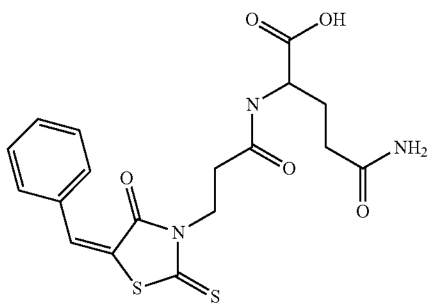 [SMILES: NC(=O)CCC(NC(=O)CCN1C(=O)/C(=C\c2ccccc2)SC1=S)C(=O)O] | 421.5 |
| IIb-246 | 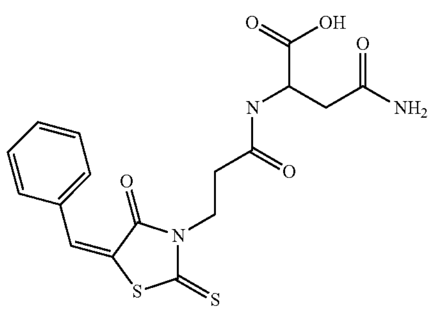 [SMILES: NC(=O)CC(NC(=O)CCN1C(=O)/C(=C\c2ccccc2)SC1=S)C(=O)O] | 407.5 |
| IIb-247 | 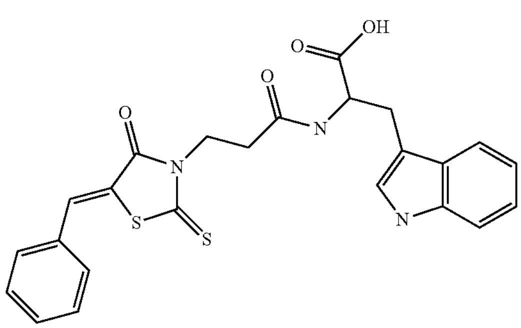 [SMILES: O=C(CCN1C(=O)/C(=C/c2ccccc2)SC1=S)NC(Cc1c[nH]c2ccccc12)C(=O)O] | 479.6 |

TABLE 7-continued
Phenmethylene-Thiazole Alkanoic Acids ($R^3$ = OH)
| ID | Structure | MW |
|---|---|---|
| IIb-248 | 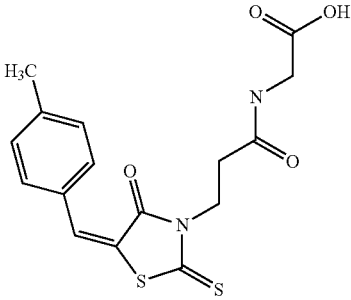 [SMILES: Cc1ccc(/C=C2/SC(=S)N(CCC(=O)NCC(=O)O)C2=O)cc1] | 364.4 |
| IIb-249 | 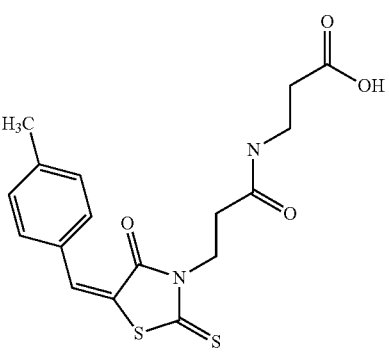 [SMILES: Cc1ccc(/C=C2/SC(=S)N(CCC(=O)NCCC(=O)O)C2=O)cc1] | 378.5 |
| IIb-250 | 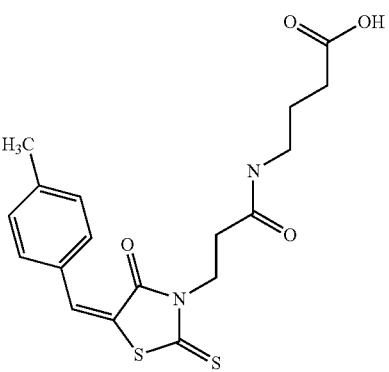 [SMILES: Cc1ccc(/C=C2/SC(=S)N(CCC(=O)NCCCC(=O)O)C2=O)cc1] | 392.5 |
| IIb-251 | 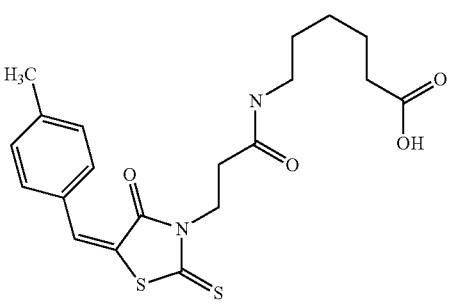 [SMILES: Cc1ccc(/C=C2/SC(=S)N(CCC(=O)NCCCCCC(=O)O)C2=O)cc1] | 420.6 |

TABLE 7-continued

Phenmethylene-Thiazole Alkanoic Acids (R³ = OH)

| ID | Structure | MW |
|---|---|---|
| IIb-252 | 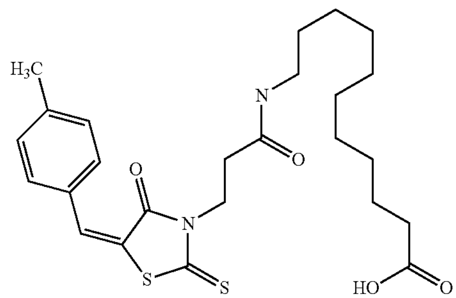 [SMILES: Cc1ccc(/C=C2/SC(=S)N(CCC(=O)NCCCCCCCCCCC(=O)O)C2=O)cc1] | 490.7 |
| IIb-253 | 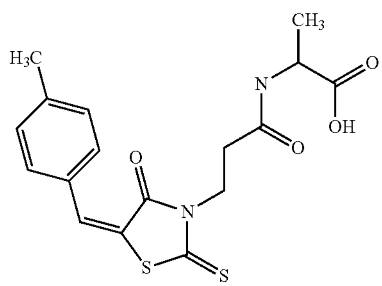 [SMILES: Cc1ccc(/C=C2/SC(=S)N(CCC(=O)NC(C)C(=O)O)C2=O)cc1] | 378.5 |
| IIb-254 | 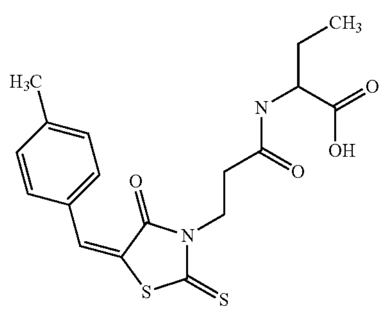 [SMILES: CCC(NC(=O)CCN1C(=O)/C(=C\c2ccc(C)cc2)SC1=S)C(=O)O] | 392.5 |
| IIb-255 | 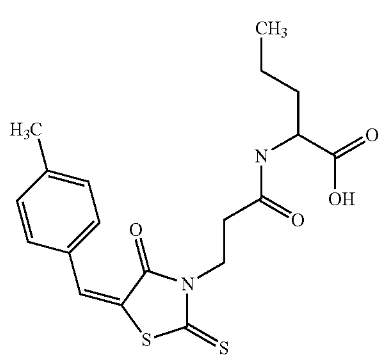 [SMILES: CCCC(NC(=O)CCN1C(=O)/C(=C\c2ccc(C)cc2)SC1=S)C(=O)O] | 406.5 |

TABLE 7-continued

Phenmethylene-Thiazole Alkanoic Acids ($R^3$ = OH)

| ID | Structure | MW |
|---|---|---|
| IIb-256 | 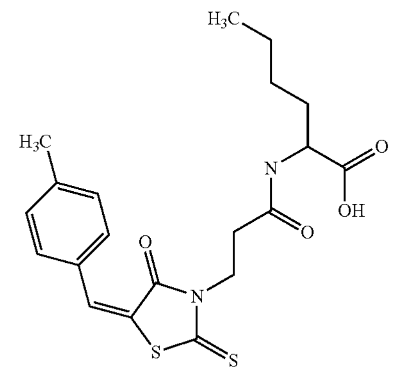 [SMILES: CCCCC(NC(=O)CCN1C(=O)/C(=C\c2ccc(C)cc2)SC1=S)C(=O)O] | 420.6 |
| IIb-257 | 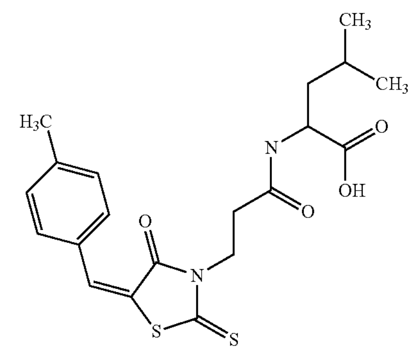 [SMILES: Cc1ccc(/C=C2/SC(=S)N(CCC(=O)NC(CC(C)C)C(=O)O)C2=O)cc1] | 420.6 |
| IIb-258 | 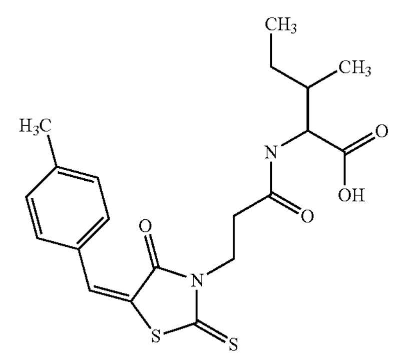 [SMILES: CCC(C)C(NC(=O)CCN1C(=O)/C(=C\c2ccc(C)cc2)SC1=S)C(=O)O] | 420.6 |
| IIb-259 | 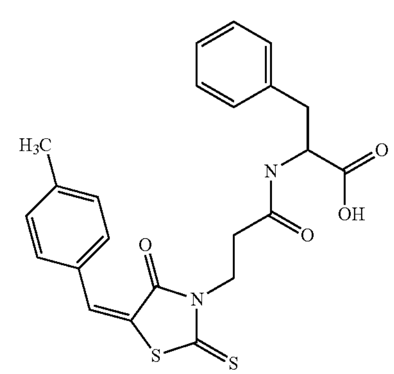 [SMILES: Cc1ccc(/C=C2/SC(=S)N(CCC(=O)NC(Cc3ccccc3)C(=O)O)C2=O)cc1] | 454.6 |

TABLE 7-continued
Phenmethylene-Thiazole Alkanoic Acids (R³ = OH)
| ID | Structure | MW |
|---|---|---|
| IIb-260 | 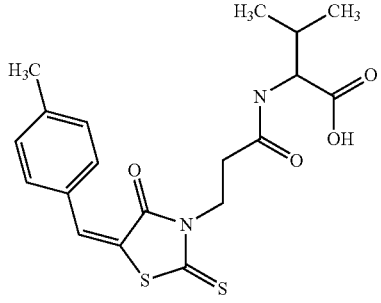 [SMILES: Cc1ccc(/C=C2/SC(=S)N(CCC(=O)NC(C(=O)O)C(C)C)C2=O)cc1] | 406.5 |
| IIb-261 | 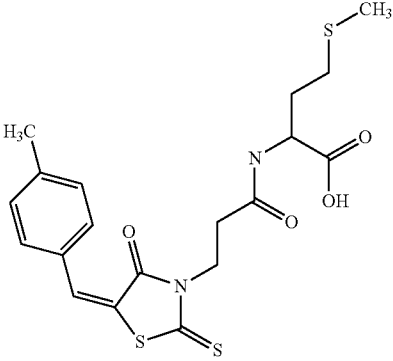 [SMILES: CSCCC(NC(=O)CCN1C(=O)/C(=C\c2ccc(C)cc2)SC1=S)C(=O)O] | 438.6 |
| IIb-262 | 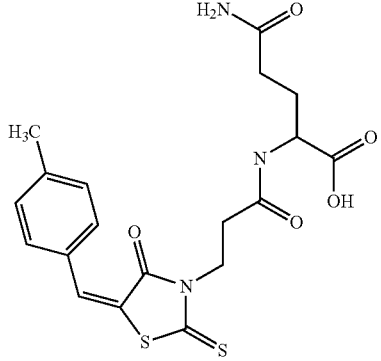 [SMILES: Cc1ccc(/C=C2/SC(=S)N(CCC(=O)NC(CCC(N)=O)C(=O)O)C2=O)cc1] | 435.5 |
| IIb-263 | 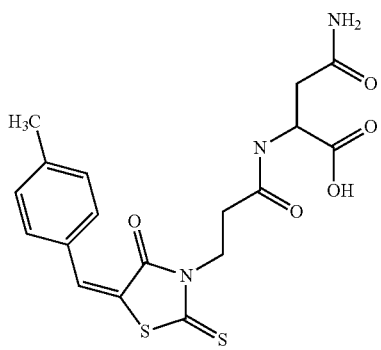 [SMILES: Cc1ccc(/C=C2/SC(=S)N(CCC(=O)NC(CC(N)=O)C(=O)O)C2=O)cc1] | 421.5 |

TABLE 7-continued

Phenmethylene-Thiazole Alkanoic Acids (R³ = OH)

| ID | Structure | MW |
|---|---|---|
| IIb-264 | 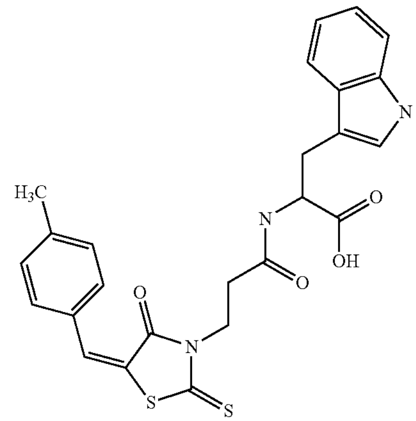 [SMILES: Cc1ccc(/C=C2/SC(=S)N(CCC(=O)NC(Cc3c[nH]c4ccccc34)C(=O)O)C2=O)cc1] | 493.6 |
| IIb-265 | 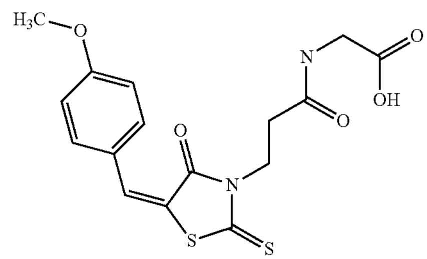 [SMILES: COc1ccc(/C=C2/SC(=S)N(CCC(=O)NCC(=O)O)C2=O)cc1] | 380.4 |
| IIb-266 | 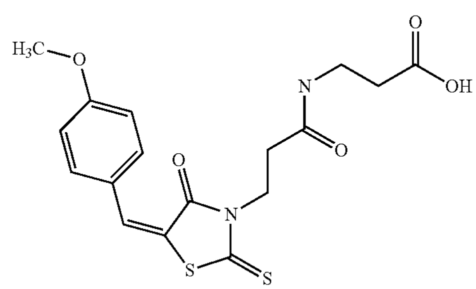 [SMILES: COc1ccc(/C=C2/SC(=S)N(CCC(=O)NCCC(=O)O)C2=O)cc1] | 394.5 |
| IIb-267 | 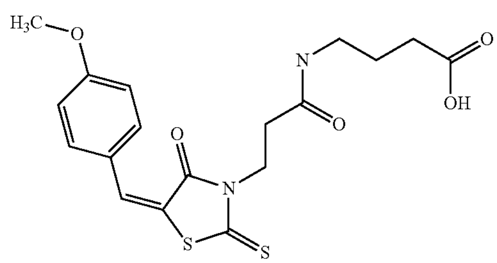 [SMILES: COc1ccc(/C=C2/SC(=S)N(CCC(=O)NCCCC(=O)O)C2=O)cc1] | 408.5 |
| IIb-268 | 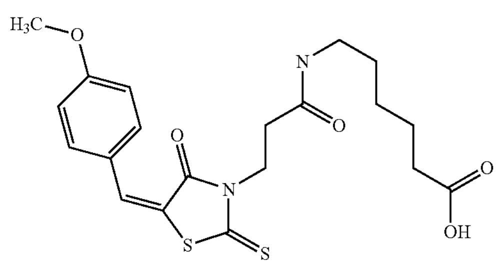 [SMILES: COc1ccc(/C=C2/SC(=S)N(CCC(=O)NCCCCCC(=O)O)C2=O)cc1] | 436.6 |

TABLE 7-continued

Phenmethylene-Thiazole Alkanoic Acids ($R^3$ = OH)

| ID | Structure | MW |
|---|---|---|
| IIb-269 | 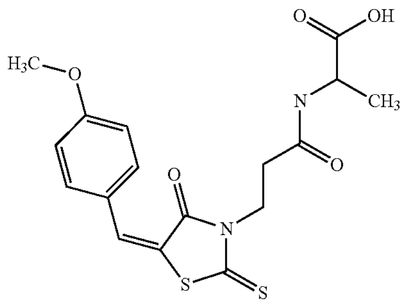 [SMILES: COc1ccc(/C=C2/SC(=S)N(CCC(=O)NC(C)C(=O)O)C2=O)cc1] | 394.5 |
| IIb-270 | 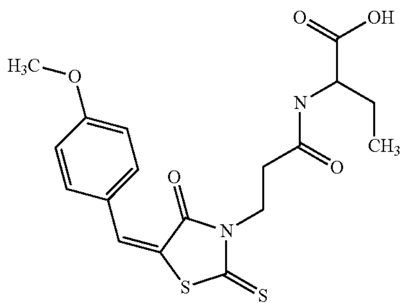 [SMILES: CCC(NC(=O)CCN1C(=O)/C(=C\c2ccc(OC)cc2)SC1=S)C(=O)O] | 408.5 |
| IIb-271 | 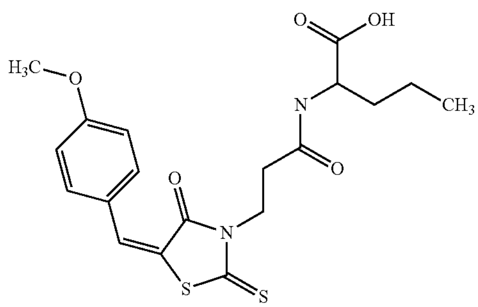 [SMILES: CCCC(NC(=O)CCN1C(=O)/C(=C\c2ccc(OC)cc2)SC1=S)C(=O)O] | 422.5 |
| IIb-272 | 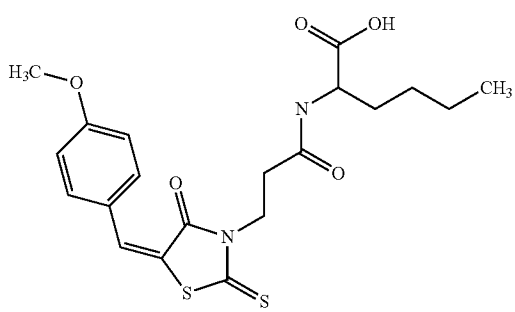 [SMILES: CCCCC(NC(=O)CCN1C(=O)/C(=C\c2ccc(OC)cc2)SC1=S)C(=O)O] | 436.6 |
| IIb-273 | 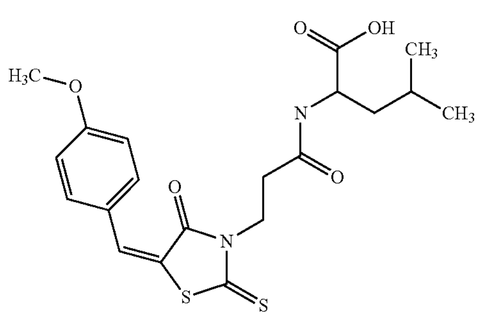 [SMILES: COc1ccc(/C=C2/SC(=S)N(CCC(=O)NC(CC(C)C)C(=O)O)C2=O)cc1] | 436.6 |

TABLE 7-continued

Phenmethylene-Thiazole Alkanoic Acids ($R^3$ = OH)

| ID | Structure | MW |
|---|---|---|
| IIb-274 | 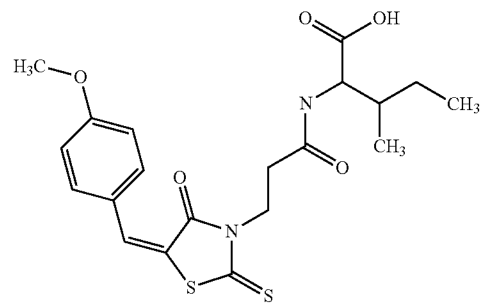 [SMILES: CCC(C)C(NC(=O)CCN1C(=O)/C(=C\c2ccc(OC)cc2)SC1=S)C(=O)O] | 436.6 |
| IIb-275 | 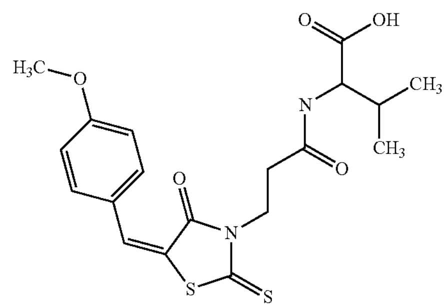 [SMILES: COc1ccc(/C=C2/SC(=S)N(CCC(=O)NC(C(=O)O)C(C)C)C2=O)cc1] | 422.5 |
| IIb-276 | 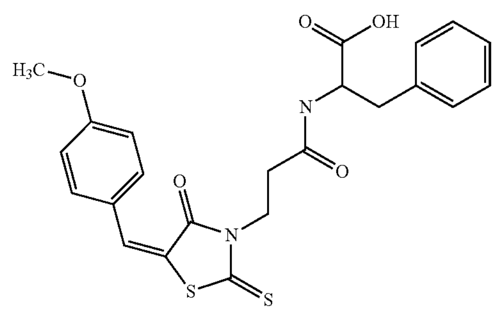 [SMILES: COc1ccc(/C=C2/SC(=S)N(CCC(=O)NC(Cc3ccccc3)C(=O)O)C2=O)cc1] | 470.6 |
| IIb-277 | 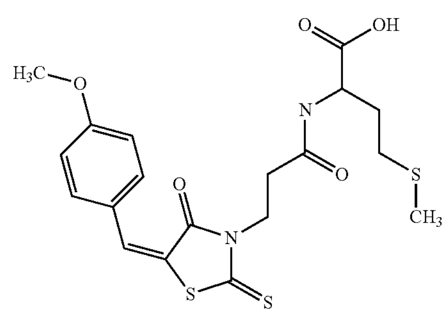 | 454.6 |
| IIb-278 | 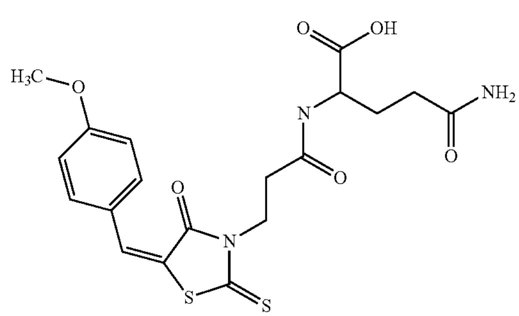 [SMILES: COc1ccc(/C=C2/SC(=S)N(CCC(=O)NC(CCC(N)=O)C(=O)O)C2=O)cc1] | 451.5 |

TABLE 7-continued

Phenmethylene-Thiazole Alkanoic Acids ($R^3$ = OH)

| ID | Structure | MW |
| --- | --- | --- |
| IIb-279 | 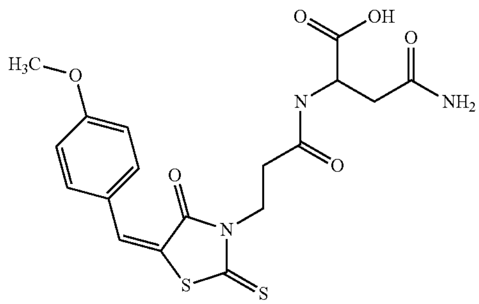 [SMILES: COc1ccc(/C=C2/SC(=S)N(CCC(=O)NC(CC(N)=O)C(=O)O)C2=O)cc1] | 437.5 |
| IIb-280 | 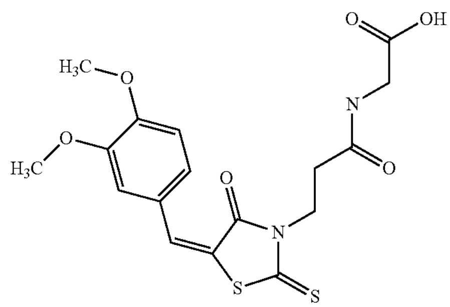 [SMILES: COc1ccc(/C=C2/SC(=S)N(CCC(=O)NCC(=O)O)C2=O)cc1OC] | 410.5 |
| IIb-281 | 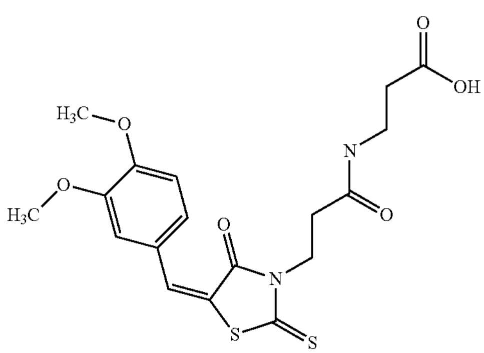 [SMILES: COc1ccc(/C=C2/SC(=S)N(CCC(=O)NCCC(=O)O)C2=O)cc1OC] | 424.5 |
| IIb-282 | 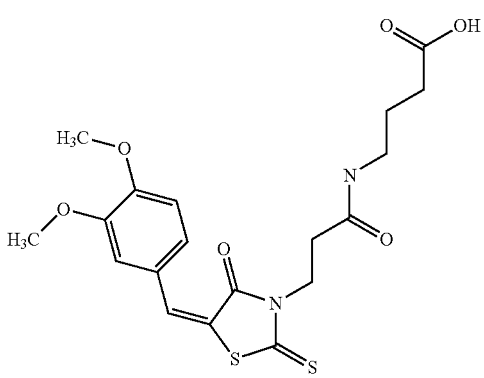 [SMILES: COc1ccc(/C=C2/SC(=S)N(CCC(=O)NCCCC(=O)O)C2=O)cc1OC] | 438.5 |

TABLE 7-continued

Phenmethylene-Thiazole Alkanoic Acids ($R^3$ = OH)

| ID | Structure | MW |
|---|---|---|
| IIb-283 | 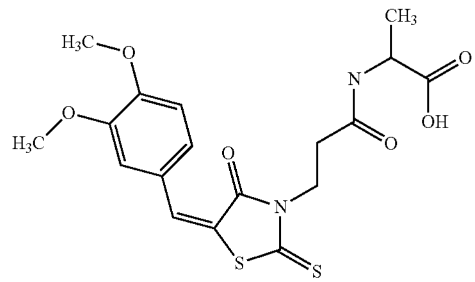 [SMILES: COc1ccc(/C=C2/SC(=S)N(CCC(=O)NC(C)C(=O)O)C2=O)cc1OC] | 424.5 |
| IIb-284 | 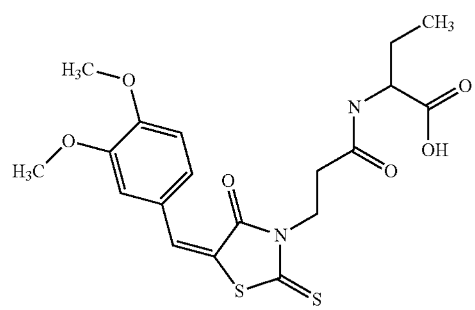 [SMILES: CCC(NC(=O)CCN1C(=O)/C(=C\c2ccc(OC)c(OC)c2)SC1=S)C(=O)O] | 438.5 |
| IIb-285 | 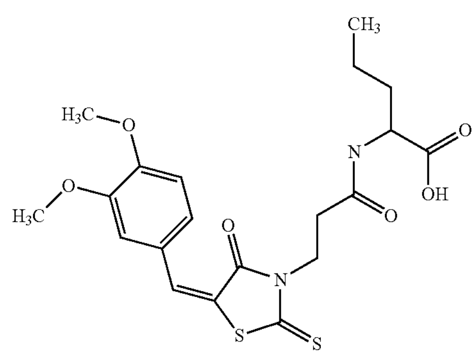 [SMILES: CCCC(NC(=O)CCN1C(=O)/C(=C\c2ccc(OC)c(OC)c2)SC1=S)C(=O)O] | 452.6 |
| IIb-286 | 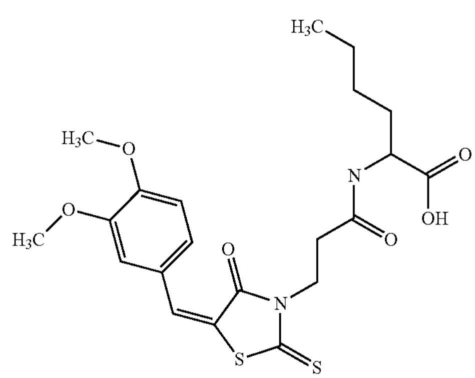 [SMILES: CCCCC(NC(=O)CCN1C(=O)/C(=C\c2ccc(OC)c(OC)c2)SC1=S)C(=O)O] | 466.6 |

TABLE 7-continued

Phenmethylene-Thiazole Alkanoic Acids ($R^3$ = OH)

| ID | Structure | MW |
|---|---|---|
| IIb-287 | 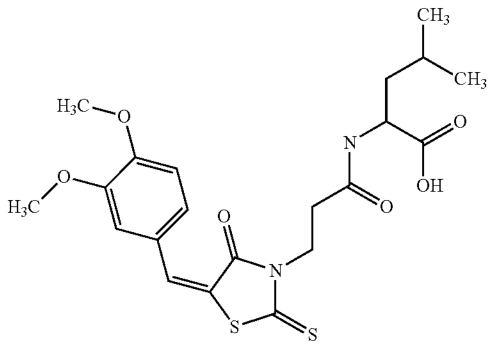 [SMILES: COc1ccc(/C=C2/SC(=S)N(CCC(=O)NC(CC(C)C)C(=O)O)C2=O)cc1OC] | 466.6 |
| IIb-288 | 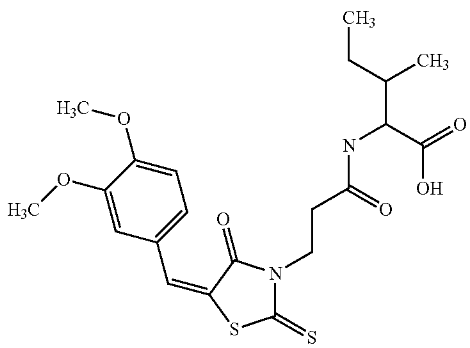 [SMILES: CCC(C)C(NC(=O)CCN1C(=O)/C(=C\c2ccc(OC)c(OC)c2)SC1=S)C(=O)O] | 466.6 |
| IIb-289 | 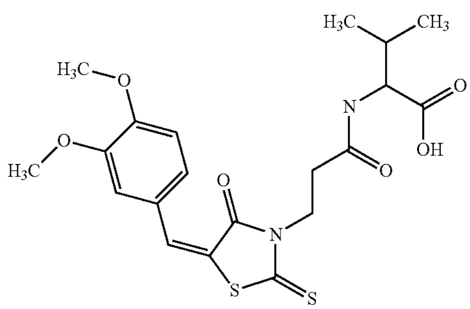 [SMILES: COc1ccc(/C=C2/SC(=S)N(CCC(=O)NC(C(=O)O)C(C)C)C2=O)cc1OC] | 452.6 |
| IIb-290 | 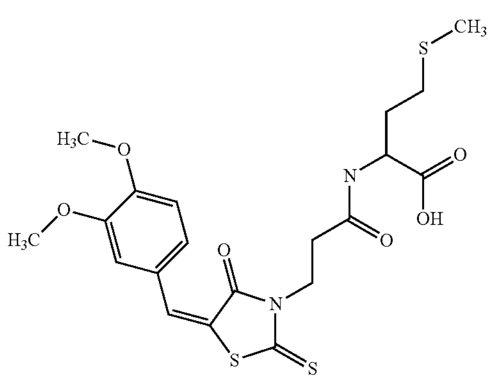 | 484.6 |

TABLE 7-continued

Phenmethylene-Thiazole Alkanoic Acids ($R^3$ = OH)

| ID | Structure | MW |
|---|---|---|
| IIb-291 | 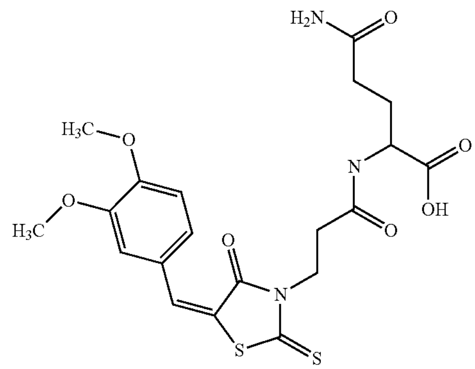 [SMILES: COc1ccc(/C=C2/SC(=S)N(CCC(=O)NC(CCC(N)=O)C(=O)O)C2=O)cc1OC] | 481.6 |
| IIb-292 | 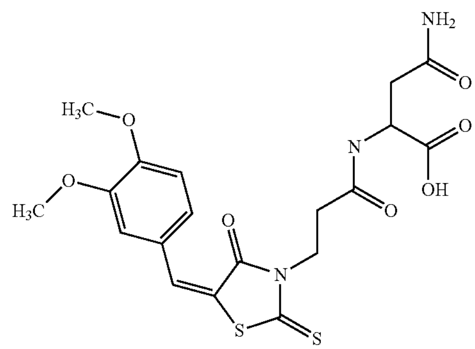 [SMILES: COc1ccc(/C=C2/SC(=S)N(CCC(=O)NC(CC(N)=O)C(=O)O)C2=O)cc1OC] | 467.5 |
| IIb-293 | 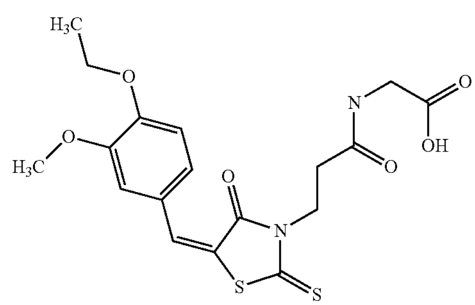 [SMILES: CCOc1ccc(/C=C2/SC(=S)N(CCC(=O)NCC(=O)O)C2=O)cc1OC] | 424.5 |
| IIb-294 | 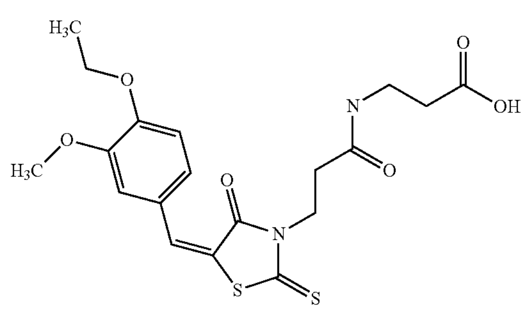 [SMILES: CCOc1ccc(/C=C2/SC(=S)N(CCC(=O)NCCC(=O)O)C2=O)cc1OC] | 438.5 |

TABLE 7-continued

Phenmethylene-Thiazole Alkanoic Acids ($R^3$ = OH)

| ID | Structure | MW |
|---|---|---|
| IIb-295 | 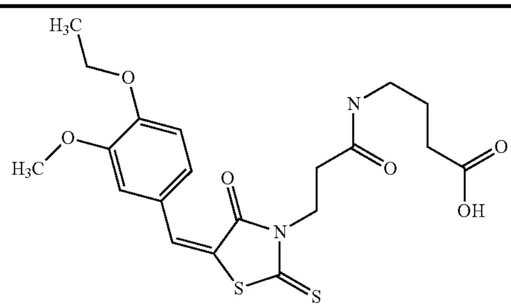 | 452.6 |
| IIb-296 | 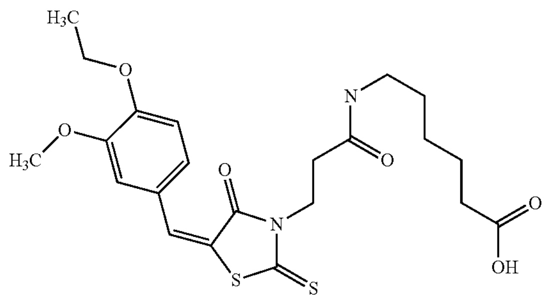 [SMILES: CCOc1ccc(/C=C2/SC(=S)N(CCC(=O)NCCCCCC(=O)O)C2=O)cc1OC] | 480.6 |
| IIb-297 | 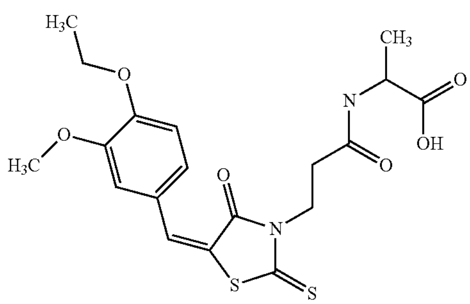 [SMILES: CCOc1ccc(/C=C2/SC(=S)N(CCC(=O)NC(C)C(=O)O)C2=O)cc1OC] | 438.5 |
| IIb-298 | 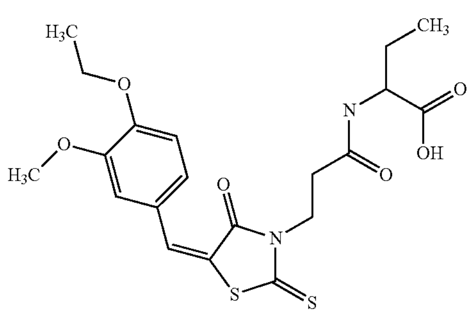 [SMILES: CCOc1ccc(/C=C2/SC(=S)N(CCC(=O)NC(CC)C(=O)O)C2=O)cc1OC] | 452.6 |
| IIb-299 | 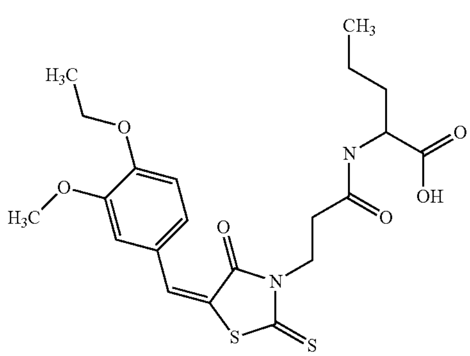 [SMILES: CCCC(NC(=O)CCN1C(=O)/C(=C\c2ccc(OCC)c(OC)c2)SC1=S)C(=O)O] | 466.6 |

TABLE 7-continued

Phenmethylene-Thiazole Alkanoic Acids (R³ = OH)

| ID | Structure | MW |
| --- | --- | --- |
| IIb-300 | 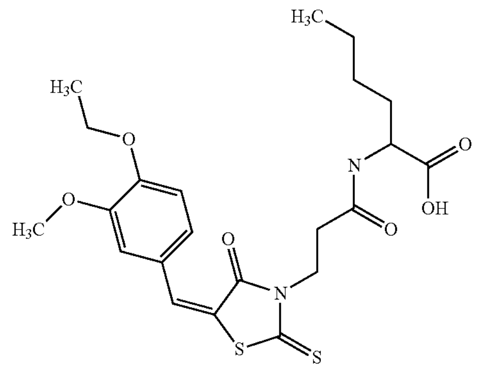 [SMILES: CCCCC(NC(=O)CCN1C(=O)/C(=C\c2ccc(OCC)c(OC)c2)SC1=S)C(=O)O] | 480.6 |
| IIb-301 | 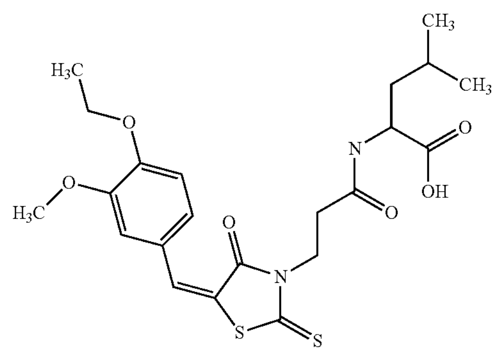 [SMILES: CCOc1ccc(/C=C2/SC(=S)N(CCC(=O)NC(CC(C)C)C(=O)O)C2=O)cc1OC] | 480.6 |
| IIb-302 | 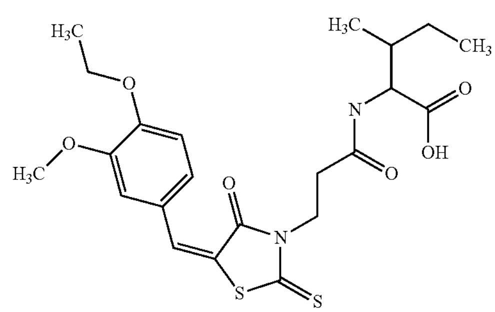 [SMILES: CCOc1ccc(/C=C2/SC(=S)N(CCC(=O)NC(C(=O)O)C(C)CC)C2=O)cc1OC] | 480.6 |
| IIb-303 | 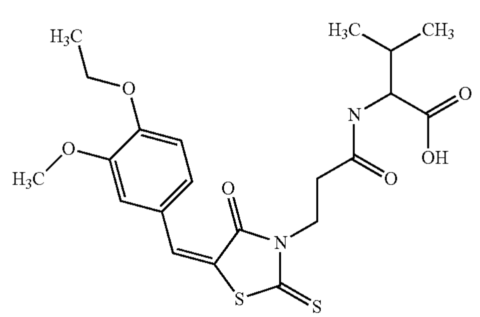 [SMILES: CCOc1ccc(/C=C2/SC(=S)N(CCC(=O)NC(C(=O)O)C(C)C)C2=O)cc1OC] | 466.6 |

TABLE 7-continued

Phenmethylene-Thiazole Alkanoic Acids ($R^3$ = OH)

| ID | Structure | MW |
|---|---|---|
| IIb-304 | 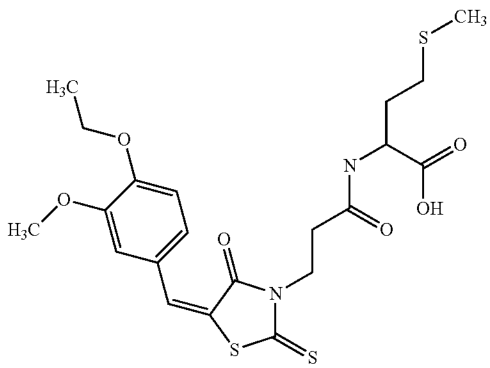 | 498.6 |
| IIb-305 | 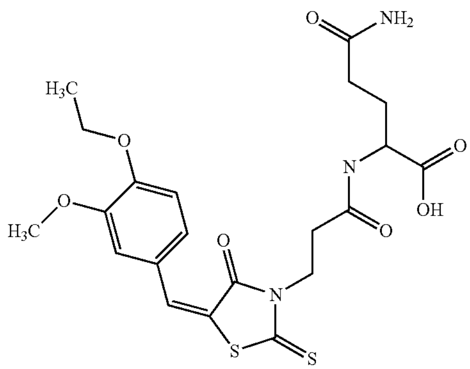 [SMILES: CCOc1ccc(/C=C2/SC(=S)N(CCC(=O)NC(CCC(N)=O)C(=O)O)C2=O)cc1OC] | 495.6 |
| IIb-306 | 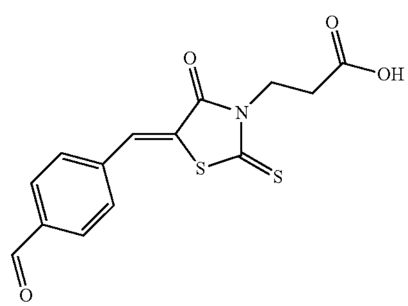 [SMILES: O=Cc1ccc(/C=C2\SC(=S)N(CCC(=O)O)C2=O)cc1] | 321.4 |
| IIb-307 | 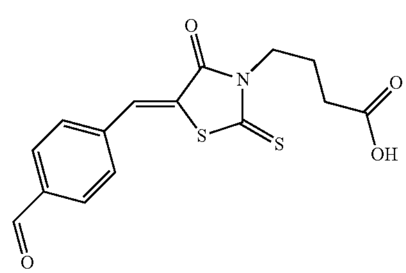 [SMILES: O=Cc1ccc(/C=C2\SC(=S)N(CCCC(=O)O)C2=O)cc1] | 335.4 |
| IIb-308 | 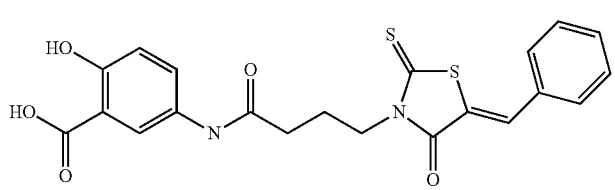 [SMILES: O=C(CCCN1C(=O)/C(=C/c2ccccc2)SC1=S)Nc1ccc(O)c(C(=O)O)c1] | 442.5 |

TABLE 7-continued

Phenmethylene-Thiazole Alkanoic Acids ($R^3$ = OH)

| ID | Structure | MW |
|---|---|---|
| IIb-309 | 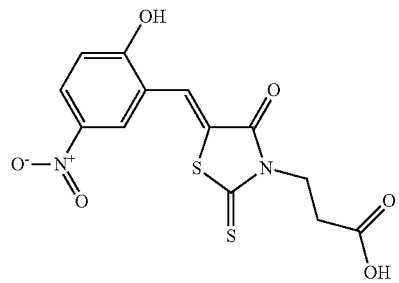 [SMILES: O=C(O)CCN1C(=O)/C(=C/c2cc([N+](=O)[O-])ccc2O)SC1=S] | 354.4 |
| IIb-310 | 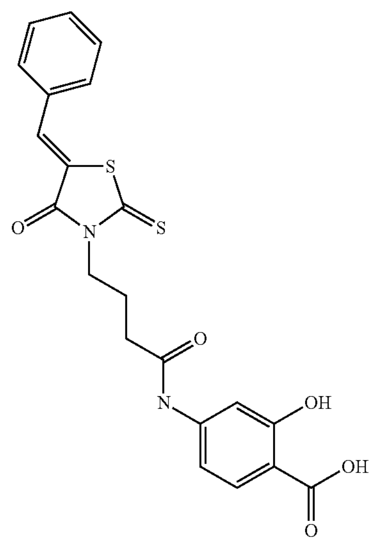 [SMILES: O=C(CCCN1C(=O)/C(=C/c2ccccc2)SC1=S)Nc1ccc(C(=O)O)c(O)c1] | 442.5 |
| IIb-311 | 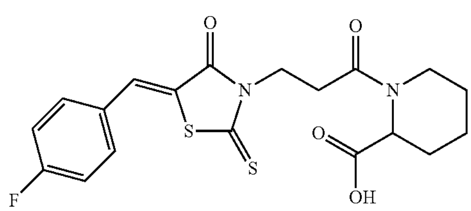 [SMILES: O=C(O)C1CCCCN1C(=O)CCN1C(=O)/C(=C/c2ccc(F)cc2)SC1=S] | 422.5 |
| IIb-312 | 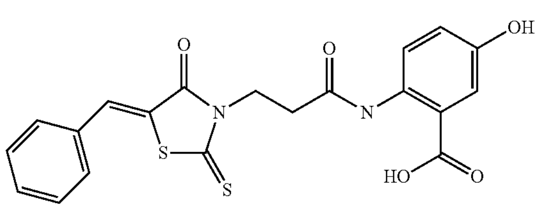 [SMILES: O=C(CCN1C(=O)/C(=C/c2ccccc2)SC1=S)Nc1ccc(O)cc1C(=O)O] | 428.5 |

TABLE 7-continued

Phenmethylene-Thiazole Alkanoic Acids ($R^3$ = OH)

| ID | Structure | MW |
| --- | --- | --- |
| IIb-313 | 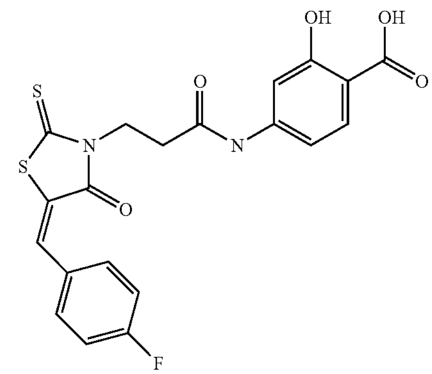 [SMILES: O=C(CCN1C(=O)/C(=C\c2ccc(F)cc2)SC1=S)Nc1ccc(C(=O)O)c(O)c1] | 446.5 |
| IIb-314 | 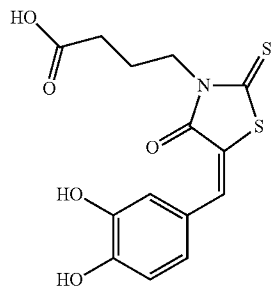 [SMILES: O=C(O)CCCN1C(=O)/C(=C\c2ccc(O)c(O)c2)SC1=S] | 339.4 |
| IIb-315 | 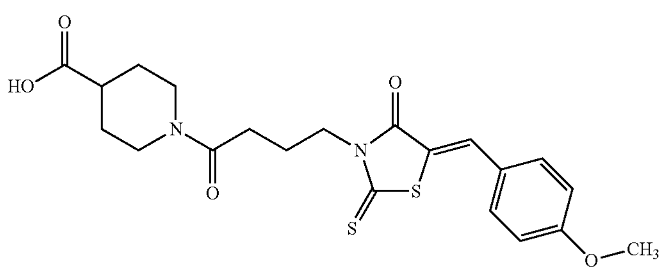 [SMILES: COc1ccc(/C=C2\SC(=S)N(CCCC(=O)N3CCC(C(=O)O)CC3)C2=O)cc1] | 448.6 |
| IIb-316 | 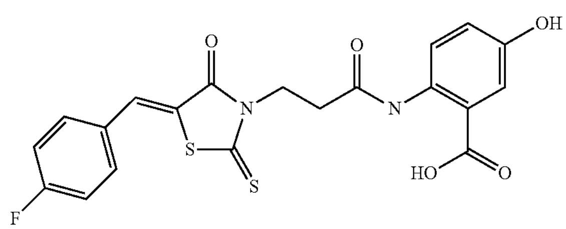 [SMILES: O=C(CCN1C(=O)/C(=C/c2ccc(F)cc2)SC1=S)Nc1ccc(O)cc1C(=O)O] | 446.5 |
| IIb-317 | 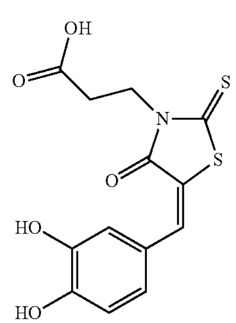 [SMILES: O=C(O)CCN1C(=O)/C(=C\c2ccc(O)c(O)c2)SC1=S] | 325.4 |

TABLE 7-continued

Phenmethylene-Thiazole Alkanoic Acids ($R^3$ = OH)

| ID | Structure | MW |
|---|---|---|
| IIb-318 | 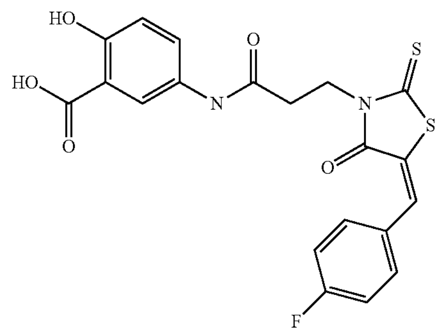 [SMILES: O=C(CCN1C(=O)/C(=C\c2ccc(F)cc2)SC1=S)Nc1ccc(O)c(C(=O)O)c1] | 446.5 |
| IIb-319 | 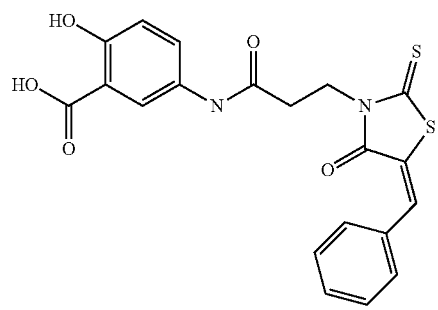 [SMILES: O=C(CCN1C(=O)/C(=C\c2ccccc2)SC1=S)Nc1ccc(O)c(C(=O)O)c1] | 428.5 |
| IIb-320 | 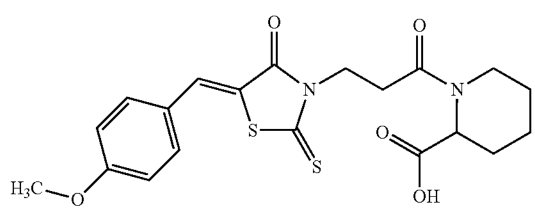 [SMILES: COc1ccc(/C=C2\SC(=S)N(CCC(=O)N3CCCCC3C(=O)O)C2=O)cc1] | 434.5 |
| IIb-321 | 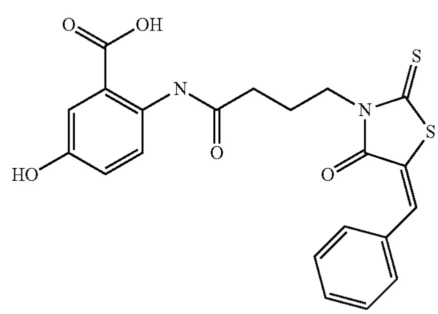 [SMILES: O=C(CCCN1C(=O)/C(=C\c2ccccc2)SC1=S)Nc1ccc(O)cc1C(=O)O] | 442.5 |
| IIb-322 | 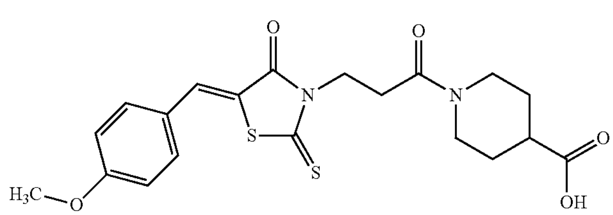 [SMILES: COc1ccc(/C=C2\SC(=S)N(CCC(=O)N3CCC(C(=O)O)CC3)C2=O)cc1] | 434.5 |

TABLE 7-continued

Phenmethylene-Thiazole Alkanoic Acids (R³ = OH)

| ID | Structure | MW |
|---|---|---|
| IIb-323 | 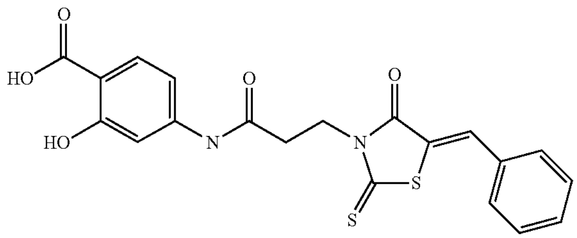 [SMILES: O=C(CCN1C(=O)/C(=C/c2ccccc2)SC1=S)Nc1ccc(C(=O)O)c(O)c1] | 428.5 |
| IIb-324 | 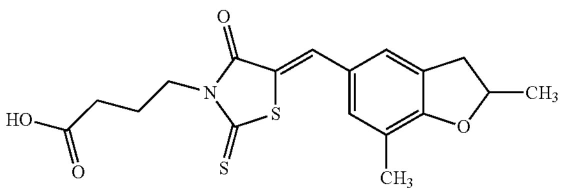 [SMILES: Cc1cc(/C=C2\SC(=S)N(CCCC(=O)O)C2=O)cc2c1OC(C)C2] | 377.5 |
| IIb-325 | 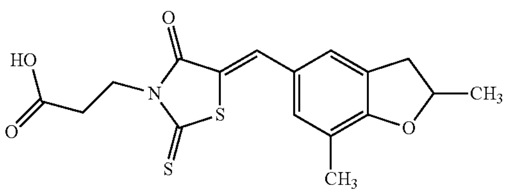 [SMILES: Cc1cc(/C=C2\SC(=S)N(CCC(=O)O)C2=O)cc2c1OC(C)C2] | 363.5 |
| IIb-326 | 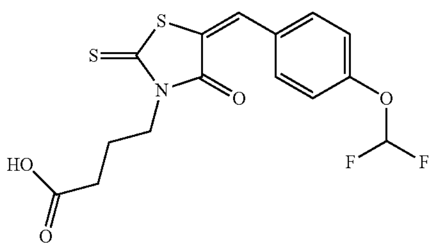 [SMILES: O=C(O)CCCN1C(=O)/C(=C\c2ccc(OC(F)F)cc2)SC1=S] | 373.4 |
| IIb-327 | 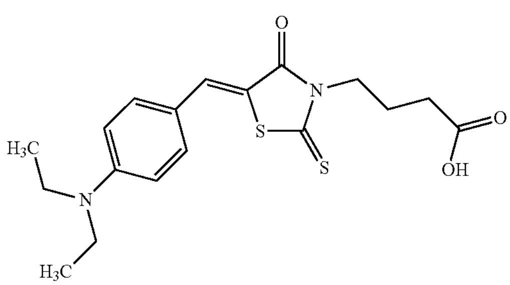 [SMILES: CCN(CC)c1ccc(/C=C2\SC(=S)N(CCCC(=O)O)C2=O)cc1] | 378.5 |
| IIb-328 | 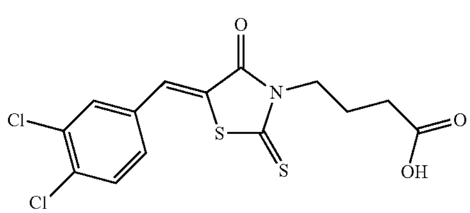 [SMILES: O=C(O)CCCN1C(=O)/C(=C/c2ccc(Cl)c(Cl)c2)SC1=S] | 376.3 |

TABLE 7-continued
Phenmethylene-Thiazole Alkanoic Acids ($R^3$ = OH)
| ID | Structure | MW |
|---|---|---|
| IIb-329 | 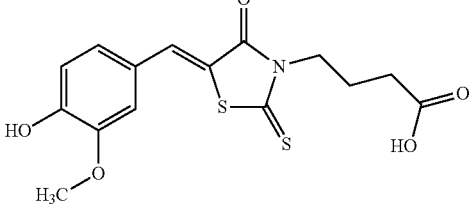 | 353.4 |
| IIb-330 | 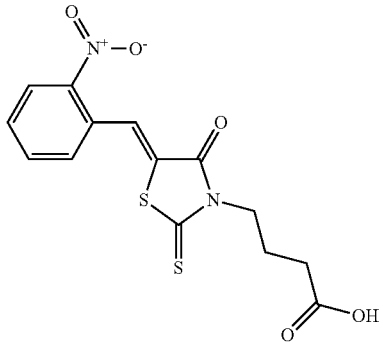 [SMILES: O=C(O)CCCN1C(=O)/C(=C/c2ccccc2[N+](=O)[O-])SC1=S] | 352.4 |
| IIb-331 | 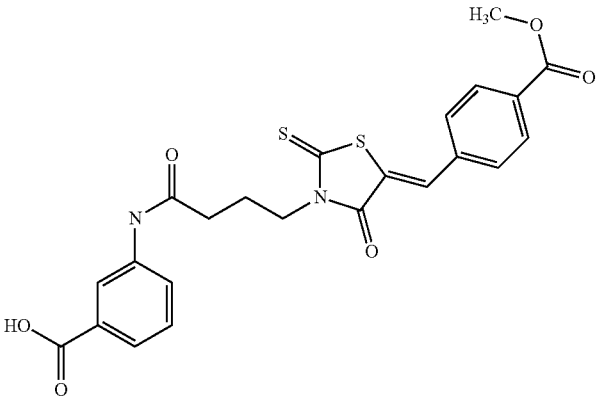 [SMILES: COC(=O)c1ccc(/C=C2\SC(=S)N(CCCC(=O)Nc3cccc(C(=O)O)c3)C2=O)cc1] | 484.6 |
| IIb-332 | 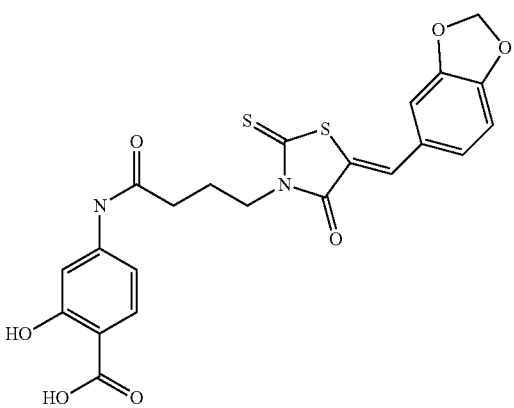 [SMILES: O=C(CCCN1C(=O)/C(=C/c2ccc3c(c2)OCO3)SC1=S)Nc1ccc(C(=O)O)c(O)c1] | 486.5 |

TABLE 7-continued

Phenmethylene-Thiazole Alkanoic Acids ($R^3$ = OH)

| ID | Structure | MW |
| --- | --- | --- |
| IIb-333 | 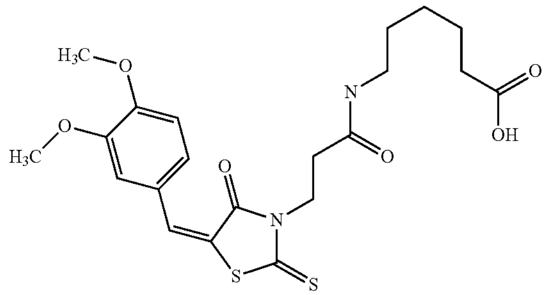 [SMILES: COc1ccc(/C=C2/SC(=S)N(CCC(=O)NCCCCCC(=O)O)C2=O)cc1OC] | 466.6 |
| IIb-334 | 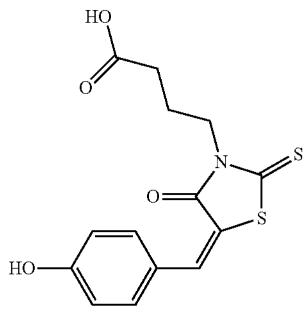 [SMILES: O=C(O)CCCN1C(=O)/C(=C\c2ccc(O)cc2)SC1=S] | 323.4 |
| IIb-335 | 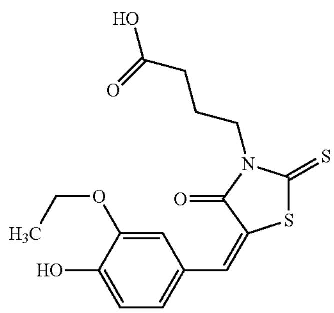 [SMILES: CCOc1cc(/C=C2/SC(=S)N(CCCC(=O)O)C2=O)ccc1O] | 367.4 |
| IIb-336 | 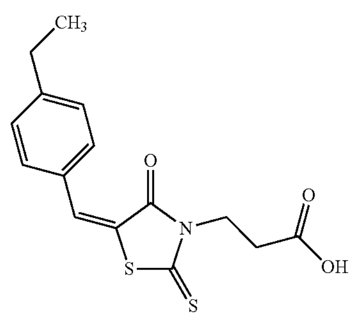 [SMILES: CCc1ccc(/C=C2/SC(=S)N(CCC(=O)O)C2=O)cc1] | 321.4 |
| IIb-337 | 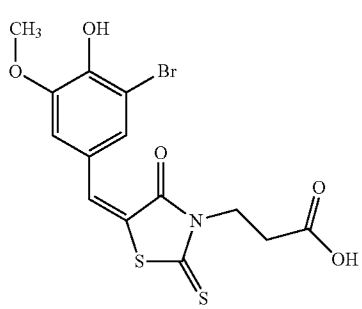 [SMILES: COc1cc(/C=C2/SC(=S)N(CCC(=O)O)C2=O)cc(Br)c1O] | 418.3 |

TABLE 7-continued

Phenmethylene-Thiazole Alkanoic Acids ($R^3$ = OH)

| ID | Structure | MW |
| --- | --- | --- |
| IIb-338 | 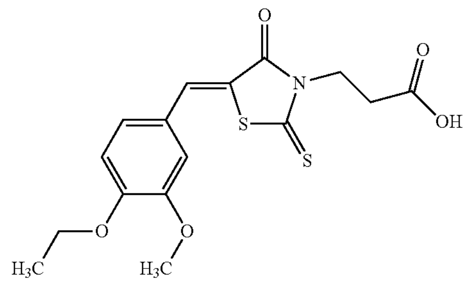 [SMILES: CCOc1ccc(/C=C2\SC(=S)N(CCC(=O)O)C2=O)cc1OC] | 367.4 |
| IIb-339 | 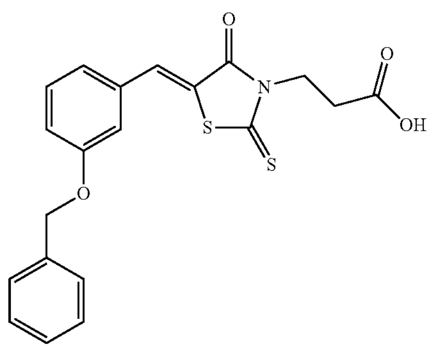 [SMILES: O=C(O)CCN1C(=O)/C(=C/c2cccc(OCc3ccccc3)c2)SC1=S] | 399.5 |
| IIb-340 | 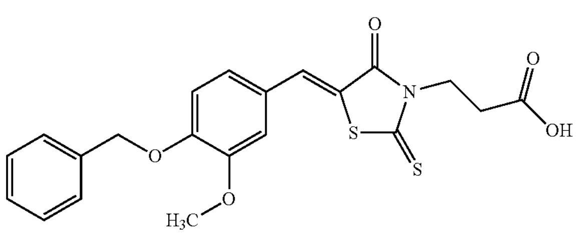 [SMILES: COc1cc(/C=C2\SC(=S)N(CCC(=O)O)C2=O)ccc1OCc1ccccc1] | 429.5 |
| IIb-341 | 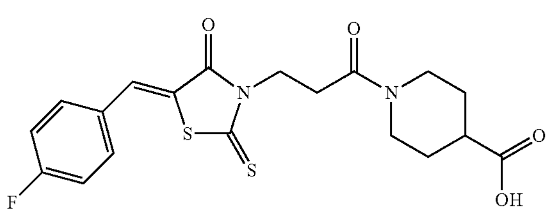 [SMILES: O=C(O)C1CCN(C(=O)CCN2C(=O)/C(=C/c3ccc(F)cc3)SC2=S)CC1] | 422.5 |

TABLE 7-continued

Phenmethylene-Thiazole Alkanoic Acids (R³ = OH)

| ID | Structure | MW |
|---|---|---|
| IIb-342 | 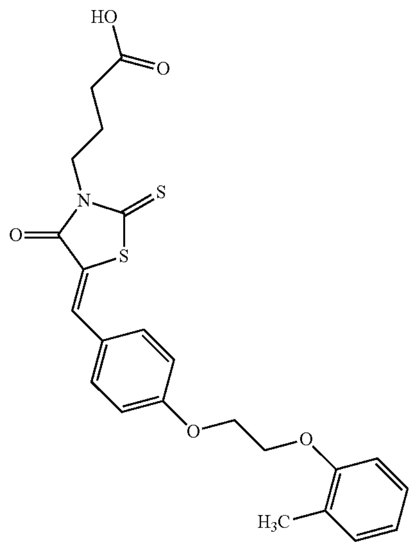 [SMILES: Cc1ccccc1OCCOc1ccc(/C=C2\SC(=S)N(CCCC(=O)O)C2=O)cc1] | 457.6 |
| IIb-343 | 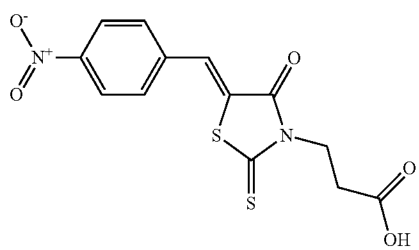 [SMILES: O=C(O)CCN1C(=O)/C(=C/c2ccc([N+](=O)[O-])cc2)SC1=S] | 338.4 |
| IIb-344 | 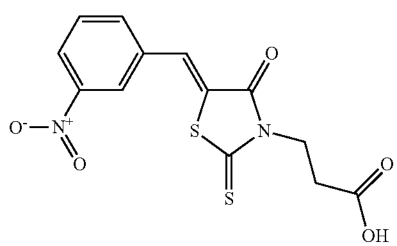 [SMILES: O=C(O)CCN1C(=O)/C(=C/c2cccc([N+](=O)[O-])c2)SC1=S] | 338.4 |
| IIb-345 | 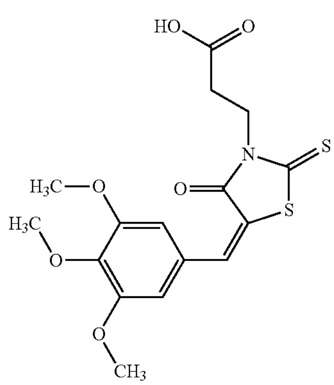 [SMILES: COc1cc(/C=C2/SC(=S)N(CCC(=O)O)C2=O)cc(OC)c1OC] | 383.4 |

TABLE 7-continued

Phenmethylene-Thiazole Alkanoic Acids ($R^3$ = OH)

| ID | Structure | MW |
|---|---|---|
| IIb-346 | 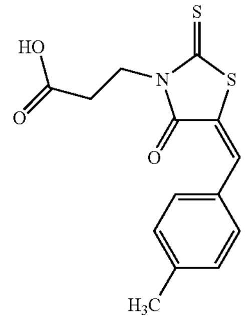 [SMILES: Cc1ccc(/C=C2/SC(=S)N(CCC(=O)O)C2=O)cc1] | 307.4 |
| IIb-347 | 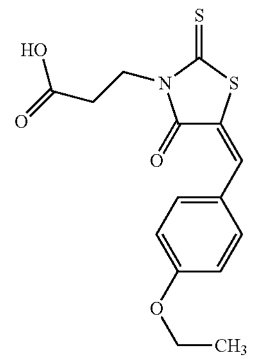 [SMILES: CCOc1ccc(/C=C2/SC(=S)N(CCC(=O)O)C2=O)cc1] | 337.4 |
| IIb-348 | 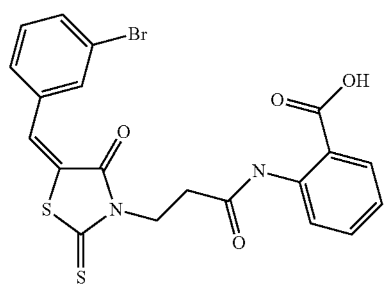 [SMILES: O=C(CCN1C(=O)/C(=C\c2cccc(Br)c2)SC1=S)Nc1ccccc1C(=O)O] | 491.4 |
| IIb-349 | 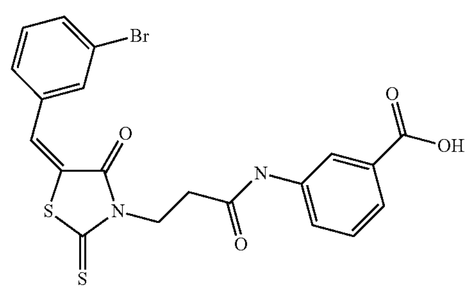 [SMILES: O=C(CCN1C(=O)/C(=C\c2cccc(Br)c2)SC1=S)Nc1cccc(C(=O)O)c1] | 491.4 |
| IIb-350 | 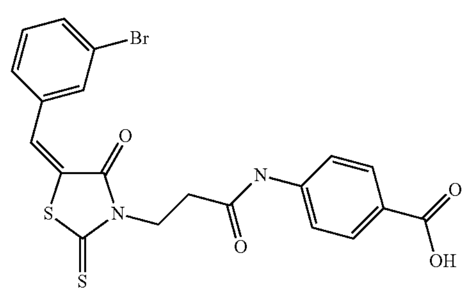 [SMILES: O=C(CCN1C(=O)/C(=C\c2cccc(Br)c2)SC1=S)Nc1ccc(C(=O)O)cc1] | 491.4 |

TABLE 7-continued

Phenmethylene-Thiazole Alkanoic Acids (R³ = OH)

| ID | Structure | MW |
|---|---|---|
| IIb-351 | 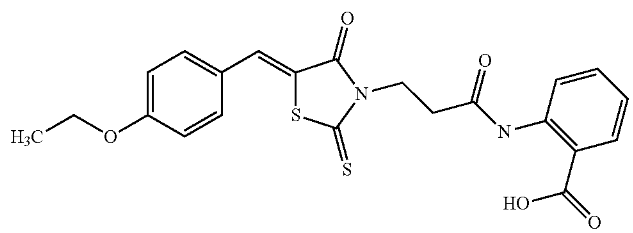 [SMILES: CCOc1ccc(/C=C2\SC(=S)N(CCC(=O)Nc3ccccc3C(=O)O)C2=O)cc1] | 456.5 |
| IIb-352 | 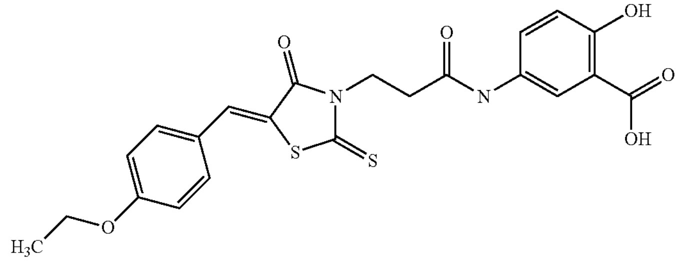 [SMILES: CCOc1ccc(/C=C2\SC(=S)N(CCC(=O)Nc3ccc(O)c(C(=O)O)c3)C2=O)cc1] | 472.5 |
| IIb-353 | 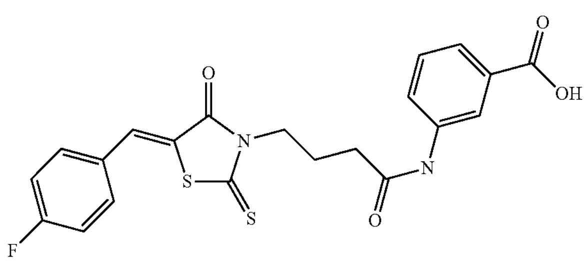 [SMILES: O=C(CCCN1C(=O)/C(=C/c2ccc(F)cc2)SC1=S)Nc1cccc(C(=O)O)c1] | 444.5 |
| IIb-354 | 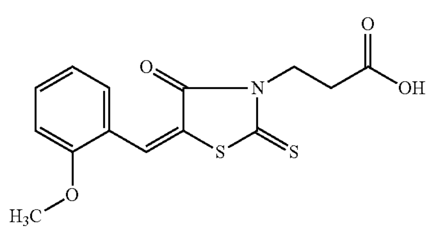 [SMILES: COc1ccccc1/C=C1/SC(=S)N(CCC(=O)O)C1=O] | 323.4 |
| IIb-355 | 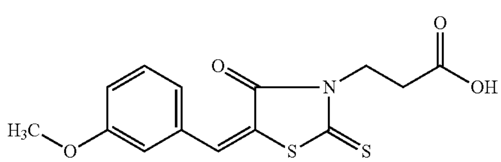 [SMILES: COc1cccc(/C=C2/SC(=S)N(CCC(=O)O)C2=O)c1] | 323.4 |
| IIb-356 | 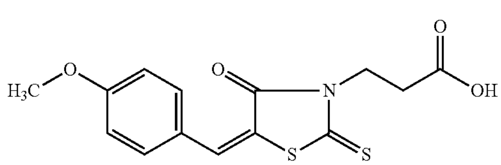 [SMILES: COc1ccc(/C=C2/SC(=S)N(CCC(=O)O)C2=O)cc1] | 323.4 |

TABLE 7-continued

Phenmethylene-Thiazole Alkanoic Acids ($R^3$ = OH)

| ID | Structure | MW |
| --- | --- | --- |
| IIb-357 | 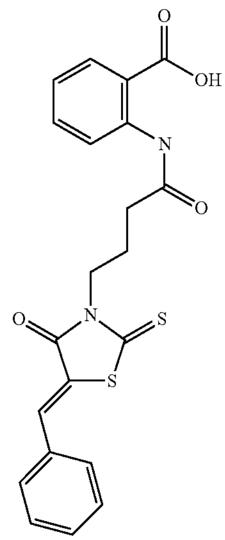 [SMILES: O=C(CCCN1C(=O)/C(=C/c2ccccc2)SC1=S)Nc1ccccc1C(=O)O] | 426.5 |
| IIb-358 | 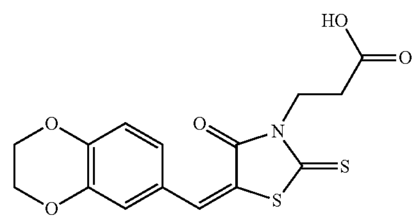 [SMILES: O=C(O)CCN1C(=O)/C(=C\c2ccc3c(c2)OCCO3)SC1=S] | 351.4 |
| IIb-359 | 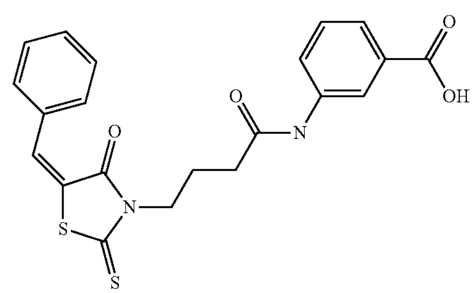 [SMILES: O=C(CCCN1C(=O)/C(=C\c2ccccc2)SC1=S)Nc1cccc(C(=O)O)c1] | 426.5 |
| IIb-360 | 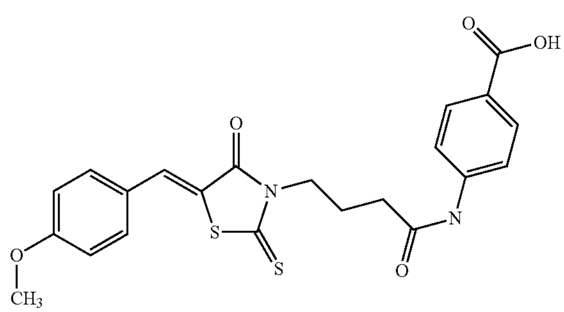 [SMILES: COc1ccc(/C=C2\SC(=S)N(CCCC(=O)Nc3ccc(C(=O)O)cc3)C2=O)cc1] | 456.5 |

TABLE 7-continued

Phenmethylene-Thiazole Alkanoic Acids ($R^3$ = OH)

| ID | Structure | MW |
|---|---|---|
| IIb-361 | 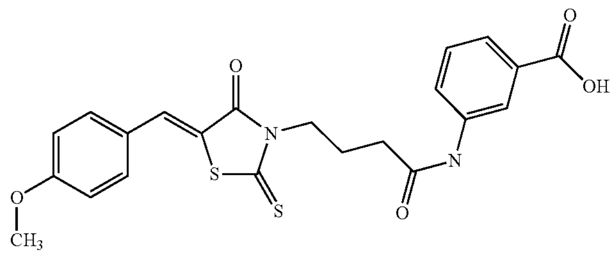 [SMILES: COc1ccc(/C=C2\SC(=S)N(CCCC(=O)Nc3cccc(C(=O)O)c3)C2=O)cc1] | 456.5 |
| IIb-362 | 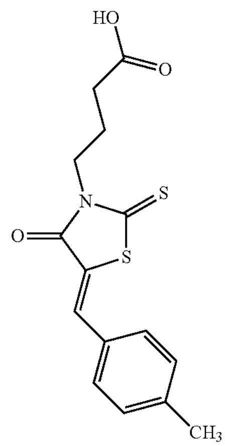 [SMILES: Cc1ccc(/C=C2\SC(=S)N(CCCC(=O)O)C2=O)cc1] | 321.4 |
| IIb-363 | 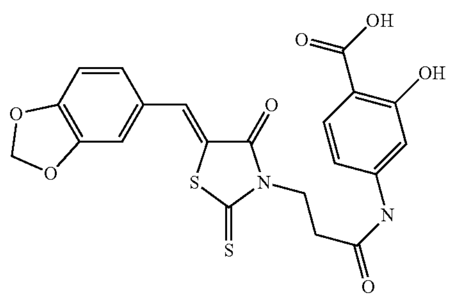 [SMILES: O=C(CCN1C(=O)/C(=C/c2ccc3c(c2)OCO3)SC1=S)Nc1ccc(C(=O)O)c(O)c1] | 472.5 |
| IIb-364 | 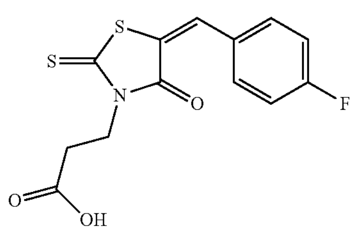 [SMILES: O=C(O)CCN1C(=O)/C(=C\c2ccc(F)cc2)SC1=S] | 311.4 |
| IIb-365 | 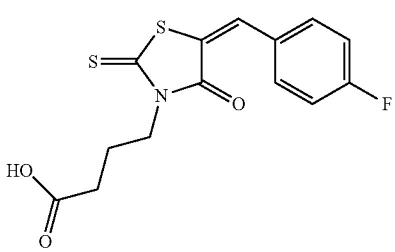 [SMILES: O=C(O)CCCN1C(=O)/C(=C\c2ccc(F)cc2)SC1=S] | 325.4 |

TABLE 7-continued

Phenmethylene-Thiazole Alkanoic Acids (R³ = OH)

| ID | Structure | MW |
|---|---|---|
| IIb-366 | 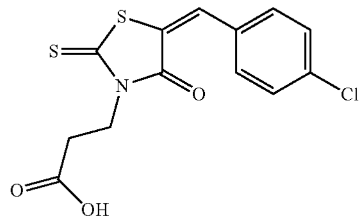 [SMILES: O=C(O)CCN1C(=O)/C(=C\c2ccc(Cl)cc2)SC1=S] | 327.8 |
| IIb-367 | 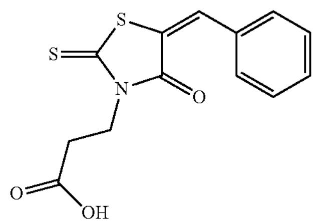 [SMILES: O=C(O)CCN1C(=O)/C(=C\c2ccccc2)SC1=S] | 293.4 |
| IIb-368 | 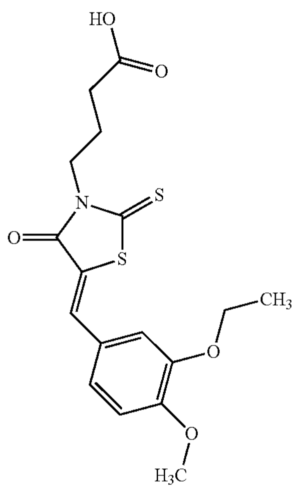 [SMILES: CCOc1cc(/C=C2\SC(=S)N(CCCC(=O)O)C2=O)ccc1OC] | 381.5 |
| IIb-369 | 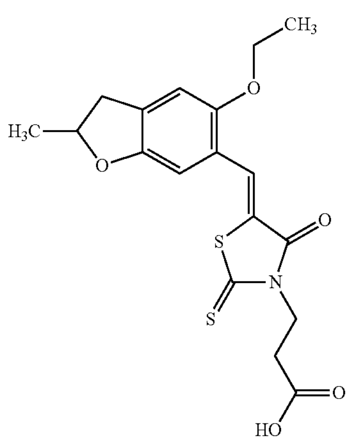 [SMILES: CCOc1cc2c(cc1/C=C1\SC(=S)N(CCC(=O)O)C1=O)OC(C)C2] | 393.5 |

TABLE 7-continued

Phenmethylene-Thiazole Alkanoic Acids (R³ = OH)

| ID | Structure | MW |
|---|---|---|
| IIb-370 | 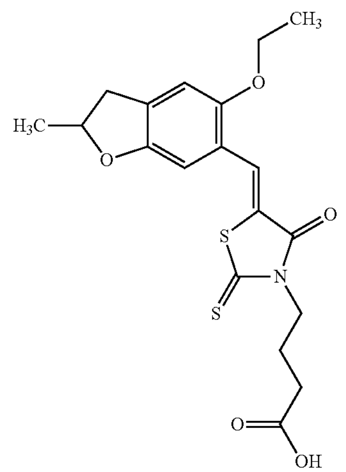 [SMILES: CCOc1cc2c(cc1/C=C1\SC(=S)N(CCCC(=O)O)C1=O)OC(C)C2] | 407.5 |
| IIb-371 | 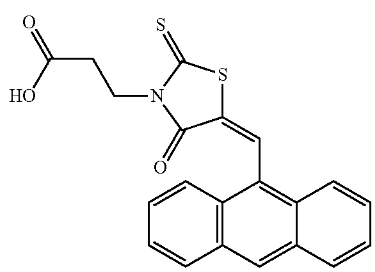 [SMILES: O=C(O)CCN1C(=O)/C(=C\c2c3ccccc3cc3ccccc23)SC1=S] | 393.5 |
| IIb-372 | 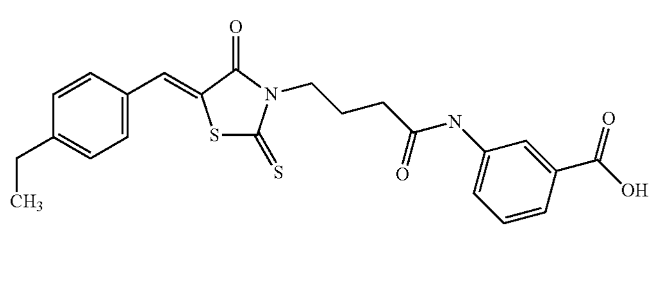 [SMILES: CCc1ccc(/C=C2\SC(=S)N(CCCC(=O)Nc3cccc(C(=O)O)c3)C2=O)cc1] | 454.6 |
| IIb-373 | 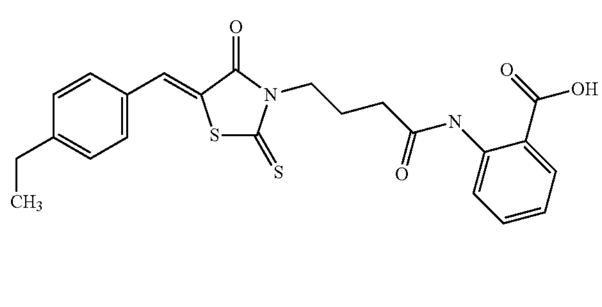 [SMILES: CCc1ccc(/C=C2\SC(=S)N(CCCC(=O)Nc3ccccc3C(=O)O)C2=O)cc1] | 454.6 |

TABLE 7-continued

Phenmethylene-Thiazole Alkanoic Acids ($R^3$ = OH)

| ID | Structure | MW |
|---|---|---|
| IIb-374 | 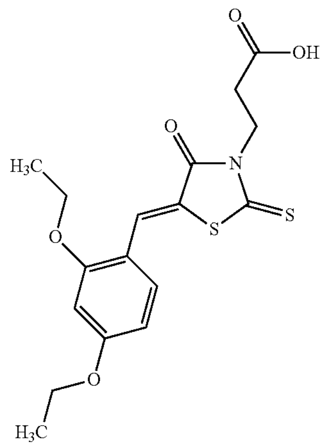 [SMILES: CCOc1ccc(/C=C2\SC(=S)N(CCC(=O)O)C2=O)c(OCC)c1] | 381.5 |
| IIb-375 | 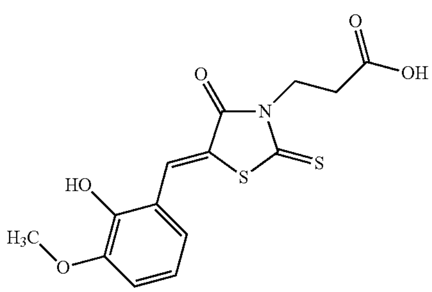 [SMILES: COc1cccc(/C=C2\SC(=S)N(CCC(=O)O)C2=O)c1O] | 339.4 |
| IIb-376 | 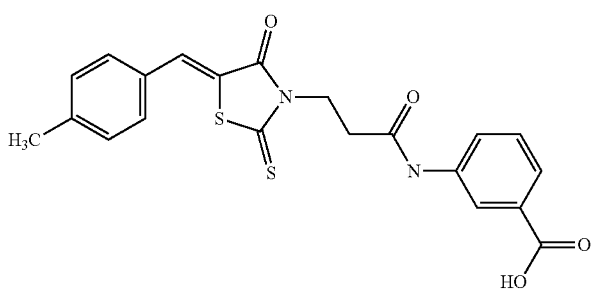 [SMILES: Cc1ccc(/C=C2\SC(=S)N(CCC(=O)Nc3cccc(C(=O)O)c3)C2=O)cc1] | 426.5 |
| IIb-377 | 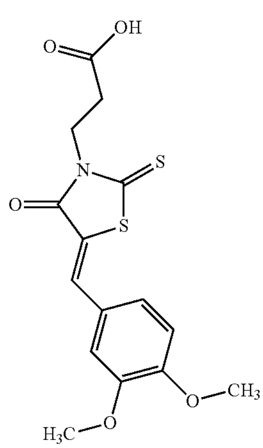 [SMILES: COc1ccc(/C=C2\SC(=S)N(CCC(=O)O)C2=O)cc1OC] | 353.4 |

TABLE 7-continued

Phenmethylene-Thiazole Alkanoic Acids ($R^3$ = OH)

| ID | Structure | MW |
|---|---|---|
| IIb-378 | 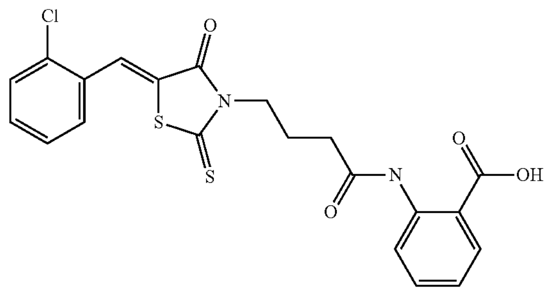 [SMILES: O=C(CCCN1C(=O)/C(=C/c2ccccc2Cl)SC1=S)Nc1ccccc1C(=O)O] | 461.0 |
| IIb-379 | 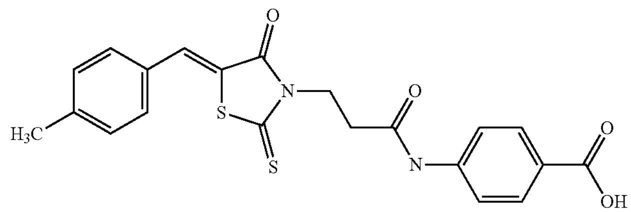 [SMILES: Cc1ccc(/C=C2\SC(=S)N(CCC(=O)Nc3ccc(C(=O)O)cc3)C2=O)cc1] | 426.5 |
| IIb-380 | 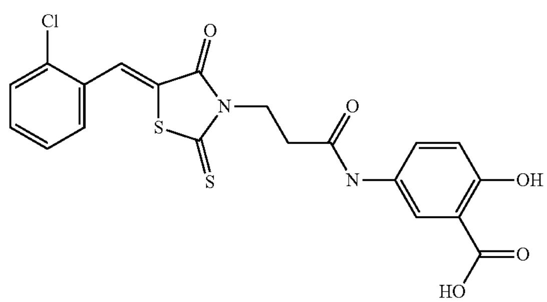 [SMILES: O=C(CCN1C(=O)/C(=C/c2ccccc2Cl)SC1=S)Nc1ccc(O)c(C(=O)O)c1] | 462.9 |
| IIb-381 | 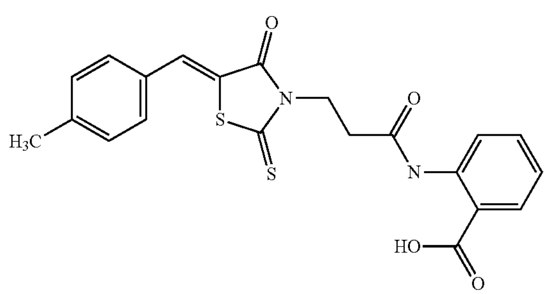 [SMILES: Cc1ccc(/C=C2\SC(=S)N(CCC(=O)Nc3ccccc3C(=O)O)C2=O)cc1] | 426.5 |
| IIb-382 | 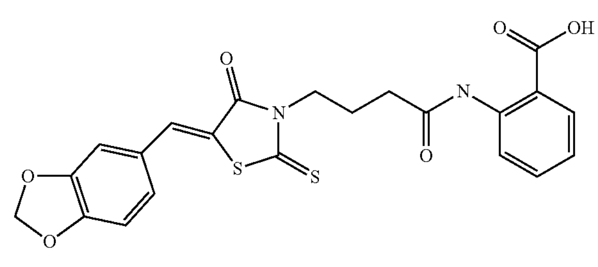 [SMILES: O=C(CCCN1C(=O)/C(=C/c2ccc3c(c2)OCO3)SC1=S)Nc1ccccc1C(=O)O] | 470.5 |

TABLE 7-continued

Phenmethylene-Thiazole Alkanoic Acids ($R^3$ = OH)

| ID | Structure | MW |
| --- | --- | --- |
| IIb-383 | 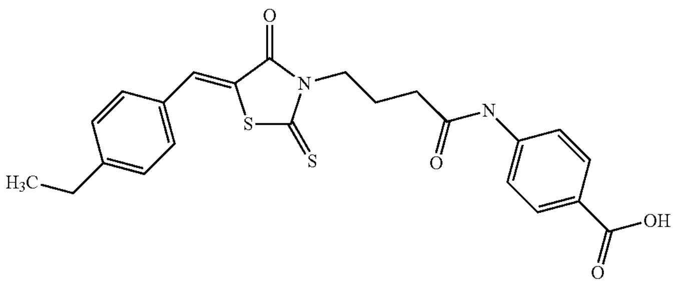 [SMILES: CCc1ccc(/C=C2\SC(=S)N(CCCC(=O)Nc3ccc(C(=O)O)cc3)C2=O)cc1] | 454.6 |
| IIb-384 | 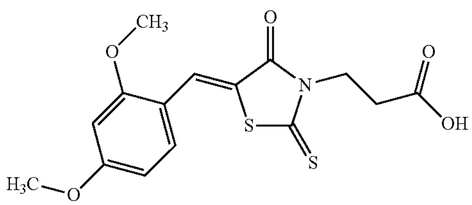 [SMILES: COc1ccc(/C=C2\SC(=S)N(CCC(=O)O)C2=O)c(OC)c1] | 353.4 |
| IIb-385 | 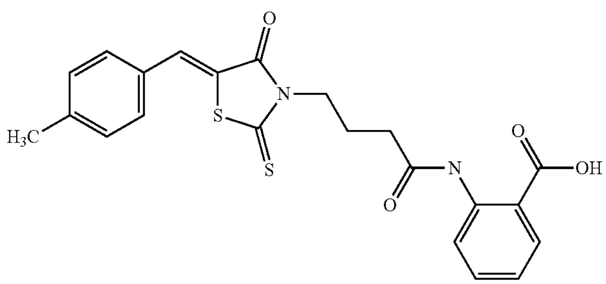 [SMILES: Cc1ccc(/C=C2\SC(=S)N(CCCC(=O)Nc3ccccc3C(=O)O)C2=O)cc1] | 440.5 |
| IIb-386 | 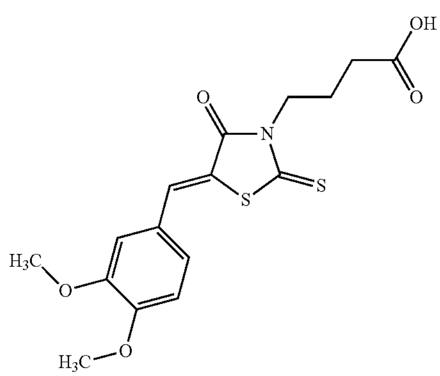 [SMILES: COc1ccc(/C=C2\SC(=S)N(CCCC(=O)O)C2=O)cc1OC] | 367.4 |
| IIb-387 | 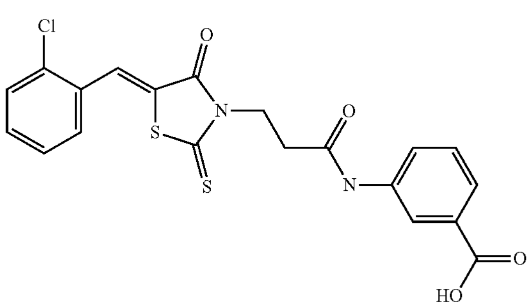 [SMILES: O=C(CCN1C(=O)/C(=C/c2ccccc2Cl)SC1=S)Nc1cccc(C(=O)O)c1] | 446.9 |

TABLE 7-continued

Phenmethylene-Thiazole Alkanoic Acids ($R^3$ = OH)

| ID | Structure | MW |
|---|---|---|
| IIb-388 | 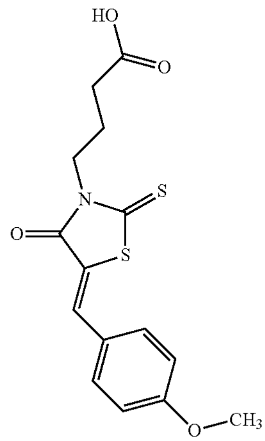 [SMILES: COc1ccc(/C=C2\SC(=S)N(CCCC(=O)O)C2=O)cc1] | 337.4 |
| IIb-389 | 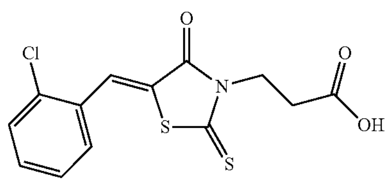 [SMILES: O=C(O)CCN1C(=O)/C(=C/c2ccccc2Cl)SC1=S] | 327.8 |
| IIb-390 | 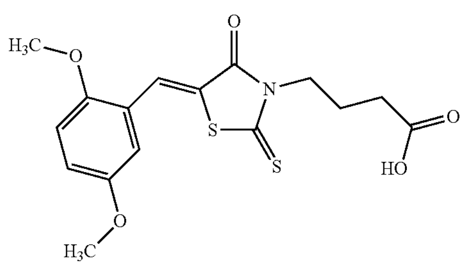 [SMILES: COc1ccc(OC)c(/C=C2\SC(=S)N(CCCC(=O)O)C2=O)c1] | 367.4 |
| IIb-391 | 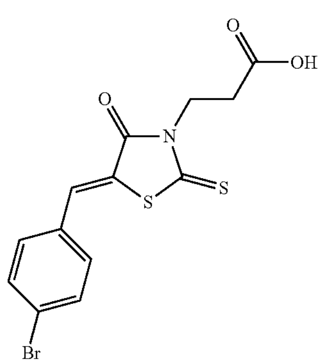 [SMILES: O=C(O)CCN1C(=O)/C(=C/c2ccc(Br)cc2)SC1=S] | 372.3 |

TABLE 7-continued

Phenmethylene-Thiazole Alkanoic Acids (R³ = OH)

| ID | Structure | MW |
|---|---|---|
| IIb-392 | 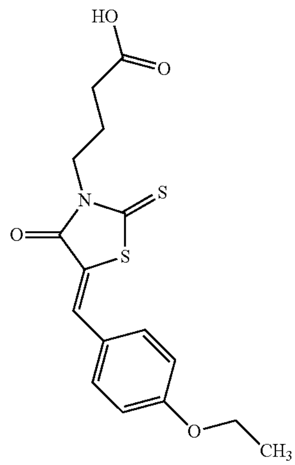 [SMILES: CCOc1ccc(/C=C2\SC(=S)N(CCCC(=O)O)C2=O)cc1] | 351.4 |
| IIb-393 | 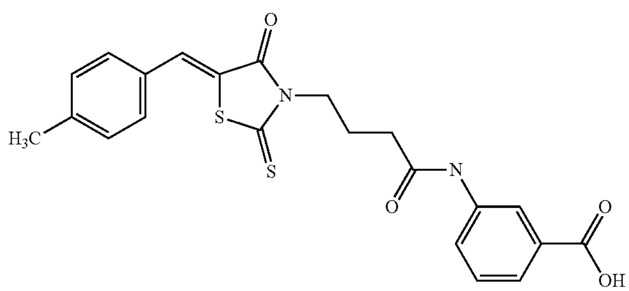 [SMILES: Cc1ccc(/C=C2\SC(=S)N(CCCC(=O)Nc3cccc(C(=O)O)c3)C2=O)cc1] | 440.5 |
| IIb-394 | 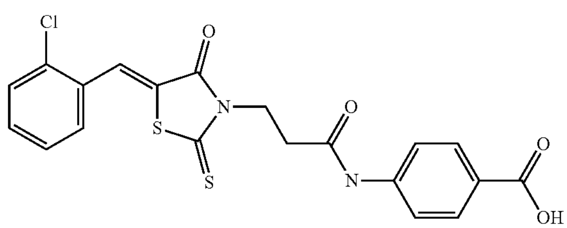 [SMILES: O=C(CCN1C(=O)/C(=C/c2ccccc2Cl)SC1=S)Nc1ccc(C(=O)O)cc1] | 446.9 |
| IIb-395 | 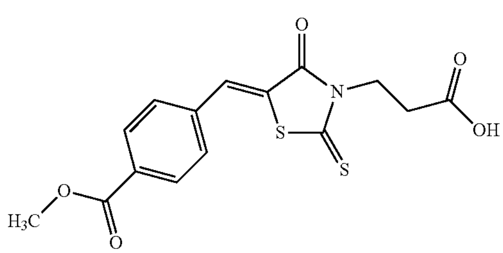 [SMILES: COC(=O)c1ccc(/C=C2\SC(=S)N(CCC(=O)O)C2=O)cc1] | 351.4 |
| IIb-396 | 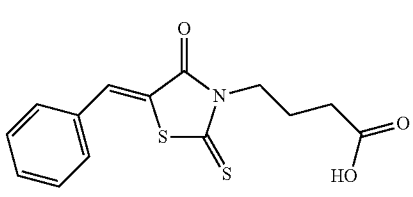 [SMILES: O=C(O)CCCN1C(=O)/C(=C/c2ccccc2)SC1=S] | 307.4 |

TABLE 7-continued

Phenmethylene-Thiazole Alkanoic Acids ($R^3$ = OH)

| ID | Structure | MW |
|---|---|---|
| IIb-397 | 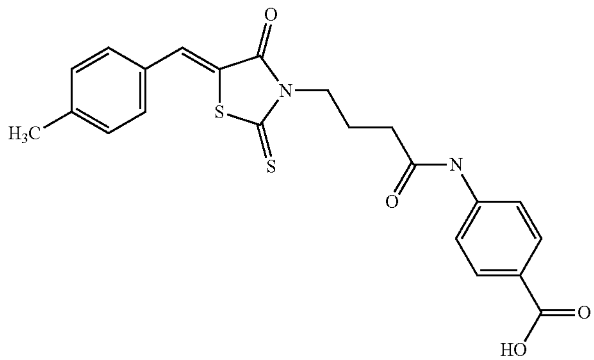 [SMILES: Cc1ccc(/C=C2\SC(=S)N(CCCC(=O)Nc3ccc(C(=O)O)cc3)C2=O)cc1] | 440.5 |
| IIb-398 | 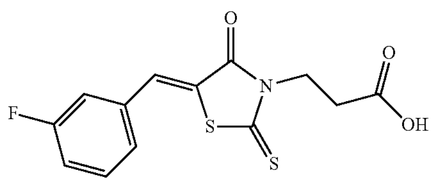 [SMILES: O=C(O)CCN1C(=O)/C(=C/c2cccc(F)c2)SC1=S] | 311.4 |
| IIb-399 | 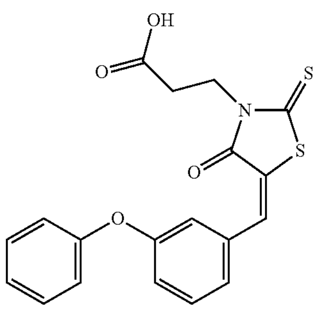 [SMILES: O=C(O)CCN1C(=O)/C(=C\c2cccc(Oc3ccccc3)c2)SC1=S] | 385.5 |
| IIb-400 | 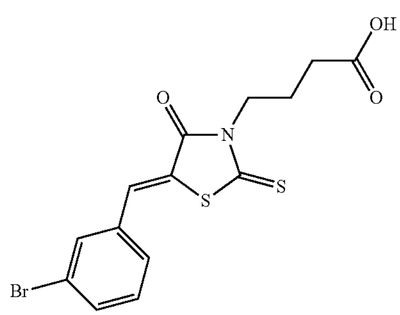 [SMILES: O=C(O)CCCN1C(=O)/C(=C/c2cccc(Br)c2)SC1=S] | 386.3 |
| IIb-401 | 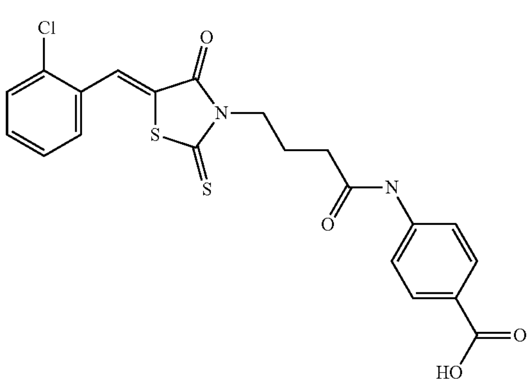 [SMILES: O=C(CCCN1C(=O)/C(=C/c2ccccc2Cl)SC1=S)Nc1ccc(C(=O)O)cc1] | 461.0 |

TABLE 7-continued

Phenmethylene-Thiazole Alkanoic Acids ($R^3$ = OH)

| ID | Structure | MW |
| --- | --- | --- |
| IIb-402 | 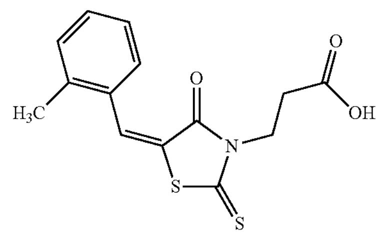 [SMILES: Cc1ccccc1/C=C1/SC(=S)N(CCC(=O)O)C1=O] | 307.4 |
| IIb-403 | 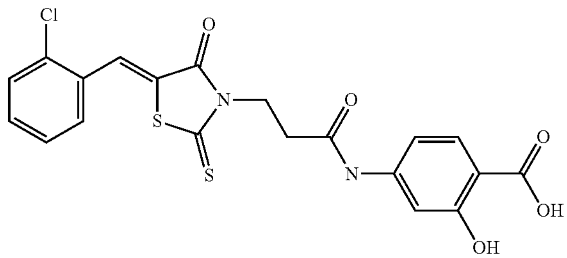 [SMILES: O=C(CCN1C(=O)/C(=C/c2ccccc2Cl)SC1=S)Nc1ccc(C(=O)O)c(O)c1] | 462.9 |
| IIb-404 | 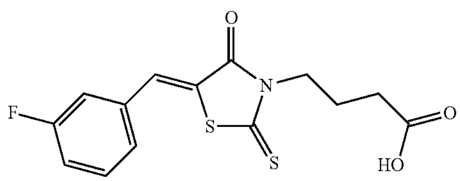 [SMILES: O=C(O)CCCN1C(=O)/C(=C/c2cccc(F)c2)SC1=S] | 325.4 |
| IIb-405 | 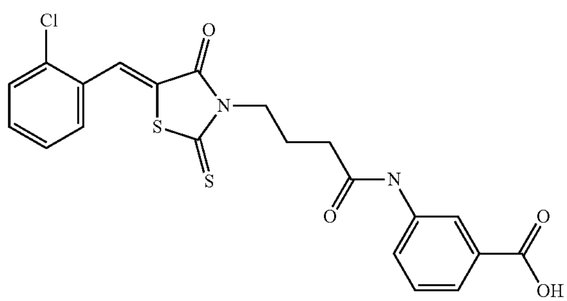 [SMILES: O=C(CCCN1C(=O)/C(=C/c2ccccc2Cl)SC1=S)Nc1cccc(C(=O)O)c1] | 461.0 |
| IIb-406 | 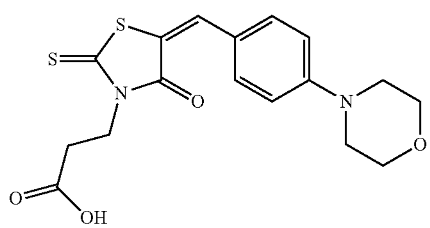 [SMILES: O=C(O)CCN1C(=O)/C(=C\c2ccc(N3CCOCC3)cc2)SC1=S] | 378.5 |
| IIb-407 | 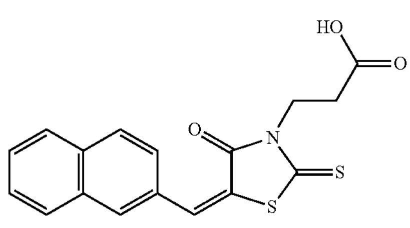 [SMILES: O=C(O)CCN1C(=O)/C(=C\c2ccc3ccccc3c2)SC1=S] | 343.4 |

TABLE 7-continued

Phenmethylene-Thiazole Alkanoic Acids ($R^3$ = OH)

| ID | Structure | MW |
|---|---|---|
| IIb-408 | 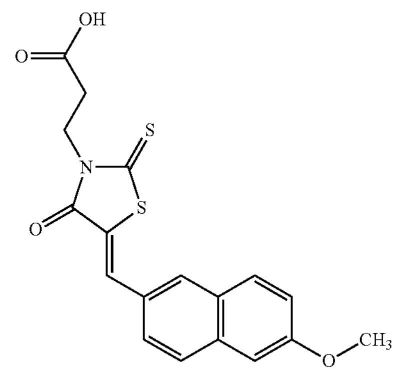 [SMILES: COc1ccc2cc(/C=C3\SC(=S)N(CCC(=O)O)C3=O)ccc2c1] | 373.5 |
| IIb-409 | 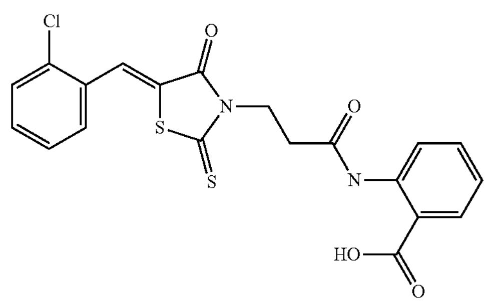 [SMILES: O=C(CCN1C(=O)/C(=C/c2ccccc2Cl)SC1=S)Nc1ccccc1C(=O)O] | 446.9 |
| IIb-410 | 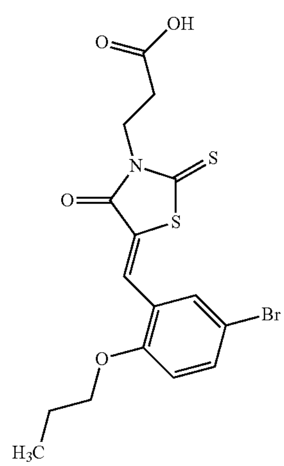 [SMILES: CCCOc1ccc(Br)cc1/C=C1\SC(=S)N(CCC(=O)O)C1=O] | 430.3 |
| IIb-411 | 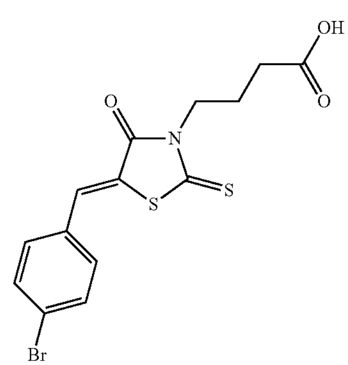 [SMILES: O=C(O)CCCN1C(=O)/C(=C/c2ccc(Br)cc2)SC1=S] | 386.3 |

TABLE 7-continued

Phenmethylene-Thiazole Alkanoic Acids ($R^3$ = OH)

| ID | Structure | MW |
|---|---|---|
| IIb-412 | 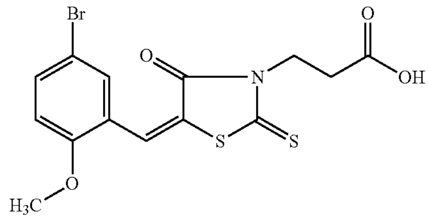 [SMILES: COc1ccc(Br)cc1/C=C1/SC(=S)N(CCC(=O)O)C1=O] | 402.3 |
| IIb-413 | 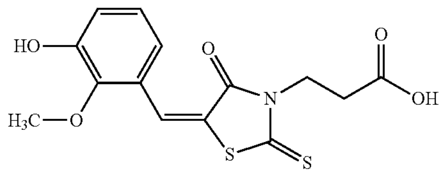 [SMILES: COc1c(O)cccc1/C=C1/SC(=S)N(CCC(=O)O)C1=O] | 339.4 |
| IIb-414 | 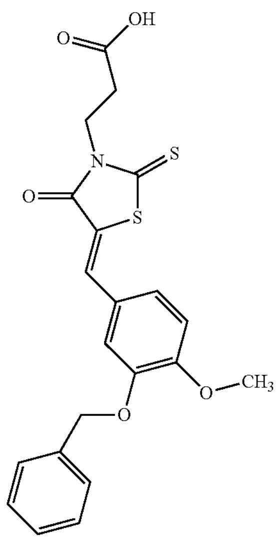 [SMILES: COc1ccc(/C=C2\SC(=S)N(CCC(=O)O)C2=O)cc1OCc1ccccc1] | 429.5 |
| IIb-415 | 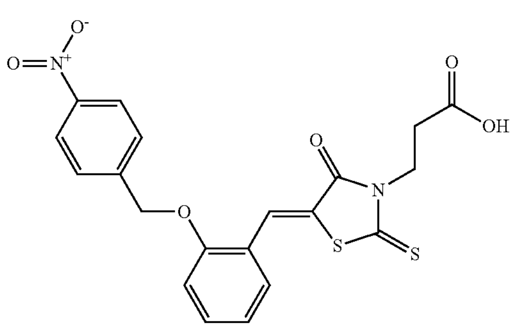 [SMILES: O=C(O)CCN1C(=O)/C(=C/c2ccccc2OCc2ccc([N+](=O)[O-])cc2)SC1=S] | 444.5 |

TABLE 8

Pyridyl And Quinolinyl Methylenyl Alkanoic Acids (R³ = OH)

| ID | Structure | MW |
|---|---|---|
| IIb-416 | 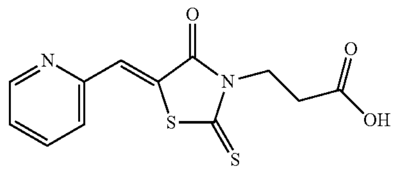 [SMILES: O=C(O)CCN1C(=O)/C(=C/c2ccccn2)SC1=S] | 294.4 |
| IIb-417 | 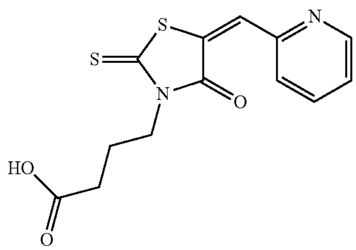 [SMILES: O=C(O)CCCN1C(=O)/C(=C\c2ccccn2)SC1=S] | 308.4 |
| IIb-418 | 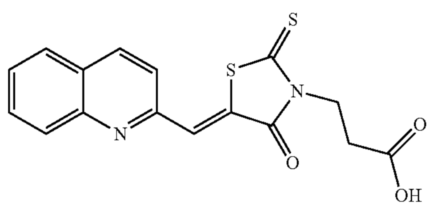 [SMILES: O=C(O)CCN1C(=O)/C(=C/c2ccc3ccccc3n2)SC1=S] | 344.4 |
| IIb-419 | 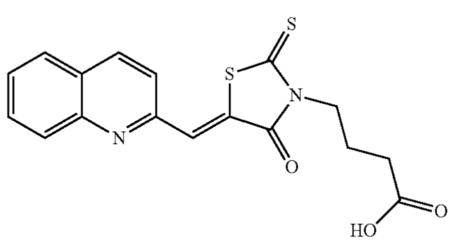 [SMILES: O=C(O)CCCN1C(=O)/C(=C/c2ccc3ccccc3n2)SC1=S] | 358.4 |
| IIb-420 | 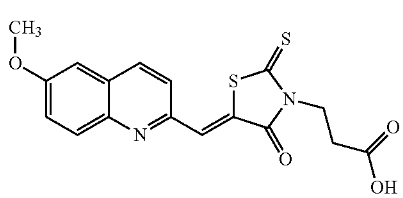 [SMILES: COc1ccc2nc(/C=C3\SC(=S)N(CCC(=O)O)C3=O)ccc2c1] | 374.4 |
| IIb-421 | 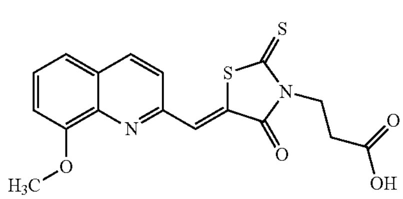 [SMILES: COc1cccc2ccc(/C=C3\SC(=S)N(CCC(=O)O)C3=O)nc12] | 374.4 |

TABLE 8-continued

Pyridyl And Quinolinyl Methylenyl Alkanoic Acids (R³ = OH)

| ID | Structure | MW |
|---|---|---|
| IIb-422 | 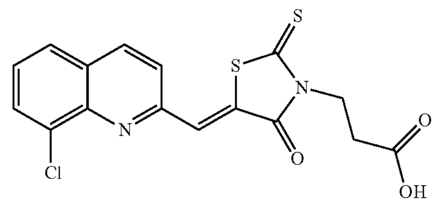 [SMILES: O=C(O)CCN1C(=O)/C(=C/c2ccc3cccc(Cl)c3n2)SC1=S] | 378.9 |
| IIb-423 | 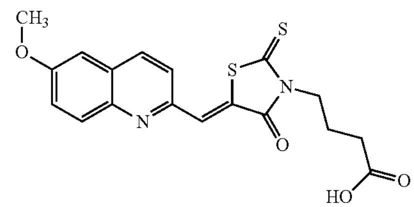 [SMILES: COc1ccc2nc(/C=C3\SC(=S)N(CCCC(=O)O)C3=O)ccc2c1] | 388.5 |
| IIb-424 | 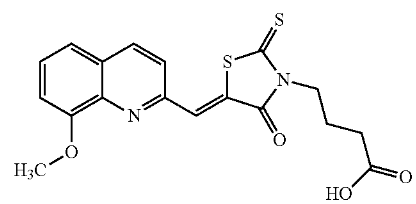 [SMILES: COc1cccc2ccc(/C=C3\SC(=S)N(CCCC(=O)O)C3=O)nc12] | 388.5 |
| IIb-425 | 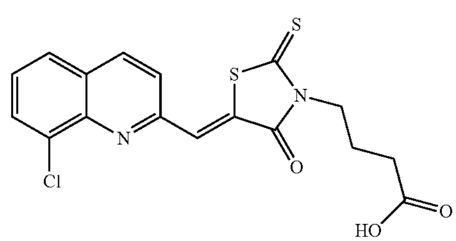 [SMILES: O=C(O)CCCN1C(=O)/C(=C/c2ccc3cccc(Cl)c3n2)SC1=S] | 392.9 |
| IIb-426 | 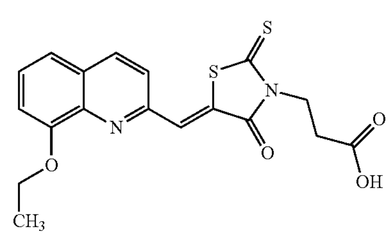 [SMILES: CCOc1cccc2ccc(/C=C3\SC(=S)N(CCC(=O)O)C3=O)nc12] | 388.5 |
| IIb-427 | 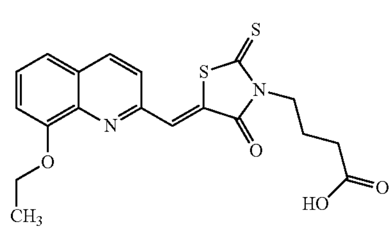 [SMILES: CCOc1cccc2ccc(/C=C3\SC(=S)N(CCCC(=O)O)C3=O)nc12] | 402.5 |

TABLE 8-continued
Pyridyl And Quinolinyl Methylenyl Alkanoic Acids ($R^3$ = OH)
| ID | Structure | MW |
|---|---|---|
| IIb-428 | 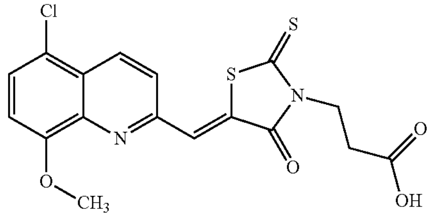 [SMILES: COc1ccc(Cl)c2ccc(/C=C3\SC(=S)N(CCC(=O)O)C3=O)nc12] | 408.9 |
| IIb-429 | 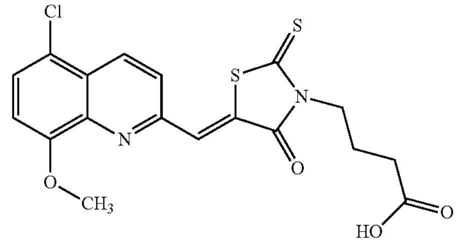 [SMILES: COc1ccc(Cl)c2ccc(/C=C3\SC(=S)N(CCCC(=O)O)C3=O)nc12] | 422.9 |
TABLE 9
Thiophenylmethylenyl Alkanoic Acids And Amides ($R^3$ = O— And NH—)
| ID | Structure | MW |
|---|---|---|
| IIb-430 | 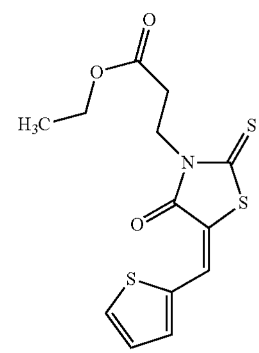 [SMILES: CCOC(=O)CCN1C(=O)/C(=C\c2cccs2)SC1=S] | 327.4 |
| IIb-431 | 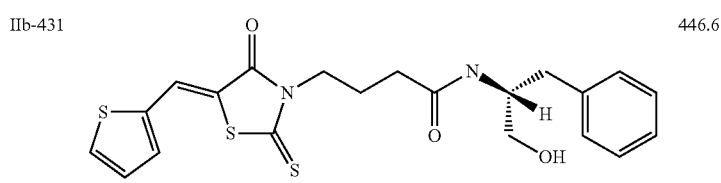 | 446.6 |
| IIb-432 | 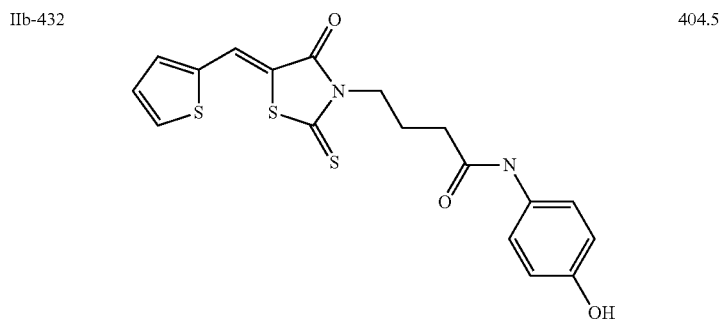 | 404.5 |

TABLE 9-continued

Thiophenylmethylenyl Alkanoic Acids And Amides (R³ = O— And NH—)

| ID | Structure | MW |
|---|---|---|
| IIb-433 | 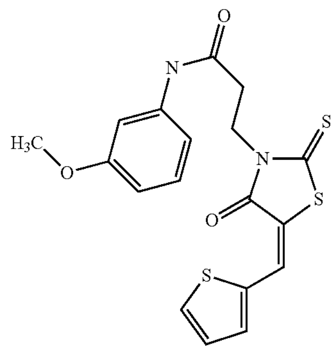 [SMILES: COc1cccc(NC(=O)CCN2C(=O)/C(=C\c3cccs3)SC2=S)c1] | 404.5 |
| IIb-434 | 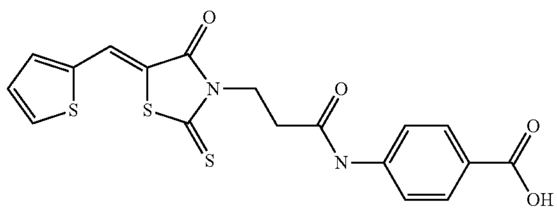 [SMILES: O=C(CCN1C(=O)/C(=C/c2cccs2)SC1=S)Nc1ccc(C(=O)O)cc1] | 418.5 |
| IIb-435 | 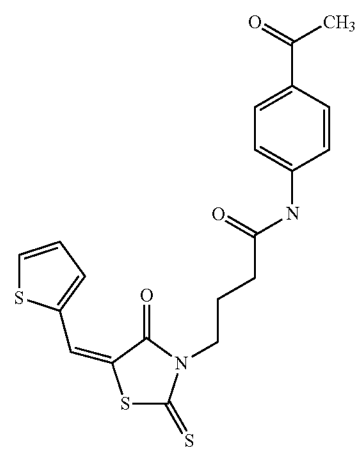 [SMILES: CC(=O)c1ccc(NC(=O)CCCN2C(=O)/C(=C\c3cccs3)SC2=S)cc1] | 430.6 |
| IIb-436 | 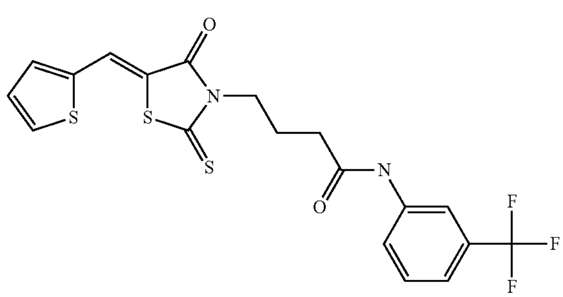 [SMILES: O=C(CCCN1C(=O)/C(=C/c2cccs2)SC1=S)Nc1cccc(C(F)(F)F)c1] | 456.5 |
| IIb-437 | 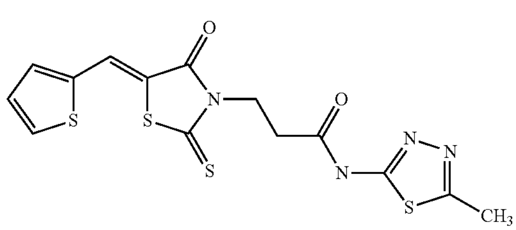 [SMILES: Cc1nnc(NC(=O)CCN2C(=O)/C(=C/c3cccs3)SC2=S)s1] | 396.5 |

TABLE 9-continued

Thiophenylmethylenyl Alkanoic Acids And Amides ($R^3$ = O— And NH—)

| ID | Structure | MW |
|---|---|---|
| IIb-438 | 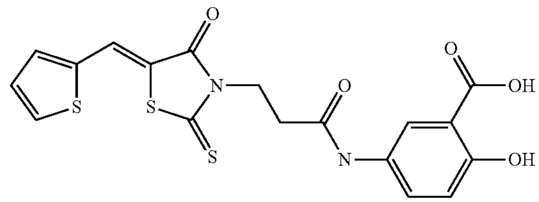 [SMILES: O=C(CCN1C(=O)/C(=C/c2cccs2)SC1=S)Nc1ccc(O)c(C(=O)O)c1] | 434.5 |
| IIb-439 | 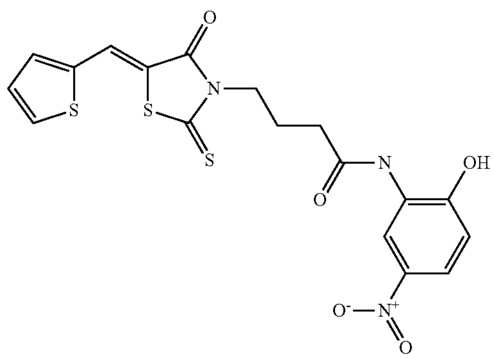 [SMILES: O=C(CCCN1C(=O)/C(=C/c2cccs2)SC1=S)Nc1cc([N+](=O)[O-])ccc1O] | 449.5 |
| IIb-440 | 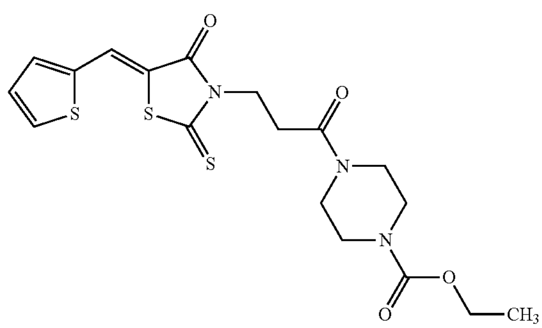 [SMILES: CCOC(=O)N1CCN(C(=O)CCN2C(=O)/C(=C/c3cccs3)SC2=S)CC1] | 439.6 |
| IIb-441 | 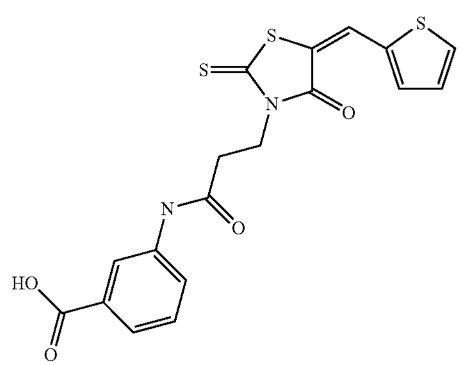 [SMILES: O=C(CCN1C(=O)/C(=C\c2cccs2)SC1=S)Nc1cccc(C(=O)O)c1] | 418.5 |
| IIb-442 | 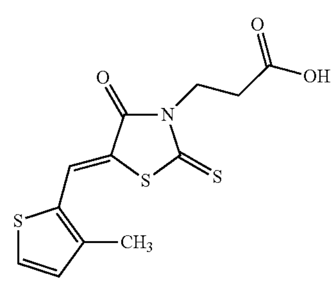 [SMILES: Cc1ccsc1/C=C1\SC(=S)N(CCC(=O)O)C1=O] | 313.4 |

TABLE 9-continued

Thiophenylmethylenyl Alkanoic Acids And Amides ($R^3$ = O— And NH—)

| ID | Structure | MW |
|---|---|---|
| IIb-443 | 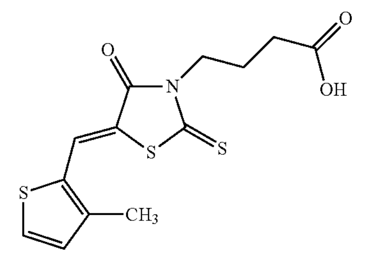 [SMILES: Cc1ccsc1/C=C1\SC(=S)N(CCCC(=O)O)C1=O] | 327.4 |
| IIb-444 | 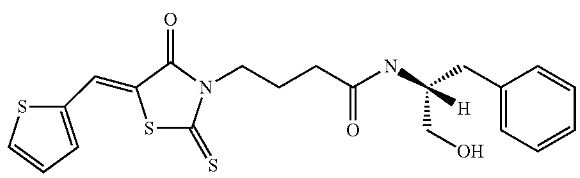 [SMILES: O=C(CCCN1C(=O)/C(=C/c2cccs2)SC1=S)N[C@@H](CO)Cc1ccccc1] | 446.6 |
| IIb-445 | 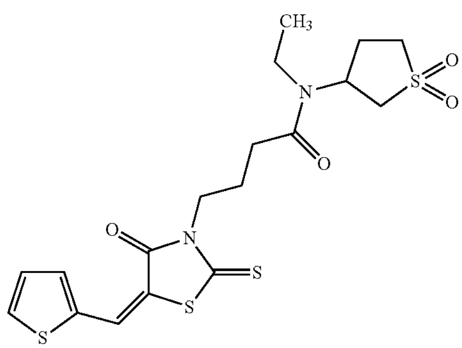 [SMILES: CCN(C(=O)CCCN1C(=O)/C(=C\c2cccs2)SC1=S)C1CCS(=O)(=O)C1] | 458.6 |
| IIb-446 | 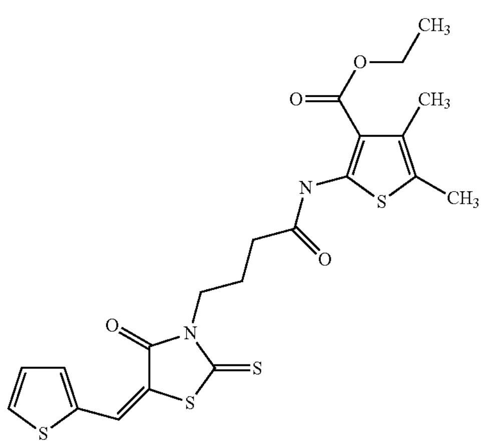 [SMILES: CCOC(=O)c1c(NC(=O)CCCN2C(=O)/C(=C\c3cccs3)SC2=S)sc(C)c1C] | 494.7 |
| IIb-447 | 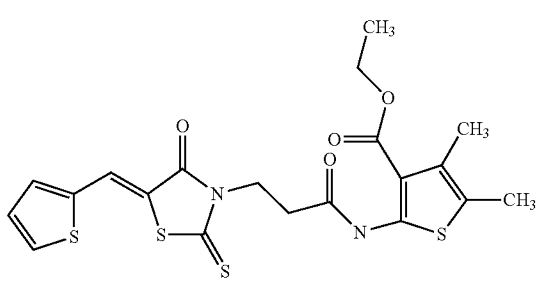 [SMILES: CCOC(=O)c1c(NC(=O)CCN2C(=O)/C(=C/c3cccs3)SC2=S)sc(C)c1C] | 480.6 |

TABLE 9-continued
Thiophenylmethylenyl Alkanoic Acids And Amides (R³ = O— And NH—)
| ID | Structure | MW |
|---|---|---|
| IIb-448 | 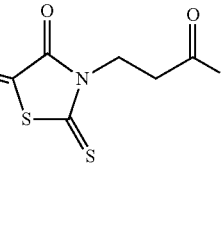 | 476.0 |
| IIb-449 | 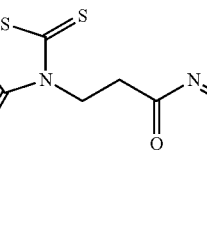 | 438.6 |
| IIb-450 | 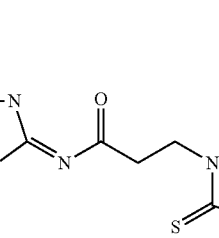 | 395.5 |
| IIb-451 | 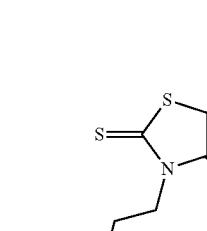 | 458.7 |
| IIb-452 | 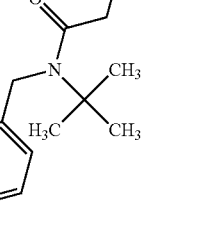 | 410.6 |

TABLE 9-continued

Thiophenylmethylenyl Alkanoic Acids And Amides ($R^3$ = O— And NH—)

| ID | Structure | MW |
|---|---|---|
| IIb-453 | 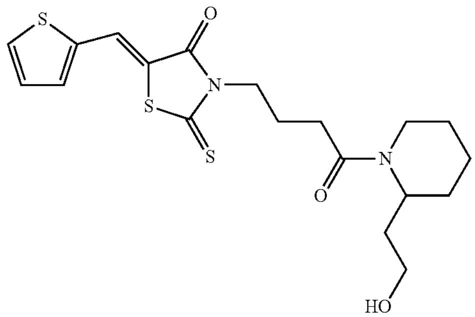 [SMILES: O=C1/C(=C/c2cccs2)SC(=S)N1CCCC(=O)N1CCCCC1CCO] | 424.6 |
| IIb-454 | 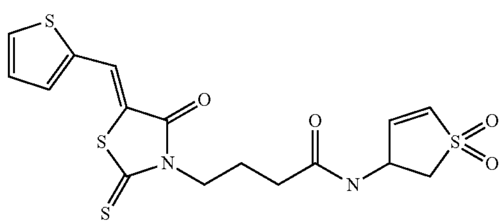 [SMILES: O=C(CCCN1C(=O)/C(=C/c2cccs2)SC1=S)NC1C=CS(=O)(=O)C1] | 428.6 |
| IIb-455 | 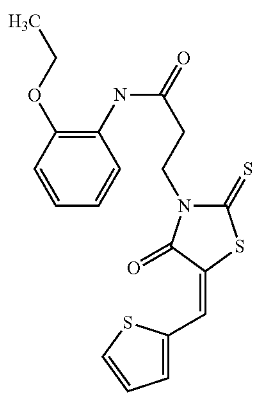 [SMILES: CCOc1ccccc1NC(=O)CCN1C(=O)/C(=C\c2cccs2)SC1=S] | 418.6 |
| IIb-456 | 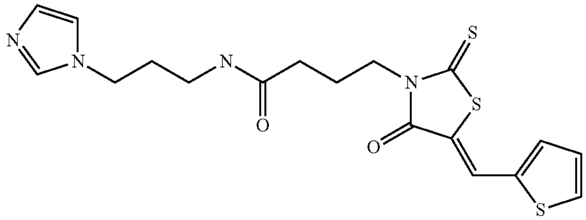 [SMILES: O=C(CCCN1C(=O)/C(=C/c2cccs2)SC1=S)NCCCn1ccnc1] | 420.6 |
| IIb-457 | 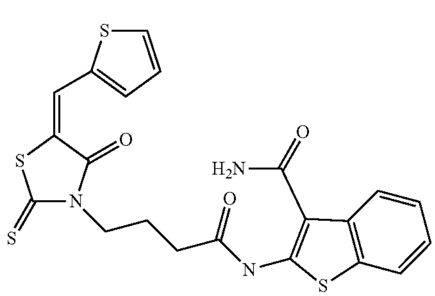 [SMILES: NC(=O)c1c(NC(=O)CCCN2C(=O)/C(=C\c3cccs3)SC2=S)sc2ccccc12] | 487.6 |

TABLE 9-continued

Thiophenylmethylenyl Alkanoic Acids And Amides ($R^3$ = O— And NH—)

| ID | Structure | MW |
|---|---|---|
| IIb-458 | 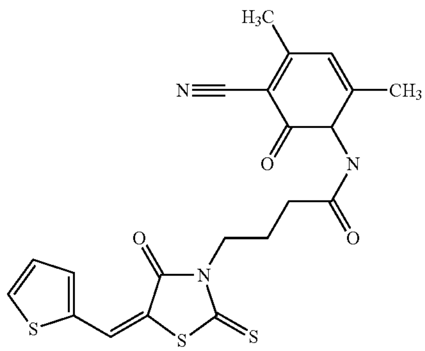 [SMILES: CC1=CC(C)=C(C#N)C(=O)C1NC(=O)CCCN1C(=O)/C(=C\c2cccs2)SC1=S] | 457.6 |
| IIb-459 | 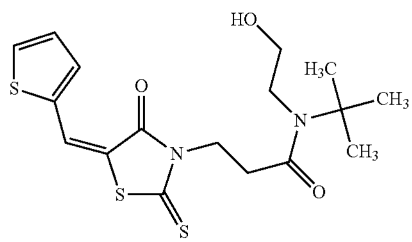 [SMILES: CC(C)(C)N(CCO)C(=O)CCN1C(=O)/C(=C\c2cccs2)SC1=S] | 398.6 |
| IIb-460 | 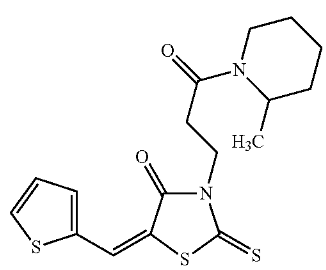 [SMILES: CC1CCCCN1C(=O)CCN1C(=O)/C(=C\c2cccs2)SC1=S] | 380.6 |
| IIb-461 | 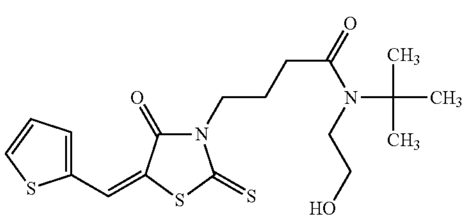 [SMILES: CC(C)(C)N(CCO)C(=O)CCCN1C(=O)/C(=C\c2cccs2)SC1=S] | 412.6 |
| IIb-462 | 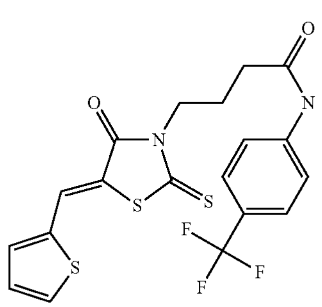 [SMILES: O=C(CCCN1C(=O)/C(=C/c2cccs2)SC1=S)Nc1ccc(C(F)(F)F)cc1] | 456.5 |

TABLE 9-continued

Thiophenylmethylenyl Alkanoic Acids And Amides (R³ = O— And NH—)

| ID | Structure | MW |
|---|---|---|
| IIb-463 | 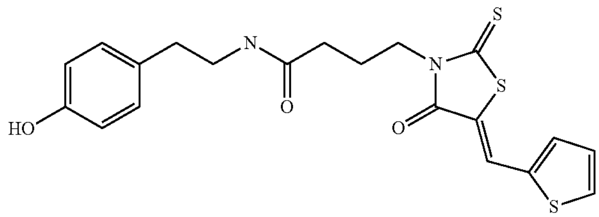 [SMILES: O=C(CCCN1C(=O)/C(=C/c2cccs2)SC1=S)NCCc1ccc(O)cc1] | 432.6 |
| IIb-464 | 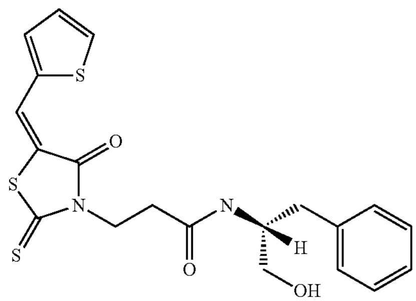 [SMILES: O=C(CCN1C(=O)/C(=C\c2cccs2)SC1=S)N[C@@H](CO)Cc1ccccc1] | 432.6 |
| IIb-465 | 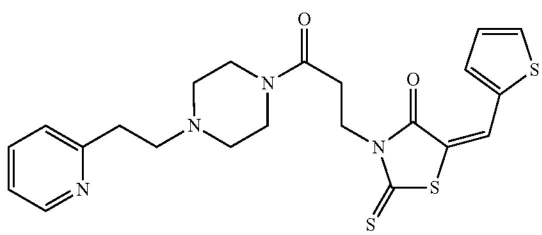 [SMILES: O=C(CCN1C(=O)/C(=C\c2cccs2)SC1=S)N1CCN(CCc2ccccn2)CC1] | 472.7 |
| IIb-466 | 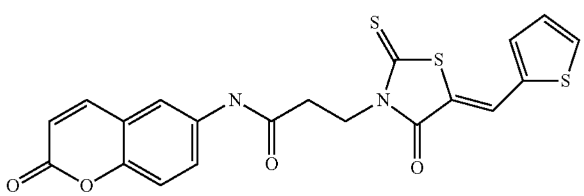 [SMILES: O=C(CCN1C(=O)/C(=C/c2cccs2)SC1=S)Nc1ccc2oc(=O)ccc2c1] | 442.5 |
| IIb-467 | 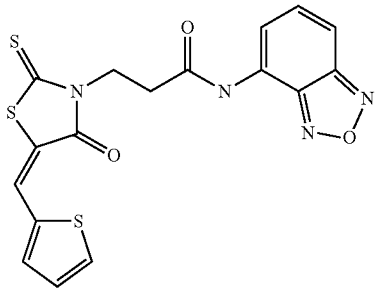 [SMILES: O=C(CCN1C(=O)/C(=C\c2cccs2)SC1=S)Nc1cccc2nonc12] | 416.5 |
| IIb-468 | 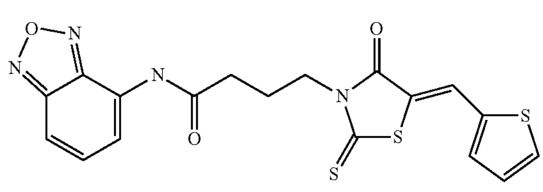 [SMILES: O=C(CCCN1C(=O)/C(=C/c2cccs2)SC1=S)Nc1cccc2nonc12] | 430.5 |

TABLE 9-continued

Thiophenylmethylenyl Alkanoic Acids And Amides ($R^3$ = O— And NH—)

| ID | Structure | MW |
| --- | --- | --- |
| IIb-469 | 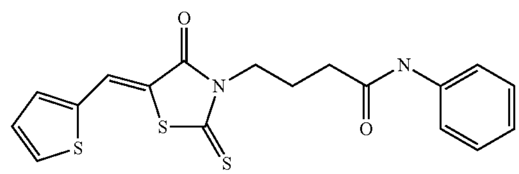 [SMILES: O=C(CCCN1C(=O)/C(=C/c2cccs2)SC1=S)Nc1ccccc1] | 388.5 |
| IIb-470 | 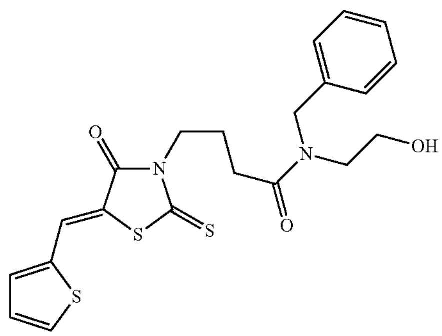 [SMILES: O=C(CCCN1C(=O)/C(=C/c2cccs2)SC1=S)N(CCO)Cc1ccccc1] | 446.6 |
| IIb-471 | 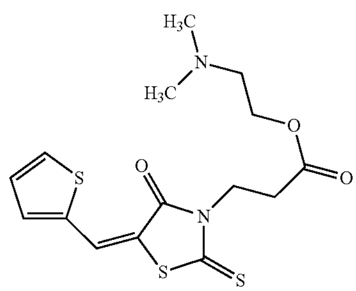 [SMILES: CN(C)CCOC(=O)CCN1C(=O)/C(=C\c2cccs2)SC1=S] | 370.5 |
| IIb-472 | 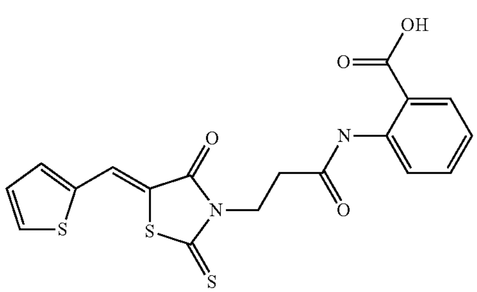 [SMILES: O=C(CCN1C(=O)/C(=C/c2cccs2)SC1=S)Nc1ccccc1C(=O)O] | 418.5 |
| IIb-473 | 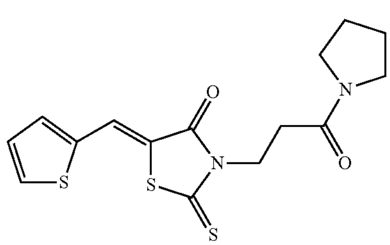 [SMILES: O=C(CCN1C(=O)/C(=C/c2cccs2)SC1=S)N1CCCC1] | 352.5 |

TABLE 9-continued

Thiophenylmethylenyl Alkanoic Acids And Amides ($R^3$ = O— And NH—)

| ID | Structure | MW |
|---|---|---|
| IIb-474 | 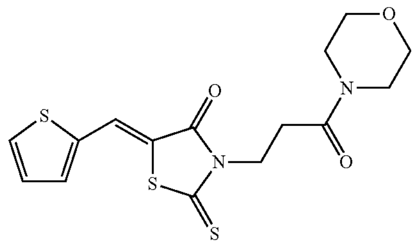 [SMILES: O=C(CCN1C(=O)/C(=C/c2cccs2)SC1=S)N1CCOCC1] | 368.5 |
| IIb-475 | 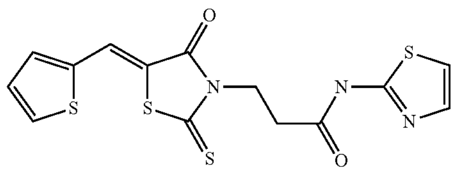 [SMILES: O=C(CCN1C(=O)/C(=C/c2cccs2)SC1=S)Nc1nccs1] | 381.5 |
| IIb-476 | 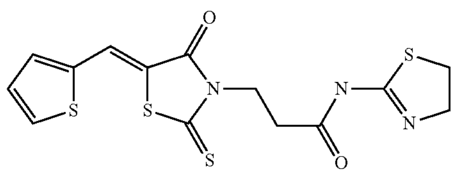 [SMILES: O=C(CCN1C(=O)/C(=C/c2cccs2)SC1=S)NC1=NCCS1] | 383.5 |
| IIb-477 | 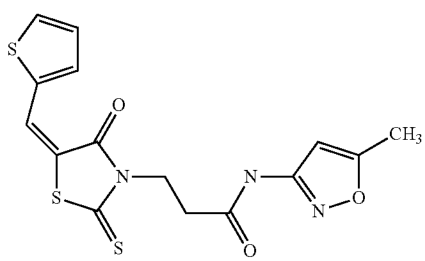 [SMILES: Cc1cc(NC(=O)CCN2C(=O)/C(=C\c3cccs3)SC2=S)no1] | 379.5 |
| IIb-478 | 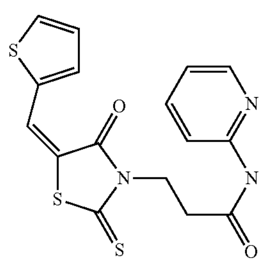 [SMILES: O=C(CCN1C(=O)/C(=C\c2cccs2)SC1=S)Nc1ccccn1] | 375.5 |
| IIb-479 | 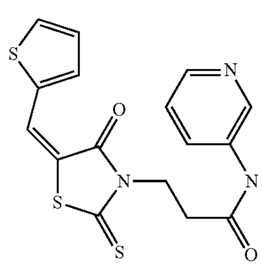 [SMILES: O=C(CCN1C(=O)/C(=C\c2cccs2)SC1=S)Nc1cccnc1] | 375.5 |
| IIb-480 | 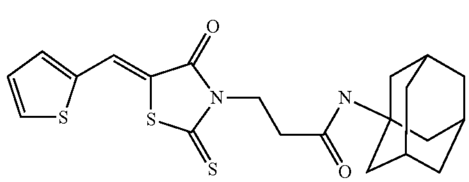 [SMILES: O=C(CCN1C(=O)/C(=C/c2cccs2)SC1=S)NC12CC3CC(CC(C3)C1)C2] | 432.6 |

TABLE 9-continued
Thiophenylmethylenyl Alkanoic Acids And Amides (R³ = O— And NH—)
| ID | Structure | MW |
|---|---|---|
| IIb-481 | 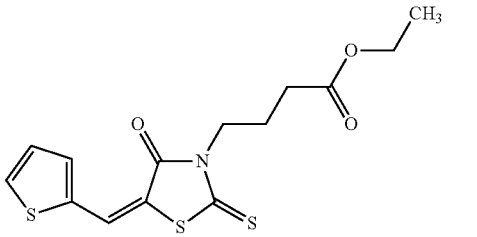 [SMILES: CCOC(=O)CCCN1C(=O)/C(=C\c2cccs2)SC1=S] | 341.5 |
| IIb-482 | 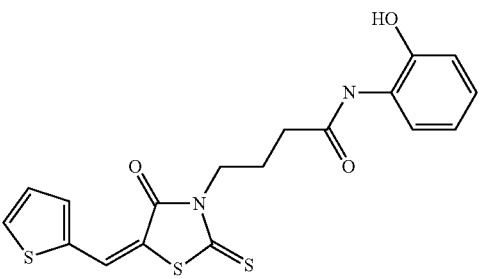 [SMILES: O=C(CCCN1C(=O)/C(=C\c2cccs2)SC1=S)Nc1ccccc1O] | 404.5 |
| IIb-483 | 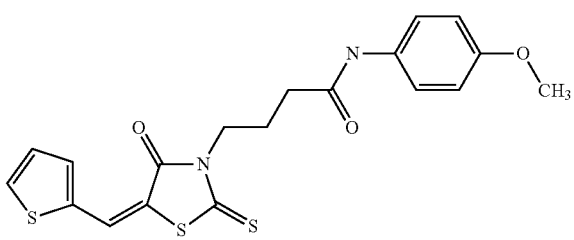 [SMILES: COc1ccc(NC(=O)CCCN2C(=O)/C(=C\c3cccs3)SC2=S)cc1] | 418.6 |
| IIb-484 | 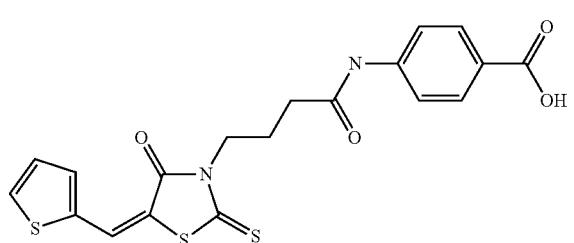 [SMILES: O=C(CCCN1C(=O)/C(=C\c2cccs2)SC1=S)Nc1ccc(C(=O)O)cc1] | 432.5 |
| IIb-485 | 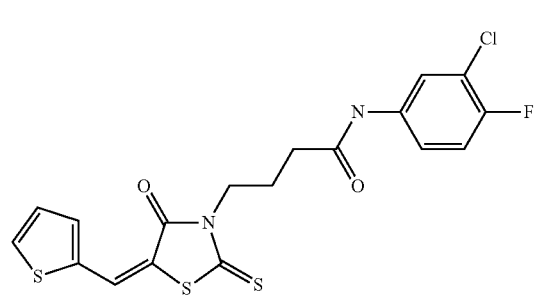 [SMILES: O=C(CCCN1C(=O)/C(=C\c2cccs2)SC1=S)Nc1ccc(F)c(Cl)c1] | 441.0 |

TABLE 9-continued

Thiophenylmethylenyl Alkanoic Acids And Amides ($R^3$ = O— And NH—)

| ID | Structure | MW |
|---|---|---|
| IIb-486 | 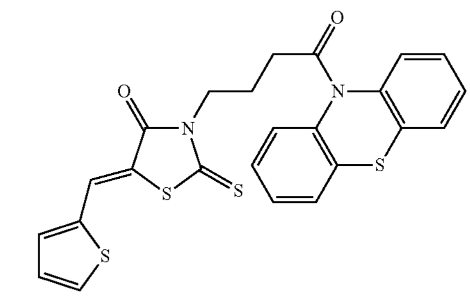 [SMILES: O=C1/C(=C/c2cccs2)SC(=S)N1CCCC(=O)N1c2ccccc2Sc2ccccc21] | 494.7 |
| IIb-487 | 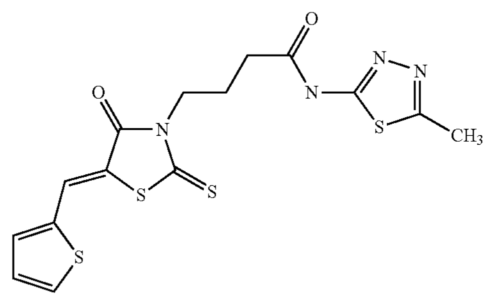 [SMILES: Cc1nnc(NC(=O)CCCN2C(=O)/C(=C/c3cccs3)SC2=S)s1] | 410.6 |
| IIb-488 | 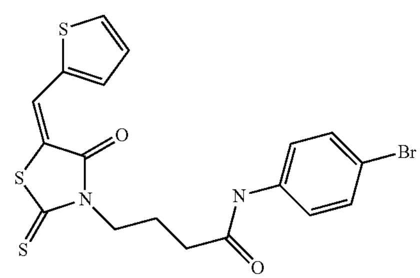 [SMILES: O=C(CCCN1C(=O)/C(=C\c2cccs2)SC1=S)Nc1ccc(Br)cc1] | 467.4 |
| IIb-489 | 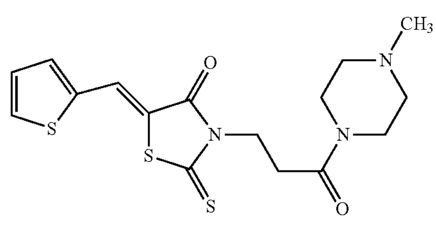 [SMILES: CN1CCN(C(=O)CCN2C(=O)/C(=C/c3cccs3)SC2=S)CC1] | 381.5 |
| IIb-490 | 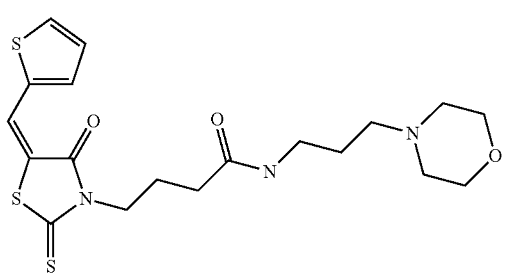 [SMILES: O=C(CCCN1C(=O)/C(=C\c2cccs2)SC1=S)NCCCN1CCOCC1] | 439.6 |

TABLE 9-continued

Thiophenylmethylenyl Alkanoic Acids And Amides ($R^3$ = O— And NH—)

| ID | Structure | MW |
|---|---|---|
| IIb-491 | 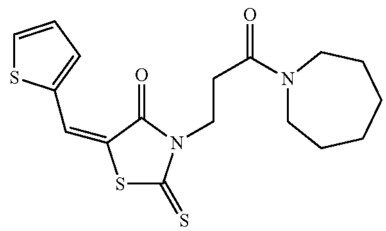 [SMILES: O=C(CCN1C(=O)/C(=C\c2cccs2)SC1=S)N1CCCCCC1] | 380.6 |
| IIb-492 | 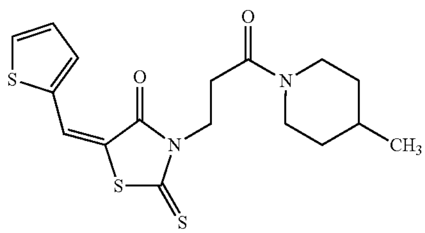 [SMILES: CC1CCN(C(=O)CCN2C(=O)/C(=C\c3cccs3)SC2=S)CC1] | 380.6 |
| IIb-493 | 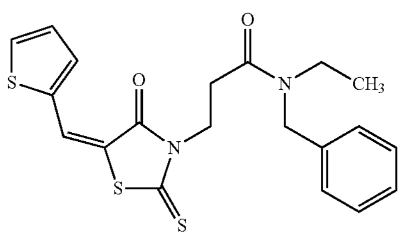 [SMILES: CCN(Cc1ccccc1)C(=O)CCN1C(=O)/C(=C\c2cccs2)SC1=S] | 416.6 |
| IIb-494 | 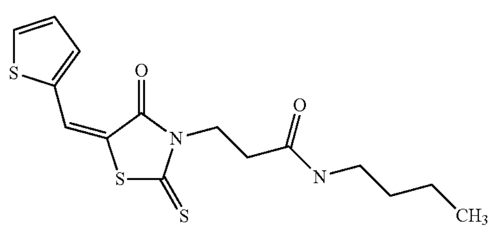 [SMILES: CCCCNC(=O)CCN1C(=O)/C(=C\c2cccs2)SC1=S] | 354.5 |
| IIb-495 | 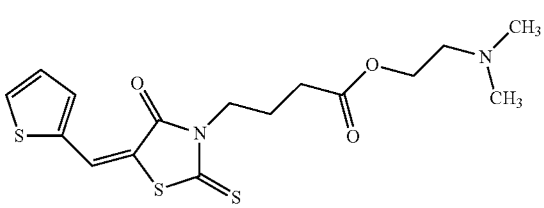 [SMILES: CN(C)CCOC(=O)CCCN1C(=O)/C(=C\c2cccs2)SC1=S] | 384.5 |
| IIb-496 | 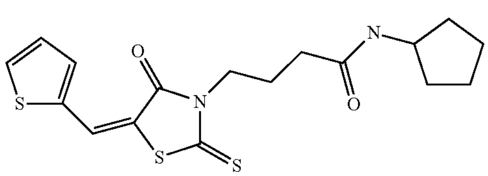 [SMILES: O=C(CCCN1C(=O)/C(=C\c2cccs2)SC1=S)NC1CCCC1] | 380.6 |

TABLE 9-continued

Thiophenylmethylenyl Alkanoic Acids And Amides ($R^3$ = O— And NH—)

| ID | Structure | MW |
|---|---|---|
| IIb-497 | 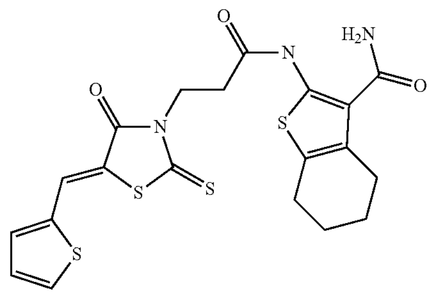 [SMILES: NC(=O)c1c(NC(=O)CCN2C(=O)/C(=C/c3cccs3)SC2=S)sc2c1CCCC2] | 477.6 |
| IIb-498 | 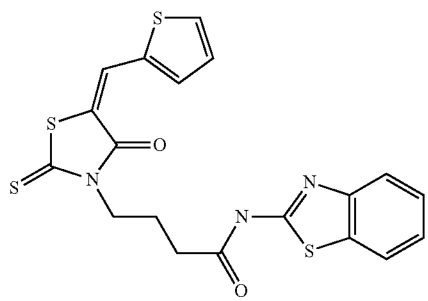 [SMILES: O=C(CCCN1C(=O)/C(=C\c2cccs2)SC1=S)Nc1nc2ccccc2s1] | 445.6 |
| IIb-499 | 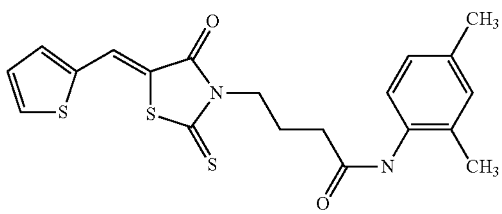 [SMILES: Cc1ccc(NC(=O)CCCN2C(=O)/C(=C/c3cccs3)SC2=S)c(C)c1] | 416.6 |
| IIb-500 | 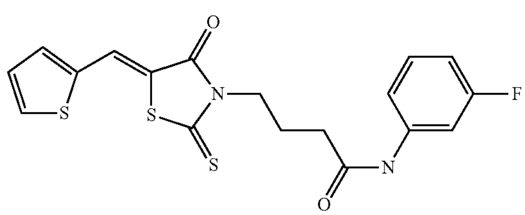 [SMILES: O=C(CCCN1C(=O)/C(=C/c2cccs2)SC1=S)Nc1cccc(F)c1] | 406.5 |
| IIb-501 | 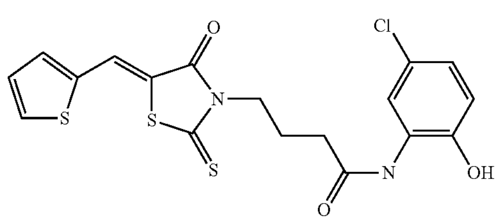 [SMILES: O=C(CCCN1C(=O)/C(=C/c2cccs2)SC1=S)Nc1cc(Cl)ccc1O] | 439.0 |
| IIb-502 | 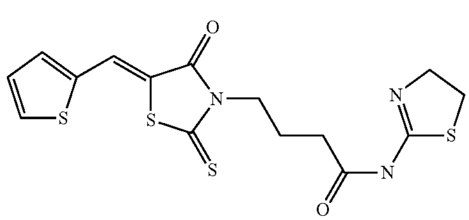 [SMILES: O=C(CCCN1C(=O)/C(=C/c2cccs2)SC1=S)NC1=NCCS1] | 397.6 |

TABLE 9-continued

Thiophenylmethylenyl Alkanoic Acids And Amides ($R^3$ = O— And NH—)

| ID | Structure | MW |
|---|---|---|
| IIb-503 | 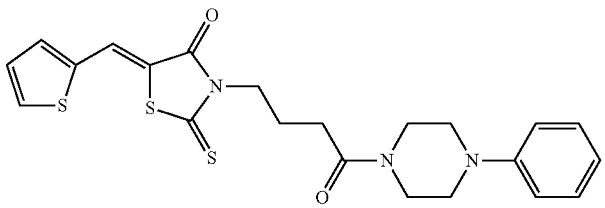 [SMILES: O=C(CCCN1C(=O)/C(=C/c2cccs2)SC1=S)N1CCN(c2ccccc2)CC1] | 457.6 |
| IIb-504 | 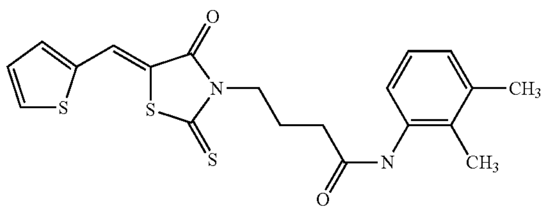 [SMILES: Cc1cccc(NC(=O)CCCN2C(=O)/C(=C/c3cccs3)SC2=S)c1C] | 416.6 |
| IIb-505 | 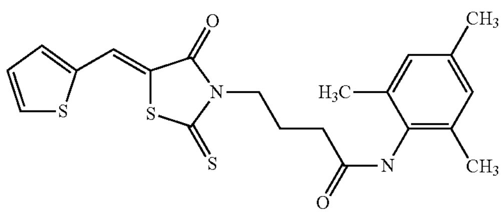 [SMILES: Cc1cc(C)c(NC(=O)CCCN2C(=O)/C(=C/c3cccs3)SC2=S)c(C)c1] | 430.6 |
| IIb-506 | 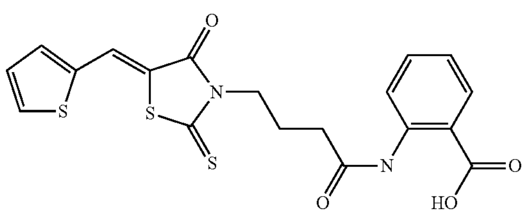 [SMILES: O=C(CCCN1C(=O)/C(=C/c2cccs2)SC1=S)Nc1ccccc1C(=O)O] | 432.5 |
| IIb-507 | 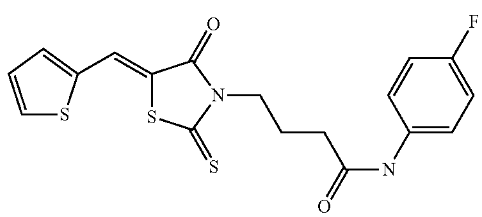 [SMILES: O=C(CCCN1C(=O)/C(=C/c2cccs2)SC1=S)Nc1ccc(F)cc1] | 406.5 |
| IIb-508 | 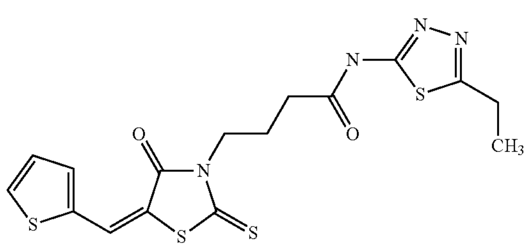 [SMILES: CCc1nnc(NC(=O)CCCN2C(=O)/C(=C\c3cccs3)SC2=S)s1] | 424.6 |
| IIb-509 | 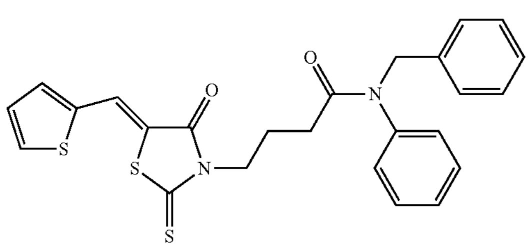 [SMILES: O=C1/C(=C/c2cccs2)SC(=S)N1CCCC(=O)N(Cc1ccccc1)c1ccccc1] | 478.7 |

TABLE 9-continued

Thiophenylmethylenyl Alkanoic Acids And Amides ($R^3$ = O— And NH—)

| ID | Structure | MW |
|---|---|---|
| IIb-510 | 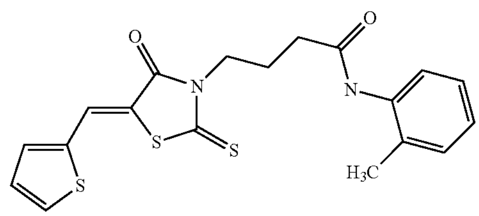 [SMILES: Cc1ccccc1NC(=O)CCCN1C(=O)/C(=C/c2cccs2)SC1=S] | 402.6 |
| IIb-511 | 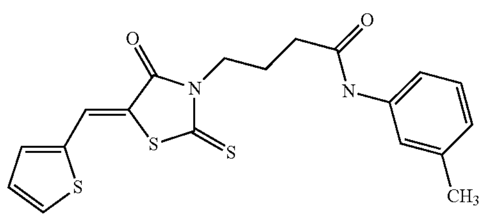 [SMILES: Cc1cccc(NC(=O)CCCN2C(=O)/C(=C/c3cccs3)SC2=S)c1] | 402.6 |
| IIb-512 | 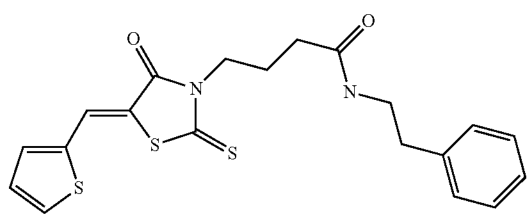 [SMILES: O=C(CCCN1C(=O)/C(=C/c2cccs2)SC1=S)NCCc1ccccc1] | 416.6 |
| IIb-513 | 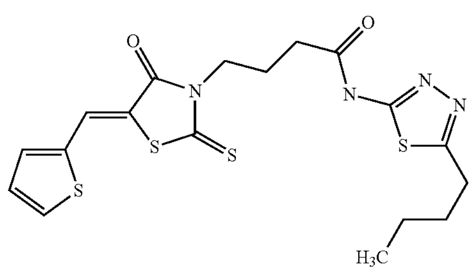 [SMILES: CCCCc1nnc(NC(=O)CCCN2C(=O)/C(=C/c3cccs3)SC2=S)s1] | 452.6 |
| IIb-514 | 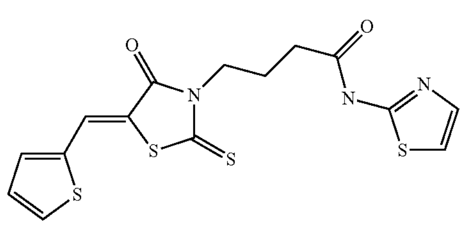 [SMILES: O=C(CCCN1C(=O)/C(=C/c2cccs2)SC1=S)Nc1nccs1] | 395.5 |
| IIb-515 | 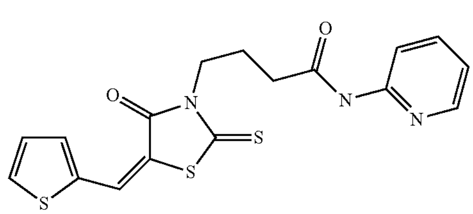 [SMILES: O=C(CCCN1C(=O)/C(=C\c2cccs2)SC1=S)Nc1ccccn1] | 389.5 |

TABLE 9-continued

Thiophenylmethylenyl Alkanoic Acids And Amides ($R^3$ = O— And NH—)

| ID | Structure | MW |
|---|---|---|
| IIb-516 | 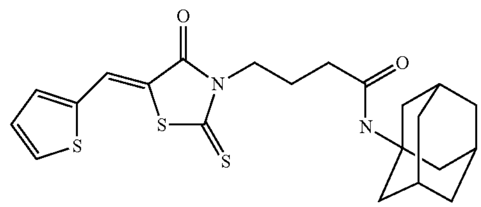 [SMILES: O=C(CCCN1C(=O)/C(=C/c2cccs2)SC1=S)NC12CC3CC(CC(C3)C1)C2] | 446.7 |
| IIb-517 | 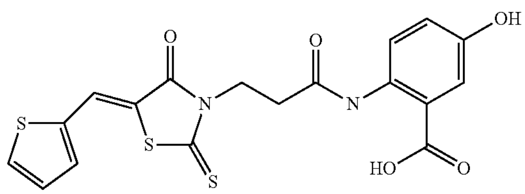 [SMILES: O=C(CCN1C(=O)/C(=C/c2cccs2)SC1=S)Nc1ccc(O)cc1C(=O)O] | 434.5 |
| IIb-518 | 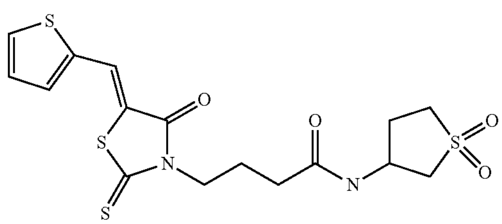 [SMILES: O=C(CCCN1C(=O)/C(=C/c2cccs2)SC1=S)NC1CCS(=O)(=O)C1] | 430.6 |
| IIb-519 | 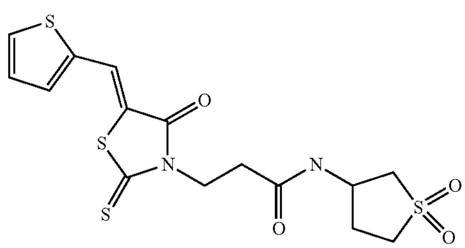 [SMILES: O=C(CCN1C(=O)/C(=C/c2cccs2)SC1=S)NC1CCS(=O)(=O)C1] | 416.6 |
| IIb-520 | 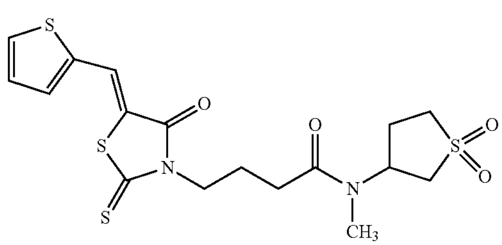 [SMILES: CN(C(=O)CCCN1C(=O)/C(=C/c2cccs2)SC1=S)C1CCS(=O)(=O)C1] | 444.6 |
| IIb-521 | 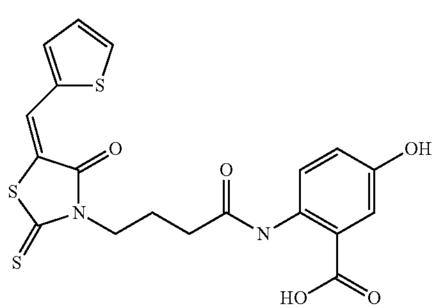 [SMILES: O=C(CCCN1C(=O)/C(=C\c2cccs2)SC1=S)Nc1ccc(O)cc1C(=O)O] | 448.5 |

TABLE 9-continued

Thiophenylmethylenyl Alkanoic Acids And Amides (R³ = O— And NH—)

| ID | Structure | MW |
|---|---|---|
| IIb-522 | 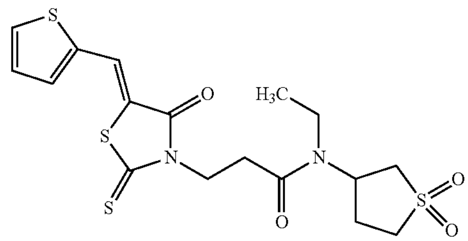 [SMILES: CCN(C(=O)CCN1C(=O)/C(=C/c2cccs2)SC1=S)C1CCS(=O)(=O)C1] | 444.6 |
| IIb-523 | 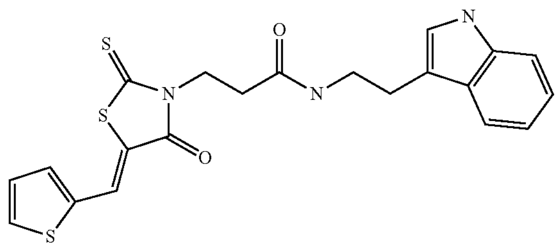 [SMILES: O=C(CCN1C(=O)/C(=C/c2cccs2)SC1=S)NCCc1c[nH]c2ccccc12] | 441.6 |
| IIb-524 | 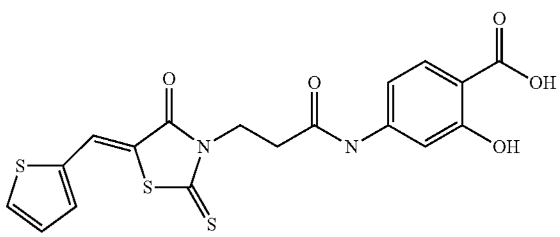 [SMILES: O=C(CCN1C(=O)/C(=C/c2cccs2)SC1=S)Nc1ccc(C(=O)O)c(O)c1] | 434.5 |
| IIb-525 | 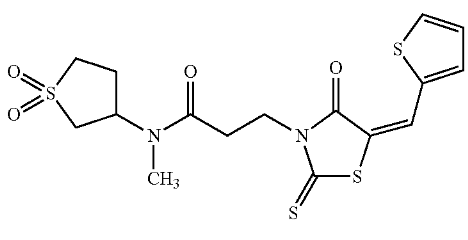 [SMILES: CN(C(=O)CCN1C(=O)/C(=C\c2cccs2)SC1=S)C1CCS(=O)(=O)C1] | 430.6 |
| IIb-526 | 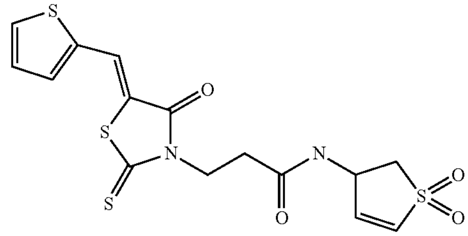 [SMILES: O=C(CCN1C(=O)/C(=C/c2cccs2)SC1=S)NC1C=CS(=O)(=O)C1] | 414.5 |
| IIb-527 | 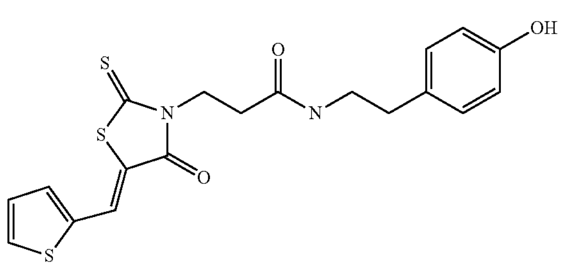 [SMILES: O=C(CCN1C(=O)/C(=C/c2cccs2)SC1=S)NCCc1ccc(O)cc1] | 418.6 |

TABLE 9-continued

Thiophenylmethylenyl Alkanoic Acids And Amides ($R^3$ = O— And NH—)

| ID | Structure | MW |
|---|---|---|
| IIb-528 | 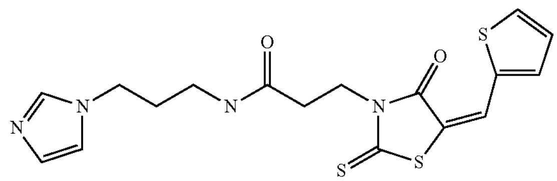 [SMILES: O=C(CCN1C(=O)/C(=C\c2cccs2)SC1=S)NCCCn1ccnc1] | 406.6 |
| IIb-529 | 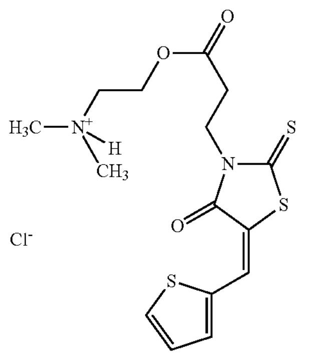 [SMILES: [Cl-] ; C[NH+](C)CCOC(=O)CCN1C(=O)/C(=C\c2cccs2)SC1=S] | 407.0 |
| IIb-530 | 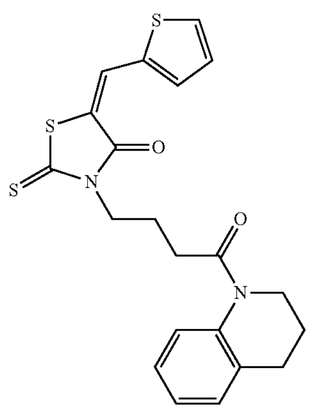 [SMILES: O=C1/C(=C\c2cccs2)SC(=S)N1CCCC(=O)N1CCCc2ccccc21] | 428.6 |
| IIb-531 | 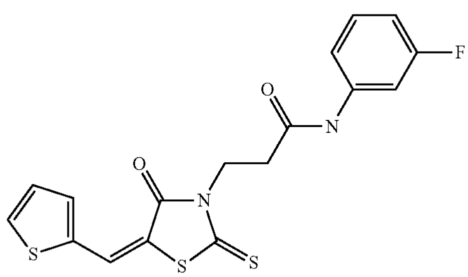 [SMILES: O=C(CCN1C(=O)/C(=C\c2cccs2)SC1=S)Nc1cccc(F)c1] | 392.5 |
| IIb-532 | 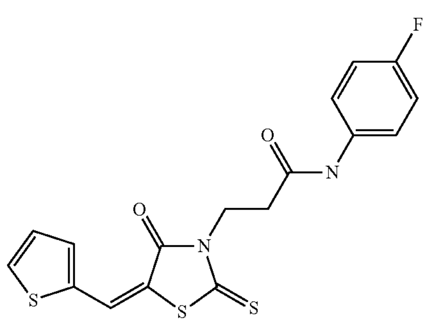 [SMILES: O=C(CCN1C(=O)/C(=C\c2cccs2)SC1=S)Nc1ccc(F)cc1] | 392.5 |

TABLE 9-continued

Thiophenylmethylenyl Alkanoic Acids And Amides ($R^3$ = O— And NH—)

| ID | Structure | MW |
|---|---|---|
| IIb-533 | 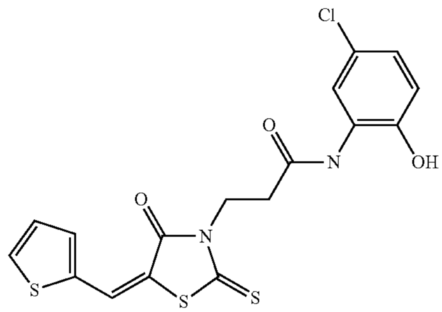 [SMILES: O=C(CCN1C(=O)/C(=C\c2cccs2)SC1=S)Nc1cc(Cl)ccc1O] | 424.9 |
| IIb-534 | 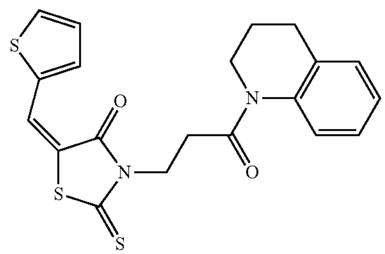 [SMILES: O=C1/C(=C\c2cccs2)SC(=S)N1CCC(=O)N1CCCc2ccccc21] | 414.6 |
| IIb-535 | 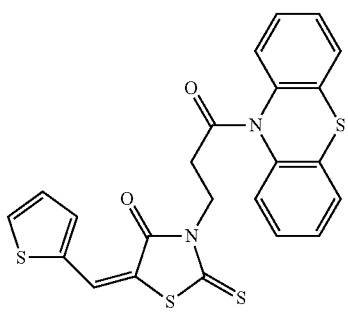 [SMILES: O=C1/C(=C\c2cccs2)SC(=S)N1CCC(=O)N1c2ccccc2Sc2ccccc21] | 480.7 |
| IIb-536 | 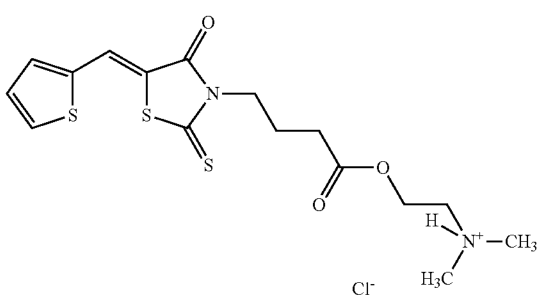 [SMILES: C[NH+](C)CCOC(=O)CCCN1C(=O)/C(=C/c2cccs2)SC1=S ; [Cl-]] | 421.0 |
| IIb-537 | 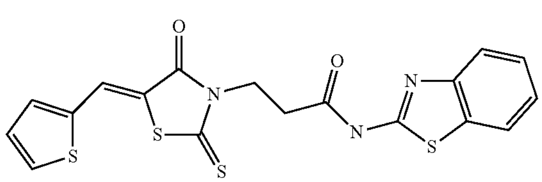 [SMILES: O=C(CCN1C(=O)/C(=C/c2cccs2)SC1=S)Nc1nc2ccccc2s1] | 431.6 |
| IIb-538 | 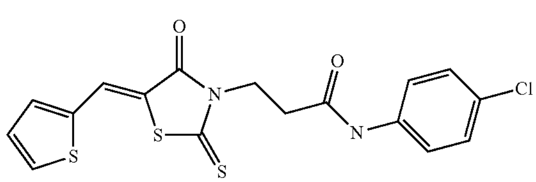 [SMILES: O=C(CCN1C(=O)/C(=C/c2cccs2)SC1=S)Nc1ccc(Cl)cc1] | 409.0 |

TABLE 9-continued

Thiophenylmethylenyl Alkanoic Acids And Amides ($R^3$ = O— And NH—)

| ID | Structure | MW |
|---|---|---|
| IIb-539 | 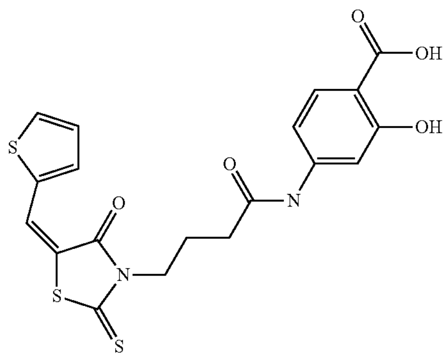 [SMILES: O=C(CCCN1C(=O)/C(=C\c2cccs2)SC1=S)Nc1ccc(C(=O)O)c(O)c1] | 448.5 |
| IIb-540 | 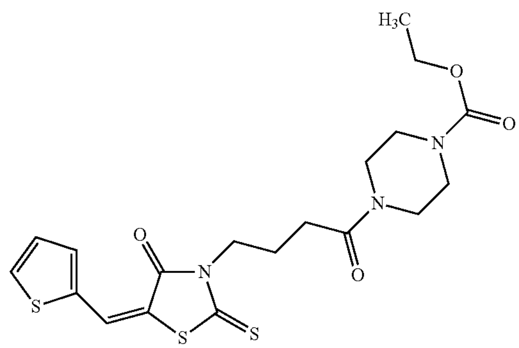 [SMILES: CCOC(=O)N1CCN(C(=O)CCCN2C(=O)/C(=C\c3cccs3)SC2=S)CC1] | 453.6 |
| IIb-541 | 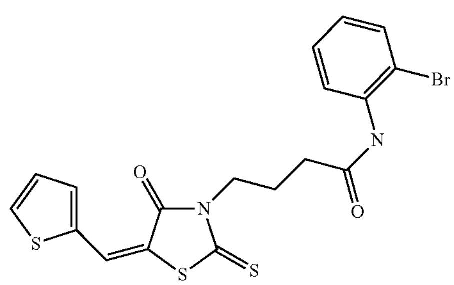 [SMILES: O=C(CCCN1C(=O)/C(=C\c2cccs2)SC1=S)Nc1ccccc1Br] | 467.4 |
| IIb-542 | 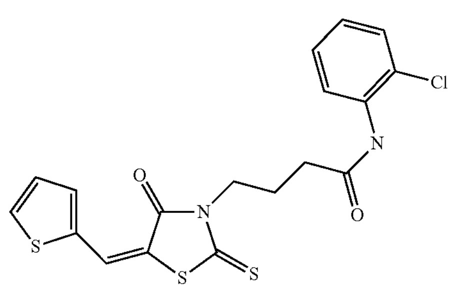 [SMILES: O=C(CCCN1C(=O)/C(=C\c2cccs2)SC1=S)Nc1ccccc1Cl] | 423.0 |
| IIb-543 | 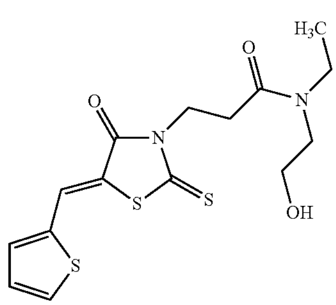 [SMILES: CCN(CCO)C(=O)CCN1C(=O)/C(=C/c2cccs2)SC1=S] | 370.5 |

TABLE 9-continued
Thiophenylmethylenyl Alkanoic Acids And Amides ($R^3$ = O— And NH—)
| ID | Structure | MW |
|---|---|---|
| IIb-544 | 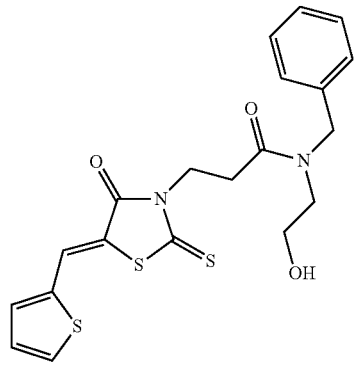 [SMILES: O=C(CCN1C(=O)/C(=C/c2cccs2)SC1=S)N(CCO)Cc1ccccc1] | 432.6 |
| IIb-545 | 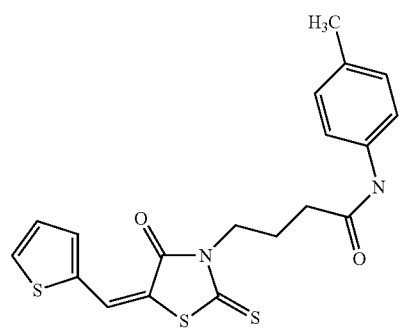 [SMILES: Cc1ccc(NC(=O)CCCN2C(=O)/C(=C\c3cccs3)SC2=S)cc1] | 402.6 |
| IIb-546 | 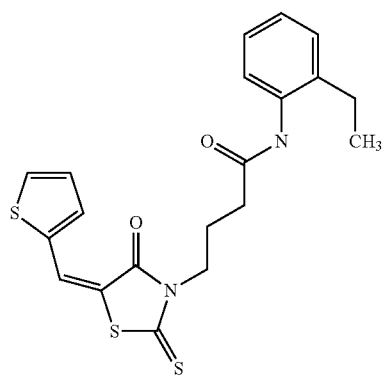 [SMILES: CCc1ccccc1NC(=O)CCCN1C(=O)/C(=C\c2cccs2)SC1=S] | 416.6 |
| IIb-547 | 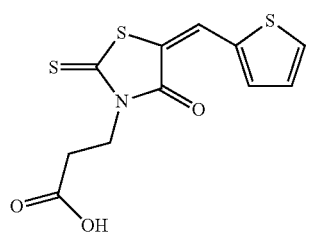 [SMILES: O=C(O)CCN1C(=O)/C(=C\c2cccs2)SC1=S] | 299.4 |

TABLE 9-continued

Thiophenylmethylenyl Alkanoic Acids And Amides ($R^3$ = O— And NH—)

| ID | Structure | MW |
|---|---|---|
| IIb-548 | 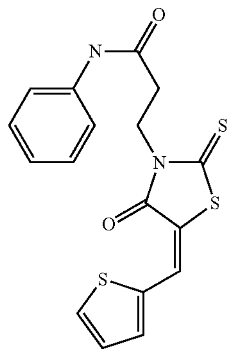 [SMILES: O=C(CCN1C(=O)/C(=C\c2cccs2)SC1=S)Nc1ccccc1] | 374.5 |
| IIb-549 | 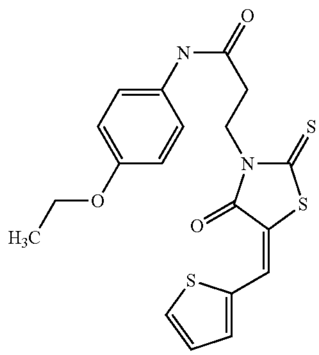 [SMILES: CCOc1ccc(NC(=O)CCN2C(=O)/C(=C\c3cccs3)SC2=S)cc1] | 418.6 |
| IIb-550 | 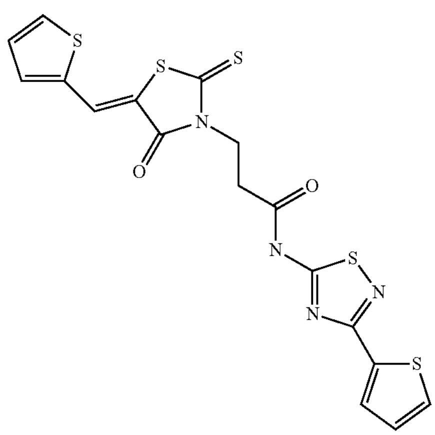 [SMILES: O=C(CCN1C(=O)/C(=C/c2cccs2)SC1=S)Nc1nc(-c2cccs2)ns1] | 464.6 |
| IIb-551 | 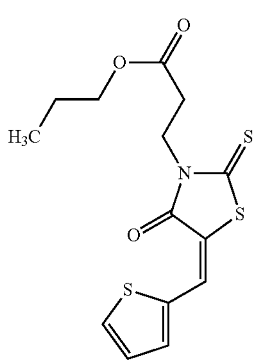 [SMILES: CCCOC(=O)CCN1C(=O)/C(=C\c2cccs2)SC1=S] | 341.5 |

TABLE 9-continued

Thiophenylmethylenyl Alkanoic Acids And Amides ($R^3$ = O— And NH—)

| ID | Structure | MW |
|---|---|---|
| IIb-552 | 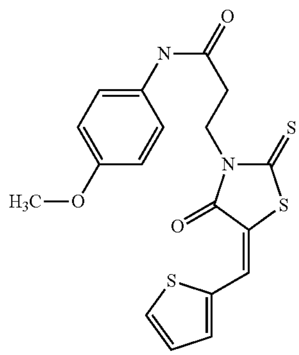 [SMILES: COc1ccc(NC(=O)CCN2C(=O)/C(=C\c3cccs3)SC2=S)cc1] | 404.5 |
| IIb-553 | 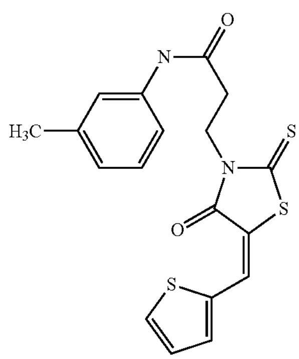 [SMILES: Cc1cccc(NC(=O)CCN2C(=O)/C(=C\c3cccs3)SC2=S)c1] | 388.5 |
| IIb-554 | 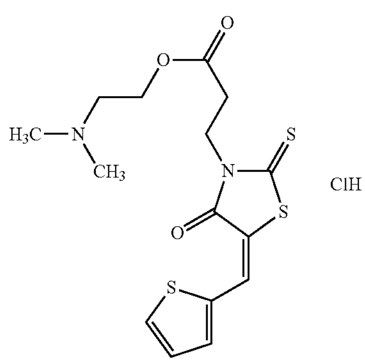 [SMILES: CN(C)CCOC(=O)CCN1C(=O)/C(=C\c2cccs2)SC1=S ; Cl] | 407.0 |
| IIb-555 | 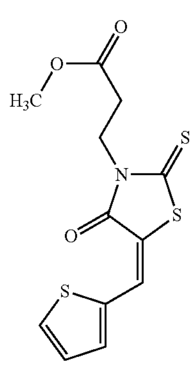 [SMILES: COC(=O)CCN1C(=O)/C(=C\c2cccs2)SC1=S] | 313.4 |

TABLE 9-continued

Thiophenylmethylenyl Alkanoic Acids And Amides ($R^3$ = O— And NH—)

| ID | Structure | MW |
|---|---|---|
| IIb-556 | 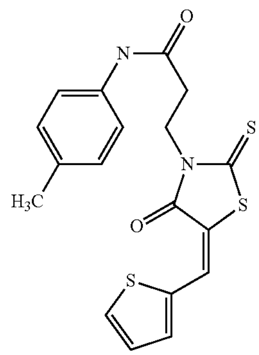 [SMILES: Cc1ccc(NC(=O)CCN2C(=O)/C(=C\c3cccs3)SC2=S)cc1] | 388.5 |
| IIb-557 | 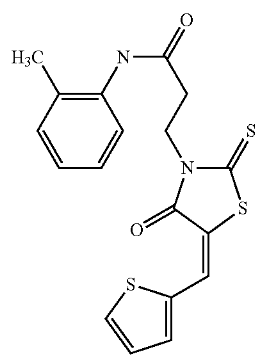 [SMILES: Cc1ccccc1NC(=O)CCN1C(=O)/C(=C\c2cccs2)SC1=S] | 388.5 |
| IIb-558 | 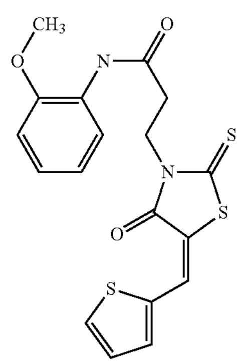 [SMILES: COc1ccccc1NC(=O)CCN1C(=O)/C(=C\c2cccs2)SC1=S] | 404.5 |
| IIb-559 | 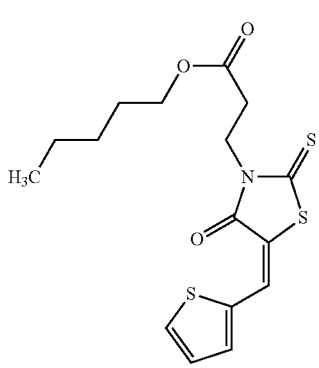 [SMILES: CCCCCOC(=O)CCN1C(=O)/C(=C\c2cccs2)SC1=S] | 369.5 |

TABLE 9-continued

Thiophenylmethylenyl Alkanoic Acids And Amides (R³ = O— And NH—)

| ID | Structure | MW |
|---|---|---|
| IIb-560 | 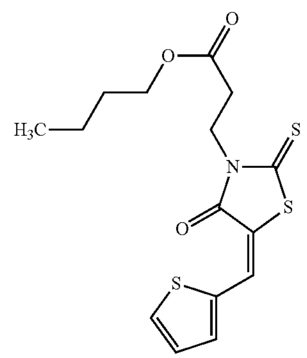 [SMILES: CCCCOC(=O)CCN1C(=O)/C(=C\c2cccs2)SC1=S] | 355.5 |
| IIb-561 | 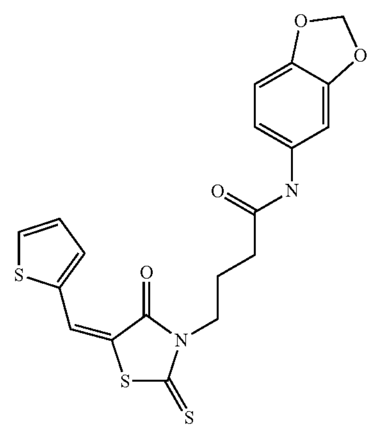 [SMILES: O=C(CCCN1C(=O)/C(=C\c2cccs2)SC1=S)Nc1ccc2c(c1)OCO2] | 432.5 |
| IIb-562 | 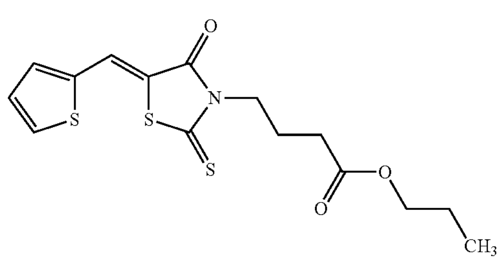 [SMILES: CCCOC(=O)CCCN1C(=O)/C(=C/c2cccs2)SC1=S] | 355.5 |
| IIb-563 | 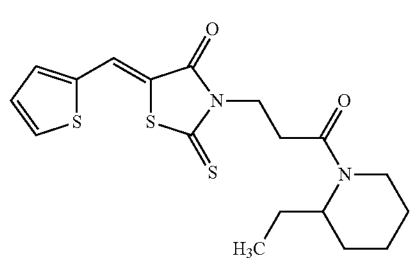 [SMILES: CCC1CCCCN1C(=O)CCN1C(=O)/C(=C/c2cccs2)SC1=S] | 394.6 |

TABLE 9-continued

Thiophenylmethylenyl Alkanoic Acids And Amides ($R^3$ = O— And NH—)

| ID | Structure | MW |
|---|---|---|
| IIb-564 | 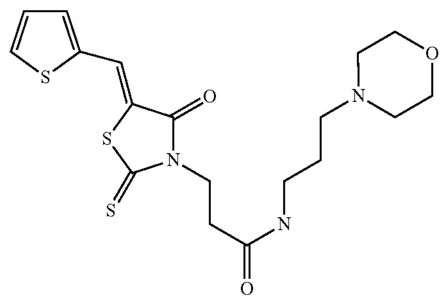 [SMILES: O=C(CCN1C(=O)/C(=C/c2cccs2)SC1=S)NCCCN1CCOCC1] | 425.6 |
| IIb-565 | 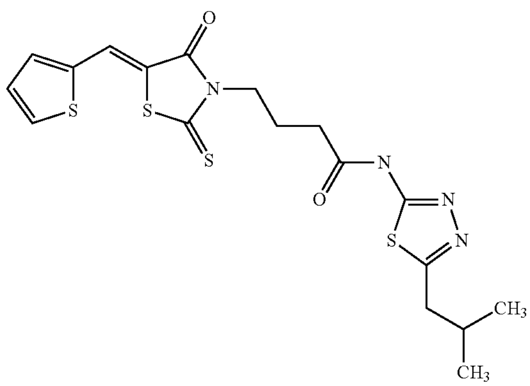 [SMILES: CC(C)Cc1nnc(NC(=O)CCCN2C(=O)/C(=C/c3cccs3)SC2=S)s1] | 452.6 |
| IIb-566 | 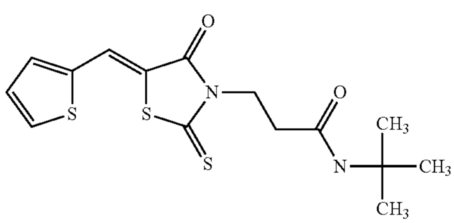 [SMILES: CC(C)(C)NC(=O)CCN1C(=O)/C(=C/c2cccs2)SC1=S] | 354.5 |
| IIb-567 | 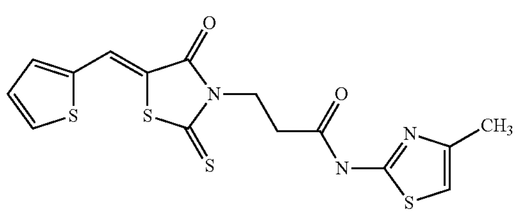 [SMILES: Cc1csc(NC(=O)CCN2C(=O)/C(=C/c3cccs3)SC2=S)n1] | 395.5 |
| IIb-568 | 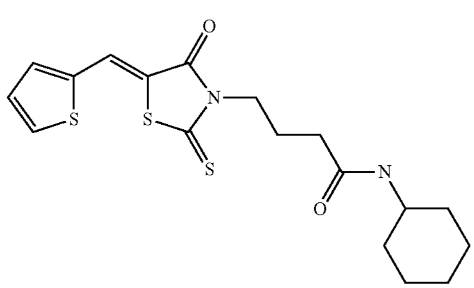 [SMILES: O=C(CCCN1C(=O)/C(=C/c2cccs2)SC1=S)NC1CCCCC1] | 394.6 |

TABLE 9-continued

Thiophenylmethylenyl Alkanoic Acids And Amides ($R^3$ = O— And NH—)

| ID | Structure | MW |
|---|---|---|
| IIb-569 | 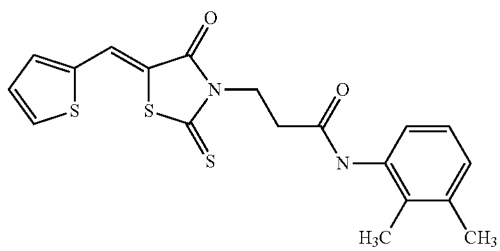 [SMILES: Cc1cccc(NC(=O)CCN2C(=O)/C(=C/c3cccs3)SC2=S)c1C] | 402.6 |
| IIb-570 | 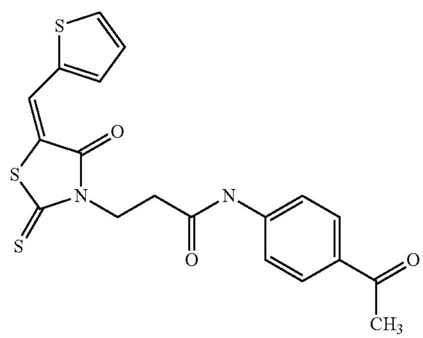 [SMILES: CC(=O)c1ccc(NC(=O)CCN2C(=O)/C(=C\c3cccs3)SC2=S)cc1] | 416.5 |
| IIb-571 | 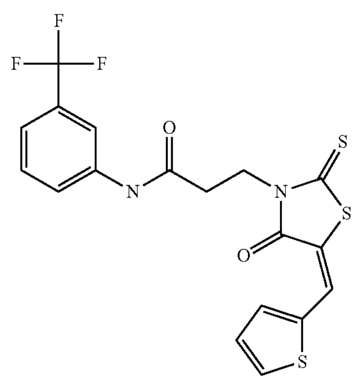 [SMILES: O=C(CCN1C(=O)/C(=C\c2cccs2)SC1=S)Nc1cccc(C(F)(F)F)c1] | 442.5 |
| IIb-572 | 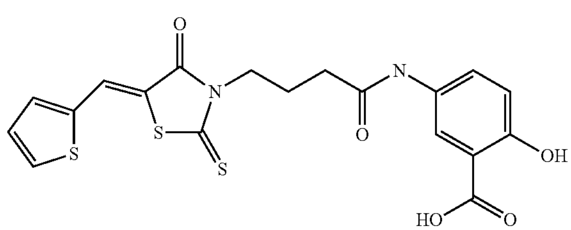 [SMILES: O=C(CCCN1C(=O)/C(=C/c2cccs2)SC1=S)Nc1ccc(O)c(C(=O)O)c1] | 448.5 |
| IIb-573 | 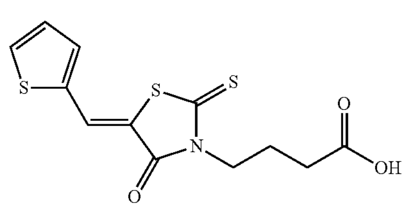 [SMILES: O=C(O)CCCN1C(=O)/C(=C/c2cccs2)SC1=S] | 313.4 |

TABLE 9-continued

Thiophenylmethylenyl Alkanoic Acids And Amides ($R^3$ = O— And NH—)

| ID | Structure | MW |
|---|---|---|
| IIb-574 | 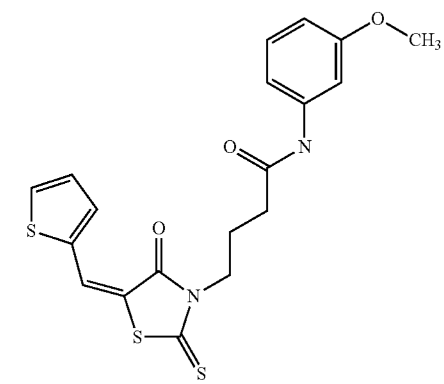 [SMILES: COc1cccc(NC(=O)CCCN2C(=O)/C(=C\c3cccs3)SC2=S)c1] | 418.6 |
| IIb-575 | 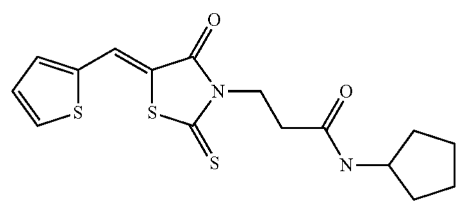 [SMILES: O=C(CCN1C(=O)/C(=C/c2cccs2)SC1=S)NC1CCCC1] | 366.5 |
| IIb-576 | 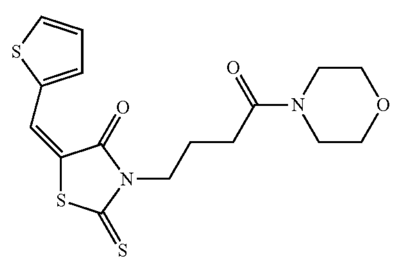 [SMILES: O=C(CCCN1C(=O)/C(=C\c2cccs2)SC1=S)N1CCOCC1] | 382.5 |
| IIb-577 | 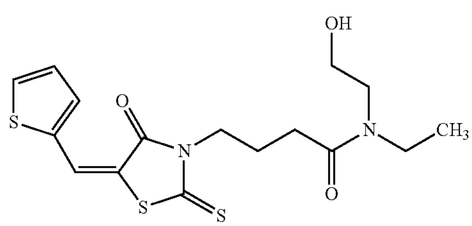 [SMILES: CCN(CCO)C(=O)CCCN1C(=O)/C(=C\c2cccs2)SC1=S] | 384.5 |
| IIb-578 | 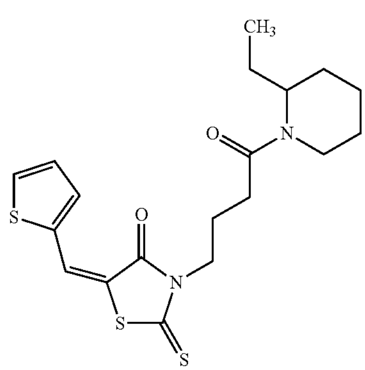 [SMILES: CCC1CCCCN1C(=O)CCCN1C(=O)/C(=C\c2cccs2)SC1=S] | 408.6 |

TABLE 9-continued
Thiophenylmethylenyl Alkanoic Acids And Amides ($R^3$ = O— And NH—)
| ID | Structure | MW |
|---|---|---|
| IIb-579 | 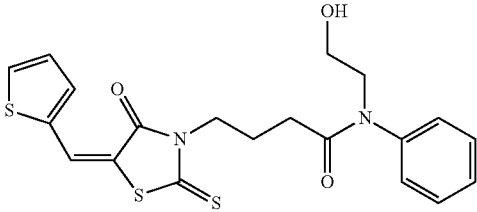 [SMILES: O=C1/C(=C\c2cccs2)SC(=S)N1CCCC(=O)N(CCO)c1ccccc1] | 432.6 |
| IIb-580 | 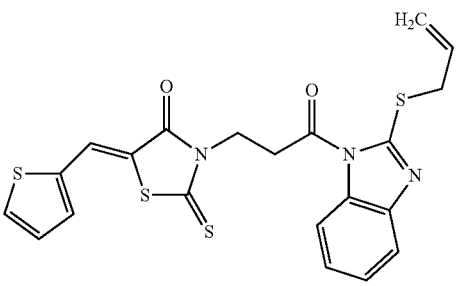 [SMILES: C=CCSc1nc2ccccc2n1C(=O)CCN1C(=O)/C(=C/c2cccs2)SC1=S] | 471.6 |
| IIb-581 | 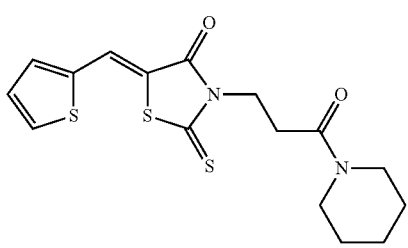 [SMILES: O=C(CCN1C(=O)/C(=C/c2cccs2)SC1=S)N1CCCCC1] | 366.5 |
| IIb-582 | 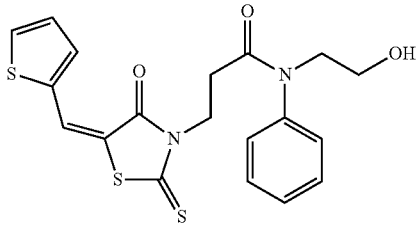 [SMILES: O=C1/C(=C\c2cccs2)SC(=S)N1CCC(=O)N(CCO)c1ccccc1] | 418.6 |
| IIb-583 | 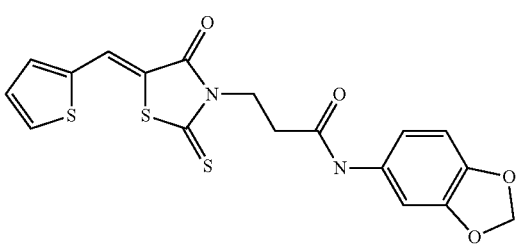 [SMILES: O=C(CCN1C(=O)/C(=C/c2cccs2)SC1=S)Nc1ccc2c(c1)OCO2] | 418.5 |
| IIb-584 | 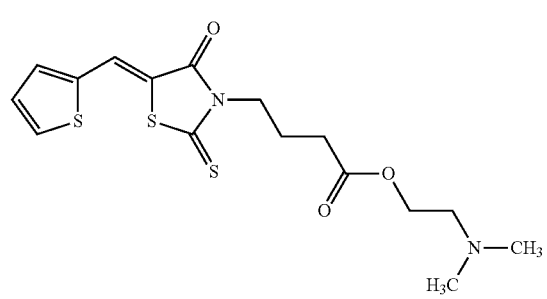 | 421.0 |

TABLE 9-continued
Thiophenylmethylenyl Alkanoic Acids And Amides ($R^3$ = O— And NH—)
| ID | Structure | MW |
|---|---|---|
| IIb-585 | 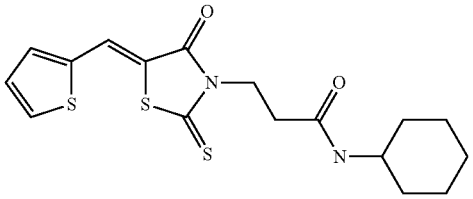 [SMILES: O=C(CCN1C(=O)/C(=C/c2cccs2)SC1=S)NC1CCCCC1] | 380.6 |
| IIb-586 | 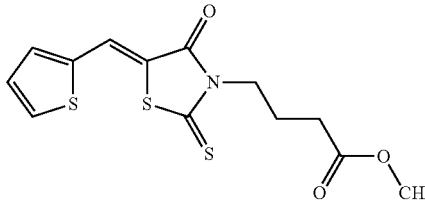 | 327.4 |
| IIb-587 | 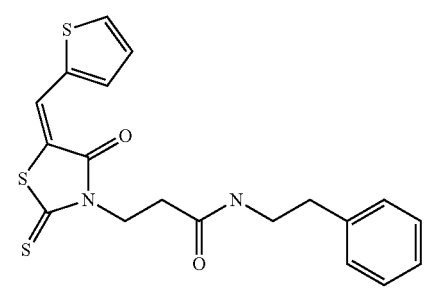 [SMILES: O=C(CCN1C(=O)/C(=C\c2cccs2)SC1=S)NCCc1ccccc1] | 402.6 |
| IIb-588 | 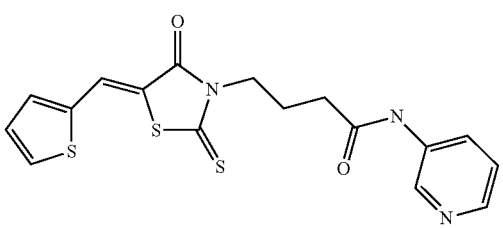 [SMILES: O=C(CCCN1C(=O)/C(=C/c2cccs2)SC1=S)Nc1cccnc1] | 389.5 |
| IIb-589 | 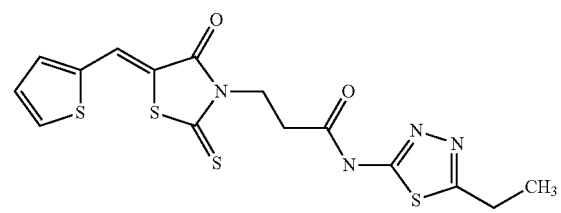 [SMILES: CCc1nnc(NC(=O)CCN2C(=O)/C(=C/c3cccs3)SC2=S)s1] | 410.6 |
| 590 | 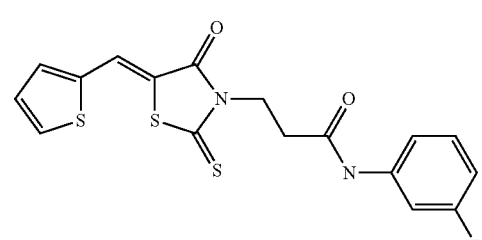 | 453.4 |

TABLE 9-continued

Thiophenylmethylenyl Alkanoic Acids And Amides ($R^3$ = O— And NH—)

| ID | Structure | MW |
|---|---|---|
| IIb-591 | 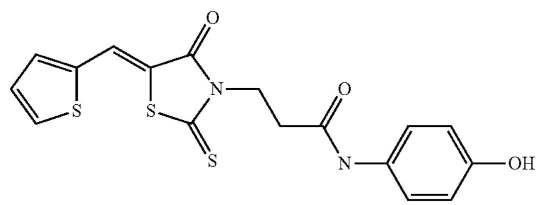 [SMILES: O=C(CCN1C(=O)/C(=C/c2cccs2)SC1=S)Nc1ccc(O)cc1] | 390.5 |
| IIb-592 | 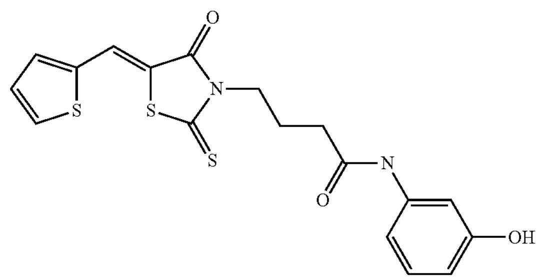 [SMILES: O=C(CCCN1C(=O)/C(=C/c2cccs2)SC1=S)Nc1cccc(O)c1] | 404.5 |
| IIb-593 | 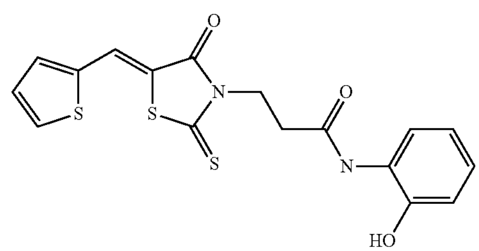 [SMILES: O=C(CCN1C(=O)/C(=C/c2cccs2)SC1=S)Nc1ccccc1O] | 390.5 |
| IIb-594 | 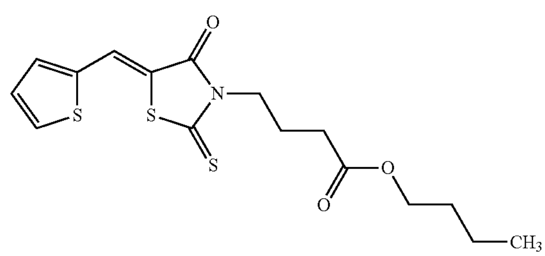 [SMILES: CCCCOC(=O)CCCN1C(=O)/C(=C/c2cccs2)SC1=S] | 369.5 |
| IIb-595 | 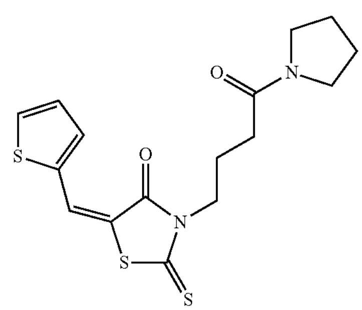 [SMILES: O=C(CCCN1C(=O)/C(=C\c2cccs2)SC1=S)N1CCCC1] | 366.5 |
| IIb-596 | 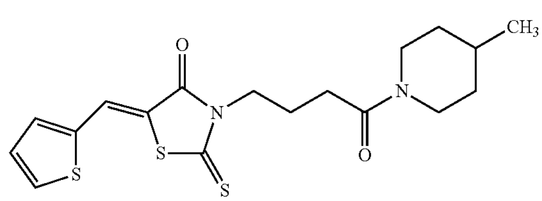 [SMILES: CC1CCN(C(=O)CCCN2C(=O)/C(=C/c3cccs3)SC2=S)CC1] | 394.6 |

TABLE 9-continued

Thiophenylmethylenyl Alkanoic Acids And Amides ($R^3$ = O— And NH—)

| ID | Structure | MW |
|---|---|---|
| IIb-597 | 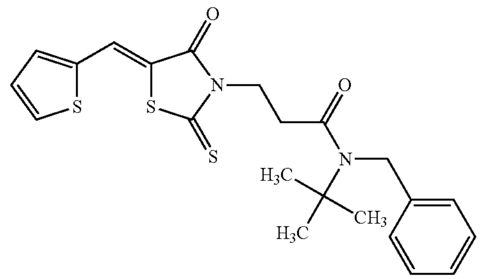 [SMILES: CC(C)(C)N(Cc1ccccc1)C(=O)CCN1C(=O)/C(=C/c2cccs2)SC1=S] | 444.6 |
| IIb-598 | 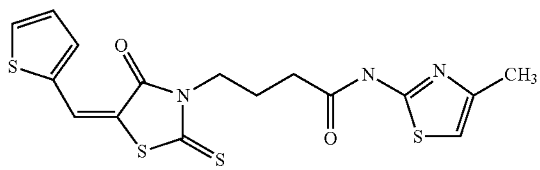 [SMILES: Cc1csc(NC(=O)CCCN2C(=O)/C(=C\c3cccs3)SC2=S)n1] | 409.6 |
| IIb-599 | 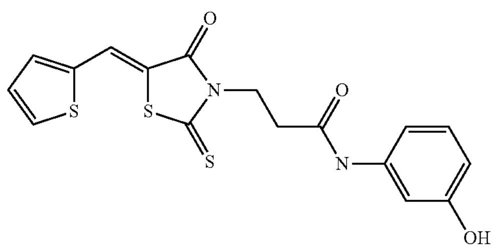 [SMILES: O=C(CCN1C(=O)/C(=C/c2cccs2)SC1=S)Nc1cccc(O)c1] | 390.5 |
| IIb-600 | 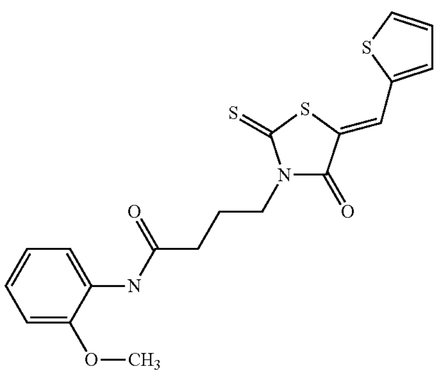 [SMILES: COc1ccccc1NC(=O)CCCN1C(=O)/C(=C/c2cccs2)SC1=S] | 418.6 |
| IIb-601 | 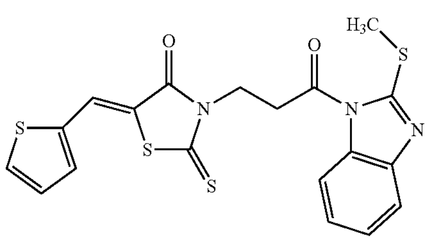 [SMILES: CSc1nc2ccccc2n1C(=O)CCN1C(=O)/C(=C/c2cccs2)SC1=S] | 445.6 |
| IIb-602 | 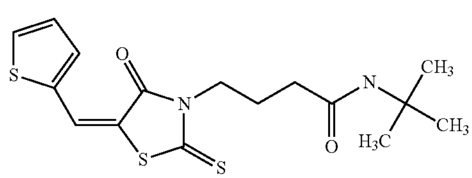 [SMILES: CC(C)(C)NC(=O)CCCN1C(=O)/C(=C\c2cccs2)SC1=S] | 368.5 |

TABLE 9-continued

Thiophenylmethylenyl Alkanoic Acids And Amides ($R^3$ = O— And NH—)

| ID | Structure | MW |
|---|---|---|
| IIb-603 | 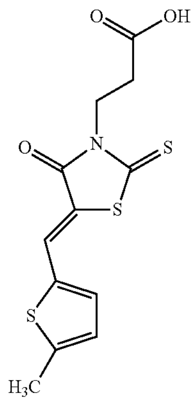 [SMILES: Cc1ccc(/C=C2\SC(=S)N(CCC(=O)O)C2=O)s1] | 313.4 |
| IIb-604 | 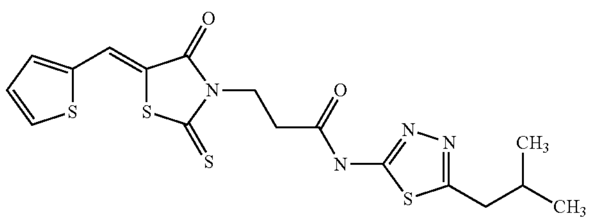 [SMILES: CC(C)Cc1nnc(NC(=O)CCN2C(=O)/C(=C/c3cccs3)SC2=S)s1] | 438.6 |
| IIb-605 | 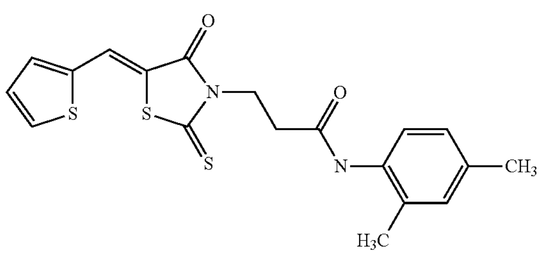 [SMILES: Cc1ccc(NC(=O)CCN2C(=O)/C(=C/c3cccs3)SC2=S)c(C)c1] | 402.6 |
| IIb-606 | 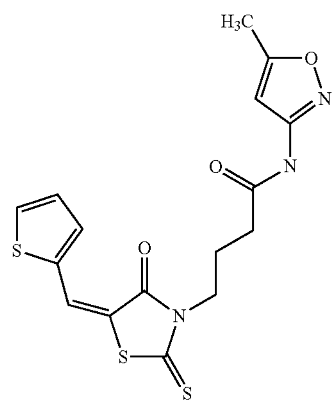 [SMILES: Cc1cc(NC(=O)CCCN2C(=O)/C(=C\c3cccs3)SC2=S)no1] | 393.5 |
| IIb-607 | 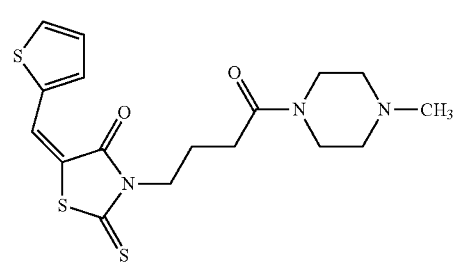 [SMILES: CN1CCN(C(=O)CCCN2C(=O)/C(=C\c3cccs3)SC2=S)CC1] | 395.6 |

TABLE 9-continued

Thiophenylmethylenyl Alkanoic Acids And Amides ($R^3$ = O— And NH—)

| ID | Structure | MW |
|---|---|---|
| IIb-608 | 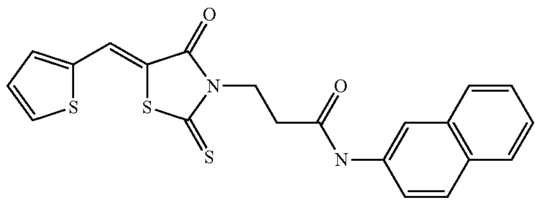 [SMILES: O=C(CCN1C(=O)/C(=C/c2cccs2)SC1=S)Nc1ccc2ccccc2c1] | 424.6 |
| IIb-609 | 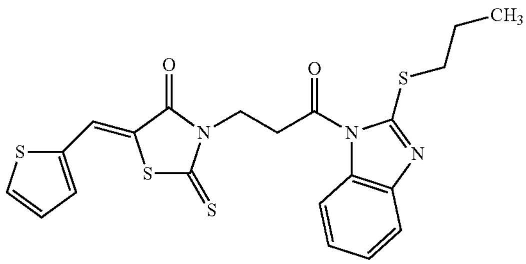 [SMILES: CCCSc1nc2ccccc2n1C(=O)CCN1C(=O)/C(=C/c2cccs2)SC1=S] | 459.6 |
| IIb-610 | 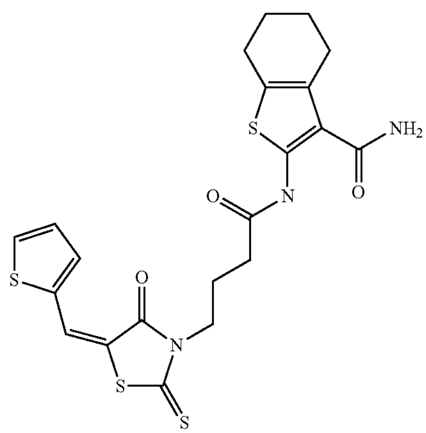 [SMILES: NC(=O)c1c(NC(=O)CCCN2C(=O)/C(=C\c3cccs3)SC2=S)sc2c1CCCC2] | 491.7 |
| IIb-611 | 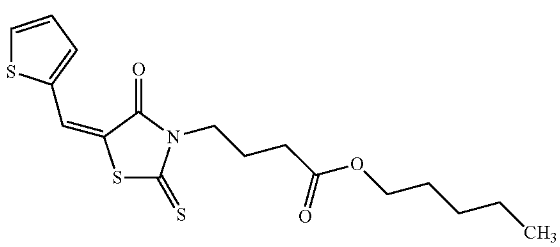 [SMILES: CCCCCOC(=O)CCCN1C(=O)/C(=C\c2cccs2)SC1=S] | 383.6 |
| IIb-612 | 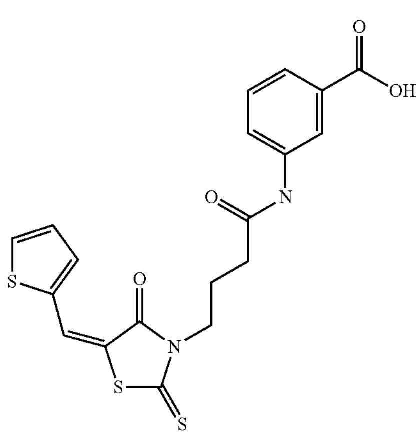 [SMILES: O=C(CCCN1C(=O)/C(=C\c2cccs2)SC1=S)Nc1cccc(C(=O)O)c1] | 432.5 |

TABLE 9-continued

Thiophenylmethylenyl Alkanoic Acids And Amides ($R^3$ = O— And NH—)

| ID | Structure | MW |
|---|---|---|
| IIb-613 | 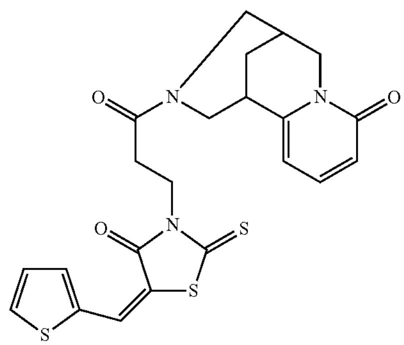 [SMILES: O=C(CCN1C(=O)/C(=C\c2cccs2)SC1=S)N1CC2CC(C1)c1cccc(=O)n1C2] | 471.6 |
| IIb-614 | 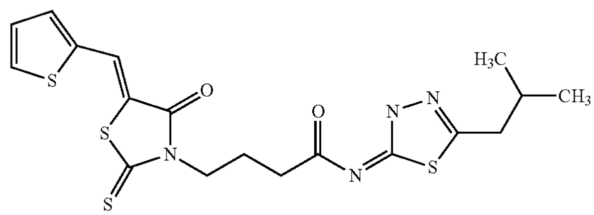 [SMILES: CC(C)Cc1n[nH]/c(=N\C(=O)CCCN2C(=O)/C(=C/c3cccs3)SC2=S)s1] | 452.6 |
| IIb-615 | 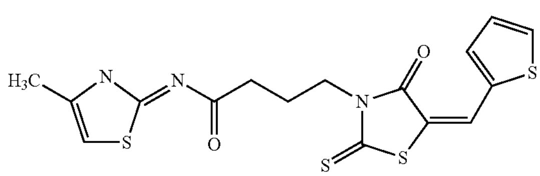 [SMILES: Cc1cs/c(=N\C(=O)CCCN2C(=O)/C(=C\c3cccs3)SC2=S)[nH]1] | 409.6 |
| IIb-616 | 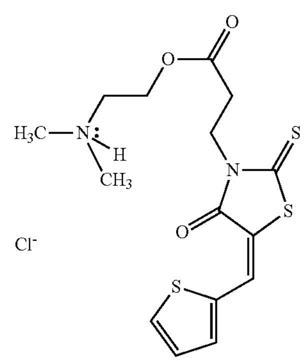 | 407.0 |
| IIb-617 | 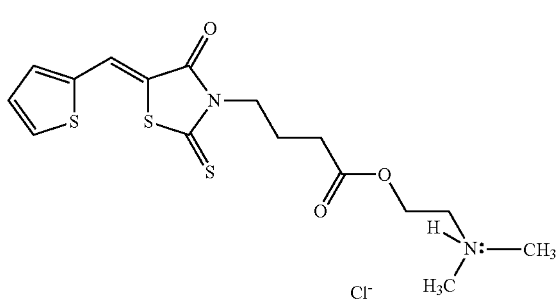 | 421.0 |

TABLE 10

5-[[2,5-Dimethyl-1H-Pyrrol-3-Yl]Methylene]-2,4-Thiazolidinediones

| ID | Structure |
|---|---|
| IIc-1 | 4-(CO₂H)phenyl-N-pyrrole(2,5-diMe)-3-CH=thiazolidinedione-N-(4-chlorophenyl) |
| IIc-2 | N-(3-chlorophenyl)-thiazolidinedione-5-CH=pyrrole(2,5-diMe)-N-(4-CO₂H-phenyl) |
| IIc-3 | 3-pyridyl-N-pyrrole(2,5-diMe)-3-CH=thiazolidinedione-N-Ph |
| IIc-4 | N-(2-chlorophenyl)-thiazolidinedione-5-CH=pyrrole(2,5-diMe)-N-(3-pyridyl) |
| IIc-5 | N-(3-chlorophenyl)-thiazolidinedione-5-CH=pyrrole(2,5-diMe)-N-(4-bromo-1-naphthyl) |
| IIc-6 | 2-(MeO₂C)phenyl-N-pyrrole(2,5-diMe)-3-CH=thiazolidinedione-N-(2-fluorophenyl) |

TABLE 10-continued

5-[[2,5-Dimethyl-1H-Pyrrol-3-Yl]Methylene]-2,4-Thiazolidinediones

| ID | Structure |
|---|---|
| IIc-7 | 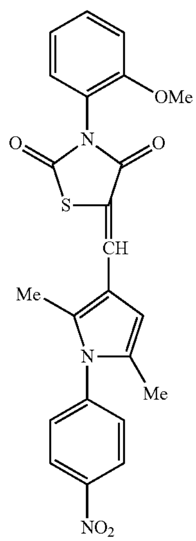 [SMILES: COc1ccccc1N1C(=O)SC(=Cc2cc(C)n(-c3ccc([N+](=O)[O-])cc3)c2C)C1=O] |
| IIc-8 | 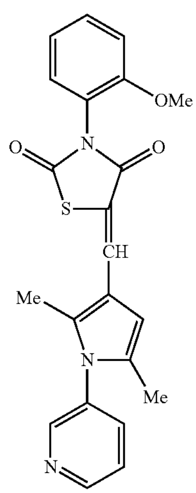 [SMILES: COc1ccccc1N1C(=O)SC(=Cc2cc(C)n(-c3cccnc3)c2C)C1=O] |
| IIc-9 | 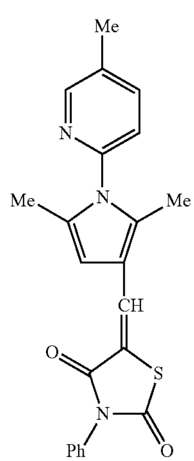 [SMILES: Cc1ccc(-n2c(C)cc(C=C3SC(=O)N(c4ccccc4)C3=O)c2C)nc1] |
| IIc-10 | 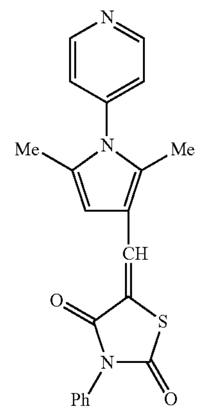 [SMILES: Cc1cc(C=C2SC(=O)N(c3ccccc3)C2=O)c(C)n1-c1ccncc1] |
| IIc-11 | 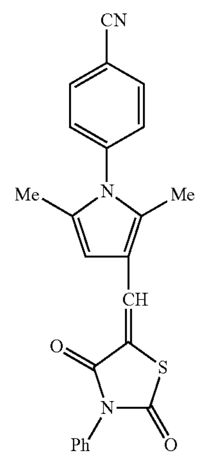 [SMILES: Cc1cc(C=C2SC(=O)N(c3ccccc3)C2=O)c(C)n1-c1ccc(C#N)cc1] |
| IIc-12 | 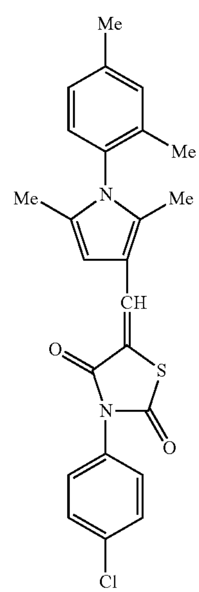 [SMILES: Cc1ccc(-n2c(C)cc(C=C3SC(=O)N(c4ccc(Cl)cc4)C3=O)c2C)c(C)c1] |

TABLE 10-continued
5-[[2,5-Dimethyl-1H-Pyrrol-3-Yl]Methylene]-2,4-Thiazolidinediones
| ID | Structure |
|---|---|
| IIc-13 | 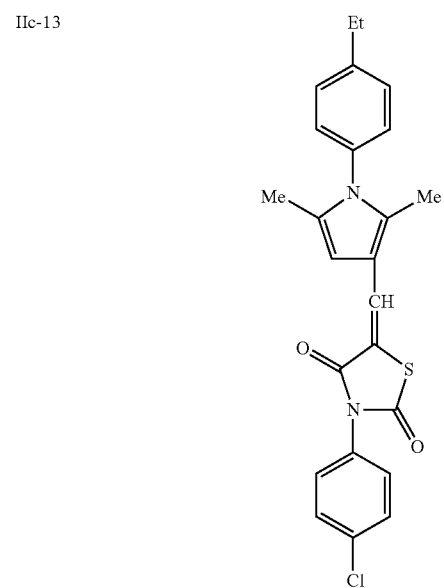 |
| IIc-14 | 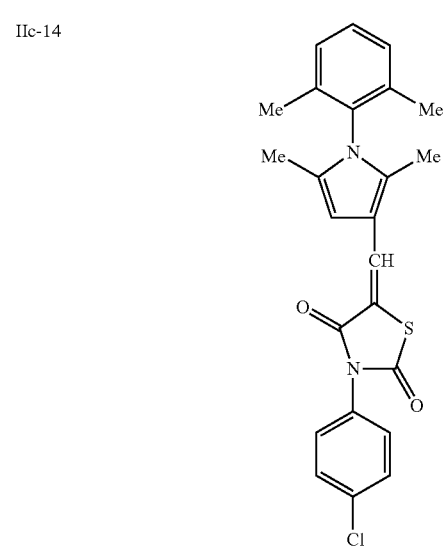 |
| IIc-15 | (structure shown) |
| IIc-16 | (structure shown) |

TABLE 10-continued
5-[[2,5-Dimethyl-1H-Pyrrol-3-Yl]Methylene]-2,4-Thiazolidinediones
| ID | Structure |
|---|---|
| IIc-17 | 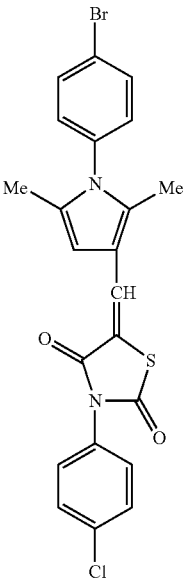 |
| IIc-19 | 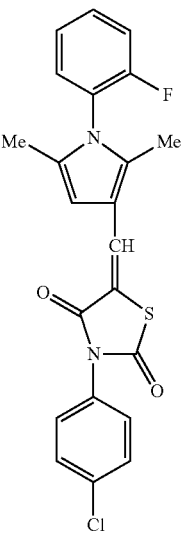 [SMILES: Cc1cccc(C)c1-n1c(C)cc(C=C2SC(=O)N(c3ccc(Cl)cc3)C2=O)c1C] |
| IIc-18 | 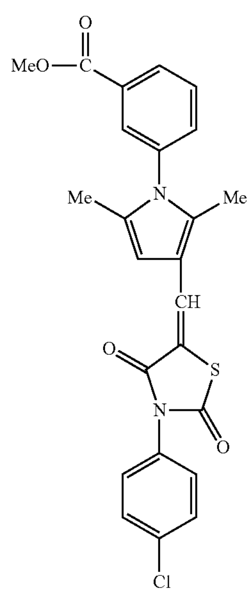 [SMILES: COC(=O)c1cccc(-n2c(C)cc(C=C3SC(=O)N(c4ccc(Cl)cc4)C3=O)c2C)c1] |
| IIc-20 | 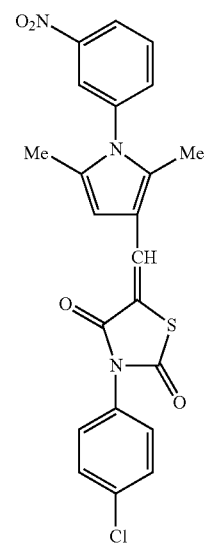 [SMILES: Cc1cc(C=C2SC(=O)N(c3ccc(Cl)cc3)C2=O)c(C)n1-c1cccc([N+](=O)[O-])c1] |

TABLE 10-continued
5-[[2,5-Dimethyl-1H-Pyrrol-3-Yl]Methylene]-2,4-Thiazolidinediones
| ID | Structure |
|---|---|
| IIc-21 | 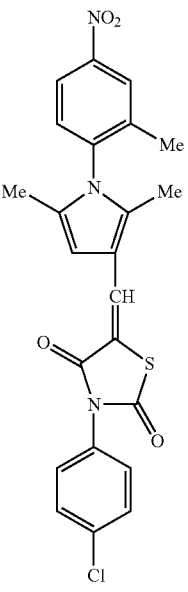 |
| IIc-22 | 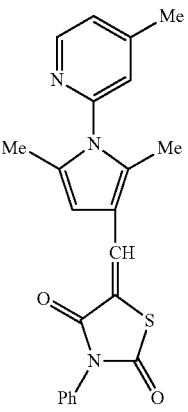 [SMILES: Cc1ccnc(-n2c(C)cc(C=C3SC(=O)N(c4ccccc4)C3=O)c2C)c1] |
| IIc-23 | 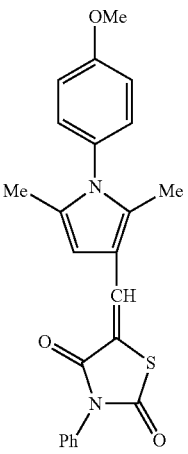 |
| IIc-24 | 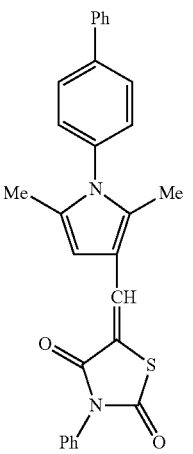 |
| IIc-25 | 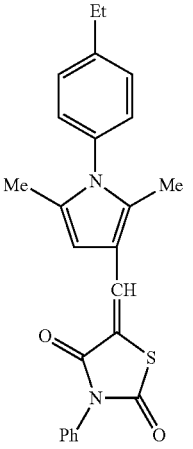 |
| IIc-26 | 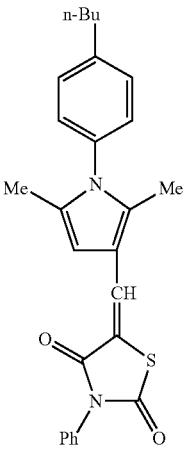 |

TABLE 10-continued

5-[[2,5-Dimethyl-1H-Pyrrol-3-Yl]Methylene]-2,4-Thiazolidinediones

| ID | Structure |
|---|---|
| IIc-27 | 4-OAc-phenyl on N of pyrrole |
| IIc-28 | 2,5-dimethylphenyl on N of pyrrole |
| IIc-29 | benzo[1,3]dioxol-5-yl on N of pyrrole |
| IIc-30 | 3-(methoxycarbonyl)phenyl on N of pyrrole |
| IIc-31 | 1,2,5-triphenylpyrrole derivative |
| IIc-32 | 2-chloro-4-(methoxycarbonyl)phenyl on N of pyrrole |
| IIc-33 | 4-(4-bromobenzyloxy)phenyl on N of pyrrole |

TABLE 10-continued

5-[[2,5-Dimethyl-1H-Pyrrol-3-Yl]Methylene]-2,4-Thiazolidinediones

| ID | Structure |
|---|---|
| IIc-34 | (4-carboxyphenyl on pyrrole N) |
| IIc-35 | (4-methyl-3-nitrophenyl on pyrrole N) |
| IIc-36 | (3-ethoxycarbonyl-4,5-dimethylthien-2-yl on pyrrole N) |
| IIc-37 | (4-(4-fluorobenzyloxy)phenyl on pyrrole N) |
| IIc-38 | (5-chloro-2-methoxyphenyl on pyrrole N) |
| IIc-39 | (2-ethylphenyl on pyrrole N) |

TABLE 10-continued
5-[[2,5-Dimethyl-1H-Pyrrol-3-Yl]Methylene]-2,4-Thiazolidinediones
| ID | Structure |
|---|---|
| IIc-40 | 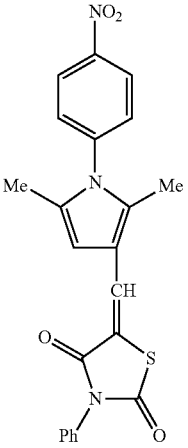 |
| IIc-41 | 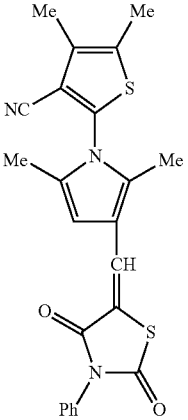 [SMILES: Cc1sc(-n2c(C)cc(C=C3SC(=O)N(c4ccccc4)C3=O)c2C)c(C#N)c1C] |
| IIc-42 | 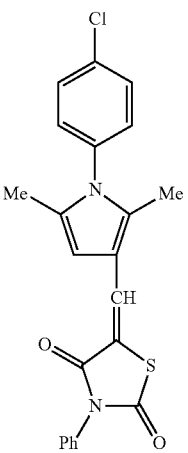 |
| IIc-43 | 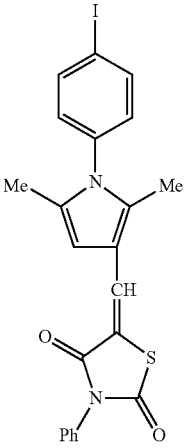 |
| IIc-44 | 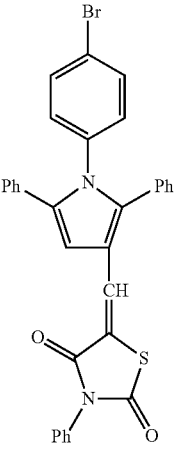 [SMILES: O=C1SC(=Cc2cc(-c3ccccc3)n(-c3ccc(Br)cc3)c2-c2ccccc2)C(=O)N1c1ccccc1] |
| IIc-45 | 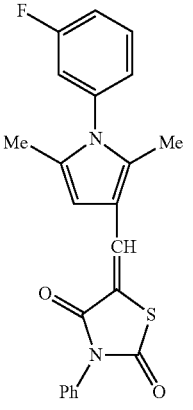 [SMILES: Cc1cc(C=C2SC(=O)N(c3ccccc3)C2=O)c(C)n1-c1cccc(F)c1] |

TABLE 10-continued
5-[[2,5-Dimethyl-1H-Pyrrol-3-Yl]Methylene]-2,4-Thiazolidinediones
| ID | Structure |
|---|---|
| IIc-46 | 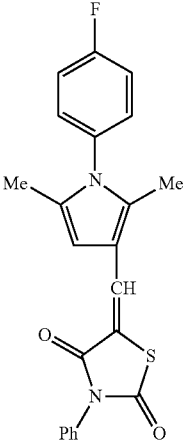 |
| IIc-47 | 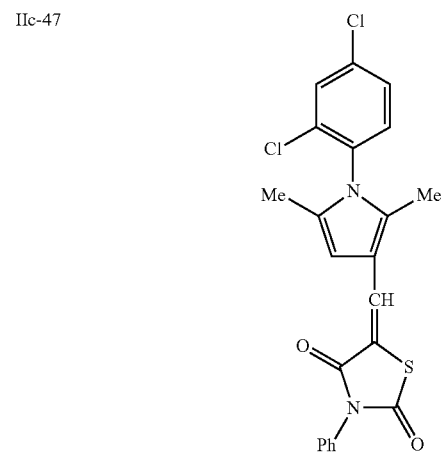 |
| IIc-48 | 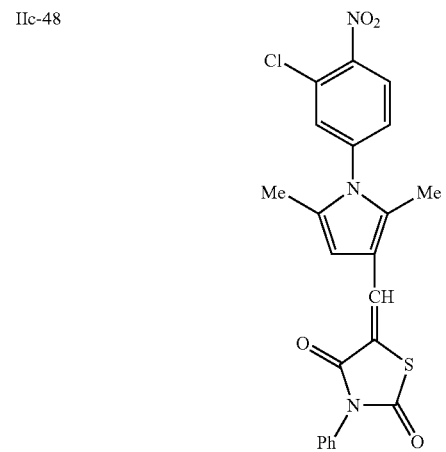 |
TABLE 10-continued
5-[[2,5-Dimethyl-1H-Pyrrol-3-Yl]Methylene]-2,4-Thiazolidinediones
| ID | Structure |
|---|---|
| IIc-49 | 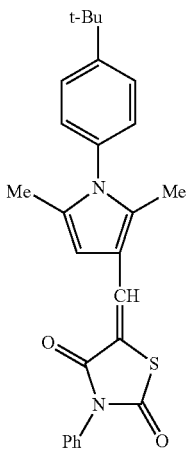 [SMILES: Cc1cc(C=C2SC(=O)N(c3ccccc3)C2=O)c(C)n1-c1ccc(C(C)(C)C)cc1] |
| IIc-50 | 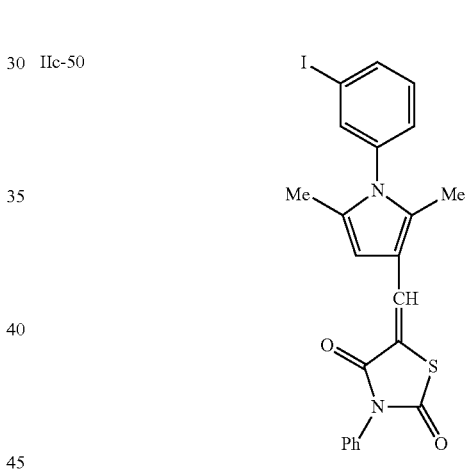 |
| IIc-51 | 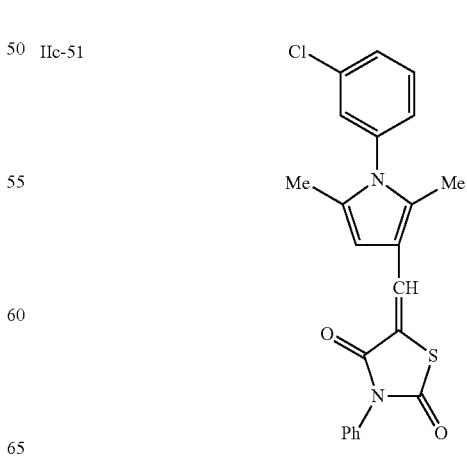 |

TABLE 10-continued

5-[[2,5-Dimethyl-1H-Pyrrol-3-Yl]Methylene]-2,4-Thiazolidinediones

| ID | Structure |
|---|---|
| IIc-52 | 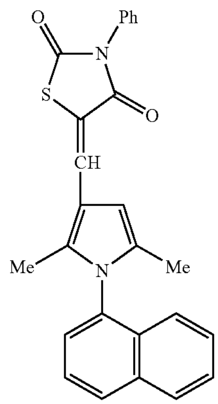 [SMILES: Cc1cc(C=C2SC(=O)N(c3ccccc3)C2=O)c(C)n1-c1cccc2ccccc12] |
| IIc-53 | 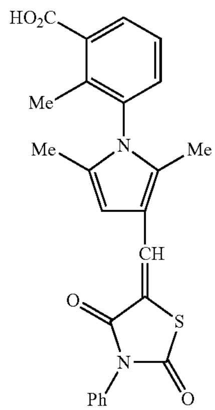 [SMILES: Cc1c(C(=O)O)cccc1-n1c(C)cc(C=C2SC(=O)N(c3ccccc3)C2=O)c1C] |
| IIc-54 | 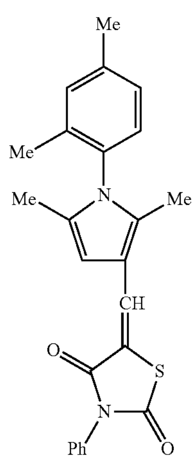 [SMILES: Cc1ccc(-n2c(C)cc(C=C3SC(=O)N(c4ccccc4)C3=O)c2C)c(C)c1] |
| IIc-55 | |
| IIc-56 | |
| IIc-57 | |

TABLE 10-continued

5-[[2,5-Dimethyl-1H-Pyrrol-3-Yl]Methylene]-2,4-Thiazolidinediones

| ID | Structure |
|---|---|
| IIc-58 | (structure) |
| IIc-59 | (structure) |
| IIc-60 | (structure) |
| IIc-61 | (structure) |
| IIc-62 | (structure) |
| IIc-63 | (structure) |

TABLE 10-continued

5-[[2,5-Dimethyl-1H-Pyrrol-3-Yl]Methylene]-2,4-Thiazolidinediones

| ID | Structure |
|---|---|
| IIc-64 | (4-chlorobenzyloxy)phenyl substituted structure |
| IIc-65 | 4-methylphenyl substituted structure |
| IIc-66 | 4-nitrophenyl, 2,5-diphenyl pyrrole structure |
| IIc-67 | 5-chloro-2-methylphenyl substituted structure |
| IIc-68 | (2-fluorobenzyloxy)phenyl substituted structure |
| IIc-69 | 3-carboxyphenyl substituted structure |

TABLE 10-continued

5-[[2,5-Dimethyl-1H-Pyrrol-3-Yl]Methylene]-2,4-Thiazolidinediones

| ID | Structure |
|---|---|
| IIc-70 | 4-NHAc-phenyl on pyrrole N |
| IIc-71 | 4-(4-nitrophenylthio)phenyl on pyrrole N |
| IIc-72 | 2-(methoxycarbonyl)phenyl on pyrrole N |
| IIc-73 | 4-OEt-phenyl on pyrrole N |
| IIc-74 | 4-iodo-3-methylphenyl on pyrrole N |
| IIc-75 | 4-nitro-2-methylphenyl on pyrrole N |

TABLE 10-continued

5-[[2,5-Dimethyl-1H-Pyrrol-3-Yl]Methylene]-2,4-Thiazolidinediones

| ID | Structure |
|---|---|
| IIc-76 | 2,3-dimethylphenyl on pyrrole N |
| IIc-77 | 2-fluorophenyl on pyrrole N |
| IIc-78 | 4-[(5-nitropyridin-2-yl)oxy]phenyl on pyrrole N |
| IIc-79 | naphthalen-2-yl on pyrrole N |
| IIc-80 | 4-chloro-3-(methoxycarbonyl)phenyl on pyrrole N |
| IIc-81 | 3,5-dimethylphenyl on pyrrole N |
| IIc-82 | 4-chlorophenyl on pyrrole N, with 2,5-diphenyl pyrrole |

TABLE 10-continued

5-[[2,5-Dimethyl-1H-Pyrrol-3-Yl]Methylene]-2,4-Thiazolidinediones

| ID | Structure |
|---|---|
| IIc-83 | (2,5-dichlorophenyl on pyrrole N) |
| IIc-84 | (4-(2,4-dichlorobenzyloxy)phenyl on pyrrole N) |
| IIc-85 | (3-chloro-2-methylphenyl on pyrrole N) |
| IIc-86 | (2-chlorophenyl on pyrrole N) |
| IIc-87 | (2-carboxyphenyl on pyrrole N) |
| IIc-88 | (4-methyl-3-(methoxycarbonyl)phenyl on pyrrole N) |

TABLE 10-continued

5-[[2,5-Dimethyl-1H-Pyrrol-3-Yl]Methylene]-2,4-Thiazolidinediones

| ID | Structure |
|---|---|
| IIc-89 | 2,3-dichlorophenyl on N of 2,5-dimethylpyrrole; pyrrole-3-CH=thiazolidine-2,4-dione N-Ph |
| IIc-90 | 3,4-dichlorophenyl on N of 2,5-dimethylpyrrole; pyrrole-3-CH=thiazolidine-2,4-dione N-Ph |
| IIc-91 | 4-(adamantyl)phenyl on N of 2,5-dimethylpyrrole; pyrrole-3-CH=thiazolidine-2,4-dione N-Ph |
| IIc-92 | 4-isopropylphenyl on N of 2,5-dimethylpyrrole; pyrrole-3-CH=thiazolidine-2,4-dione N-Ph |
| IIc-93 | 3-chloro-4-fluorophenyl on N of 2,5-dimethylpyrrole; pyrrole-3-CH=thiazolidine-2,4-dione N-Ph |
| IIc-94 | 4-(2-chlorobenzyloxy)phenyl on N of 2,5-dimethylpyrrole; pyrrole-3-CH=thiazolidine-2,4-dione N-Ph |
| IIc-95 | 4-hydroxyphenyl on N of 2,5-dimethylpyrrole; pyrrole-3-CH=thiazolidine-2,4-dione N-Ph |

TABLE 10-continued

5-[[2,5-Dimethyl-1H-Pyrrol-3-Yl]Methylene]-2,4-Thiazolidinediones

| ID | Structure |
|---|---|
| IIc-96 | 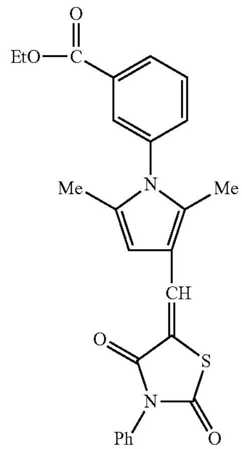 [SMILES: CCOC(=O)c1cccc(-n2c(C)cc(C=C3SC(=O)N(c4ccccc4)C3=O)c2C)c1] |
| IIc-97 | 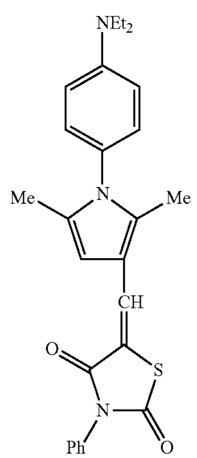 |
| IIc-98 | 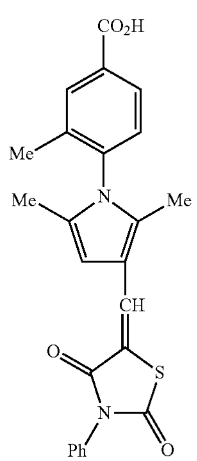 [SMILES: Cc1cc(C(=O)O)ccc1-n1c(C)cc(C=C2SC(=O)N(c3ccccc3)C2=O)c1C] |
| IIc-99 | |
| IIc-100 | |
| IIc-101 | |

TABLE 10-continued

5-[[2,5-Dimethyl-1H-Pyrrol-3-Yl]Methylene]-2,4-Thiazolidinediones

| ID | Structure |
|---|---|
| IIc-102 | 4-Br-C6H4 on pyrrole N; 2,5-dimethylpyrrol-3-yl methylene thiazolidinedione, N-Ph |
| IIc-103 | 3,4-diMe-C6H3 on pyrrole N; 2,5-dimethylpyrrol-3-yl methylene thiazolidinedione, N-Ph |
| IIc-104 | 4-NMe2-C6H4 on pyrrole N; 2,5-dimethylpyrrol-3-yl methylene thiazolidinedione, N-Ph |
| IIc-105 | 2-MeO-4-NO2-C6H3 on pyrrole N; 2,5-dimethylpyrrol-3-yl methylene thiazolidinedione, N-Ph |
| IIc-106 | 5-HO2C-2-Cl-C6H3 on pyrrole N; 2,5-dimethylpyrrol-3-yl methylene thiazolidinedione, N-Ph |
| IIc-107 | N-Ph on pyrrole; 2,5-dimethylpyrrol-3-yl methylene thiazolidinedione, N-Ph |

TABLE 10-continued

5-[[2,5-Dimethyl-1H-Pyrrol-3-Yl]Methylene]-2,4-Thiazolidinediones

| ID | Structure |
|---|---|
| IIc-108 | 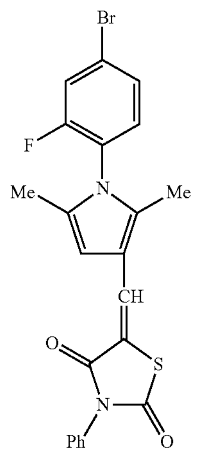 [SMILES: Cc1cc(C=C2SC(=O)N(c3ccccc3)C2=O)c(C)n1-c1ccc(Br)cc1F] |
| IIc-109 | 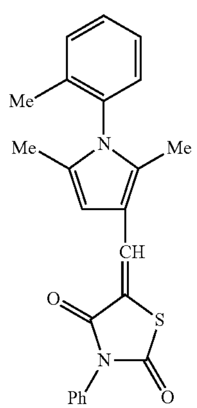 [SMILES: Cc1ccccc1-n1c(C)cc(C=C2SC(=O)N(c3ccccc3)C2=O)c1C] |
| IIc-110 | 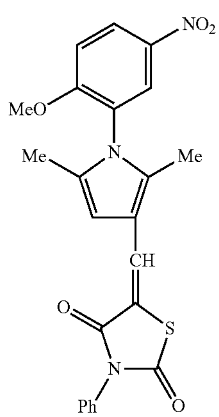 [SMILES: COc1ccc([N+](=O)[O-])cc1-n1c(C)cc(C=C2SC(=O)N(c3ccccc3)C2=O)c1C] |
| IIc-111 | |
| IIc-112 | |
| IIc-113 | |

A number of representative oxazoles and thiazole derivatives of this invention, as listed below in Table 11, were tested for their inhibitory activity and $IC_{50}$ were calculated. For the purpose of Table 11 below, activity of each compound is determined using the luciferase assay method in *Drosophila* Clone 8 cells.

TABLE 11
| ID | C#* | Structure | MW | IC50 (μM) |
|---|---|---|---|---|
| IIa-66 | C6 | 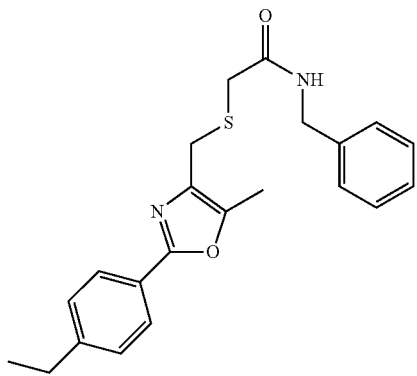 [SMILES: CCc1ccc(-c2nc(CSCC(=O)NCc3ccccc3)c(C)o2)cc1] | 380.51 | 3.51 |
| IIa-333 | C3 | 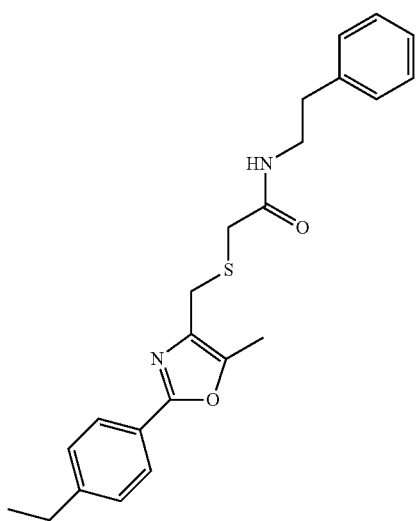 [SMILES: CCc1ccc(-c2nc(CSCC(=O)NCCc3ccccc3)c(C)o2)cc1] | 394.54 | 4.18 |
| IIa-719 | C1 | 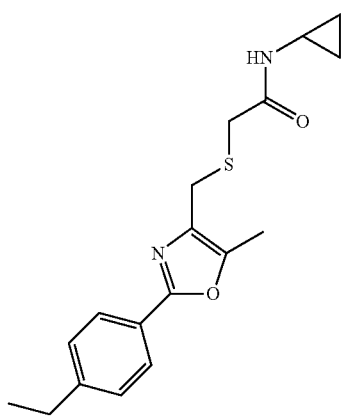 [SMILES: CCc1ccc(-c2nc(CSCC(=O)NC3CC3)c(C)o2)cc1] | 330.45 | 1.58 |

TABLE 11-continued

IC₅₀ Values of Exemplary Compounds

| ID | C#* | Structure | MW | IC50 (μM) |
|---|---|---|---|---|
| IIa-722 | C13 | 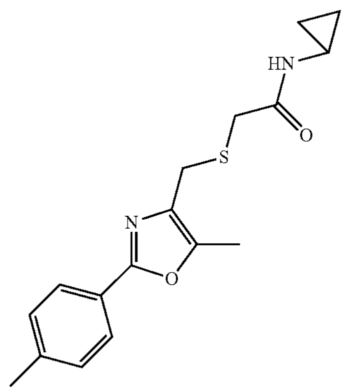 [SMILES: Cc1ccc(-c2nc(CSCC(=O)NC3CC3)c(C)o2)cc1] | 316.43 | 1259.72 |
| IIa-2102 | C8 | 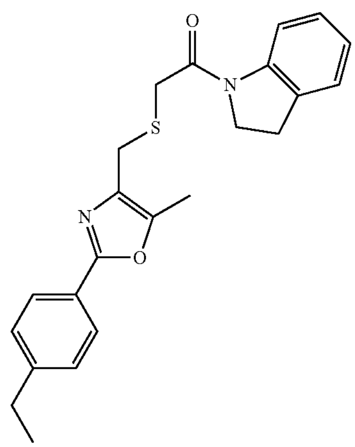 [SMILES: CCc1ccc(-c2nc(CSCC(=O)N3CCc4ccccc43)c(C)o2)cc1] | 392.52 | 1.10 |
| IIb-143 | C5 | 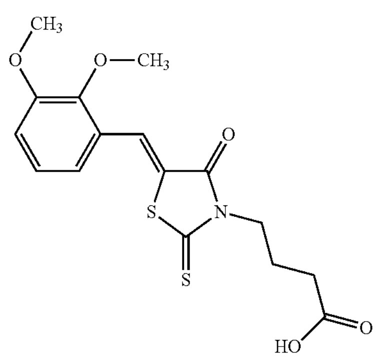 [SMILES: COc1cccc(/C=C2\SC(=S)N(CCCC(=O)O)C2=O)c1OC] | 367.4 | 3.06 |
| IIb-432 | C10 | 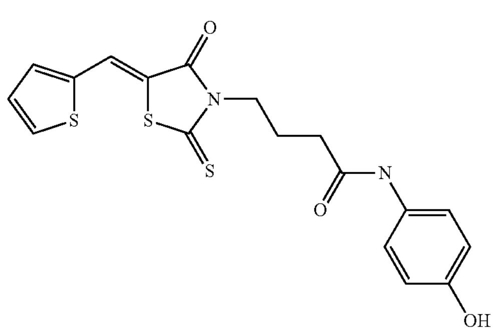 [SMILES: O=C(CCCN1C(=O)/C(=C/c2cccs2)SC1=S)Nc1ccc(O)cc1] | 404.5 | 4.76 |

TABLE 11-continued

IC$_{50}$ Values of Exemplary Compounds

| ID | C#* | Structure | MW | IC50 (μM) |
|---|---|---|---|---|
| IIc-3 | C14 | 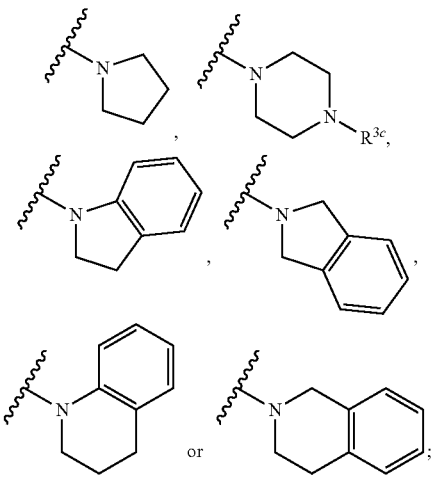 | 375.4 | 3.24 |

*see FIG.s 3-12

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS® /DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A pharmaceutical composition comprising a pharmaceutically acceptable carrier and a pharmaceutically effective amount of a compound according to formula I:

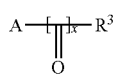
I wherein A is A$^1$;
A$^1$ is

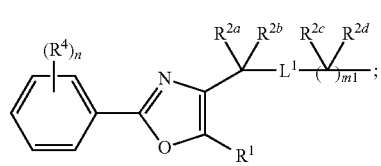

x is 1;
L$^1$ is S, SO or SO$_2$;
m1 is 1, 2 or 3; n is 1, 2, 3, 4 or 5;
each R$^1$, R$^{2a}$, R$^{2b}$, R$^{2c}$, and R$^{2d}$ is independently selected from hydrogen, halo, and substituted or unsubstituted C$_1$-C$_6$ alkyl;
R$^3$ is NR$^{3a}$R$^{3b}$; and
one of R$^{3a}$ and R$^{3b}$ is substituted or unsubstituted alkyl, substituted or unsubstituted benzyl, substituted or unsubstituted phenethyl, cycloheptyl, cyclohexyl, cyclohexyl substituted with methyl or dimethyl, substituted or unsubstituted cyclopentyl, substituted or unsubstituted cyclobutyl, or substituted or unsubstituted cyclopropyl; and the other is H or substituted or unsubstituted alkyl; or
NR$^{3a}$R$^{3b}$ is:

and wherein R$^{3c}$ is H or alkyl;
each R$^4$ is independently selected from alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, heteroaryloxy, substituted or unsubstituted heteroaryl, substituted or unsubstituted heteroalkyl, hydroxy, nitro, and thiol; and a pharmaceutically acceptable salt, solvate or prodrug thereof;

and stereoisomers, isotopic variants and tautomers thereof.

2. The pharmaceutical composition of claim 1 wherein the carrier is a parenteral carrier, oral or topical carrier.

3. The pharmaceutical composition according to claim 1, wherein the compound is according to formula IIa:

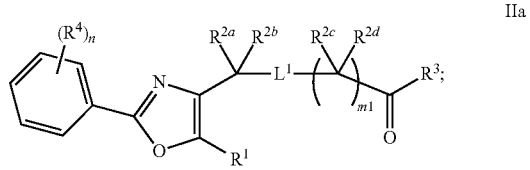

and wherein $L^1$, m1, n, $R^1$, $R^{2a}$, $R^{2b}$, $R^{2c}$, $R^{2d}$, $R^3$, and $R^4$, are as in claim 1.

4. The pharmaceutical composition according to claim 3, wherein $R^1$ is H, halo, or substituted or unsubstituted $C_1$-$C_6$ alkyl.

5. The pharmaceutical composition according to claim 3, wherein $R^3$ is $NR^{3a}R^{3b}$; and;
one of $R^{3a}$ and $R^{3b}$ is substituted or unsubstituted alkyl, substituted or unsubstituted benzyl, substituted or unsubstituted phenethyl, cycloheptyl, cyclohexyl, cyclohexyl substituted with methyl or dimethyl, substituted or unsubstituted cyclopentyl, substituted or unsubstituted cyclobutyl, or substituted or unsubstituted cyclopropyl; and the other is H.

6. The pharmaceutical composition according to claim 3, wherein $R^3$ is $NR^{3a}R^{3b}$; and
$NR^{3a}R^{3b}$ is:

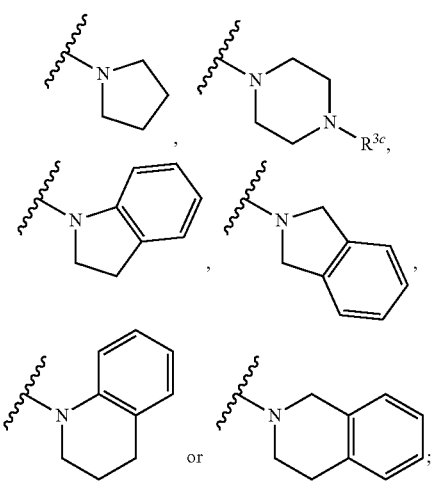

and wherein $R^{3c}$ is H or alkyl.

7. The pharmaceutical composition according to claim 1, wherein the compound is according to formula IVa:

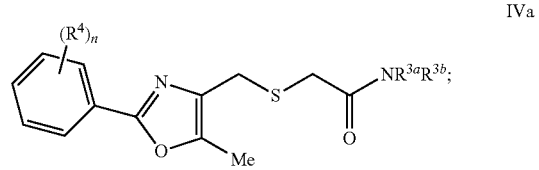

wherein n, and $R^4$ are as in claim 1; and one of $R^{3a}$ and $R^{3b}$ is substituted or unsubstituted alkyl, substituted or unsubstituted benzyl, substituted or unsubstituted phenethyl, cycloheptyl, cyclohexyl, cyclohexyl substituted with methyl or dimethyl, substituted or unsubstituted cyclopentyl, substituted or unsubstituted cyclobutyl, or substituted or unsubstituted cyclopropyl; and the other is H; or $NR^{3a}R^{3b}$ is:

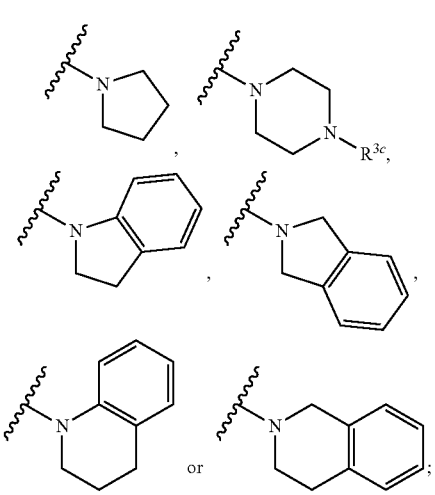

and wherein $R^{3c}$ is H or alkyl.

8. The pharmaceutical composition according to claim 7, wherein n is 1; and $R^4$ is alkyl, alkoxy, or haloalkyl.

9. The pharmaceutical composition according to claim 7, wherein one of $R^{3a}$ and $R^{3b}$ is substituted or unsubstituted benzyl, substituted or unsubstituted phenethyl, cycloheptyl, cyclohexyl, cyclohexyl substituted with methyl or dimethyl, substituted or unsubstituted cyclopentyl, substituted or unsubstituted cyclobutyl, or substituted or unsubstituted cyclopropyl; and the other is H.

10. The pharmaceutical composition according to claim 1, wherein the compound is according to formula VIIa, VIIb, VIIc or VIId:

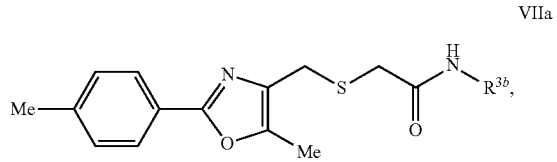

VIIb

[Structure: Et-phenyl-oxazole(Me)-CH2-S-CH2-C(O)-NH-R^{3b}]

VIIc

[Structure: MeS-phenyl-oxazole(Me)-CH2-S-CH2-C(O)-NH-R^{3b}] or

VIId

[Structure: MeO-phenyl-oxazole(Me)-CH2-S-CH2-C(O)-NH-R^{3b}].

wherein R^{3b} is substituted or unsubstituted alkyl, benzyl, substituted or unsubstituted phenethyl, cyclohexyl, cyclohexyl substituted with methyl or dimethyl, substituted or unsubstituted cyclopentyl, substituted or unsubstituted cyclobutyl, or substituted or unsubstituted cyclopropyl.

11. The pharmaceutical composition according to claim 1, wherein the compound is according to formula VIIIa, VIIIb, VIIIc, or VIIId:

VIIIa

[Structure: Me-phenyl-oxazole(Me)-CH2-S-CH2-C(O)-N(Cy)]

VIIIb

[Structure: Et-phenyl-oxazole(Me)-CH2-S-CH2-C(O)-N(Cy)]

VIIIc

[Structure: MeS-phenyl-oxazole(Me)-CH2-S-CH2-C(O)-N(Cy)] or

VIIId

[Structure: MeO-phenyl-oxazole(Me)-CH2-S-CH2-C(O)-N(Cy)].

wherein Cy is

[Pyrrolidine N-linked], [Piperazine N-linked with N-R^{3c}],

[Indoline N-linked], [Isoindoline N-linked],

[Tetrahydroquinoline N-linked] or [Tetrahydroisoquinoline N-linked];

and wherein R^{3c} is H or alkyl.

12. The pharmaceutical composition according to claim 1, wherein the compound is according to formula XIIa, XIIb, XIIc or XIId:

XIIa

[Structure: Me-phenyl-oxazole(Me)-CH2-S-CH2-C(O)-tetrahydroisoquinoline],

XIIb

[Structure: Et-phenyl-oxazole(Me)-CH2-S-CH2-C(O)-tetrahydroisoquinoline],

XIIc

[Structure: MeS-phenyl-oxazole(Me)-CH2-S-CH2-C(O)-tetrahydroisoquinoline] or

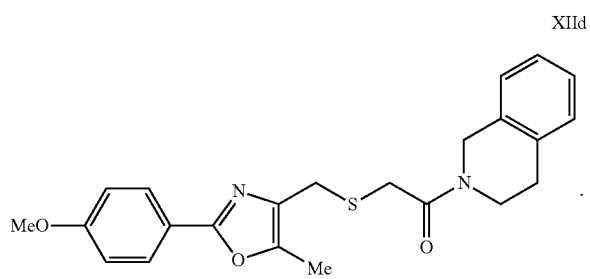

XIId

13. The pharmaceutical composition according to claim 1, wherein the compound is according to formula XIIIa, XIIIb, XIIIc or XIIId:

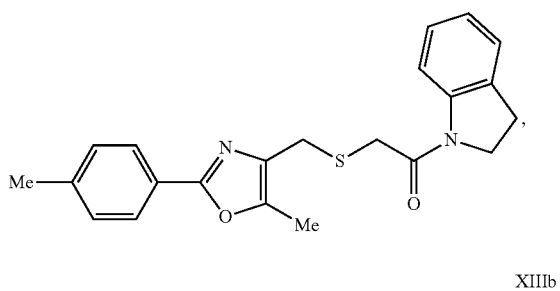

XIIIa

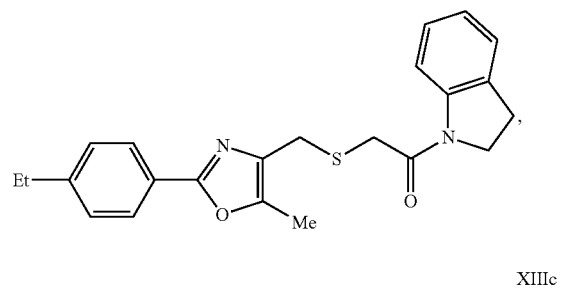

XIIIb

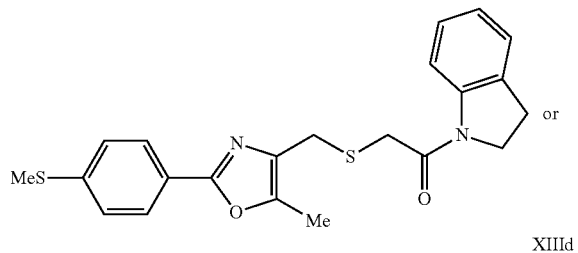

XIIIc or

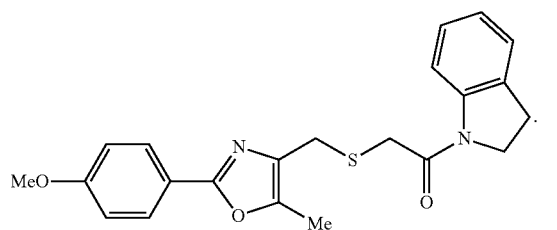

XIIId

14. A pharmaceutical composition comprising a pharmaceutically acceptable carrier and a pharmaceutically effective amount of a compound, wherein the compound is according to formula XIa, XIb, XIc or XId:

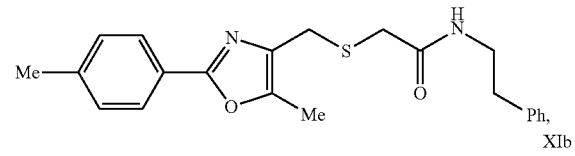

XIa

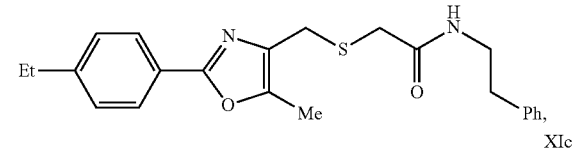

XIb

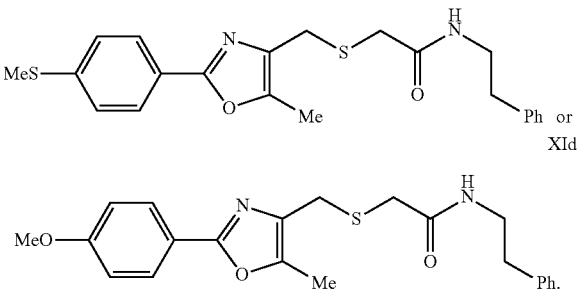

XIc or

XId

15. A pharmaceutical composition comprising a pharmaceutically acceptable carrier and a pharmaceutically effective amount of a compound, wherein the compound is selected from Table 1.

16. A pharmaceutical composition comprising a pharmaceutically acceptable carrier and a pharmaceutically effective amount of a compound, wherein the compound is selected from Table 2.

17. A pharmaceutical composition comprising a pharmaceutically acceptable carrier and a pharmaceutically effective amount of a compound, wherein the compound is selected from Table 4.

18. A pharmaceutical composition comprising a pharmaceutically acceptable carrier and a pharmaceutically effective amount of a compound according to formula I:

I wherein A is $A^1$;

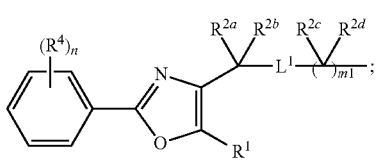

$A^1$ is
x is 1;
$L^1$ is S, SO or $SO_2$;
m1 is 1, 2 or 3; n is 1, 2, 3, 4 or 5;
each $R^1$, $R^{2a}$, $R^{2b}$, $R^{2c}$, and $R^{2d}$ is independently selected from hydrogen, halo, and substituted or unsubstituted $C_1$-$C_6$ alkyl;
$R^3$ is $NR^{3a}R^{3b}$; and
one of $R^{3a}$ and $R^{3b}$ is substituted or unsubstituted alkyl, substituted or unsubstituted benzyl, substituted or unsubstituted phenethyl, substituted or unsubstituted cyclopentyl, substituted or unsubstituted cyclobutyl, or substituted or unsubstituted cyclopropyl; and the other is H or substituted or unsubstituted alkyl; or $NR^{3a}R^{3b}$ is:

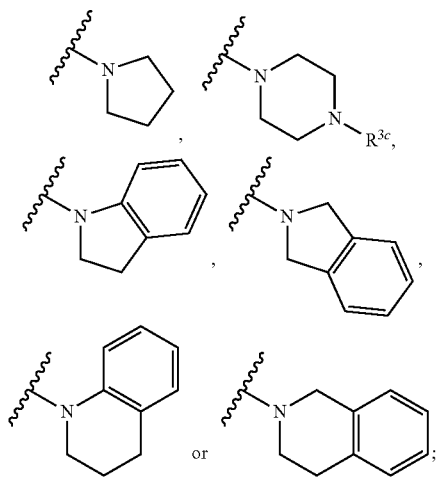

and wherein $R^{3c}$ is H or alkyl;

each $R^4$ is independently selected from alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, heteroaryloxy, substituted or unsubstituted heteroaryl, substituted or unsubstituted heteroalkyl, hydroxy, nitro, and thiol; and a pharmaceutically acceptable salt, solvate or prodrug thereof;

and stereoisomers, isotopic variants and tautomers thereof.

* * * * *